US010017481B2

(12) United States Patent
Obrecht et al.

(10) Patent No.: US 10,017,481 B2
(45) Date of Patent: Jul. 10, 2018

(54) CONFORMATIONALLY CONSTRAINED, FULLY SYNTHETIC MACROCYCLIC COMPOUNDS

(71) Applicant: POLYPHOR AG, Allschwil (CH)

(72) Inventors: Daniel Obrecht, Bättwil (CH); Philipp Ermert, Allschwil (CH); Said Oumouch, Mulhouse (FR); Arnaud Piettre, Hundsbach (FR); Jean-François Gosalbes, Huningue (FR); Marc Thommen, Nuglar (CH)

(73) Assignee: Polyphor AG, Allschwil (CH)

( * ) Notice: Subject to any disclaimer, the term of this patent is extended or adjusted under 35 U.S.C. 154(b) by 0 days.

(21) Appl. No.: 14/385,689

(22) PCT Filed: Mar. 15, 2013

(86) PCT No.: PCT/EP2013/055368

§ 371 (c)(1),
(2) Date: Sep. 16, 2014

(87) PCT Pub. No.: WO2013/139697

PCT Pub. Date: Sep. 26, 2013

(65) Prior Publication Data

US 2015/0051183 A1 Feb. 19, 2015

(30) Foreign Application Priority Data

Mar. 17, 2012 (EP) .................................... 12001830

(51) Int. Cl.

| | |
|---|---|
| *C07D 273/02* | (2006.01) |
| *C07D 498/04* | (2006.01) |
| *C07D 498/18* | (2006.01) |
| *C07D 498/08* | (2006.01) |
| *C07D 515/18* | (2006.01) |
| *C07D 291/08* | (2006.01) |
| *C07D 515/06* | (2006.01) |
| *C07D 515/22* | (2006.01) |
| *C07D 515/08* | (2006.01) |

(52) U.S. Cl.

CPC ......... *C07D 273/02* (2013.01); *C07D 291/08* (2013.01); *C07D 498/04* (2013.01); *C07D 498/08* (2013.01); *C07D 498/18* (2013.01); *C07D 515/06* (2013.01); *C07D 515/08* (2013.01); *C07D 515/18* (2013.01); *C07D 515/22* (2013.01)

(58) Field of Classification Search

CPC combination set(s) only.
See application file for complete search history.

(56) References Cited

U.S. PATENT DOCUMENTS 4,228,239 A 10/1980 Higashide et al.

FOREIGN PATENT DOCUMENTS

| | | |
|---|---|---|
| FR | 2 409 307 A1 | 6/1979 |
| GB | 2 002 759 A | 2/1979 |
| WO | WO 2006/074501 A1 | 7/2006 |

OTHER PUBLICATIONS

Majer et al., 2010, caplus an 2010:1465997.*
Sheh et al., 1987, caplus an 1987:526732.*
Buijnsters et al., 2009, caplus an 2009:1142128.*
Jenkins et al., 2014, caplus an 2014:1548146.*
LTB4, 2017, http://www.webmd.com/allergies/singulair-leukotriene-inhibitors.*
BB3-1, 2017, https://arizona.pure.elsevier.com/en/publications/metabolic-stability-and-tumor-inhibition-of-bombesingrp-receptor-.*
BB3-2, 2017, https://miami.pure.elsevier.com/en/publications/effective-inhibition-of-experimental-human-ovarian-cancers-with-a.*
BB3-3, 2017, https://link.springer.com/article/10.1007/BF01221028.*
Papatsonis, 2005, https://www.ncbi.nlm.nih.gov/pubmed/16034931.*
Kubek et al., Pediatric Neurology, vol. 26, No. 1, 9-17,2002.*
Virobay-2, 2014, http://www.virobayinc.com/docs/Neuroscience_Annual_Meeting.pdf.*
Virobay, 2012, http://www.virobayinc.com/docs/LEO_Pharma_Virobay.pdf.*

(Continued)

*Primary Examiner* — Sun Jae Yoo
(74) *Attorney, Agent, or Firm* — Birch, Stewart, Kolasch & Birch, LLP

(57) ABSTRACT

The conformationally restricted, spatially defined macrocyclic ring system of formula (I) is constituted by three distinct molecular parts: Template A, conformation Modulator B and Bridge C. Macrocycles described by this ring system I are readily manufactured by parallel synthesis or combinatorial chemistry in solution or on solid phase. They are designed to interact with a variety of specific biological target classes, examples being agonistic or antagonistic activity on G-protein coupled receptors (GPCRs), inhibitory activity on enzymes or antimicrobial activity. In particular, these macrocycles show inhibitory activity on endothelin converting enzyme of subtype 1 (ECE-1) and/or the cysteine protease cathepsin S (CatS), and/or act as antagonists of the oxytocin (OT) receptor, thyrotropin-releasing hormone (TRH) receptor and/or leukotriene B4 (LTB4) receptor, and/or as agonists of the bombesin 3 (BB3) receptor, and/or show antimicrobial activity against at least one bacterial strain. Thus they are showing great potential as medicaments for a variety of diseases.

(I)

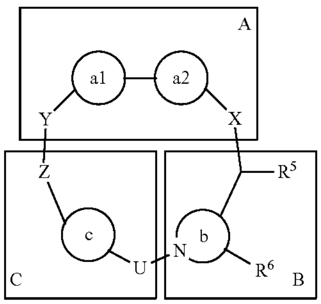

15 Claims, No Drawings

(56) References Cited

OTHER PUBLICATIONS

E-1, 2008, https://www.ncbi.nlm.nih.gov/pubmed/18767389.*

Obesity, 2017, http://www.webmd.com/diet/obesity/tc/obesity-medications.*

Graves, 2017, http://www.mayoclinic.org/diseases-conditions/graves-disease/basics/treatment/con-20025811.*

MS, 2017,http://www.webmd.com/multiple-sclerosis/guide/ms-treatment#1.*

Bergman et al., 1999, caplus an 1999:282203.*

Jones et al., 2008, caplus an 2008:1383654.*

Voskressensky et al., 2013, caplus an 2013:1506395.*

International Search Report, issued in PCT/EP2013/055368, dated May 3, 2013.

* cited by examiner

CONFORMATIONALLY CONSTRAINED, FULLY SYNTHETIC MACROCYCLIC COMPOUNDS

Macrocyclic natural and synthetic products have played a crucial role in the development of new drugs, especially as anti-infectives (F. von Nussbaum, M. Brands, B. Hinzen, S. Weigand, D. Häbich, *Angew. Chem. Int. Ed. Engl.* 2006, 45, 5072-5129; D. Obrecht, J. A. Robinson, F. Bernardini, C. Bisang, S. J. DeMarco, K. Moehle, F. O. Gombert, *Curr. Med. Chem.* 2009, 16, 42-65), as anti-cancer drugs and in other therapeutic areas (C. E. Ballard, H. Yu, B. Wang, *Curr. Med. Chem.* 2002, 9, 471-498; F. Sarabia, S. Chammaa, A. S. Ruiz, L. M. Ortiz, F. J. Herrera, *Curr. Med. Chem.* 2004, 11, 1309-1332). They often display remarkable biological activities, and many macrocycles or their derivatives have been successfully developed into drugs (L. A. Wessjohann, E. Ruijter, D. Garcia-Rivera, W. Brandt, *Mol. Divers.* 2005, 9, 171-186; D. J. Newman, G. M. Gragg, K. M. Snader, *J. Nat. Prod.* 2003, 66, 1022-1037). The chemical diversity of macrocyclic natural products is immense and provides a tremendous source of inspiration for drug design.

Macrocyclic natural and synthetic products generally exhibit semi-rigid backbone conformations placing appended substituents into well-defined spatial orientation. Certain ring sizes are preferred (L. A. Wessjohann, E. Ruijter, D. Garcia-Rivera, W. Brandt, *Mol. Divers.* 2005, 9, 171-186), e.g. 16-membered rings are frequently found in oxygen-containing macrocycles, such as polyketides (M. Q. Zhang, B. Wilkinson, *Curr. Opin. Biotechnol.* 2007, 18, 478-488). It is hypothesized that semi-rigid scaffolds possess some of the favorable binding properties of rigid molecules (entropy), yet still retaining enough flexibility to adapt suitable conformations in the binding event (induced fit).

Macrocyclic natural and synthetic products are generally classified according to the chemical nature of the backbone, e.g. cyclic peptides (Y. Hamady, T. Shioiri, *Chem. Rev.* 2005, 105, 4441-4482; N.-H. Tan, J. Zhou, *Chem. Rev.* 2006, 106, 840-895); cyclic depsipeptides (F. Sarabia, S. Chammaa, A. S. Ruiz, L. M. Ortiz, F. J. Herrera, *Curr. Med. Chem.* 2004, 11, 1309-1332); macrocyclic lactones (macrolactones) and macrolides; macrocyclic lactams (macrolactams), macrocyclic amines, macrocyclic ethers, macrocyclic ureas and urethanes, and others. The conformational, physico-chemical, pharmacological and pharmacodynamic properties of macrocyclic natural and synthetic compounds depend largely on the ring size, the chemical nature of the backbone, and of appended groups (L. A. Wessjohann, E. Ruijter, D. Garcia-Rivera, W. Brandt, *Mol. Divers.* 2005, 9, 171-186). By modifying these three parameters nature has created a virtually unlimited repertoire of molecular diversity. Despite their undisputed interesting biological properties, many natural products show limitations for drug development, such as low metabolic stability, i.e. short half lives, lack of or insufficient oral bioavailability as well as low tissue penetration and membrane permeability which renders them not amenable for intracellular targets. In addition, their high structural complexity imposes severe limitations to synthetic accessibility, often leaving fermentation or recombinant methods as sole options; thus making complex quality control and development processes necessary and leading to high production costs.

The present invention describes novel, fully synthetic, macrocyclic natural product-like molecules of type I (Scheme 1), accessible through a modular approach by connecting suitably protected building blocks A, B and C to a linear precursor followed by subsequent intramolecular cyclization.

Building blocks A serve as conformation-inducing templates ("Template") and are based on appropriately substituted and protected divalent biaryl-derivatives. Biaryl as used in this context shall comprise all possible pairwise combinations of aromatic carbocyclic and/or aromatic heterocyclic ring systems connected by a $C_{sp}{}^2$-$C_{sp}{}^2$ single bond, i.e. aryl-aryl, heteroaryl-heteroaryl, aryl-heteroaryl and heteroaryl-aryl.

Scheme 1: Macrocycles of Type I

I

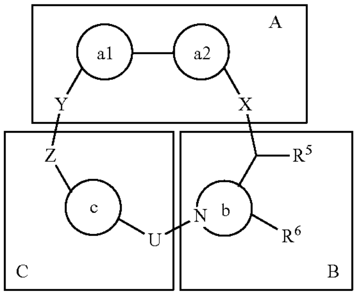

Building blocks B are corresponding to appropriately substituted and protected primary, secondary or tertiary aminoalcohols and are functioning as conformational modulators ("Modulator") by influencing the conformation of the macrocycle, e.g. through cis/trans-isomerization of amides.

Within the macrocycles backbone of I the building blocks A and B are connected via the "Bridge" C composed of one to three appropriately and independently substituted subunits c1, c2 and c3, which in turn are derived from suitably substituted and protected precursors, like, but not limited to, appropriately substituted and protected amino acids or amine derivatives.

Scheme 2: Building Blocks of Macrocyle I

"Template" A:

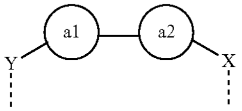

"Modulator" B:

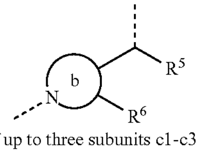

"Bridge" C comprised of up to three subunits c1-c3 (n = 0 - 1):

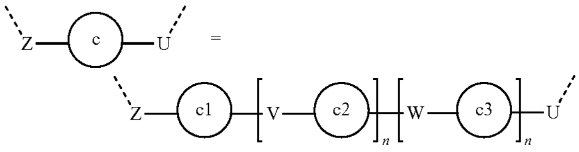

The connectivity —X— between Template A and Modulator B is defined by an ether (X═O) or thioether (X═S)

bond; while that between A and Bridge C is defined by the structural element —Y—Z— as detailed below. As sulfur atoms of such a thioether linkage can easily and selectively be oxidized to the corresponding sulfoxides (S═O) or sulfones ($S(═O)_2$), these higher oxidation states are also part of the invention.

X =
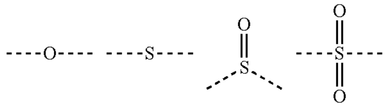

Z =
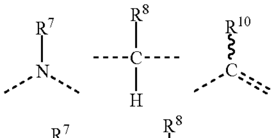

Y—Z =
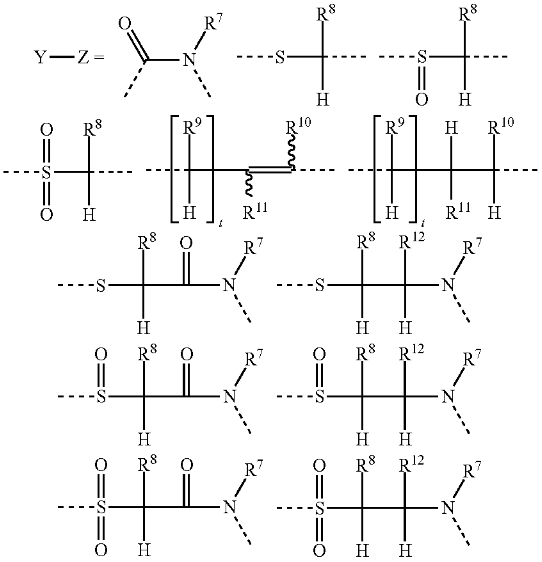

U =
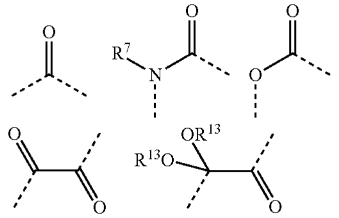

V or W =
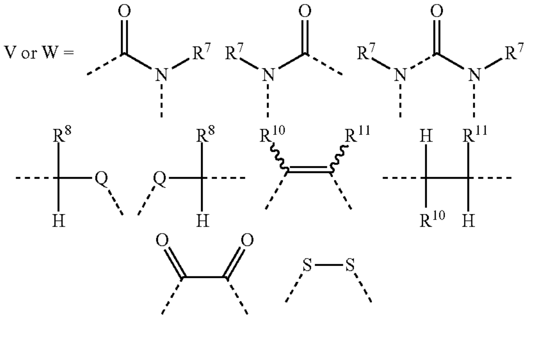

The generic connection —Y—Z— between A and C corresponds in most exemplified cases to a secondary or tertiary amide bond (—C(═O)—$NR^7$—). Alternative connectivities —Y—Z— are thioethers (—S—$CHR^8$—) and its oxidation products, i.e. sulfoxides (—S(═O)—$CHR^8$—) or sulfones (—$S(═O)_2$—$CHR^8$—), as well as olefinic moieties (—$(CHR^9)_t$—$CR^{11}$═$CR^{10}$—) and their reduced aliphatic analogs (—$(CHR^9)_t$—$CHR^{11}$—$CHR^{10}$—). Furthermore, in case of Templates A carrying a thiophenolic Y-group (Y═S) an additional two carbon spacer can be easily introduced by reacting with β-halo carboxyl or β-halo carbonyl compounds prior to processing with the C building blocks; thus providing access to —Y—Z— groups of type —S—$CHR^8$—C(═O)—$NR^7$—, —S—$CHR^8$—$CHR^{12}$—$NR^7$—, —S—$CHR^8$—$CHR^{12}$—$NR^7$— and their corresponding S-oxidized congeners.

The functional moiety U connects Bridge C with the nitrogen atom of Modulator B. In most cases this is realized by an amide bond, in which case the moiety U corresponds to a carbonyl group (—C(═O)—). Alternatively, U can be defined as a carbamoyl moiety (—$NR^7$—C(═O)—) leading to a urea (including the N-atom of B) as functional connection between B and C. Similarly, a carboxyl group (—O—C(═O)—) as U describes a carbamate linkage between B and C. In addition, U can represent an oxalyl group (—C(═O)—C(═O)—) or the corresponding acetal (—C(—$OR^{13})_2$—C(═O)—).

As mentioned before, the Bridge C itself comprises one to three (1-3) appropriately and independently substituted subunits c1, c2 and c3, which in turn are independently connected to each other by the generic groups V or W which can correspond to an amide bond (—C(═O)$NR^7$—) and the corresponding inverse amide (—$NR^7$C(═O)—), the methylene-heteroatom linkages —$CHR^8$-Q- and -Q-$CHR^8$—, an alkene[1,2]diyl moiety (—$CHR^{10}$═$CHR^{11}$—) or its reduced form as alkane[1,2]diyl (—$CHR^{10}$—$CHR^{11}$—), an oxalyl group (—C(═O)—C(═O)—) or a disulfide bridge (—S—S—).

The spatial orientation of the substituents in macrocycles I is modulated by the ring size and the stereochemical connectivity within building blocks A, B and C. Therefore the macrocyclic backbone as well as the substituents contribute to the biological activity of compounds of type I.

Compounds of this invention are characterized by macrocyclic backbones containing an aromatic ether/thioether linkage and one or more tertiary amide bonds. In other cases secondary amide bonds, aliphatic ether linkages, ethylidene or ethylene moieties are exemplified as part of the backbone.

Ether linkages in macrocyclic molecules favorably influence physico-chemical and pharmacological properties, such as solubility in aqueous solutions, metabolic stability against proteolytic degradation, cell permeability and oral absorption (K. X. Chen et al., *J. Med. Chem.* 2006, 49, 995-1005). In addition, tertiary amide bonds containing macrocycles are well-known for increased proteolytic stability, cell permeability and oral bioavailability compared to the parent molecules with secondary amide bonds (E. Biron, J. Chatterjee, O. Ovadia, D. Langenegger, J. Brueggen, D. Hoyer, H. A. Schmid, R. Jelinek, C. Gilon, A. Hoffmann, H. Kessler, *Angew. Chem. Int. Ed.* 2008, 47, 1-6; J. Chatterjee, O. Ovadia, G. Zahn, L. Marinelli, A. Hoffmann, C. Gilon, H. Kessler, *J. Med. Chem.* 2007, 50, 5878-5881). For instance, the cyclic undecapeptide cyclosporin A (INN: Ciclosporin), which is used as immunosuppressant in organ transplants, contains seven N-methylated amino acids and possesses good oral bioavailability when formulated appropriately (P. R. Beauchesne, N. S. C. Chung, K. M. Wasan, *Drug Develop. Ind. Pharm.* 2007, 33, 211-220).

A well documented process in protein folding events is the peptidyl cis/trans isomerization of proline or pipecolic acid containing polypeptides and proteins. In vivo this process is mediated by peptidyl prolyl cis/trans isomerases such as the cyclophilins, the FK506-binding proteins and the parvulins (A. Bell, P. Monaghan, A. P. Page, *Int. J. Parasitol.* 2006, 36, 261-276). Besides their role in protein folding and in the immune system, peptidyl prolyl cis/trans isomerases have been implicated in cell cycle control (P. E. Shaw, *EMBO Reports* 2002, 3, 521-526) and therefore constitute interesting pharmaceutical targets. In the context of this invention it is worth mentioning that both FK506 and cyclosporin A are macrocyclic natural products interacting with the FK506-binding protein and cyclophilins, respectively.

An interesting structural motif found in several natural products consist of a macrocylic ring system with a biaryl moiety as backbone element. Such biaryls, which are composed of two aromatic or heteroaromatic rings connected via a single bond, are the outstanding characteristic of a number of antibacterial macrocyclic peptide classes, like the biphenomycins, arylomycins and aciculitins; not to mention the glycopeptide antibiotics with the vancomycins as most prominent representatives (L. Feliu, M. Planas, *Int. J. Pept. Res. Ther.* 2005, 11, 53-97).

For many extra- and intracellular biological targets the quest for small molecule hits has been disappointing; this is especially true if protein-protein interactions are involved (J. A. Robinson, S. DeMarco, F. Gombert, K. Moehle, D. Obrecht, *Drug Disc. Today* 2008, 13, 944-951). These so-called "difficult targets" include e.g. receptor tyrosine kinases, growth factor receptors, transcription modulators, and chaperones. Interestingly, several natural and synthetic macrocyclic compounds have been described as promising starting points for drug discovery programs around such difficult targets (D. Obrecht, J. A. Robinson, F. Bernardini, C. Bisang, S. J. DeMarco, K. Moehle, F. O. Gombert, *Curr. Med. Chem.* 2009, 16, 42-65).

The novel macrocycles of type I described in the embodiments of this invention are designed to combine unique features of natural macrocyclic compounds with beneficial physico-chemical and pharmacological properties of small molecules, e.g.:

- Natural product-like structural complexity
- Good aqueous solubility
- High metabolic stability
- Improved oral bioavailability
- Enhanced membrane permeability
- Extra- and intracellular targets amenable
- Improved tissue penetration
- Small molecule-like pharmacokinetics
- Modular chemical synthesis
- Synthesis process well suited for parallelization
- Reasonable production costs
- Small molecule-like QC and development processes The Main Embodiment of the current invention of novel and fully synthetic macrocyclic compounds I according Scheme 1 (detailed in Scheme 2 and Scheme 3) is defined by groups of selected building blocks A, B and C as shown in Table 1 to Table 3 and by the appending substituents $R^1$-$R^{57}$ as detailed below.

As shortly indicated before, Template A exerts an important conformational constraint on products of type I. These structural effects of A depend on (i) the dihedral angle between the two $C_{sp}{}^2$-$C_{sp}{}^2$ connected aromatic rings $A_B$ and $A_C$ that are defining the Template A entity; (ii) the relative orientation of the attachment vectors of —X— and —Y— and (iii) the spatial distance between the groups —X— and —Y—.

One possible general preparative access to the corresponding building blocks of type A consists of an $C_{sp}{}^2$-$C_{sp}{}^2$-coupling between appropriately functionalized arene and/or heteroarenes (R. M. Kellogg et al., *Org. Process Res. Dev.* 2010, 14, 30-47; A. de Meijere, F. Diederich (eds), *Metal-*

*Catalyzed Cross-Coupling Reactions,* 2nd ed., Wiley-VCH 2004; especially for macrocyclic biaryls cf. Q. Wang, J. Zhu, *Chimia* 2011, 65, 168-174, and literature cited therein). Therefore the template A can be described by its two aryl/heteroaryl constituents $A_B$ and $A_C$, wherein $A_B$ is defined as that structural half of A that is directly connected with building block B and $A_C$ as that half that is directly bound to building block C. In case of a biphenyl derivative as Template A such disconnection can be illustrated e.g. as:

Scheme 4: Dissection of Template A into its constituents $A_B$ and $A_C$

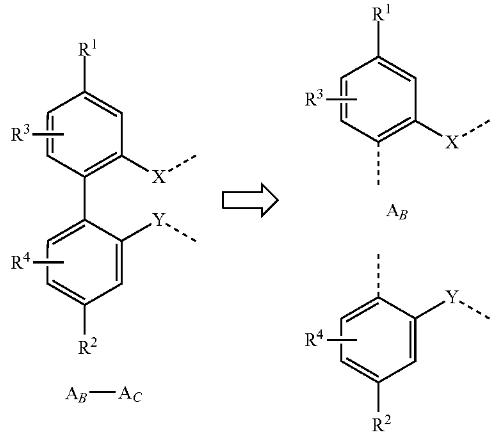

A $A_B$—$A_C$ $A_B$ $A_C$

In general, Template A of this invention is a divalent radical that is defined by the combinatorial connection of its two constituent aryl/heterorayl moieties $A_B$ and $A_C$ selected from Table 1 and Table 2.

TABLE 1

| Constituents $A_B$1-$A_B$65 of Template A | |
|---|---|
| 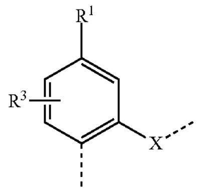 | $A_B$1 |
| 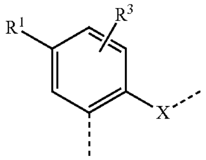 | $A_B$2 |
| 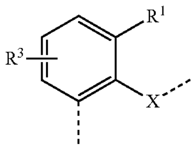 | $A_B$3 |

TABLE 1-continued
| Constituents $A_B1$-$A_B65$ of Template A | |
|---|---|
| 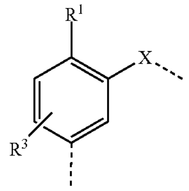 | $A_B4$ |
| 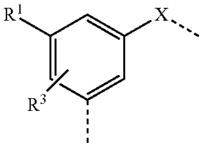 | $A_B5$ |
| 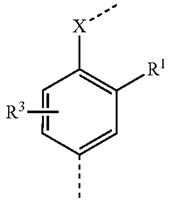 | $A_B6$ |
| 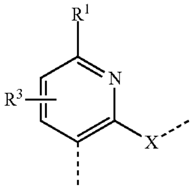 | $A_B7$ |
| 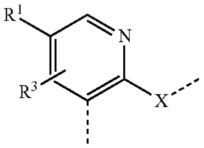 | $A_B8$ |
| 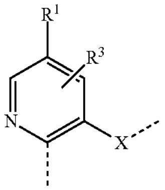 | $A_B9$ |
| 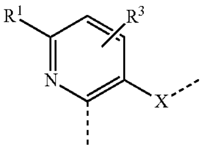 | $A_B10$ |
| 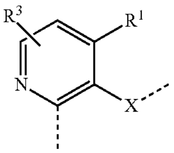 | $A_B11$ |
TABLE 1-continued
| Constituents $A_B1$-$A_B65$ of Template A | |
|---|---|
| 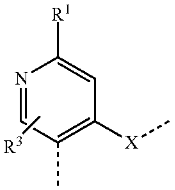 | $A_B12$ |
| 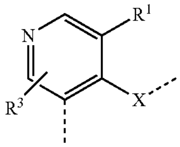 | $A_B13$ |
| 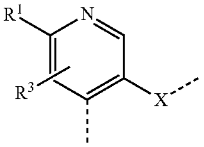 | $A_B14$ |
| 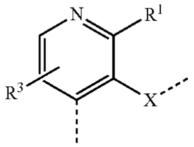 | $A_B15$ |
| 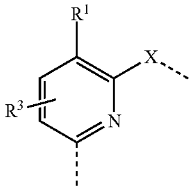 | $A_B16$ |
| 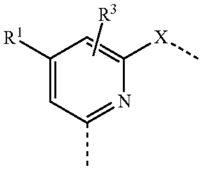 | $A_B17$ |
| 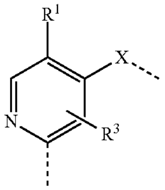 | $A_B18$ |
| 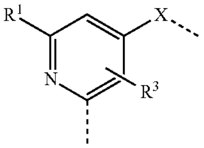 | $A_B19$ |

TABLE 1-continued
| Constituents $A_B1$-$A_B65$ of Template A | |
|---|---|
| 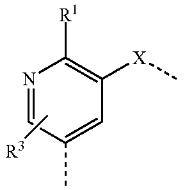 | $A_B20$ |
| 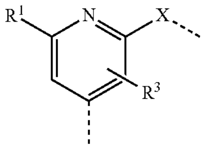 | $A_B21$ |
| 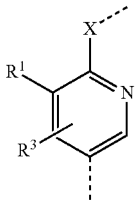 | $A_B22$ |
| 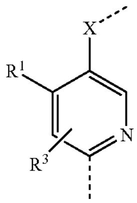 | $A_B23$ |
| 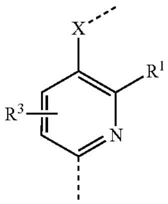 | $A_B24$ |
| 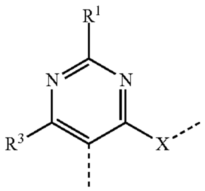 | $A_B25$ |
| 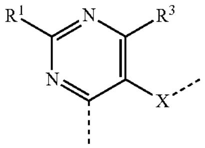 | $A_B26$ |
| 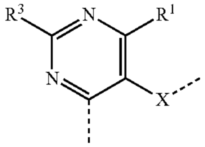 | $A_B27$ |
| 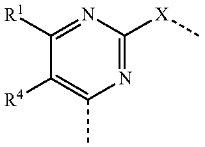 | $A_B28$ |
| 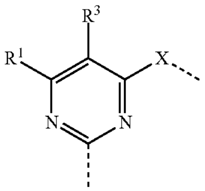 | $A_B29$ |
| 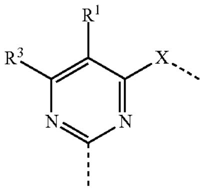 | $A_B30$ |
| 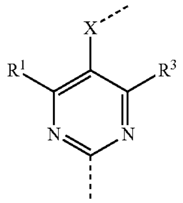 | $A_B31$ |
| 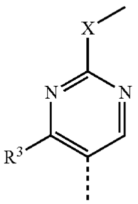 | $A_B32$ |
| 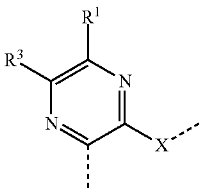 | $A_B33$ |
| 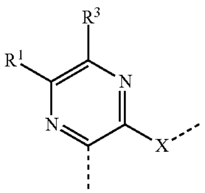 | $A_B34$ |
| 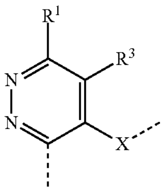 | $A_B35$ |

TABLE 1-continued
| Constituents $A_B1$-$A_B65$ of Template A | |
|---|---|
| 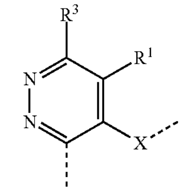 | $A_B36$ |
| 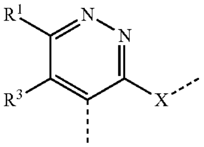 | $A_B37$ |
| 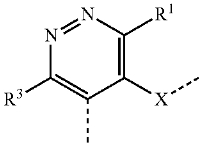 | $A_B38$ |
| 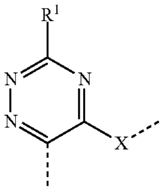 | $A_B39$ |
| 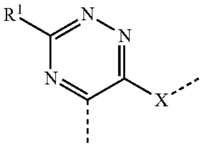 | $A_B40$ |
| 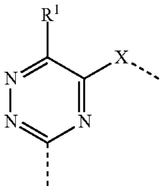 | $A_B41$ |
| 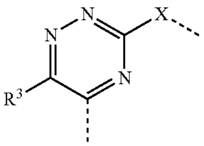 | $A_B42$ |
| 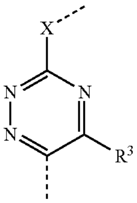 | $A_B43$ |
TABLE 1-continued
| Constituents $A_B1$-$A_B65$ of Template A | |
|---|---|
| 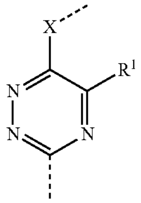 | $A_B44$ |
| 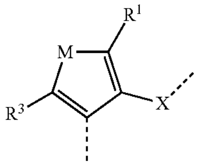 | $A_B45$ |
| 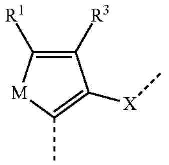 | $A_B46$ |
| 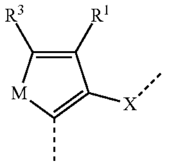 | $A_B47$ |
| 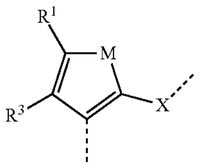 | $A_B48$ |
| 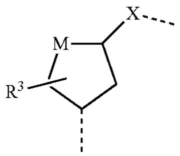 | $A_B49$ |
| 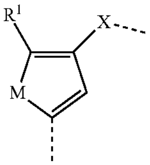 | $A_B50$ |
| 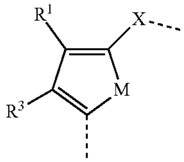 | $A_B51$ |
| 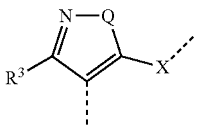 | $A_B52$ |

TABLE 1-continued
| Constituents $A_B$1-$A_B$65 of Template A | |
|---|---|
| 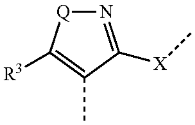 | $A_B$53 |
| 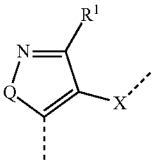 | $A_B$54 |
| 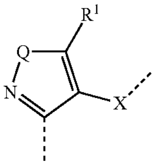 | $A_B$55 |
| 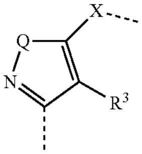 | $A_B$56 |
| 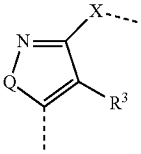 | $A_B$57 |
| 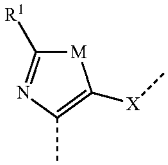 | $A_B$58 |
| 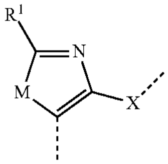 | $A_B$59 |
| 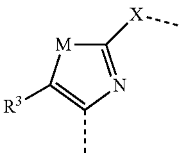 | $A_B$60 |
| 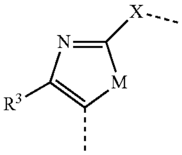 | $A_B$61 |
TABLE 1-continued
| Constituents $A_B$1-$A_B$65 of Template A | |
|---|---|
| 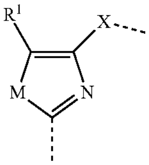 | $A_B$62 |
| 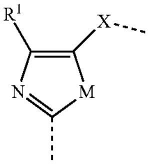 | $A_B$63 |
| 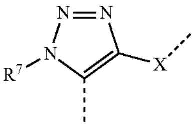 | $A_B$64 |
| 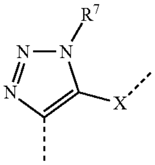 | $A_B$65 |
TABLE 2
| Constituents $A_C$1-$A_C$66 of Template A | |
|---|---|
| 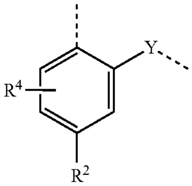 | $A_C$1 |
| 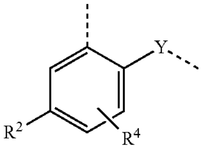 | $A_C$2 |
| 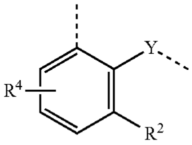 | $A_C$3 |
| 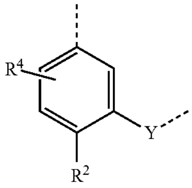 | $A_C$4 |

TABLE 2-continued
| Constituents $A_C1$-$A_C66$ of Template A | |
|---|---|
| 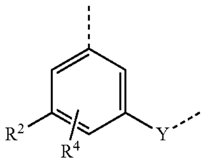 | $A_C5$ |
| 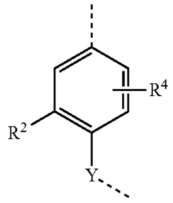 | $A_C6$ |
| 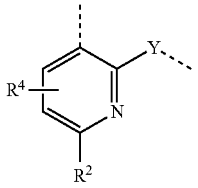 | $A_C7$ |
| 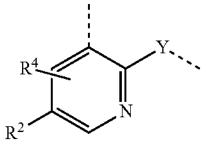 | $A_C8$ |
| 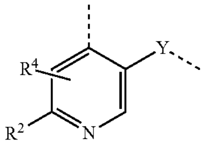 | $A_C9$ |
| 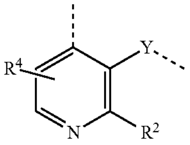 | $A_C10$ |
| 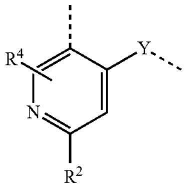 | $A_C11$ |
| 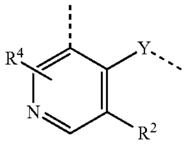 | $A_C12$ |
| 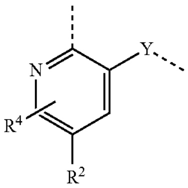 | $A_C13$ |
TABLE 2-continued
| Constituents $A_C1$-$A_C66$ of Template A | |
|---|---|
| 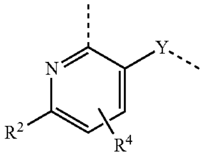 | $A_C14$ |
| 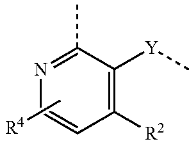 | $A_C15$ |
| 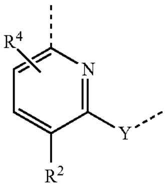 | $A_C16$ |
| 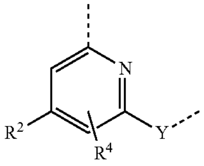 | $A_C17$ |
| 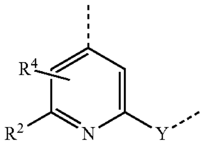 | $A_C18$ |
| 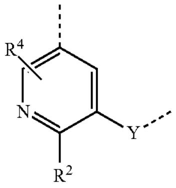 | $A_C19$ |
| 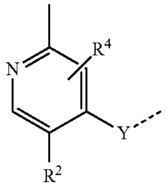 | $A_C20$ |
| 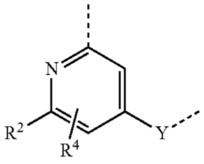 | $A_C21$ |

TABLE 2-continued
Constituents $A_C1$-$A_C66$ of Template A
| | |
|---|---|
| 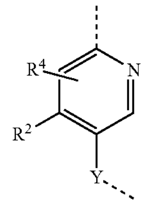 | $A_C22$ |
| 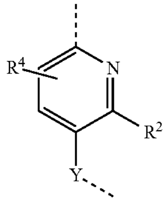 | $A_C23$ |
| 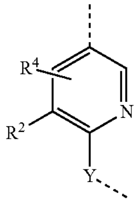 | $A_C24$ |
| 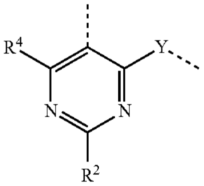 | $A_C25$ |
| 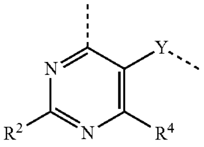 | $A_C26$ |
| 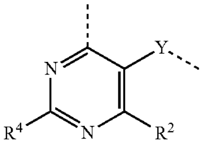 | $A_C27$ |
| 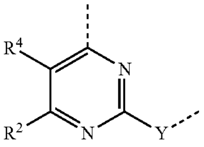 | $A_C28$ |
| 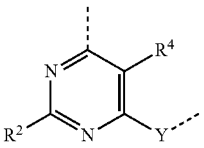 | $A_C29$ |
TABLE 2-continued
Constituents $A_C1$-$A_C66$ of Template A
| | |
|---|---|
| 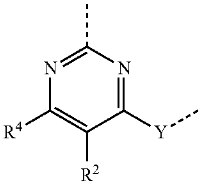 | $A_C30$ |
| 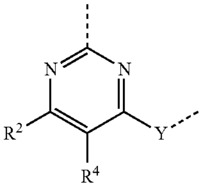 | $A_C31$ |
| 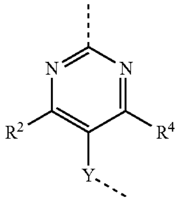 | $A_C32$ |
| 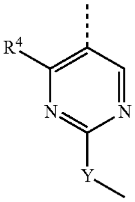 | $A_C33$ |
| 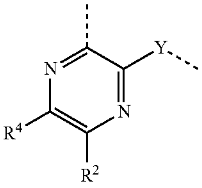 | $A_C34$ |
| 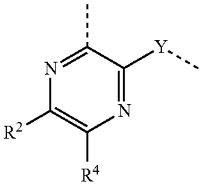 | $A_C35$ |
| 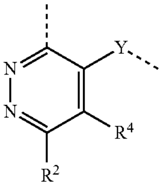 | $A_C36$ |
| 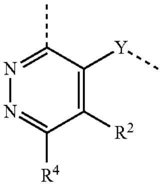 | $A_C37$ |

TABLE 2-continued
Constituents $A_C1$-$A_C66$ of Template A
$A_C38$
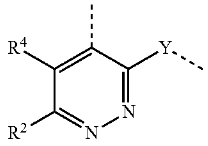
$A_C39$
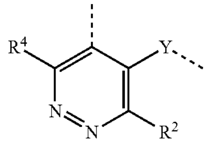
$A_C40$
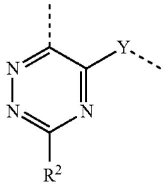
$A_C41$
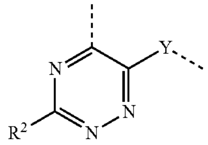
$A_C42$
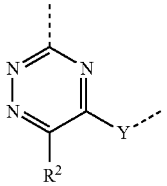
$A_C43$
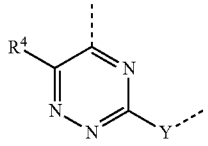
$A_C44$
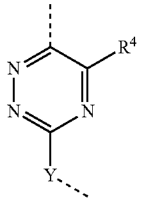
$A_C45$
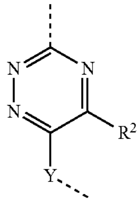
TABLE 2-continued
Constituents $A_C1$-$A_C66$ of Template A
$A_C46$
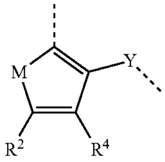
$A_C47$
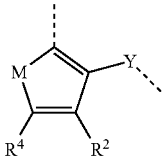
$A_C48$
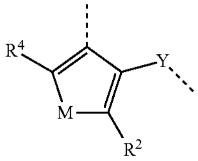
$A_C49$
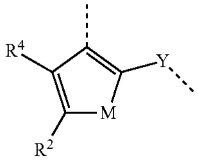
$A_C50$
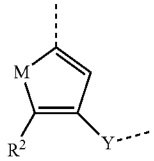
$A_C51$
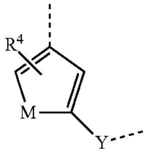
$A_C52$
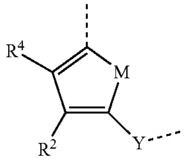
$A_C53$
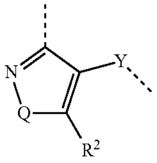
$A_C54$
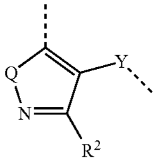

TABLE 2-continued

| Constituents $A_C1$-$A_C66$ of Template A | |
|---|---|
| 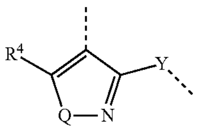 | $A_C55$ |
| 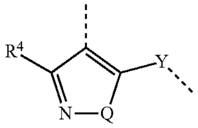 | $A_C56$ |
| 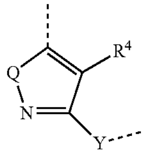 | $A_C57$ |
| 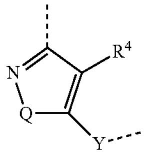 | $A_C58$ |
| 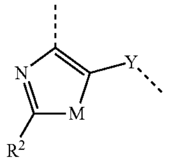 | $A_C59$ |
| 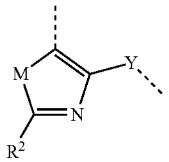 | $A_C60$ |
| 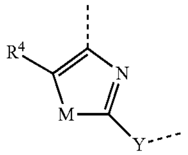 | $A_C61$ |
| 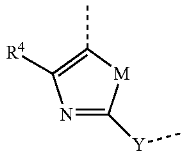 | $A_C62$ |
| 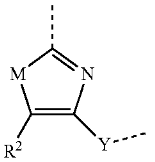 | $A_C63$ |
| 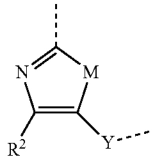 | $A_C64$ |
| 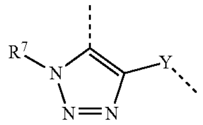 | $A_C65$ |
| 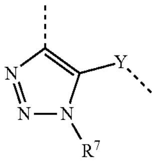 | $A_C66$ |

The Modulator B is a divalent radical selected from the groups of Table 3. B1-B10 are optionally substituted primary or secondary amines carrying a moiety of type —$CHR^5$-LG, wherein LG is a suitable leaving group that can be replaced by the nucleophilic groups on Template A forming an ether (—O—) or a thioether (—S—) linkage (as well as its oxidized variations —S(═O)— and —$S(=O)_2$—) between building blocks of type A and B. Examples of appropriate LGs include —OH, which is in situ transformed into the active LG during Mitsunobu reactions, or halogens, like —Br or —I, which are amenable to $S_N$ reactions.

For most examples of this invention, the amine nitrogen of Modulator B forms a secondary or tertiary amide bond with the carboxyl group of the Bridge C. By virtue of inducing peptidyl cis-trans isomerizations or stabilizing cis amide bonds, building blocks of type B can function as conformational modulators in macrocycles of type I.

TABLE 3

| Radicals B1-B10 | |
|---|---|
| 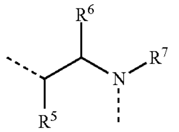 | B1 |
| 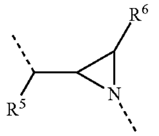 | B2 |
| 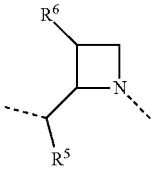 | B3 |

TABLE 3-continued

| Radicals B1-B10 | |
|---|---|
| 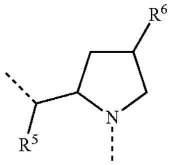 | B4 |
| 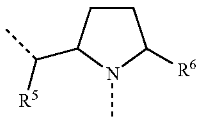 | B5 |
| 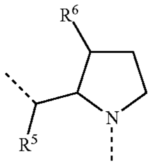 | B6 |
| 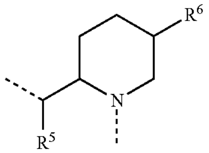 | B7 |

TABLE 3-continued

| Radicals B1-B10 | |
|---|---|
| 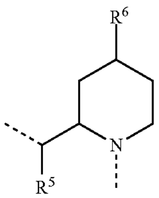 | B8 |

TABLE 3-continued

| Radicals B1-B10 | |
|---|---|
| 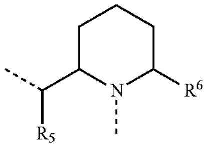 | B9 |
| 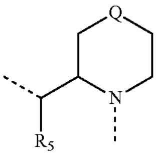 | B10 |

The Bridge C is a divalent radical selected from the groups of Table 4. This divalent moiety C may consist of one to three (1-3) subunits c1 to c3, i.e. (i) —Z-c1-U—, (ii) —Z-c1-V-c2-U— and (iii) —X-c1-V-c2-W-c3-U—. As a consequence Bridge C directly influences the ring size of the macrocycle and can therefore be regarded as spacer or linker. This Bridge C is joined to Template A via its terminal group Z (i.e. N-terminus in case of an amino acid) and to Modulator B via its terminal group U (i.e. C-terminus in case of an amino acid) to form the macrocyclic ring of type I. Thus C contributes to the backbone of macrocycle I with its carbon chains as well as with its functional groups Z, W, V and U (cf. Scheme 2 and 3).

TABLE 4

| Generic Representations of Bridge C | |
|---|---|
| 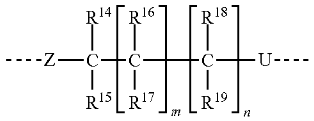 | C1 |
| 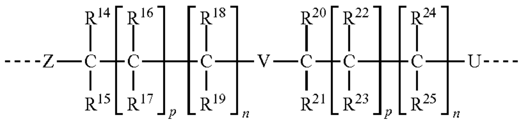 | C2 |
| 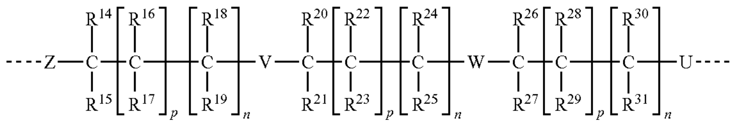 | C3 |

According to the preceding definitions, macrocycles I contain at least one amide bond or isosteric surrogate thereof. As emphasized in the introduction, tertiary amides generally show various ratios of cis and trans conformations in solution. In striking contrast secondary amides strongly prefer trans conformations. Such occurrence of cis and/or trans conformations in macrocyclic natural products containing tertiary amide groups is well documented. In some cases a rapid equilibration by peptidyl cis-trans isomerization is observed, whereas in other cases discrete cis and trans tertiary amide bonds are detected as two stable conformers in solution at room temperature. Consequently all possible stereoisomers, explicitly including atropisomers, conformers or rotamers of macrocycles of type I are part of this invention.

The substituents attached to the Main Embodiment of macrocycle I or its constituents A, B or C, are defined as follows:

$R^1$ and $R^2$ are independently defined as H; F; Cl; Br; I; $CF_3$; $OCF_3$; $OCHF_2$; $NO_2$; CN; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_qNR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qSO_2R^{38}$; —$(CR^{32}R^{33})_qR^{39}$; —$(CR^{32}R^{33})_q R^{40}$; —$(CR^{32}R^{33})_qR^{41}$; or —$(CR^{32}R^{33})_q R^{44}$;

$R^3$ and $R^4$ are independently defined as H; F; Cl; $CF_3$; $OCF_3$; $OCHF_2$; $NO_2$; CN; $C_{1-24}$-alkyl; cycloalkyl; heterocycloalkyl; aryl; heteroaryl; aryl-$C_{1-12}$-alkyl; heteroaryl-$C_{1-12}$-alkyl; $C_{1-12}$-alkoxy or aryloxy;

$R^5$ is H; $CF_3$; $C_{1-24}$-alkyl; cycloalkyl; heterocycloalkyl; aryl; heteroaryl; aryl-$C_{1-12}$-alkyl; or heteroaryl-$C_{1-12}$-alkyl;

$R^6$ is H; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_qNR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qSO_2R^{38}$; —$(CR^{32}R^{33})_qR^{39}$; —$(CR^{32}R^{33})_sR^{40}$; or —$(CR^{32}R^{33})_qR^{41}$; or —$(CR^{32}R^{33})_qR^{44}$;

$R^7$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; or an N-protecting group;

$R^8$ and $R^9$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{10}$, $R^{11}$ and $R^{12}$ are independently defined as H; $C_{1-24}$-alkyl; or cycloalkyl;

$R^{13}$ is $C_{1-24}$-alkyl or cycloalkyl;

$R^{14}$, $R^{20}$ and $R^{26}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_qNR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qSO_2R^{38}$; —$(CR^{32}R^{33})_qR^{39}$; —$(CR^{32}R^{33})_s R^{40}$; —$(CR^{32}R^{33})_qR^{41}$; or —$(CR^{32}R^{33})_q R^{44}$;

$R^{15}$, $R^{17}$, $R^{19}$, $R^{21}$, $R^{23}$, $R^{25}$, $R^{27}$, $R^{29}$ and $R^{31}$ are independently defined as H; $C_{1-24}$-alkyl; cycloalkyl; or heterocycloalkyl;

$R^{16}$, $R^{22}$ and $R^{28}$ are independently defined as H; $CF_3$; $C_{1-24}$-alkyl; cycloalkyl; heterocycloalkyl; aryl; heteroaryl; aryl-$C_{1-12}$-alkyl; or heteroaryl-$C_{1-12}$-alkyl;

$R^{18}$, $R^{24}$ and $R^{30}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{32}R^{33})_qOR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_q NR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_q COOR^{36}$; —$(CR^{32}R^{33})_qCONR^7R^{35}$; —$(CR^{32}R^{33})_q SO_2NR^7R^{35}$; —$(CR^{32}R^{33})_qCOR^{37}$; or —$(CR^{32}R^{33})_q R^{44}$;

$R^{32}$ is H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{51}R^{53})_qOR^{45}$; —$(CR^{51}R^{53})_qSR^{45}$; —$(CR^{51}R^{53})_qNR^7R^{45}$; —$(CR^{51}R^{53})_qOCONR^7R^{45}$; —$(CR^{51}R^{53})_qNR^{74}COOR^{36}$; —$(CR^{51}R^{53})_qNR^7COR^{37}$; —$(CR^{51}R^{53})_qNR^7CONR^7R^{45}$; —$(CR^{51}R^{53})_qNR^7SO_2R^{38}$; —$(CR^{51}R^{53})_qNR^7SO_2NR^7R^{45}$; —$(CR^{51}R^{53})_qCOOR^{36}$; —$(CR^{51}R^{53})_qCONR^7R^{45}$; —$(CR^{51}R^{53})_qSO_2NR^7R^{45}$; —$(CR^{51}R^{53})_qCOR^{37}$; —$(CR^{51}R^{53})_qSO_2R^{38}$; —$(CR^{51}R^{53})_qR^{39}$; —$(CR^{51}R^{53})_s R^{40}$; —$(CR^{51}R^{53})_qR^{41}$; or —$(CR^{51}R^{53})_q R^{44}$;

$R^{33}$ is H; $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{34}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{51}R^{53})_rOR^{45}$; —$(CR^{51}R^{53})_rNR^7R^{45}$; —$(CR^{51}R^{53})_rOCONR^7R^{35}$; —$(CR^{51}R^{53})_rNR^7COOR^{36}$; —$(CR^{51}R^{53})_rNR^7COR^{38}$; —$(CR^{51}R^{53})_rNR^7CONR^7R^{45}$; —$(CR^{51}R^{53})_rNR^7SO_2R^{38}$; —$(CR^{51}R^{53})_qCOOR^{36}$; —$(CR^{51}R^{53})_qCONR^7R^{45}$; —$(CR^{51}R^{53})_qSO_2NR^7R^{45}$; —$(CR^{51}R^{53})_qCOR^{38}$; —$(CR^{51}R^{53})_qSO_2R^{38}$; —$(CR^{51}R^{53})_qR^{39}$; —$(CR^{51}R^{53})_s R^{40}$; —$(CR^{51}R^{53})_qR^{41}$; or —$(CR^{51}R^{53})_q R^{44}$;

$R^{35}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; an N-protecting group; —$(CR^{32}R^{33})_rOR^{45}$; —$(CR^{32}R^{33})_rNR^7R^{45}$; —$(CR^{32}R^{33})_rOCONR^7R^{45}$; —$(CR^{32}R^{33})_rNR^7COOR^{36}$; —$(CR^{32}R^{33})_rNR^7CONR^7R^{50}$; —$(CR^{32}R^{33})_rNR^7SO_2R^{38}$; —$(CR^{32}R^{33})_rNR^7SO_2NR^7R^{50}$; —$(CR^{32}R^{33})_qCOOR^{36}$; —$(CR^{32}R^{33})_rNR^7COR^{37}$; —$(CR^{32}R^{33})_qCONR^7R^{50}$; —$(CR^{32}R^{33})_qCOR^{37}$; —$(CR^{32}R^{33})_qSO_2R^{38}$; —$(CR^{32}R^{33})_qSO_2NR^7R^{50}$; —$(CR^{32}R^{33})_qR^{39}$; —$(CR^{32}R^{33})_sR^{40}$; —$(CR^{32}R^{33})_qR^{41}$; or —$(CR^{32}R^{33})_q R^{44}$;

$R^{36}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; or an O/S-protecting group;

$R^{37}$ is $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{51}R^{53})_qOR^{45}$; —$(CR^{51}R^{53})_qSR^{45}$; —$(CR^{51}R^{53})_qNR^7R^{45}$; —$(CR^{51}R^{53})_qOCONR^7R^{45}$; —$(CR^{51}R^{53})_qNR^7COOR^{36}$; —$(CR^{51}R^{53})_qNR^7COR^{38}$; —$(CR^{51}R^{53})_qNR^7CONR^7R^{45}$; —$(CR^{51}R^{53})_qNR^7SO_2R^{38}$; —$(CR^{51}R^{53})_qNR^7SO_2NR^7R^{45}$; —$(CR^{51}R^{53})_qCOOR^{36}$; —$(CR^{51}R^{53})_qCONR^7R^{45}$; —$(CR^{51}R^{53})_qSO_2NR^7R^{45}$; —$(CR^{51}R^{53})_tCOR^{44}$; —$(CR^{51}R^{53})_qSO_2R^{38}$; —$(CR^{51}R^{53})_tR^{39}$; —$(CR^{51}R^{53})_u R^{40}$; —$(CR^{51}R^{53})_tR^{41}$; or —$(CR^{51}R^{53})_t R^{44}$;

$R^{38}$ is $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{39}$ is aryl; heteroaryl; —$C_6H_2R^3R^4R^{46}$; or a group of one of the formulae H1-H34 listed in Table 5.
TABLE 5
| Groups of Formulae H1-H34 | |
|---|---|
| 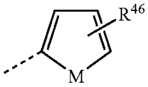 | H1 |
| 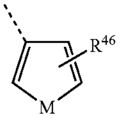 | H2 |
| 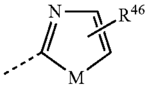 | H3 |
| 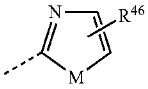 | H4 |
| 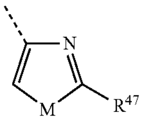 | H5 |
| 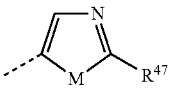 | H6 |
| 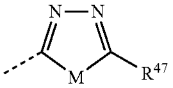 | H7 |
| 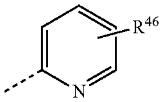 | H8 |
| 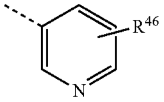 | H9 |
| 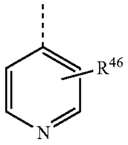 | H10 |
| 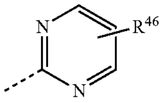 | H11 |
| 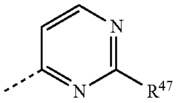 | H12 |
| 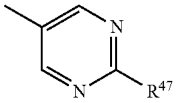 | H13 |
TABLE 5-continued
| Groups of Formulae H1-H34 | |
|---|---|
| 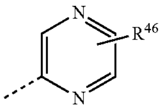 | H14 |
| 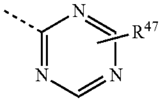 | H15 |
| 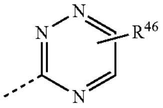 | H16 |
| 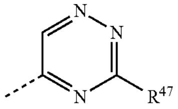 | H17 |
| 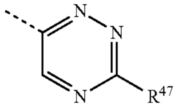 | H18 |
| 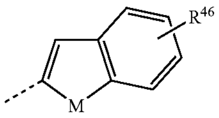 | H19 |
| 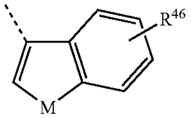 | H20 |
| 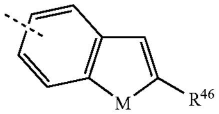 | H21 |
| 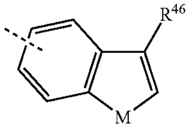 | H22 |
| 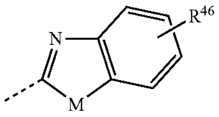 | H23 |
| 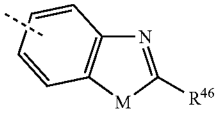 | H24 |
| 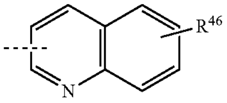 | H25 |
| 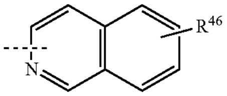 | H26 |

TABLE 5-continued
Groups of Formulae H1-H34
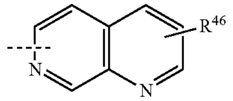
H27
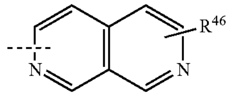
H28
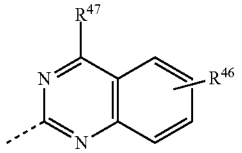
H29
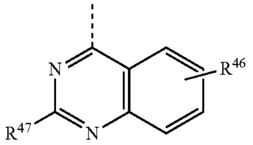
H30
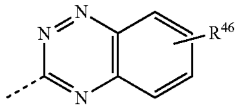
H31
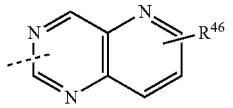
H32
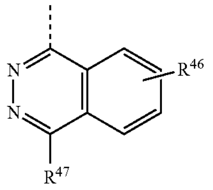
H33
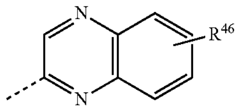
H34
$R^{40}$ is a group of one of formulae H35-H41 as shown in Table 6 below.
TABLE 6
Groups of Formulae H35-H41
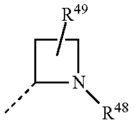
H35
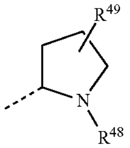
H36
TABLE 6-continued
Groups of Formulae H35-H41
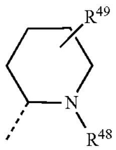
H37
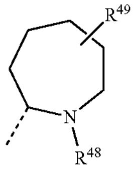
H38
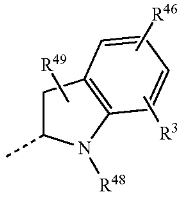
H39
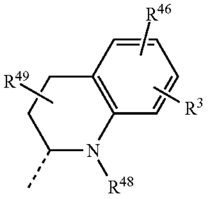
H40
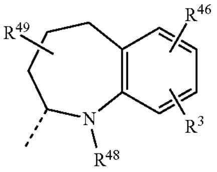
H41
$R^{41}$ is a group of one of formulae H42-H50 as shown in Table 7 below.
TABLE 7
Groups of Formulae H42-H50
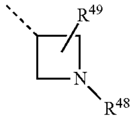
H42
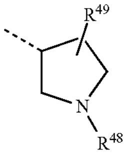
H43
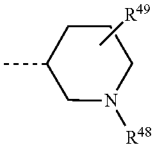
H44

TABLE 7-continued

| Groups of Formulae H42-H50 | |
|---|---|
| 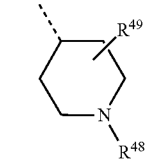 | H45 |
| 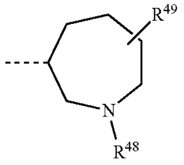 | H46 |
| 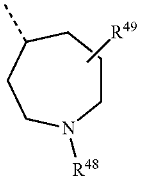 | H47 |
| 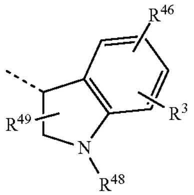 | H48 |
| 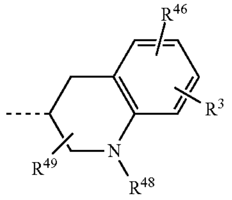 | H49 |
| 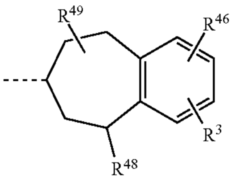 | H50 |

$R^{42}$ and $R^{43}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{44}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; or a group of one of the formulae H51-H55 as shown in Table 8 below.

TABLE 8

| Groups of Formulae H51-H55 | |
|---|---|
| 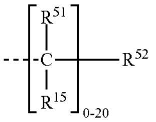 | H51 |
| 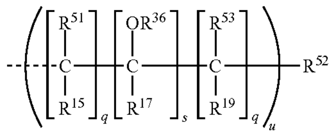 | H52 |
| 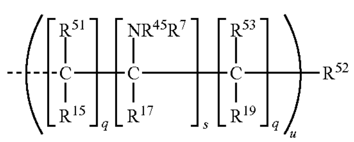 | H53 |
| 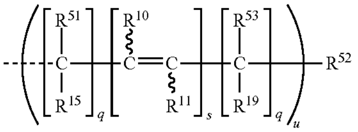 | H54 |
| 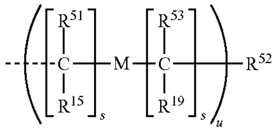 | H55 |

$R^{45}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; an N-protecting group; $-(CR^{51}R^{53})_rOR^{36}$; $-(CR^{51}R^{53})_rNR^7R^{57}$; $-(CR^{51}R^{53})_rOCONR^7R^{57}$; $-(CR^{51}R^{53})_rNR^7CONR^7R^{57}$; $-(CR^{51}R^{53})_rNR^7COR^{38}$; $-(CR^{51}R^{53})_rNR^7SO_2NR^7R^{57}$; $-(CR^{51}R^{53})_rNR^7SO_2R^{38}$; $-(CR^{51}R^{53})_qCOOR^{36}$; $-(CR^{51}R^{53})_qCOR^{38}$; $-(CR^{51}R^{53})_qSO_2R^{38}$; $-(CR^{51}R^{53})_qR^{39}$; $-(CR^{51}R^{53})_sR^{40}$; $-(CR^{51}R^{53})_qR^{41}$; or $-(CR^{51}R^{53})_sR^{44}$;

$R^{46}$ is H; F; Cl; $CF_3$; $OCF_3$; $OCHF_2$; $NO_2$; CN; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; $-(CR^{51}R^{53})_qOR^{36}$; $-(CR^{51}R^{53})_qSR^{36}$; $-(CR^{51}R^{53})_qNR^7R^{57}$; $-(CR^{51}R^{53})_qOCONR^7R^{57}$; $-(CR^{51}R^{53})_qNR^7COOR^{36}$; $-(CR^{51}R^{53})_qNR^7COR^{38}$; $-(CR^{51}R^{53})_qNR^7CONR^7R^{45}$; $-(CR^{51}R^{53})_qNR^7SO_2R^{38}$; $-(CR^{51}R^{53})_qNR^7SO_2NR^7R^{45}$; $-(CR^{51}R^{53})_qCOOR^{36}$; $-(CR^{51}R^{53})_qCONR^7R^{45}$; $-(CR^{51}R^{53})_qSO_2NR^7R^{45}$; $-(CR^{51}R^{53})_qCOR^{38}$; $-(CR^{51}R^{53})_qSO_2R^{38}$; or $-(CR^{51}R^{53})_qR^{44}$;

$R^{47}$ is H; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; or $-NR^7R^{45}$;

$R^{48}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; an N-protecting group; $-(CR^{51}R^{53})_rOR^{45}$; $-(CR^{51}R^{53})_rSR^{45}$; $-(CR^{51}R^{53})_rNR^7R^{45}$; $-(CR^{51}R^{53})_rOCONR^7R^{45}$; $-(CR^{51}R^{53})_rNR^7COOR^{36}$; $-(CR^{51}R^{53})_rNR^7COR^{38}$; $-(CR^{51}R^{53})_rNR^7CONR^7R^{45}$; $-(CR^{51}R^{53})_rNR^7SO_2R^{38}$; $-(CR^{51}R^{53})_rNR^7SO_2NR^7R^{45}$; $-(CR^{51}R^{53})_q$ $COOR^{36}$; $—(CR^{51}R^{53})_qCONR^7R^{45}$; $—(CR^{51}R^{53})_rSO_2NR^7R^{45}$; $—(CR^{51}R^{53})_qCOR^{38}$; $—(CR^{51}R^{53})_qSO_2R^{38}$; or $—(CR^{51}R^{53})_sR^{44}$;

$R^{49}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{51}R^{53})_qOR^{36}$; $—(CR^{51}R^{53})_qSR^{36}$; $—(CR^{51}R^{53})_qNR^7R^{45}$; $—(CR^{51}R^{53})_qNR^7COOR^{36}$; $—(CR^{51}R^{53})_qNR^7COR^{38}$; $—(CR^{51}R^{53})_q NR^7SO_2R^{38}$; $—(CR^{51}R^{53})_qNR^7CONR^7R^{45}$; $—(CR^{51}R^{53})_qCOOR^{36}$; $—(CR^{51}R^{53})_q CONR^7R^{45}$; $—(CR^{51}R^{53})_qCOR^{38}$; or $—(CR^{51}R^{53})_q R^{44}$;

$R^{50}$ is H; $C_{1-24}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{42}R^{43})_tOR^{36}$; $—(CR^{42}R^{43})_tNR^7R^{57}$; $—(CR^{42}R^{43})_tCOOR^{36}$; or $—(CR^{42}R^{43})_tCONR^7R^{57}$;

$R^{52}$ is H; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—OR^{36}$; $—NR^7R^{57}$; $—NR^7COR^{38}$; $—NR^7COOR^{36}$; $—NR^7SO_2R^{38}$; $—NR^7CONR^7R^{57}$; $—COOR^{36}$; $—CONR^7R^{57}$; $—C(=NR^7)NR^7R^{57}$; $—NR^7C(=NR^7)NR^7R^{57}$; or a group of one of the formulae H56-H110 as shown in Table 9 below.

TABLE 9

| Groups of Formulae H56-H110 | |
|---|---|
| 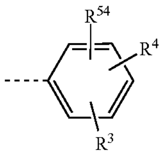 | H56 |
| 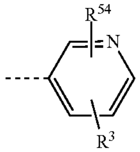 | H57 |
| 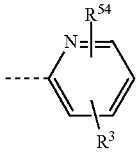 | H58 |
| 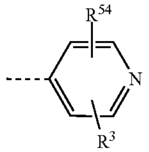 | H59 |
| 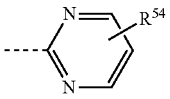 | H60 |
| 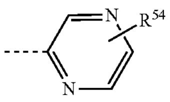 | H61 |

TABLE 9-continued

| Groups of Formulae H56-H110 | |
|---|---|
| 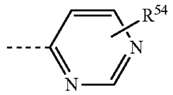 | H62 |
| 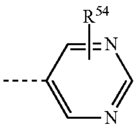 | H63 |
| 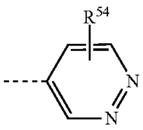 | H64 |
| 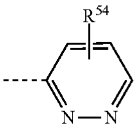 | H65 |
| 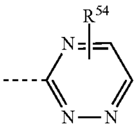 | H66 |
| 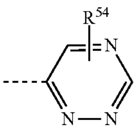 | H67 |
| 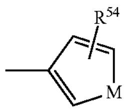 | H68 |
| 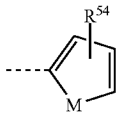 | H69 |
| 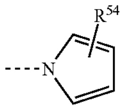 | H70 |
| 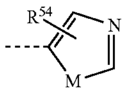 | H71 |
| 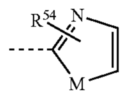 | H72 |
| 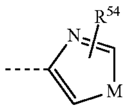 | H73 |

TABLE 9-continued
| Groups of Formulae H56-H110 | |
|---|---|
| 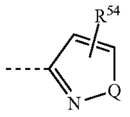 | H74 |
| 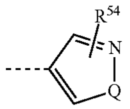 | H75 |
| 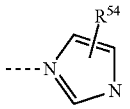 | H76 |
| 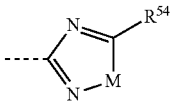 | H77 |
| 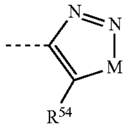 | H78 |
| 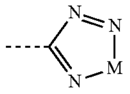 | H79 |
| 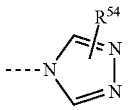 | H80 |
| 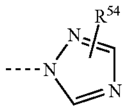 | H81 |
| 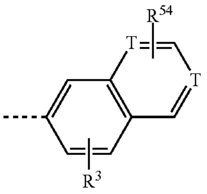 | H82 |
| 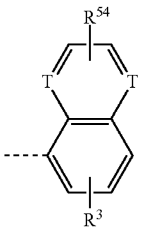 | H83 |
TABLE 9-continued
| Groups of Formulae H56-H110 | |
|---|---|
| 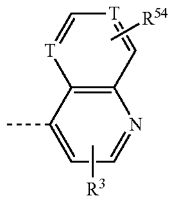 | H84 |
| 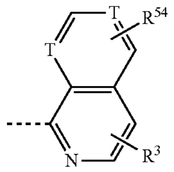 | H85 |
| 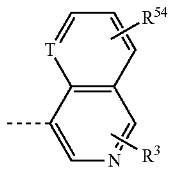 | H86 |
| 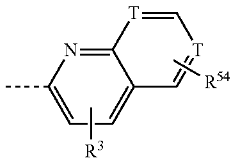 | H87 |
| 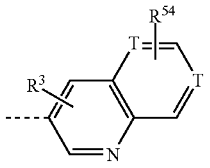 | H88 |
| 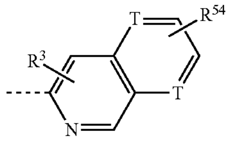 | H89 |
| 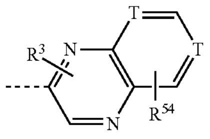 | H90 |
| 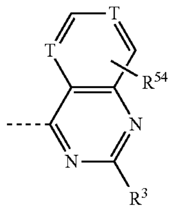 | H91 |

TABLE 9-continued
Groups of Formulae H56-H110
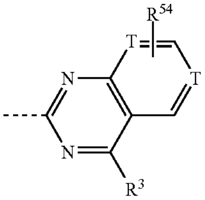
H92
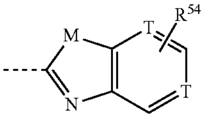
H93
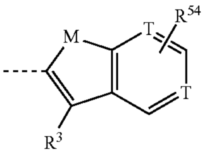
H94
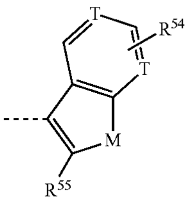
H95
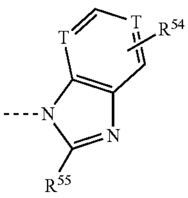
H96
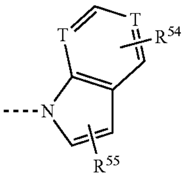
H97
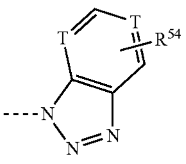
H98
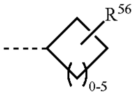
H99
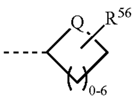
H100
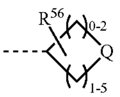
H101
TABLE 9-continued
Groups of Formulae H56-H110
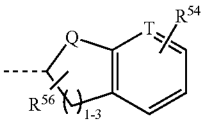
H102
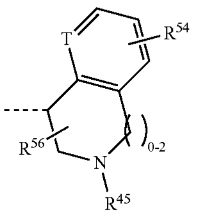
H103
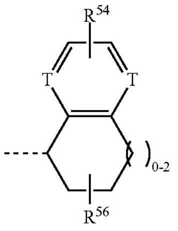
H104
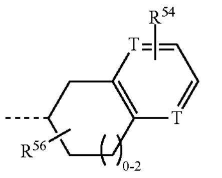
H105
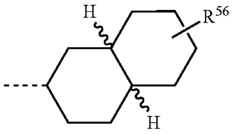
H106
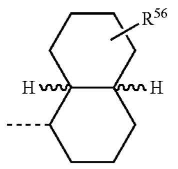
H107
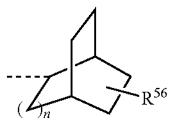
H108
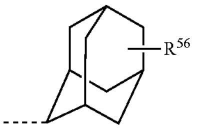
H109
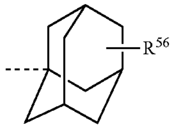
H110
$R^{54}$ is H; F; $CF_3$; $OCF_3$; $OCHF_2$; $NO_2$; CN; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; —$OR^{36}$; —$NR^7R^{57}$; —$NR^7COR^{38}$; —$NR^7SO_2R^{38}$; —$NR^7CONR^7R^{57}$; —$COR^{38}$; or —$SO_2R^{38}$;

$R^{55}$ is H; $CF_3$; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; —$COOR^{36}$; or —$CONR^7R^{45}$;

$R^{56}$ is H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{42}R^{43})_sOR^{36}$; —$(CR^{42}R^{43})_sNR^7R^{45}$; —$(CR^{42}R^{43})_qCOOR^{36}$; or —$(CR^{42}R^{43})_qCONR^7R^{45}$;

$R^{57}$ is H; $C_{1-24}$-alkyl; $C_{2-24}$-alkenyl; cycloalkyl; aryl; aryl-$C_{1-12}$-alkyl; or an N-protecting group.

Taken together, the following pairs of substituents can form optionally substituted cycloalkyl or heterocycloalkyl moieties: ($R^5$ and $R^6$); ($R^7$ and $R^{14}$); ($R^7$ and $R^{16}$); ($R^7$ and $R^{18}$); ($R^7$ and $R^{20}$); ($R^7$ and $R^{22}$); ($R^7$ and $R^{24}$); ($R^7$ and $R^{26}$); ($R^7$ and $R^{28}$); ($R^7$ and $R^{30}$); ($R^7$ and $R^{35}$); ($R^7$ and $R^{45}$); ($R^7$ and $R^{57}$); ($R^{13}$ and $R^{13}$); ($R^{14}$ and $R^{16}$); ($R^{14}$ and $R^{18}$); ($R^{15}$ and $R^{51}$); ($R^{19}$ and $R^{51}$); ($R^{20}$ and $R^{22}$); ($R^{20}$ and $R^{24}$); ($R^{26}$ and $R^{28}$); ($R^{26}$ and $R^{30}$); ($R^{32}$ and $R^{33}$); ($R^{42}$ and $R^{43}$); or ($R^{51}$ and $R^{53}$).

In addition, the structural elements —$NR^7R^{35}$; or —$NR^{44}R^{45}$ can form one of the groups of formulae H111-H118 as shown in Table 10 below.

TABLE 10

Heterocyclic Groups Defined by Linking the Residues of the Disubstituted Amino Groups —$NR^7R^{35}$ or —$NR^{44}R^{45}$.

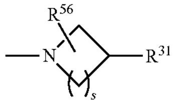
H111

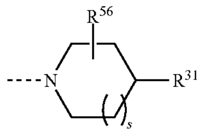
H112

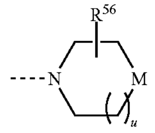
H113

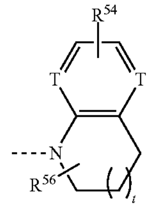
H114

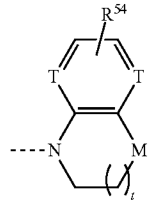
H115

TABLE 10-continued

Heterocyclic Groups Defined by Linking the Residues of the Disubstituted Amino Groups —$NR^7R^{35}$ or —$NR^{44}R^{45}$.

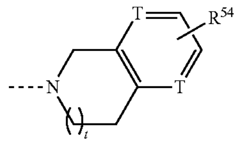
H116

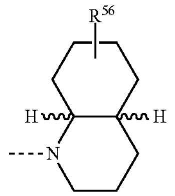
H117

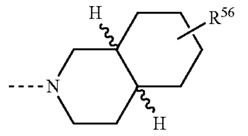
H118

Generic atoms and connector groups in the aforementioned structures are:

Z, Y, X, W, V, U as defined by Scheme 3;

T is $CR^{54}$ or N;

Q is O; S; or $NR^{35}$;

M is O; S; or $NR^7$.

The indices in the aforementioned structures are defined as:

m is an integer of 0-8;

n is an integer of 0-1;

p is an integer of 0-4;

q is an integer of 0-4;

r is an integer of 2-4;

s is an integer of 1-4;

t is an integer of 0-2;

u is an integer of 1-2.

For the avoidance of doubt, some of the aforementioned substituents, for example, but not limited to, $R^7$, $R^{16}$, $R^{17}$, $R^{18}$, $R^{19}$, $R^{22}$, $R^{23}$, $R^{24}$, $R^{25}$, $R^{28}$, $R^{29}$, $R^{30}$, $R^{31}$, $R^{32}$, $R^{33}$, $R^{42}$, $R^{43}$, $R^{45}$, $R^{46}$, and $R^{49}$; the indices as well as the generic atoms/connector groups (Z, Y, X, W, V, U, T, Q, M) can occur several times within the same molecular entity. In such a case each of them shall be selected independently from others specified by the same symbol.

"Salts" as understood herein are especially, but not limited to, the pharmaceutically acceptable salts of compounds of formula I. Such salts are formed, for example, as acid addition salts with organic or inorganic acids, from compounds of type I with a basic nitrogen atom. Suitable inorganic acids are, for example, halogen acids, such as hydrochloric acid, sulfuric acid, or phosphoric acid. Suitable organic acids are, for example, carboxylic, phosphonic, sulfonic or sulfamic acids; like acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzene-sulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

As used in this description, the term "alkyl", taken alone or in combinations (i.e. as part of another group, such as "aryl-$C_{1-6}$-alkyl"), designates saturated, straight-chain or branched hydrocarbon radicals and may be optionally substituted. The term "$C_{x-y}$-alkyl" (x and y each being an integer) refers to an alkyl group as defined before containing x to y carbon atoms. For example a $C_{1-6}$-alkyl group contains one to six carbon atoms. Representative examples of alkyl groups include methyl, ethyl, n-propyl, iso-propyl, n-butyl, iso-butyl, sec-butyl, tert-butyl, n-pentyl, n-hexyl and the like.

The term "alkenyl", taken alone or in combinations, designates straight chain or branched hydrocarbon radicals containing at least one or, depending on the chain length, up to four olefinic double bonds. Such alkenyl moieties are optionally substituted and can independently exist as E or Z configurations per double bond, which are all part of the invention. The term "$C_{x-y}$-alkenyl" (x and y each being an integer) refers to an alkenyl group as defined before, containing x to y carbon atoms.

The term "alkynyl" designates straight chain or branched hydrocarbon radicals containing at least one or, depending on the chain length, up to four triple bonds. The term "$C_{x-y}$-alkynyl" (x and y each being an integer) refers to an alkynyl group as defined before, containing x to y carbon atoms.

The term "cycloalkyl" refers to a saturated or partially unsaturated alicyclic moiety having from three to ten carbon atoms and may be optionally substituted. Examples of this moiety include, but are not limited to, cyclohexyl, norbornyl, decalinyl and the like.

The term "heterocycloalkyl" describes a saturated or partially unsaturated mono- or bicyclic moiety having from two to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4]nonane and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as F, Cl, Br, $CF_3$, OH, $OCF_3$, $OCHF_2$, $NH_2$, $N(CH_3)_2$, $NO_2$, CN, $C_{1-6}$-alkyl, $C_{2-6}$-alkenyl, $C_{2-6}$-alkynyl, phenyl or phenoxy.

The term "heteroaryl", taken alone or in combinations, designates aromatic heterocyclic radicals containing one or two five- and/or six-membered rings, at least one of them containing up to four heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "aryl-$C_{x-y}$-alkyl", as used herein, refers to an $C_{x-y}$-alkyl group as defined above, substituted by an aryl group, as defined above. Representative examples of aryl-$C_{x-y}$-alkyl moieties include, but are not limited to, benzyl, 1-phenylethyl, 2-phenylethyl, 3-phenylpropyl, 2-phenylpropyl and the like.

The term "heteroaryl-$C_{x-y}$-alkyl", as used herein, refers to an $C_{x-y}$-alkyl group as defined above, substituted by a heteroaryl group, as defined above. Examples of heteroaryl-$C_{x-y}$-alkyl groups include pyridin-3-ylmethyl, (1H-pyrrol-2-yl)ethyl and the like.

The terms "alkoxy" and "aryloxy", taken alone or in combinations, refer to the groups of —O-alkyl and —O-aryl respectively, wherein an alkyl group or an aryl group is as defined above. The term "$C_{x-y}$-alkoxy" (x and y each being an integer) refers to an —O-alkyl group as defined before containing x to y carbon atoms attached to an oxygen atom. Representative examples of alkoxy groups include methoxy, ethoxy, n-propoxy, iso-propoxy, n-butoxy, tert-butoxy and the like. Examples of aryloxy include e.g. phenoxy.

"Amino" designates primary, secondary or tertiary amines. Particular secondary and tertiary amines are alkylamines, dialkylamines, arylamines, diarylamines, arylalkylamines and diarylamines wherein the alkyl or aryl is as herein defined and optionally substituted.

The term "N-protecting group", as use herein, refers to the following commonly known groups, suitable to protect a nitrogen atom: allyloxycarbonyl (Alloc), tert-butoxycarbonyl (Boc), benzyloxycarbonyl (Cbz), 9-fluorenylmethoxycarbonyl (Fmoc), 2- or 4-nitrobenzenesulfonyl (Ns), 2-(trimethylsilyl)ethoxycarbonyl (Teoc), 2,2,2-Trichloroethoxycarbonyl (Troc), p-methoxybenzyl (PMB), 3,4-dimethoxybenzyl (DMB), triphenylmethyl (trityl, Tr), or 2-chlorotrityl (CTC).

The term "O/S-protecting group", as use herein, refers to the following commonly known groups, suitable to protect either an oxygen and/or a sulfur atom: tert-butyldimethylsilyl (TBDMS), tert-butyldiphenylsilyl (TBDPS), acetyl (Ac), pivaloyl (Piv), tert-butyl, 2-(trimethylsilyl)ethoxymethyl (SEM), methoxymethyl (MOM), triphenylmethyl (trityl, Tr), p-methoxybenzyl (PMB), 3,4-dimethoxybenzyl (DMB), or 2-(Trimethylsilyl)ethyl (TMSE).

A person skilled in the art might find easily corresponding equivalents for the above mentioned protecting groups which are considered to be as well comprised by the gist of the current invention. Examples of suitable protecting groups are as detailed in P. G. M. Wuts, T. W. Greene, *Greene's Protective Groups in Organic Synthesis*, John Wiley and Sons, 4th Edition, 2006.

The term "optionally substituted" is in general intended to mean that a group, such as, but not limited to $C_{x-y}$-alkyl, $C_{x-y}$-alkenyl, $C_{x-y}$-alkynyl, cycloalkyl, aryl, heteroaryl, heterocycloalkyl, $C_{x-y}$-alkoxy and aryloxy may be substituted with one or more substituents independently selected from amino (—$NH_2$), dimethylamino, nitro (—$NO_2$), halogen (F, Cl, Br, I), $CF_3$, cyano (—CN), hydroxy, methoxy, ethoxy, phenyloxy, benzyloxy, acetoxy, oxo (═O), carboxy, carboxamide, methyl, ethyl, n-propyl, iso-propyl, cyclo-propyl, phenyl, benzyl, sulfonic acid, sulfate, phosphonic acid, phosphate, phosphonate, or —$SR^a$, —$S(O)R^a$, —$S(O)_2R^a$, —$R^a$, —$C(O)R^a$, —$C(O)OR^a$, —$C(O)NR^bR^c$, —$C(=NR^a)NR^bR^c$, —$OR^a$, —$OC(O)R^a$, —$OC(O)OR^a$, —$OC(O)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^b$, —$NR^aC(O)OR^b$, —$NR^aC(O)NR^bR^c$, —$NR^aC(=NR^d)NR^bR^c$, —$NR^aS(O)R^b$, —$NR^aS(O)_2R^b$, wherein $R^a$, $R^b$, $R^c$, and $R^d$ are each independently hydrogen, $C_{1-6}$-alkyl, $C_{2-6}$-alkenyl, $C_{2-6}$-alkynyl, cycloalkyl, aryl, heteroaryl, or heterocycloalkyl as described herein; or $R^b$ and $R^c$ may be taken together with the N-atom to which they are attached forming heterocycloalkyl or heteroaryl. These groups in turn can be substituted with one or more moieties selected from the group consisting of halogen (F, Cl, Br, or I), hydroxyl, amino, mono-, di- or tri-$C_{1-6}$-alkylamino, mono-, di- or tri-arylamino, hydroxy, carboxy, $C_{1-6}$-alkoxy, aryloxy, nitro, cyano, sulfonic acid, sulfate, phosphonic acid, phosphate, or phosphonate.

As used herein, all groups that can be substituted in one embodiment are indicated to be "optionally substituted", unless otherwise specified.

The embodiments of the present invention shall include so-called "prodrugs" of the compounds of this invention. In general, such prodrugs will be functional derivatives of the compounds, which in vivo are readily convertible into the required compound. Conventional procedures for the selection and preparation of suitable prodrug derivatives are described, for example, in Hans Bundgaard, *Design of Prodrugs*, Elsevier, 1985; and in Valentino J. Stella et al., *Prodrugs: Challenges and Rewards*, Springer, 1st ed., 2007.

The term "isomer" comprises species of identical chemical formula, constitution and thus molecular mass, such as but not limited to C═C-double bond or amide cis/trans isomers, rotamers, conformers and diastereomers.

All possible stereoisomers—explicitly including atropisomers—conformers and rotamers as well as salts, solvates, clathrates, N-oxides, or isotopically enriched or enantiomerically enriched versions of the macrocycles of type I are part of this invention.

In a Preferred Embodiment of this invention, macrocycles of type I are defined by groups of selected building blocks A, B and C and substituents $R^1$-$R^{57}$. The connectivities between the building blocks of the preferred embodiment are defined as shown in Scheme 5.

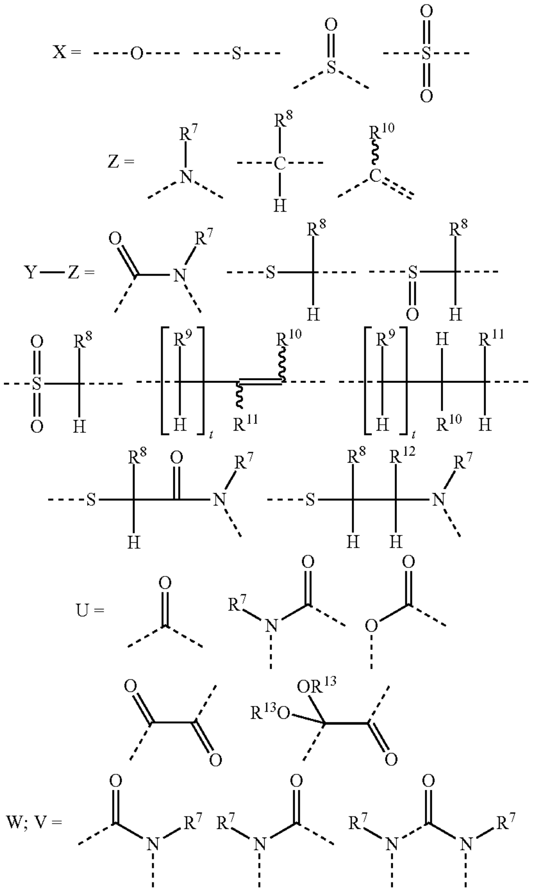

-continued

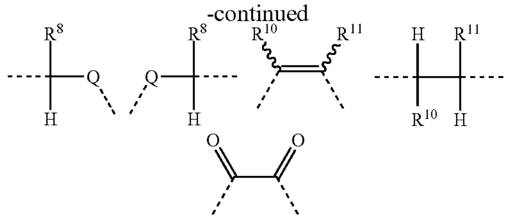

The biaryl Template A of the Preferred Embodiment is selected from $A_B$1-$A_C$1; $A_B$1-$A_C$2; $A_B$1-$A_C$3; $A_B$1-$A_C$4; $A_B$1-$A_C$5; $A_B$1-$A_C$6; $A_B$1-$A_C$8; $A_B$1-$A_C$9; $A_B$1-$A_C$11; $A_B$1-$A_C$12; $A_B$1-$A_C$13; $A_B$1-$A_C$19; $A_B$1-$A_C$22; $A_B$1-$A_C$24; $A_B$1-$A_C$49; $A_B$1-$A_C$51; $A_B$2-$A_C$1; $A_B$2-$A_C$2; $A_B$2-$A_C$3; $A_B$2-$A_C$4; $A_B$2-$A_C$5; $A_B$2-$A_C$11; $A_B$2-$A_C$12; $A_B$2-$A_C$51; $A_B$3-$A_C$1; $A_B$3-$A_C$2; $A_B$3-$A_C$3; $A_B$3-$A_C$4; $A_B$3-$A_C$5; $A_B$3-$A_C$11; $A_B$3-$A_C$12; $A_B$4-$A_C$1; $A_B$4-$A_C$2; $A_B$4-$A_C$3; $A_B$4-$A_C$4; $A_B$4-$A_C$5; $A_B$4-$A_C$6; $A_B$4-$A_C$11; $A_B$4-$A_C$12; $A_B$4-$A_C$19; $A_B$4-$A_C$22; $A_B$4-$A_C$24; $A_B$4-$A_C$49; $A_B$4-$A_C$51; $A_B$4-$A_C$59; $A_B$5-$A_C$1; $A_B$5-$A_C$2; $A_B$5-$A_C$3; $A_B$5-$A_C$4; $A_B$5-$A_C$5; $A_B$5-$A_C$11; $A_B$5-$A_C$12; $A_B$5-$A_C$51; $A_B$5-$A_C$59; $A_B$6-$A_C$1; $A_B$6-$A_C$4; $A_B$6-$A_C$8; $A_B$6-$A_C$9; $A_B$6-$A_C$11; $A_B$6-$A_C$13; $A_B$6-$A_C$16; $A_B$6-$A_C$18; $A_B$6-$A_C$19; $A_B$6-$A_C$20; $A_B$6-$A_C$30; $A_B$6-$A_C$31; $A_B$6-$A_C$49; $A_B$6-$A_C$51; $A_B$9-$A_C$6; $A_B$9-$A_C$49; $A_B$10-$A_C$6; $A_B$11-$A_C$6; $A_B$12-$A_C$2; $A_B$12-$A_C$5; $A_B$12-$A_C$11; $A_B$12-$A_C$12; $A_B$13-$A_C$2; $A_B$13-$A_C$5; $A_B$13-$A_C$11; $A_B$13-$A_C$12; $A_B$13-$A_C$5; $A_B$13-$A_C$11; $A_B$13-$A_C$12; $A_B$14-$A_C$49; $A_B$20-$A_C$2; $A_B$20-$A_C$6; $A_B$20-$A_C$49; $A_B$23-$A_C$4; $A_B$23-$A_C$49; $A_B$26-$A_C$2; $A_B$26-$A_C$5; $A_B$26-$A_C$11; $A_B$26-$A_C$12; $A_B$40-$A_C$2; $A_B$40-$A_C$5; $A_B$40-$A_C$11; $A_B$40-$A_C$12; $A_B$45-$A_C$49; $A_B$45-$A_C$52; $A_B$45-$A_C$57; $A_B$45-$A_C$58; $A_B$45-$A_C$65; $A_B$45-$A_C$66; $A_B$46-$A_C$57; $A_B$46-$A_C$58; $A_B$47-$A_C$58; $A_B$49-$A_C$49; $A_B$50-$A_C$57; $A_B$50-$A_C$58; $A_B$50-$A_C$61; $A_B$51-$A_C$49; $A_B$51-$A_C$61; $A_B$53-$A_C$2; $A_B$53-$A_C$5; $A_B$53-$A_C$11; $A_B$53-$A_C$12; $A_B$58-$A_C$2; $A_B$58-$A_C$5; $A_B$58-$A_C$11; $A_B$58-$A_C$12; $A_B$59-$A_C$2; $A_B$59-$A_C$5; $A_B$59-$A_C$11; $A_B$59-$A_C$12; or $A_B$59-$A_C$61.

The preferred Modulator B is selected from

B1; B4; B5; B6; B7; B8; B9 or B10;

and the preferred Bridge C from

C1; C2; or C3.

The substituents $R^1$-$R^{57}$ attached to the Preferred Embodiment of macrocycle I are as defined as shown below.

$R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $-(CR^{32}R^{33})_qOR^{34}$; $-(CR^{32}R^{33})_qSR^{34}$; $-(CR^{32}R^{33})_qNR^7R^{35}$; $-(CR^{32}R^{33})_qOCONR^7R^{35}$; $-(CR^{32}R^{33})_qNR^7COOR^{36}$; $-(CR^{32}R^{33})_qNR^7COR^{37}$; $-(CR^{32}R^{33})_qNR^7CONR^7R^{35}$; $-(CR^{32}R^{33})_qNR^7SO_2R^{38}$; $-(CR^{32}R^{33})_qNR^7SO_2NR^7R^{35}$; $-(CR^{32}R^{33})_qCOOR^{36}$; $-(CR^{32}R^{33})_qCONR^7R^{35}$; $-(CR^{32}R^{33})_qSO_2NR^7R^{35}$; $-(CR^{32}R^{33})_qCOR^{37}$; $-(CR^{32}R^{33})_qSO_2R^{38}$; $-(CR^{32}R^{33})_qR^{39}$; $-(CR^{32}R^{33})_qR^{40}$; $-(CR^{32}R^{33})_qR^{41}$; or $-(CR^{32}R^{33})_qR^{44}$;

$R^3$ and $R^4$ are independently defined as H; F; Cl; $CF_3$; $OCF_3$; $OCHF_2$; $NO_2$; CN; $C_{1-6}$-alkyl; cycloalkyl; $C_{1-6}$-alkoxy or aryloxy;

$R^5$ is H; $CF_3$; $C_{1-6}$-alkyl; or cycloalkyl;

$R^6$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $-(CR^{32}R^{33})_qOR^{34}$; $-(CR^{32}R^{33})_q$ $SR^{34}$; —$(CR^{32}R^{33})_qNR^7R^{35}$; —$(CR^{32}R^{33})_q$ $OCONR^7R^{35}$; —$(CR^{32}R^{33})_qNR^7COOR^{36}$; —$(CR^{32}R^{33})_qNR^7COR^{37}$; —$(CR^{32}R^{33})_qNR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qSO_2R^{38}$; —$(CR^{32}R^{33})_qR^{39}$; —$(CR^{32}R^{33})_sR^{40}$; —$(CR^{32}R^{33})_qR^{41}$; or —$(CR^{32}R^{33})_qR^{44}$;

$R^7$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^8$ and $R^9$ are independently defined as H; $CF_3$; $C_{1-6}$-alkyl; cycloalkyl; heterocycloalkyl;

$R^{10}$, $R^{11}$ and $R^{12}$ are independently defined as H; $C_{1-6}$-alkyl; or cycloalkyl;

$R^{13}$ is $C_{1-6}$-alkyl;

$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_q$ $NR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_q$ $COOR^{36}$; —$(CR^{32}R^{33})_qCONR^7R^{35}$; —$(CR^{32}R^{33})_q$ $SO_2NR^7R^{35}$; —$(CR^{32}R^{33})_qCOR^{37}$; —$(CR^{32}R^{33})_q$ $SO_2R^{38}$; —$(CR^{32}R^{33})_qR^{39}$; —$(CR^{32}R^{33})_s$ $R^{40}$; —$(CR^{32}R^{33})_qR^{41}$; or —$(CR^{32}R^{33})_q$ $R^{44}$;

$R^{15}$, $R^{17}$, $R^{19}$, $R^{21}$, $R^{23}$, $R^{25}$, $R^{27}$, $R^{29}$ and $R^{31}$ are independently defined as H; or $C_{1-6}$-alkyl;

$R^{16}$, $R^{22}$ and $R^{28}$ are independently defined as H; $CF_3$; or $C_{1-6}$-alkyl;

$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; —$(CR^{32}R^{33})_q$ $OR^{34}$; —$(CR^{32}R^{33})_qNR^7R^{35}$; —$(CR^{32}R^{33})_q$ $OCONR^7R^{35}$; —$(CR^{32}R^{33})_qNR^7COOR^{36}$; —$(CR^{32}R^{33})_qNR^7COR^{37}$; —$(CR^{32}R^{33})_q$ $NR^7CONR^7R^{35}$; —$(CR^{32}R^{33})_qNR^7SO_2R^{38}$; —$(CR^{32}R^{33})_qNR^7SO_2NR^7R^{35}$; —$(CR^{32}R^{33})_q$ $COOR^{36}$; —$(CR^{32}R^{33})_qCONR^7R^{35}$; —$(CR^{32}R^{33})_q$ $SO_2NR^7R^{35}$; —$(CR^{32}R^{33})_qCOR^{37}$; or —$(CR^{32}R^{33})_q$ $R^{44}$;

$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{51})_qOR^{45}$; —$(CR^{42}R^{51})_q$ $SR^{45}$; —$(CR^{42}R^{51})_qNR^7R^{45}$; —$(CR^{42}R^{51})_q$ $OCONR^7R^{45}$; —$(CR^{42}R^{51})_qNR^7COOR^{36}$; —$(CR^{42}R^{51})_qNR^7COR^{38}$; —$(CR^{42}R^{51})_q$ $NR^7CONR^7R^{45}$; —$(CR^{42}R^{51})_qNR^7SO_2R^{38}$; —$(CR^{42}R^{51})_qNR^7SO_2NR^7R^{45}$; —$(CR^{42}R^{51})_q$ $COOR^{36}$; —$(CR^{42}R^{51})_qCONR^7R^{45}$; —$(CR^{42}R^{51})_q$ $SO_2NR^7R^{45}$; —$(CR^{42}R^{51})_qCOR^{38}$; —$(CR^{42}R^{51})_q$ $SO_2R^{38}$; —$(CR^{42}R^{51})_qR^{39}$; —$(CR^{42}R^{51})_sR^{40}$; —$(CR^{42}R^{51})_qR^{41}$; or —$(CR^{42}R^{51})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; heteroaryl-$C_{1-6}$-alkyl; —$(CR^{42}R^{51})_rOR^{45}$; —$(CR^{42}R^{51})_rNR^7R^{45}$; —$(CR^{42}R^{51})_rOCONR^7R^{35}$; —$(CR^{42}R^{51})_r$ $NR^7COOR^{36}$; —$(CR^{42}R^{51})_rNR^7COR^{38}$; —$(CR^{42}R^{51})_r$ $NR^7CONR^7R^{45}$; —$(CR^{42}R^{51})_rNR^7SO_2R^{38}$; —$(CR^{42}R^{51})_qCOOR^{36}$; —$(CR^{42}R^{51})_qCONR^7R^{45}$; —$(CR^{42}R^{51})_qSO_2NR^7R^{45}$; —$(CR^{42}R^{51})_qCOR^{38}$; —$(CR^{42}R^{51})_qSO_2R^{38}$; —$(CR^{42}R^{51})_qR^{39}$; —$(CR^{42}R^{51})_s$ $R^{40}$; —$(CR^{42}R^{51})_qR^{41}$; or —$(CR^{42}R^{51})_q$ $R^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$alkyl; an N-protecting group; —$(CR^{32}R^{33})_rOR^{45}$; —$(CR^{32}R^{33})_rNR^7R^{45}$; —$(CR^{32}R^{33})_rOCONR^7R^{45}$; —$(CR^{32}R^{33})_rNR^7COOR^{36}$; —$(CR^{32}R^{33})_rNR^7COR^{37}$; —$(CR^{32}R^{33})_rNR^7CONR^7R^{45}$; —$(CR^{32}R^{33})_r$ $NR^7SO_2R^{38}$; —$(CR^{32}R^{33})_rNR^7SO_2NR^7R^{45}$; —$(CR^{32}R^{33})_qCOOR^{36}$; —$(CR^{32}R^{33})_qCONR^7R^{45}$; —$(CR^{32}R^{33})_qCOR^{37}$; —$(CR^{32}R^{33})_qSO_2R^{38}$; —$(CR^{32}R^{33})_qSO_2NR^7R^{50}$; —$(CR^{32}R^{33})_qR^{39}$; —$(CR^{32}R^{33})_sR^{40}$; —$(CR^{32}R^{33})_qR^{41}$; or —$(CR^{32}R^{33})_q$ $R^{44}$;

$R^{36}$ is H; $C_{1-6}$-alkyl; cycloalkyl; aryl; aryl-$C_1$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; —$(CR^{42}R^{51})_qOR^{45}$; —$(CR^{42}R^{51})_qSR^{45}$; —$(CR^{42}R^{51})_q$ $NR^7R^{45}$; —$(CR^{42}R^{51})_sOCONR^7R^{45}$; —$(CR^{42}R^{51})_s$ $NR^7COOR^{36}$; —$(CR^{42}R^{51})_qNR^7COR^{44}$; —$(CR^{42}R^{51})_s$ $NR^7CONR^7R^{45}$; —$(CR^{42}R^{51})_s$ $NR^7SO_2R^{38}$; —$(CR^{42}R^{51})_sR^7SO_2NR^7R^{45}$; —$(CR^{42}R^{51})_qCOOR^{36}$; —$(CR^{42}R^{51})_qCONR^7R^{45}$; —$(CR^{42}R^{51})_qSO_2NR^7R^{45}$; —$(CR^{42}R^{51})_rCOR^{38}$; —$(CR^{42}R^{51})_qSO_2R^{38}$; —$(CR^{42}R^{51})_rR^{39}$; —$(CR^{42}R^{51})_u$ $R^{40}$; —$(CR^{42}R^{51})_t$ $R^{41}$; or —$(CR^{42}R^{51})_rR^{44}$;

$R^{38}$ is $C_{1-6}$-alkyl; $C_{2-6}$-alkenyl; cycloalkyl; heterocycloalkyl; aryl; heteroaryl; aryl-$C_{1-6}$-alkyl; or heteroaryl-$C_{1-6}$-alkyl;

$R^{42}$ and $R^{43}$ are independently defined as H; F; $CF_3$; $C_{1-6}$-alkyl; $C_{2-6}$-alkenyl; cycloalkyl; heterocycloalkyl; aryl-$C_{1-6}$-alkyl; or heteroaryl-$C_{1-6}$-alkyl;

$R^{44}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or a group of one of the formulae H51-H55 as shown in Table 8 above.

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{42}R^{51})_rOR^{36}$; —$(CR^{42}R^{51})_rNR^7R^{57}$; —$(CR^{42}R^{51})_rOCONR^7R^{57}$; —$(CR^{42}R^{51})_rNR^7CONR^7R^{57}$; —$(CR^{42}R^{51})_r$ $NR^7COR^{38}$; —$(CR^{42}R^{51})_rNR^7SO_2R^{38}$; —$(CR^{42}R^{51})_r$ $NR^7SO_2NR^7R^{57}$; —$(CR^{42}R^{51})_qCOOR^{36}$; —$(CR^{42}R^{51})_qCOR^{38}$; —$(CR^{42}R^{51})_qSO_2R^{33}$; —$(CR^{42}R^{51})_qR^{39}$; —$(CR^{42}R^{51})_sR^{40}$; —$(CR^{42}R^{51})_q$ $R^{41}$; or —$(CR^{42}R^{51})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$(CR^{42}R^{51})_qOR^{36}$; —$(CR^{42}R^{51})_qSR^{36}$; —$(CR^{42}R^{51})_q$ $NR^7R^{57}$; —$(CR^{42}R^{51})_qOCONR^7R^{57}$; —$(CR^{42}R^{51})_q$ $NR^{44}COOR^{36}$; —$(CR^{42}R^{51})_qNR^7COR^{38}$; —$(CR^{42}R^{51})_qNR^7CONR^7R^{45}$; —$(CR^{42}R^{51})_q$ $NR^7SO_2R^{38}$; —$(CR^{42}R^{51})_qNR^7SO_2NR^7R^{45}$; —$(CR^{42}R^{51})_qCOOR^{36}$; —$(CR^{42}R^{51})_qCONR^7R^{45}$; —$(CR^{42}R^{51})_qSO_2NR^7R^{45}$; —$(CR^{42}R^{51})_qCOR^{38}$; —$(CR^{42}R^{51})_qSO_2R^{38}$; or —$(CR^{42}R^{51})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or —$NR^7R^{45}$;

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{42}R^{51})_rOR^{45}$; —$(CR^{42}R^{51})_rSR^{45}$; —$(CR^{42}R^{51})_rNR^7R^{45}$;

—$(CR^{42}R^{51})_r$OCONR$^7$R$^{45}$; —$(CR^{42}R^{51})_r$NR$^7$COOR$^{36}$; —$(CR^{42}R^{51})_r$NR$^7$COR$^{38}$; —$(CR^{42}R^{51})_r$NR$^7$CONR$^7$R$^{45}$; —$(CR^{42}R^{51})_r$NR$^7$SO$_2$R$^{38}$; —$(CR^{42}R^{51})_r$NR$^7$SO$_2$NR$^7$R$^{45}$; —$(CR^{42}R^{51})_q$COOR$^{36}$; —$(CR^{42}R^{51})_q$CONR$^7$R$^{45}$; —$(CR^{42}R^{51})_r$SO$_2$NR$^7$R$^{45}$; —$(CR^{42}R^{51})_q$COR$^{38}$; —$(CR^{42}R^{51})_q$SO$_2$R$^{38}$; or —$(CR^{42}R^{51})_s$R$^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{51})_q$OR$^{36}$; —$(CR^{42}R^{51})_q$SR$^{36}$; —$(CR^{42}R^{51})_q$NR$^7$R$^{45}$; —$(CR^{42}R^{51})_q$NR$^7$COOR$^{36}$; —$(CR^{42}R^{51})_q$NR$^7$COR$^{38}$; —$(CR^{42}R^{51})_q$NR$^7$SO$_2$R$^{38}$; —$(CR^{42}R^{51})_q$NR$^7$CONR$^7$R$^{45}$; —$(CR^{42}R^{51})_q$COOR$^{36}$; —$(CR^{42}R^{51})_q$CONR$^7$R$^{45}$; —$(CR^{42}R^{51})_q$COR$^{38}$; or —$(CR^{42}R^{51})_q$R$^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_t$OR$^{36}$; —$(CR^{42}R^{43})_t$NR$^7$R$^{57}$; —$(CR^{42}R^{43})_t$COOR$^{36}$; or —$(CR^{42}R^{43})_t$CONR$^7$R$^{57}$;

$R^{52}$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —OR$^{36}$; —NR$^7$R$^{57}$; —NR$^7$COR$^{38}$; —NR$^7$COOR$^{36}$; —NR$^7$SO$_2$R$^{38}$; —NR$^7$CONR$^7$R$^{57}$; —COOR$^{36}$; —CONR$^7$R$^{57}$; —C(=NR$^7$)NR$^7$R$^{57}$; —NR$^7$C(=NR$^7$)NR$^7$R$^{57}$; or a group of one of the formulae H56-H110 as shown in Table 9 above.

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —OR$^{36}$; —NR$^7$R$^{57}$; —NR$^7$COR$^{38}$; —NR$^7$SO$_2$R$^{38}$; —NR$^7$CONR$^7$R$^{57}$; —COR$^{38}$; or —SO$_2$R$^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; —COOR$^{36}$; or —CONR$^7$R$^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_s$OR$^{36}$; —$(CR^{42}R^{43})_s$NR$^7$R$^{45}$; —$(CR^{42}R^{43})_q$COOR$^{36}$; or —$(CR^{42}R^{43})_q$CONR$^7$R$^{45}$;

$R^{57}$ is H; $C_{1-6}$-alkyl; $C_{2-6}$-alkenyl; cycloalkyl; aryl-$C_{1-6}$-alkyl; or an N-protecting group.

Defined as for the Main Embodiment (vide supra) are i) the generic atoms and connector groups Z, Y, X, W, V, U, T, Q and M; ii) the indices m, n, p, q, r, s, t and u; as well as iii) pairs of substituents that can be define additional cyclic structural elements.

In a Further Preferred Embodiment of this invention, the macrocycles of type I are defined by groups of selected building blocks A, B and C and substituents $R^1$-$R^{57}$ as follows. The connectivities between these building blocks are defined as for the Preferred Embodiment and as shown in Scheme 5 above.

The biaryl Template A of the Further Preferred Embodiment is selected from $A_B1$-$A_C1$; $A_B1$-$A_C4$; $A_B1$-$A_C6$; $A_B1$-$A_C8$; $A_B1$-$A_C9$; $A_B1$-$A_C11$; $A_B1$-$A_C13$; $A_B1$-$A_C19$; $A_B1$-$A_C22$; $A_B1$-$A_C24$; $A_B1$-$A_C49$; $A_B1$-$A_C51$; $A_B2$-$A_C4$; $A_B2$-$A_C51$; $A_B4$-$A_C1$; $A_B4$-$A_C4$; $A_B4$-$A_C6$; $A_B4$-$A_C19$; $A_B4$-$A_C22$; $A_B4$-$A_C24$; $A_B4$-$A_C49$; $A_B4$-$A_C51$; $A_B4$-$A_C59$; $A_B5$-$A_C51$; $A_B5$-$A_C59$; $A_B6$-$A_C1$; $A_B6$-$A_C4$; $A_B6$-$A_C8$; $A_B6$-$A_C9$; $A_B6$-$A_C11$; $A_B6$-$A_C13$; $A_B6$-$A_C16$; $A_B6$-$A_C18$; $A_B6$-$A_C19$; $A_B6$-$A_C20$; $A_B6$-$A_C30$; $A_B6$-$A_C31$; $A_B6$-$A_C49$; $A_B6$-$A_C51$; $A_B9$-$A_C6$; $A_B9$-$A_C49$; $A_B14$-$A_C49$; $A_B20$-$A_C6$; $A_B20$-$A_C49$; $A_B23$-$A_C4$; $A_B23$-$A_C49$; $A_B45$-$A_C49$; $A_B45$-$A_C52$; $A_B45$-$A_C57$; $A_B45$-$A_C58$; $A_B45$-$A_C65$; $A_B45$-$A_C66$; $A_B46$-$A_C57$; $A_B46$-$A_C58$; $A_B49$-$A_C49$; $A_B50$-$A_C57$; $A_B50$-$A_C58$; $A_B50$-$A_C61$; $A_B51$-$A_C49$; $A_B51$-$A_C61$; or $A_B59$-$A_C61$.

The further preferred Modulator B is selected from B1; B4; B5; B6; or B7;

and the further preferred Bridge of type C from C1; C2; or C3.

The substituents $R^1$-$R^{57}$ attached to the Further Preferred Embodiment of macrocycle I are as defined as described below.

$R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$(CR^{32}R^{33})_q$OR$^{34}$; —$(CR^{32}R^{33})_q$SR$^{34}$; —$(CR^{32}R^{33})_q$NR$^7$R$^{35}$; —$(CR^{32}R^{33})_q$OCONR$^7$R$^{35}$; —$(CR^{32}R^{33})_q$NR$^7$COOR$^{36}$; —$(CR^{32}R^{33})_q$NR$^7$COR$^{37}$; —$(CR^{32}R^{33})_q$NR$^7$CONR$^7$R$^{35}$; —$(CR^{32}R^{33})_q$NR$^7$SO$_2$R$^{38}$; —$(CR^{32}R^{33})_q$COOR$^{36}$; —$(CR^{32}R^{33})_q$CONR$^7$R$^{35}$; —$(CR^{32}R^{33})_q$SO$_2$NR$^7$R$^{35}$; —$(CR^{32}R^{33})_q$COR$^{37}$; —$(CR^{32}R^{33})_q$R$^{39}$; —$(CR^{32}R^{33})_q$R$^{40}$; —$(CR^{32}R^{33})_q$R$^{41}$; or —$(CR^{32}R^{33})_q$R$^{44}$.

$R^3$ and $R^4$ are independently defined as H; F; Cl; $CF_3$; $OCF_3$; $OCHF_2$; $NO_2$; CN; $C_{1-6}$-alkyl; or $C_{1-6}$-alkoxy;

$R^5$ is H; $CF_3$; or $C_{1-6}$-alkyl;

$R^6$ is H; $C_3$; $C_{1-6}$-alkyl; $C_{2-6}$-alkenyl; cycloalkyl; heterocycloalkyl; aryl; heteroaryl; aryl-$C_1$-alkyl; heteroaryl-$C_{1-6}$-alkyl; —$(CR^{32}R^{33})_q$OR$^{34}$; —$(CR^{32}R^{33})_q$SR$^{34}$; —$(CR^{32}R^{33})_q$NR$^7$R$^{35}$; —$(CR^{32}R^{33})_q$OCONR$^7$R$^{35}$; —$(CR^{32}R^{33})_q$NR$^7$COOR$^{36}$; —$(R^{32}R^{33})_q$NR$^7$COR$^{37}$; —$(CR^{32}R^{33})_q$NR$^7$CONR$^7$R$^{35}$; —$(CR^{32}R^{33})_q$NR$^7$SO$_2$R$^{38}$; —$(R^{32}R^{33})_q$COOR$^{36}$; —$(CR^{32}R^{33})_q$CONR$^7$R$^{35}$; —$(CR^{32}R^{33})_q$SO$_2$NR$^7$R$^{35}$; —$(CR^{32}R^{33})_q$COR$^{37}$; —$(CR^{32}R^{33})_q$R$^{39}$; —$(CR^{32}R^{33})_s$R$^{40}$; —$(CR^{32}R^{33})_q$R$^{41}$; or —$(CR^{32}R^{33})_q$R$^{44}$;

$R^7$, $R^8$, $R^9$, $R^{10}$, $R^{11}$, $R^{12}$ and $R^{13}$ are defined as in the Preferred Embodiment;

$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{32}R^{33})_q$OR$^{34}$; —$(CR^{32}R^{33})_q$SR$^{34}$; —$(CR^{32}R^{33})_q$NR$^7$R$^{35}$; —$(CR^{32}R^{33})_q$OCONR$^7$R$^{35}$; —$(CR^{32}R^{33})_q$NR$^7$COOR$^{36}$; —$(CR^{32}R^{33})_q$NR$^7$COR$^{37}$; —$(CR^{32}R^{33})_q$NR$^7$CONR$^7$R$^{35}$; —$(CR^{32}R^{33})_q$NR$^7$SO$_2$R$^{38}$; —$(CR^{32}R^{33})_q$COOR$^{36}$; —$(CR^{32}R^{33})_q$CONR$^7$R$^{35}$; —$(CR^{32}R^{33})_q$SO$_2$NR$^7$R$^{35}$; —$(CR^{32}R^{33})_q$COR$^{37}$; —$(CR^{32}R^{33})_q$R$^{39}$; —$(CR^{32}R^{33})_s$R$^{40}$; —$(CR^{32}R^{33})_q$ R$^{41}$; or —$(CR^{32}R^{33})_q$R$^{44}$;

$R^{15}$, $R^{16}$, $R^{17}$, $R^{19}$, $R^{21}$, $R^{22}$, $R^{23}$, $R^{25}$, $R^{27}$, $R^{28}$, $R^{29}$ and $R^{31}$ are defined as in the Preferred Embodiment;

$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; —$(CR^{32}R^{33})_q$OR$^{34}$; —$(CR^{32}R^{33})_q$NR$^7$R$^{37}$; —$(CR^{32}R^{33})_q$OCONR$^7$R$^{35}$; —$(CR^{32}R^{33})_q$NR$^7$COOR$^{36}$; —$(CR^{32}R^{33})_q$NR$^7$COR$^{37}$; —$(CR^{32}R^{33})_q$NR$^7$CONR$^7$R$^{35}$; —$(CR^{32}R^{33})_q$NR$^7$SO$_2$R$^{38}$; —$(CR^{32}R^{33})_q$COOR$^{36}$; —$(CR^{32}R^{33})_q$CONR$^7$R$^{35}$; —$(CR^{32}R^{33})_q$COR$^{37}$; or —$(CR^{32}R^{33})_q$R$^{44}$;

$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_q$OR$^{45}$; —$(CR^{42}R^{43})_q$SR$^{45}$; —$(CR^{42}R^{43})_q$NR$^7$R$^{45}$; —$(CR^{42}R^{43})_q$NR$^7$COOR$^{36}$; —$(CR^{42}R^{43})_q$NR$^7$COR$^{38}$;

—$(CR^{42}R^{43})_q$ $COOR^{36}$; —$(CR^{42}R^{43})_qCONR^7R^{45}$; —$(CR^{42}R^{43})COR^{38}$; —$(CR^{42}R^{43})_qR^{39}$; —$(CR^{42}R^{43})_sR^{40}$; —$(CR^{42}R^{43})_qR^{41}$; or —$(CR^{42}R^{43})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; —$(CR^{42}R^{43})_rOR^{45}$; —$(CR^{42}R^{43})_rNR^7R^{45}$; —$(CR^{42}R^{43})_rOCONR^7R^{35}$; —$(CR^{42}R^{43})_rNR^7COOR^{36}$; —$(CR^{42}R^{43})_rNR^7COR^{38}$; —$(CR^{42}R^{43})_rNR^7CONR^7R^{45}$; —$(CR^{42}R^{43})_rNR^7SO_2R^{38}$; —$(CR^{42}R^{43})_qCOOR^{36}$; —$(CR^{42}R^{43})_qCONR^7R^{45}$; —$(CR^{42}R^{43})_qCOR^{38}$; —$(CR^{42}R^{43})_qR^{39}$; —$(CR^{42}R^{43})_sR^{40}$; —$(CR^{42}R^{43})_qR^{41}$; or —$(CR^{42}R^{43})_qR^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{32}R^{33})_rOR^{45}$; —$(CR^{32}R^{33})_rNR^7R^{45}$; —$(CR^{32}R^{33})_rOCONR^7R^{45}$; —$(CR^{32}R^{33})_rNR^7COOR^{36}$; —$(CR^{32}R^{33})_rNR^7COR^{37}$; —$(CR^{32}R^{33})_rNR^7CONR^7R^{50}$; —$(CR^{32}R^{33})_rNR^7SO_2R^{38}$; —$(CR^{32}R^{33})_qCOOR^{36}$; —$(CR^{32}R^{33})_qCONR^7R^{45}$; —$(CR^{32}R^{33})_qCOR^{38}$; —$(CR^{32}R^{33})_qR^{39}$; —$(CR^{32}R^{33})_sR^{40}$; —$(CR^{32}R^{33})_qR^{41}$; or —$(CR^{32}R^{33})_qR^{44}$;

$R^{36}$ is H; $C_{1-6}$-alkyl; cycloalkyl; aryl; aryl-$C_{1-6}$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; —$(CR^{42}R^{43})_qOR^{45}$; —$(CR^{42}R^{43})_qSR^{45}$; —$(CR^{42}R^{43})_qNR^7R^{45}$; —$(CR^{42}R^{43})_sOCONR^7R^{45}$; —$(CR^{42}R^{43})_sNR^7COOR^{36}$; —$(CR^{42}R^{43})_sNR^7COR^{44}$; —$(CR^{42}R^{43})_sNR^7CONR^7R^{45}$; —$(CR^{42}R^{43})_sNR^7SO_2R^{38}$; —$(CR^{42}R^{43})_qCOOR^{36}$; —$(CR^{42}R^{43})CONR^7R^{45}$; —$(CR^{42}R^{43})_tCOR^{38}$; —$(CR^{42}R^{43})_tR^{39}$; —$(CR^{42}R^{43})_uR^{40}$; —$(CR^{42}R^{43})_tR^{41}$; or —$(CR^{42}R^{43})_tR^{44}$;

$R^{38}$, $R^{42}$, $R^{43}$ and $R^{44}$ are defined as in the Preferred Embodiment;

$R^{39}$, $R^{40}$, and $R^{41}$ are as defined in the Main Embodiment;

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{42}R^{43})_rOR^{36}$; —$(CR^{42}R^{43})_rNR^7R^{57}$; —$(CR^{42}R^{43})_rOCONR^7R^{57}$; —$(CR^{42}R^{43})_rNR^7CONR^7R^{57}$; —$(CR^{42}R^{43})_rNR^7COR^{38}$; —$(CR^{42}R^{43})_rNR^7SO_2R^{38}$; —$(CR^{42}R^{43})_qCOOR^{36}$; —$(CR^{42}R^{43})_qCOR^{38}$; —$(CR^{42}R^{43})_qR^{39}$; —$(CR^{42}R^{43})_sR^{40}$; —$(CR^{42}R^{43})_qR^{41}$; or —$(CR^{42}R^{43})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$(CR^{42}R^{43})_qOR^{36}$; —$(CR^{42}R^{43})_qNR^7R^{57}$; —$(CR^{42}R^{43})_qNR^7COR^{38}$; —$(CR^{42}R^{43})_qCOOR^{36}$; —$(CR^{42}R^{43})_qCONR^7R^{45}$; —$(CR^{42}R^{43})_qSO_2NR^7R^{45}$; —$(CR^{42}R^{43})_qCOR^{38}$; or —$(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or —$NR^7R^{45}$.

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{42}R^{43})_rOR^{45}$; —$(CR^{42}R^{43})_rSR^{45}$; —$(CR^{42}R^{43})_rNR^7R^{45}$; —$(CR^{42}R^{43})_rOCONR^7R^{45}$; —$(CR^{42}R^{43})_rNR^7COOR^{36}$; —$(CR^{42}R^{43})_rNR^7COR^{38}$; —$(CR^{42}R^{43})_rNR^7CONR^7R^{45}$; —$(CR^{42}R^{43})_rNR^7SO_2R^{38}$; —$(CR^{42}R^{43})_qCOOR^{36}$; —$(CR^{42}R^{43})_qCONR^7R^{45}$; —$(CR^{42}R^{43})_qCOR^{38}$; or —$(CR^{42}R^{43})_sR^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_qOR^{36}$; —$(CR^{42}R^{43})_qNR^7R^{45}$; —$(CR^{42}R^{43})NR^7COR^{38}$; —$(CR^{42}R^{43})_qNR^7SO_2R^{38}$; —$(CR^{42}R^{43})_qCOOR^{36}$; —$(CR^{42}R^{43})_qCONR^7R^{45}$; —$(CR^{42}R^{43})_qCOR^{38}$; or —$(CR^{42}R^{43})_qR^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_tOR^{36}$; —$(CR^{42}R^{43})_tNR^7R^{57}$; —$(CR^{42}R^{43})_tCOOR^{36}$; or —$(CR^{42}R^{43})_tCONR^7R^{57}$;

$R^{52}$ is defined as in the Preferred Embodiment;

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$OR^{36}$; —$NR^7R^{57}$; —$NR^7COR^{38}$; —$NR^7SO_2R^{38}$; —$NR^7CONR^7R^{57}$; —$COR^{38}$; or —$SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; —$COOR^{36}$; or —$CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_sOR^{36}$; —$(CR^{42}R^{43})_sNR^7R^{45}$; —$(CR^{42}R^{43})_qCOOR^{36}$; or —$(CR^{42}R^{43})_qCONR^7R^{45}$;

$R^{57}$ is defined as in the Preferred Embodiment;

as are (vide supra) i) the generic atoms and connector groups Z, Y, X, W, V, U, T, Q and M; ii) the indices m, n, p, q, r, s, t and u; as well as iii) the pairs of substituents that can be define additional cyclic structural elements.

In a Particularly Preferred Embodiment of this invention, the macrocycles of type I are defined by groups of selected building blocks A, B and C and substituents $R^1$-$R^{57}$ as follows. The connectivities between these building blocks are defined as for the Preferred Embodiment and as shown in Scheme 5 above.

The biaryl Template A of the Particularly Preferred Embodiment is selected from $A_B1$-$A_C1$; $A_B1$-$A_C4$; $A_B1$-$A_C19$; $A_B2$-$A_C4$; $A_B4$-$A_C1$; $A_B4$-$A_C4$; $A_B4$-$A_C19$; $A_B4$-$A_C59$; $A_B5$-$A_C51$; $A_B5$-$A_C59$; $A_B6$-$A_C31$; $A_B9$-$A_C6$; or $A_B46$-$A_C58$.

The particularly preferred Modulator building block of type B and the Bridge of type C are selected as described in the Further Preferred Embodiment.

The substituents $R^1$-$R^{57}$ attached to the Particularly Preferred Embodiment of macrocycle I are as defined as described below.

$R^1$ and $R^2$ are defined as in the Further Preferred Embodiment;

$R^3$ and $R^4$ are independently defined as H; F; $CF_3$; $OCF_3$; $OCHF_2$; CN; or $C_{1-6}$-alkoxy;

$R^5$ is H; $CF_3$; or $C_{1-6}$-alkyl;

$R^6$ is defined as in the Further Preferred Embodiment;

$R^7$, $R^8$, $R^9$, $R^{10}$, $R^{11}$, $R^{12}$ and $R^{13}$ are defined as in the Preferred Embodiment;

$R^{14}$, $R^{20}$ and $R^{26}$ are defined as in the Further Preferred Embodiment;

$R^{15}$, $R^{16}$, $R^{17}$, $R^{19}$, $R^{21}$, $R^{22}$, $R^{23}$, $R^{25}$, $R^{27}$, $R^{28}$, $R^{29}$ and $R^{31}$ are defined as in the Preferred Embodiment, $R^{18}$, $R^{24}$, $R^{30}$ and $R^{32}$ are defined as in the Further Preferred Embodiment;

$R^{33}$ is H; or $C_{1-6}$-alkyl;

$R^{34}$, $R^{35}$, $R^{36}$ and $R^{37}$ are defined as in the Further Preferred Embodiment;

$R^{38}$, $R^{42}$, $R^{43}$ and $R^{44}$ are defined as in the Preferred Embodiment;

$R^{39}$, $R^{40}$, and $R^{41}$ are as defined in the Main Embodiment;

$R^{45}$ is defined as in the Further Preferred Embodiment;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $—(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $—NR^7R^{45}$;

$R^{48}$ is defined as in the Further Preferred Embodiment;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or $—(CR^{42}R^{43})_qR^{44}$;

$R^{50}$ is defined as in the Further Preferred Embodiment;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_tOR^{36}$; $—(CR^{42}R^{43})_tNR^7R^{57}$; $—(CR^{42}R^{43})_tCOOR^{36}$; or $—(CR^{42}R^{43})_tCONR^7R^{57}$;

$R^{52}$ is defined as in the Preferred Embodiment;

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—OR^{36}$; $—NR^7R^{57}$; $—NR^7COR^{38}$; $—NR^7SO_2R^{38}$; $—NR^7CONR^7R^{57}$; $—COR^{38}$; or $—SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; $—COOR^{36}$; or $—CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_sOR^{36}$; $—(CR^{42}R^{43})_sNR^7R^{45}$; $—(CR^{42}R^{43})_qCOOR^{36}$; or $—(CR^{42}R^{43})_qCONR^7R^{45}$;

$R^{57}$ is defined as in the Preferred Embodiment; as are (vide supra) i) the generic atoms and connector groups Z, Y, X, W, V, U, T, Q and M; ii) the indices m, n, p, q, r, s, t and u; as well as iii) the pairs of substituents that can be define additional cyclic structural elements.

In an Specific Representation of the Particularly Preferred Embodiment the Bridge C is represented by $$---[-C_{AA}-]_{1-3}---$$

wherein $C_{AA}$ is an amino acid selected from the readily accessible amino acids listed in Table 11. Even though only one stereoisomer, usually the L-enantiomer, is cited within Table 11, it is understood that the complementary enantiomer is also part to the embodiment. Also not listed explicitly, but part of the embodiment are the simple N-methyl derivatives of the listed amino acids.

TABLE 11

Structures representing subunits $C_{AA}$ of Bridge C (continued on the following pages)

| Code | Chemical Name |
|---|---|
| Ala | L-Alanine |
| Arg | L-Arginine |
| Asn | L-Asparagine |
| Asp | L-Aspartic acid |
| Cys | L-Cysteine |
| Glu | L-Glutamic acid |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Apa | 3-Amino-propanoic acid |
| H-$\beta^3$-HAla-OH | (3S)-3-Amino-butyric acid |
| H-$\beta^3$-HVal-OH | (3R)-3-Amino-4-methyl-valeric acid |
| H-$\beta^3$-HIle-OH | (3R,4S)-3-Amino-4-methyl-hexanoic acid |
| H-$\beta^3$-HLeu-OH | (3S)-3-Amino-5-methyl-hexanoic acid |
| H-$\beta^3$-HMet-OH | (3S)-3-Amino-5-methylthio pentanoic acid |
| H-$\beta^3$-HTyr-OH | (3S)-3-Amino-4-(4'-hydroxyphenyl)-butyric acid |
| H-$\beta^3$-HHis-OH | (3S)-3-Amino-4-(imidazole-4'-yl)-butyric acid |
| H-$\beta^3$-HPhe-OH | (3S)-3-Amino-4-phenyl butyric acid |
| H-$\beta^3$-HTrp-OH | (3S)-3-Amino-4-(indol-3'-yl)-butyric acid |
| H-$\beta^3$-HSer-OH | (3R)-3-Amino-4-hydroxy-butyric acid |
| H-$\beta^3$-HAsp-OH | 3-Amino-pentanedioic acid |
| H-$\beta^3$-HGlu-OH | (3S)-3-Amino-hexanedioic acid |
| H-$\beta^3$-HLys-OH | (3S)-3,7-Diamino-heptanoic acid |
| H-$\beta^3$-HArg-OH | (3S)-3-Amino-6-guanidino-hexanoic-acid |
| H-$\beta^3$-HCys-OH | (3R)-3-Amino-4-mercapto-butyric acid |
| H-$\beta^3$-HAsn-OH | (3S)-3-Amino-4-carbamoyl-butyric acid |
| H-$\beta^3$-HGln-OH | (3S)-3-Amino-5-carbamoyl-pentanoic acid |

TABLE 11-continued

Structures representing subunits $C_{AA}$ of Bridge C (continued on the following pages)

| Code | Chemical Name |
|---|---|
| H-$\beta^3$-HThr-OH | (3R,4R)-3-Amino-4-hydroxy-pentanoic acid |
| Gaba | 4-Amino-butyric acid |
| H-$\gamma^4$-DiHAla-OH | (4S)-4-Amino-pentanoic acid |
| H-$\gamma^4$-DiHVal-OH | (4R)-4-Amino-5-methyl-hexanoic acid |
| H-$\gamma^4$-DiHIle-OH | (4R,5S)-4-Amino-5-methyl-heptanoic acid |
| H-$\gamma^4$-DiHLeu-OH | (4R)-4-Amino-6-methyl-heptanoic acid |
| H-$\gamma^4$-DiHMet-OH | (4R)-4-Amino-6-methylthio-hexanoic acid |
| H-$\gamma^4$-DiHTyr-OH | (4R)-4-Amino-5-(4'-hydroxyphenyl)-pentanoic acid |
| H-$\gamma^4$-DiHHis-OH | (4R)-4-Amino-5-(imidazole-4'-yl)-pentanoic acid |
| H-$\gamma^4$-DiHPhe-OH | (4R)-4-Amino-5-phenyl-pentanoic acid |
| H-$\gamma^4$-DiHTrp-OH | (4R)-4-Amino-5-(indol-3'-yl)-pentanoic acid |
| H-$\gamma^4$-DiHSer-OH | (4R)-4-Amino-5-hydroxy-pentanoic acid |
| H-$\gamma^4$-DiHAsp-OH | (4R)-4-Amino-hexanedioic acid |
| H-$\gamma^4$-DiHGlu-OH | 4-Amino-heptanedioic acid |
| H-$\gamma^4$-DiHLys-OH | (4S)-4,8-Diamino-octanoic acid |
| H-$\gamma^4$-DiHArg-OH | (4S)-4-Amino-7-guanidino-heptanoic-acid |
| H-$\gamma^4$-DiHCys-OH | (4R)-4-Amino-5-mercapto-pentanoic acid |
| H-$\gamma^4$-DiHAsn-OH | (4R)-4-Amino-5-carbamoyl-pentanoic acid |
| H-$\gamma^4$-DiHGln-OH | (3S)-3-Amino-5-carbamoyl-hexanoic acid |
| H-$\gamma^4$-DiHThr-OH | (4R,5R)-4-Amino-5-hydroxy-hexanoic acid |
| Cit | L-Citrulline |
| Orn | L-Ornithine |
| tBuA | L-t-Butylalanine |
| Sar | Sarcosine |
| Pen | L-Penicillamine |
| tBuG | L-tert-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC($NH_2$)═NH) | L-meta-Amidinophenylalanine |
| Phe(pC($NH_2$)═NH) | L-para-Amidinophenylalanine |
| Phe(mNHC($NH_2$)═NH) | L-meta-Guanidinophenylalanine |
| Phe(pNHC($NH_2$)═NH) | L-para-Guanidinophenylalanine |
| 2Pal | (2S)-2-Amino-3-(pyridine-2'-yl)-propionic acid |
| 4Pal | (2S)-2-Amino-3-(pyridine-4'-yl)-propionic acid |
| Phg | L-Phenylglycine |
| Cha | L-Cyclohexylalanine |
| $C_4$al | L-3-Cyclobutylalanine |
| $C_5$al | L-3-Cyclopentylalanine |
| Nle | L-Norleucine |
| 2-Nal | L-2-Naphthylalanine |
| 1-Nal | L-1-Naphthylalanine |
| 4ClPhe | L-4-Chlorophenylalanine |
| 3ClPhe | L-3-Chlorophenylalanine |
| 2ClPhe | L-2-Chlorophenylalanine |
| 3,4$Cl_2$Phe | L-3,4-Dichlorophenylalanine |
| 4FPhe | L-4-Fluorophenylalanine |
| 3FPhe | L-3-Fluorophenylalanine |
| 2FPhe | L-2-Fluorophenylalanine |
| Thi | L-β-2-Thienylalanine |
| Tza | L-2-Thiazolylalanine |
| Mso | L-Methionine sulfoxide |
| AcLys | N-Acetyllysine |
| Dap | 2,3-Diaminopropionic acid |
| Dab | 2,4-Diaminobutyric acid |
| Dbu | (2S)-2,3-Diamino-butyric acid |
| Abu | γ-Aminobutyric acid (GABA) |
| Aha | ε-Aminohexanoic acid |
| Aib | α-Aminoisobutyric acid |
| ACC | 1-Amino cyclopropane carboxylic acid |
| ACBC | 1-Amino cyclobutane carboxylic acid |
| ACPC | 1-Amino cyclopentane carboxylic acid |
| 1-ACHC | 1-Amino cyclohexane carboxylic acid |
| 2-ACHC | 2-Amino cyclohexane carboxylic acid |
| 3-ACHC | 3-Amino cyclohexane carboxylic acid |
| 4-ACHC | 4-Amino cyclohexane carboxylic acid |
| Y(Bzl) | L-O-Benzyltyrosine |
| H(Bzl) | (3S)-2-Amino-3-(1'-benzylimidazole-4'-yl)-propionic acid |
| Bip | L-(4-phenyl)phenylalanine |
| S(Bzl) | L-O-Benzylserine |
| T(Bzl) | L-O-Benzylthreonine |
| alloT | (2S,3S)-2-Amino-3-hydroxy-butyric acid |
| Leu3OH | (2S,3R)-2-Amino-3-hydroxy-4-methyl-pentanoic acid |
| hAla | L-Homo-alanine |
| hArg | L-Homo-arginine |
| hCys | L-Homo-cysteine |

TABLE 11-continued

Structures representing subunits $C_{AA}$ of Bridge C (continued on the following pages)

| Code | Chemical Name |
|---|---|
| hGlu | L-Homo-glutamic acid |
| hGln | L-Homo-glutamine |
| hHis | L-Homo-histidine |
| hIle | L-Homo-isoleucine |
| hLeu | L-Homo-leucine |
| hNle | L-Homo-norleucine |
| hLys | L-Homo-lysine |
| hMet | L-Homo-Methionine |
| hPhe | L-Homo-phenylalanine |
| hSer | L-Homo-serine |
| hThr | L-Homo-threonine |
| hTrp | L-Homo-tryptophan |
| hTyr | L-Homo-tyrosine |
| hVal | L-Homo-valine |
| hCha | L-Homo-cyclohexylalanine |
| Bpa | L-4-Benzoylphenylalanine |
| OctG | L-Octylglycine |
| Tic | (3S)-1,2,3,4-Tetrahydroisoquinoline-3-carboxylic acid |
| Tiq | (1S)-1,2,3,4-Tetrahydroisoquinoline-1-carboxylic acid |
| Oic | (2S,3aS,7aS)-1-Octahydro-1H-indole-2-carboxylic acid |
| 4AmPyrr1 | (2S,4S)-4-Amino-pyrrolidine-2-carboxylic acid |
| 4AmPyrr2 | (2S,4R)-4-Amino-pyrrolidine-2-carboxylic acid |
| 4PhePyrr1 | (2S,4R)-4-Phenyl-pyrrolidine-2-carboxylic acid |
| 4PhePyrr2 | (2S,4S)-4-Phenyl-pyrrolidine-2-carboxylic acid |
| 5PhePyrr1 | (2S,5R)-5-Phenyl-pyrrolidine-2-carboxylic acid |
| 5PhePyrr2 | (2S,5S)-5-Phenyl-pyrrolidine-2-carboxylic acid |
| 4Hyp1 | (4S)-L-Hydroxyproline |
| 4Hyp2 | (4R)-L-Hydroxyproline |
| 4Mp1 | (4S)-L-Mercaptoproline |
| 4Mp2 | (4R)-L-Mercaptoproline |
| Pip | L-Pipecolic acid |
| H-$\beta^3$-HCit-OH | (3S)-3-Amino-6-carbamidyl-hexanoic acid |
| H-$\beta^3$-HOrn-OH | (3S)-3,6-Diamino-hexanoic acid |
| H-$\beta^3$-HtBuA-OH | (3S)-3-Amino-5,5-dimethyl-hexanoic acid |
| H-$\beta^3$-HSar-OH | N-Methyl-3-amino-propionic acid |
| H-$\beta^3$-HPen-OH | (3R)-3-Amino-4-methyl-4-mercapto-pentanoic acid |
| H-$\beta^3$-HtBuG-OH | (3R)-3-Amino-4,4-dimethyl-pentanoic acid |
| H-$\beta^3$-H4AmPhe-OH | (3S)-3-Amino-4-(4'-aminophenyl)-butyric acid |
| H-$\beta^3$-H3AmPhe-OH | (3S)-3-Amino-4-(3'-aminophenyl)-butyric acid |
| H-$\beta^3$-H2AmPhe-OH | (3S)-3-Amino-4-(2'-aminophenyl)-butyric acid |
| H-$\beta^3$-HPhe(mC(NH$_2$)=NH)—OH | (3S)-3-Amino-4-(3'-amidinophenyl)-butyric acid |
| H-$\beta^3$-HPhe(pC(NH$_2$)=NH)—OH | (3S)-3-Amino-4-(4'-amidinophenyl)-butyric acid |
| H-$\beta^3$-HPhe(mNHC(NH$_2$)=NH)—OH | (3S)-3-Amino-4-(3'-guanidinophenyl)-butyric acid |
| H-$\beta^3$-HPhe(pNHC(NH$_2$)=NH)—OH | (3S)-3-Amino-4-(4'-guanidino-phenyl)-butyric acid |
| H-$\beta^3$-H2Pal-OH | (3S)-3-Amino-4-(pyridine-2'-yl)-butyric acid |
| H-$\beta^3$-H4Pal-OH | (3S)-3-Amino-4-(pyridine-4'-yl)-butyric acid |
| H-$\beta^3$-HPhg-OH | (3R)-3-Amino-3-phenyl-propionic acid |
| H-$\beta^3$-HCha-OH | (3S)-3-Amino-4-cyclohexyl-butyric acid |
| H-$\beta^3$-HC$_4$al-OH | (3S)-3-Amino-4-cyclobutyl-butyric acid |
| H-$\beta^3$-HC$_5$al-OH | (3S)-3-Amino-4-cyclopentyl-butyric acid |
| H-$\beta^3$-HNle-OH | (3S)-3-Amino-heptanoic acid |
| H-$\beta^3$-H2Nal-OH | (3S)-3-Amino-4-(2'-naphthyl)-butyric acid |
| H-$\beta^3$-H1Nal-OH | (3S)-3-Amino-4-(1'-naphthyl)-butyric acid |
| H-$\beta^3$-H4ClPhe-OH | (3S)-3-Amino-4-(4'-chlorophenyl)-butyric acid |
| H-$\beta^3$-H3ClPhe-OH | (3S)-3-Amino-4-(3'-chlorophenyl)-butyric acid |
| H-$\beta^3$-H2ClPhe-OH | (3S)-3-Amino-4-(2'-chlorophenyl)-butyric acid |
| H-$\beta^3$-H3,4Cl$_2$Phe-OH | (3S)-3-Amino-4-(3',4'-dichlorophenyl)-butyric acid |
| H-$\beta^3$-H4FPhe-OH | (3S)-3-Amino-4-(4'-fluorophenyl)-butyric acid |
| H-$\beta^3$-H3FPhe-OH | (3S)-3-Amino-4-(3'-fluorophenyl)-butyric acid |
| H-$\beta^3$-H2FPhe-OH | (3S)-3-Amino-4-(2'-fluorophenyl)-butyric acid |
| H-$\beta^3$-HThi-OH | (3R)-3-Amino-4-(2'-thienyl)-butyric acid |
| H-$\beta^3$-HTza-OH | (3R)-3-Amino-4-(2'-thiazolyl)-butyric acid |
| H-$\beta^3$-HMso-OH | (3R)-3-Amino-4-methylsulfoxyl-butyric acid |
| H-$\beta^3$-HAcLys-OH | (3S)-7-Acetylamino-3-amino-heptanoic acid |
| H-$\beta^3$-HDpr-OH | (3R)-3,4-diamino-butyric acid |
| H-$\beta^3$-HA$_2$Bu—OH | (3S)-3,5-Diamino-pentanoic acid |
| H-$\beta^3$-HDbu-OH | (3R)-3,4-Diamino-pentanoic acid |
| H-$\beta^3$-HAib-OH | Amino-dimethyl acetic acid |
| H-$\beta^3$-HCyp-OH | 1-Amino-cyclopentane-1-yl-acetic acid |
| H-$\beta^3$-HY(Bzl)-OH | (3S)-3-Amino-4-(4'-benzyloxyphenyl)-butyric acid |
| H-$\beta^3$-HH(Bzl)-OH | (3S)-3-Amino-4-(1'-benzylimidazole-4'-yl)-butyric acid |
| H-$\beta^3$-HBip-OH | (3S)-3-Amino-4-biphenylyl-butyric acid |

TABLE 11-continued

| Structures representing subunits $C_{AA}$ of Bridge C (continued on the following pages) | |
|---|---|
| Code | Chemical Name |
| H-$\beta^3$-HS(Bzl)-OH | (3S)-3-Amino-4-(benzyloxy)-butyric acid |
| H-$\beta^3$-HT(Bzl)-OH | (3R,4R)-3-Amino-4-benzyloxy-pentanoic acid |
| H-$\beta^3$-HalloT-OH | (3R,4S)-3-Amino-4-hydroxy-pentanoic acid |
| H-$\beta^3$-HLeu3OH—OH | (3R,4R)-3-Amino-4-hydroxy-5-methyl-hexanoic acid |
| H-$\beta^3$-HhAla-OH | (3S)-3-Amino-pentanoic acid |
| H-$\beta^3$-HhArg-OH | (3S)-3-Amino-7-guanidino-heptanoic acid |
| H-$\beta^3$-HhCys-OH | (3R)-Amino-5-mercapto-pentanoic acid |
| H-$\beta^3$-HhGlu-OH | (3S)-3-Amino-heptanedioic acid |
| H-$\beta^3$-HhGln-OH | (3S)-3-Amino-6-carbamoyl hexanoic acid |
| H-$\beta^3$-HhHis-OH | (3S)-3-Amino-5-(imidazole-4'-yl)-pentanoic acid |
| H-$\beta^3$-HhIle-OH | (3S,5S)-3-Amino-5-methyl-heptanoic acid |
| H-$\beta^3$-HhLeu-OH | (3S)-3-Amino-6-methyl-heptanoic acid |
| H-$\beta^3$-HhNle-OH | (3S)-3-Amino-octanoic acid |
| H-$\beta^3$-DiAoc-OH | (3S)-3,8-Diamino-octanoic acid |
| H-$\beta^3$-HhMet-OH | (3S)-3-Amino-6-methylthio-hexanoic acid |
| H-$\beta^3$-HhPe-OH | (3S)-3-Amino-5-phenyl-pentanoic acid |
| H-$\beta^3$-HhSer-OH | (3S)-3-Amino-5-hydroxy-pentanoic acid |
| H-$\beta^3$-HhThr-OH | (3S,5R)-3-Amino-5-hydroxy-hexanoic acid |
| H-$\beta^3$-HhTrp-OH | (3S)-3-Amino-5-(indol-3'-yl)-pentanoic acid |
| H-$\beta^3$-HhThr-OH | (3S)-3-Amino-5-(4'-hydroxyphenyl)-pentanoic acid |
| H-$\beta^3$-HhCha-OH | (3S)-3-Amino-5-cyclohexyl-pentanoic acid |
| H-$\beta^3$-HBpa-OH | (3S)-3-Amino-4-(4'-benzoylphenyl)-butyric acid |
| H-$\beta^3$-HOctG-OH | (3S)-3-Amino-undecanoic acid |
| H-$\beta^3$-HNle-OH | (3S)-3-Amino-heptanoic acid |
| H-$\beta^3$-HTic-OH | (3S)-1,2,3,4-Tetrahydroisoquinoline-3-yl-acetic acid |
| H-$\beta^3$-HTiq-OH | (1S)-1,2,3,4-Tetrahydroisoquinoline-1-acetic acid |
| H-$\beta^3$-HOic-OH | (2S,3aS,7aS)-1-Octahydro-1H-indole-2-yl-acetic acid |
| H-$\beta^3$-H4AmPyrr1-OH | (2S,4S)-4-Amino-pyrrolidine-2-acetic acid |
| H-$\beta^3$-H4AmPyrr2-OH | (2S,4R)-4-Amino-pyrrolidine-2-acetic acid |
| H-$\beta^3$-H4PhePyrr1-OH | (2S,4R)-4-Phenyl-pyrrolidine-2-acetic acid |
| H-$\beta^3$-H4PhePyrr2-OH | (2S,4S)-4-Phenyl-pyrrolidine-2-acetic acid |
| H-$\beta^3$-H5PhePyrr1-OH | (2S,5R)-5-Phenyl-pyrrolidine-2-acetic acid |
| H-$\beta^3$-H5PhePyrr2-OH | (2S,5S)-5-Phenyl-pyrrolidine-2-acetic acid |
| H-$\beta^3$-H4Hyp1-OH | (2S,4S)-4-Hydroxy-pyrrolidine-2-acetic acid |
| H-$\beta^3$-H4Hyp2-OH | (2S,4R)-4-Hydroxy-pyrrolidine-2-acetic acid |
| H-$\beta^3$-H4Mp1-OH | (2R,4S)-4-Mercapto-pyrrolidine-2-acetic acid |
| H-$\beta^3$-H4Mp2-OH | (2R,4R)-4-Mercapto-pyrrolidine-2-acetic acid |
| H-$\beta^3$-HPip-OH | (2S)-Piperidine-2-acetic acid |
| H-$\beta^3$-HPro-OH | (2S)-Pyrrolidine-2-acetic acid |
| Ahb | 4-Amino-2-hydroxy butyric acid |
| H-$\gamma^4$-DiHCit-OH | (4S)-4-Amino-7-carbamidyl-heptanoic acid |
| H-$\gamma^4$-DiHOrn-OH | (4S)-4,7-Diamino-heptanoic acid |
| H-$\gamma^4$-DiHtBuA-OH | (4R)-4-Amino-6,6-dimethyl-heptanoic acid |
| H-$\gamma^4$-DiHSar-OH | N-Methyl-4-amino-butyric acid |
| H-$\gamma^4$-DiHPen-OH | (4R)-4-Amino-5-methyl-5-mercapto-hexanoic acid |
| H-$\gamma^4$-DiHtBuG-OH | (4R)-4-Amino-5,5-dimethyl-hexanoic acid |
| H-$\gamma^4$-DiH4AmPhe-OH | (4R)-4-Amino-5-(4'-aminophenyl)-pentanoic acid |
| H-$\gamma^4$-DiH3AmPhe-OH | (4R)-4-Amino-5-(3'-aminophenyl)-pentanoic acid |
| H-$\gamma^4$-DiH2AmPhe-OH | (4R)-4-Amino-5-(2'-aminophenyl)-pentanoic acid |
| H-$\gamma^4$-DiHPhe(mC($NH_2$)=NH)—OH | (4R)-4-Amino-5-(3'-amidinophenyl)-pentanoic acid |
| H-$\gamma^4$-DiHPhe(pC($NH_2$)=NH)—OH | (4R)-4-Amino-5-(4'-amidinophenyl)-pentanoic acid |
| H-$\gamma^4$-DiHPhe(mNHC($NH_2$)=NH)—OH | (4R)-4-Amino-5-(3'-guanidino-phenyl)-pentanoic acid |
| H-$\gamma^4$-DiHPhe(pNHC($NH_2$)=NH)—OH | (4R)-4-Amino-5-(4'-guanidino-phenyl)-pentanoic acid |
| H-$\gamma^4$-DiH2Pal-OH | (4R)-4-Amino-5-(pyridine-4'-yl)-pentanoic acid |
| H-$\gamma^4$-DiH4Pal-OH | (4R)-4-Amino-5-(pyridine-4'-yl)-pentanoic acid |
| H-$\gamma^4$-DiHPhg-OH | (4R)-4-Amino-4-phenyl-butyric acid |
| H-$\gamma^4$-DiHCha-OH | (4R)-4-Amino-5-cyclohexyl-pentanoic acid |
| H-$\gamma^4$-DiH$C_4$al-OH | (4R)-4-Amino-5-cyclobutyl-pentanoic acid |
| H-$\gamma^4$-DiH$C_5$al-OH | (4R)-4-Amino-5-cyclopentyl-pentanoic acid |
| H-$\gamma^4$-DiHNle-OH | (4S)-4-Amino-octanoic acid |
| H-$\gamma^4$-DiH2Nal-OH | (4S)-4-Amino-5-(2'-naphthyl)-pentanoic acid |
| H-$\gamma^4$-DiH1Nal-OH | (4S)-4-Amino-5-(1'-naphthyl)-pentanoic acid |
| H-$\gamma^4$-DiH4ClPhe-OH | (4R)-4-Amino-5-(4'-chlorophenyl)-pentanoic acid |
| H-$\gamma^4$-DiH3ClPhe-OH | (4R)-4-Amino-5-(3'-chlorophenyl)-pentanoic acid |
| H-$\gamma^4$-DiH2ClPhe-OH | (4R)-4-Amino-5-(2'-chlorophenyl)-pentanoic acid |
| H-$\gamma^4$-DiH3,4$Cl_2$Phe-OH | (4R)-4-Amino-5-(3',4'-dichloro-phenyl)-pentanoic acid |
| H-$\gamma^4$-DiH4FPhe-OH | (4R)-4-Amino-5-(4'-fluorophenyl)-pentanoic acid |
| H-$\gamma^4$-DiH3FPhe-OH | (4R)-4-Amino-5-(3'-fluorophenyl)-pentanoic acid |
| H-$\gamma^4$-DiH2FPhe-OH | (4R)-4-Amino-5-(2'-fluorophenyl)-pentanoic acid |
| H-$\gamma^4$-DiHThi-OH | (4R)-4-Amino-5-(2'-thienyl)-pentanoic acid |
| H-$\gamma^4$-DiHTza-OH | (4R)-4-Amino-5-(2'-thiazolyl)-pentanoic acid |
| H-$\gamma^4$-DiHMso-OH | (4R)-4-Amino-5-methylsulfoxyl-pentanoic acid |

TABLE 11-continued

Structures representing subunits $C_{A4}$ of Bridge C (continued on the following pages)

| Code | Chemical Name |
|---|---|
| H-$\gamma^4$-DiHAcLys-OH | (4S)-8-Acetylamino-4-amino-ocatanoic acid |
| H-$\gamma^4$-DiHDpr-OH | (4R)-4,5-diamino-pentanoic acid |
| H-$\gamma^4$-DiHA$_2$Bu—OH | (4R)-4,5-Diamino-hexanoic acid |
| H-$\gamma^4$-DiHDbu-OH | (4R)-4,5-Diamion-hexanoic acid |
| H-$\gamma^4$-DiHAib-OH | 3-Amino-3,3-dimethyl propionic acid |
| H-$\gamma^4$-DiHCyp-OH | (1'-Amino-cyclopentane-1'-yl)-3-propionic acid |
| H-$\gamma^4$-DiHY(Bzl)-OH | (4R)-4-Amino-5-(4'-benzyloxyphenyl)-pentanoic acid |
| H-$\gamma^4$-DiHH(Bzl)-OH | (4R)-4-Amino-5-(1'-benzylimidazole-4'-yl)-pentanoic acid |
| H-$\gamma^4$-DiHBip-OH | (4R)-4-Amino-5-biphenylyl-pentanoic acid |
| H-$\gamma^4$-DiHS(Bzl)-OH | (4S)-4-Amino-5-(benzyloxy)-pentanoic acid |
| H-$\gamma^4$-DiHT(Bzl)-OH | (4R,5R)-4-Amino-5-benzyloxy-hexanoic acid |
| H-$\gamma^4$-DiHalloT-OH | (4R,5S)-4-Amino-5-hydroxy-hexanoic acid |
| H-$\gamma^4$-DiHLeu3OH—OH | (4R,5R)-4-Amino-5-hydroxy-6-methyl-heptanoic acid |
| H-$\gamma^4$-DiHhAla-OH | (4S)-4-Amino-hexanoic acid |
| H-$\gamma^4$-DiHhArg-OH | (4S)-4-Amino-8-guanidino-octanoic acid |
| H-$\gamma^4$-DiHhCys-OH | (4R)-Amino-6-mercapto-hexanoic acid |
| H-$\gamma^4$-DiHhGlu-OH | (4S)-4-Amino-ocatanedioic acid |
| H-$\gamma^4$-DiHhGln-OH | (4S)-4-Amino-7-carbamoyl-heptanoic acid |
| H-$\gamma^4$-DiHhHis-OH | (4S)-4-Amino-6-(imidazole-4'-yl)-hexanoic acid |
| H-$\gamma^4$-DiHhIle-OH | (4S,6S)-4-Amino-6-methyl-octanoic acid |
| H-$\gamma^4$-DiHhLeu-OH | (4S)-4-Amino-7-methyl-ocatanoic acid |
| H-$\gamma^4$-DiHhNle-OH | (4S)-4-Amino-nonanoic acid |
| H-$\gamma^4$-DiHhLys-OH | (4S)-4,9-Diamino-nonanoic acid |
| H-$\gamma^4$-DiHhMet-OH | (4R)-4-Amino-7-methylthioheptanoic acid |
| H-$\gamma^4$-DiHhPhe-OH | (4S)-4-Amino-6-phenyl-hexanoic acid |
| H-$\gamma^4$-DiHhSer-OH | (4R)-4-Amino-6-hydroxy-hexanoic acid |
| H-$\gamma^4$-DiHhThr-OH | (4R,6R)-4-Amino-6-hydroxy-heptanoic acid |
| H-$\gamma^4$-DiHhTrp-OH | (4S)-4-Amino-6-(indol-3'-yl)-hexanoi cacid |
| H-$\gamma^4$-DiHhTyr-OH | (4S)-4-Amino-6-(4'-hydroxyphenyl)-hexanoic acid |
| H-$\gamma^4$-DiHhCha-OH | (4R)-4-Amino-5-cyclohexyl-pentanoic acid |
| H-$\gamma^4$-DihBpa-OH | (4R)-4-Amino-5-(4'-benzoylphenyl)-pentanoic acid |
| H-$\gamma^4$-DiHOctG-OH | (4S)-4-Amino-dodecanoic acid |
| H-$\gamma^4$-DiHNle-OH | (4S)-4-Amino-octanoic acid |
| H-$\gamma^4$-DiHTic-OH | (3R)-1',2',3',4'-Tetrahydroisoquinoline-3'-yl-3-propionic acid |
| H-$\gamma^4$-DiHTiq-OH | (1'R)-1',2',3',4'-Tetrahydroisoquinoline-1'-yl-3-propionic acid |
| H-$\gamma^4$-DiHOic-OH | (2'S,3'aS,7'aS)-1'-Octahydro-1H-indole-2'-yl-3-propionic acid |
| H-$\gamma^4$-DiH4AmPyrr1-OH | (2'R,4'S)-4'-Amino-pyrrolidine-2'-yl-3-propionic acid |
| H-$\gamma^4$-DiH4AmPyrr2-OH | (2'R,4'R)-4'-Amino-pyrrolidine-2'-yl-3-propionic acid |
| H-$\gamma^4$-DiH4PhePyrr1-OH | (2'R,4'R)-4'-Phenyl-pyrrolidine-2'-yl-3-propionic acid |
| H-$\gamma^4$-DiH4PhePyrr2-OH | (2'R,4'S)-4'-Phenyl-pyrrolidine-2'-yl-3-propionic acid |
| H-$\gamma^4$-DiH5PhePyrr1-OH | (2'S,5'R)-5'-Phenyl-pyrrolidine-2'-yl-3-propionic acid |
| H-$\gamma^4$-DiH5PhePyrr2-OH | (2'S,5'S)-5'-Phenyl-pyrrolidine-2'-yl-3-propionic acid |
| H-$\gamma^4$-DiH4Hyp1-OH | (2'R,4'S)-4'-Hydroxy-pyrrolidine-2'-yl-2-propionic acid |
| H-$\gamma^4$-DiH4Hyp2-OH | (2'R,4'R)-4'-Hydroxy-pyrrolidine-2'-yl-3-propionic acid |
| H-$\gamma^4$-DiH4Mp1-OH | (2'R,4'S)-4'-Mercapto-pyrrolidine-2'-yl-3-propionic acid |
| H-$\gamma^4$-DiH4Mp2-OH | (2'R,4'R)-4'-Mercapto-pyrrolidine-2'-yl-3-propionic acid |
| H-$\gamma^4$-DiHPip-OH | (2'S)-Piperidine-2'-yl-3-propionic acid |
| H-$\gamma^4$-DiHPro-OH | (2'S)-Pyrrolidine-2'-yl-3-propionic acid |
| (AEt)G | N-(2-Aminoethyl)glycine |
| (APr)G | N-(3-Amino-n-propyl)glycine |
| (ABu)G | N-(4-Amino-n-butyl)glycine |
| (APe)G | N-(5-Amino-n-pentyl)glycine |
| (GuEt)G | N-(2-Guanidinoethyl)glycine |
| (GuPr)G | N-(3-Guanidino-n-propyl)glycine |
| (GuBu)G | N-(4-Guanidino-n-butyl)glycine |
| (GuPe)G | N-(5-Guanidino-n-pentyl)glycine |
| (PEG$_3$-NH$_2$)G | N—[$H_2N$—$(CH_2)_3$—$(OCH_2$—$CH_2)_2$—$O(CH_2)_3$]glycine |
| (Me)G | N-Methylglycine |
| (Et)G | N-Ethylglycine |
| (Bu)G | N-Butylglycine |
| (Pe)G | N-Pentylglycine |
| (Ip)G | N-Isopropylglycine |
| (2MePr)G | N-(2-Methylpropyl)glycine |
| (3MeBu)G | N-(3-Methylbutyl)glycine |
| (1MePr)G | (1S)-N-(1-Methylpropyl)glycine |
| (2MeBu)G | (2S)-N-(2-Methylbutyl)glycine |
| (MthEt)G | N-(Methylthioethyl)glycine |
| (MthPr)G | N-(Methylthiopropyl)glycine |
| (Ben)G | N-(Benzyl)glycine |
| (PhEt)G | N-(2-Phenylethyl)glycine |
| (HphMe)G | N-([4'-hydroxyphenyl]methyl)glycine |
| (HphEt)G | N-(2-[4'-hydroxyphenyl]ethyl)glycine |

TABLE 11-continued

| Structures representing subunits $C_{AA}$ of Bridge C (continued on the following pages) | |
|---|---|
| Code | Chemical Name |
| (ImMe)G | N-(Imidazol-5-yl-methyl)glycine |
| (ImEt)G | N-(2-(Imidazol-5'-yl)ethyl)glycine |
| (InMe)G | N-(Indol-2-yl-methyl)glycine |
| (InEt)G | N-(2-(Indol-2'-yl)ethyl)glycine |
| (CboMe)G | N-(Carboxymethyl)glycine |
| (CboEt)G | N-(2-Carboxyethyl)glycine |
| (CboPr)G | N-(3-Carboxypropyl)glycine |
| (CbaMe)G | N-(Carbamoylmethyl)glycine |
| (CbaEt)G | N-(2-Carbamoylethyl)glycine |
| (CbaPr)G | N-(3-Carbamoylpropyl)glycine |
| (HyEt)G | N-(2-Hydroxyethyl)glycine |
| (HyPr)G | (2R)-N-(2-Hydroxypropyl)glycine |
| (Mcet)G | N-(2-Mercaptoethyl)glycine |
| Nip | (S)-Nipecotic acid/(S)-3-Piperidinecarboxylic acid |
| INip | Isonipecotic acid/4-Piperidinecarboxylic acid |
| PCA | (S)-2-Piperazinecarboxylic acid |
| (S)betaPro | (S)-β-Proline/(S)-Pyrrolidine-3-carboxylic acid |

In a Specific Embodiment of this invention, the macrocycles of formula I are selected from the following list (Table 12).

TABLE 12

| IUPAC Names of the Examples (continued on the following pages) | |
|---|---|
| Example | IUPAC Name |
| Ex. 1 | benzyl N-[(12R,16S,18S)-16-[(tert-butoxycarbonyl)amino]-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 2 | tert-butyl N-[(12R,16S,18S)-12-amino-8,13-dioxo-20-oxa-9,14-diazatetracyclo[19.3.1.$0^{2,7}$.$0^{14,18}$]pentacosa-1(25),2,4,6,21,23-hexaen-16-yl]carbamate |
| Ex. 3 | benzyl N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 4 | tert-butyl N-[(12R,16S,18S)-12-{[2-(1-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]carbamate |
| Ex. 5 | N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 6 | methyl N-[(12R,16S,18S)-12-{[2-(1-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]carbamate |
| Ex. 7 | N-[(12R,16S,18S)-8,13-dioxo-16-{[2-(1-pyrrolidinyl)acetyl]amino}-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 8 | N-[(12R,16S,18S)-16-(dimethylamino)-8,13-dioxo-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 9 | (12R,16S,18S)-12,16-diamino-20-oxa-9,14-diazatetracyclo[19.3.1.$0^{2,7}$.$0^{14,18}$]pentacosa-1(25),2,4,6,21,23-hexaene-8,13-dione |
| Ex. 10 | benzyl N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 11 | N-[(12R,16S,18S)-12-amino-8,13-dioxo-20-oxa-9,14-diazatetracyclo[19.3.1.$0^{2,7}$.$0^{14,18}$]pentacosa-1(25),2,4,6,21,23-hexaen-16-yl]-2-(2-naphthyl)acetamide |
| Ex. 12 | 2-(dimethylamino)-N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]acetamide |
| Ex. 13 | 3-methyl-N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]butanamide |
| Ex. 14 | benzyl N-[(12R,16S,18S)-8,13-dioxo-16-[(phenoxycarbonyl)amino]-20-oxa-9,14-diazatetracyclo[19.3.1.$0^{2,7}$.$0^{14,18}$]pentacosa-1(25),2,4,6,21,23-hexaen-12-yl]carbamate |
| Ex. 15 | benzyl N-[(10S,12S,16S)-12-[(tert-butoxycarbonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]carbamate |

TABLE 12-continued

| IUPAC Names of the Examples (continued on the following pages) | |
|---|---|
| Example | IUPAC Name |
| Ex. 16 | tert-butyl N-[(10S,12S,16S)-16-amino-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]carbamate |
| Ex. 17 | benzyl N-[(10S,12S,16S)-12-amino-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]carbamate |
| Ex. 18 | benzyl N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]carbamate |
| Ex. 19 | N-[(10S,12S,16S)-16-amino-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 20 | 2-(dimethylamino)-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 21 | N-[(10S,12S,16S)-16-[(cyclopropylsulfonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 22 | N-[(10S,12S,16S)-20-methyl-16-{[(methylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 23 | 2-methoxy-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 24 | 3-methyl-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]butanamide |
| Ex. 25 | N-[(10S,12S,16S)-20-methyl-15,21-dioxo-16-[(2-phenylacetyl)amino]-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 26 | N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]benzamide |
| Ex. 27 | N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]butanamide |
| Ex. 28 | N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]pentanamide |
| Ex. 29 | 2-{[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]amino}acetic acid |
| Ex. 30 | 2-(dimethylamino)-N-[(10S,12S,16S)-20-methyl-12-{[(methylamino)carbothioyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 31 | 2-(dimethylamino)-N-[(10S,12S,16S)-20-methyl-15,21-dioxo-12-[(2-sulfanylacetyl)amino]-8-oxa-14,20-diazatetracyclo[20.3.1.$0^{2,7}$.$0^{10,14}$]hexacosa-1(26),2,4,6,22,24-hexaen-16-yl]acetamide |
| Ex. 32 | 2-(dimethylamino)-N-[(10S,12S,16S)-20-methyl-15,21-dioxo-12-{[2-(tritylsulfanyl)acetyl]amino}-8-oxa-14,20-diazatetracyclo[20.3.1.$0^{2,7}$.$0^{10,14}$]hexacosa-1(26),2,4,6,22,24-hexaen-16-yl]acetamide |
| Ex. 33 | 2-(dimethylamino)-N-[(10S,12S,16S)-20-methyl-12-{[(methylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 34 | 2-(dimethylamino)-N-[(10S,12S,16S)-12-({[3-(dimethylamino)anilino]carbonyl}amino)-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 35 | 2-(dimethylamino)-N-[(10S,12S,16S)-20-methyl-12-{[(2-naphthylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 36 | 2-(dimethylamino)-N-[(10S,12S,16S)-20-methyl-12-[(methylsulfonyl)amino]-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 37 | N-[(10S,12S,16S)-12-[(benzylsulfonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]-2-(dimethylamino)acetamide |
| Ex. 38 | tert-butyl N-[(10S,12S,16S)-16-{[2-(dimethylamino)acetyl]amino}-20-methyl-15,21-dioxo-8-oxa-14,20- |

TABLE 12-continued

IUPAC Names of the Examples (continued on the following pages)

| Example | IUPAC Name |
|---|---|
| | diazatetracyclo[20.3.1.0$^{2,7}$.0$^{10,14}$]hexacosa-1(26),2,4,6,22,24-hexaen-12-yl]carbamate |
| Ex. 39 | N-[(10S,12S,16S)-12-amino-20-methyl-15,21-dioxo-8-oxa-14,20-diazatetracyclo[20.3.1.0$^{2,7}$.0$^{10,14}$]hexacosa-1(26),2,4,6,22,24-hexaen-16-yl]-2-(dimethylamino)acetamide |
| Ex. 40 | ethyl 2-{[(10S,12S,16S)-16-{[2-(dimethylamino)acetyl]amino}-20-methyl-15,21-dioxo-8-oxa-14,20-diazatetracyclo[20.3.1.0$^{2,7}$.0$^{10,14}$]hexacosa-1(26),2,4,6,22,24-hexaen-12-yl]amino}acetate |
| Ex. 41 | benzyl (10R,15S)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxylate |
| Ex. 42 | (10R,15S)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxylic acid |
| Ex. 43 | (10R,15S)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 44 | (10R,15S)-4-methoxy-N,10,16-trimethyl-12,17-dioxo-8-oxa-11,16-diazatricyclo[16.3.1.0$^{2,7}$]docosa-1(22),2,4,6,18,20-hexaene-15-carboxamide |
| Ex. 45 | (10R,15S)-4-methoxy-10,16-dimethyl-12,17-dioxo-N-phenyl-8-oxa-11,16-diazatricyclo[16.3.1.0$^{2,7}$]docosa-1(22),2,4,6,18,20-hexaene-15-carboxamide |
| Ex. 46 | (10R,15S)-4-methoxy-10,16-dimethyl-15-(1-pyrrolidinylcarbonyl)-8-oxa-11,16-diazatricyclo[16.3.1.0$^{2,7}$]docosa-1(22),2,4,6,18,20-hexaene-12,17-dione |
| Ex. 47 | (10R,15S)-N-[2-(dimethylamino)ethyl]-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 48 | tert-butyl N-[3-({[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]carbonyl}amino)propyl]carbamate |
| Ex. 49 | (10R,15S)-N-(3-aminopropyl)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 50 | (10R,15S)-4-methoxy-10,16-dimethyl-12,17-dioxo-N-(3-pyridinylmethyl)-8-oxa-11,16-diazatricyclo[16.3.1.0$^{2,7}$]docosa-1(22),2,4,6,18,20-hexaene-15-carboxamide |
| Ex. 51 | (10R,15S)-4-methoxy-N-(2-methoxyethyl)-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 52 | (10R,15S)-N-cyclopropyl-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 53 | (10R,15S)-4-methoxy-10,16-dimethyl-12,17-dioxo-N-(2,2,2-trifluoroethyl)-8-oxa-11,16-diazatricyclo[16.3.1.0$^{2,7}$]docosa-1(22),2,4,6,18,20-hexaene-15-carboxamide |
| Ex. 54 | (10R,15S)-N-isobutyl-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 55 | (10R,15S)-N-(2-hydroxyethyl)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 56 | tert-butyl 2-({[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]carbonyl}amino)acetate |
| Ex. 57 | 2-({[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]carbonyl}amino)acetic acid |
| Ex. 58 | (10R,15S)-4-methoxy-10,16-dimethyl-12,17-dioxo-N-[(1S)-1-phenylethyl]-8-oxa-11,16-diazatricyclo[16.3.1.0$^{2,7}$]docosa-1(22),2,4,6,18,20-hexaene-15-carboxamide |
| Ex. 59 | (10R,15S)-N-[2-(dimethylamino)ethyl]-4-methoxy-N,10,16-trimethyl-12,17-dioxo-8-oxa-11,16-diazatricyclo[16.3.1.0$^{2,7}$]docosa-1(22),2,4,6,18,20-hexaene-15-carboxamide |
| Ex. 60 | (10R,15S)-4-methoxy-10,16-dimethyl-N-(1-naphthylmethyl)-12,17-dioxo-8-oxa-11,16-diazatricyclo[16.3.1.0$^{2,7}$]docosa-1(22),2,4,6,18,20-hexaene-15-carboxamide |
| Ex. 61 | (10R,15S)-4-methoxy-10,16-dimethyl-N-(2-naphthylmethyl)-12,17-dioxo-8-oxa-11,16-diazatricyclo[16.3.1.0$^{2,7}$]docosa-1(22),2,4,6,18,20-hexaene-15-carboxamide |
| Ex. 62 | (10R,15S)-15-(hydroxymethyl)-4-methoxy-10,16-dimethyl-8-oxa-11,16-diazatricyclo[16.3.1.0$^{2,7}$]docosa-1(22),2,4,6,18,20-hexaene-12,17-dione |
| Ex. 63 | (10R,15S)-4-methoxy-10,16-dimethyl-15-[(3-pyridinyloxy)methyl]-8-oxa-11,16-diazatricyclo[16.3.1.0$^{2,7}$]docosa-1(22),2,4,6,18,20-hexaene-12,17-dione |

TABLE 12-continued

| IUPAC Names of the Examples (continued on the following pages) | |
|---|---|
| Example | IUPAC Name |
| Ex. 64 | (10R,15S)-15-(azidomethyl)-4-methoxy-10,16-dimethyl-8-oxa-11,16-diazatricyclo[16.3.1.0$^{2,7}$]docosa-1(22),2,4,6,18,20-hexaene-12,17-dione |
| Ex. 65 | (10R,15S)-15-(aminomethyl)-4-methoxy-10,16-dimethyl-8-oxa-11,16-diazatricyclo[16.3.1.0$^{2,7}$]docosa-1(22),2,4,6,18,20-hexaene-12,17-dione |
| Ex. 66 | N-{[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]methyl}-2-phenylacetamide |
| Ex. 67 | [(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]methyl N-phenylcarbamate |
| Ex. 68 | benzyl (9S,14S)-9,15-dimethyl-11,16-dioxo-7-oxa-10,15-diazatricyclo[15.3.1.1$^{2,6}$]docosa-1(21),2(22),3,5,17,19-hexaene-14-carboxylate |
| Ex. 69 | (9S,14S)-9,15-dimethyl-11,16-dioxo-7-oxa-10,15-diazatricyclo[15.3.1.1$^{2,6}$]docosa-1(21),2(22),3,5,17,19-hexaene-14-carboxylic acid |
| Ex. 70 | (9S,14S)-N,9,15-trimethyl-11,16-dioxo-7-oxa-10,15-diazatricyclo[15.3.1.1$^{2,6}$]docosa-1(21),2(22),3,5,17,19-hexaene-14-carboxamide |
| Ex. 71 | (9S,14S)-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex. 72 | (9S,14S)-9,15-dimethyl-11,16-dioxo-N-phenyl-7-oxa-10,15-diazatricyclo[15.3.1.1$^{2,6}$]docosa-1(21),2(22),3,5,17,19-hexaene-14-carboxamide |
| Ex. 73 | (9S,14S)-9,15-dimethyl-11,16-dioxo-N-phenethyl-7-oxa-10,15-diazatricyclo[15.3.1.1$^{2,6}$]docosa-1(21),2(22),3,5,17,19-hexaene-14-carboxamide |
| Ex. 74 | (9S,14S)-9,15-dimethyl-N-(1-naphthylmethyl)-11,16-dioxo-7-oxa-10,15-diazatricyclo[15.3.1.1$^{2,6}$]docosa-1(21),2(22),3,5,17,19-hexaene-14-carboxamide |
| Ex. 75 | (9S,14S)-9,15-dimethyl-11,16-dioxo-N-(3-pyridinylmethyl)-7-oxa-10,15-diazatricyclo[15.3.1.1$^{2,6}$]docosa-1(21),2(22),3,5,17,19-hexaene-14-carboxamide |
| Ex. 76 | (9S,14S)-9,15-dimethyl-11,16-dioxo-N-[(1S)-1-phenylethyl]-7-oxa-10,15-diazatricyclo[15.3.1.1$^{2,6}$]docosa-1(21),2(22),3,5,17,19-hexaene-14-carboxamide |
| Ex. 77 | (9S,14S)-N-(2-methoxyethyl)-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex. 78 | (9S,14S)-9,15-dimethyl-11,16-dioxo-N-(2,2,2-trifluoroethyl)-7-oxa-10,15-diazatricyclo[15.3.1.1$^{2,6}$]docosa-1(21),2(22),3,5,17,19-hexaene-14-carboxamide |
| Ex. 79 | (9S,14S)-N-cyclopropyl-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex. 80 | (9S,14S)-N-isobutyl-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex. 81 | (9S,14S)-N-(2-hydroxyethyl)-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex. 82 | tert-butyl 2-({[(9S,14S)-9,15-dimethyl-11,16-dioxo-7-oxa-10,15-diazatricyclo[15.3.1.1$^{2,6}$]docosa-1(21),2(22),3,5,17,19-hexaen-14-yl]carbonyl}amino)acetate |
| Ex. 83 | 2-({[(9S,14S)-9,15-dimethyl-11,16-dioxo-7-oxa-10,15-diazatricyclo[15.3.1.1$^{2,6}$]docosa-1(21),2(22),3,5,17,19-hexaen-14-yl]carbonyl}amino)acetic acid |
| Ex. 84 | (9S,14S)-N-[2-(dimethylamino)ethyl]-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex. 85 | (9S,14S)-9,15-dimethyl-11,16-dioxo-N-[3-(1-pyrrolidinyl)propyl]-7-oxa-10,15-diazatricyclo[15.3.1.1$^{2,6}$]docosa-1(21),2(22),3,5,17,19-hexaene-14-carboxamide |
| Ex. 86 | (9S,14S)-14-(1-azetanylcarbonyl)-9,15-dimethyl-7-oxa-10,15-diazatricyclo[15.3.1.1$^{2,6}$]docosa-1(21),2(22),3,5,17,19-hexaene-11,16-dione |
| Ex. 87 | (9S,14S)-9,15-dimethyl-14-(morpholinocarbonyl)-7-oxa-10,15-diazatricyclo[15.3.1.1$^{2,6}$]docosa-1(21),2(22),3,5,17,19-hexaene-11,16-dione |
| Ex. 88 | (9S,14S)-9,15-dimethyl-N-[(1-methyl-1H-imidazol-4-yl)methyl]-11,16-dioxo-7-oxa-10,15-diazatricyclo[15.3.1.1$^{2,6}$]docosa-1(21),2(22),3,5,17,19-hexaene-14-carboxamide |
| Ex. 89 | (9S,14S)-9,15-dimethyl-N-(2-naphthylmethyl)-11,16-dioxo-7-oxa-10,15-diazatricyclo[15.3.1.1$^{2,6}$]docosa-1(21),2(22),3,5,17,19-hexaene-14-carboxamide |

TABLE 12-continued

IUPAC Names of the Examples (continued on the following pages)

| Example | IUPAC Name |
|---|---|
| Ex. 90 | benzyl (9S,11R)-11-[(tert-butoxycarbonyl)amino]-14,20-dioxo-7-oxa-13,16,19,23-tetraazatetracyclo[19.3.1.$1^{2,6}$.$0^{9,13}$]hexacosa-1(25),2(26),3,5,21,23-hexaene-16-carboxylate |
| Ex. 91 | tert-butyl N-[(9S,11R)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate |
| Ex. 92 | benzyl (9S,11R)-11-amino-14,20-dioxo-7-oxa-13,16,19,23-tetraazatetracyclo[19.3.1.$1^{2,6}$.$0^{9,13}$]hexacosa-1(25),2(26),3,5,21,23-hexaene-16-carboxylate |
| Ex. 93 | (9S,11R)-11-amino-7-oxa-13,16,19,23-tetraazatetracyclo[19.3.1.$1^{2,6}$.$0^{9,13}$]hexacosa-1(25),2(26),3,5,21,23-hexaene-14,20-dione |
| Ex. 94 | tert-butyl N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate |
| Ex. 95 | (9S,11R)-11-amino-16-methyl-7-oxa-13,16,19,23-tetraazatetracyclo[19.3.1.$1^{2,6}$.$0^{9,13}$]hexacosa-1(25),2(26),3,5,21,23-hexaene-14,20-dione |
| Ex. 96 | N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-2-(2-naphthyl)acetamide |
| Ex. 97 | tert-butyl N-[(9S,11R)-16-(3-fluorobenzyl)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate |
| Ex. 98 | (9S,11R)-11-amino-16-(3-fluorobenzyl)-7-oxa-13,16,19,23-tetraazatetracyclo[19.3.1.$1^{2,6}$.$0^{9,13}$]hexacosa-1(25),2(26),3,5,21,23-hexaene-14,20-dione |
| Ex. 99 | N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]acetamide |
| Ex. 100 | N-[(9S,11R)-16-(3-fluorobenzyl)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]acetamide |
| Ex. 101 | N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-2-(1-naphthyl)acetamide |
| Ex. 102 | N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-N'-phenylurea |
| Ex. 103 | N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]benzenesulfonamide |
| Ex. 104 | tert-butyl N-[(9S,11R)-16-[2-(dimethylamino)acetyl]-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate |
| Ex. 105 | (9S,11R)-11-amino-16-[2-(dimethylamino)acetyl]-7-oxa-13,16,19,23-tetraazatetracyclo[19.3.1.$1^{2,6}$.$0^{9,13}$]hexacosa-1(25),2(26),3,5,21,23-hexaene-14,20-dione |
| Ex. 106 | N-[(9S,11R)-16-[2-(dimethylamino)acetyl]-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-2-phenylacetamide |
| Ex. 107 | N-[(9S,11R)-16-[2-(dimethylamino)acetyl]-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]cyclopropanesulfonamide |
| Ex. 108 | N-[(9S,11R)-16-[2-(dimethylamino)acetyl]-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-N'-methylurea |
| Ex. 109 | tert-butyl N-[(9S,11R)-16-(cyclopropylsulfonyl)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate |
| Ex. 110 | (9S,11R)-11-amino-16-(cyclopropylsulfonyl)-7-oxa-13,16,19,23-tetraazatetracyclo[19.3.1.$1^{2,6}$.$0^{9,13}$]hexacosa-1(25),2(26),3,5,21,23-hexaene-14,20-dione |
| Ex. 111 | N-[(9S,11R)-16-(cyclopropylsulfonyl)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]benzamide |
| Ex. 112 | tert-butyl N-[(9S,11R)-16-[(methylamino)carbonyl]-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate |
| Ex. 113 | (9S,11R)-11-amino-N-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaene-16-carboxamide |
| Ex. 114 | (95,11R)-11-[(3-fluorobenzoyl)amino]-N-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaene-16-carboxamide |

TABLE 12-continued

IUPAC Names of the Examples (continued on the following pages)

| Example | IUPAC Name |
|---|---|
| Ex. 115 | allyl N-[(135,16R)-16-methyl-14-oxo-18-oxa-8-thia-15-azatricyclo[17.3.1.0$^{2,7}$]tricosa-1(23),2,4,6,19,21-hexaen-13-yl]carbamate |
| Ex. 116 | (135,16R)-13-amino-16-methyl-18-oxa-8-thia-15-azatricyclo[17.3.1.0$^{2,7}$]tricosa-1(23),2,4,6,19,21-hexaen-14-one |
| Ex. 117 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-naphthyl)acetamide |
| Ex. 118 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(2-naphthyl)acetamide |
| Ex. 119 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-pyrrolidinyl)acetamide |
| Ex. 120 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]nicotinamide |
| Ex. 121 | 3-methyl-N-[(13S,16R)-16-methyl-14-oxo-18-oxa-8-thia-15-azatricyclo[17.3.1.0$^{2,7}$]tricosa-1(23),2,4,6,19,21-hexaen-13-yl]butanamide |
| Ex. 122 | methyl N-[(13S,16R)-16-methyl-14-oxo-18-oxa-8-thia-15-azatricyclo[17.3.1.0$^{2,7}$]tricosa-1(23),2,4,6,19,21-hexaen-13-yl]carbamate |
| Ex. 123 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]cyclopropanesulfonamide |
| Ex. 124 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]benzenesulfonamide |
| Ex. 125 | N-methyl-N'-[(13S,16R)-16-methyl-14-oxo-18-oxa-8-thia-15-azatricyclo[17.3.1.0$^{2,7}$]tricosa-1(23),2,4,6,19,21-hexaen-13-yl]urea |
| Ex. 126 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-N'-(3-pyridinyl)urea |
| Ex. 127 | (13S,16R)-13-(isobutylamino)-16-methyl-18-oxa-8-thia-15-azatricyclo[17.3.1.0$^{2,7}$]tricosa-1(23),2,4,6,19,21-hexaen-14-one |
| Ex. 128 | (13S,16R)-13-(isopentylamino)-16-methyl-18-oxa-8-thia-15-azatricyclo[17.3.1.0$^{2,7}$]tricosa-1(23),2,4,6,19,21-hexaen-14-one |
| Ex. 129 | allyl N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]carbamate |
| Ex. 130 | (13S,16R)-13-amino-16-methyl-18-oxa-8$\lambda^6$-thia-15-azatricyclo[17.3.1.0$^{2,7}$]tricosa-1(23),2,4,6,19,21-hexaene-8,8,14-trione |
| Ex. 131 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]-2-(1-naphthyl)acetamide |
| Ex. 132 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]-2-(2-naphthyl)acetamide |
| Ex. 133 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]-2-(1-pyrrolidinyl)acetamide |
| Ex. 134 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]nicotinamide |
| Ex. 135 | 3-methyl-N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]butanamide |
| Ex. 136 | methyl N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]carbamate |
| Ex. 137 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]cyclopropanesulfonamide |
| Ex. 138 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]benzenesulfonamide |
| Ex. 139 | N-methyl-N'-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]urea |
| Ex. 140 | N-[(13S,16R)-16-methyl-8,8,14-trioxo-18-oxa-8$\lambda^6$-thia-15-azatricyclo[17.3.1.0$^{2,7}$]tricosa-1(23),2,4,6,19,21-hexaen-13-yl]-N'-(3-pyridinyl)urea |
| Ex. 141 | (13S,16R)-13-(isobutylamino)-16-methyl-18-oxa-8$\lambda^6$-thia-15-azatricyclo[17.3.1.0$^{2,7}$]tricosa-1(23),2,4,6,19,21-hexaene-8,8,14-trione |
| Ex. 142 | (13S,16R)-13-(isopentylamino)-16-methyl-18-oxa-8$\lambda^6$-thia-15-azatricyclo[17.3.1.0$^{2,7}$]tricosa-1(23),2,4,6,19,21-hexaene-8,8,14-trione |
| Ex. 143 | allyl N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]carbamate |
| Ex. 144 | (10R,13S)-13-amino-10-methyl-8-oxa-18-thia-11,21-diazatricyclo[17.3.1.0$^{2,7}$]tricosa-1(23),2,4,6,19,21-hexaen-12-one |
| Ex. 145 | (10R,13S)-13-(dimethylamino)-10-methyl-8-oxa-18-thia-11,21-diazatricyclo[17.3.1.0$^{2,7}$]tricosa-1(23),2,4,6,19,21-hexaen-12-one |
| Ex. 146 | (10R,13S)-13-(isobutylamino)-10-methyl-8-oxa-18-thia-11,21-diazatricyclo[17.3.1.0$^{2,7}$]tricosa-1(23),2,4,6,19,21-hexaen-12-one |

TABLE 12-continued

| IUPAC Names of the Examples (continued on the following pages) | |
|---|---|
| Example | IUPAC Name |
| Ex. 147 | (10R,13S)-13-[(3-fluorobenzyl)amino]-10-methyl-8-oxa-18-thia-11,21-diazatricyclo[17.3.1.0$^{2,7}$]tricosa-1(23),2,4,6,19,21-hexaen-12-one |
| Ex. 148 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]acetamide |
| Ex. 149 | 2-methoxy-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]acetamide |
| Ex. 150 | 2-(dimethylamino)-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]acetamide |
| Ex. 151 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]nicotinamide |
| Ex. 152 | 3-methyl-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]butanamide |
| Ex. 153 | tert-butyl N-(3-{[(10R,13S)-10-methyl-12-oxo-8-oxa-18-thia-11,21-diazatricyclo[17.3.1.0$^{2,7}$]tricosa-1(23),2,4,6,19,21-hexaen-13-yl]amino}-3-oxopropyl)carbamate |
| Ex. 154 | 3-amino-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]propanamide |
| Ex. 155 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]-2-(1-naphthyl)acetamide |
| Ex. 156 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]-2-(2-naphthyl)acetamide |
| Ex. 157 | 3,3,3-trifluoro-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]propanamide |
| Ex. 158 | 3-fluoro-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]benzamide |
| Ex. 159 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]-N'-(3-pyridinyl)urea |
| Ex. 160 | N-methyl-N'-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]urea |
| Ex. 161 | tert-butyl 3-[({[(10R,13S)-10-methyl-12-oxo-8-oxa-18-thia-11,21-diazatricyclo[17.3.1.0$^{2,7}$]tricosa-1(23),2,4,6,19,21-hexaen-13-yl]amino}carbonyl)amino]propanoate |
| Ex. 162 | 3-[({[(10R,13S)-10-methyl-12-oxo-8-oxa-18-thia-11,21-diazatricyclo[17.3.1.0$^{2,7}$]tricosa-1(23),2,4,6,19,21-hexaen-13-yl]amino}carbonyl)amino]propanoic acid |
| Ex. 163 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]methanesulfonamide |
| Ex. 164 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]cyclopropanesulfonamide |
| Ex. 165 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]benzenesulfonamide |
| Ex. 166 | methyl N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]carbamate |
| Ex. 167 | 2-methoxyethyl N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]carbamate |
| Ex. 168 | allyl N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]carbamate |
| Ex. 169 | (10R,13S)-13-amino-10-methyl-8-oxa-18λ$^{6}$-thia-11,21-diazatricyclo[17.3.1.0$^{2,7}$]tricosa-1(23),2,4,6,19,21-hexaene-12,18,18-trione |
| Ex. 170 | (10R,13S)-13-(dimethylamino)-10-methyl-8-oxa-18λ$^{6}$-thia-11,21-diazatricyclo[17.3.1.0$^{2,7}$]tricosa-1(23),2,4,6,19,21-hexaene-12,18,18-trione |
| Ex. 171 | (10R,13S)-13-(isobutylamino)-10-methyl-8-oxa-18λ$^{6}$-thia-11,21-diazatricyclo[17.3.1.0$^{2,7}$]tricosa-1(23),2,4,6,19,21-hexaene-12,18,18-trione |
| Ex. 172 | (10R,13S)-13-[(3-fluorobenzyl)amino]-10-methyl-8-oxa-18λ$^{6}$-thia-11,21-diazatricyclo[17.3.1.0$^{2,7}$]tricosa-1(23),2,4,6,19,21-hexaene-12,18,18-trione |
| Ex. 173 | N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]acetamide |
| Ex. 174 | 2-methoxy-N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]acetamide |
| Ex. 175 | 2-(dimethylamino)-N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]acetamide |
| Ex. 176 | N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]nicotinamide |

TABLE 12-continued

IUPAC Names of the Examples (continued on the following pages)

| Example | IUPAC Name |
|---|---|
| Ex. 177 | 3-methyl-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]butanamide |
| Ex. 178 | tert-butyl N-(3-{[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]amino}-3-oxopropyl)carbamate |
| Ex. 179 | 3-amino-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]propanamide |
| Ex. 180 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]-2-(1-naphthyl)acetamide |
| Ex. 181 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]-2-(2-naphthyl)acetamide |
| Ex. 182 | 3,3,3-trifluoro-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]propanamide |
| Ex. 183 | 3-fluoro-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]benzamide |
| Ex. 184 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]-N'-(3-pyridinyl)urea |
| Ex. 185 | N-methyl-N'-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]urea |
| Ex. 186 | tert-butyl 3-[({[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]amino}carbonyl)amino]propanoate |
| Ex. 187 | 3-[({[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]amino}carbonyl)amino]propanoic acid |
| Ex. 188 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]methanesulfonamide |
| Ex. 189 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]cyclopropanesulfonamide |
| Ex. 190 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]benzenesulfonamide |
| Ex. 191 | methyl N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]carbamate |
| Ex. 192 | 2-methoxyethyl N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]carbamate |
| Ex. 193a | (9S,16S,19R)-16-benzyl-19,20-dimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193c | (9S,19S)-19-benzyl-20-methyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193d | (9S,19S)-19-benzyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193e | (9S,16R,19S)-19-benzyl-16,17,20-trimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193f | (9S,16R)-16,17,20-trimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193g | (9S,16R,19S)-19-benzyl-16,17-dimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193h | (9S,16S)-16-benzyl-21-methyl-7-oxa-13,17,21,25-tetraazatetracyclo[21.3.1.1$^{2,6}$.0$^{9,13}$]octacosa-1(27),2(28),3,5,23,25-hexaene-14,18,22-trione |
| Ex. 194b | 3-[(9S,16R,19S)-16,17,20-trimethyl-14,18,21-trioxo-7-oxa-13,17,20,24-tetraazatetracyclo[20.3.1.1$^{2,6}$.0$^{9,13}$]heptacosa-1(26),2(27),3,5,22,24-hexaen-19-yl]propanoic acid |
| Ex. 195a | (9S,16R,22S)-16,17,20,22,23-pentamethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone |
| Ex. 195b | (9S,16R,22S)-16,17,22-trimethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone |

TABLE 12-continued

| IUPAC Names of the Examples (continued on the following pages) | |
|---|---|
| Example | IUPAC Name |
| Ex. 195e | (9S,19R,22S)-16,19,20,22,23-pentamethyl-7-oxa-13,16,20,23,27-pentaazatetracyclo[23.3.1.1$^{2,6}$.0$^{9,13}$]triaconta-1(29),2(30),3,5,25,27-hexaene-14,17,21,24-tetrone |
| Ex. 195f | (9S,18S,22R)-16,18,19,22,23-pentamethyl-7-oxa-13,16,19,23,27-pentaazatetracyclo[23.3.1.1$^{2,6}$.0$^{9,13}$]triaconta-1(29),2(30),3,5,25,27-hexaene-14,17,20,24-tetrone |
| Ex. 195g | (9S,18S,21R)-18-benzyl-21,22-dimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone |
| Ex. 195h | (9S,18S,21R)-18-benzyl-16,21-dimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone |
| Ex. 195j | (9S,18S,21R)-18-benzyl-16,21,22-trimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone |
| Ex. 196c | 3-[(9S,16R,19S,22S)-16,17,19,23-tetramethyl-14,18,21,24-tetraoxo-7-oxa-13,17,20,23,27-pentaazatetracyclo[23.3.1.1$^{2,6}$.0$^{9,13}$]triaconta-1(29),2(30),3,5,25,27-hexaen-22-yl]propanoic acid |
| Ex. 196i | 3-[(9S,15S,18R,21S)-18-benzyl-15,22-dimethyl-14,17,20,23-tetraoxo-7-oxa-13,16,19,22,26-pentaazatetracyclo[22.3.1.1$^{2,6}$.0$^{9,13}$]nonacosa-1(28),2(29),3,5,24,26-hexaen-21-yl]propanoic acid |
| Ex. 196k | 3-[(9S,15R,18S,21S)-18-benzyl-15,22-dimethyl-14,17,20,23-tetraoxo-7-oxa-13,16,19,22,26-pentaazatetracyclo[22.3.1.1$^{2,6}$.0$^{9,13}$]nonacosa-1(28),2(29),3,5,24,26-hexaen-21-yl]propanoic acid |
| Ex. 197d | (9S,16R,19S,22R)-19-(4-aminobutyl)-16,17,22-trimethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone |
| Ex. 198 | benzyl (10S,12S)-12-[(tert-butoxycarbonyl)amino]-15,21-dioxo-8-oxa-3,14,17,20-tetraazatetracyclo[20.2.2.0$^{2,7}$.0$^{10,14}$]hexacosa-1(24),2,4,6,22,25-hexaene-17-carboxylate |
| Ex. 199 | benzyl (10S,12S)-12-amino-15,21-dioxo-8-oxa-3,14,17,20-tetraazatetracyclo[20.2.2.0$^{2,7}$.0$^{10,14}$]hexacosa-1(24),2,4,6,22,25-hexaene-17-carboxylate |
| Ex. 200 | tert-butyl N-[(10S,12S)-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]carbamate |
| Ex. 201 | tert-butyl N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]carbamate |
| Ex. 202 | (10S,12S)-12-amino-17-methyl-8-oxa-3,14,17,20-tetraazatetracyclo[20.2.2.0$^{2,7}$.0$^{10,14}$]hexacosa-1(24),2,4,6,22,25-hexaene-15,21-dione |
| Ex. 203 | N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-2-(1-naphthyl)acetamide |
| Ex. 204 | 3-methyl-N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]butanamide |
| Ex. 205 | N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-N'-(3-pyridinyl)urea |
| Ex. 206 | N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]benzenesulfonamide |
| Ex. 207 | tert-butyl N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]carbamate |
| Ex. 208 | (10S,12S)-12-amino-17-[2-(dimethylamino)acetyl]-8-oxa-3,14,17,20-tetraazatetracyclo[20.2.2.0$^{2,7}$.0$^{10,14}$]hexacosa-1(24),2,4,6,22,25-hexaene-15,21-dione |
| Ex. 209 | N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-2-phenylacetamide |
| Ex. 210 | N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-N'-methylurea |
| Ex. 211 | N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]cyclopropanesulfonamide |
| Ex. 212 | benzyl (10S,12S)-12-(acetylamino)-15,21-dioxo-8-oxa-3,14,17,20-tetraazatetracyclo[20.2.2.0$^{2,7}$.0$^{10,14}$]hexacosa-1(24),2,4,6,22,25-hexaene-17-carboxylate |
| Ex. 213 | N-[(10S,12S)-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]acetamide |

TABLE 12-continued

| IUPAC Names of the Examples (continued on the following pages) | |
|---|---|
| Example | IUPAC Name |
| Ex. 214 | N-[(10S,12S)-17-(3-fluorobenzyl)-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 215 | N-[(10S,12S)-15,21-dioxo-17-[2-(1-pyrrolidinyl)acetyl]-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 216 | (10S,12S)-12-(acetylamino)-15,21-dioxo-N-phenyl-8-oxa-3,14,17,20-tetraazatetracyclo[20.2.2.$0^{2,7}$.$0^{10,14}$]hexacosa-1(24),2,4,6,22,25-hexaene-17-carboxamide |
| Ex. 217 | N-[(10S,12S)-15,21-dioxo-17-(phenylsulfonyl)-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 218 | 3-({[(10S,12S)-12-(acetylamino)-15,21-dioxo-8-oxa-3,14,17,20-tetraazatetracyclo[20.2.2.$0^{2,7}$.$0^{10,14}$]hexacosa-1(24),2,4,6,22,25-hexaen-17-yl]carbonyl}amino)propanoic acid |
| Ex. 219 | tert-butyl 3-({[(10S,12S)-12-(acetylamino)-15,21-dioxo-8-oxa-3,14,17,20-tetraazatetracyclo[20.2.2.$0^{2,7}$.$0^{10,14}$]hexacosa-1(24),2,4,6,22,25-hexaen-17-yl]carbonyl}amino)propanoate |
| Ex. 220 | methyl (8S,17S,19S)-17-[(tert-butoxycarbonyl)amino]-24-fluoro-6,14-dioxo-10,21-dioxa-4-thia-7,15-diazatetracyclo[20.3.1.$1^{2,5}$.$0^{15,19}$]heptacosa-1(26),2,5(27),12,22,24-hexaene-8-carboxylate |
| Ex. 221 | methyl (8S,17S,19S)-17-[(tert-butoxycarbonyl)amino]-24-fluoro-6,14-dioxo-10,21-dioxa-4-thia-7,15-diazatetracyclo[20.3.1.$1^{2,5}$.$0^{15,19}$]heptacosa-1(26),2,5(27),22,24-pentaene-8-carboxylate |
| Ex. 222 | methyl (8S,17S,19S)-17-amino-24-fluoro-6,14-dioxo-10,21-dioxa-4-thia-7,15-diazatetracyclo[20.3.1.$1^{2,5}$.$0^{15,19}$]heptacosa-1(26),2,5(27),22,24-pentaene-8-carboxylate |
| Ex. 223 | methyl (8S,17S,19S)-24-fluoro-6,14-dioxo-17-[(2-phenylacetyl)amino]-10,21-dioxa-4-thia-7,15-diazatetracyclo[20.3.1.$1^{2,5}$.$0^{15,19}$]heptacosa-1(26),2,5(27),22,24-pentaene-8-carboxylate |
| Ex. 224 | (8S,17S,19S)-24-fluoro-6,14-dioxo-17-[(2-phenylacetyl)amino]-10,21-dioxa-4-thia-7,15-diazatetracyclo[20.3.1.$1^{2,5}$.$0^{15,19}$]heptacosa-1(26),2,5(27),22,24-pentaene-8-carboxylic acid |
| Ex. 225 | (8S,17S,19S)-24-fluoro-6,14-dioxo-17-[(2-phenylacetyl)amino]-10,21-dioxa-4-thia-7,15-diazatetracyclo[20.3.1.$1^{2,5}$.$0^{15,19}$]heptacosa-1(26),2,5(27),22,24-pentaene-8-carboxamide |
| Ex. 226 | (8S,17S,19S)-24-fluoro-N-isobutyl-6,14-dioxo-17-[(2-phenylacetyl)amino]-10,21-dioxa-4-thia-7,15-diazatetracyclo[20.3.1.$1^{2,5}$.$0^{15,19}$]heptacosa-1(26),2,5(27),22,24-pentaene-8-carboxamide |
| Ex. 227 | methyl (8S,12E,18S,20S)-18-[(tert-butoxycarbonyl)amino]-25-fluoro-6,15-dioxo-10,22-dioxa-4-thia-7,16-diazatetracyclo[21.3.1.$1^{2,5}$.$0^{16,20}$]octacosa-1(27),2,5(28),12,23,25-hexaene-8-carboxylate |
| Ex. 228 | (8S,12E,18S,20S)-18-[(tert-butoxycarbonyl)amino]-25-fluoro-6,15-dioxo-10,22-dioxa-4-thia-7,16-diazatetracyclo[21.3.1.$1^{2,5}$.$0^{16,20}$]octacosa-1(27),2,5(28),12,23,25-hexaene-8-carboxylic acid |
| Ex. 229 | methyl (8S,12E,18S,20S)-18-amino-25-fluoro-6,15-dioxo-10,22-dioxa-4-thia-7,16-diazatetracyclo[21.3.1.$1^{2,5}$.$0^{16,20}$]octacosa-1(27),2,5(28),12,23,25-hexaene-8-carboxylate |
| Ex. 230 | methyl (8S,12E,18S,20S)-25-fluoro-18-[2-(2-naphthyl)acetyl]amino-6,15-dioxo-10,22-dioxa-4-thia-7,16-diazatetracyclo[21.3.1.$1^{2,5}$.$0^{16,20}$]octacosa-1(27),2,5(28),12,23,25-hexaene-8-carboxylate |
| Ex. 231 | tert-butyl N-[(8S,12E,18S,20S)-25-fluoro-8-[(isobutylamino)carbonyl]-6,15-dioxo-10,22-dioxa-4-thia-7,16-diazatetracyclo[21.3.1.$1^{2,5}$.$0^{16,20}$]octacosa-1(27),2,5(28),12,23,25-hexaen-18-yl]carbamate |
| Ex. 232 | (8S,12E,18S,20S)-18-amino-25-fluoro-N-isobutyl-6,15-dioxo-10,22-dioxa-4-thia-7,16-diazatetracyclo[21.3.1.$1^{2,5}$.$0^{16,20}$]octacosa-1(27),2,5(28),12,23,25-hexaene-8-carboxamide |
| Ex. 233 | (8S,12E,18S,20S)-25-fluoro-N-isobutyl-6,15-dioxo-18-[(3-pyridinylcarbonyl)amino]-10,22-dioxa-4-thia-7,16-diazatetracyclo[21.3.1.$1^{2,5}$.$0^{16,20}$]octacosa-1(27),2,5(28),12,23,25-hexaene-8-carboxamide |
| Ex. 234 | tert-butyl N-[(8S,12E,18S,20S)-8-(anilinocarbonyl)-25-fluoro-6,15-dioxo-10,22-dioxa-4-thia-7,16-diazatetracyclo[21.3.1.$1^{2,5}$.$0^{16,20}$]octacosa-1(27),2,5(28),12,23,25-hexaen-18-yl]carbamate |
| Ex. 235 | (8S,12E,18S,20S)-18-amino-25-fluoro-6,15-dioxo-N-phenyl-10,22-dioxa-4-thia-7,16-diazatetracyclo[21.3.1.$1^{2,5}$.$0^{16,20}$]octacosa-1(27),2,5(28),12,23,25-hexaene-8-carboxamide |
| Ex. 236 | methyl (8S,12E,18S,20S)-25-fluoro-6,15-dioxo-18-[(2-phenylacetyl)amino]-10,22-dioxa-4-thia-7,16-diazatetracyclo[21.3.1.$1^{2,5}$.$0^{16,20}$]octacosa-1(27),2,5(28),12,23,25-hexaene-8-carboxylate |
| Ex. 237 | (8S,12E,18S,20S)-25-fluoro-6,15-dioxo-18-[(2-phenylacetyl)amino]-10,22-dioxa-4-thia-7,16-diazatetracyclo[21.3.1.$1^{2,5}$.$0^{16,20}$]octacosa-1(27),2,5(28),12,23,25-hexaene-8-carboxylic acid |

TABLE 12-continued

| IUPAC Names of the Examples (continued on the following pages) | |
|---|---|
| Example | IUPAC Name |
| Ex. 238 | methyl (8S,12E,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylate |
| Ex. 239 | (8S,12E 18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid |
| Ex. 240 | (8S,12E,18S,20S)-25-fluoro-N-isobutyl-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxamide |
| Ex. 241 | (8S,12E,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid |
| Ex. 242 | methyl (8S,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate |
| Ex. 243 | (8S,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylic acid |
| Ex. 244 | methyl (8S,18S,20S)-18-amino-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate |
| Ex. 245 | methyl (8S,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate |
| Ex. 246 | tert-butyl N-[(8S,18S,20S)-8-(anilinocarbonyl)-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate |
| Ex. 247 | (8S,18S,20S)-18-amino-25-fluoro-6,15-dioxo-N-phenyl-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 248 | methyl (8S,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$]octacosa-1(27),2,5(28),23,25-pentaene-8-carboxylate |
| Ex. 249 | (8S,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylic acid |
| Ex. 250 | methyl (8S,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate |
| Ex. 251 | (8S,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$]octacosa-1(27),2,5(28),23,25-pentaene-8-carboxylic acid |
| Ex. 252 | (8S,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylic acid |
| Ex. 253 | tert-butyl N-[(8S,18S,20S)-25-fluoro-8-[(isobutylamino)carbonyl]-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate |
| Ex. 254 | (8S,18S,20S)-18-amino-25-fluoro-N-isobutyl-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 255 | (8S,18S,20S)-25-fluoro-N-isobutyl-6,15-dioxo-18-[(3-pyridinylcarbonyl)amino]-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 256 | tert-butyl N-[(8S,18S,20S)-8-[(4-chloroanilino)carbonyl]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate |
| Ex. 257 | (8S,18S,20S)-18-amino-N-(4-chlorophenyl)-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 258 | tert-butyl N-[(8S,18S,20S)-25-fluoro-6,15-dioxo-8-(3-toluidinocarbonyl)-10,22-dioxa-4-thia-7,16-diazatetracyclo[21.3.1.1$^{2,5}$.0$^{16,20}$]octacosa-1(27),2,5(28),23,25-pentaen-18-yl]carbamate |
| Ex. 259 | (8S,18S,20S)-18-amino-25-fluoro-N-(3-methylphenyl)-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 260 | tert-butyl N-[(8S,18S,20S)-8-[(benzylamino)carbonyl]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate |
| Ex. 261 | (8S,18S,20S)-18-amino-N-benzyl-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide |

TABLE 12-continued

| IUPAC Names of the Examples (continued on the following pages) | |
|---|---|
| Example | IUPAC Name |
| Ex. 262 | benzyl N-[(9S,11S,15S)-11-[(4-bromobenzyl)oxy]-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]carbamate |
| Ex. 263 | (9S,11S,15S)-15-amino-11-hydroxy-18,21-dimethyl-7-oxa-3-thia-13,18,21,22-tetraazatetracyclo[18.2.1.0$^{2,6}$.0$^{9,13}$]tricosa-1(22),2(6),4,20(23)-tetraene-14,19-dione |
| Ex. 264 | (9S,11S,15S)-15-amino-11-(benzyloxy)-18,21-dimethyl-7-oxa-3-thia-13,18,21,22-tetraazatetracyclo[18.2.1.0$^{2,6}$.0$^{9,13}$]tricosa-1(22),2(6),4,20(23)-tetraene-14,19-dione |
| Ex. 265 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(2-naphthyl)acetamide |
| Ex. 266 | N-[(9S,11S,15S)-11-(benzyloxy)-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]acetamide |
| Ex. 267 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(1-naphthyl)acetamide |
| Ex. 268 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-3-methylbutanamide |
| Ex. 269 | 3-fluoro-N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]benzamide |
| Ex. 270 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]benzenesulfonamide |
| Ex. 271 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]methanesulfonamide |
| Ex. 272 | methyl N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]carbamate |
| Ex. 273 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N'-methylurea |
| Ex. 274 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N'-(3-pyridinyl)urea |
| Ex. 275 | N-[(9S,11S,15S)-11-methoxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(2-naphthyl)acetamide |
| Ex. 276 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N'-(2-naphthyl)urea |
| Ex. 277 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-phenylacetamide |
| Ex. 278 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-3-methoxybenzamide |
| Ex. 279 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-naphthalenesulfonamide |
| Ex. 280 | 3-(4-fluorophenyl)-N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]propanamide |
| Ex. 281 | N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(1H-indol-3-yl)acetamide |
| Ex. 282 | (9S,11S,15S)-11-hydroxy-18,21-dimethyl-15-{[2-(2-naphthyl)ethyl]amino}-7-oxa-3-thia-13,18,21,22-tetraazatetracyclo[18.2.1.0$^{2,6}$.0$^{9,13}$]tricosa-1(22),2(6),4,20(23)-tetraene-14,19-dione |
| Ex. 283 | (9S,11S,15S)-15-[(4-fluorobenzyl)amino]-11-hydroxy-18,21-dimethyl-7-oxa-3-thia-13,18,21,22-tetraazatetracyclo[18.2.1.0$^{2,6}$.0$^{9,13}$]tricosa-1(22),2(6),4,20(23)-tetraene-14,19-dione |
| Ex. 284a | benzyl N-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| EX. 284b | benzyl N-[(13R,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 285 | (13S,19S)-13-amino-4,8-dimethyl-23-nitro-21-oxa-3,8,15,27-tetraazatetracyclo[20.2.2.1$^{2,6}$.0$^{15,19}$]heptacosa-1(24),2(27),3,5,22,25-hexaene-7,14-dione |

TABLE 12-continued

| IUPAC Names of the Examples (continued on the following pages) | |
|---|---|
| Example | IUPAC Name |
| Ex. 286 | benzyl N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 287 | benzyl N-[(13S,19S)-23-(acetylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 288 | N-[(13S,19S)-13-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 289 | N-(2-chlorophenyl)-N'-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]urea |
| Ex. 290 | N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-N'-(2-chlorophenyl)urea |
| Ex. 291 | N-[(13S,19S)-13-{[(2-chloroanilino)carbonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide |
| Ex. 292 | N-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide |
| Ex. 293 | N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide |
| Ex. 294 | N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide |
| Ex. 295 | N-[(13S,19S)-13-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide |
| Ex. 296 | benzyl N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 297 | benzyl N-[(13S,19S)-4,8-dimethyl-7,14-dioxo-23-(2-pyrimidinylamino)-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 298 | (13S,19S)-13-amino-4,8-dimethyl-23-(2-pyrimidinylamino)-21-oxa-3,8,15,27-tetraazatetracyclo[20.2.2.1$^{2,6}$.0$^{15,19}$]heptacosa-1(24),2(27),3,5,22,25-hexaene-7,14-dione |
| Ex. 299 | N-[(13S,19S)-13-(dimethylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 300 | N-[(13S,19S)-23-(acetylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-2-phenylacetamide |
| Ex. 301 | N-[(13S,19S)-13-{[(3-chlorophenyl)sulfonyl]amino}-4.8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 302 | N-[(13S,19S)-13-{[(isobutylamino)carbonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 303 | N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-4-fluorobenzamide |
| Ex. 304 | N-[(13S,19S)-13-[(3-fluorobenzyl)amino]-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide |
| Ex. 305 | benzyl N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]carbamate |
| Ex. 306 | (15R,16aS)-15-amino-10-methyl-10,11,15,16,16a,17-hexahydro-14H-dibenzo[i,k]pyrrolo[2,1-c][1,4,7]oxadiazacyclododecine-9,12-dione |
| Ex. 307 | (15R,16aS)-15-(dimethylamino)-10-methyl-10,11,15,16,16a,17-hexahydro-14H-dibenzo[i,k]pyrrolo[2,1-c][1,4,7]oxadiazacyclododecine-9,12-dione |
| Ex. 308 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]acetamide |
| Ex. 309 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-methylbutanamide |
| Ex. 310 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(2-naphthyl)acetamide |

TABLE 12-continued

IUPAC Names of the Examples (continued on the following pages)

| Example | IUPAC Name |
|---|---|
| Ex. 311 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(1-naphthyl)acetamide |
| Ex. 312 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(dimethylamino)acetamide |
| Ex. 313 | tert-butyl N-(3-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino-3-oxopropyl)carbamate |
| Ex. 314 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-aminopropanamide |
| Ex. 315 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-fluorobenzamide |
| Ex. 316 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]isonicotinamide |
| Ex. 317 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N'-methylurea |
| Ex. 318 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N'-(3-pyridinyl)urea |
| Ex. 319 | 2-methoxyethyl N-[(15R,16aS)-10-methyl-9,12-dioxo-9,10,11,12,15,16,163,17-octahydro-14H-dibenzo[i,k]pyrrolo[2,1-c][1,4,7]oxadiazacyclododecin-15-yl]carbamate |
| Ex. 320 | tert-butyl 3-[({[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino}carbonyl)amino]propanoate |
| Ex. 321 | 3-[({[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino}carbonyl)amino]propanoic acid |
| Ex. 322 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]methanesulfonamide |
| Ex. 323 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]benzenesulfonamide |
| Ex. 324 | (15R,16aS)-15-[(3-fluorobenzyl)amino]-10-methyl-10,11,15,16,16a,17-hexahydro-14H-dibenzo[i,k]pyrrolo[2,1-c][1,4,7]oxadiazacyclododecine-9,12-dione |
| Ex. 325 | (15R,16aS)-15-(isobutylamino)-10-methyl-10,11,15,16,16a,17-hexahydro-14H-dibenzo[i,k]pyrrolo[2,1-c][1,4,7]oxadiazacyclododecine-9,12-dione |
| Ex. 326 | N''-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N,N,N',N'-tetramethylguanidine |
| Ex. 327 | benzyl (16S,18S)-16-[(tert-butoxycarbonyl)amino]-7,13-dioxo-4-(trifluoromethyl)-5,20-dioxa-3,8,11,14-tetraazatetracyclo[19.3.1.$0^{2,6}$.$0^{14,18}$]pentacosa-1(25),2(6),3,21,23-pentaene-11-carboxylate |
| Ex. 328 | tert-butyl N-[(16S,18S)-7,13-dioxo-4-(trifluoromethyl)-5,20-dioxa-3,8,11,14-tetraazatetracyclo[19.3.1.$0^{2,6}$.$0^{14,18}$]pentacosa-1(25),2(6),3,21,23-pentaen-16-yl]carbamate |
| Ex. 329 | benzyl (165,18S)-16-amino-7,13-dioxo-4-(trifluoromethyl)-5,20-dioxa-3,8,11,14-tetraazatetracyclo[19.3.1.$0^{2,6}$.$0^{14,18}$]pentacosa-1(25),2(6),3,21,23-pentaene-11-carboxylate |
| Ex. 330 | allyl N-[(12R,16S,18S)-16-[(tert-butoxycarbonyl)amino]-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 331 | allyl N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 332 | 2-(1H-imidazol-1-yl)-N-[(12R,16S,18S)-12-{[2-(1-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]acetamide |
| Ex. 333 | N-[(12R,16S,18S)-8,13-dioxo-16-{[(3-pyridinylamino)carbonyl]amino}-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 334 | 2-(3-chlorophenyl)-N-[(12R,16S,18S)-8,13-dioxo-16-{[2-(1-pyrrolidinyl)acetyl]amino}-20-oxa-9,14-diazatetracyclo[19.3.1.$0^{2,7}$.$0^{14,18}$]pentacosa-1(25),2,4,6,21,23-hexaen-12-yl]acetamide |

TABLE 12-continued

IUPAC Names of the Examples (continued on the following pages)

| Example | IUPAC Name |
|---|---|
| Ex. 335 | 2-cyclohexyl-N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]acetamide |
| Ex. 336 | N-[(12R,16S,18S)-12-{[(1-naphthylamino)carbonyl]amino}-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide |
| Ex. 337 | N-[(12R,16S,18S)-12-[(benzylsulfonyl)amino]-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide |
| Ex. 338 | benzyl N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]carbamate |
| Ex. 339 | N-[(12R,16S,18S)-12-amino-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide |
| Ex. 340 | N-[(12R,16S,18S)-12-{[2-(1-naphthyl)ethyl]amino}-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide |
| Ex. 341 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(1-naphthyl)acetamide |
| Ex. 342 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 343 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-N'-(2-naphthyl)urea |
| Ex. 344 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-naphthalenesulfonamide |
| Ex. 345 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-3-(2-naphthyl)propanamide |
| Ex. 346 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-3-phenylpropanamide |
| Ex. 347 | 2-(dimethylamino)-N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]acetamide |
| Ex. 348 | benzyl (9S,11R)-11-{[2-(2-naphthyl)acetyl]amino}-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxylate |
| Ex. 349 | N-[(9S,11R)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 350 | N-[(9S,11R)-16-(3-fluorobenzoyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 351 | N-[(9S,11R)-16-benzyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 352 | N-[(9S,11R)-14,20-dioxo-16-phenethyl-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 353 | N-[(9S,11R)-14,20-dioxo-16-(3-phenylpropyl)-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 354 | N-[(9S,11R)-16-isopentyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 355 | N-[(9S,11R)-16-isobutyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 356 | 2-(dimethylamino)ethyl (9S,11R)-11-{[2-(2-naphthyl)acetyl]amino}-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxylate |
| Ex. 357 | N-[(9S,11R)-16-[2-(dimethylamino)ethyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 358 | 3,3-dimethyl-N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]butanamide |

Synthesis of the Building Blocks

Readily available examples of amino acids representing subunits of the Bridge C are detailed to the level of fully-defined structures in Table 11. Additional analogs can be accessed smoothly, and a plethora of literature precedents are published. Therefore this section focuses on synthetic approaches towards building blocks of the Template A and the Modulator B.

Functional groups not involved in ring connections of the macrocyclic backbone can be diversified by standard methods of organic synthesis, preferably by parallel/combinatorial chemistry introducing so-called high variation substituents. These derivatization methods are well-known to those skilled in the art and do not require further exemplification (selected references: A. R. Katritzky et al. (eds), *Comprehensive Functional Group Transformations*, Pergamon, 1995; S. Patai, Z. Rappoport (eds), *Chemistry of Functional Groups*, Wiley, 1999; J. March, *Advanced Organic Chemistry,* 4 ed., Wiley, 1992; D. Obrecht, J. M. Villalgordo (eds), *Solid-Supported Combinatorial and Parallel Synthesis of Small-Molecular-Weight Compound Libraries*, Pergamon, 1998; W. Bannwarth et al. (eds), *Combinatorial Chemistry: From Theory to Application,* 2 ed., Wiley-VCH 2006).

a) Synthesis of Template a Building Blocks

Over the last decades the coupling to suitably functionalized aromatic or heteroaromatic compounds has reached a highly mature status providing an easy and reliable route to biaryl derivatives of nearly any substitution pattern (cf. leading reviews covering several types of coupling reactions and the references cited therein: R. M. Kellogg et al., *Org. Process Res. Dev.* 2010, 14, 30-47; A. de Meijere, F. Diederich (eds), *Metal-Catalyzed Cross-Coupling Reactions,* 2nd ed., Wiley-VCH 2004; with focus on heteroaromatic substrates: G. Zeni, R. C. Larock, *Chem. Rev.* 2006, 106, 4644-4680; especially for macrocyclic biaryls: Q. Wang, J. Zhu, *Chimia* 2011, 65, 168-174). Most prominent among these coupling reactions is definitely the Suzuki-Miyaura cross coupling of aryl boronic acid derivatives with aryl halides under palladium catalysis (N. Miyaura, A. Suzuki, *Chem. Rev.* 1995, 95, 2457-2483; S. Kotha et al., *Tetrahedron* 2002, 58, 9633-9695; S. L. Buchwald et al., *J. Am. Chem. Soc.* 2005, 127, 4685-4696). Special catalysts, especially the Nolan's catalysts make the Suzuki-Miyaura reaction also amenable to highly sterically hindered substrates (S. P. Nolan et al., *J. Am. Chem. Soc.* 2003, 125, 16194-16195; S. P. Nolan et al., *Org. Lett.* 2005, 7, 1829-1832). More recent developments broadened the scope of the Suzuki coupling from aryl halides to other substrates like aryl mesylates (F. Y. Kwong et al., *Angew. Chem. Int. Ed.* 2008, 47, 8059-8063) or aryl carbamates, carbonates and sulfamates (N. K. Garg et al., *J. Am. Chem. Soc.* 2009, 131, 17748-17749).

The biaryl compounds obtained by such coupling protocols might require further functional group transformations as described below.

General Functional Group Interconversions

The majority of the Templates A are carrying an aromatic or heteroaromatic hydroxy (—OH) or sulfanyl (thiol) group (—SH) in the $A_B$ substructure and a carboxylic acid group (—COOH) or sulfanyl moiety (—SH) or its respective oxidation products in the Ac substructure.

As more phenolic precursors are commercially available than the corresponding thiophenols, a transformation of a phenol into a thiophenol might be required. Alternatively thiophenols might be derived from the corresponding aryl halides or diazonium salts. Selected functional group transformations for introducing a sulfanyl group (—SH), i.e. Ar/Hetar-X→Ar/Hetar-SH (X═OH, F, Cl, Br, I, $N_2^+$), are the compiled below (T-I to T-VII):

T-I: A sequence of broad applicability is the transformation of a phenol into a thiocarbamate with N,N-dimethylthiocarbamoyl chloride, followed by Newman-Kwart rearrangement and subsequent hydrolysis (A. Gallardo-Godoy et al., *J. Med. Chem.* 2005, 48, 2407-2419; P. Beaulieu et al., *Bioorg. Med. Chem. Lett.* 2006, 16, 4987-4993; H. Sugiyama et al., *Chem. Pharm. Bull.* 2007, 55, 613-624; S. Lin et al., *Org. Prep. Proced. Int.* 2000; 547-556).

T-II: The direct transformation of an —OH adjacent to a pyridinic nitrogen (i.e. equivalent to the pyridone tautomer) can be accomplished by heating with $P_2S_5$ (K. Hirai et al., *Heterocycles* 1994, 38, 277-280).

T-III: As an alternative to phenols, halogen-substituted (esp. with F or Cl) aromatic ring systems might serve as precursors. In case the halogen is in a position activated by an electron withdrawing group in ortho- or para-position the —SH moiety or a protected surrogate can be introduced under mild conditions by nucleophilic aromatic substitution reactions ($S_NAr$) (G. J. Atwell et al., *J. Med. Chem.* 1994, 37, 371-380). Especially in the field of heterocyclic compounds, where the electron withdrawing effect is exerted by pyridine-like nitrogen atoms, this type of substitution is often utilized (S. McCombie et al., *Heterocycles,* 1993, 35, 93-97).

T-IV: Similarly, in Sandmeyer-type reactions a diazonium group (—$N_2^+$) can be replaced (C. Mukherjee, E. Biehl, *Heterocycles* 2004, 63, 2309-2318).

T-V: In positions not activated for an $S_NAr$ the substitution of halogen atoms (esp. Br or I) can be accomplished via the corresponding organolithium or Grignard reagents (J. L. Kice, A. G. Kutateladze, *J. Org. Chem.* 1993, 58, 917-923; P. C. Kearney et al., *J. Am. Chem. Soc.* 1993, 115, 9907-9919). Alternatively, transition metal-catalyzed transformations are feasible for this type of reaction, e.g. Cu-catalyzed substitution with benzothioic S-acid (N. Sawada et al., *Tetrahedron Lett.* 2006, 47, 6595-6597), or Pd-catalyzed substitution with KS—Si(i-Pr)$_3$ followed by desilylation of the introduced —SSi(i-Pr)$_3$ group (A. M. Rane et al., *Tetrahedron Lett.* 1994, 35, 3225-3226).

The thus introduced —SH moieties constitute a thiabridge —S— in the later macrocyclic products and can be selectively transformed into higher oxidation states. Therefore the building blocks with sulfanyl moieties are also regarded as building blocks for the introduction of sulfinyl (—S(═O)—; i.e. sulfoxide) and sulfonyl (—S(═O)$_2$—; i.e. sulfone) moieties. Suitable oxidation methods are:

T-VI: The selective oxidation of a thioether (—S—) to a sulfoxide (—S(═O)—) can be highly selectively and mildly achieved with hexamethylenetetramine-bromine HMTAB (K. Choudhary et al.; *J. Phys. Org. Chem.* 2000, 13, 283-292); under these conditions primary hydroxyl groups for example are not affected. In a number of related reactions chlorotrimethylsilane showed high selectivity, too (Y.-J. Chen et al., *Tetrahedron Lett.* 2000, 41, 5233-5236).

T-VII: Stronger oxidants directly transfer the sulfanyl (—S—) into the sulfonyl group (—S(═O)$_2$—). Among the many reagents mentioned in literature the system periodic acid/chromium(VI)oxide for example can be applied in the presence of C═C-double bonds (US2007/293548 A1).

Hydroxyl groups attached to aromatic rings (Ar—OH or Heteroaryl-OH) in turn, if not already part of a synthesized or commercially available biaryl, can be introduced by various methods, e.g. H-I to H-IV:

H-I: Analogously to T-III) the hydroxy group or its surrogate can be introduced by an $S_NAr$ reaction of halogen atoms, esp. Cl or F, ortho or para to an electron withdrawing substituent (W. Cantrell, *Tetrahedron Lett.* 2006, 47, 4249-4251) or to a pyridinic nitrogen atom (S. D. Taylor et al., *J. Org. Chem.* 2006, 71, 9420-9430).

H-II: Sandmeyer-type hydroxylations of aromatic amines via intermediate diazonium salts (P. Madsen et al., *J. Med. Chem.* 2002, 45, 5755-5775).

H-III: The substitution of halogen atoms (esp. Br and I), which are not activated for an $S_NAr$, can be achieved by transition metal-catalyzed C—O-couplings. Predominant are Pd-catalysts (K. W. Anderson et al., *J. Am. Chem. Soc.* 2006, 128, 10694-10695; B. J. Gallon et al., *Angew. Chem., Int. Ed.* 2007, 46, 7251-7254), but also others find application, like Cu-catalysts (J. E. Ellis, S. R. Lenger, *Synth. Commun.* 1998, 28, 1517-1524).

H-IV: Of broad scope is also a two-step process which first transforms halogen atoms (Cl, Br and I) into a boronate and then oxidatively cleaves the carbon-boron bond to the phenol (J. R. Vyvyan et al., *J. Org. Chem.* 2004, 69, 2461-2468).

The carboxylic acid group of the biaryl A building blocks, if not already present in commercially available coupling precursors, can be introduced by standard procedures like C-I to C-IV:

C-I: The oxidation of functional groups like hydroxymethyl ($—CH_2—OH$) or aldehyde ($—C(═O)H$) can be achieved under mild conditions (G. V. M. Sharma et al., *Synth. Commun.* 2000, 30, 397-406; C. Wiles et al., *Tetrahedron Lett.* 2006, 47, 5261-5264). Also methyl groups on benzene rings can be oxidized; however, as harsh reaction conditions are usually required, its applicability is limited. In contrast, the relatively acidic methyl groups ortho or para to a pyridine nitrogen can be oxidized under milder conditions; making this the method of choice for many pyridine analogs (T. R. Kelly, F. Lang, *J. Org. Chem.* 1996, 61, 4623-4633).

C-II: Halogen atoms can easily be replaced by a carboxyl group or surrogate thereof, e.g. by halogen metal exchange and subsequent carboxylation of the intermediate Grignard or organolithium species (C. G. Screttas, B. R. Steele, *J. Org. Chem.* 1989, 54, 1013-1017), or by utilizing Mander's reagent (methyl cyanoformate) (A. Lepretre et al., *Tetrahedron* 2000, 56, 265-274).

C-III: In the case that acidified ring positions are to be carboxylated, a viable method is deprotonation with a strong base (usually tert-butyl lithium) followed by carboxylation of the intermediate organolithium species in analogy to C-II).

C-IV: Hydrolysis of ester, amide or nitrile groups. The CN group in turn can easily be introduced by treating organic halides with CuCN (Rosenmund-von Braun reaction: C. F. Koelsch, A. G. Whitney, *J. Org. Chem.,* 1941, 6, 795-803).

Applied to commercially available starting materials or biarlys obtained by coupling route, these general transformations offer a tool box for accessing a huge variety of Templates A. Additional literature examples are cited below within the sections on specific derivatives.

b) Synthesis of Modulator B Building Blocks

The Modulator B moieties of macrocycle I are derived from appropriately substituted aminoalcohols, wherein the amino and alcohol group, which contribute to the ring connectivity, are separated by 2-4 C-atoms.

If not already present in a commercial building block, the substituent $R^6$ can be introduced by standard nucleophilic addition of organometallic reagents to carbonyl or carboxyl derivatives. Alkyl (as $R^6$) substituted analogs of B1 and derivatives of B2-B10 with no additional C-substituent on their ring system are commercially available, as are many derivatives with an amino ($—NH_2$) or alcohol ($—OH$) substituent as $R^6$. In the such cases the diversification of the substitution pattern can be easily achieved by standard transformations of the free amine or hydroxy functionalities.

Possible pathways to more complex pyrrolidine derivatives of type B4-B6 or piperidine derivatives of type B7-B9 rely on the same strategy: Intramolecular cyclization reactions are the predominant route applicable to diversely substituted substrates. Amines carrying a residue with a leaving group in the ω-position lead directly to the desired saturated ring systems by intramolecular nucleophilic substitution (G. Ceulemans et al., *Tetrahedron* 1997, 53, 14957-14974; S. H. Kang, D. H. Ryu, *Tetrahedron Lett.* 1997, 38, 607-610; J. L. Ruano et al., *Synthesis* 2006, 687-691). Also N-haloamines can be directly transformed into the desired compounds by a Hofmann-Löffler-Freytag reaction (M. E. Wolff, *Chem. Rev.* 1963, 63, 55-64). Alternatively, amines carrying two substituents, each with an alkene or alkyne bond, can be subjected to a ring closing metathesis (RCM) reaction (Y. Coquerel, J. Rodriguez, *Eur. J. Org. Chem.* 2008, 1125-1132) and subsequent reduction of the partially unsaturated ring to the saturated heterocycle.

Another possible access, reduction of aromatic five- or six-membered heterocycles to their saturated analogs, is described in the literature. Due to the large number of commercially available pyridines this approach is especially useful for the synthesis of the piperidine system (J. Bolos et al., *J. Heterocycl. Chem.* 1994, 31, 1493-1496; A. Solladie-Cavallo et al., *Tetrahedron Lett.* 2003, 44, 8501-8504; R. Naef et al., *J. Agric. Food Chem.* 2005, 53, 9161-9164).

General Processes for the Synthesis of Macrocyclic Compounds I

General procedures for the synthesis of libraries of macrocyclic compounds of general structure I are described below. It will be immediately apparent to those skilled in the art how these procedures have to be modified for the synthesis of individual macrocyclic compounds of type I.

The macrocyclic compounds of this invention are obtained by cyclization of suitable linear precursors which are derived from optionally substituted bifunctional hydroxy- or mercapto biaryls/heteroaryls $X-A_B-A_C-Y$ (Template $A_B-A_C$), substituted amino alcohols B (Modulator), and one to three building blocks forming Bridge C.

Hydroxy- or mercapto biaryls/heteroaryls $X-A_B-A_C-Y$ consist of two optionally substituted building blocks $X-A_B$ and $A_C-Y$. Building blocks $X-A_B$ comprise hydroxyaryl, hydroxyheteroaryl-, mercaptoaryl- and mercaptoheteroaryl compounds. Building blocks $A_c-Y$ comprise carboxyaryl-, carboxyheteroaryl-, mercaptoaryl-, mercaptoheteroaryl, alkenylaryl, and alkenylheteroaryl compounds. $X-A_B$ and $A_C-Y$ are six-membered aromatic or five- or six-membered heteroaromatic rings. Templates $X-A_B-A_C-Y$ can be obtained by combination of two six-membered rings, two five-membered rings or a five- and a six-membered ring. The building blocks $X-A_B$ and $A_C-Y$ are connected by a carbon-carbon bond to form the biaryls $X-A_B-A_C-Y$.

Variable substituents are introduced by pre- or postcyclative derivatization of one or more orthogonally protected functional group (e.g. amino groups, carboxyl groups, hydroxyl groups) attached to B, C or A. Variable R-groups may also be introduced as side chain motifs of the subunits of Bridge C.

The macrocyclic products of this invention can be prepared either in solution or on solid support.

The essential ring closure reaction is possible between any of the building blocks; and macrocycles I are obtained by e.g.

Macrolactamization between C and B;

Macrolactamization between $A_B$-$A_C$ and C;

Macrolactamization between any two subunits of Bridge C;

Arylether or arylthioether formation between $A_B$-$A_C$ and B;

Arylthioether formation between $A_B$-$A_C$ and C;

Biaryl synthesis by coupling reaction (e.g. Suzuki coupling) between $A_B$ and $A_C$;

Ring closing metathesis (RCM) reaction between any two subunits of C or upon formation of such a subunit;

Ring closing metathesis reaction between $A_B$-$A_C$ and C.

SW-1: Synthesis Workflow for the Preparation of Side-Chain Protected Macrocycles I by Macrolactamization in Solution Macrocycles of structure I with orthogonally protected exocyclic functional groups (attachment points for derivatizations) are prepared in solution by the process outlined below. Throughout all steps the orthogonal protection of the side chains stays intact and is not affected by protecting group manipulations of the main chain.

a1) Condensation of an appropriately protected hydroxy- or mercapto-biaryl/heteroaryl carboxylic acid $PG^1$-X-$A_B$-$A_C$-$CO_2H$ and a suitable C-terminally and side-chain protected C-subunit building block H—$NR^7$-c1-CO—$OPG^2$ to form $PG^1$-X-$A_B$-$A_C$-$CONR^7$-c1-CO—$OPG^2$;

b1) If required, deprotection of the aryl/heteroaryl hydroxy or mercapto group;

c1) Aryl/heteroaryl ether or thioether formation with a suitably N-protected amino alcohol $PG^3$-B-OH leading to the fully protected linear precursor $PG^3$-B-X-$A_B$-$A_C$-$CONR^7$-c1-CO—$OPG^2$;

d1) Cleavage of the "main chain" protective groups affording the free amino acid H—B—X-$A_B$-$A_C$-$CONR^7$-c1-CO—OH, which is subjected to macrocyclization e1) Intramolecular amide coupling to cyclo(B—X-$A_B$-$A_C$-$CONR^7$-c1-CO—) as macrocyclic product.

In addition to the steps described above, chain elongation by one or two additional C-subunits (c2, c3) and subsequent macrolactamization starts with coupling of a second suitably C-protected amino acid to the free carboxylic acid functionality of the product obtained by N-reprotection of the product of step d1. Cleavage of the main chain protective groups and either macrolactamization or repetition of the chain elongation steps and macrolactamization provides either cyclo(B—X-$A_B$-$A_C$-$CONR^7$-c1-$CONR^7$-c2-CO—) or cyclo(B—X-$A_B$-$A_C$-$CONR^7$-c1-$CONR^7$-c2-$CONR^7$-c3-CO—).

The free carboxylic acid functionality of the N-reprotected product derived from any of the three linear macrolactamization precursors (product of step d1, or corresponding product after coupling of one or two additional C-subunits) can be further elaborated by chain extensions/homologizations (e.g. Arndt-Eistert reaction) or functional group interconversions like Curtius rearrangement ultimately affording homologous macrocycles or those where the connection between Modulator B and Bridge C corresponds to a urea moiety.

SW-2: Synthesis Workflow for the Preparation of Side-Chain Protected Macrocycles I by Macrolactamization in Solution As an alternative to SW-1 the intermediate H—X-$A_B$-$A_C$-Y-Z-c1-CO—$OPG^2$ (product of step b1) can be prepared by a2) S-alkylation of a suitable mercapto-substituted haloaryl/heteroaryl compound Hal-$A_C$-SH (Hal represents a halogen atom) with a C-terminally and side-chain protected C-subunit building block LG-$CHR^8$-c1-CO—$OPG^2$ (LG represents a leaving group like halide, alkyl-, arylsulfonate or activated OH like e.g. under Mitsunobu conditions);

b2) Suzuki coupling reaction between the product of step a2) and a suitable hydroxyl-substituted boronic acid or boronic ester HX-$A_B$-$B(OR)_2$ leading to HX-$A_B$-$A_C$-S—$CHR^8$-c1-CO—$OPG^2$.

In analogy, amide coupling of a suitable C-terminally and side-chain protected C-subunit building block H—$NR^7$-c1-CO—$OPG^2$ to a haloaryl/heteroaryl carboxylic acid Hal-$A_C$-CO—OH and subsequent Suzuki biaryl coupling reaction with a suitable hydroxyl-substituted boronic acid or boronic ester would provide H—X-$A_B$-$A_C$-$CONR^7$-c1-CO—$OPG^2$.

Possible subsequent steps are as described in SW-1, providing cyclo(B—X-$A_B$-$A_C$-Y-Z-c1-CO—) with Y—Z=$CONR^7$, S—$CHR^8$.

Oxidation of cyclo(B—X-$A_B$-$A_C$-S—$CHR^8$-c1-CO—) leads to the corresponding sulfoxides cyclo(B—X-$A_B$-$A_C$-SO—$CHR^8$-c1-CO—) or sulfone cyclo(B—X-$A_B$-$A_C$-$SO_2$—$CHR^8$-c1-CO—).

SW-3: Synthesis Workflow for the Preparation of Side-Chain Protected Macrocycles I by Macrolactamization in Solution As an alternative to SW-1 the protected cyclization precursor $PG^3$-B-X-$A_B$-$A_C$-$CONR^7$-c1-CO—$OPG^2$ can also be synthesized by an inverted order of reaction steps:

a3) Arylether or arylthioether formation between a hydroxyl or mercapto-aryl/heteroaryl ester H—X-$A_B$-$A_C$-CO—$OPG^4$ and a suitably protected amino alcohol $PG^3$-B-OH to afford $PG^3$-B-X-$A_B$-$A_C$-CO—$OPG^4$.

Further more, $PG^3$-B-X-$A_B$-$A_C$-CO—$OPG^4$ can also be obtained by arylether or arylthio ether formation between a suitably protected aminoalcohol $PG^3$-B-OH and an optionally substituted hydroxyl- or mercaptoaryl halide or heteroaryl halide HX-$A_B$-Hal leading to $PG^3$-B-X-$A_B$-Hal and subsequent coupling of an optionally substituted alkoxycarbonyl aryl or heteroaryl boronic acid or boronic ester $(RO)_2B$-$A_C$-CO—$OPG^4$.

b3) Deprotection of the carboxylic acid group to $PG^3$-B-X-$A_B$-$A_C$-CO—OH;

c3) Condensation with a C-terminally and side-chain protected building block H—$NR^7$-c1-CO—$OPG^2$ to $PG^3$-B-X-$A_B$-$A_C$-$CONR^7$-c1-CO—$OPG^2$.

Possible subsequent steps are as described in SW-1.

In analogy to step c3), $PG^3$-B-X-$A_B$-$A_C$-$CO_2H$ can be coupled to a previously formed di- or tripeptide leading to protected cyclization precursors such as $PG^3$-B-X-$A_B$$A_C$-$CONR^7$-c1-$CONR^7$-c2-CO—$OPG^2$ or $PG^3$-B-X-$A_B$-$A_C$-$CONR^7$-c1-$CONR^7$-c2-$CONR^7$-c3-CO—$OPG^2$. If applying this approach for the synthesis of macrocycles I, the synthesis is best performed by preparation of the linear N-terminal deprotected cyclization precursor on solid support, followed by release from resin and cyclization as well as cleavage of side chain protective groups in solution, as detailed in SW4.

SW-4: Synthesis Workflow for the Preparation of Side-Chain Protected Macrocycles I by Combined Solid Phase and Solution Phase Chemistry Macrocyclic compounds of general formula I with highly variable side chain motifs in Bridge C can advantageously be prepared in parallel array synthesis applying a combination of solid phase and solution phase synthesis methodologies.

The solid support (polymer, resin) is preferably a trityl resin e.g. chlorotrityl chloride resin (cross-linked with 1-5% divinylbenzene), which is useful as polymer-bound protective group for carboxylic acids (D. Obrecht, J.-M. Villalgordo, *Solid-Supported Combinatorial and Parallel Synthe-*

*sis of Small-Molecular-Weight Compound Libraries*, Tetrahedron Organic Chemistry Series, Vol. 17, Pergamon 1998; K. Barlos et al., *Int. J. Peptide Protein Res.* 1991, 37, 513-520; K. Barlos et al., *Angew. Chem. Int. Ed.* 1991, 30, 590-593).

a4) The suitably side-chain protected C-subunit $PG^5NR^7$-c2-CO—OH is attached to the solid support;

b4) The N-terminal protective group is cleaved;

c4) The suitably side-chain protected C-subunit $PG^5NR^7$-c1-CO—OH is coupled; subsequent N-terminal deprotection leads to $HNR^7$-c1-CO—$NR^7$-c2-CO—O-chlorotrityl resin;

d4) Coupling of a suitably side chain protected building block $PG^3$-B-X-$A_B$-$A_C$-CO—OH (cf. SW-3, product of step b3) and cleavage of the N-terminal protective group;

e4) Release of the linear main-chain deprotected macrolactamization precursor H—B—X-$A_B$-$A_C$-$CONR^7$-c1-$CONR^7$-c2-CO—OH from the resin;

f4) Macrolactamization to cyclo(B—X-$A_B$-$A_C$-$CONR^7$-c1-$CONR^7$-c2-CO—).

g4) Optional: Cleavage of protective groups of side-chain functions.

Immobilization of an amino acid $PG^5NR^7$-c3-CO—OH and two additional amino acid coupling/deprotection cycles would lead to $HNR^7$-c1-CO—$NR^7$-c2-CO—$NR^7$-c3-CO—O-chlorotrityl resin. Possible subsequent steps are as described above, providing cyclo(B—X-$A_B$-$A_C$-$CONR^7$-c1-$CONR^7$-c2-CO—$NR^7$-c3-CO—).

The ring closure of linear precursors like H—B—X-$A_B$-$A_C$-$CONR^7$-c1-$CONR^7$-c2-CO—OH may be achieved using soluble coupling reagents as described below or by engaging polymer-supported coupling reagents such as N-cyclohexyl-carbodiimide-N'-methylpolystyrene or N-alkyl-2-chloro pyridinium triflate resin (S. Crosignani et al, *Org. Lett.* 2004, 6, 4579-4582).

Further viable alternatives for the synthesis of macrocycles I by combined application of solid phase and solution phase conditions could involve macrolactamization in other positions, e.g. between two subunits in Bridge C. Alternative cyclization precursors like H—$NR^7$-c2-CO—B—X-$A_B$-$A_C$-$CONR^7$-c1-CO—OH can be obtained from the same building blocks (as described for SW4) by changing the sequence of coupling/deprotection steps.

SW-5: Synthesis Workflow for the Preparation of Side-Chain Protected Macrocycles I by Ring-Closing Metathesis in Solution Ring-closing metathesis (RCM) of olefinic precursors was applied for the synthesis of subunits of Bridge C, wherein e.g. c2=c2'−c2":

a5) Coupling of an optionally substituted alkenyl amine building block H—$NR^7$-c1-V-c2'=$CH_2$ with suitably protected carboxylic acid derivatives $PG^1$-X-$A_B$-$A_C$-$CO_2H$ to afford $PG^1$-X-$A_B$-$A_C$-CO—$NR^7$-c1-V-c2'=$CH_2$;

b5) if required release of the aryl/heteroaryl hydroxyl or mercapto group;

c5) Arylether or arylthioether formation between H—X-$A_B$-$A_C$-CO—$NR^7$-c1-V-c2'=$CH_2$ and $PG^3$-B-OH leading to $PG^3$-B-X-$A_B$-$A_C$-CO—$NR^7$-c1-V-c2'=$CH_2$ d5) Cleavage of the N-terminal protective group leading to H—B—X-$A_B$-$A_C$-CO—$NR^7$-c1-V-c2'=$CH_2$ e5) Coupling of a suitable (optionally substituted and suitably protected) enoic acid to $H_2C$=c2"-CO—B—X-$A_B$-$A_C$-CO—$NR^7$-c1-V-c2'=$CH_2$;

f5) Ring-closing metathesis to cyclo(c2"-CO—B—X-$A_B$-$A_C$-CO—$NR^7$-c1-V-c2') [=cyclo(B—X-$A_B$-$A_C$-CO—$NR^7$-c1-V-c2-CO—)]

g5) Optional: Hydrogenation of the newly formed C—C double bond of the metathesis product.

In addition, it is also feasible to prepare olefinic macrocycles with modified Bridges C such as cyclo(B—X-$A_B$-$A_C$-Y-Z-c1-V-c2-CO—$NR^7$-c3-CO—), or cyclo(B—X-$A_B$-$A_C$-Y-Z-c1-CO—), and subsequently the respective hydrogenated analogs.

General Procedures for Synthetic Steps Utilized in SW-1 to SW-5

In all general procedures below Y—Z represents CONR" or SCHR".

Amidation Reactions (Steps a1, c3, a5, e5)

An appropriately protected (preferably as acetyloxy or acetylmercapto) and optionally substituted biaryl/heteroaryl carboxylic acid ($PG^3$-X-$A_B$-$A_C$-$CO_2H$) or a more advanced intermediate like $PG^3$-B-X-$A_B$-$A_C$-$CO_2H$ is condensed with a suitably protected amino acid ester H—$NR^7$-c1-CO—$OPG^2$ or an amine H—$NR^7$-c1-V-c2'=$CH_2$ in the presence of a coupling reagent (e.g. benzotriazole derivatives like HBTU, HCTU, BOP, PyBOP; their aza analogs like HATU; or carbodiimides like EDC; others like PyClu, T3P), an auxiliary base (e.g. i-$Pr_2NEt$, $Et_3N$, pyridine, collidine) in solvents like $CH_2Cl_2$, DMF, pyridine. Benzotriazole-based coupling reagents and carbodiimides can be used together with suitable auxiliary reagents HOBt or HOAt.

Hydroxybiaryl/heteroaryl carboxylic acids H—X-$A_B$-$A_C$-$CO_2H$ do not necessarily require protection of the phenolic OH-group and can directly be coupled with the H—$NR^7$-c1-CO—$OPG^2$ to the free phenol derivative H—X-$A_B$-$A_C$-$CONR^7$-c1-CO—$OPG^2$.

As an alternative, the amidation can also be accomplished with the corresponding acid derivatives like acid chlorides, anhydrides, or active esters.

Deprotection of Aromatic Hydroxy or Mercapto Groups (Steps b1, b5)

Deacylation of $PG^1$-X-$A_B$-$A_C$-$CONR^7$-c1-CO—$OPG^2$ or $PG^1$-X-$A_B$-$A_C$-CO—$NR^7$-c1-V-c2'=$CH_2$ to the corresponding free hydroxyl or mercapto aryl/heteroaryl amide H—X-$A_B$-$A_C$-$CONR^7$-c1-CO—$OPG^2$ or H—X-$A_B$-$A_C$-CO—$NR^7$-c1-V-c2'=$CH_2$ is achieved by aminolysis, which is advantageously carried out with a dialkylaminoalkyl amine in solvents like degassed THF at 0-25° C. Acyl amine side products formed in the course of the reaction are easily removed by extraction with acidic aqueous solutions.

Arylether or Arylthioether Formation Between A and B (Steps c1, a3, c5)

Alkylation of the phenol or thiophenol like H—X-$A_B$-$A_C$-Y-Z-c1-CO—$OPG^2$, H—X-$A_B$-$A_C$-CO—$OPG^4$, or H—X-$A_B$-$A_C$-CO—$NR^7$-c1-V-c2'=$CH_2$ with a suitably N-protected amino alcohol $PG^3$-B-OH to the ether or thioether $PG^3$-B-X-$A_B$-$A_C$-Y-Z-c1-CO—$OPG^2$, $PG^3$-B-X-$A_B$-$A_C$-CO—$OPG^4$, or $PG^3$-B-X-$A_B$-$A_C$-CO—$NR^7$-c1-V-c2'=$CH_2$ is accomplished with azodicarboxylic acid derivatives such as DEAD, DIAD, TMAD or ADDP in the presence of trialkyl or triaryl phosphines in solvents like benzene, toluene, $CH_2Cl_2$, $CHCl_3$ or THF at 0° C. to room temperature. As a variation, the reaction is performed with CMBP in toluene at temperatures of 20-110° C.

In an alternative approach, the alcohol $PG^3$-B-OH is converted into the corresponding sulfonate (e.g. mesylate, tosylate or triflate) or halide (e.g. chloride, bromide or iodide) and subsequently treated with the phenol/thiophenol H—X-$A_B$-$A_C$-CO—$OPG^4$ in the presence of an auxiliary base such as NaH or $K_2CO_3$ in solvents like DMF, DMSO, NMP, HMPA, or THF, to yield $PG^3$-B-X-$A_B$-$A_C$-CO—$OPG^4$.

Cleavage of the Main Chain Protective Groups (Step d1)

Simultaneous or stepwise cleavage of the main chain protective groups provides the linear amino acids as cyclization precursors. The preferred protecting groups are Alloc as $PG^3$ and/or allylester as $PG^2$, which can be cleaved simultaneously by palladium catalysts (e.g. $Pd(PPh_3)_4$) in the presence of 1,3-dimethyl barbituric acid in solvents like $CH_2Cl_2$ or EtOAc or mixtures thereof.

Also applied were Boc as $PG^3$ and methyl, ethyl or tert-butyl ester as $PG^2$. Boc and groups and t-Bu esters are cleaved either with TFA in $CH_2Cl_2$ or with HCl-dioxane. Methyl or ethyl esters are best saponified with aq. LiOH in mixtures of MeOH and THF.

Macrolactamization (Steps e1, f4)

Macrolactamization occurs upon treatment of the cyclization precursor with coupling reagents like T3P or FDPP (if required in the presence of an auxiliary base such as $i\text{-}Pr_2NEt$) in solvents like $CH_2Cl_2$ or DMF under high dilution conditions and at temperatures ranging from 20 to 100° C.

Due to their synthetic importance, macrolactamizations are a well-investigated class of transformations. The favorable application of FDPP as cyclization mediator is described e.g. by J. Dudash et al., *Synth. Commun.* 1993, 23, 349-356; and R. Samy et al., *J. Org. Chem.* 1999, 64, 2711-2728. Many other coupling reagents were successfully utilized in related head to tail cyclizations and might be applied instead; examples include benzotriazole derivatives like HBTU, HCTU, PyBOP; or their aza analogs such as HATU, as well as DPPA, and carbodiimides like EDC or DIC (P. Li, P. P. Roller, *Curr. Top. Med. Chem.* 2002, 2, 325-341; D. L. Boger et al., *J. Am. Chem. Soc.* 1999, 121, 10004-10011). Still another route to macrolactams relies on the intramolecular reaction of an active ester with an in situ released amino group (e.g. by carbamate deprotection or azide reduction) as demonstrated in the synthesis of peptide alkaloids and vancomycin model systems (U. Schmidt et al., *J. Org. Chem.* 1982, 47, 3261-3264; K. C. Nicolaou et al., *Chem. Commun.* 1997, 1899-1900).

Ring-Closing Metathesis (RCM) (Step f5)

Ring-closing metathesis (RCM) of olefinic precursors to macrocyclic compounds is well documented (e.g. A. Fürstner et al., *Chem. Eur. J.* 2001, 7, 4811-4820) and supplements the macrocyclization strategies described above.

The ring-closing metathesis is conveniently performed in solvents like $CH_2Cl_2$ or toluene at temperatures of 20-100° C. in the presence of indenylidene-ruthenium complexes such as [1,3-bis(2,4,6-trimethylphenyl)-2-imidazolidinylidene]dichloro-[(2-isopropoxy)(5-pentafluorobenzoylamino)benzylidene]ruthenium(II); dichloro-(3-phenyl-1H-inden-1-ylidene)bis(tricyclohexyl-phosphine)-ruthenium (II); [1,3-bis(2,4,6-trimethylphenyl)-2-imidazolidinylidene]-dichloro-(3-phenyl-1H-inden-1-ylidene(tri-cyclohexylphosphine)-ruthenium(II); or [1,3-bis (2,4,6-tri-methylphenyl)-2-imidazolidinylidene]-dichloro-(3-phenyl-1H-inden-1-ylidene)(pyridyl)ruthenium(II) (S. Monsaert et al., *Eur. J. Inorg. Chem.* 2008, 432-440 and references cited therein).

In addition to ring closing transformations described above, biaryl coupling reactions such as intramolecular Suzuki coupling and Suzuki-Miyaura conditions have been applied to prepare macrocyclic compounds with biaryl motifs (M. Kaiser et al., *Org. Lett.* 2003, 5, 3435-3437; R. Lépine et al., *Org. Lett.* 2005, 7, 2981-2984).

The coupling of arylboronato-carboxylic acids to amines is also described (cf ref. above, M. Kaiser et al., R. Lépine et al.); therefore the synthesis of linear precursors Hal-$A_B$-X-B—CO-c1-$NR^7$—CO-$A_C$-$B(OR)_2$ (Hal represents a halogen atom or a triflate, $B(OR)_2$ a boronic acid or boronic ester functionality) an their cyclization in a Pd-catalyzed coupling reaction is a feasible alternative.

General Procedures for Synthetic Steps in SW-4

Synthesis of Linear Cyclization Precursors on Solid Support (Steps a4 to e4)

Chlorotrityl resins are frequently used in solid phase peptide synthesis. Therefore, attachment of Fmoc- or Alloc-protected amino acids to these resins as well as subsequent deprotection steps and coupling/deprotection of additional amino acids are well described (K. Barlos et al., *Int. J. Peptide Protein Res.* 1991, 37, 513-520; K. Barlos et al., *Angew. Chem. Int. Ed.* 1991, 30, 590-593). For the examples of the present invention, chlorotrityl chloride resin (matrix: copoly(styrene-1% DVB) is treated with an N-terminally Fmoc-protected amino acid in $CH_2Cl_2$ in the presence of an auxiliary base like $i\text{-}Pr_2NEt$. Fmoc deprotection (DBU, DMF) and coupling/deprotection of Fmoc- or Alloc-protected amino acids provides a linear, N-terminally deprotected cyclization precursor, still attached to the resin. Fmoc- or Alloc-protected amino acids are coupled in the presence of reagents like HATU or PyBOP in DMF in the presence of $i\text{-}Pr_2NEt$. Alloc protective groups were removed by treatment of the carbamate with $Pd(PPh_3)_4$ and phenylsilane in $CH_2Cl_2$. The linear cyclization precursor is then released by treatment of the resin with HFIP in $CH_2Cl_2$ (R. Bollhagen et al. *J. Chem. Soc. Chem. Commun.* 1994, 2559-2560). It is well known, that peptides can also be cleaved from the resin using TFA in $CH_2Cl_2$ or mixtures of acetic acid, 2,2,2-trifluoroethanol and $CH_2Cl_2$ (K. Barlos et al., *Int. J. Peptide Protein Res.* 1991, 37, 513-520). The subsequent macrolactaminzation step is described above.

SW-6: Synthesis Workflow for Derivatizations of Attachment Points in Solution

The macrocyclic compounds obtained according to SW-1 to SW-3 and SW-5 can be further modified by transformations involving functional groups like, but not limited to, amino, carboxyl or hydroxyl groups. In addition, aromatic halides or sulfonates can be subjected to transition-metal catalyzed C—C or C-heteroatom-coupling reactions. The orthogonal protection of the attachment points allows stepwise deprotections and derivatizations which are carried out in a parallel fashion to generate substance libraries:

a6) Cleavage of the first protective group;

b6) Derivatization of the unmasked functional group;

c6) Cleavage of the second protective group;

d6) Derivatization of the liberated functional group; etc.

General Procedures for Synthetic Steps Utilized in SW-6

Protecting Group Cleavage (Steps a6 and c6)

The utilized amine protecting groups (e.g. Boc, Cbz, Teoc, Alloc, Fmoc, etc.), carboxylic acid protecting groups (e.g. tert-butyl, benzyl, allyl, methyl, etc.) or alcohol protecting groups (e.g. tert-butyl, benzyl, allyl, acetyl, benzoyl, pivaloyl) are removed under standard conditions (P. G. M. Wuts, T. W. Greene, *Greene's Protective Groups in Organic Synthesis*, John Wiley and Sons, 4th Edition, 2006; P. J. Koncienski, *Protecting Groups,* 3rd ed., Georg Thieme Verlag 2005).

Aryl nitro groups are reduced to anilines.

Attachment Point Derivatizations (Steps b6 and d6)

Derivatizations of the liberated functional groups are based on standard synthesis procedures (A. R. Katritzky et al. (eds), *Comprehensive Functional Group Transformations*, Pergamon, 1995; S. Patai, Z. Rappoport (eds), *Chemistry of Functional Groups*, Wiley, 1999; J. March, *Advanced Organic Chemistry,* 4 ed., Wiley, 1992; leading reviews for Mitsunobu reaction: O. Mitsunobu, *Synthesis* 1981, 1-28; D. L. Hughes, *Org. Reactions*; Wiley, 1992, Vol. 42; leading reviews for reductive amination/alkylation: A. F. Abdel-Magid et al., *J. Org. Chem.* 1996, 61, 3849; E. W. Baxter, A. B. Reitz, *Org. Reactions*, Wiley, 2002, Vol. 59).

Such prototypical transformations include, but are not limited to:

(i) Amino group derivatizations such as
- Amidations with carbonyl chlorides, carboxylic acid anhydrides, active esters; or with carboxylic acids in the presence of coupling reagents (cf. the general procedures);
- Formation of sulfonamides with sulfonyl chlorides;
- Reductive alkylation with carbonyl compounds; or alkylation with alkyl halides, alkylsulfonates or Michael acceptors;
- Formation of ureas by reacting with isocyanates or their equivalents like carbamoyl chlorides or hydroxysuccinimidyl esters;
- Transformation into thioureas with isothiocyanates or their equivalents;
- Carbamate formation by reacting with chloroformates or their surrogates such as hydroxysuccinimidyl carbonates;
- N-arylation to the corresponding N-aryl or N-heteroaryl derivatives with activated aromatic or heteroaromatic halides or sulfonates in the presence of an auxiliary base and/or transition metal catalyst like Pd or Cu catalyst (e.g. Buchwald-Hartwig coupling).

(ii) Carboxyl group derivatizations like
- Amidation with amines in the presence of a coupling reagent;
- Esterification with alcohols.
- Reduction to alcohols (also obtained by reduction of the corresponding esters)

(iii) Alcoholic hydroxyl group derivatizations such as
- Alkylation to alkyl ethers with alkyl halides or alkylsulfonates, trialkyloxonium tetrafluoroborates;
- Transformation into aryl or heteroaryl ethers by reaction with (a) phenols in the presence of azodicarboxylic acid derivatives and triaryl or trialkyl phosphines (Mitsunobu type reactions); or (b) suitably activated aryl or heteroaryl halides or sulfonates;
- Conversion into carbamates by reaction with isocyanates;
- Conversion into primary amines (obtained e.g. by hydrogenation of azides, which in turn are prepared by the reaction of an alcohol with DPPA, $PPh_3$, and DEAD) and derivatization of these amines as described above;
- Oxidation to carbonyl compounds, which in turn can be further elaborated by e.g. reductive amination, Wittig reaction or related olefination reactions, etc.;
- Esterification with carboxylic acids or their activated surrogates.

(iv) Aryl halide or sulfonate derivatizations by e.g. Suzuki, Sonogashira, Buchwald, Negishi or Kumada coupling reactions etc.

SW-7: Synthesis Workflow for Derivatizations of Functional Groups at the Solid Phase As a possible alternative to SW-6, macrocyclic compounds I with one or more orthogonally protected exocyclic functional groups and one free primary amino group can be converted into fully derivatized products on solid support as previously described for related macrocyclic compounds (WO2011/014973) by:

a7) Attachment of the macrocyclic amine to an appropriately functionalized solid support by reductive amination;

b7) Acylation, carbamoylation, or sulfonylation, of the secondary amine functionality generated in the previous step a7 or conversion of this secondary amine functionality into carbamates;

c7) Removal of the protecting group from the second attachment point;

d7) Derivatization of the liberated second functional group whereby e.g. amino groups can be alkylated or converted into amides, ureas, thioureas carbamates, or sulfonamides; and carboxylic acid moieties can be transformed into amides or esters;

e7) Repetitions of steps c7 and d7 if a third, fourth etc. attachment point is available;

f7) Release of the final product from the solid support.

In case of macrocyclic carboxylic acids the attachment to a polymer-supported amine is followed by derivatizations and release in analogy to c7 to f7:

a8) Attachment of an amine to an appropriately functionalized solid support by reductive amination;

b8) Coupling of the macrocyclic carboxylic acid to the polymer-supported amine of step a8;

c8-f8) Derivatizations and release in analogy to steps c7-f7.

General Procedures for Synthetic Steps Utilized in SW-7

The Functionalized Solid Support

The solid support (polymer, resin) is preferably a derivative of polystyrene cross-linked with 1-5% divinylbenzene, of polystyrene coated with polyethyleneglycol (Tentagel™), or of polyacrylamide (D. Obrecht, J.-M. Villalgordo, *Solid-Supported Combinatorial and Parallel Synthesis of Small-Molecular-Weight Compound Libraries*, Tetrahedron Organic Chemistry Series, Vol. 17, Pergamon 1998). It is functionalized by means of a linker, i.e. an α,ω-bifunctional spacer molecule with an anchoring group for the solid support on one end, and on the other end by means of a selectively cleavable functional group that is used for subsequent transformations and finally for release of the product. For the examples of the present invention linkers are used that release an N-acyl (amide, urea, carbamate) or an N-sulfonyl (sulfonamide) derivative under acidic conditions. These kinds of linkers have been applied in the backbone amide linker (BAL) strategy for solid-phase synthesis of linear and cyclic peptides (K. J. Jensen et al., *J. Am. Chem. Soc.* 1998, 120, 5441-5452; J. Alsina et al., *Chem. Eur. J.* 1999, 5, 2787-2795) and heterocyclic compounds as well (T. F. Herpin et al., *J. Comb. Chem.* 2000, 2, 513-521; M. del Fresno et al., *Tetrahedron Lett.* 1998, 39, 2639-2642; N. S. Gray et al., *Tetrahedron Lett.* 1997, 38, 1161-1164).

Examples of such functionalized resins include DFPE polystyrene (2-(3,5-dimethoxy-4-formylphenoxy)ethyl polystyrene), DFPEM polystyrene (2-(3,5-dimethoxy-4-formylphenoxy)ethoxymethyl polystyrene), FMPB resins (4-(4-formyl-3-methoxy-phenoxy)butyryl AM-resin), FMPE polystyrene HL (2-(4-formyl-3-methoxyphenoxy) ethyl polystyrene HL), FMPB NovaGel™ (4-(4-formyl-3-methoxyphenoxy)butyryl NovaGel; a PEG PS resin).

Attachment of the Macrocyclic Amine to the Functionalized Resin (Steps a7 and b7) and Subsequent N-Acylation or N-Sulfonylation The macrocyclic primary amine is attached to the functionalized solid support by reductive amination preferably with $NaBH(OAc)_3$ as reducing agent in 1,2-dichloroethane and in the presence of trimethyl orthoformate or $i\text{-}Pr_2NEt$.

The use of reductive aminations for such processes as well as the subsequent N-acylation or N-sulfonylation are well-documented; for example $NaBH_3CN$ in DMF or in methanol, or $NaBH(OAc)_3$ in DMF/acetic acid or in dichloromethane/acetic acid have been used (cf. references cited for the functionalized solid support). The N-acylation is favorably conducted with carboxylic acids in the presence of coupling reagents like PyBOP, PyBroP, or HATU or with carboxylic acid fluorides/chlorides or carboxylic acid anhydrides.

Deprotection (steps c7)

The second attachment point is an Alloc or Fmoc protected amino group or a carboxyl group protected as allyl ester. Standard methods (cf. SW-6) are applied for their deprotection and derivatization.

Release from the Resin (Step f7)

The final products are detached from the solid support by acids dissolved in organic solvents and/or $H_2O$. The use of TFA in dichloromethane, of TFA in dichloromethane in the presence of a scavenger such as $H_2O$ or dimethyl sulfide, or of TFA/$H_2O$ and TFA/$H_2O$/dimethylsulfide has been described (cf. references cited for the functionalized solid support).

Attachment of the Macrocyclic Carboxylic Acid to the Functionalized Resin (Steps a8 and b8)

A primary amine is attached to the functionalized solid support by reductive amination preferably using $NaBH(OAc)_3$ in 1,2-dichloroethane in the presence of trimethyl orthoformate.

Subsequent acylation with the macrocyclic carboxylic acids is favorably conducted in the presence of coupling reagents like HATU, PyBOP, or PyBroP.

It is worth mentioning that the initially attached primary amine corresponds to an attachment point derivatization of the carboxylic acid.

Properties and Usefulness

The macrocycles of type I of the present invention interact with specific biological targets. In particular, they show i) inhibitory activity on endothelin converting enzyme of subtype 1 (ECE-1), ii) inhibitory activity on the cysteine protease cathepsin S (CatS), iii) antagonistic activity on the oxytocin (OT) receptor), iv) antagonistic activity on the thyrotropin-releasing hormone (TRH) receptor), v) agonistic activity on the bombesin 3 (BB3) receptor, vi) antagonistic activity on the leukotriene B4 (LTB4) receptor, and/or vii) antimicrobial activity against at least one bacterial strain, in particular *Staphylococcus aureus* or *Streptococcus pneumoniae*.

Accordingly, these compounds are useful for the prevention or treatment of i) diseases resulting from abnormally high plasma or tissue levels of the potent vasoconstrictive peptide endothelin-1 (ET-1), like systemic and pulmonary hypertension, cerebral vasospasm and stroke, asthma, cardiac and renal failure, atherosclerosis, preeclampsia, benign prostatic hyperplasia, and carcinogenesis (S. De Lombaert et al., *J. Med. Chem.* 2000, 43, 488-504); ii) a wide range of diseases related to Cathepsin S, including neuropathic hyperalgesia, obesity, and in particular diseases of the immune system, like rheumatoid arthritis (RA), multiple sclerosis (MS), myasthenia gravis, transplant rejection, diabetes, Sjøgrens syndrome, Grave's disease, systemic lupus erythematosis, osteoarthritis, psoriasis, idiopathic thrombocytopenic purpura, allergic rhinitis, asthma, atherosclerosis, and chronic obstructive pulmonary disease (COPD) (O. Irie et al., *J. Med. Chem.* 2008, 51, 5502-5505; WO2009/1112826); iii) diseases and conditions associated to an overexpression of oxytocin (OT), like preterm delivery (P. D. Williams, D. J. Pettibone, *Curr. Pharm. Des.* 1996, 2, 41-58; A. D. Borthwick, *J. Med. Chem.* 2010, 53, 6525-6538); iv) diseases related to a dysfunction in the homoeostatic system of the thyrotropin-releasing hormone (TRH), such as infantile spasms, generalized and refractory partial seizures, edematous and destructive forms of acute pancreatitis, and certain inflammatory disorders (e.g. autoimmune diseases, inflammatory bowel diseases, cancer-related fatigue or depression, and Alzheimer's disease) (P.-Y. Deng et al., *J. Physiol.* 2006, 497-511; J. Kamath et al., *Pharmacol. Ther.* 2009, 121, 20-28); v) diseases related to a dysfunction of the bombesin 3 (BB3) receptor, like obesity and impairment of glucose metabolism, disorders of lung development, pulmonary diseases, CNS disorders and carcinogenesis (R. T. Jensen, *Pharmacol. Rev.* 2008, 60, 1-42); vi) diseases potentially treatable by blockade of the leukotriene B4 (LTB4) receptor, especially inflammatory and allergic diseases like asthma, acute respiratory distress syndrome (ARDS), acute lung injury (ALI), chronic obstructive pulmonary disease (COPD), rheumatoid arthritis (RA) and inflammatory bowel disease (IBD), allergic rhinitis, atopic dermatitis, allergic conjunctivitis, obliterative bronchiolitis after lung transplantation, or interstitial lung diseases (R. A. Goodnow, Jr., et al., *J. Med. Chem.* 2010, 53, 3502-3516; E. W. Gelfand et al., H. Ohnishi et., *Allergol. Int.* 2008, 57, 291-298); and/or vii) a wide range of infections caused by microorganisms, in particular strains of *Staphylococcus aureus* or *Streptococcus pneumonia*, comprising infections related to: a) respiratory diseases like cystic fibrosis, emphysema, asthma or pneumonia, b) skin or soft tissue diseases such as surgical wounds, traumatic wounds, burn wounds or herpes, smallpox, rubella or measles, c) gastrointestinal diseases including epidemic diarrhea, necrotizing enterocolitis, typhlitis or gastroenteritis or pancreatitis, d) eye diseases such as keratitis and endophthalmitis, e) ear diseases, e.g. otitis, f) CNS diseases including brain abscess and meningitis or encephalitis, g) bone diseases such as osteochondritis and osteomyelitis, h) cardiovascular diseases like endocartitis and pericarditis, or i) genitourinal diseases such as epididymitis, prostatitis and urethritis (R. P. Rennie, *Handb. Exp. Pharmacol.* 2012, 211, 45-65; W. Bereket et al., *Eur. Rev. Med. Pharmacol. Sci.* 2012, 16, 1039-1044; D. P. Calfee, *Curr. Opin. Infect. Dis.* 2012, 25, 385-394). Additional uses of antimicrobial macrocycles of type I comprise the treatment or prevention of microbial infections in plants and animals or as disinfectants or preservatives for materials such as foodstuff, cosmetics, medicaments and other nutrient-containing materials.

The macrocycles, as such or after further optimization, may be administered per se or may be applied as an appropriate formulation together with carriers, diluents or excipients well-known in the art.

When used to treat or prevent the diseases mentioned above the macrocycles can be administered singly, as mixtures of several macrocycles, or in combination with other pharmaceutically active agents. The macrocycles can be administered per se or as pharmaceutical compositions.

Pharmaceutical compositions comprising macrocycles of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active macrocycles into preparations which can be used pharmaceutically. Proper formulation depends upon the method of administration chosen.

For topical administration the macrocycles of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the macrocycles of type I may be formulated in adequate solutions, preferably in physiologically compatible buffers such as Hank's solution, Ringer's solution, or physiological saline buffer. The solutions may contain formulatory agents such as suspending, stabilizing and/or dispersing agents. Alternatively, the macrocycles of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated per se or by combining the active macrocycles of the invention with pharmaceutically acceptable carriers well known in the art. Such carriers enable the macrocycles of type I to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, (e.g. lactose, sucrose, mannitol or sorbitol) or such as cellulose preparations (e.g. maize starch, wheat starch, rice starch, potato starch, gelatin, gum tragacanth, methyl cellulose, hydroxypropylmethyl cellulose, sodium carboxymethylcellulose); and/or granulating agents; and/or binding agents such as polyvinylpyrrolidone (PVP). If desired, desintegrating agents may be added, such as cross-linked polyvinylpyrrolidones, agar, or alginic acid or a salt thereof, such as sodium alginate. Solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the macrocycles of the invention are conveniently delivered in form of an aerosol spray from pressurized packs or a nebulizer, with the use of a suitable propellant, e.g. hydrofluoroalkanes (HFA) such as HFA 134a (1,1,1,2,-tetrafluoroethane); carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the macrocycles of the invention and a suitable powder base such as lactose or starch.

The compounds may also be formulated in rectal or vaginal compositions such as suppositories together with appropriate suppository bases like cocoa butter or other glycerides.

In addition to the formulations described above, the macrocycles of the invention may also be formulated as depot preparations. Such slow release, long acting formulations may be administered by implantation (e.g. subcutaneously or intramuscularly) or by intramuscular injection. For the manufacture of such depot preparations the macrocycles of the invention may be formulated with suitable polymeric or hydrophobic materials (e.g. as an emulsion in an acceptable oil) or with ion exchange resins, or as sparingly soluble salts.

Furthermore, other pharmaceutical delivery systems may be employed such as liposomes and emulsions. Certain organic solvents such as dimethylsulfoxide may also be employed. Additionally, the macrocycles of type I may be delivered using a sustained-release system, such as semipermeable matrices of solid polymers containing the therapeutic agent. Various sustained-release materials have been established and are well-known by those skilled in the art. Sustained-release capsules may, depending on their chemical nature, release the compounds over a period of a few days up to several months. Depending on the chemical nature and the biological stability of the therapeutic agent, additional strategies for stabilization may be employed.

As the macrocycles of the invention may contain charged residues, they may be included in any of the above-described formulations as such or as pharmaceutically acceptable salts. Pharmaceutically acceptable salts tend to be more soluble in aqueous and other protic solvents than the corresponding free base or acid forms.

The macrocycles of the invention, or compositions thereof, will generally be used in an amount effective to achieve the intended purpose. It is understood that the amount used will depend on a particular application.

For example, the therapeutically effective dose for systemic administration can be estimated initially from in vitro assays: A dose can be formulated in animal models to achieve a circulating macrocycle concentration range that includes the $IC_{50}$ or $EC_{50}$ as determined in the cell culture (i.e. the concentration of a test compound that shows half maximal inhibitory concentration in case of antagonists or half maximal effective concentration in case agonists). Such information can be used to more accurately determine useful doses in humans.

Initial dosages can also be determined from in vivo data, e.g. animal models, using techniques that are well known in the art.

Dosage amounts for applications such as gastroparesis or schizophrenia etc. may be adjusted individually to provide plasma levels of the active compound that are sufficient to maintain the therapeutic effect. Therapeutically effective serum levels may be achieved by administering multiple doses each day.

In cases of local administration or selective uptake, the effective local concentration of the macrocycles of the invention may not be related to plasma concentration.

Those having the ordinary skill in the art will be able to optimize therapeutically effective dosages without undue experimentation.

The amount of macrocycle administered will, of course, be dependent on the subject being treated, on the subject's weight, the severity of the affliction, the method of administration and the judgment of the prescribing physician.

Normally, a therapeutically effective dose of the macrocycles described herein will provide therapeutic benefit without causing substantial toxicity.

Toxicity of the macrocycles can be determined by standard pharmaceutical procedures in cell cultures or experimental animals, e.g., by determining the $LD^{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from cell culture assays and animal studies can be used in formulating a dosage range that is not toxic for use in humans. The dosage of the macrocycles of the invention lies preferably within a range of circulating concentrations that include the effective dose with little or no toxicity. The dosage may vary within the range depending upon the dosage form and the route of administration. The exact formulation, route of administration and dose can be chosen by the individual physician in view of the patient's condition (cf. E. Fingl et al. in L. Goodman und A. Gilman (eds), *The Pharmacological Basis of Therapeutics*, 5$^{th}$ ed. 1975, Ch. 1, p. 1).

Another embodiment of the present invention may also include compounds, which are identical to the compounds of formula I, except that one or more atoms are replaced by an atom having an atomic mass number or mass different from the atomic mass number or mass usually found in nature, e.g. compounds enriched in $^2$H (D), $^3$H, $^{11}$C, $^{14}$C, $^{125}$I etc. These isotopic analogs and their pharmaceutical salts and formulations are considered useful agents in therapy and/or diagnostics, for example, but not limited to, fine-tuning of in vivo half-life.

EXAMPLES

The following examples illustrate the invention in more detail but are not intended to limit its scope in any way. Before specific examples are described in detail the used abbreviations and applied general methods are listed.

Ac: acetyl
addn: addition
ADDP: azodicarboxylic dipiperidide
Alloc: allyloxycarbonyl
AllocCl: allyl chloroformate
AllocOSu: allyloxycarbonyl-N-hydroxysuccinimide
AM-resin: aminomethyl resin
AM-PS: aminomethyl polystyrene
aq.: aqueous
arom.: aromatic
Bn: benzyl
BOP: (benzotriazol-1-yloxy)tris(dimethylamino)phosphonium hexafluorophosphate
Boc: tert-butoxycarbonyl
br.: broad
Cbz: benzyloxycarbonyl
CbzCl: benzyl chloroformate
CbzOSu: N-(benzyloxycarbonyloxy)succinimide
Cl-HOBt: 6-chloro-1-hydroxybenzotriazole
CMBP: cyanomethylenetributyl-phosphorane
m-CPBA: 3-chloroperbenzoic acid
d: day(s) or doublet (spectral)
DBU: 1,8-diazabicyclo[5.4.0]undec-7-ene
DCE: 1,2-dichloroethane
DEAD: diethyl azodicarboxylate
DFPE polystyrene: 2-(3,5-dimethoxy-4-formylphenoxy) ethyl polystyrene
DIAD: diisopropyl azodicarboxylate
DIC: N,N'-diisopropylcarbodiimide
DMAP: 4-(dimethylamino)pyridine
DME: 1,2-dimethoxyethane
DMF: dimethylformamide
DMSO: dimethyl sulfoxide
DPPA: diphenyl phosphoryl azide
DVB: divinylbenzene
EDC: 1-[3-(dimethylamino)propyl]-3-ethylcarbodiimide
equiv.: equivalent
Et: ethyl
Et$_3$N: triethylamine
Et$_2$O: diethyl ether
EtOAc: ethyl acetate
EtOH: ethanol
exp.: experimental
FC: flash chromatography
FDPP: pentafluorophenyl diphenylphosphinate
FI-MS: flow injection mass spectrometry
Fmoc: 9-fluorenylmethoxycarbonyl
Fmoc-Cl: Fmoc chloride, 9-fluorenylmethyl chloroformate
Fmoc-OSu: (9H-fluoren-9-yl)methyl 2,5-dioxopyrrolidin-1-yl carbonate (or 9-fluorenylmethyl-succinimidyl carbonate)
h: hour(s)
HATU: O-(7-azabenzotriazol-1-yl)-N,N,N',N'-tetramethyluronium hexafluorophosphate
HBTU: O-(benzotriazol-1-yl)-N,N,N',N'-tetramethyluronium hexafluorophosphate
mCPBA: 3-chloroperbenzoic acid
HCTU: O-(6-chlorobenoztriazol-1-yl)-N,N,N',N'-tetramethyluronium hexafluorophosphate
HFIP: Hexafluoroisopropanol (1,1,1,3,3,3-hexafluoro-2-propanol)
HL: high loading
HOAt: 1-hydroxy-7-azabenzotriazole
HOBt.H$_2$O: 1-hydroxybenzotriazole hydrate
HMPA: hexamethylphosphoramide
i.v.: in vacuo
m: multiplet (spectral)
MeCN: acetonitrile
MeOH: methanol
Me: methyl
NMP: 1-methyl-2-pyrrolidinone
Ns: 2-nitrobenzenesulfonyl; 4-nitrobenzenesulfonyl
PdCl$_2$(PPh$_3$)$_2$: bis(triphenylphosphine)palladium (II) dichloride
Pd(dppf)Cl$_2$.CH$_2$Cl$_2$: [1,1'-bis(diphenylphosphino)ferrocene]dichloropalladium (II), complex with dichloromethane
Pd(PPh$_3$)$_4$: tetrakis(triphenylphosphine)palladium(0)
PEG PS resin: polyethyleneglycol coated polystyrene resin
PG: protective group
Ph: phenyl
PPh$_3$: triphenylphosphine
prep.: preparative
i-Pr: isopropyl
i-Pr$_2$NEt: N-ethyl-N,N-diisopropylamine
i-PrOH: isopropanol
PyBOP: (benzotriazol-1-yloxy)tripyrrolidinophosphonium hexafluorophosphate
PyBroP: bromotripyrrolidinophosphonium hexafluorophosphate
PyClu: N,N,N',N'-bis-(tetramethylene)-chloroforamidinium hexafluorophosphate
q: quartet (spectral)
quant.: quantitative
quint: quintet (spectral)
rt: room temperature
s: singlet (spectral)
sat.: saturated
soln: solution
TBAF: tetrabutylammonium fluoride
t: triplet (spectral)
Teoc: 2-(trimethylsilyl)ethoxycarbonyl
tert.: tertiary
TFA: trifluoroacetic acid
THF: tetrahydrofuran
TLC: thin layer chromatography TMAD: tetramethylazodicarboxamide T3P=T3P™: propanephosphonic acid cyclic anhydride p-TsOH: p-toluenesulfonic acid Umicore M72 SIMes (RD): [1,3-bis(2,4,6-trimethylphenyl)-2-imidazolidinylidene]dichloro-[(2-isopropoxy)(5-pentafluorobenzoylamino)benzylidene]ruthenium(II)

General Methods

TLC: Merck (silica gel 60 F254, 0.25 mm).

Flash chromatography (FC): Fluka silica gel 60 (0.04-0.063 mm) and Interchim Puriflash IR 60 silica gel (0.04-0.063 mm).

I. Analytical HPLC-MS methods:

$R_t$ in min (purity at 220 nm in %), m/z $[M+H]^+$

UV wave length 220 nm, 254 nm

MS: Electrospray Ionization

Volume of injection: 5 μL

Method 1

LC-MS: Agilent HP1100 (DAD detector)

Column: Ascentis Express™ C18 2.7 μm, 3×50 mm (53811U—Supelco Inc.)

Mobile Phases: A: 0.1% TFA in Water; B: 0.085% TFA in MeCN

Column oven temperature: 55° C.

Gradient:

| Time [min.] | Flow [mL/min] | % A | % B |
|---|---|---|---|
| 0 | 1.3 | 97 | 3 |
| 0.05 | 1.3 | 97 | 3 |
| 2.95 | 1.3 | 3 | 97 |
| 3.15 | 1.3 | 3 | 97 |
| 3.17 | 1.3 | 97 | 3 |
| 3.2 | 1.3 | 97 | 3 |

Method 1a: MS scan range: 95-1800 Da; centroid mode, positive mode 40V, scan time: 1 sec Method 1b: MS scan range: 95-800 Da; centroid mode, positive mode 40V, scan time: 1 sec Method 1c: MS scan range: 95-1800 Da; centroid mode, positive mode 20V, scan time: 1 sec Method 1d: MS scan range: 95-1800 Da; profile mode, positive mode 40V, scan time: 1 sec Method 1e: MS scan range: 95-1800 Da; profile mode, positive mode 80V, scan time: 1 sec Method 1f: MS scan range: 95-1800 Da; profile mode, positive mode 20V, scan time: 1 sec Method 1g: MS scan range: 95-1800 Da; centroid mode, positive mode 80V, scan time: 1 sec Method 2

LC-MS: Agilent HP1100 (DAD detector)

Column: Ascentis Express™ C18 2.7 μm, 3×50 mm (53811U—Supelco Inc.)

Mobile Phases: A: Ammonium Bicarbonate 1 mM in Water—pH=10 in Water; B: MeCN

Column oven temperature: 55° C.

Gradient:

| Time [min.] | Flow [mL/min] | % A | % B |
|---|---|---|---|
| 0 | 1.3 | 97 | 3 |
| 0.05 | 1.3 | 97 | 3 |
| 2.95 | 1.3 | 3 | 97 |
| 3.15 | 1.3 | 3 | 97 |

-continued

| Time [min.] | Flow [mL/min] | % A | % B |
|---|---|---|---|
| 3.17 | 1.3 | 97 | 3 |
| 3.2 | 1.3 | 97 | 3 |

Method 2a: MS scan range: 95-800 Da; centroid mode, negative mode 40V scan time: 1 sec Method 2b: MS scan range: 95-1800 Da; centroid mode, negative mode 40V scan time: 1 sec Method 2c: MS scan range: 95-1800 Da; centroid mode, positive mode 40V scan time: 1 sec Method 2d: MS scan range: 95-1800 Da; centroid mode, positive mode 20V scan time: 1 sec Method 2e: MS scan range: 95-800 Da; centroid mode, positive mode 40V scan time: 1 sec Method 2f: MS scan range: 95-1800 Da; profile mode, positive mode 40V scan time: 1 sec Method 3

LC-MS: Dionex Ultimate 3000 RS (DAD detector)

Column: Ascentis Express™ C18 2.7 μm, 2.1×50 mm (53822-U—Supelco Inc.)

Mobile Phases: A: 0.1% TFA in Water; B: 0.085% TFA in MeCN

Column oven temperature: 55° C.

Gradient:

| Time [min.] | Flow [mL/min] | % A | % B |
|---|---|---|---|
| 0 | 1.4 | 97 | 3 |
| 0.05 | 1.4 | 97 | 3 |
| 1.95 | 1.4 | 3 | 97 |
| 2.15 | 1.4 | 3 | 97 |
| 2.18 | 1.4 | 97 | 3 |
| 2.3 | 1.4 | 97 | 3 |

Method 3a: MS scan range: 95-1800 Da; centroid mode, positive mode 40V scan time: 1 sec Method 3b: MS scan range: 95-1800 Da; profile mode, positive mode 40V scan time: 1 sec Method 4

LC-MS: Agilent HP1100 (DAD detector)

Column: Ascentis Express™ F5 2.7 μm, 3×50 mm (53576-U—Supelco Inc.)

Mobile Phases: A: 0.1% TFA in Water; B: 0.085% TFA in MeCN

Column oven temperature: 55° C.

Method 4a and method 4b

Gradient:

| Time [min.] | Flow [mL/min] | % A | % B |
|---|---|---|---|
| 0 | 1.3 | 70 | 30 |
| 0.05 | 1.3 | 70 | 30 |
| 2.95 | 1.3 | 30 | 97 |
| 3.15 | 1.3 | 30 | 97 |
| 3.17 | 1.3 | 70 | 30 |
| 3.2 | 1.3 | 70 | 30 |

Method 4a: MS scan range: 95-1800 Da; centroid mode, positive mode 40V, scan time: 1 sec Method 4b: MS scan range: 95-1800 Da; profile mode, positive mode 40V, scan time: 1 sec Method 4c Gradient:

| Time [min.] | Flow [mL/min] | % A | % B |
|---|---|---|---|
| 0 | 1.3 | 97 | 3 |
| 0.05 | 1.3 | 97 | 3 |
| 2.95 | 1.3 | 3 | 97 |
| 3.15 | 1.3 | 3 | 97 |
| 3.17 | 1.3 | 97 | 3 |
| 3.2 | 1.3 | 97 | 3 |

Method 4c: MS scan range: 95-1800 Da; centroid mode, positive mode 20V, scan time: 1 sec Method 5

LC-MS: Agilent HP1100 (DAD detector)

Column: Atlantis™ T3 3 μm, 2.1×50 mm (186003717—Waters AG)

Mobile Phases: A: 0.1% TFA in Water; B: 0.085% TFA in MeCN

Column oven temperature: 55° C.

Gradient:

| Time [min.] | Flow [mL/min] | % A | % B |
|---|---|---|---|
| 0 | 0.8 | 100 | 0 |
| 0.1 | 0.8 | 100 | 0 |
| 2.9 | 0.8 | 50 | 50 |
| 2.95 | 0.8 | 3 | 97 |
| 3.2 | 0.8 | 3 | 97 |
| 3.22 | 0.8 | 100 | 100 |
| 3.3 | 0.8 | 100 | 100 |

Method 5a: MS scan range: 95-1800 Da; centroid mode, positive mode 40V, scan time: 1 sec II. Preparative HPLC methods:

1. Reverse Phase—Acidic Conditions

Method 1a

Column: XBridge™ C18 5 μm, 30×150 mm (Waters AG)

Mobile phases:

A: 0.1% TFA in Water/Acetonitrile 98/2 v/v

B: 0.1% TFA Acetonitrile

Method 1b

Column: XBridge™ C18 5 μm, 30×100 mm (Waters AG)

Mobile phases:

A: 0.1% TFA in Water/Acetonitrile 98/2 v/v

B: 0.1% TFA Acetonitrile

Method 1c

Column: Gemini-NX™ C18 5 μm, 30×100 mm (Phenomenex Inc.)

Mobile phases:

A: 0.1% TFA in Water/Acetonitrile 98/2 v/v

B: 0.1% TFA Acetonitrile

Method 1d

Column: XBridge™ Prep C18 10 μm, 50×250 mm (Waters AG)

Mobile phases:

A: 0.1% TFA in Water/Acetonitrile 98/2 v/v

B: Acetonitrile

Flow rate: 150 mL/min

2. Reverse Phase—Basic conditions

Method 2a

Column: XBridge™ C18 5 μm, 30×150 mm (Waters AG)

Mobile phases:

A: 10 mM Ammonium Bicarbonate pH 10/Acetonitrile 98/2 v/v

B: Acetonitrile

Method 2b

Column: XBridge™ C18 5 μm, 30×100 mm (Waters AG)

Mobile phases:

A: 10 mM Ammonium Bicarbonate pH 10/Acetonitrile 98/2 v/v

B: Acetonitrile

3. Normal Phase

Method 3

Column: VP 100/21 NUCLEOSIL™ 50-10, 21×100 mm (Macherey-Nagel AG)

Mobile phases:

A: Hexane

B: Ethylacetate

C: Methanol

FI-MS: Agilent HP1100; m/z $[M+H]^+$

NMR Spectroscopy: Bruker Avance 300, $^1$H-NMR (300 MHz) in the indicated solvent at ambient temperature. Chemical shifts δ in ppm, coupling constants J in Hz.

SPECIFIC EXAMPLES

In the examples below and if no other sources are cited, leading reference for standard conditions of protecting group manipulations (protection and deprotection) are 1) P. G. M. Wuts, T. W. Greene, *Greene's Protective Groups in Organic Synthesis*, John Wiley and Sons, 4th Edition, 2006; 2) P. J. Koncienski, *Protecting Groups,* 3rd ed., Georg Thieme Verlag 2005; and 3) M. Goodman (ed.), *Methods of Organic Chemistry* (Houben-Weyl), Vol E22a, Synthesis of Peptides and Peptidomimetics, Georg Thieme Verlag 2004.

Starting Materials

Template A Building Blocks (Scheme 5):

3'-Hydroxybiphenyl-2-carboxylic acid (1) is commercially available.

Methyl 3'-hydroxybiphenyl-2-carboxylate (2)

Thionyl chloride (7.7 mL, 105 mmol) was added at 0° C. to a soln of 1 (4.5 g, 21.0 mmol) in MeOH (55 mL). The mixture was stirred for 10 min at 0° C. and then heated to reflux for 4 h. Evaporation of the volatiles, aqueous workup (EtOAc, sat. aq. $NaHCO_3$ soln; $Na_2SO_4$) and FC (hexane/EtOAc 5:1) afforded the ester 2 (4.34 g, 90%).

Data of 2: $C_{14}H_{12}O_3$ (228.2). $^1$H-NMR (DMSO-$d_6$): 9.52 (br. s, OH); 7.68 (dd, J=1.1, 7.6, 1H); 7.59 (dt, J=1.5, 7.6, 1H); 7.47 (dt, J=1.3, 7.5, 1H); 7.40 (dd, J=0.9, 7.6, 1H); 7.20 (t-like m, J=8.0, 1H); 6.75 (m, 1H); 6.70-6.67 (m, 2H); 3.59 (s, 3H).

2'-Hydroxybiphenyl-3-carboxylic acid (3) is commercially available.

Methyl 2'-hydroxybiphenyl-3-carboxylate (4)

Thionyl chloride (6.8 mL, 93 mmol) was added at 0° C. to a soln of 3 (4.0 g, 18.6 mmol) in MeOH (60 mL). The mixture was stirred for 10 min at 0° C. and then heated to reflux for 3 h. Evaporation of the volatiles and aqueous workup (EtOAc, sat. aq. $NaHCO_3$ soln; $Na_2SO_4$) afforded the ester 4 (3.68 g, 86%).

Data of 4: $C_{14}H_{12}O_3$ (228.2). LC-MS (method 2a): $R_t$=1.95 (98), 226.9 ([M−H]⁻). $^1$H-NMR (DMSO-$d_6$): 9.66 (s, 1H); 8.16 (t, J=1.6, 1H); 7.89 (d-like m, 1H); 7.81 (d-like m, 1H); 7.56 (t, J=7.7, 1H); 7.29 (dd, J=1.7, 7.6, 1H); 7.20 (t-like m, 1H); 6.98-6.88 (m, 2H); 3.87 (s, 3H).

2'-Hydroxy-5'-methoxybiphenyl-3-carboxylic acid (5) is commercially available.

Methyl 2'-hydroxy-5'-methoxybiphenyl-3-carboxylate (6)

Thionyl chloride (5.14 mL, 71 mmol) was added at 0° C. to a soln of 5 (5.74 g, 23.5 mmol) in MeOH (100 mL). The mixture was heated to reflux for 2 h. Evaporation of the volatiles, aqueous workup (EtOAc, sat. aq. $NaHCO_3$ soln; $Na_2SO_4$) and FC (hexane/EtOAc 4:1) afforded the ester 6 (5.1 g, 84%).

Data of 6: $C_{15}H_{14}O_4$ (258.3). $^1$H-NMR (DMSO-$d_6$): 9.18 (s, OH); 8.17 (t, J=1.7, 1H); 7.89 (td, J=1.4, 7.8, 1H); 7.82 (td, J=1.5, 8.0, 1H); 7.56 (t, J=7.8, 1H); 6.91-6.78 (m, 3H); 3.87 (s, 3H); 3.72 (s, 3H).

3'-Hydroxybiphenyl-3-carboxylic acid (7) is commercially available.

Methyl 3'-hydroxybiphenyl-3-carboxylate (8)

Thionyl chloride (4.1 mL, 56 mmol) was added at 0° C. to a soln of 7 (4.0 g, 18.6 mmol) in MeOH (160 mL). The mixture was heated to reflux for 2 h. Evaporation of the volatiles, filtration of the residue through a pad of silica gel (EtOAc) and FC (hexane/EtOAc 93:7 to 0:100) afforded the ester 8 (4.0 g, 94%).

Data of 8: $C_{14}H_{12}O_3$ (228.2). LC-MS (method 2a): $R_t$=1.90 (98), 227.3 ([M−H]⁻). $^1$H-NMR (DMSO-$d_6$): 9.63 (br. s, OH); 8.13 (t, J=1.6, 1H); 7.96-7.88 (m, 2H), 7.61 (t, J=7.7, 1H); 7.29 (t, J=7.8, 1H); 7.10 (m, 1H); 7.06 (t, J=2.0, 1H); 6.81 (m, 1H); 3.89 (s, 3H).

5-(3-Hydroxyphenyl)nicotinic acid (9) is commercially available.

5-(3-Acetoxyphenyl)nicotinic acid (10)

At 0° C. acetic anhydride (18.8 mL, 0.2 mol) was added dropwise to a soln of 5-(3-hydroxyphenyl)nicotinic acid (9; 7.13 g, 0.033 mol) in 4 M aq. NaOH soln (41.4 mL, 0.166 mol). The mixture was stirred for 1 h. A precipitate was formed. The mixture was diluted with 4 M aq. NaOH soln (41.4 mL, 0.166 mol). More acetic anhydride (18.8 mL, 0.2 mol) was added and stirring was continued for 2 h followed by the addition of $H_2O$ (50 mL). The mixture was acidified to pH 1 by addition of 3 M aq. HCl soln. The solid was filtered, washed ($H_2O$) and dried i.v. to afford 10.HCl (8.22 g, 84%).

Data of 10.HCl: $C_{14}H_{11}NO_4$.HCl (257.2, free base). LC-MS (method 1b): $R_t$=1.22 (99), 258.0 ([M+H]⁺). $^1$H-NMR (DMSO-$d_6$): 13.62 (very br. s, 1H); 9.12 (d, J=2.0, 1H); 9.07 (d, J=1.3, 1H); 8.46 (s, 1H); 7.71 (d, J=7.7, 1H); 7.63 (s, 1H); 7.57 (t, J=7.9, 1H); 7.23 (d, J=8.0, 1H); 2.31 (s, 3H).

2-Bromothiophenol (11) is commercially available.

3-Hydroxyphenylboronic acid (12) is commercially available.

5-Bromopyridine-3-thiol (13) was prepared as described in the literature (S. A. Thomas et al. *Bioorg. Med. Chem. Lett.* 2006, 16, 3740-3744).

2-Hydroxyphenylboronic acid (14) is commercially available.

4-(3-Hydroxypyridin-2-yl)benzoic acid (92) is commercially available.

Methyl 4-(3-hydroxypyridin-2-yl)benzoate (93)

Thionyl chloride (7.6 mL, 104 mmol) was added at 4° C. to a soln of 92 (4.5 g, 21.0 mmol) in MeOH (130 mL). The mixture was heated to 70° C. for 14 h and concentrated. The residue was dissolved in $CHCl_3$ (200 mL) and EtOH (20 mL) and treated with aq. $NaHCO_3$ soln (100 mL). The organic phase was separated, the aq. phase was extracted repeatedly with $CHCl_3$. The combined organic phases were dried ($Na_2SO_4$), filtered and concentrated to afford the ester 93 (4.45 g, 92%).

Data of 93: $C_{13}H_{11}NO_3$ (229.2). LC-MS (method 1a): $R_t$=1.07 (90), 230.1 ([M+H]⁺). $^1$H-NMR (DMSO-$d_6$): 10.40 (br. s, OH), 8.32-8.18 (m, 3H); 8.02 (d, J=8.6, 2 H), 7.38 (dd, J=1.4, 8.2, 1H); 7.26 (dd, J=4.4, 8.2, 1H); 3.88 (s, 3H).

4-(3-Fluoro-5-hydroxyphenyl)thiophene-2-carboxylic acid (98)

At rt, a solution of tert-butyl 2,2,2-trichloroacetimidate (27.7 mL, 155 mmol) in $CH_2Cl_2$ (50 mL) was added dropwise to a soln of 4-bromothiophene-2-carboxylic acid (94; 16.0 g, 77.3 mmol) in $CH_2Cl_2$ (150 mL). The mixture was stirred for 16 h. A precipitate was formed, which was removed by filtration. The filtrate was concentrated. FC (hexane/EtOAc 99:1 to 97:3) yielded 95 (18.7 g, 92%).

Sat. aq. $NaHCO_3$ soln (183 mL) was added to a soln of 95 (17.2 g, 65.2 mmol), 3-fluoro-5-hydroxyphenylboronic acid (96; 15.3 g, 97.9 mmol) and $Pd(PPh_3)_4$ (3.77 g, 3.26 mmol) in dioxane (517 mL). The mixture was heated to reflux for 2 h. Aqueous workup (EtOAc, sat. aq. $Na_2CO_3$ soln, sat. aq. NaCl soln; $Na_2SO_4$) and FC (hexane/EtOAc 90:10) afforded 97 (12.55 g, 65%).

TFA (150 mL) was added at rt to a mixture of 97 (12.5 g, 42.6 mmol) in $CH_2Cl_2$ (150 mL). The soln was stirred for 2.5 h and concentrated to give 98 (10.3 g, quant. yield).

Data of 98: $C_{11}H_7FO_3S$ (238.2). $^1$H-NMR (DMSO-$d_6$): 13.23 (br. s, 1H); 10.03 (br. s, 1H); 8.21 (d, J=1.6, 1H); 8.05 (d, J=1.6, 1H); 7.05 (m, 1H); 6.95 (t, J=1.7, 1H), 6.53 (td, J=2.2, 10.7, 1H).

3-(Allyloxy)-N-methoxy-N-methylthiophene-2-carboxamide (102)

At 0° C., allyl bromide (18.1 mL, 209 mmol) was added dropwise to a mixture of 3-hydroxythiophene-2-carboxylic acid (99; 10.0 g, 69.8 mmol) and $K_2CO_3$ (48.2 g, 349 mmol) in DMF (255 mL). The mixture was allowed to stir for 2 h at 0° C. to rt. The mixture was filtered and the residue was washed with EtOAc. The filtrate was concentrated, followed by an aqueous workup ($Et_{20}$, 1 M aq. HCl soln, sat. aq. $NaHCO_3$ soln, $H_2O$; $Na_2SO_4$) to give ester 100 (15.5 g).

At rt, 2 M aq. LiOH soln (346 mL, 691 mmol) was added to a soln of the crude ester 100 (15.5 g) in DME (315 mL). The mixture was heated to 50° C. for 16 h and concentrated. The residue was distributed between $H_2O$ and EtOAc. The aqueous phase was acidified with 1 M aq. HCl soln and repeatedly extracted with EtOAc. The combined organic layer was dried ($Na_2SO_4$), filtered and concentrated to afford the acid 101 (11.5 g, 90%).

At 5° C., i-$Pr_2NEt$ (42.3 mL, 249 mmol) was added dropwise to a mixture of 101 (11.45 g, 62.2 mmol), N,O-dimethylhydroxylamine hydrochloride (7.28 g, 74.6 mmol), EDC-HCl (14.3 g, 74.6 mmol), $HOBt.H_2O$ (11.4 g, 74.6 mmol) and DMAP (1.52 g, 12.4 mmol) in DMF (116 mL). The mixture was allowed to warm to rt over 5 h followed by an aqueous workup (EtOAc, 1 M aq. HCl soln; $Na_2SO_4$) and FC (hexane/EtOAc 2:1) to afford 102 (9.69 g, 69%).

Data of 102: $C_{10}H_{13}NO_3S$ (227.3). LC-MS (method 1c): $R_t$=1.59 (92), 228.1 ([M+H]$^+$).

tert-Butyl 3-(3-hydroxythiophen-2-yl)-1-methyl-1H-pyrazole-5-carboxylate (106)

n-Butyllithium (1.6 M in hexane; 41.9 mL, 67.0 mmol) was added dropwise within 10 min at −55 to −50° C. to a soln of tert-butyl propiolate (103; 8.76 mL, 63.8 mmol) in dry THF (200 mL). The mixture was allowed to stir at −40° C. for 1.5 h. The mixture was cooled to −78° C. A soln of 102 (7.25 g, 31 9 mmol) in THF (66 mL) was added within 10 min with the temperature not exceeding −64° C. The mixture was stirred for 0.5 h at −78° C., then warmed to −40° C. and allowed to slowly warm to 0° C. over 3 h. The mixture was poured into 1 M aq. $KHSO_4$ soln and extracted with EtOAc. The organic phase was dried ($Na_2SO_4$) and concentrated. FC (hexane/EtOAc 90:10 to 70:30) afforded the ketone 104 (8.34 g, 89%).

Methylhydrazine (1.0 mL, 18.8 mmol) was added at rt to a soln of 104 (4.6 g, 16 mmol) in EtOH (62 mL). Stirring was continued for 1 h and the volatiles were evaporated. Aqueous workup (EtOAc, sat. aq. $NaHCO_3$ soln; $Na_2SO_4$) and FC (hexane/EtOAc 90:10) gave pyrazole 105 (4.25 g, 84%).

Data of 105: $C_{16}H_{20}N_2O_3S$ (320.4). LC-MS (method 4a): $R_t$=1.80 (96), 321.2 ([M+H]$^+$). $^1$H-NMR (DMSO-$d_6$): 7.40 (d, J=5.5, 1H); 7.08 (s, 1H); 7.07 (d, J ca 5.9, 1H); 6.06 (m, 1H); 5.43 (qd, J=1.7, 17.3, 1H); 5.29 (qd, J=1.6, 10.6, 1H); 4.69 (td, J=1.6, 5.0, 2 H); 4.05 (s, 3H); 1.55 (s, 9H).

Phenylsilane (15.0 mL, 121 mmol) was added to a soln of 105 (7.75 g, 24 mmol) and $Pd(PPh_3)_4$ (1.4 g, 1.2 mmol) in THF (78 mL). The mixture was stirred at rt for 16 h. More $Pd(PPh_3)_4$ (0.8 g, 0.7 mmol) and phenylsilane (6.0 mL, 48 mmol) were added and stirring was continued for 24 h. The volatiles were evaporated followed by an aqueous workup (EtOAc, 1 M $NH_4Cl$ soln) and FC (hexane/EtOAc 90:10) to yield 106 (5.75 g, 84%).

Data of 106: $C_{13}H_{16}N_2O_3S$ (280.3). LC-MS (method 1a): $R_t$=2.40 (94), 281.2 ([M+H]$^+$). $^1$H-NMR (DMSO-$d_6$): 10.01 (br. s, 1H); 7.24 (d, J=5.3, 1H); 7.04 (s, 1H); 6.72 (d, J=5.3, 1H); 4.04 (s, 3H); 1.55 (s, 9H).

2-(4-Hydroxy-3-nitrophenyl)-6-methylpyrimidine-4-carboxylic acid (110)

Sat. aq. $Na_2CO_3$ soln (52.5 mL) was added to a soln of methyl 2-chloro-6-methylpyrimidine-4-carboxylate (107; 5.0 g, 26.8 mmol), 4-methoxy-3-nitrophenylboronic acid (108; 6.86 g, 34.8 mmol) and $PdCl_2(PPh_3)_2$ (0.94 g, 1.3 mmol) in dioxane (175 mL). The mixture was heated to reflux for 4 h and partially concentrated, followed by an aqueous workup (EtOAc, 1 M aq. HCl soln; sat. aq. NaCl soln; $Na_2SO_4$). The crude product was suspended in $CH_2Cl_2$/MeOH 2:1; the solid was filtered, washed (MeOH) and dried i.v to afford 109.HCl (3.7 g, 42%). The filtrate was concentrated and purified by FC($CH_2Cl_2$/MeOH 100:0 to 70:30) to give 109.HCl (3.87 g, 44%).

A mixture of 109.HCl (7.5 g, 23.1 mmol) and LiCl (4.9 g, 11.5 mmol) in DMF (100 mL) was heated to 145° C. for 18 h. The volatiles were mostly evaporated. The residue was cooled to 0° C. and treated with 1 M aq. HCl soln (250 mL). The resulting suspension was sonicated and filtered. The solid material was washed ($Et_2O$) and dried. The solid material was suspended in $CH_2Cl_2$/$Et_2O$ 1:4, filtered and dried to give 110.HCl (6.5 g, 80%).

Data of 110.HCl: $C_{12}H_9N_3O_5$.HCl (free base, 275.2). LC-MS (method 1a): $R_t$=1.73 (83), 276.0 ([M+H]$^+$). $^1$H-NMR (DMSO-$d_6$): 8.91 (d, J=1.9, 1H); 8.56 (dd, J=1.9, 8.8, 1H); 7.80 (s, 1H); 7.30 (d, J=8.8, 1H); 2.63 (s, 3H).

2-Iodophenol (111) is commercially available.

2-(Ethoxycarbonyl)phenylboronic acid (112) is commercially available.

Ethyl 2-(4,4,5,5-tetramethyl-1,3,2-dioxaborolan-2-yl) benzoate (113) is commercially available.

4-(3-Hydroxyphenyl)-2-(trifluoromethyl)oxazole-5-carboxylic acid (117)

The aminoacrylic acid ester 115 was prepared according to J. H. Lee et al, *J. Org. Chem.* 2007, 72, 10261.

The 2-(trifluoromethyl)oxazole 116 was prepared as described by F. Zhao et al. *J. Org. Chem.* 2011, 76, 10338 for similar compounds:

A degassed soln of 115 (2.15 g, 9.72 mmol) in DCE (500 mL) was warmed to 45° C. [Bis(trifluoroacetoxy)iodo] benzene (5.02 g, 11.67 mmol) was added in one portion, and stirring at 45° C. was continued for 16 h. Evaporation of the volatiles and FC (hexane/EtOAc 98:2) afforded 116 (1.55 g, 50%).

Data of 116: $C_{14}H_{12}F_3NO_4$ (315.2). $^1$H-NMR (DMSO-$d_6$): 7.62-7.57 (m, 2H); 7.45 (t, J=8.0, 1H); 7.11 (m, 1H); 4.38 (q, J=7.1, 2 H); 3.81 (s, 3H); 1.31 (t, J=7.1, 3 H). At 0° C., $BBr_3$ (1 M in THF; 24.2 mL, 24.2 mmol) was added dropwise to a soln of 116 (1.5 g, 4.85 mmol) in $CH_2Cl_2$ (3.5 mL). The mixture was stirred for 16 h at 0° C. to rt, slowly added onto ice-cold water (500 mL) and extracted with EtOAc. The organic phase was washed (sat. aq. NaCl soln), dried ($Na_2SO_4$), filtered and concentrated. FC (hexane/EtOAc 75:25 to 0:100, then $CH_2Cl_2$/MeOH 90:10) afforded 117 (1.24 g, 95%).

Data of 117: $C_{11}H_6F_3NO_4$ (273.2). $^1$H-NMR (DMSO-$d_6$): 9.54 (br. s, 1H), 7.71-7.65 (m, 2H); 7.23 (t, J=7.9, 1H); 6.80 (m, 1H).

Modulator B Building Blocks (Scheme 6):

tert-Butyl (3S,5S)-5-(hydroxymethyl)pyrrolidin-3-ylcarbamate hydrochloride (15.HCl) is commercially available.

(2S,4S)-Allyl 4-(tert-butoxycarbonylamino)-2-(hydroxymethyl)-pyrrolidine-1-carboxylate (16) was prepared by Alloc protection of the secondary amino group of 15.HCl with allyl chloroformate in $CH_2Cl_2$ in the presence of aq. $NaHCO_3$ soln applying standard conditions.

Data of 16: $C_{14}H_{24}N_2O_5$ (300.4). $^1$H-NMR (DMSO-$d_6$): 7.12 (br. d, J=6.1, 1H); 5.91 (m, 1H); 5.27 (m, 1H); 5.18 (m, 1H); 4.49 (m, 2H); ca 3.9 (br. m, 1H); 3.89-3.57 (several m, 4H); 3.48 (dd, J=3.1, 10.6, 1H); 2.95 (br. m, 1H); 2.21 (br. m, 1H); 1.75 (br. m, 1H); 1.38 (s, 9H).

tert-Butyl (3R,5S)-5-(hydroxymethyl)pyrrolidin-3-ylcarbamate hydrochloride (17.HCl) is commercially available.

(2S,4R)-Allyl 4-(tert-butoxycarbonylamino)-2-(hydroxylmethyl)-pyrrolidin-1-carboxylate (18) was prepared by Alloc protection of the secondary amino group of 17.HCl with allyl chloroformate in $CH_2Cl_2$ in the presence of aq. $NaHCO_3$ soln applying standard conditions.

Data of 18: $C_{14}H_{24}N_2O_5$ (300.4). $^1$H-NMR (DMSO-$d_6$): 7.08 (br. d, J=7.1, 1H); 5.91 (m, 1H); 5.26 (br. m, 1H); 5.18 (br. d, J ca 10.4, 1H); 4.52 (br. m, 2H), ca 4.1 (br. m, 2H); 3.82 (br. m, 1H); ca 3.5-3.35 (br. s-like m, 3H); 3.19 (br. m, 1H); 2.05 (br. m, 1H); 1.79 (br. m, 1H); 1.38 (s, 9H).

N-Boc-L-alaninol (19) is commercially available.

N-Boc-D-alaninol (20) is commercially available.

(S)-tert-Butyl 2-(hydroxymethyl)pyrrolidine-1-carboxylate (21) is commercially available.

(2S,4S)-Allyl 4-(4-bromobenzyloxy)-2-(hydroxymethyl) pyrrolidine-1-carboxylate (118) was prepared as described in the preceding patent application (WO 2011/014973 A2).

(S)-(+)-Prolinol (119) is commercially available.

(S)-Allyl 2-(hydroxymethyl)pyrrolidine-1-carboxylate (120) was prepared by Alloc protection of the secondary amino group of (S)-(+)-prolinol (119) with allyl chloroformate in dioxane in the presence of aq. $NaHCO_3$ soln applying standard conditions.

Data of 120: $C_9H_{15}NO_3$ (185.2). FI-MS: 186.1 ($[M+H]^+$). $^1$H-NMR (DMSO-$d_6$): 5.92 (m, 1H); 5.28 (br. dd-like m, 1H); 5.18 (br. dd-like m, 1H); 4.72 (br. not resolved m, 1H); 4.60-4.45 (br. not resolved m, 2H); 3.73 (br. not resolved m, 1H); 3.50 (br. not resolved m, 1H); 3.35-3.25 (br. not resolved m, 3H); 2.0-1.75 (br. not resolved m, 4H).

(2S,4R)-tert-Butyl 4-amino-2-(hydroxymethyl)pyrrolidine-1-carboxylate hydrochloride (121.HCl) is commercially available.

(2S,4R)-tert-Butyl 4-(benzyloxycarbonylamino)-2-(hydroxymethyl)pyrrolidine-1-carboxylate (122) was prepared by Cbz protection of the primary amino group of 121.HCl with benzyl chloroformate in $CH_2Cl_2$ in the presence of aq. $Na_2CO_3$ soln applying standard conditions.

Data of 122: $C_{18}H_{26}N_2O_5$ (350.4). LC-MS (method 1c): $R_t$=1.89 (95), 351.3 ($[M+H]^+$). $^1$H-NMR (DMSO-$d_6$): 7.49 (d, J=6.8, 1H); 7.42-7.28 (m, 5H); 5.02 (s, 2H); 4.76 (br. s, 1H); 4.13 (br. not resolved m, 1H), 3.76 (br. not resolved m, 1H); 3.40 (m, 3 H; partially superimposed by $H_2O$ signal); 3.11 (dd; J=6.4, 10.6, 1H); 2.07 (br. not resolved m, 1H); 1.82 (br. not resolved m, 1H); 1.38 (s, 9H).

Building Blocks for Subunits of Bridge C (Scheme 7):

(R)-Allyl 4-amino-2-(benzyloxycarbonylamino)butanoate toluene-4-sulfonate (22.pTsOH) was prepared as described for the (S)-enantiomer in the preceding patent application (WO 2011/014973 A2).

(S)-Allyl 2-(benzyloxycarbonylamino)-(5-methylamino) pentanoate hydrochloride (23.HCl), (S)-5-allyl 1-benzyl 2-(methylamino)pentanedioate hydrochloride (24.HCl) and (S)-5-allyl 1-benzyl 2-aminopentanedioate hydrochloride (25.HCl) were prepared as described in the preceding patent application (WO 2011/014973 A2).

Ethyl 2-((2-aminoethyl)(benzyloxycarbonyl)amino)acetate hydrochloride (28.HCl)

Ethyl 2-(2-(tert-butoxycarbonylamino)ethylamino)acetate hydrochloride (26.HCl; 25.0 g, 88 mmol) was added to a mixture of dioxane (250 mL) and 1 M aq. $Na_2CO_3$ soln (250 mL). After 5 min, CbzCl (17.0 g, 98 mmol) was slowly added and the mixture was stirred for 2 h. Aqueous workup (EtOAc, sat. aq. $NaHCO_3$; $Na_2SO_4$) and FC (hexane/EtOAc 8:2 to 1:1) afforded 27 (29.0 g, 85%). A solution of 27 (29.5 g, 77.5 mmol) in 4 M HCl-dioxane (300 mL) was stirred at rt for 2 h and concentrated. The residue was washed with $Et_2O$ to give 28.HCl (24.3 g, 99%).

Data of 28.HCl: $C_{14}H_{20}N_2O_4$.HCl (280.3, free base). LC-MS (method 1a): $R_t$=1.33 (99), 281.1 ($[M+H]^+$). $^1$H-NMR (DMSO-$d_6$): 8.05 (br. s, $NH_3^+$); 7.39-7.28 (m, 5 arom. H); 5.12, 5.07 (2 s; 2H); 4.16-4.04 (m, 4H); 3.54 (m, 2H); 2.97 (br m, 2H); 1.19, 1.32 (2 t, J=7.1, 3 H).

(S)-Methyl 2-(tert-butoxycarbonylamino)-6-hydroxyhexanoate (30)

At 0° C., iodomethane (8.18 mL, 131 mmol) was added to a suspension of Boc-L-6-hydroxynorleucine (29; 25 g, 101 mmol) and $NaHCO_3$ (42.5 g, 505 mmol) in DMF (790 mL). The mixture was stirred at 0° C. to rt for 16 h. The mixture was filtered. The filtrate was distributed between EtOAc and 1 M aq. HCl soln. The organic layer was subsequently washed with $H_2O$, sat. aq. $NaHCO_3$ soln and sat. aq. NaCl soln. The organic phase was dried ($Na_2SO_4$), filtered, and concentrated to afford 30 (24.54 g, 92%).

Data of 30: $C_{12}H_{23}NO_5$ (261.3). FI-MS: 262.0 ($[M+H]^+$). $^1$H-NMR (DMSO-$d_6$): 7.21 (d, J=7.8, 1H); 4.36 (t, J=5.2, 1H); 3.92 (m, 1H); 3.61 (s, 3H); 3.36 (q, J=5.8, 2 H); 1.59 (m, 2H); 1.44 (s, 9H); 1.44-1.26 (m, 4H).

(S)-3-(((9H-Fluoren-9-yl)methoxy)carbonylamino)-4-phenylbutanoic acid (31; Fmoc-β$^3$-homoPhe-OH) is commercially available.

3-((((9H-Fluoren-9-yl)methoxy)carbonyl)(methyl) amino)propanoic acid (33; Fmoc-NMe-β-Ala-OH) was prepared from 3-(methylamino)propanoic acid hydrochloride (32.HCl) applying Fmoc-OSu and $Na_2CO_3$ in $H_2O$ and dioxane.

Data of 33: $C_{19}H_{19}NO_4$ (325.3). LC-MS (method 1a): $R_t$=1.95 (96), 326.0 ($[M+H]^+$).

3-(((9H-Fluoren-9-yl)methoxy)carbonylamino)propanoic acid (34; Fmoc-β-Ala-OH) is commercially available.

Synthesis of (R)-3-((((9H-Fluoren-9-yl)methoxy)carbonyl)(methyl)amino)butanoic acid (40; Fmoc-NMe-β$^3$-homoDAla-OH)

At 0° C., 4 M HCl-dioxane (37.8 mL, 151 mmol) was added dropwise to a mixture of (R)-homo-β-alanine (35; 13.0 g, 126 mmol) in $CH_2Cl_2$ (170 mL). $PCl_5$ (31.5 g, 151 mmol) was added to the suspension. The mixture was stirred at 0° C. to rt for 15 h. A clear solution resulted. The volatiles were evaporated. The residue was dissolved in $CH_2Cl_2$ (150 mL). Allyl alcohol (10.3 mL, 151 mmol) was added slowly and the mixture was stirred for 2 h at rt. The volatiles were evaporated to afford crude 36.HCl (25.6 g).

Pyridine (115 mL) was added to a soln of crude 36.HCl (25.5 g) in $CH_2Cl_2$ (275 mL). The mixture was cooled to 0° C., followed by the addition of 4-nitrobenzenesulfonyl chloride (63 g, 284 mmol). The mixture was stirred at 0° C. to rt for 16 h. Aq. workup ($CH_2Cl_2$, 1 M aq. HCl soln; $Na_2SO_4$) and FC (hexane/EtOAc 9:1 to 1:1) yielded 37 (26.7 g, 64%).

$K_2CO_3$ (56 g, 404 mmol) was added to a solution of 37 (26.5 g, 81 mmol) in DMF (295 mL). Iodomethane (50 mL, 807 mmol) was added at 0° C. and the mixture was allowed to warm to rt over 3 h. Aq. workup (EtOAc, 1 M aq. HCl soln, sat. aq. NaCl soln; $Na_2SO_4$) gave crude 38 (27.6 g).

$K_2CO_3$ (16.7 g, 121 mmol) was added to a soln of crude 38 (13.8 g, ca 40 mmol) in $CH_3CN$ (275 mL). The mixture was degassed, cooled to 0° C. and treated with thiophenol (6.15 mL, 60 mmol). The mixture was stirred at 0° C. to rt for 15 h. $H_2O$ (115 mL) and (in portions) Fmoc-Cl (10.5 g, 40.3 mmol) were added. Stirring was continued for 3 h followed by an aq. workup (EtOAc, sat. aq. $Na_2CO_3$; $Na_2SO_4$) and FC (hexane/EtOAc 95:5 to 70:30). The material obtained (11.5 g) was purified again by FC (hexane/$CH_2Cl_2$ 8:2, then $CH_2Cl_2$, then $CH_2Cl_2$/EtOAc) to give 39 (9.2 g, 60%). A degassed soln of 39 (18.3 g, 48.2 mmol) in $CH_2Cl_2$ (175 mL)/EtOAc (210 mL) was treated with $Pd(PPh_3)_4$ (0.9 g, 0.77 mmol) and 1,3-dimethylbarbituric acid (9.04 g, 57.9 mmol) for 3 h at rt. The volatiles were evaporated. FC ($CH_2Cl_2$/MeOH 100:0 to 80:20) afforded 40 (7.55 g, 46%) and impure material which was further purified by prep. HPLC (method 1d) to give more 40 (5.61 g, 34%).

Data of 40: $C_{20}H_{21}NO_4$ (339.4). LC-MS (method 1a): $R_t$=2.03 (96), 340.1 ($[M+H]^+$). $^1$H-NMR (DMSO-$d_6$): 12.2 (br. s, 1H); 7.89 (d, J=7.4, 2 H); 7.65 (br. s, 2H); 7.41 (t, J=7.4, 2 H); 7.33 (t, J=7.3, 2 H); 4.40-4.24 (m, 4H), 2.67 (s, 3H); 2.45-2.30 (br. m, 2H); 1.37 (br. d, 3H).

Allyl 2-((2-aminoethyl)(benzyloxycarbonyl)amino)acetate hydrochloride (125.HCl)

At 4° C., $LiOH.H_2O$ (6.36 g, 152 mmol) was added to a soln of 27 (28.82 g, 75.8 mmol) in MeOH (86 mL), $H_2O$ (85 mL) and THF (270 mL). The mixture was stirred for 18 h at rt, acidified with 1 M aq. HCl soln (500 mL) and extracted with EtOAc. The organic phase was dried ($Na_2SO_4$), filtered and concentrated to give 123 (26.5 g, 99%). $NaHCO_3$ (17.7 g, 210 mmol) was added to a soln of 123 (37.1 g, 105.4 mmol) in DMF (530 mL). The mixture was stirred for 5 min followed by the addn of allyl bromide (18.0 mL; 208 mmol). The mixture was stirred at rt for 18 h. More $NaHCO_3$ (2.0 g, 24 mmol) and allyl bromide (2.0 mL; 23.1 mmol) were added and stirring was continued for 4 h. Aq. Workup (EtOAc, 1 M aq. HCl soln; $Na_2SO_4$) and FC($CH_2Cl_2$/MeOH 99.5:0.5 to 98:2) afforded 124 (38.8 g, 94%).

A soln of 124 (22.5 g, 53.3 mmol) in dioxane (23 mL) was treated at rt with 4 M HCl in dioxane (80 mL) for 3 h. Dioxane (50 mL) was added and stirring was continued for 1 h. The volatiles were evaporated and the residue was washed ($Et_2O$) and dried i.v. to yield 125.HCl (17.0 g, 97%).

Data of 125.HCl: $C_{15}H_{20}N_2O_4$.HCl (free base, 292.3). FI-MS: 292.9 ($[M+H]^+$). $^1$H-NMR (DMSO-$d_6$): 8.03 (br s, 3H); 7.39-7-28 (m, 5H); 5.87 (m, 1H); 5.35-5.17 (m, 2H); 5.12, 5.07 (2 s, 2H); 4.59 (m, 2H); 4.16 (d, J=7.5, 2 H); 3.54 (q-like m, 2H); 2.97 (br m, 2H).

All Fmoc-α-amino acids and Fmoc-N-methyl-α-amino acids applied in the synthesis of Core 10 and Core 11 are commercially available:

Fmoc-L-alanine (Fmoc-Ala-OH)
Fmoc-N-methyl-L-alanine (Fmoc-NMe-Ala-OH)
Fmoc-D-alanine (Fmoc-DAla-OH)
Fmoc-N-methyl-D-alanine (Fmoc-NMe-DAla-OH)
Fmoc-N-methyl-L-glutamic acid 5 tert.-butyl ester (Fmoc-NMe-Glu(OtBu)-OH)
Fmoc-glycine (Fmoc-Gly-OH)
N-α-Fmoc-N-ε-Boc-L-lysine (Fmoc-Lys(Boc)-OH)
Fmoc-L-phenylalanine (Fmoc-Phe-OH)
Fmoc-N-methyl-L-phenylalanine (Fmoc-NMe-Phe-OH)
Fmoc-D-phenylalanine (Fmoc-DPhe-OH)
Fmoc-N-methyl-D-phenylalanine (Fmoc-NMe-DPhe-OH)
Fmoc-sarcosine (Fmoc-Sar-OH)

(S)-Methyl 3-(allyloxy)-2-aminopropanoate hydrochloride (129)

A soln of Boc-serine (126; 14.0 g, 68.2 mmol) in DMF (143 mL) was cooled to 0° C. $NaHCO_3$ (17.2 g 205 mmol) was added and the mixture was stirred for 15 min. Iodomethane (8.5 mL, 136 mmol) was added dropwise. The mixture was stirred at 0° C. to rt for 16 h and again cooled to 0° C. More iodomethane (4.2 mL, 67 mmol) was slowly added and stirring was continued for 3 h. The mixture was diluted with $H_2O$ and extracted with EtOAc. The organic phase was washed (sat. aq. NaCl soln), dried ($Na_2SO_4$), filtered and concentrated to give crude 127 (14.2 g).

A soln of crude 127 (14.2 g) and $Pd(PPh_3)_4$ (0.64 g) in THF (416 mL) was degassed. Carbonic acid allyl methyl ester (9.6 g, 82.8 mmol) was added and the mixture was heated to 60° C. for 2 h. The volatiles were evaporated. FC (hexane/EtOAc 9:1) afforded 128 (11.4 g, 79%)

A soln of 128 (11.4 g, 43.9 mmol) in dioxane (110 mL) was treated with 4 M HCl in dioxane (110 mL) for 4 h at rt. Additional 4 M HCl in dioxane (30 mL) was added and stirring was continued for 30 min. The volatiles were evaporated and the residue was washed with $Et_2O$ to give 129.HCl (8.3 g, 96%).

Data of 129.HCl: $C_7H_{13}NO_3$.HCl (159.2, free base). FI-MS: 160.0 ($[M+H]^+$). $^1$H-NMR (DMSO-$d_6$): 8.70 (br. s, 3H); 5.85 (m, 1H); 5.29 (qd, J=1.7, 17.3, 1H), 5.19 (qd, J=1.5, 10.4, 1H); 4.33 (t, J=3.6, 1H); 4.07-3.93 (m, 2H); 3.86-3.78 (m, 2H); 3.76 (s, 3H).

(S)-Allyl 2-(benzyloxycarbonylamino)-4-(methylamino) butanoate hydrochloride (130.HCl) and (S)-Allyl 2-(benzyloxycarbonylamino)-6-(methylamino) hexanoate hydrochloride (131.HCl) were prepared described in the preceding patent application (WO 2011/014973 A2).

Sarcosine tert-butylester hydrochloride (132.HCl) is commercially available.

Core 01: Synthesis of Ex. 1, Ex. 2 and Ex. 3 (Scheme 8)

Synthesis of the Mitsunobu Product 41

At 0° C., ADDP (7.08 g, 28.1 mmol) was added in portions to a mixture of phenol 2 (4.27 g, 18.7 mmol), alcohol 16 (6.18 g, 20.6 mmol) and $PPh_3$ (7.36 g, 28.1 mmol) in $CHCl_3$ (110 mL). The stirred mixture was allowed to warm to rt over 15 h.

The volatiles were evaporated. The residue was suspended in $CH_2Cl_2$ and filtered. The filtrate was concentrated and purified by FC (hexane/EtOAc 4:1) to yield 41 (5.98 g, 62%).

Data of 41: $C_{28}H_{34}N_2O_7$ (510.6). LC-MS (method 1a): $R_t$=2.58 (94), 511.2 ($[M+H]^+$).

Synthesis of the Acid 42

Aq. LiOH soln (2 M; 11 mL, 22.0 mmol) was added to a solution of ester 41 (5.65 g, 11.1 mmol) in MeOH (11 mL) and THF (19 mL). The mixture was heated to 65° C. for 4 h, partially concentrated, acidified with 1 M aq. HCl soln to pH 1 and extracted twice with EtOAc. The combined organic layer was washed (sat. aq. NaCl soln), dried ($Na_2SO_4$), filtered and concentrated to give 42 (4.46 g, 81%).

Data of 42: $C_{27}H_{32}N_2O_7$ (496.6). LC-MS (method 1a): $R_t$=2.28 (90), 497.2 ($[M+H]^+$).

Synthesis of the Amide 43

A solution of acid 42 (4.46 g, 9.0 mmol), amine 22.pTsOH (5.6 g, 11 mmol), HATU (5.1 g, 13 mmol), HOAt (1.8 g, 13 mmol) in DMF (70 mL) was cooled to 0° C., followed by the addition of i-$Pr_2$NEt (6.2 mL, 36 mmol). The mixture was allowed to warm to rt over 15 h. The mixture was diluted with 0.5 M aq. HCl soln and extracted twice with EtOAc. The combined organic layer was washed (sat. aq. NaCl soln), dried ($Na_2SO_4$), filtered and concentrated. FC (hexane/EtOAc 1:1) of the crude product afforded 43 (5.56 g, 80%).

Data of 43: $C_{42}H_{50}N_4O_{10}$ (770.9). LC-MS (method 1a): $R_t$=2.55 (95), 771.3 ($[M+H]^+$).

Synthesis of Amino Acid 44

A degassed solution of amide 43 (5.55 g, 7.2 mmol) and 1,3-dimethylbarbituric acid (2.5 g, 16 mmol) in $CH_2Cl_2$ (40 mL) and EtOAc (40 mL) was treated with $Pd(PPh_3)_4$ (0.41 g, 0.36 mmol) at rt. After 2 h, more $CH_2Cl_2$ (40 mL) and $Pd(PPh_3)_4$ (0.41 g, 0.36 mmol) were added and stirring was continued for 1 h. The volatiles were evaporated. The solid was suspended in EtOAc, filtered, washed (EtOAc) and dried i.v. to afford 44 (3.94 g, 83%).

Data of 44: $C_{35}H_{42}N_4O_8$ (646.7). LC-MS (method 1a): $R_t$=1.75 (97), 647.2 ($[M+H]^+$).

Synthesis of Ex. 1

The amino acid 44 (2.77 g, 4.28 mmol) was added in portions over 2 h to a solution of T3P (50% in EtOAc; 13 mL, 22.1 mmol) and i-$Pr_2$NEt (5.8 mL, 34.3 mmol) in dry $CH_2Cl_2$ (800 mL). Stirring was continued for 30 min. The mixture was washed (sat. aq. $NaHCO_3$ soln.), dried ($Na_2SO_4$), filtered and concentrated. FC($CH_2Cl_2$/THF 9:1) of the crude product yielded Ex. 1 (2.35 g, 87%).

Data of Ex. 1: $C_{35}H_{40}N_4O_7$ (628.7). LC-MS (method 1a): $R_t$=2.17 (94), 629.2 ($[M+H]^+$). $^1$H-NMR (DMSO-$d_6$): 8.18 (br. t, 1H); 7.67 (d, J=7.2, 1H); 7.52-7.23 (m, 11H); 7.11-7.06 (m, 2H); 6.98 (d, J=8.1, 1H); 4.98 (s, 2H); 4.64 (br. m, 1H); ca 4.3-4.0 (several br. m, 4H); 3.85 (br. m, 1H); 3.10 (br. m, 1H); 2.98 (m, 1H); 2.31 (br. m, 1H); ca 2.0-1.75 (br. m, 2H); 1.53 (br. m, 1H); 1.41 (s, 9H); 0.83 (br. m, 1H).

Synthesis of Ex. 2

A soln of Ex. 1 (300 mg, 0.477 mmol) in MeOH (6.0 mL) was hydrogenated for 16 h at rt and normal pressure in the presence of palladium hydroxide on activated charcoal (moistened with 50% $H_2O$; 63 mg). The mixture was filtered through a pad of celite. The solid was washed with MeOH. The combined filtrate and washings were concentrated. FC($CH_2Cl_2$/MeOH 95:5 to 80:20) gave Ex. 2 (206 mg, 87%).

Data of Ex. 2: $C_{27}H_{34}N_4O_5$ (494.6). LC-MS (method 1a): $R_t$=1.60 (99), 495.2 ($[M+H]^+$). $^1$H-NMR (DMSO-$d_6$): 8.21 (t-like m, 1H); 7.52-7.36 (m, 5H); 7.21 (br. d, 1H), 7.15-7.00 (m, 2H); 7.00 (s, 1H), 4.43 (br. not resolved m, 1H); 4.24-4.01 (m, 3H); 3.89 (q-like m, 1H); 3.58-3.12 (several br. m, 3H); 2.98 (dd, J=6.2, 12.1, 1H); 2.33 (m, 1H); 1.89 (m, 1H); 1.65-1.55 (br. not resolved m, 2H); 1.41 (s, 9H).

Synthesis of Ex. 3

A soln of Ex. 1 (750 mg, 1.19 mmol) in $CH_2Cl_2$ (5 mL) was cooled to 0° C. TFA (2.0 mL) was slowly added and the mixture was stirred at 0° C. to rt for 4 h. The volatiles were evaporated. The residue was taken up in $CHCl_3$ and concentrated.

The residue was taken up in $CH_2Cl_2$ (6 mL), treated with 4 M HCl in dioxane (2 mL) to give a precipitate. The volatiles were evaporated. The treatment with $CH_2Cl_2$/4 M HCl in dioxane was repeated. The residue was suspended in $Et_2O$, filtered, washed ($Et_2O$) and dried i.v. to afford Ex. 3.HCl (613 mg, 90%).

Data of Ex. 3.HCl: $C_{30}H_{32}N_4O_5$.HCl (528.6, free base). LC-MS (method 1a): $R_t$=1.55 (99), 529.1 ($[M+H]^+$).

Core 01: Synthesis of Ex. 330, Ex. 331 and the Resin 133 (Scheme 8)

Synthesis of Ex. 330

Sat. aq. $NaHCO_3$ soln (131 mL) and $H_2O$ (53.5 mL) were added to a soln of Ex. 2 (14.4 g, 29 mmol) in dioxane (131 mL) and THF (78 mL). The mixture was cooled to 0° C. Allyl chloroformate (3.71 mL, 34.9 mmol) was slowly added. Stirring was continued for 2 h at 0° C. to rt. The mixture was diluted with sat. aq. $Na_2CO_3$ soln and extracted with $CH_2Cl_2$. The organic phase was dried ($Na_2SO_4$), filtered and concentrated to give Ex. 330 (16.18 g, 96%).

Data of Ex. 330: $C_{31}H_{38}N_4O_7$ (578.6). LC-MS (method 1c): $R_t$=2.06 (97), 578.9 ($[M+H]^+$).

Synthesis of Ex. 331

At 0° C., TFA (40.6 mL) was added to a soln of Ex. 330 (15.8 g, 27.3 mmol) in $CH_2Cl_2$ (160 mL). The cooling bath was removed and stirring was continued for 2 h. The volatiles were evaporated. The residue was dissolved in $CHCl_3$ (76 mL) and 4 M HCl in dioxane (14.0 mL) was added. The volatiles were evaporated. The residue was again taken up in $CHCl_3$ (76 mL), treated with 4 M HCl in dioxane (14.0 mL) and concentrated. The residue was distributed between sat. aq. $Na_2CO_3$ soln and EtOAc. The organic layer was separated, the aqueous layer repeatedly extracted with EtOAc. The combined organic phases were concentrated. The residue was dissolved in $CH_2Cl_2$ (200 mL). Then 4 M HCl in dioxane (17.7 mL) was slowly added to give a thick precipitate. The volatiles were evaporated. The residue was suspended in $Et_2O$, filtered, washed ($Et_2O$) and dried i.v. to afford Ex. 331.HCl (12.5 g, 89%).

Data of Ex. 331.HCl: $C_{26}H_{30}N_4O_5$.HCl (free base, 478.5). LC-MS (method 1a): $R_t$=1.36 (96), 479.2 ($[M+H]^+$). $^1$H-NMR (DMSO-$d_6$): 8.43 (br. s, 3H); 8.27 (br. t, J ca 5.3, 1H); 7.67 (d, J=6.9, 1H); 7.52-7.37 (m, 5H); 7.12-7.09 (m, 2H); 7.02 (d, J=8.8, 1H); 5.88 (m, 1H); 5.26 (dd, J=1.2, 17.2, 1H); 5.17 (dd, J=1.1, 10.4, 1H); 4.67 (br. m, not resolved, 1H); 4.43 (d, J=5.2, 2 H); 4.31-4.11 (m, 4H); 3.56 (br. m, not resolved, 1H); 3.31-3.16 (br. m, 2H); 3.19 (dd, J=8.1, 12.1, 1H); 2.60 (m, 1H); 2.12 (m, 1H); 1.83 (br. m, 1H); 1.47 (br. m, 1H).

Synthesis of the Resin 133

Under Ar, DFPE polystyrene (1% DVB, 100-200 mesh, loading 0.87 mmol/g; 11.1 g, 9.6 mmol) was swollen in DCE (110 mL) for 1 h. Ex. 331.HCl (5.7 g, 10.6 mmol) and i-$Pr_2$NEt (4.9 mL, 28.9 mmol) were added. The mixture was shaken at rt for 1 h. $NaBH(OAc)_3$ (4.09 g, 19.3 mmol) was added and the mixture was shaken for 20 h. The resin was filtered and successively washed with MeOH twice, then three times each with DCE, 10% i-$Pr_2$NEt in DMF, DMF, $CH_2Cl_2$ and MeOH. The resin was dried i.v. to give 133 (15.73 g; loading 0.6 mmol/g).

Procedure D:

Core 01: Synthesis of Final Products on Solid Support

Synthesis of Resin 134

1) First Derivatization Step

Resin 133 (loading 0.6 mmol/g; 96 mg, 0.055 mmol) was swollen in DMF (1 mL) for 60 min and filtered. The resin was resuspended in DMF/$CH_2Cl_2$ 1:1 (1 mL). i-$Pr_2$NEt (8 equiv.) the carboxylic acid $R^{III}CO_2H$ (4 equiv.) and HATU (4 equiv.) or the succinimidyl carbamate $R^{III}NHCO_2Su$ (4 equiv.) were added. The mixture was shaken for 1 h and filtered. The resin was washed with DMF. The coupling step was repeated. The resin was washed three times with DMF.

2) Cleavage of the Alloc Group

The resin was suspended in $CH_2Cl_2$ (1 mL). Phenylsilane (10 equiv.) and $Pd(PPh_3)_4$ (0.2 equiv.) were added, then the mixture was shaken for 15 min and filtered. The deprotection step was repeated. The resin was filtered, washed three times each with $CH_2Cl_2$, DMF, twice with MeOH and three times with $CH_2Cl_2$.

3) Second Derivatization Step

The resin was resuspended in DMF/$CH_2Cl_2$ 1:1 (1 mL). i-$Pr_2$NEt (8 equiv.) and the carboxylic acid $R^{IV}CO_2H$ (4 equiv.) and PyBOP (4 equiv.) or the isocyanate $R^{IV}NCO$ (4 equiv) or the sulfonyl chlorides $R^{IV}SO_2Cl$ (4 equiv) and DMAP (1 equiv.) were added. The mixture was shaken for 1 h and filtered. The resin was filtered, washed three times with DMF to afford resin 134.

Release of the Final Products

The resin 134 was treated with 20% TFA in $CH_2Cl_2$ (1 mL) for 30 min, filtered and washed with $CH_2Cl_2$. The cleavage step was repeated once. The combined filtrates and washings were concentrated. The residue was treated with $CH_3CN$, evaporated and dried i.v. Purification of the crude product by normal phase or reverse phase prep. HPLC afforded Ex. 7 and Ex. 332-Ex. 337.

Core 01: Synthesis of Selected Advanced Intermediates and Final Products (Scheme 8)

Synthesis on Solid Support:

Ex. 7.$CF_3CO_2H$ (6.6 mg, 15%) was obtained by treatment of resin 133 (0.6 mmol/g, 96 mg, 0.055 mmol) with 1-pyrrolidineacetic acid (in total 57 mg, 0.44 mmol; first coupling step) and with 1-naphthaleneacetic acid (41 mg, 0.22 mmol, second coupling step) according to procedure D. The product was purified by prep. HPLC (method 1a).

Data of Ex. 7.$CF_3CO_2H$: cf. Table 13b.

$^1$H-NMR (DMSO-$d_6$): 9.94 (br. s, 1H); 8.77 (d, J=5.3, 1H); 8.65 (d, J=7.7, 1H); 8.06 (t, J=5.4, 1H); 8.01 (m, 1H); 7.92 (m, 1H); 7.81 (d, J=7.9, 1H); 7.55-7.37 (m, 8H); 7.34 (t, J=8.0, 1H); 7.09-7.05 (m, 2H); 6.91 (dd, J=2.0, 8.2, 1H); 4.58 (br. not resolved m, 1H); 4.44 (br. not resolved m, 1H); 4.19 (dd, J=4.9, 11.5, 1H); 4.12-4.00 (m, 5H); 3.94 (d, J=14.9, 1H); 3.87 (d, J=14.9, 1H); ca 3.6-3.5 (br m, 2H), 3.30 (1H, superimposed by $H_2O$ signal); 3.07-3.02 (br. m, 4H); 2.15-1.84 (br. m, 7H); 1.67 (br. m, 1H).

Ex. 332.$CF_3CO_2H$ (21 mg, 48%) was obtained by treatment of resin 133 (0.6 mmol/g, 96 mg, 0.055 mmol) with imidazol-1-yl acetic acid (in total 55 mg, 0.44 mmol; first coupling step) and with 1-naphthaleneacetic acid (41 mg, 0.22 mmol, second coupling step) according to procedure D. The product was purified by prep. HPLC (method 1a).

Data of Ex. 332.$CF_3CO_2H$: cf. Table 13b.

Ex. 333.$CF_3CO_2H$ (29 mg, 65%) was obtained by treatment of resin 133 (0.6 mmol/g, 96 mg, 0.055 mmol) with 2,5-dioxopyrrolidin-1-yl pyridine-3-ylcarbamate (in total 103 mg, 0.44 mmol; first coupling step) and with 1-naphthaleneacetic acid (41 mg, 0.22 mmol, second coupling step) according to procedure D. The product was purified by prep. HPLC (method 1a).

Data of Ex. 333.$CF_3CO_2H$: cf. Table 13b.

Ex. 334.$CF_3CO_2H$ (16 mg, 38%) was obtained by treatment of resin 133 (0.6 mmol/g, 96 mg, 0.055 mmol) with 1-pyrrolidineacetic acid (in total 57 mg, 0.44 mmol; first coupling step) and with 3-chlorophenylacetic acid (37 mg, 0.22 mmol, second coupling step) according to procedure D. The product was purified by prep. HPLC (method 1a).

Data of Ex. 334.$CF_3CO_2H$: cf. Table 13b.

Ex. 335.$CF_3CO_2H$ (11 mg, 26%) was obtained by treatment of resin 133 (0.6 mmol/g, 96 mg, 0.055 mmol) with 1-pyrrolidineacetic acid (in total 57 mg, 0.44 mmol; first coupling step) and with cyclohexylacetic acid (31 mg, 0.22 mmol, second coupling step) according to procedure D. The product was purified by prep. HPLC (method 1a).

Data of Ex. 335.$CF_3CO_2H$: cf. Table 13b.

Ex. 336.$CF_3CO_2H$ (6 mg, 13%) was obtained by treatment of resin 133 (0.6 mmol/g, 96 mg, 0.055 mmol) with 1-pyrrolidineacetic acid (in total 57 mg, 0.44 mmol; first coupling step) and with 1-naphthyl isocyanate (0.031 mL, 0.22 mmol, second coupling step) according to procedure D. The product was purified by prep. HPLC (method 1a).

Data of Ex. 336.$CF_3CO_2H$: cf. Table 13b.

$^1$H-NMR (DMSO-$d_6$): 9.94 (br. s, 1H); 8.81 (d, J=4.9, 1H); 8.63 (s, 1H); 8.27 (t, J=5.6, 1H); 8.06 (d, J=8.0, 1H); 7.96 (dd, J=1.0, 7.6, 1H); 7.89 (d, J ca 9.3, 1H); 7.59-7.38 (m, 9H); 7.16-7.13 (m, 2H); 7.04-6.99 (t-like m, 2H); 4.82 (br. not resolved m, 1H); 4.45 (t-like m, 1H); 4.29 (dd, J=5.9, 11.5, 1H); 4.22-4.13 (br. m, 3H); 4.01 (s, 2H); 3.65-3.45 (br. m, 3H); 3.25-3.0 (br. m, 4H); 2.45 (m, 1H); 2.10-1.70 (br. m, 7H).

Synthesis in Solution:

Synthesis of Ex. 4

At rt, i-$Pr_2$NEt (0.27 mL, 1.57 mmol) was added to a soln of Ex. 2 (258 mg, 0.52 mmol), 1-naphthaleneacetic acid (117 mg, 0.63 mmol), HATU (298 mg, 0.78 mmol) and HOAt (107 mg, 0.78 mmol) in DMF (4.3 mL). The mixture was stirred at rt for 15 h and distributed between $CH_2Cl_2$ and 1 M aq. $Na_2CO_3$ soln. The organic phase was separated, washed ($H_2O$), dried ($Na_2SO_4$), filtered and concentrated. FC (hexane/EtOAc 34:66 to 0:100) afforded Ex. 4 (267 mg, 77%).

Data of Ex. 4: cf. Table 13b

Synthesis of Ex. 5

A soln of Ex. 4 (220 mg, 0.33 mmol) in dioxane (4.0 mL) was treated with 4 M HCl-dioxane (1.0 mL) for 2 h. The volatiles were evaporated to afford Ex. 5.HCl (208 mg, quant.)

Data of Ex. 5.HCl: cf. Table 13b

Synthesis of Ex. 7

At rt, i-$Pr_2$NEt (0.057 mL, 0.33 mmol) was added to a soln of Ex. 5.HCl (50 mg, 0.08 mmol), 1-Pyrrolidineacetic acid (22 mg, 0.17 mmol), HATU (63 mg, 0.17 mmol) and HOAt (23 mg, 0.17 mmol) in DMF (1.2 mL). The mixture was stirred at rt for 4 h and distributed between EtOAc and sat. aq. $NaHCO_3$ soln. The organic phase was dried ($Na_2SO_4$), filtered and concentrated. FC($CH_2Cl_2$/MeOH 100:0 to 95:5) afforded Ex. 7 (40 mg, 71%).

Data of Ex. 7: $C_{40}H_{43}N_5O_5$ (673.8). LC-MS (method 1a): $R_t$=1.70 (96), 674.2 ($[M+H]^+$).

Synthesis of Ex. 14

At 0° C., phenyl chloroformate (87 mg, 0.55 mmol) was slowly added to a mixture of Ex. 3 (285 mg, 0.50 mmol) in $CH_2Cl_2$ (5 mL) and sat. aq. $Na_2CO_3$ soln (1.7 mL). Stirring was continued for 2 h. Aqueous workup (EtOAc, sat. aq.

$NaHCO_3$ soln., $Na_2SO_4$) and FC (EtOAc) afforded Ex. 14 (315 mg, 96%)

Data of Ex. 14: cf. Table 13b

Core 02: Synthesis of Ex. 15, Ex. 16 and Ex. 17 (Scheme 9)

Synthesis of the Mitsunobu Product 45

At 0° C., a solution of TMAD (7.57 g, 43.9 mmol) in benzene (80 mL) was added dropwise to a degassed solution of the phenol 4 (3.68 g, 16.1 mmol), alcohol 16 (4.40 g, 14.65 mmol) and $PPh_3$ (11.5 g, 43.9 mmol) in benzene (80 mL). The stirred mixture was allowed to warm to rt over 15 h.

The volatiles were evaporated. The residue was suspended in hexane and filtered. The filtrate was concentrated and purified by FC (hexane/EtOAc 5:1) to yield 45 (5.45 g, 73%).

Data of 45: $C_{28}H_{34}N_2O_7$ (510.6). LC-MS (method 1c): $R_t$=2.67 (97), 511.2 ([M+H]$^+$).

Synthesis of the Acid 46

At 0° C., aq. LiOH soln (2 M; 10.6 mL, 21.1 mmol) was added to a solution of ester 45 (5.4 g, 10.6 mmol) in MeOH (10 mL) and THF (20 mL). The mixture was allowed to warm to rt over 16 h. The volatiles were evaporated. The residue was taken up in 1 M aq. HCl soln and extracted twice with EtOAc. The combined organic layer was dried ($Na_2SO_4$), filtered and concentrated. FC (hexane/EtOAc 2:1 to 0:100 then EtOAc/MeOH 100:0 to 90:10 gave 46 (4.48 g, 85%).

Data of 46: $C_{27}H_{32}N_2O_7$ (496.6). LC-MS (method 1c): $R_t$=2.29 (99), 497.2 ([M+H]$^+$).

Synthesis of the Amide 47

A solution of acid 46 (4.28 g, 8.6 mmol), amine 23.HCl (4.6 g, 10.3 mmol), HATU (4.9 g, 12.9 mmol) and HOAt (1.76 g, 12.9 mmol) in DMF (80 mL) was cooled to 0° C., followed by the addition of i-$Pr_2$NEt (5.9 mL, 34.5 mmol). The mixture was allowed to warm to rt over 15 h. The mixture was diluted with $H_2O$ and EtOAc. The organic layer was washed (aq. 1 M HCl soln, sat. aq. NaCl soln), dried ($Na_2SO_4$), filtered and concentrated. FC (hexane/EtOAc 1:1) of the crude product afforded 47 (6.1 g, 89%).

Data of 47: $C_{44}H_{54}N_4O_{10}$ (798.9). LC-MS (method 1a): $R_t$=2.72 (97), 799.4 ([M+H]$^+$).

Synthesis of Amino Acid 48

A degassed solution of 47 (6.14 g, 7.7 mmol) and 1,3-dimethylbarbituric acid (2.64 g, 16.9 mmol) in $CH_2Cl_2$ (70 mL) and EtOAc (42 mL) was treated with $Pd(PPh_3)_4$ (0.44 g, 0.38 mmol) at rt for 1 h. The volatiles were evaporated. FC (EtOAc, then $CH_2Cl_2$/MeOH 98:2 to 80:20) afforded 48 (4.64 g, 89%).

Data of 48: $C_{37}H_{46}N_4O_8$ (674.8). LC-MS (method 1a): $R_t$=1.86 (97), 675.3 ([M+H]$^+$).

Synthesis of Ex. 15

A soln of the amino acid 48 (1.12 g, 1.66 mmol) in $CH_2Cl_2$ (60 mL) was added dropwise over 2 h by syringe pump to a soln of T3P (50% in EtOAc; 2.45 mL, 4.15 mmol) and i-$Pr_2$NEt (1.14 mL, 6.64 mmol) in dry $CH_2Cl_2$ (770 mL). Evaporation of the volatiles, aq. workup (EtOAc, sat. aq. $NaHCO_3$ soln; $Na_2SO_4$) and FC (hexane/EtOAc 50:50 to 0:100) yielded Ex. 15 (0.96 g, 88%).

Data of Ex. 15: $C_{37}H_{44}N_4O_7$ (656.7). LC-MS (method 1d): $R_t$=2.29 (97), 657.3 ([M+H]$^+$). $^1$H-NMR (DMSO-$d_6$): 7.6-7.0 (br. m, 13H); 7.13 (d, J=7.9, 1H); 7.03 (t, J=7.3, 1H); 5.01 (br. s, 2H); 4.37 (br. d, J ca 9.7, 1H); ca 4.25-3.7 (several br. m, 4H); 3.25 (br. m, 1H); 2.95 (br. s, 3H); 2.64 (br. m, 1H); 2.40 (br. m, 1H); 2.18 (br. m, 1H); ca. 1.85-1.0 (several br. m, 6H); 1.37 (s, 9H).

Synthesis of Ex. 16

A soln of Ex. 15 (1.3 g, 2.0 mmol) in MeOH (60 mL) was hydrogenated for 4 h at rt and normal pressure in the presence of palladium hydroxide on activated charcoal (moistened with 50% $H_2O$; 240 mg). The mixture was filtered through a pad of celite and $Na_2SO_4$. The solid was washed with MeOH. The combined filtrate and washings were concentrated to give Ex. 16 (1.03 g, 99%).

Data of Ex. 16: $C_{29}H_{38}N_4O_5$ (522.6). LC-MS (method 1a): $R_t$=1.68 (97), 523.1 ([M+H]$^+$).

Synthesis of Ex. 17

A soln of Ex. 15 (600 mg, 0.91 mmol) in dioxane (6 mL) was treated with 4 M HCl in dioxane (6 mL) at rt for 1 h followed by evaporation of the volatiles. The residue was taken up in $CHCl_3$ and concentrated to afford Ex. 17 (571 mg, quant. yield).

Data of Ex. 17.HCl: $C_{32}H_{36}N_4O_5$.HCl (556.6, free base). LC-MS (method 1a): $R_t$=1.65 (96), 557.2 ([M+H]$^+$).

Core 02: Synthesis of Selected Advanced Intermediates and Final Products (Scheme 9)

Synthesis of Ex. 18

At 0° C., i-$Pr_2$NEt (0.635 mL, 3.71 mmol) was added dropwise to a soln of Ex. 17.HCl (550 mg, 0.93 mmol), 2-naphthaleneacetic acid (207 mg, 1.11 mmol), HATU (529 mg, 1.39 mmol) and HOAt (189 mg, 1.39 mmol) in DMF (10 mL). The mixture was stirred at 0° C. for 4 h and distributed between EtOAc and 0.2 M aq. HCl soln. The organic phase was separated, washed ($H_2O$, sat. aq. NaCl soln), dried ($Na_2SO_4$), filtered and concentrated. FC (EtOAc) afforded Ex. 18 (530 mg, 79%).

Data of Ex. 18: cf. Table 14b

Synthesis of Ex. 19

A soln of Ex. 18 (520 mg, 0.72 mmol) in MeOH (5 mL) was hydrogenated for 4 h at rt and normal pressure in the presence of palladium hydroxide on activated charcoal (moistened with 50% $H_2O$; 94 mg). The mixture was filtered through a pad of celite. The solid was washed with MeOH. The combined filtrate and washings were concentrated to give Ex. 19 (412 mg, 97%).

Data of Ex. 19: cf. Table 14b

Synthesis of Ex. 20 i-$Pr_2$NEt (0.043 mL, 0.25 mmol) was added to a soln of Ex. 19 (50 mg, 0.085 mmol), 2-(dimethylamino)acetic acid (17 mg, 0.17 mmol), HATU (64 mg, 0.17 mmol) and HOAt (23 mg, 0.17 mmol). The mixture was stirred at rt for 15 h and distributed between $CH_2Cl_2$ and sat. aq. $Na_2CO_3$ soln.

The organic phase was separated, dried ($Na_2SO_4$), filtered and concentrated. FC($CH_2Cl_2$/MeOH 95:5 to 90:10) afforded Ex. 20 (17 mg, 30%).

Data of Ex. 20: cf. Table 14b

Synthesis of Ex. 25

Phenylacetyl chloride (0.013 mL, 0.098 mmol) was added at 0° C. to a soln of Ex. 19 (50 mg, 0.085 mmol) and pyridine (0.034 mL, 0.42 mmol) in $CH_2Cl_2$ (0.5 mL). The mixture was stirred at 0° C. for 2 h followed by the addition of more phenylacetyl chloride (0.006 mL, 0.045 mmol). Stirring was continued for 1 h. Evaporation of the volatiles and prep. HPLC (method 1a) afforded Ex. 25 (36 mg, 60%).

Data of Ex. 25: cf. Table 14b

Synthesis of Ex. 26

Benzoyl chloride (0.012 mL, 0.10 mmol) was added at 0° C. to a soln of Ex. 19 (50 mg, 0.085 mmol) and pyridine (0.034 mL, 0.42 mmol) in $CH_2Cl_2$ (0.5 mL). The mixture was stirred at 0° C. for 2 h followed by evaporation of the volatiles and prep. HPLC (method 1a) to afford Ex. 26 (40 mg, 67%).

Data of Ex. 26: cf. Table 14b

Core 03: Synthesis of Ex. 41, Ex. 42, Ex. 50 and Ex. 62-Ex. 67 (Scheme 10)

Synthesis of the Mitsunobu Product 49

At 0° C., ADDP (7.32 g, 29.0 mmol) was added in portions to a mixture of phenol 6 (5.0 g, 19.4 mmol), alcohol 20 (5.08 g, 29.0 mmol) and $PPh_3$ (7.62 g, 29.0 mmol) in $CHCl_3$ (82 mL). The stirred mixture was allowed to warm to rt over 15 h.

More 20 (5.08 g, 29.0 mmol), $PPh_3$ (7.62 g, 29.0 mmol) and finally ADDP (7.32 g, 29.0 mmol) were added at 0° C. Stirring was continued at rt for 6 h. The mixture was filtered. The filtrate was concentrated and purified by FC (hexane/EtOAc 90:10 to 80:20) to yield 49 (7.57 g, 94%).

Data of 49: $C_{23}H_{29}NO_6$ (415.5). LC-MS (method 1a): $R_t$=2.54 (99), 416.2 ($[M+H]^+$).

Synthesis of the Acid 50

At 0° C., aq. LiOH soln (2 M; 27 mL, 54.0 mmol) was added dropwise to a solution of ester 49 (7.44 g, 17.9 mmol) in MeOH (27 mL) and THF (50 mL). The mixture was stirred at rt for 5 h, partially concentrated, acidified with 1 M aq. HCl soln and extracted twice with EtOAc. The combined organic layer was dried ($Na_2SO_4$), filtered and concentrated to give 50 (7.1 g, 98%).

Data of 50: $C_{22}H_{27}NO_6$ (401.4). LC-MS (method 1a): $R_t$=2.20 (98), 402.1 ($[M+H]^+$).

Synthesis of the Amide 51

A solution of acid 50 (7.0 g, 17.4 mmol), amine 24.HCl (6.86 g, 20.9 mmol), HATU (9.95 g, 26.2 mmol) and HOAt (3.56 g, 26.2 mmol) in DMF (180 mL) was cooled to 0° C., followed by the addition of i-$Pr_2$NEt (11.9 mL, 69.7 mmol). The mixture was allowed to warm to rt over 7 h. More 24.HCl (6.86 g, 20.9 mmol) was added and stirring continued for 15 h. The mixture was diluted with 1 M aq. HCl soln and extracted twice with EtOAc. The combined organic layer was washed ($H_2O$, sat. aq. NaCl soln), dried ($Na_2SO_4$), filtered and concentrated. FC (hexane/EtOAc 2:1) of the crude product afforded 51 (10.05 g, 85%).

Data of 51: $C_{38}H_{46}N_2O_9$ (674.8). LC-MS (method 1a): $R_t$=2.69 (97), 675.2 ($[M+H]^+$).

Synthesis of the Amino Ester 52

A soln of 51 (10.0 g, 14.8 mmol) in dioxane (10 mL) was treated at rt with 4 M HCl in dioxane (40 mL) for 5 h. The volatiles were evaporated. The residue was taken up in $CH_2Cl_2$ and concentrated to afford 52.HCl (9.2 g, quant. yield).

Data of 52.HCl: $C_{33}H_{38}N_2O_7$.HCl (574.6, free base). LC-MS (method 1a): $R_t$=1.94 (94), 575.2 ($[M+H]^+$).

Synthesis of Amino Acid 53

A degassed solution of ester 52 (9.2 g, 15 mmol) and 1,3-dimethylbarbituric acid (2.8 g, 18 mmol) in $CH_2Cl_2$ (30 mL) and EtOAc (60 mL) was treated with $Pd(PPh_3)_4$ (1.8 g, 1.5 mmol) at rt for 2 h. The volatiles were evaporated. FC ($CH_2Cl_2$/MeOH 98:2 to 70:30) afforded 53 (8.2 g, quant.).

Data of 53: $C_{30}H_{34}N_2O_7$ (534.6). LC-MS (method 1a): $R_t$=1.70 (94), 535.2 ($[M+H]^+$).

Synthesis of Ex. 41

A soln of the amino acid 53 (4.0 g, 7.5 mmol) in $CH_2Cl_2$ (80 mL) was added dropwise over 2 h by syringe pump to a soln of T3P (50% in EtOAc; 11.0 mL, 18.7 mmol) and i-$Pr_2$NEt (5.12 mL, 29.9 mmol) in dry $CH_2Cl_2$ (1360 mL). Evaporation of the volatiles, aq. workup ($CH_2Cl_2$, sat. aq. $NaHCO_3$ soln; $Na_2SO_4$) and FC (hexane/EtOAc 20:80 to 0:100) yielded Ex. 41 (3.0 g, 77%).

Data of Ex. 41: $C_{30}H_{32}N_2O_6$ (516.5). LC-MS (method 1d): $R_t$=2.14 (96), 517.0 ($[M+H]^+$). $^1$H-NMR ($CDCl_3$): 7.78 (s, 1H); 7.50-7.35 (m, 7H); 7.25 (m, 1H), 6.92-6.82 (m, 3H); 5.59 (d, J=8.4, 1H); 5.32 (d, J=12.2, 1H); 5.26 (d, J=12.2, 1H); 4.78 (d, J=11.9, 1H); 4.16 (q-like m, 1H); 3.81 (s, 3H); 3.71 (d, J=9.0, 1H); 3.38 (t-like m, 1H); 2.98 (s, 3H); 2.64 (br. t, J ca. 12.7, 1H); 2.37 (dd, J=5.6, 16.2, 1H); 2.01-1.90 (m, 2H); 1.24 (d, J=6.8, 3 H).

Synthesis of Ex. 42

A soln of Ex. 41 (2.0 g, 3.87 mmol) in MeOH (30 mL) was hydrogenated for 2 h at rt and normal pressure in the presence of palladium hydroxide on activated charcoal (moistened with 50% $H_2O$; 220 mg). The mixture was filtered through a pad of celite. The solid was washed with MeOH. The combined filtrate and washings were concentrated to give Ex. 42 (1.77 g, quant. yield).

Data of Ex. 42: $C_{23}H_{26}N_2O_6$ (426.5). LC-MS (method 1d): $R_t$=1.55 (93), 427.0 ($[M+H]^+$). $^1$H-NMR (DMSO-$d_6$): 13.2 (br. s, 1H); 8.03 (d, J=8.2, 1H); 7.59 (s, 1H); 7.46-7.41 (m, 2H); 7.16 (m, 1H); 7.04 (d, J=8.9, 1H); 6.90 (dd, J=3.0, 8.8, 1H); 6.83 (d, J=3.0, 1H); 4.13 (dd, J=3.0, 12.2, 1H); 4.03-3.91 (m, 2H); 3.74 (s, 3H); 3.52 (t, J=9.2, 1H); 2.86 (s, 3H); 2.39 (br. t, J ca 13.2, 1H); 2.19 (br. dd, J ca 4.9, 15.9, 1H); 1.99 (d-like m, 1H); 1.86 (m, 1H); 1.03 (d, J=6.6, 3 H).

Core 03: Synthesis of Selected Advanced Intermediates and Final Products (Scheme 10)

Synthesis of Ex. 62

A soln of Ex. 41 (50 mg, 0.1 mmol) in THF (1 mL) was cooled to 0° C. $LiBH_4$ (5 mg, 0.213 mmol) and MeOH (3.9

μL, 0.1 mmol) in THF (0.5 mL) were added. The mixture was stirred at rt for 20 h followed by the addition of acetone (0.1 mL). Aqueous workup ($CHCl_3$, 1 M aq. HCl soln, $H_2O$, sat. aq. $NaHCO_3$ soln, sat. aq. NaCl soln; $Na_2SO_4$) and FC($CH_2Cl_2$/MeOH 100:0 to 90:10) yielded Ex. 62 (25 mg, 61%).

Data of Ex. 62: $C_{23}H_{28}N_2O_5$ (412.5). LC-MS (method 1a): $R_t$=1.49 (97), 413.0 ([M+H]$^+$). $^1$H-NMR (DMSO-$d_6$): 7.90 (d, J=8.2, 1H); 7.56-7.53 (m, 2H); 7.41-7.32 (m, 2H); 7.00 (d, J=8.9, 1H); 6.89 (dd, J=3.1, 8.9, 1H); 6.80 (d, J=3.1, 1H); 5.05 (t, J=5.3, 1H); 4.01-3.87 (m, 2H); 3.74 (s, 3H); 3.74 (m, 1H); 3.61-3.38 (m, 3H); 2.78 (s, 3H); 2.11 (dd, J=5.6, 15.9, 1H); 1.99 (br. t, 1H); 1.85 (br. t, 1H); 1.45 (dt, J=6.1, 12.7, 1H); 1.00 (d, J=6.7, 3 H).

Synthesis of Ex. 63

At 0° C., DEAD (40% in toluene; 0.05 mL, 0.109 mmol) was slowly added to a soln of Ex. 62 (30 mg, 0.073 mmol), 3-hydroxypyridine (8.3 mg, 0.087 mmol) and $PPh_3$ (29 mg, 0.109 mmol) in degassed benzene/THF 1:1 (2 mL). The mixture was stirred at rt for 16 h and concentrated. FC($CH_2Cl_2$/MeOH 100:0 to 90:10) afforded Ex. 63 (26 mg, 73%).

Data of Ex. 63: $C_{28}H_{31}N_3O_5$ (489.5). LC-MS (method 1a): $R_t$=1.44 (95), 490.1 ([M+H]$^+$).

Synthesis of Ex. 64

At 0° C., DEAD (40% in toluene; 0.83 mL, 1.82 mmol) was slowly added to a soln of Ex. 62 (250 mg, 0.61 mmol), $PPh_3$ (477 mg, 1.82 mmol) and DPPA (0.394 mL; 1.82 mmol) in degassed benzene (10 mL). The mixture was stirred for 30 min at rt and for 1 h at 50° C. The volatiles were evaporated. The residue was suspended in $Et_2O$. The solid was collected to afford Ex. 64 (169 mg, 63%).

Data of Ex. 64: $C_{23}H_{27}N_5O_4$ (437.5). LC-MS (method 1a): $R_t$=1.86 (94), 438.2 ([M+H]$^+$).

Synthesis of Ex. 65

A soln of Ex. 64 (166 mg, 0.38 mmol) in MeOH/$CH_2Cl_2$ 2:1 (3 mL) was hydrogenated at rt for 4 h in the presence of palladium hydroxide on activated charcoal (moistened with 50% $H_2O$; 71 mg). The mixture was filtered through a pad of celite. The solid was washed with MeOH. The combined filtrate and washings were concentrated. The residue was dissolved in $CHCl_3$ and evaporated. The residue was dissolved in $CH_2Cl_2$ (3 mL), treated with 4 M HCl-dioxane (0.285 mL, 1.1 mmol). A precipitate was obtained which was filtered and washed (EtOAc) to afford Ex. 65.HCl (149 mg, 87%).

Data of Ex. 65.HCl: $C_{23}H_{29}N_3O_4$ (411.5). LC-MS (method 1a): $R_t$=1.35 (86), 412.2 ([M+H]$^+$).

Synthesis of Ex. 66

At 0° C., i-$Pr_2$NEt (0.076 mL, 0.45 mmol) was added dropwise to a soln of Ex. 65.HCl (50 mg, 0.11 mmol), phenylacetic acid (18 mg, 0.13 mmol), HATU (64 mg, 0.17 mmol) and HOAt (23 mg, 0.167 mmol) in DMF (0.5 mL). The mixture was stirred at 0° C. for 2 h. Aq. workup (EtOAc, 0.2 M HCl soln, $H_2O$, sat. aq. NaCl soln; $Na_2SO_4$) and prep. HPLC (method 3) afforded Ex. 66 (33 mg, 55%).

Data of Ex. 66: $C_{31}H_{35}N_3O_5$ (529.6). LC-MS (method 1a): $R_t$=1.89 (91), 530.2 ([M+H]$^+$).

Synthesis of Ex. 67 i-$Pr_2$NEt (0.031 mL, 0.18 mmol) was added to a soln of Ex. 62 (50 mg, 0.12 mmol) and phenyl isocyanate (17 mg, 0.15 mmol) in THF/DMF 1:1 (1.0 mL). The mixture was stirred at rt for 16 h followed by an aq. workup ($CHCl_3$, sat. aq. $Na_2CO_3$ soln; $Na_2SO_4$) and prep. HPLC (method 3) to afford Ex. 67 (46 mg, 72%).

Data of Ex. 67: $C_{30}H_{33}N_3O_6$ (531.6). LC-MS (method 1a): $R_t$=2.06 (90), 532.2 ([M+H]$^+$).

Synthesis of Ex. 50

3-Picolylamine (0.014 mL, 0.141 mmol) and i-$Pr_2$NEt (0.06 mL, 0.352 mmol) were slowly added to a cold solution of Ex. 42 (50 mg, 0.117 mmol), HATU (67 mg, 0.176 mmol) and HOAt (24 mg, 0.176 mmol) in DMF (0.5 mL). The mixture was stirred for 2 h at 4° C., followed by an aqueous workup ($CH_2Cl_2$, 1 M aq. HCl soln, sat. aq. NaCl soln; $Na_2SO_4$) and purification by prep HPLC (method 1c) to give Ex. 50.$CF_3CO_2H$ (28 mg, 37%).

Data of Ex. 50.$CF_3CO_2H$: cf. Table 15b.

$^1$H-NMR (DMSO-$d_6$ and $D_2O$): 8.90 (br. s, 1H); 8.50 (very br. s, 1H); 7.56 (s, 1H); 7.40 (br. s, 1H); 7.30 (very br. s, 1H); 7.01 (m, 2H); 6.88 (dd, J=2.9, 8.9, 1H); 6.78 (d, J=2.7, 1H); 4.60 (br. not resolved m, 2H); 4.08 (br. d, J=9.8, 1H); 3.98-3.89 (br. m, 2H); 3.71 (s, 3H); 3.51 (t, J=9.2, 1H); 2.84 (s, 3H); 2.43 (br. not resolved m, 1H), 2.21 (br. m, 1H); 1.96-1.76 (m, 2H); 1.00 (d, J=6.5, 3 H).

An analytical sample of Ex. 50.$CF_3CO_2H$ was dissolved in $CH_2Cl_2$ and washed with sat. aq. $Na_2CO_3$ soln. The organic phase was separated, dried ($Na_2SO_4$) and concentrated to give Ex. 50.

Data of Ex. 50: $^1$H-NMR (DMSO-$d_6$): 8.88 (t, J=6.0, 1H); 8.59 (d, J=1.6, 1H); 8.56 (dd, J=1.5, 4.8, 1H); 8.09 (d, J=8.2, 1H); 7.82 (td, J=1.9, 7.9, 1H); 7.67 (s, 1H); 7.50-7.44 (m, 2H); 7.32 (t, J=7.6, 1H); 7.13-7.08 (m, 2H); 6.95 (dd; J=3.1, 8.9, 1H); 6.87 (d, J=3.1, 1H); 4.43-4.40 (m, 2H); 4.15-3.96 (m, 3H); 3.80 (s, 3H); 3.57 (t, J ca 9.0, 1H); 2.91 (s, 3H); ca 2.5 (1H, superimposed by DMSO-d signal); 2.26 (br. dd, 1H); 1.98 (br. dd, 1H), 1.81 (dt; J=5.3, 10.0, 1H); 1.08 (d, J=6.7, 3 H).

Core 04: Synthesis of Ex. 68 and Ex. 69 (Scheme 11)

Synthesis of the Mitsunobu Product 54

ADDP (6.61 g, 26.2 mmol) was added to a mixture of the phenol 8 (3.98 g, 17.5 mmol), the alcohol 19 (4.59 g, 26.2 mmol) and $PPh_3$ (6.87 g, 26.2 mmol) in $CHCl_3$ (160 mL). The mixture was stirred at rt for 15 h. Silica gel (20 g) was added. The volatiles were evaporated and the residue was purified by FC (hexane/EtOAc 5:1) to give 54 (3.2 g, 48%).

Data of 54: $C_{22}H_{27}NO_5$ (385.5). LC-MS (method 2b): $R_t$=2.56 (90), 384.0 ([M−H]$^-$).

Synthesis of the Acid 55

LiOH.$H_2O$ (1.6 g, 38 mmol) was added to a solution of ester 54 (4.89 g, 12.7 mmol) in THF (72 mL), MeOH (24 mL) and $H_2O$ (24 mL). The mixture was stirred at rt for 4.5 h, partially concentrated, diluted with $H_2O$ (30 mL), acidified with 1 M aq. HCl soln (ca 40 mL) and extracted twice with EtOAc. The combined organic layer was dried ($Na_2SO_4$), filtered and concentrated to give 55 (4.67 g, 99%).

Data of 55: $C_{21}H_{25}NO_5$ (371.4). LC-MS (method 2a): $R_t$=1.32 (98), 369.9 ([M−H]$^-$).

Synthesis of the Amide 56

PyClu (2.2 g, 6.62 mmol) and i-$Pr_2NEt$ (2.95 mL, 17.3 mmol) were successively added to a solution of acid 55 (2.14 g, 5.76 mmol) and amine 24.HCl (2.52 g, 7.7 mmol), in DMF (50 mL). The mixture was stirred at rt for 1 h followed by an aq. workup ($Et_2O$, 0.5 M aq. HCl soln, $H_2O$, sat. aq. NaCl soln; $Na_2SO_4$). FC (hexane/EtOAc 7:3 to 4:6) afforded 56 (2.29 g, 61%).

Data of 56: $C_{37}H_{44}N_2O_8$ (644.8). LC-MS (method 1a): $R_t$=2.69 (95), 645.3 ([M+H]$^+$).

Synthesis of the Amino Ester 57

A soln of 56 (5.6 g, 8.66 mmol) in dry $CH_2Cl_2$ (75 mL) was treated with TFA (15 mL) at rt for 1 h. The volatiles were evaporated. Aq. workup ($CH_2Cl_2$, sat. aq. $NaHCO_3$ soln, sat. aq. NaCl soln; $Na_2SO_4$) of the residue gave 57 (4.93 g, quant. yield).

Data of 57: $C_{32}H_{36}N_2O_6$ (544.6). LC-MS (method 1a): $R_t$=1.88 (93), 545.2 ([M+H]$^+$).

Synthesis of Amino Acid 58

A degassed solution of ester 57 (4.7 g, 8.66 mmol) and 1,3-dimethylbarbituric acid (1.62 g, 10.4 mmol) in $CH_2Cl_2$ (73 mL) and EtOAc (73 mL) was treated with $Pd(PPh_3)_4$ (0.3 g, 0.26 mmol) at rt for 1.5 h. The volatiles were evaporated. The solid was suspended in EtOAc (200 mL), filtered and washed (EtOAc). The solid was suspended in $CH_2Cl_2$. The volatiles were evaporated. The residue was dried i.v. to yield 58 (3.94 g, 90%).

Data of 58: $C_{29}H_{32}N_2O_6$ (504.6). LC-MS (method 1a): $R_t$=1.61 (91), 505.2 ([M+H]$^+$).

Synthesis of Ex. 68

A soln of the amino acid 58 (3.45 g, 6.8 mmol) in $CH_2Cl_2$ (150 mL) was added dropwise over 2 h by syringe pump to a soln of T3P (50% in EtOAc; 10 mL, 17.1 mmol) and i-$Pr_2NEt$ (4.7 mL, 27.4 mmol) in dry $CH_2Cl_2$ (1250 mL). Partial evaporation of the volatiles, aq. workup (sat. aq. $NaHCO_3$ soln; $Na_2SO_4$) and FC($CH_2Cl_2$/MeOH 98.5:1.5) yielded Ex. 68 (2.57 g, 78%).

Data of Ex. 68: $C_{29}H_{30}N_2O_5$ (486.5). LC-MS (method 1d): $R_t$=2.23 (95), 486.9 ([M+H]$^+$).

Synthesis of Ex. 69

A soln of Ex. 68 (2.5 g, 5.2 mmol) in MeOH (50 mL) and $CH_2Cl_2$ (25 mL) was hydrogenated for 2 h at rt and normal pressure in the presence of palladium on activated charcoal (moistened with 50% $H_2O$; 1.9 g). The mixture was filtered through a pad of celite. The solid was washed with MeOH/$CH_2Cl_2$ 2:1. The combined filtrate and washings were concentrated to give Ex. 69 (2.0 g, 98%).

Data of Ex. 69: $C_{22}H_{24}N_2O_5$ (396.4). LC-MS (method 1a): $R_t$=1.58 (98), 397.1 ([M+H]$^+$). $^1$H-NMR (DMSO-$d_6$): 13.05 (br. s, 1H); 8.21 (br. s, 1H); 7.86-7.17 (several m, 6.33H); 7.06 (s, 0.66H); 6.96 (d, J=8.2, 0.66H); 6.90 (dd, J=1.9, 8.2, 0.33H); 4.49-4.31 (m, 1.66H); 4.15 (s, 2H); 3.57 (t, J=11.8, 0.33H); 2.91, 2.86 (2 br. s, 3H); 2.45-2.20 (m, 2.33H); 2.2-2.0 (m, 1.66H); 1.15-1.12 (2 d, 3H).

Core 05: Synthesis of Ex. 90, Ex. 91 and Ex. 92 (Scheme 12)

Synthesis of Amide 59

A mixture of acid 10.HCl (9.34 g, 31.8 mmol), amine 28.HCl (13.1 g, 41.3 mmol), HATU (19.3 g, 51 mmol) and HOAt (6.93 g, 51 mmol) in DMF (75 mL) was cooled to 0° C., followed by the addition of i-$Pr_2NEt$ (21.6 mL, 127 mmol). The mixture was stirred for 4 h and concentrated to ca 50% of its volume. The mixture was diluted with 1 M aq. HCl soln and extracted twice with EtOAc. The combined organic layer was washed ($H_2O$, sat. aq. $NaHCO_3$ soln,), dried ($Na_2SO_4$), filtered and concentrated. FC (hexane/EtOAc 50:50 to 20:80) of the crude product afforded 59 (13.4 g, 80%).

Data of 59: $C_{28}H_{29}N_3O_7$ (519.5). LC-MS (method 1a): $R_t$=1.89 (98), 520.0 ([M+H]$^+$).

Synthesis of Phenol 60

At 0° C. 3-(dimethylamino)propylamine (12.0 mL, 95.4 mmol) was slowly added to a soln of 59 (16.53 g, 31.8 mmol) in THF (110 mL). The soln was allowed to warm to rt over 2 h. Aqueous workup (EtOAc, 1 M aq. HCl soln, sat. aq. $NaHCO_3$ soln; $Na_2SO_4$) yielded 60 (14.45 g, 95%).

Data of 60: $C_{26}H_{27}N_3O_6$ (477.5). LC-MS (method 1a): $R_t$=1.67 (97), 478.1 ([M+H]$^+$).

Synthesis of the Mitsunobu Product 61

The phenol 60 (4.35 g, 9.1 mmol) and the alcohol 18 (3.56 g, 11.8 mmol) were dissolved in toluene (39 mL). CMBP (3.0 mL, 11.4 mmol) was added and the mixture was heated to reflux for 0.5 h. More CMBP (0.31 mL, 1.2 mmol) was added and the mixture was refluxed for 0.5 h followed by evaporation of the volatiles and FC (hexane/EtOAc 50:50 to 0:100) to afford 61 (5.25 g, 77%).

Data of 61: $C_{40}H_{49}N_5O_{10}$ (759.8). LC-MS (method 1a): $R_t$=2.24 (92), 760.2 ([M+H]$^+$).

Synthesis of the Amino Acid 63

A soln of 61 (11.8 g, 16 mmol) in THF (59 mL) and MeOH (30 mL) was treated with 2 M aq. LiOH soln (31 mL, 62 mmol) at rt for 2 h. The volatiles were partially evaporated. The remaining mixture was acidified to pH ca 1 by addition of 3 M aq. HCl soln and repeatedly extracted with EtOAc. The combined organic phase was dried ($Na_2SO_4$) and concentrated to afford crude acid 62 (12.6 g).

1,3-Dimethylbarbituric acid (3.2 g, 20.5 mmol) and acid 62 (12.5 g) were dissolved in $CH_2Cl_2$/EtOAc 1:1 (300 mL). The mixture was degassed, treated with $Pd(PPh_3)_4$ (1.98 g, 1.71 mmol) and stirred at rt for 2 h. The volatiles were evaporated. The residue was suspended in EtOAc and filtered to give 63 (9.80 g, 97%).

Data of 63: $C_{34}H_{41}N_5O_8$ (647.7). LC-MS (method 1c): $R_t$=1.51 (83), 648.1 ([M+H]$^+$).

Synthesis of Ex. 90

A soln of the amino acid 63 (2.0 g, 3.1 mmol) in DMF (50 mL) was added dropwise over 2 h by syringe pump to a soln of T3P (50% in EtOAc; 9.1 mL, 15 mmol) and i-$Pr_2NEt$ (4.2 mL, 25 mmol) in dry $CH_2Cl_2$ (600 mL). Partial evaporation of the volatiles, aq. workup (sat. aq. $NaHCO_3$ soln; $Na_2SO_4$) and FC($CH_2Cl_2$/MeOH 100:0 to 97:3) yielded Ex. 90 (1.18 g, 60%).

Data of Ex. 90: $C_{34}H_{39}N_5O_7$ (629.7). LC-MS (method 1d): $R_t$=2.00 (99), 630.0 ($[M+H]^+$). $^1$H-NMR (DMSO-$d_6$): 9.68, 9.62 (2 s, 1H); 9.18 (s, 1H); 9.11 (s, 1H); 8.97 (s, 1H); 8.41 (br. s, 1H); 7.58 (d, J=7.5, 1H); 7.40 (t, J=7.9, 1H); 7.40-7.20 (m, 5H); 7.17 (m, 1H); 6.94 (d, J=8.0, 1H); 5.15 (d, J=12.1, 0.5H); 5.12 (s, 1H); 5.01 (d, J=12.9, 0.5H); 4.55-4.15 (m, 4H); 4.15-3.5 (several m, 5H); 3.5-3.1 (several m, 3H); 2.11 (m, 1H); 1.91 (m, 1H); 1.40 (s, 9H).

Synthesis of Ex. 91

A soln of Ex. 90 (200 mg, 0.32 mmol) in MeOH (5 mL) was hydrogenated for 2 h at rt and normal pressure in the presence of palladium hydroxide on activated charcoal (moistened with 50% $H_2O$; 50 mg). The mixture was filtered through a pad of celite. The solid was washed with MeOH. The combined filtrate and washings were concentrated to give Ex. 91 (150 mg, 95%).

Data of Ex. 91: $C_{26}H_{33}N_5O_5$ (495.6). LC-MS (method 1a): $R_t$=1.48 (97), 496.1 ($[M+H]^+$). $^1$H-NMR (DMSO-$d_6$): 9.73 (br. s, 1H); 9.26 (t, J=1.9, 1H); 9.18 (d, J=1.9, 1H); 8.94 (d, J=1.9, 1H); 8.51 (s, 1H); 7.59 (d, J=7.7, 1H); 7.40 (t, J=7.9, 1H); 7.26 (d, J=6.5, 1H); 6.94 (dd; J=1.9, 8.1, 1H); 4.5-4.4 (m, 2H); 4.26 (m, 1H); 3.89 (t, J ca. 11.5, 1H); 3.67 (dd, J=7.2, 9.7, 1H); 3.53 (d, J=17.9, 1H); 3.39 (d, J=17.8, 1H); 3.21-3.08 (m, 3H); 2.55 (m, 1H); ca 2.45 (m, 1H); 2.11 (m, 1H); 1.89 (m, 1H); 1.40 (s, 9H).

Synthesis of Ex. 92

A soln of Ex. 90 (200 mg, 0.32 mmol) in dioxane (2 mL) was treated with 4 M HCl in dioxane (2 mL) for 15 h. The volatiles were evaporated. Purification by prep. HPLC (method 1c) afforded Ex. 92.2$CF_3CO_2H$ (89 mg, 37%) and Ex. 93.3$CF_3CO_2H$ (34 mg, 17%).

Data of Ex. 92.2 $CF_3CO_2H$: $C_{29}H_{31}N_5O_5$ (529.6, free base). LC-MS (method 1a): $R_t$=1.38 (98), 530.1 ($[M+H]^+$).

Data of Ex. 93.3 $CF_3CO_2H$: Cf Table 17b

Core 05: Synthesis of Selected Advanced Intermediates and Final Products (Scheme 12)

Synthesis of Ex. 94

A soln of Ex. 91 (137 mg, 0.28 mmol) in DCE (4.0 mL) was cooled to 0° C. Aq. formaldehyde soln. (36.5%; 0.104 mL, 1.38 mmol) was added followed by acetic acid (0.019 mL, 0.332 mmol) and $NaBH(OAc)_3$ (234 mg, 1.106 mmol). The mixture was stirred at 0° C. for 4 h followed by an aq. workup ($CH_2Cl_2$, sat. aq. $NaHCO_3$ soln). FC ($CH_2Cl_2$/MeOH 100:0 to 95:5) afforded Ex. 94 (119 mg, 84%).

Data of Ex. 94: cf. Table 17b $^1$H-NMR (DMSO-$d_6$): 9.60 (br. s, 1H); 9.21 (t, J=1.9, 1H); 9.17 (d, J=1.9, 1H); 8.93 (d, J=1.9, 1H), 8.48 (s, 1H); 7.58 (d, J=7.7, 1H); 7.39 (t, J=8.0, 1H); 7.28 (d, J=6.4, 1H); 6.94 (dd, J=1.9, 8.1, 1H); 4.45-4.41 (br, m, 2H); 4.26 (m, 1H); 3.88 (br. t, J ca 11.5, 1H); 3.68 (dd, J=7.2, 9.7, 1H); 3.45 (d, J=17.6, 1H); 3.89-3.21 (m, 3H, signal partially superimposed by $H_2O$ signal); 3.15 (t-like m, J ca 9, 1H); 2.62 (br. not resolved m, 2H), 2.37 (s, 3H); 2.11 (m, 1H); 1.90 (m, 1H); 1.41 (s, 9H).

Synthesis of Ex. 95

A soln of Ex. 94 (100 mg, 0.196 mmol) in dioxane (1.0 mL) was treated with 4 M HCl-dioxane (1.0 mL) for 2 h. The volatiles were evaporated to afford Ex. 95.3HCl (116 mg, quant.).

Data of Ex. 95.3HCl: cf. Table 17b

Synthesis of Ex. 96

At 0° C., i-$Pr_2NEt$ (0.11 mL, 0.65 mmol) was slowly added to a soln of Ex. 95.3HCl (97 mg, 0.19 mmol), 2-naphthaleneacetic acid (49 mg, 0.26 mmol), HATU (124 mg, 0.326 mmol) and HOAt (44 mg, 0.323 mmol) in DMF (1.0 mL). The mixture was stirred at at 0° C. for 2 h and distributed between $CH_2Cl_2$ and 1 M aq. HCl soln. The organic phase was washed (sat. aq. NaCl soln), dried ($Na_2SO_4$), filtered and concentrated. FC ($CH_2Cl_2$/MeOH 100:0 to 95:5) and prep. HPLC (method 1b) afforded Ex. 96.2$CF_3CO_2H$ (62 mg, 41%).

Data of Ex. 96: cf. Table 17b $^1$H-NMR (DMSO-$d_6$): Ca. 9.7 (very br. s, 1H); 9.28 (very br. s, 1H); 9.14 (br. s, 1H); 8.96 (very br. s, 1H); 8.62 (d, J=5.4, 1H); 8.54 (br. s, 1H); 8.30 (br. s, 1H); 7.90-7.85 (m, 3H); 7.77 (s, 1H); 7.65 (d, J=7.6, 1H); 7.53-7.41 (m, 4H); 6.98 (d, J=8.3, 1H); 4.55-4.33 (2 br. not resolved m, 5H); 4.01 (t, J=11.2, 1H); 3.85 (br. t, J ca 8.4, 1H); 3.65 (br. not resolved m, 2H); 3.63 (s, 2H); 3.39 (br. not resolved m, 2H); 3.11 (t, J=9.0, 1H); 2.89 (s, 3H); 2.26 (m, 1H); 2.04 (m, 1H).

Synthesis of Ex. 101

A soln of 1-naphthaleneacetic acid (43 mg, 0.23 mmol) and T3P (50% in DMF; 0.17 mL; 0.29 mmol) in DMF (0.3 mL) was added dropwise to a suspension of Ex. 95.3HCl (50 mg, 0.096 mmol) in DMF (0.2 mL). The mixture was stirred at rt for 15 h followed by an aqueous workup ($CHCl_3$, sat. aq. $Na_2CO_3$ soln; $Na_2SO_4$) and purification by prep. HPLC (method 1a) to afford Ex. 101.2 $CF_3CO_2H$ (38 mg, 49%).

Data of Ex. 101.2 $CF_3CO_2H$: cf. Table 17b $^1$H-NMR (DMSO-$d_6$): 9.71 (very br. s, 1H); 9.26 (d, J=1.9, 1H); 9.13 (br. s, 1H); 8.93 (d, J=1.5, 1H); 8.68 (d, J=5.6, 1H); 8.52 (br. s, 1H); 8.30 (s, 1H); 8.10 (m, 1H), 7.93 (m, 1H); 7.84 (dd, J=1.9, 7.3, 1H); 7.66 (d, J=7.7, 1H); 7.57-7.41 (m, 5H); 6.98 (dd, J=1.8, 8.3, 1H); 4.55-4.39 (2 br. not resolved m, 5H); 4.04-3.94 (m, 3H); 3.83 (br. t, J ca 8.5, 1H); 3.68 (br. not resolved m, 2H); 3.41 (br. not resolved m, 2H); 3.12 (t, J=9.0, 1H); 2.89 (s, 3H); 2.26 (m, 1H); 2.03 (m, 1H).

Synthesis of Ex. 103

At 4° C., $Et_3N$ (0.04 mL, 0.29 mmol) and then benzenesulfonyl chloride (17 mg, 0.096 mmol) were added to a soln of Ex. 95.3HCl (50 mg, 0.096 mmol) in $CH_2Cl_2$ (0.5 mL). The mixture was stirred at rt for 15 h; i-$Pr_2NEt$ (0.049 mL, 0.29 mmol) and more benzenesulfonyl chloride (17 mg, 0.096 mmol) were added. Stirring was continued for 1 h followed by an aqueous workup ($CHCl_3$, sat. aq. $Na_2CO_3$ soln, $Na_2SO_4$) and purification by prep. HPLC (method 1a) to afford Ex. 103.2 $CF_3CO_2H$ (33 mg, 44%).

Data of Ex. 103.2 $CF_3CO_2H$: cf. Table 17b $^1$H-NMR (DMSO-$d_6$): 9.69 (br. s, 1H); 9.24 (d, J=1.9, 1H); 9.09 (br. s, 1H); 8.92 (d, J=1.6, 1H); 8.47 (br. s, 1H); 8.30 (br. s, 1H); 8.22 (br. s, 1H); 7.90-7.88 (m, 2H); 7.74-7.63 (m, 4H); 7.41 (t, J=7.9, 1H); 6.93 (dd; J=1.9, 8.2, 1H); ca. 4.5-4.2 (m, 4H); 4.00 (br. not resolved m, 1H); 3.89

(t, J ca. 11.4, 1H); 3.69-3.63 (m, 3H); 3.42 (br. not resolved m, 2H); 3.23 (dd, J=8.4, 9.7; 1H); 2.91 (s, 3H); 2.02 (m, 1H); 1.88 (m, 1H).

Synthesis of Ex. 97

3-Fluorobenzaldehyde (50 mg, 0.40 mmol) was added to a soln of Ex. 91 (120 mg, 0.24 mmol) in THF (1.5 mL). The soln was stirred at rt for 1 h followed by the addn of acetic acid (0.015 mL, 0.27 mmol) and $NaBH(OAc)_3$ (154 mg, 0.73 mmol). The mixture was stirred at rt for 16 h. More 3-fluorobenzaldehyde (15 mg, 0.12 mmol) was added and stirring continued. Aq. workup ($CH_2Cl_2$, sat. aq. $Na_2CO_3$ soln; $Na_2SO_4$) and FC ($CH_2Cl_2$/MeOH) afforded Ex. 97 (117 mg, 80%).

Data of Ex. 97: cf. Table 17b

Synthesis of Ex. 98

A soln of Ex. 97 (94 mg, 0.156 mmol) in dioxane (0.8 mL) was treated with 4 M HCl-dioxane (0.8 mL) for 2 h. The volatiles were evaporated to afford Ex. 98.3HCl (91 mg, 95%).

Data of Ex. 98.3HCl: cf. Table 17b

Synthesis of Ex. 100

A soln of Ex. 98.3HCl (62 mg, 0.10 mmol) in $CH_2Cl_2$ (0.6 mL) was treated with pyridine (0.041 mL, 0.51 mmol) and acetyl chloride (16 mg, 0.2 mmol) at rt for 16 h. i-$Pr_2NEt$ (0.052 mL, 0.3 mmol) and more acetyl chloride (16 mg, 0.2 mmol) were added and stirring was continued for 24 h followed by an aqueous workup ($CHCl_3$, sat. aq. $Na_2CO_3$ soln; $Na_2SO_4$) and purification by prep. HPLC (method 1a) to afford Ex. 100.2 $CF_3CO_2H$ (50 mg, 64%).

Data of Ex. 100.2 $CF_3CO_2H$: cf. Table 17b $^1$H-NMR (DMSO-$d_6$): Ca. 9.5 (br. s, 1H); 9.23 (s, 2H); 8.96 (d, J=1.0, 1H); 8.45 (br. s, 1H); 8.17 (d, J=6.5, 1H); 7.62 (d, J=7.7, 1H); 7.42 (t, J=7.9, 1H); ca 7.4 (br. not resolved m, 1H); ca 7.35-7.25 (br. not resolved m, 2H); 7.15 (br. t-like m, 1H); 6.97 (dd; J=1.9, 8.2, 1H); 4.52-4.39 (m, 4H); ca 4.2-3.8 (br. not resolved m, 3H); 3.90 (t, J=11.3, 1H); 3.71 (t-like m, 2H); 3.49 (m, 1H); 3.33 (br. t-like m, 1H); 3.07 (t, J=9.0, 1H); 2.95 (br. not resolved m, 2H); 2.14 (m, 1H); 1.89 (m, 1H); 1.81 (s, 3H).

Core 06/07: Synthesis of Ex. 115, Ex. 116 and Ex. 129, Ex. 130 (Scheme 13)

Synthesis of the Arylbromide 65

2-Bromothiophenol (11; 2.71 mL, 23 mmol) was added to a soln of 30 (5.0 g, 19.1 mmol) and CMBP (6.02 mL, 23 mmol) in toluene (50 mL). The mixture was heated to reflux for 1 h. The volatiles were evaporated. FC (hexane/EtOAc 4:1) afforded 65 7.31 g, 88%)

Data of 65: $C_{18}H_{26}BrNO_4S$ (432.3). LC-MS (method 1c): $R_t$=2.58 (97), 434.0/431.9 ([M+H]$^+$).

Synthesis of the Biphenyl 66

Sat. aq. $NaHCO_3$ soln (37.8 mL) was added dropwise to a soln of 65 (5.0 g, 11.6 mmol), 3-hydroxyphenylboronic acid (12, 4.79 g, 34.7 mmol) and $Pd(PPh_3)_4$ (1.34 g, 1.16 mmol) in DME (150 mL). The mixture was heated to reflux for 4 h. The volatiles were evaporated and the residue was distributed between EtOAc and sat. aq. $Na_2CO_3$ soln. The organic phase was repeatedly washed (sat. aq. $Na_2CO_3$ soln), dried ($Na_2SO_4$), filtered and concentrated. FC($CH_2Cl_2$/EtOAc 100:0 to 95:5) afforded 66 (3.91 g, 75%).

Data of 66: $C_{24}H_{31}NO_5S$ (445.5). LC-MS (method 1a): $R_t$=2.46 (94), 446.1 ([M+H]$^+$).

Synthesis of the Phenol 68

At 0° C., TFA (11.9 mL) was slowly added to a soln of 66 (2.38 g, 5.34 mmol) in $CH_2Cl_2$ (24 mL). Stirring was continued for 1 h followed by evaporation of the volatiles. The residue was dissolved in $CHCl_3$ and concentrated to afford 67-$CF_3CO_2H$ as a brown oil which was dissolved in $CH_2Cl_2$ (12 mL) and cooled to 0° C. i-$Pr_2NEt$ (2.73 mL, 16.0 mmol) was slowly added. Allyl chloroformate (0.63 mL, 5.88 mmol) in $CH_2Cl_2$ (12 mL) was added over 30 min. The mixture was stirred for 2 h followed by evaporation of the volatiles. Aqueous workup (EtOAc, sat. aq. $NaHCO_3$ soln; $Na_2SO_4$) and FC (hexane/EtOAc 9:1 to 7:3) yielded 68 (2.02 g, 88%).

Data of 68: $C_{23}H_{27}NO_5S$ (429.5). LC-MS (method 1a): $R_t$=2.29 (92), 430.1 ([M+H]$^+$).

Synthesis of the Ether 69

A soln of ADDP (1.34 g, 5.31 mmol) in degassed $CHCl_3$ (5.0 mL) was added at 0° C. to a soln of 68 (1.52 g, 3.54 mmol), Boc-D-alaminol (20; 0.93 g, 5.31 mmol) and $PPh_3$ (1.39 g, 5.31 mmol) in $CHCl_3$ (20 mL). The mixture was stirred at 0° C. to rt for 16 h. More Boc-D-alaminol (20; 0.93 g, 5.31 mmol) and $PPh_3$ (1.39 g, 5.31 mmol) were added. The mixture was cooled to 0° C. followed by the slow addition of ADDP (1.34 g, 5.31 mmol) in $CHCl_3$ (5.0 mL). The mixture was stirred at rt for 16 h. The volatiles were evaporated. The residue was suspended in $Et_2O$ and filtered. The filtrate was concentrated and purified by FC (hexane/EtOAc 4:1 to 3:1) to afford 69 (1.6 g, 77%). Data of 69: $C_{31}H_{42}N_2O_7S$ (586.7). LC-MS (method 1a): $R_t$=2.78 (97), 587.1 ([M+H]$^+$).

Synthesis of the Amino Acid 71

A soln of 69 (3.2 g, 5.5 mmol) in THF (17 mL) and MeOH (17 mL) was treated at 0° C. with 1 M aq. LiOH soln (6.5 mL, 6.5 mmol). The mixture was allowed to stir at 0° C. to rt for 16 h. The volatiles were evaporated. The residue was distributed between EtOAc and 0.2 M aq. HCl soln. The organic phase was dried ($Na_2SO_4$) and concentrated to afford crude acid 70 (3.02 g) which was dissolved in dioxane (12.5 mL) and treated with 4 M HCl-dioxane (7.9 mL) for 4 h. The volatiles were evaporated. The residue was taken up in $CHCl_3$ and concentrated to afford crude 71.HCl (2.84 g, quant. yield) which was used without further purification.

Data of 71.HCl: $C_{25}H_{32}N_2O_5S$.HCl (472.6, free base). LC-MS (method 1a): $R_t$=1.76 (89), 473.1 ([M+H]$^+$).

Synthesis of Ex. 115

A soln of crude 71.HCl (0.94 g, 1.8 mmol) in $CH_2Cl_2$ (45 mL) was added over 2 h to a soln of T3P (50% in EtOAc; 2.7 mL, 4.6 mmol) and i-$Pr_2NEt$ (1.3 mL, 7.4 mmol) in $CH_2Cl_2$ (1810 mL). The soln was partially concentrated, washed with sat. aq. $NaHCO_3$ soln, dried ($Na_2SO_4$), filtered and concentrated. FC (hexane/EtOAc 8:2 to 1:1) gave Ex. 115 (0.63 g, 75%).

Data of Ex 115: $C_{25}H_{30}N_2O_4S$ (454.6). LC-MS (method 1d): $R_t$=2.35 (95), 455.0 [M+H]$^+$). $^1$H-NMR (DMSO-$d_6$):

7.57-7.52 (m, 2H); 7.38-7.21 (m, 5H); 7.01-6.95 (m, 2H); 6.90 (d, J=7.9, 1H), 5.90 (m, 1H); 5.29 (d, J=17.2, 1H); 5.17 (d, J=10.0, 1H); 4.47-4.45 (m, 2H); 4.13-3.97 (m, 3H); 3.82 (q, J=6.5, 1H); 2.60-2.57 (m, 2H); 1.57-1.09 (m, 6H); 1.19 (d, J=6.5, 3 H).

Synthesis of Ex. 116

A soln of Ex. 115 (120 mg, 0.26 mmol) in degassed EtOAc/$CH_2Cl_2$ 1:1 (2.1 mL) was treated at rt for 16 h with $Pd(PPh_3)_4$ (1.2 mg) and 1,3-dimethylbarbituric acid (49 mg, 0.32 mmol). The volatiles were evaporated and the residue purified by FC (hexane/EtOAc 50:50 to 0:100, then $CH_2Cl_2$/MeOH 100:0 to 90:10) to afford Ex. 116 (82 mg, 83%).

Data of Ex. 116: $C_{21}H_{26}N_2O_2S$ (370.5). LC-MS (method 1a): $R_t$=1.74 (95), 371.1 ([M+H]$^+$).

$^1$H-NMR (DMSO-$d_6$): 7.76 (d, J=7.1, 1H); 7.55 (m, 1H); 7.37-7.26 (m, 4H); 7.07 (t-like m, 1H); 6.98 (dd-like m, 1H); 6.87 (d-like m, J ca 7.9, 1H), 4.14-4.01 (m, 3H); 3.32 (t, J=5.0, 1H); 2.67-2.55 (m, 2H); ca 2.6 (very br. s, 2H); 1.56 (m, 1H); 1.38-1.03 (m, 5H); 1.21 (d, J=6.3, 3H).

Synthesis of Ex. 129

At 0° C., mCPBA (70%, 876 mg, 3.55 mmol) was added in portions to a soln of Ex. 115 (808 mg, 1.78 mmol) in $CH_2Cl_2$ (17 mL). The mixture was stirred at 0° C. to rt for 2 h and concentrated, followed by an aq. workup (EtOAc, sat. aq. $NaHCO_3$ soln, 1 M aq. $Na_2S_2O_3$ soln; $Na_2SO_4$). FC (hexane/EtOAc 50:50 to 0:100) gave Ex. 129 (788 mg, 91%).

Data of Ex. 129:$C_{25}H_{30}N_2O_6S$ (486.6). LC-MS (method 1a): $R_t$=1.91 (93), 487.1 ([M+H]$^+$). $^1$H-NMR (DMSO-$d_6$): 8.06 (dd, J=1.3, 7.9, 1H); 7.77 (dt, J=1.4, 7.5, 1H); 7.68 (dt, J=1.4, 7.7, 1H); 7.49-7.44 (m, 2H); 7.39 (t, J=8.0, 1H); 7.09-7.03 (m, 3H); 6.73 (s, 1H); 5.88 (m, 1H); 5.27 (d, J=17.3, 1H); 5.17 (d, J=10.3, 1H); 4.45 (d, J=4.9, 2 H); 4.08-3.96 (m, 3H); 3.75 (q-like m, J=7.6, 1H); 2.45 (br. m, 2H); 1.45-1.01 (m, 5H); 1.23 (d, J=6.8, 3 H); 1.01 (m, 1H).

Synthesis of Ex. 130

A soln of Ex. 129 (100 mg, 0.21 mmol) in degassed EtOAc/$CH_2Cl_2$ 1:1 (1.7 mL) was treated at rt for 3 h with $Pd(PPh_3)_4$ (1.0 mg) and 1.3-dimethylbarbituric acid (39 mg, 0.25 mmol). The volatiles were evaporated and the residue purified by FC (hexane/EtOAc 50:50 to 0:100, then $CH_2Cl_2$/MeOH 100:0 to 90:10) to afford Ex. 130 (82 mg, 98%).

Data of Ex. 130: $C_{21}H_{26}N_2O_4S$ (402.5). LC-MS (method 1a): $R_t$=1.48 (94), 403.0 ([M+H]$^+$).

Core 06: Synthesis of Selected Advanced Intermediates and Final Products (Scheme 13)

Synthesis of Ex. 119

At 0° C., i-$Pr_2NEt$ (0.055 mL, 0.324 mmol) was slowly added to a solution of Ex. 116 (40 mg, 0.108 mmol), 1-pyrrolidineacetic acid (17 mg, 0.13 mmol), HATU (62 mg, 0.162 mmol) and HOAt (22 mg, 0.162 mmol) in DMF (0.5 mL). The mixture was stirred for 2 h at 0° C., followed by an aqueous workup (EtOAc, sat. aq. $NaHCO_3$ soln, $H_2O$, sat. aq. NaCl soln; $Na_2SO_4$) and purification by prep HPLC (method 3) to give Ex. 119 (30 mg, 57%).

Data of Ex. 119: cf. Table 18b.

Core 08/09: Synthesis of Ex. 143, Ex. 144 and Ex. 168, Ex. 169 (Scheme 14)

Synthesis of Thioether 72

5-Bromopyridine-3-thiol (13; 1.0 g, 5.3 mmol) was added to a soln of alcohol 30 (1.06 g, 4.0 mmol) and CMBP (1.17 g, 4.85 mmol) in toluene (15 mL). The mixture was heated to reflux for 1 h. The volatiles were evaporated. FC (hexane/EtOAc 4:1) of the residue gave 72 (1.35 g, 77%).

Data of 72: $C_{17}H_{25}BrN_2O_4S$ (433.6). LC-MS (method 1c): $R_t$=2.37 (93), 433.0/435.0 ([M+H]$^+$).

Synthesis of Phenol 73

At rt, sat. aq. $NaHCO_3$ soln (17.1 mL) was added to a soln of 72 (2.65 g, 6.1 mmol), 2-hydroxyphenylboronic acid (14; 2.53 g, 18.3 mmol) and $Pd(PPh_3)_4$ (707 mg, 0.61 mmol) in DME (78 mL). The mixture was heated to reflux for 1 h followed by an aq. workup (EtOAc, sat. aq. $Na_2CO_3$ soln; $Na_2SO_4$) and FC (hexane/EtOAc 2:1 to 1:1) to afford 73 (2.42 g, 88%).

Data of 73: $C_{23}H_{30}N_2O_5S$ (446.6). LC-MS (method 1a): $R_t$=1.82 (96), 447.1 ([M+H]$^+$).

Synthesis of Phenol 75

At 0° C., a soln of 73 (500 mg, 1.12 mmol) in $CH_2Cl_2$ (4.0 mL) was treated with TFA (3.0 mL) for 2 h and concentrated. Aq. workup (EtOAc, sat. aq. $NaHCO_3$ soln; $Na_2SO_4$) afforded crude 74 which was dissolved in $CH_2Cl_2$ (4.0 mL). The soln was cooled to 0° C. A soln of AllocOSu (245 mg, 1.23 mmol) in $CH_2Cl_2$ (1.0 mL) was added dropwise. Stirring was continued for 2 h followed by an aq. workup ($CH_2Cl_2$, sat. aq. $NaHCO_3$ soln; $Na_2SO_4$) and FC (hexane/EtOAc 1:1) to yield 75 (310 mg, 64%).

Data of 75: $C_{22}H_{26}N_2O_5S$ (430.5). LC-MS (method 1a): $R_t$=1.68 (94), 431.1 ([M+H]$^+$).

Synthesis of the Ether 76

At 0° C., ADDP (967 mg, 3.83 mmol) was added in portions to a soln of alcohol 20 (672 mg, 3.83 mmol), phenol 75 (1.1 g, 2.55 mmol) and $PPh_3$ (1.0 g, 3.83 mmol) in $CHCl_3$ (15 mL). The mixture was stirred for 4 h at rt and concentrated. FC (hexane/EtOAc 4:1 to 2:1) afforded 76 (450 mg, 30%).

Data of 76: $C_{30}H_{41}N_3O_7S$ (587.7). LC-MS (method 1a): $R_t$=2.33 (87), 588.2 ([M+H]$^+$).

Synthesis of the Amino Acid 78

At 0° C., 1 M aq. LiOH (0.67 mL, 0.67 mmol) was added to a soln of 76 (430 mg, 0.73 mmol) in THF/MeOH 2:1 (1.5 mL). The mixture was stirred at 0° C. to rt for 5 h and distributed between EtOAc and 0.2 M aq. HCl soln. The organic phase was separated, dried ($Na_2SO_4$), filtered and concentrated. FC($CH_2Cl_2$/MeOH 100:0 to 80:20) gave acid 77 (288 mg) which was dissolved in dioxane (1 mL) and treated with 4 M HCl-dioxane (1.15 mL) for 6 h at rt. The volatiles were evaporated. The residue was suspended in EtOAc, filtered and dried i.v. to afford 78.2HCl (256 mg, 64%).

Data of 78.2HCl: $C_{24}H_{31}N_3O_5S$.2HCl (473.6, free base). LC-MS (method 1c): $R_t$=1.39 (92), 474.1 ([M+H]$^+$).

Synthesis of Ex. 143

A soln of 78.2HCl (200 mg, 0.37 mmol) and i-$Pr_2NEt$ (0.125 mL, 0.73 mmol) in $CH_2Cl_2$ (5 mL) was added dropwise over 2 h (syringe pump) to a soln of T3P (50% in EtOAc; 0.65 mL, 1.1 mmol) and i-$Pr_2NEt$ (0.188 mL, 1.1 mmol) in $CH_2Cl_2$ (177 mL). Aq. Workup ($CH_2Cl_2$, sat. aq. $NaHCO_3$ soln; $Na_2SO_4$) and FC (hexane/EtOAc 50:50 to 0:100) afforded Ex. 143 (105 mg, 63%).

Data of Ex. 143: $C_{24}H_{29}N_3O_4S$ (455.5). LC-MS (method 1d): $R_t$=1.66 (98), 456.0 ([M+H]$^+$). $^1$H-NMR (DMSO-$d_6$): 8.52 (d, J=2.2, 1H); 8.40 (d, J=1.9, 1H); 8.36 (s, 1H); 8.11 (d, J=5.5, 1H); 7.45-7.39 (m, 2H); 7.20 (d, J=7.6, 1H); 7.14 (d, J=8.2, 1H); 7.08 (t, J=7.5, 1H); 5.88 (m, 1H); 5.28 (d, J=16.5, 1H); 5.16 (d, J=10.4, 1 H); 4.44 (d, J=5.2, 2 H); 4.17-3.97 (m, 4H); 3.06 (m, 1H); 2.89 (m, 1H); 1.85 (m, 1H); ca 1.6-1.3 (m, 5H); 1.09 (d, J=6.3, 3 H).

Synthesis of Ex. 144

A degassed solution of Ex. 143 (200 mg, 0.44 mmol) in degassed $CH_2Cl_2$/EtOAc 1:1 (11 mL) was treated at rt for 2 h with $Pd(PPh_3)_4$ (2.0 mg) and 1,3-dimethylbarbituric acid (82 mg, 0.53 mmol). The volatiles were evaporated. FC (hexane/EtOAc 50:50 to 0:100 and then $CH_2Cl_2$/MeOH 99:1 to 95:5) gave Ex. 144 (128 mg, 78%).

Data of Ex. 144: $C_{20}H_{25}N_3O_2S$ (371.5). LC-MS (method 1a): $R_t$=1.30 (97), 371.9 ([M+H]$^+$). $^1$H-NMR (DMSO-$d_6$): 8.52 (d, J=2.2, 1H); 8.40 (d, J=2.0, 1H); 8.16 (t, J=2.1, 1H); 7.77 (d, J=6.4, 1H); 7.45-7.39 (m, 2H); 7.16 (d, J=7.9, 1H); 7.07 (dt; J=0.8, 7.1, 1H); 4.13-4.04 (m, 2H); 3.97 (br. not resolved m, 1H); 3.21 (t-like m, 1H); 3.08-2.89 (m, 2H); 2.01 (br. s, 2H); 1.74-1.18 (several m, 6H); 1.12 (d, J=6.5, 3 H).

Synthesis of Ex. 168

$H_2O_2$ (35% in $H_2O$; 0.043 mL; 0.49 mmol) was added to a soln of Ex. 143 (32 mg, 0.07 mmol) in AcOH (1.0 mL). The mixture was stirred at rt for 20 h; after 2 h and after 3 h, 16 h and 17 h more $H_2O_2$ (35% in $H_2O$; 0.043 mL; 0.49 mmol) had been added. The mixture was diluted with $H_2O$ and extracted with EtOAc. The organic phase was dried ($Na_2SO_4$), filtered and concentrated to yield Ex. 168 (28 mg, 82%).

Data of Ex. 168: $C_{24}H_{29}N_3O_6S$ (487.5). LC-MS (method 1a): $R_t$=1.78 (92), 488.1 ([M+H]$^+$). $^1$H-NMR (DMSO-$d_6$): 8.99 (d, J=2.2, 1H); 8.91 (d, J=1.9, 1H); 8.52 (s, 1H); 7.86 (d, J=4.9, 1H); 7.49-7.44 (m, 2H); 7.17-7.08 (m, 3H); 5.86 (m, 1H); 5.26 (d, J=18.6, 1H); 5.15 (d, J=9.9, 1H); 4.42 (m, 2H); 4.11-3.95 (m, 3H); 3.87 (q-like m, 1H); 3.56 (m, 1H); 3.35 (m, 1H); ca 1.70 (m, 1H); ca 1.65 (m, 1H); 1.40-1.10 (m, 4H); 1.06 (d, J=6.1, 3 H).

Synthesis of Ex. 169

A soln of Ex. 168 (2.19 g, 4.5 mmol) and 1,3-dimethylbarbituric acid (2.1 g, 13.5 mmol) in degassed EtOAc/$CH_2Cl_2$ 1:1 (65 mL) was treated at rt for 2 h with $Pd(PPh_3)_4$ (260 mg). The volatiles were evaporated and the residue purified by FC ($CH_2Cl_2$/MeOH 100:0 to 95:5) to afford Ex. 169 (1.81 g, quant. yield).

Data of Ex. 169: $C_{20}H_{25}N_3O_4S$ (403.5). LC-MS (method 1a): $R_t$=1.34 (96), 403.9 ([M+H]$^+$). $^1$H-NMR (DMSO-$d_6$): 8.97 (d, J=2.2, 1H); 8.92 (d, J=2.0, 1H); 8.39 (t, J=2.1, 1H); 7.64 (d, J=6.5, 1H); 7.49-7.42 (m, 2H); 7.17 (d, J=8.0, 1H); 7.11 (t, J=7.4, 1H); 4.11-3.97 (m, 3H); 3.63 (m, 1H); 3.40 (m, 1H); 3.07 (m, 1H); 1.98 (br. s, 2H); 1.58 (quint, J=7.1, 2 H); 1.27-1.16 (m, 2H); 1.09 (d, J=6.0, 3 H); 1.09 (m, 1H), 0.97 (m, 1H).

Core 10/11: Synthesis of the B-$A_B$-$A_C$ Fragment 84 (Scheme 15)

Synthesis of the Allylester 79

Oxalyl chloride (1.8 mL, 20.4 mmol) and DMF (26 μL) were added to a suspension of 10.HCl (2.0 g, 6.8 mmol) in $CHCl_3$ (50 mL). The mixture was stirred at rt for 1 h and concentrated (at 35° C.). The residue was suspended in THF (50 mL) and cooled to 0° C. Allyl alcohol (1.4 mL, 20.4 mmol) and $Et_3N$ (2.9 mL, 20.4 mmol) were added.

The mixture was stirred at rt for 1 h followed by an aq. workup (EtOAc, 1 M aq. HCl soln, sat. aq. $NaHCO_3$ soln, sat. aq. NaCl soln; $Na_2SO_4$). FC (hexane/EtOAc 3:1) yielded 79 (1.78 g, 88%).

Data of 79: $C_{17}H_{15}NO_4$ (297.3). LC-MS (method 1b): $R_t$=1.96 (99), 298.0 ([M+H]$^+$).

Synthesis of the Phenol 80

3-Dimethylaminopropylamine (2.3 mL, 17.9 mmol) was added at rt to a soln of 79 (1.77 g, 5.9 mmol) in THF (65 mL). The soln was stirred at rt for 3 h followed by an aq. workup (EtOAc, 1 M aq. HCl soln, sat. aq. $NaHCO_3$ soln, sat. aq. NaCl soln; $Na_2SO_4$) to afford 80 (1.27 g, 83%).

Data of 80: $C_{15}H_{13}NO_3$ (255.3). LC-MS (method 1a): $R_t$=1.65 (91), 255.9 ([M+H]$^+$).

Synthesis of the Arylether 81

A soln of ADDP (1.56 g, 6.2 mmol) in degassed $CHCl_3$ (10 mL) was slowly added to a soln of 80 (1.26 g, 4.9 mmol), (S)-tert-butyl 2-(hydroxymethyl)pyrrolidine-1-carboxylate (21; 0.83 g, 4.12 mmol) and $PPh_3$ (1.62 g, 6.2 mmol) in degassed $CHCl_3$ (20 mL). The soln was stirred at rt for 15 h followed by evaporation of the volatiles. The residue was suspended in $Et_2O$ and filtered. The filtrate was concentrated and purified by FC (hexane/EtOAc 4:1) to afford 81 (1.78 g, 98%).

Data of 81: $C_{25}H_{30}N_2O_5$ (438.5). LC-MS (method 1a): $R_t$=2.58 (98), 439.1 ([M+H]$^+$).

Synthesis of Acid 84

A soln of 81 (1.76 g, 4.0 mmol) in MeOH/THF 1:1 (30 mL) was treated with 2 M aq. LiOH soln (4.0 mL, 8.0 mmol) for 1 h at rt. The mixture was concentrated. The residue was distributed between EtOAc and 1 aq. HCl soln. The organic phase was washed (sat. aq. NaCl soln), dried ($Na_2SO_4$), filtered and concentrated to give crude 82.HCl (1.5 g) which was dissolved in dioxane (15 mL) and treated with 4 M HCl-dioxane (30 mL) for 2.5 h at rt. The mixture was concentrated and repeatedly treated with $CHCl_3$ and concentrated to obtain crude 83.2HCl (1.79 g).

To a soln of crude 83.2HCl (1.24 g) in THF (11 mL) was added 2 M aq NaOH soln (5.3 mL). The mixture was cooled to 0° C. A soln of allyl chloroformate (0.34 mL, 3.2 mmol) in THF (5 mL) was added dropwise over 30 min (syringe pump). Stirring was continued for 30 min followed by an aq.

workup ($CH_2Cl_2$, 1 M aq. HCl soln; $Na_2SO_4$) and purification by prep. HPLC (method 1d) to yield 84.$CF_3CO_2H$ (0.93 g, 67%).

Data of 84.$CF_3CO_2H$: $C_{21}H_{22}N_2O_5$.$CF_3CO_2H$ (382.4, free form). LC-MS (method 1a): $R_t$=1.80 (99), 383.0 ([M+H]$^+$). $^1$H-NMR (DMSO-$d_6$): ca 13.5 (br. s, 1H); 9.12 (s, 1H); 9.06 (d, J=1.9, 1H); 8.48 (s, 1H); 7.46-7.34 (m, 3H); 7.06 (d, J=7.4, 1H); 5.92 (m, 1H); 5.31-5.15 (m, 2H); 4.61-4.48 (m, 2H); 4.23-4.02 (m, 3H); 3.37-3.35 (m, 2H); ca 2.1-1.8 (m, 4H).

Core 10: Synthesis of Ex. 193a,c-h and Ex. 194b (Scheme 15)

Procedure C.1:

General Procedure for the Synthesis of Ex. 193a-h and Ex. 194b (Scheme 15)

1. Synthesis of resins 85a-h: Immobilisation of Fmoc-AA1-OH

2-Chlorotrityl chloride resin (matrix: copoly(styrene-1% DVB), 100-200 mesh, loading: 1.3 mmol/g; 10 g, 13 mmol) was suspended in dry $CH_2Cl_2$ (100 mL), shaken for 50 min and filtered. The resin was suspended in dry $CH_2Cl_2$ (80 mL). A soln of Fmoc-AA1-OH (10.3 mmol) and i-$Pr_2$NEt (4.4 mL, 26 mmol) in DMF (20 mL) was added. The mixture was shaken at rt for 2.7 h with $N_2$ bubbling through. The resin was filtered and washed ($CH_2Cl_2$, DMF, $CH_2Cl_2$). Capping: The resin was shaken in $CH_2Cl_2$/MeOH/i-$Pr_2$NEt 15:2:3 (100 mL) for 0.5 h and filtered. The capping step was repeated twice. The resin was filtered, washed ($CH_2Cl_2$, DMF, $CH_2Cl_2$, MeOH) and dried i.v. to afford resin 85.

| Resin | Chlorotrityl-chlorid resin | Fmoc-AA1-OH | Yield/Loading (mass increase) |
|---|---|---|---|
| 85a, h | 5 g | Fmoc-β$^3$-homoPhe-OH | 6.79 g/0.72 mmol/g |
| 85b, e, f, g | 10 g | Fmoc-NMe-β$^3$-homoDAla-OH | 13.0 g/0.78 mmol/g |
| 85c, d | 10 g | Fmoc-β-Ala-OH | 12.5 g/0.73 mmol/g |

2. Synthesis of Ex. 193a,c-h and Ex. 194b

Fmoc Cleavage: The resin 85 (90-110 mg, ca 70 μmol) was swollen, in DMF (1 mL) for 1 h and filtered. Then it was suspended in a soln of 2% v/v DBU in DMF (1 mL), shaken for 10 min, filtered off and washed (DMF). The deprotection step was repeated once. The resin was filtered and washed (DMF).

Coupling of Fmoc-AA2-OH: The resin 86 was suspended in DMF (1 mL). i-$Pr_2$NEt (280 μmol), Fmoc-AA2-OH (140 μmol) and HATU (140 μmol) were added. The mixture was shaken for 40 min, filtered and washed (DMF). The coupling step was repeated once. The resin 87 was filtered and washed (DMF).

Fmoc Cleavage: The resin was treated with 2% v/v DBU in DMF (1 mL) as described above to yield resin 88.

Coupling of Alloc-protected amino acid 84: The resin 88 was suspended in DMF (1 mL)[1)]. i-$Pr_2$NEt (560 μmol), 84 (35 mg, 70 μmol) and PyBOP (140 μmol) were added. The mixture was shaken for 1 h and filtered. The resin was washed (DMF). The coupling step was repeated once. The resin 89 was filtered and washed (DMF, $CH_2Cl_2$).

[1)] Ex. 193c,d: Coupling of 84 was performed in DMF/NMP 6:1

Alloc Cleavage: The resin 89 was suspended in $CH_2Cl_2$ (1 mL). Phenylsilane (0.18 mL; 1.45 mmol)[2)] and $Pd(PPh_3)_4$ (8 mg, 7 μmol) were added. The mixture was shaken for 15 min and filtered. The deprotection step was repeated once. The resin 90 was filtered and washed ($CH_2Cl_2$, DMF, MeOH, $CH_2Cl_2$).

[2)] Ex. 193c,d: 0.09 mL/0.7 mmol Phenylsilane was used

Release of the cyclization precursor: The resin 90 was treated with HFIP/$CH_2Cl_2$ 2:3 (1 mL) for 30 min, filtered and washed ($CH_2Cl_2$). The cleavage step was repeated once. The combined filtrates and washings were concentrated and dried i.v. to afford crude 91a-h.

Ring closure and cleavage of side chain protective groups: Crude 91 was dissolved in dry DMF (4 mL)[3)] and i-$Pr_2$NEt (96 μL; 560 μmol) was added. This soln was then added dropwise to a soln of FDPP (40 mg, 105 μmol) in DMF (20 mL)[3)]. The soln was stirred at rt for 15 h and the volatiles were evaporated. The residue was treated with sat. aq. $Na_2CO_3$ soln (4 mL) and extracted with $CHCl_3$ (9 mL). The organic layer was filtered through a pad of $MgSO_4$. The filtrate was concentrated and purified by prep. HPLC to afford Ex. 193a,c-h.

[3)] Ex. 193c,d: Ring closure was performed in a total volume of 12 mL of DMF

Crude Ex. 193b was dissolved in $CH_2Cl_2$ (0.7 mL) and treated with TFA (0.3 mL) at rt for 3 h. The volatiles were evaporated and the residue was purified by prep. HPLC to give Ex. 194b.

Purification methods applied, yields, LC-MS data and systematic names of Ex. 193a,c-h and Ex. 194b are indicated in Table 22.

Ex. 193a: $^1$H-NMR (DMSO-$d_6$): 9.21 (d, J=2.1, 1H); 8.80 (t, J=2.0, 1H); 8.64 (d, J=1.8, 1H); 8.50 (d, J=9.0, 1H); 8.30 (s, 1H); 7.65 (d, J=7.7, 1H); 7.40 (t, J=7.9, 1 H); 7.30-7.10 (m, 5H); 6.94 (dd, J=1.8, 8.2, 1H); 5.23 (q, J=7.2, 1H); 4.50 (d, J=11.6, 1H); 4.36-4.26 (m, 2H); 3.82 (t, J=11.2, 1H); 3.20-3.17 (m, 2H); 2.99-2.70 (m, 2H); 2.81 (s, 3H); ca 2.50 (m, 2H; superimposed by DMSO-d signal); 2.09-1.77 (m, 4H); 1.34 (d, J=7.2, 3 H).

Ex. 194b: $^1$H-NMR (DMSO-$d_6$, addition of $D_2O$): Two sets of signals were observed; ratio 9:1; signals of major isomer: 9.17 (d, J=2.0, 1H); 8.64 (s, 1H); 8.59 (d, J=1.7, 1H); 8.09 (s, 1H); 7.57 (d, J=7.8, 1H); 7.40 (t, J=7.9, 1H); 6.93 (dd, J=1.6, 8.2, 1H); 5.54 (t-like m, 1H); 4.56-4.53 (m, 2H); 4.31 (m, 1H); 3.68 (t, J=11.3, 1H); 3.55 (br. t-like m, 1H); 3.36 (br. q-like m, 1H); 2.81 (s, 3H); 2.80 (s, 3H); 2.62-2.60 (m, 2H); 2.31-2.27 (m, 2H); ca 2.1-1.75 (m, 6H); 1.12 (d, J=6.8; 3 H).

Core 11: Synthesis of Ex. 195a,b,e-h,j; Ex. 196c,i,k and Ex. 197d (Scheme 16)

Procedure C.2:

General Procedure for the Synthesis of Ex. 195a,b,e-h,j; Ex. 196c,i,k and Ex. 197d (Scheme 16)

1. Synthesis of Resins 135a-k: Immobilisation of Fmoc-AA1-OH

2-Chlorotrityl chloride resin (matrix: copoly(styrene-1% DVB), 100-200 mesh, loading: 1.3 mmol/g; 10 g, 13 mmol) was suspended in dry $CH_2Cl_2$ (100 mL), shaken for 50 min and filtered. The resin was suspended in dry $CH_2Cl_2$ (80 mL). A soln of Fmoc-AA1-OH (10.3 mmol) and i-$Pr_2$NEt (4.4 mL, 26 mmol) in DMF (20 mL) was added. The mixture was shaken at rt for 2.7 h with $N_2$ bubbling through. The resin was filtered and washed ($CH_2Cl_2$, DMF, $CH_2Cl_2$). Capping: The resin was shaken in $CH_2Cl_2$/MeOH/i-$Pr_2$NEt 15:2:3 (100 mL) for 0.5 h and filtered. The capping step was repeated twice. The resin was filtered, washed ($CH_2Cl_2$, DMF, $CH_2Cl_2$, MeOH) and dried i.v. to afford resin 135.

| Resin | Chlorotrityl-chlorid resin | Fmoc-AA1-OH | Yield/Loading (mass increase) |
|---|---|---|---|
| 135a-d | 10 g | Fmoc-NMe-β[3]-homoDAla-OH | 13.0 g/0.78 mmol/g |
| 135e, f, h, j | 1 g | Fmoc-Sar-OH | 1.34 g/0.80 mmol/g |
| 135g | 1 g | Fmoc-Gly-OH | 1.22 g/0.70 mmol/g |
| 135i | 1 g | Fmoc-Ala-OH | 1.28 g/0.67 mmol/g |
| 135k | 2 g | Fmoc-DAla-OH | 2.35 g/0.71 mmol/g |

2. Synthesis of Ex. 195a,b,e-h,j; Ex. 196c,i,k and Ex. 197d

Fmoc Cleavage: The resin 135 (90-107 mg, ca 70 μmol) was swollen in DMF (1 mL) for 1 h and filtered. Then it was suspended in a soln of 2% v/v DBU in DMF (1 mL), shaken for 10 min filtered and washed (DMF). The deprotection step was repeated once. The resin 136 was filtered and washed (DMF).

Coupling of Fmoc-AA2-OH: The resin 136 was suspended in DMF (1 mL). i-$Pr_2NEt$ (280 μmol), Fmoc-AA2-OH (140 μmol) and HATU (140 μmol) were added. The mixture was shaken for 40 min, filtered and washed (DMF). The coupling step was repeated once. The resin 137 was filtered and washed (DMF).

Fmoc Cleavage: The resin 137 was treated with 2% v/v DBU in DMF (1 mL) as described above to afford resin 138.

Coupling of Fmoc-AA3-OH: The resin 138 was suspended in DMF (1 mL). i-$Pr_2NEt$ (280 μmol), Fmoc-AA3-OH (140 μmol) and HATU (140 μmol) were added. The mixture was shaken for 40 min, filtered and washed (DMF). The coupling step was repeated once. The resin 139 was filtered and washed (DMF).

Fmoc Cleavage: The resin 139 was treated with 2% v/v DBU in DMF (1 mL) as described above to afford resin 140.

Coupling of Alloc-protected amino acid 84: The resin 140 was suspended in DMF (1 mL). i-$Pr_2NEt$ (560 μmol), 84 (36 mg, 84 μmol) and PyBOP (140 μmol) were added. The mixture was shaken for 1 h and filtered. The resin 141 was washed (DMF). The coupling step was repeated once. The resin was filtered and washed (DMF, $CH_2Cl_2$).

Alloc Cleavage: The resin 141 was suspended in $CH_2Cl_2$ (1 mL). Phenylsilane (0.18 mL; 1.4 mmol) and $Pd(PPh_3)_4$ (8 mg, 7 μmol) were added. The mixture was shaken for 15 min and filtered. The deprotection step was repeated once. The resin 142 was filtered and washed ($CH_2Cl_2$, DMF, MeOH, $CH_2Cl_2$).

Release of the cyclization precursor: The resin 142 was treated with HFIP/$CH_2Cl_2$ 2:3 (1 mL) for 30 min, filtered and washed ($CH_2Cl_2$). The cleavage step was repeated once. The combined filtrates and washings were concentrated, taken up in $CH_3CN$ (3 mL), concentrated and dried i.v. to afford crude 143a-k.

Ring closure and cleavage of side chain protective groups: Crude 143 was dissolved in a soln of i-$Pr_2NEt$ (98 μL; 570 μmol) in dry DMF (4 mL). This soln was then added dropwise to a soln of FDPP (41 mg, 106 μmol) in DMF (20 mL). The soln was stirred at rt for 5 h and the volatiles were evaporated. The residue was treated with sat. aq. $Na_2CO_3$ soln (4 mL) and extracted with $CHCl_3$ (9 mL). The organic layer was filtered through a pad of $MgSO_4$. The filtrate was concentrated to afford crude Ex. 195a-k. Crude products Ex. 195a,b,e-h,j were purified by prep. HPLC to afford Ex. 195a,b,e-h,j.

A soln of crude product Ex. 195c,d,i or k in TFA/$CH_2Cl_2$ 3:7 (1 mL) was stirred at rt for 3 h. The volatiles were evaporated. The residue was dissolved in $CH_2Cl_2$, concentrated, dried i.v. and purified by prep. HPLC to afford Ex. 196c,i,k or Ex. 197d, respectively.

Purification methods applied, yields, LC-MS data and systematic names of Ex. 195a, b,e-h,j; Ex. 196c,i,k and Ex. 197d are indicated in Table 23a.

Ex. 195b: $^1H$-NMR ($CD_3OD$): 9.16 (d, J=2.1, 1H); 8.97 (t, J=2.1, 1H); 8.94 (d, J=2.0, 1H); 7.57-7.39 (m, 3H); 7.00 (m, 1H); 5.23 (m, 1H); ca 4.8 (1H, superimposed by HDO signal); 4.40 (d, J=16.8, 1H); ca. 4.4 (br. m, 1H), 4.28 (dd; J=3.8, 8.1, 1H); 3.73 (d, J=16.8, 1H); 3.77-3.60 (m, 3H); 2.98 (s, 3H); 2.65 (dd, J=2.4, 13.6, 1H); 2.37 (t, J=12.8, 1H); 2.20-2.02 (m, 4H); 1.46 (d, J=7.0, 3 H); 1.15 (d, J=7.0, 3 H).

Ex. 195h: $^1H$-NMR ($CD_3OD$): Two sets of signals were observed; ratio 1:1; 9.06 (d, J=2.0, 0.5H); 9.00 (d, J=2.0, 0.5H); 8.97 (d, J=1.9, 0.5H); 8.84 (d, J=1.9, 0.5H); 8.72 (t, J=2.1, 0.5H); 8.50 (t, J=2.1, 0.5H); 7.88 (s, 0.5H); 7.65 (s, 0.5H); 7.50-7.35 (m, 2H); 7.32-7.19 (m, 3.5H); 7.09-6.93 (m, 2.5H); 5.89 (d, J=16.7, 0.5H); 5.26-5.20 (q-like m, 1H), 4.79 (q, J=7.2, 0.5H); 4.65 (dd, J ca 4.7, 11.8, 1H); 4.51 (dt-like m, 1H); 4.50 (br. m, 0.5H); 4.05 (d, J=7.2, 1H); 3.90 (t, J=9.6, 0.5H); 3.75-3.44 (m, 3.5H); 3.23 (dd, J=4.5, 13.9, 0.5H); 3.12-3.05 (m, 1H); 2.98 (s, 3H); 2.24-2.04 (m, 4H); 1.43 (d, J=7.0, 1.5H); 1.36 (d, J=7.2, 1.5H).

Core 12: Synthesis of Ex. 198, Ex. 199 and Ex. 200 (Scheme 17)

Synthesis of the Mitsunobu Product 144

CMBP (9.9 mL, 38 mmol) was added to a soln of the hydroxypyridine 93 (4.32 g, 19 mmol) and the alcohol 16 (6.5 g, 22 mmol) in toluene (200 mL). The mixture was heated to 80° C. for 1 h. The volatiles were evaporated. FC (hexane/EtOAc/MeOH gradient) afforded 144 (8.60 g, 90%).

Data of 144: $C_{27}H_{33}N_3O_7$ (511.6). LC-MS (method 1a): $R_t$=1.91 (98), 512.3 ($[M+H]^+$).

Synthesis of the Carboxylic Acid 145

A soln of the ester 144 (6.56 g, 13 mmol) in MeOH (23 mL), THF (92 mL) and $H_2O$ (23 mL) was treated with $LiOH.H_2O$ (1.6 g, 38 mmol) at rt for 16 h. $H_2O$ (50 mL) was added followed by 1 M aq. HCl soln (100 mL). The mixture was repeatedly extracted with EtOAc. The combined organic phases were washed (sat. aq. NaCl soln), dried ($Na_2SO_4$), filtered and concentrated to give 145 (6.19 g, 96%).

Data of 145: $C_{26}H_{31}N_3O_7$ (497.5). LC-MS (method 1a): $R_t$=1.62 (97), 498.0 ($[M+H]^+$).

Synthesis of Amide 146

A mixture of acid 145 (6.19 g, 12 mmol), amine 28.HCl (3.6 g, 11 mmol), and HATU (5.7 g, 15 mmol) was dissolved in DMF (197 mL), followed by the addition of i-$Pr_2NEt$ (6.6 mL, 39 mmol). The mixture was stirred for 2 h. The mixture was diluted with sat. aq. $Na_2CO_3$ soln and extracted with $CH_2Cl_2$. The organic layer was dried ($Na_2SO_4$), filtered and concentrated. The residue was dissolved in EtOAc, washed ($H_2O$, sat. aq. NaCl soln), dried ($Na_2SO_4$), filtered and concentrated. FC (hexane/EtOAc 1:3) afforded 146 (7.1 g, 74%).

Data of 146: $C_{40}H_{49}N_5O_{10}$ (759.8). LC-MS (method 1a): $R_t$=2.04 (92), 760.1 ($[M+H]^+$).

Synthesis of the Carboxylic Acid 147

A soln of the ester 146 (7.07 g, 9.3 mmol) in MeOH (57 mL), THF (171 mL) and $H_2O$ (57 mL) was treated with $LiOH.H_2O$ (1.2 g, 28 mmol) at rt for 16 h. The mixture was poured onto ice/1 M aq. HCl soln (50 mL) and repeatedly extracted with EtOAc. The combined organic phases were washed (sat. aq. NaCl soln), dried ($Na_2SO_4$), filtered and concentrated to give 147 (6.8 g, quant. yield).

Data of 147: $C_{38}H_{45}N_5O_{10}$ (731.8). LC-MS (method 1c): $R_t$=1.81 (94), 731.9 ($[M+H]^+$).

Synthesis of Amino Acid 148

A degassed solution of ester 147 (6.8 g, 9.3 mmol) and 1,3-dimethylbarbituric acid (4.4 g, 28 mmol) in $CH_2Cl_2$ (67 mL) and EtOAc (68 mL) was treated with $Pd(PPh_3)_4$ (0.54 g, 0.46 mmol) at rt for 2 h. The volatiles were evaporated. FC($CH_2Cl_2$/MeOH 99:1 to 80:20) afforded 148 (5.6 g, 93%).

Data of 148: $C_{34}H_{41}N_5O_8$ (647.7). LC-MS (method 1a): $R_t$=1.45 (91), 648.0 ($[M+H]^+$).

Synthesis of Ex. 198

A solution of 148 (1.08 g, 1.7 mmol) and $i\text{-}Pr_2NEt$ (0.86 mL, 5.0 mmol) in dry DMF (40 mL) was added over 3 h (syringe pump) to a soln of HATU (1.27 g, 3.33 mmol) in DMF (1620 mL). The volatiles were evaporated. Aq. Workup (EtOAc, sat. aq. $NaHCO_3$ soln, $H_2O$, sat. aq. NaCl soln; $Na_2SO_4$) and FC (EtOAc/MeOH 95:5) afforded Ex. 198 (0.65 g, 62%).

Data of Ex. 198: $C_{34}H_{39}N_5O_7$ (629.7). LC-MS (method 1d): $R_t$=1.61 (99), 630.3 ($[M+H]^+$). $^1$H-NMR (DMSO-$d_6$): Three sets of broad signals were observed; 8.44 (br. d, J ca 3.7, 0.5H); 8.32, 8.28 (2 d, J=3.8, 3.9, 0.5H); 7.86-7.18 (m, 13H); 5.12-4.83 (m, 2H); 4.59-3.46 (several m, 7H); 3.32-2.72 (several m, 5H); 2.40-2.25 (m, 1H), 2.15-1.90 (m, 1H); 1.40, 1.39 (2 s, 9H).

Synthesis of Ex. 199

A soln of Ex. 198 (0.85 g, 1.34 mmol) in dioxane (17 mL) was treated with 4 M HCl dioxane soln (17 mL) for 1 h at rt. The volatiles were evaporated. The residue was suspended in $Et_2O$, filtered, washed with $Et_2O$ and dried to afford Ex. 199.2HCl (836 mg; quant. yield).

Data of Ex. 199.2HCl: $C_{29}H_{31}N_5O_5$.2HCl (529.6, free base). LC-MS (method 2c): $R_t$=1.40 (94), 530.2 ($[M+H]^+$).

Synthesis of Ex. 200

A soln of Ex. 198 (1.2 g, 1.91 mmol) in MeOH (40 mL) was hydrogenated for 2 h at rt and normal pressure in the presence of palladium hydroxide on activated charcoal (moistened with 50% $H_2O$; 250 mg). The mixture was filtered through a pad of celite. The solid was washed with MeOH. The combined filtrate and washings were concentrated to give Ex. 200 (0.87 g, 92%).

Data of Ex. 200: $C_{26}H_{33}N_5O_5$ (495.6). LC-MS (method 1a): $R_t$=1.15 (97), 496.2 ($[M+H]^+$). $^1$H-NMR (DMSO-$d_6$): two sets of signals were observed; 8.38 (br. s, 0.3H); 8.33 (d, J=4.2, 0.7H), 7.75-7.41 (m, 7H), 7.18 (br. s, 1H); 4.20-4.13 (m, 2H); 3.93-3.87 (t-like m, 2H); 3.76-3.73 (d-like m, 1H); 3.14-2.70 (several m, 4H); 2.45-2.30 (m, 2H), 2.01 (d, J=15.9, 1H), 1.85 (br. not resolved m, 1H); 1.70 (d-like m, 1H); 1.41, 1.37 (2 s, 9H).

Core 13-15: Synthesis of the Common Precursor 151 (Scheme 18)

Synthesis of the Amide 149

A soln of 98 (7.96 g, 33.4 mmol), 129.HCl (7.19 g, 36.8 mmol) and BOP (16.3 g, 36.8 mmol) in DMF (120 mL) was cooled to 0° C. $i\text{-}Pr_2NEt$ (22.7 mL, 134 mmol) was slowly added and stirring was continued for 30 min. Aqueous workup (EtOAc, aq. 1 M HCl soln, sat. aq. $NaHCO_3$ soln, sat. aq. NaCl soln; $Na_2SO_4$) followed by FC (hexane/EtOAc 2:1) afforded 149 (10.8 g, 85%).

Data of 149: $C_{18}H_{18}FNO_5S$ (379.4). LC-MS (method 1a): $R_t$=1.98 (90), 380.2 ($[M+H]^+$)

Synthesis of the Amine 151

A suspension of phenol 149 (8.79 g, 23.2 mmol), alcohol 16 (8.35 g, 27.8 mmol) and $PPh_3$ (9.11 g, 34.8 mmol) in benzene (278 mL) was degassed and cooled to 0° C. DEAD (40% in toluene; 15.9 mL, 34.8 mmol) was added dropwise. The mixture was stirred at rt for 16 h and concentrated. The residue was suspended in $Et_2O$ and filtered. The filtrate was concentrated and purified by FC (hexane/EtOAc, $Et_3N$ 66:33:1) to give 150 (15.4 g).

A degassed soln of 150 (15.4 g) and 1,3-dimethylbarbituric acid (5.45 g, 34.9 mmol) in $CH_2Cl_2$ (150 mL) and EtOAc (450 mL) was treated with $Pd(PPh_3)_4$ (0.67 g, 0.58 mmol) at rt for 1 h. Aqueous workup (EtOAc, sat.aq. $NaHCO_3$ soln, sat. aq. NaCl soln; $Na_2SO_4$) and FC (EtOAc, then $CH_2Cl_2$/MeOH 95:5) afforded 151 (8.18 g, 61%).

Data of 151: $C_{28}H_{36}FN_3O_7S$ (577.6). LC-MS (method 1a): $R_t$=1.87 (96), 578.4 ($[M+H]^+$)

Core 13: Synthesis of Ex. 220, Ex. 221 and Ex. 222 (Scheme 18)

Synthesis of Amide 152

At 0° C., acryloyl chloride (0.37 mL, 4.57 mmol) was slowly added to a soln of 151 (2.2 g, 3.81 mmol) and $i\text{-}Pr_2NEt$ (0.78 mL, 4.57 mmol) in $CH_2Cl_2$ (33 mL). The mixture was stirred for 0.5 h followed by an aqueous workup ($CH_2Cl_2$, 0.1 M aq. HCl soln, sat. aq. $NaHCO_3$ soln, sat. aq. NaCl soln; $Na_2SO_4$) and FC (hexane/EtOAc 1:1 to 3:7) to afford 152 (2.21 g, 91%).

Data of 152: $C_{31}H_{38}FN_3O_8S$ (631.7). LC-MS (method 4a): $R_t$=1.60 (94), 632.1 ($[M+H]^+$)

Synthesis of Ex. 220

The catalyst Umicore M72 SIMes (RD) (64 mg, 0.075 mmol) was added in one portion to a degassed solution of 152 (240 mg, 0.38 mmol) in toluene (380 mL) and heated to 100° C. for 0.5 h. The mixture was cooled to rt. More Umicore M72 SIMes (RD) catalyst (64 mg) was added and the mixture was heated to 100° C. for 30 min; this operation was repeated once again. 2-Mercaptonicotinic acid (59 mg, 0.38 mmol) was added and the heating to 100° C. was continued for 1 h. The mixture was concentrated. Aqueous workup (EtOAc, sat. aq. $NaHCO_3$ soln; $Na_2SO_4$) and FC (hexane/EtOAc 50:50 to 0:100) followed by prep. HPLC (method 3) afforded Ex. 220 (42 mg, 18%).

Data of Ex. 220: $C_{29}H_{34}FN_3O_8S$ (603.6). LC-MS (method 1f): $R_t$=2.18 (89), 604.0 ($[M+H]^+$)

Synthesis of Ex. 221

A soln of Ex. 220 (0.49 g, 0.8 mmol)) in MeOH (80 mL) was hydrogenated for 2 h at rt and normal pressure in the presence palladium hydroxide on activated charcoal (moistened with 50% $H_2O$; 304 mg). The mixture was filtered through a pad of $Na_2SO_4$ and celite. The solid was washed with $CH_2Cl_2$/MeOH 1:1 (300 mL). The combined filtrate and washings were concentrated to give Ex. 221 (0.25 g, 51%).

Data of Ex. 221: $C_{29}H_{36}FN_3O_8S$ (605.7). LC-MS (method 2f): $R_t$=2.43 (90), 606.2 ([M+H]$^+$). $^1$H-NMR ($CDCl_3$): 8.67 (d, J=1.2, 1H); 8.01 (s, 1H); 7.69 (d, J=1.2, 1H); 7.52 (d, J=8.5, 1H); 6.98 (d, J=8.7, 1H); 6.55 (td, J=2.2, 10.2, 1H); 4.97 (td, J=2.9, 8.7, 1H); 4.82 (br. m, not resolved, 1H); 4.69 (d-like m, 1H); 4.61 (br. not resolved m, 1H); 4.31-4.22 (m, 2H); 4.04-3.90 (m, 3H); 3.80 (s, 3H); 3.74 (dd, J=2.8, 10.8, 1H); 3.65 (m, 1H); 3.46 (m, 1H); 2.53-2.41 (m, 3H); 2.02-1.88 (m, 3H); 1.48 (s, 9H).

Synthesis of Ex. 222

A soln of Ex. 221 (233 mg. 0.39 mmol) in dioxane (1 mL) was treated with 4 M HCl in dioxane (5 mL) for 2 h at rt. The volatiles were evaporated. The residue was suspended in $Et_2O$, filtered and dried i.v. to afford Ex. 222.HCl (180 mg, 86%).

Data of Ex. 222.HCl: $C_{24}H_{28}FN_3O_6S$ (505.6, free base). LC-MS (method 1d): $R_t$=1.55 (92), 506.2 ([M+H]$^+$).

Core 14: Synthesis of Ex. 227, Ex. 228 and Ex. 229 (Scheme 18)

Synthesis of Amide 153

At 0° C., i-$Pr_2$NEt (2.2 mL, 13.0 mmol) was added dropwise to a soln of 151 (2.5 g, 4.3 mmol), but-3-enoic acid (0.48 g, 5.6 mmol), HATU (2.47 g, 6.5 mmol) and HOAt (0.88 g, 6.5 mmol) in DMF (60 mL). The mixture was stirred for 1.5 h at 0° C. followed by an aqueous workup (EtOAc, 1 M aq. HCl soln, sat. aq. $NaHCO_3$ soln, sat. aq. NaCl soln; $Na_2SO_4$) and FC (hexane/EtOAc 2:1 to 1:2) to give 153 (2.36 g, 84%).

Data of 153: $C_{32}H_{40}FN_3O_8S$ (645.7). LC-MS (method 4b): $R_t$=1.67 (96), 646.2 ([M+H]$^+$).

Synthesis of Ex. 227

A solution of 153 (110 mg, 0.17 mmol) and the catalyst Umicore M72 SIMes (RD) (58 mg, 0.068 mmol) in $CH_2Cl_2$ (70 mL) was degassed and heated to reflux for 2 h. The mixture was allowed to cool to rt. 2-Mercaptonicotinic acid (106 mg, 0.68 mmol) was added. The mixture was heated to reflux for 1 h. The mixture was washed with sat. aq. $NaHCO_3$ soln. The organic phase was dried ($Na_2SO_4$), filtered and concentrated. The crude product was purified by prep. HPLC (method 3) to afford Ex. 227 (56 mg, 53%).

Data of Ex. 227: $C_{30}H_{36}FN_3O_8S$ (617.7). LC-MS (method 1d): $R_t$=2.32 (87), 618.2 ([M+H]$^+$). $^1$H-NMR (DMSO-$d_6$): 8.38 (s, 1H), 8.27-8.24 (m, 2H); 7.90 (s, 1H); 7.28-7.18 (m, 2H); 6.70 (td, J=2.1, 10.6, 1H); 5.97 (td, J=5.9, 15.8, 1H); 5.66 (td, J=4.6, 15.7, 1H); 4.75-4.63 (m, 2H); 4.31 (br. not resolved m, 1H); 4.06-3.67 (m, 7H); 3.67 (s, 3H); 3.24 (dd, J=6.4, 10.5, 1H); 3.11 (br. m, 2H); 2.30 (m, 1H); 1.92 (m, 1H); 1.39 (s, 9H).

Synthesis of Ex. 228

Trimethyltin hydroxide (263 mg; 1.46 mmol) was added to a solution of Ex. 227 (300 mg, 0.49 mmol) in DCE (15 mL). The mixture was heated to 80° C. for 16 h, followed by aqueous workup ($CH_2Cl_2$, 1 M aq. HCl soln, sat. aq. NaCl soln; $Na_2SO_4$) to afford Ex. 228 (350 mg, containing tin salts). An analytical sample was purified by prep. RP-HPLC (method 2a) followed by aqueous extraction ($CH_2Cl_2$, 1 M aq. HCl soln; $Na_2SO_4$) to give Ex. 228 (13 mg).

Data of Ex. 228: $C_{29}H_{34}FN_3O_8S$ (603.6). LC-MS (method 1a): $R_t$=2.17 (92), 604.0 ([M+H]$^+$).

Synthesis of Ex. 229

A soln of Ex. 227 (287 mg, 0.46 mmol) in dioxane (5 mL) was treated with 4 M HCl in dioxane (5 mL) for 5 h at rt and concentrated. The residue was suspended in $Et_2O$ and filtered to afford Ex. 229.HCl (240 mg, 93%).

Data of Ex. 229.HCl: $C_{25}H_{28}FN_3O_6S$.HCl (517.6, free base). LC-MS (method 1a): $R_t$=1.49 (92), 518.1 ([M+H]$^+$). $^1$H-NMR (DMSO-$d_6$): 8.38 (br. s, 4H), 8.28 (s, 1H); 8.22 (d, J=8.0, 1H); 7.82 (s, 1H); 7.29 (d, J=9.4, 1H); 6.73 (d, J=10.6, 1H); 5.98 (td, J=6.0, 15.6, 1H); 5.69 (td, J=4.8, 15.8, 1H); 4.74-4.65 (m, 2H); 4.39 (m, 1H); 4.04-3.85 (m, 5H); 3.85-3.65 (m, 2H); 3.67 (s, 3H); 3.44 (dd, J=7.1, 10.5, 1H); 3.14 (d, J=5.6, 2 H), 2.50 (m, 1H); 2.04 (m, 1H).

Core 15: Synthesis of Ex. 242, Ex. 243 and Ex. 244 (Scheme 18)

Synthesis of Ex. 242

A soln of Ex. 227 (1.5 g, 2.4 mmol)) in MeOH (75 mL) was hydrogenated for 2.5 h at rt and normal pressure in the presence of 5% palladium on activated charcoal (moistened with 50% $H_2O$; 300 mg). The mixture was filtered through a pad of celite. The solid was washed with MeOH. The combined filtrate and washings were concentrated. FC (hexane/EtOAc 1:2) gave Ex. 242 (1.37 g, 91%).

Data of Ex. 242: $C_{30}H_{38}FN_3O_8S$ (619.7). LC-MS (method 1a): $R_t$=2.47 (92), 620.0 ([M+H]$^+$). $^1$H-NMR (DMSO-$d_6$): 8.51 (d, J=1.1, 1H); 8.29 (d, J=1.1, 1H); 8.07 (d, J=7.9, 1H); 7.95 (s, 1H); 7.30-7.26 (m, 2H), 6.70 (td, J=2.1, 10.5, 1H); 4.70 (m, 1H); 4.60 (br. dd, 1H); 4.29 (br. not resolved m, 1H); 4.04-3.67 (m, 5H); 3.67 (s, 3H); 3.48 (br. not resolved m, 2H); 3.28 (m, 1H); 2.38-2.23 (m, 3H); 1.91 (m, 1H), 1.77 (m, 1H); 1.68-1.51 (m, 3H); 1.39 (s, 9H).

Synthesis of Ex. 243

Trimethyltin hydroxide (175 mg; 0.97 mmol) was added to a solution of Ex. 242 (200 mg, 0.32 mmol) in DCE (10 mL). The mixture was heated to 80° C. for 16 h, followed by aqueous workup ($CH_2Cl_2$, 1 M aq. HCl soln, sat. aq. NaCl soln; $Na_2SO_4$) to afford Ex. 243 (236 mg, containing tin salts). An analytical sample was purified by prep. RP-HPLC (method 2a) followed by aqueous extraction ($CH_2Cl_2$, 1 M aq. HCl soln; $Na_2SO_4$) to give Ex. 243 (14 mg).

Data of Ex. 243: $C_{29}H_{36}FN_3O_8S$ (605.7). LC-MS (method 1a): $R_t$=2.27 (97), 606.2 ([M+H]$^+$).

Synthesis of Ex. 244

A soln of Ex. 242 (265 mg, 0.43 mmol) in dioxane (5 mL) was treated with 4 M HCl in dioxane (5 mL) for 6 h at rt and concentrated. The residue was taken up in $CHCl_3$ and concentrated to afford Ex. 244.HCl (205 mg, 86%).

Data of Ex. 244.HCl: $C_{25}H_{30}FN_3O_6S$.HCl (519.6, free base). LC-MS (method 1d): $R_t$=1.55 (92), 520.0 ([M+H]$^+$).

$^{1}$H-NMR (DMSO-$d_6$): 8.48 (s, 1H); 8.40-8.25 (br. s, 4H); 8.05 (d, J=7.9, 1H); 7.86 (s, 1H); 7.31 (d, J=8.8, 1H); 6.73 (d, J=10.6, 1H); 4.72-4.61 (m, 2H); ca 4.4-4.3 (br. m, 2H); 4.00-3.68 (m, 5H); 3.68 (s, 3H); 3.49-3.43 (m, not resolved, 2H), ca 2.5 (m, superimposed by DMSO-d signal, 1H); 2.40-2.25 (m, 2H), 2.02 (m, 1H); 1.79-1.52 (m, 4H).

Core 15: Synthesis of Selected Advanced Intermediates and Final Products (Scheme 18)

Synthesis of Ex. 246

At 0° C., i-$Pr_2NEt$ (0.054 mL, 0.32 mmol) was added to a soln of Ex. 243 (ca. 70% w/w; 55 mg, 0.064 mmol), HATU (36 mg, 0.095 mmol), HOAt (13 mg, 0.095 mmol) and aniline (0.029 mL, 0.32 mmol) in $CH_2Cl_2$ (1.5 mL) and DMF (0.5 mL). The mixture was stirred for 30 min followed by an aqueous workup ($CH_2Cl_2$, 1 M aq. HCl soln, sat. aq. $NaHCO_3$ soln, sat. aq. NaCl soln; $Na_2SO_4$) and FC (hexane/EtOAc 2:1 to 1.1) to afford Ex. 246 (27 mg, 62%).

Data of Ex. 246: cf. Table 27b

Synthesis of Ex. 247

At 0° C., 4 M HCl in dioxane (0.20 mL) was added to a soln of Ex. 246 (25 mg, 0.037 mmol) in dioxane (0.6 mL). The mixture was stirred for 5 h at 0° C. to rt. More 4 M HCl in dioxane (0.15 mL) was added and the mixture was stirred at rt for 16 h. The volatiles were evaporated. The residue was treated with TFA (0.15 mL) in $CH_2Cl_2$ (0.75 mL) for 1 h at 0° C., followed by evaporation of the solvents, aqueous workup (EtOAc, sat.aq. $Na_2CO_3$ soln; $Na_2SO_4$) and FC($CH_2Cl_2$/MeOH 100:0 to 90:10). The purified product (13 mg) was dissolved in dioxane (0.3 mL) and treated with 4 M HCl in dioxane (0.05 mL). The volatiles were evaporated to give Ex. 247.HCl (14 mg, 60%).

Data of Ex. 247.HCl: cf. Table 27b $^{1}$H-NMR (DMSO-$d_6$): 10.18 (s, 1H); 8.48 (s, 1H); 8.30 (s, 1H); 8.15 (d, J=7.1, 1H); 8.15 (br. s, 3H); 7.85 (s, 1H); 7.59 (d, J=7.7, 2 H); 7.36-7.27 (m, 3H); 7.06 (t, J=7.4, 1H); 6.74 (dt-like m, 1H); 4.73-4.63 (m, 2H); 4.40 (br. not resolved m, 1H); 4.01-3.59 (m, 5H); 3.50-3.41 (m, 3H); 2.36 (br. t-like m, 2H); 2.04 (m, 1H); 1.90-1.45 (several not resolved m, 5H).

Synthesis of Ex. 256

Ex. 256 (8 mg, 14%) was obtained from Ex. 243 (ca. 70% w/w; 65 mg, 0.075 mmol) and 4-chloroaniline (48 mg, 0.38 mmol) by applying the method described for the synthesis of Ex. 246.

Data of Ex. 256: cf. Table 27b

Synthesis of Ex. 257

Ex. 257.HCl (4 mg, 66%) was obtained from Ex. 256 (7 mg, 0.01 mmol) by applying the method described for the synthesis of Ex. 247.HCl.

Data of Ex. 257.HCl: cf. Table 27b

Synthesis of Ex. 258

Ex. 258 (19 mg, 43%) was obtained from Ex. 243 (ca. 70% w/w; 55 mg, 0.064 mmol) and m-toluidine (0.034 mL, 0.32 mmol) by applying the method described for the synthesis of Ex. 246.

Data of Ex. 258: cf. Table 27b

Synthesis of Ex. 259

Ex. 259.HCl (10 mg, 66%) was obtained from Ex. 258 (17 mg, 0.024 mmol) by applying the method described for the synthesis of Ex. 247.HCl.

Data of Ex. 259.HCl: cf. Table 27b $^{1}$H-NMR (DMSO-$d_6$): 10.07 (s, 1H); 8.47 (s, 1H); 8.30 (s, 1H); 8.12 (d, J=7.6, 1H); 8.12 (br. s, 3H); 7.85 (s, 1H); 7.42-7.30 (m, 3H), 7.18 (t, J=7.4, 1H); 6.88 (d, J ca 7.6, 1H); 6.74 (d, J=10.3, 1H); 4.78-4.60 (m, 2H); 4.40 (br. not resolved m, 1H); 4.05-3.65 (m, 5H); 3.51-3.40 (m, 3H); 2.37 (br. t-like m, 2H); 2.27 (s, 3H); 2.01 (m, 1H); 1.90-1.45 (several not resolved m, 5H).

Core 16: Synthesis of Ex. 262, Ex. 263 and Ex. 264 (Scheme 19)

Synthesis of the Mitsunobu Product 154

CMBP (8.5 mL, 32 mmol) was added to a soln of hydroxythiophene 106 (5.69 g, 20 mmol) and alcohol 118 (9.8 g, 26 mmol) in toluene (77 mL). The mixture was heated to reflux for 2 h and concentrated. FC (hexane/EtOAc 90:10 to 20:80) gave 154 (12.68 g, 98%).

Data of 154: $C_{29}H_{34}BrN_3O_6S$ (632.6). LC-MS (method 4a): $R_t$=2.29 (93), 634.3/632.3 ($[M+H]^+$).

Synthesis of the Amino Acid 157

A soln of 154 (12.6 g, 20 mmol) in $CH_2Cl_2$ (128 mL) was treated with TFA (148 mL) and heated to reflux for 3 h. The volatiles were evaporated. The residue was suspended in toluene, concentrated and dried i.v. to give crude 155 (16.15 g, containing residual solvent), which was used without further purification.

At 0° C., i-$Pr_2NEt$ (6.85 mL, 40.3 mmol) was added to a soln of crude carboxylic acid 155 (9.27 g, ca 11.5 mmol), amine 130.HCl (5.52 g, 16.1 mmol), HATU (7.66 g, 20.1 mmol) and HOAt (2.74 g, 20.1 mmol) in DMF (170 mL). The mixture was stirred at rt for 2 h, followed by an aqueous workup (EtOAc, 1 M aq. HCl soln, sat. aq. $NaHCO_3$ soln; $Na_2SO_4$) and FC($CH_2Cl_2$/MeOH 100:0 to 95:5) to afford 156 (11.7 g; containing residual DMF), used without further purification.

A degassed solution of 156 (11.6 g) and 1,3-dimethylbarbituric acid (6.3 g, 40 mmol) in $CH_2Cl_2$ (39 mL) and EtOAc (78 mL) was treated with $Pd(PPh_3)_4$ (1.6 g, 1.3 mmol) at rt for 4 h. The volatiles were evaporated. FC (EtOAc, then $CH_2Cl_2$/MeOH 100:0 to 80:20) afforded 157 (7.6 g, 89% over the three steps).

Data of 157: $C_{34}H_{38}BrN_5O_7S$ (740.6). LC-MS (method 1a): $R_t$=1.91 (87), 740.1/742.1 ($[M+H]^+$).

Synthesis of Ex. 262

A soln of 157 (1.9 g, 2.57 mmol) in $CH_2Cl_2$ (40 mL) was added dropwise over 2 h (syringe pump) to a soln of T3P (50% in EtOAc, 7.56 mL, 12.8 mmol) and i-$Pr_2NEt$ (1.96 mL, 11.5 mmol) in $CH_2Cl_2$ (1190 mL). Stirring at rt was continued for 4 h. The volatiles were evaporated. Aqueous workup ($CH_2Cl_2$, sat. aq. $NaHCO_3$ soln.; $Na_2SO_4$) and FC (hexane/EtOAc 50:50 to 0:100) afforded Ex. 262 (1.63 g, 88%).

Data of Ex. 262: $C_{34}H_{36}BrN_5O_6S$ (722.6). LC-MS (method 1d): $R_t$=2.52 (99), 722.0/724.0 ($[M+H]^+$). $^{1}$H-NMR (DMSO-$d_6$): 7.65 (d, J=6.8, 1H); 7.49 (d, J=8.0, 2 H); 7.41-7.26 (m, 8H); 7.08 (d, J=5.4, 1H); 6.64 (s, 1H); 5.06 (s, 2H); ca 4.5-4.4 (br. m, 2H); 4.48 (s, 2H); 4.32 (br. d, J ca 8.8, 1H); 4.16 (br. m, 2H); 4.01 (m, 1H); 3.86 (s, 3H); 3.69 (br. m, 1H); 3.46-3.32 (m, 2H); 2.96 (s, 3H); 2.40-2.25 (br. m, 2H), 2.10-1.90 (br. m, 2H).

Synthesis of Ex. 263

At 0° C., $BCl_3$ (16 mL, 16 mmol) was added dropwise to a soln of Ex. 262 (2.34 g, 3.2 mmol) in $CH_2Cl_2$ (83 mL). The mixture was allowed to stir at 0° C. to rt for 16 h. The mixture was cooled to 0° C. and poured slowly into MeOH. The mixture was concentrated. Aqueous workup ($CH_2Cl_2$, sat. aq. $NaHCO_3$ soln; $Na_2SO_4$) afforded Ex. 263 (1.21 g, 89%).

Data of Ex. 263: $C_{19}H_{25}N_5O_4S$ (419.5). LC-MS (method 1d): $R_t$=1.11 (98), 420.0 ([M+H]$^+$). $^1$H-NMR (DMSO-$d_6$): 7.40 (d, J=5.5, 1H); 7.08 (d, J=5.5, 1H); 6.63 (s, 1H); 5.17 (d, J=5.1, 1H); 4.35-4.29 (m, 2H); 4.24 (dd, J=6.6, 11.9, 1H); 4.12-3.97 (m, 3H); 3.85 (s, 3H); 3.68 (d, J=7.4, 1H); 3.61 (m, 1H); 3.17 (dd, J=6.6, 10.2, 1H); 2.97 (s, 3H); 2.28-2.19 (m, 2H); 1.95 (m, 1H), 1.90-1.75 (br. not resolved m, 3H).

Synthesis of Ex. 264

At rt, TBAF (1 M in THF; 0.119 mL, 0.119 mmol) was slowly added to a soln of Ex. 262 (160 mg, 0.221 mmol) in THF (2.5 mL). The mixture was heated to reflux for 2 h, filtered through a pad of celite and concentrated. Aqueous workup ($CH_2Cl_2$, sat. aq. $NaHCO_3$ soln; $Na_2SO_4$) and FC($CH_2Cl_2$/MeOH 85:15) afforded a white solid (100 mg) was dissolved in DMF (4.0 mL) and hydrogenated for 2 h at rt and normal pressure in the presence of palladium hydroxide on activated charcoal (moistened with 50% $H_2O$; 23 mg). The volatiles were evaporated. The crude product was purified by FC ($CH_2Cl_2$/MeOH 100:0 to 80:20) to give Ex. 264 (45 mg, 40%).

Data of Ex. 264: $C_{26}H_{31}N_5O_4S$ (509.6). LC-MS (method 1a): $R_t$=1.62 (99), 510.1 ([M+H]$^+$). $^1$H-NMR (DMSO-$d_6$): 7.40 (d, J=5.5, 1H); 7.33-7.27 (m, 5H); 7.08 (d, J=5.5, 1H); 6.65 (s, 1H); 4.53 (s, 2H); 4.41-4.17 (m, 5H); 3.98 (dd, J=5.1, 9.4, 1H); 3.85 (s, 3H); 3.72 (d, J=7.0, 1H); 3.61 (m, 1H); ca 3.3 (m, superimposed by $H_2O$ signal, 1H); 2.97 (s, 3H); 2.40-1.80 (several br. m, 6H).

Core 16: Synthesis of Selected Advanced Intermediates and Final Products (Scheme 19)

Synthesis of Ex. 265

At 0° C., oxalyl chloride (0.104 mL, 1.19 mmol) and one drop of DMF were added to a soln of 2-naphthaleneacetic acid (53 mg, 0.29 mmol) in $CH_2Cl_2$ (6 mL). The mixture was stirred at rt for 1 h and concentrated. The residue was dissolved in $CH_2Cl_2$ (2.5 mL) and added dropwise to a soln of Ex. 263 (100 mg, 0.24 mmol) and i-$Pr_2$NEt (0.204 mL, 1.19 mmol) in $CH_2Cl_2$ (3.5 mL). The mixture was stirred at 0° C. for 1 h followed by an aqueous workup ($CH_2Cl_2$, sat. aq. $NaHCO_3$ soln; $Na_2SO_4$) and FC ($CH_2Cl_2$/i-PrOH 100:0 to 95:5) to yield Ex. 265 (110 mg, 78%).

Data of Ex. 265: cf. Table 28b $^1$H-NMR (DMSO-$d_6$): 8.54 (d, J=7.5, 1H); 7.89-7.85 (m, 3H); 7.78 (s, 1H); 7.52-7.44 (m, 3H); 7.40 (d, J=5.5, 1H); 7.09 (d, J=5.5, 1H); 6.44 (s, 1H); 5.14 (d, J=4.9, 1H); 4.65 (br. t, J=8.0, 1H); 4.40-4.31 (m, 2H); 4.11 (q, J ca 5.8, 1H); 4.03 (m, 1H), 3.84 (m, 1H); 3.84 (s, 3H); 3.68 (s, 2H); 3.64 (m, 1H); ca 3.30 (m, 1H, partially superimposed by $H_2O$ signal); 3.17 (dd, J=6.3, 10.5, 1H); 2.91 (s, 3H); 2.35 (m, 1H); 2.18 (m, 1H); 1.91-1.82 (m, 2H).

Synthesis of Ex. 275

Trimethyloxonium tetrafluoroborate (15 mg, 0.10 mmol) was added at 0° C. to a solution of Ex. 265 (40 mg, 0.068 mmol) and N,N,N',N'-tetramethyl-1,8-naphthalenediamine (22 mg, 0.102 mmol) in $CH_2Cl_2$ (1.0 mL). The mixture was stirred at 0° C. to rt for 4.5 h. More N,N,N',N'-tetramethyl-1,8-naphthalenediamine (32 mg, 0.15 mmol) and trimethyloxonium tetrafluoroborate (22 mg, 0.15 mmol) were added at 0° C. and stirring was continued at rt for 16 h. Aqueous workup ($CH_2Cl_2$, 2 M aq. HCl soln; $Na_2SO_4$). The residue was suspended in $CH_2Cl_2$ and filtered. The filtrate was purified by FC (EtOAc/MeOH 100:0 to 97:3) and by prep. RP-HPLC (method 1a) to afford Ex. 275 (5 mg, 12%).

Data of Ex. 275: cf. Table 28b $^1$H-NMR (DMSO-$d_6$): 8.57 (d, J=7.5, 1H); 7.90-7.85 (m, 3H); 7.80 (s, 1H); 7.54-7.45 (m, 3H); 7.39 (d, J=5.5, 1H); 7.07 (d, J=5.5, 1H); 6.62 (s, 1H); 4.65 (br. t, J=7.8, 1H); 4.40 (br. not resolved m, 1H); 4.29 (dd; J=2.7, 9.5, 1H); 3.96-3.83 (m, 2H); 3.83 (s, 3H); 3.75-3.60 (m, 2H); 3.67 (s, 2H); ca 3.3-3.2 (m, 2H, partially superimposed by $H_2O$ signal); 3.05 (s, 3H); 2.92 (s, 3H); 2.36 (m, 1H); 2.16 (m, 1H); 1.96-1.83 (m, 2H).

Synthesis of Ex. 276

At 0° C., i-$Pr_2$NEt (0.061 mL, 0.36 mmol) and 2-naphthylisocyanate (22 mg, 0.131 mmol) were added to a soln of Ex. 263 (50 mg, 0.12 mmol) in $CH_2Cl_2$ (1.0 mL). The mixture was stirred at 0° C. to rt for 60 min. Aqueous workup ($CHCl_3$, sat. aq. $Na_2CO_3$ soln; $Na_2SO_4$) and purification by prep. HPLC (method 3) afforded Ex. 276 (50 mg, 71%).

Data of Ex. 276: cf. Table 28b $^1$H-NMR (DMSO-$d_6$): 9.00 (s, 1H) 8.05 (d, J=1.8, 1H); 7.81-7.74 (m, 3H); 7.45-7.40 (m, 3H); 7.32 (dt, J=1.2, 7.5, 1H); 7.11 (d, J=5.5, 1H); 6.74 (d, J=7.3, 1H); 6.68 (s, 1H); 5.24 (d, J=5.0, 1H); 4.77 (br. t, J=7.1, 1H); 4.38-4.32 (m, 2H); 4.29 (q-like m, 1H); 4.07-4.00 (m, 2H), 3.88 (s, 3H); 3.85 (m, 1H); ca 3.30-3.20 (m, 2H, partially superimposed by $H_2O$ signal); 2.98 (s, 3H); ca 2.5 (m, 1H, superimposed by DMSO-d signal); 2.27 (m, 1H); 2.00-1.92 (m, 2H).

Core 17: Synthesis of Ex. 284a, Ex. 285 and Ex. 286 (Scheme 20)

Synthesis of Amide 158

A suspension of 110.HCl (6.2 g, 19.9 mmol) in $CH_2Cl_2$ (310 mL) was cooled to 0° C. Oxalyl chloride (5.1 mL, 59.7 mmol) was added followed by DMF (0.37 mL). The mixture was stirred for 1.5 h at rt and concentrated. The residue was suspended in $CH_2Cl_2$ and concentrated; this operation was repeated once and the residue was then dried i.v. The residue was suspended in $CH_2Cl_2$ (180 mL). A soln of 131HCl (8.86 g, 23.9 mmol) in $CH_2Cl_2$ (120 mL) was added. The mixture was cooled to 0° C. followed by the slow addn of i-$Pr_2$NEt (17.0 mL, 99.5 mmol). The mixture was stirred for 1 h at 0° C. Aqueous workup ($CH_2Cl_2$, 1 M aq. HCl soln, sat. aq. $NaHCO_3$ soln; $Na_2SO_4$) and FC (hexane/EtOAc gradient) gave 158 (8.1 g, 69%).

Data of 158: $C_{30}H_{33}N_5O_8$ (591.6). LC-MS (method 1a): $R_t$=2.43 (94), 592.1 ($[M+H]^+$).

Synthesis of the Mitsunobu Product 159

A soln of CMBP (6.58 g, 27.3 mmol) in toluene (30 mL) was added to a soln of phenol 158 (8.07 g, 13.6 mmol) and alcohol 120 (3.28 g, 17.7 mmol) in toluene (131 mL). The mixture was heated to reflux for 1 h and concentrated. FC (hexane/EtOAc 50:50 to 0:100) yielded 159 (7.9 g, 76%).

Data of 159: $C_{39}H_{46}N_6O_{10}$ (758.8). LC-MS (method 4a): $R_t$=1.91 (90), 759.2 ($[M+H]^+$).

Synthesis of the Amino Acid 160

A degassed solution of 159 (8.9 g, 11.8 mmol) and 1,3-dimethylbarbituric acid (4.4 g, 28.3 mmol) in $CH_2Cl_2$ (180 mL) and EtOAc (45 mL) was treated with $Pd(PPh_3)_4$ (1.36 g, 1.18 mmol) at rt for 2 h. The volatiles were evaporated. FC (EtOAc, then $CH_2Cl_2$/MeOH 100:0 to 40:60) afforded 160 (7.33 g, 98%; containing some impurities; used without further purification).

Data of 160: $C_{32}H_{38}N_6O_8$ (634.7). LC-MS (method 1a): $R_t$=1.65 (88), 635.2 ($[M+H]^+$).

Synthesis of Ex. 284a and Ex. 284b

A soln of 160 (500 mg, 0.79 mmol) in pyridine (40 mL) was added dropwise over 2 h (syringe pump) to a soln of HATU (900 mg, 2.36 mmol) and HOAt (322 mg, 2.36 mmol) in pyridine (1500 mL). An additional portion of HATU (900 mg, 2.36 mmol) and HOAt (322 mg, 2.36 mmol) was added to the solution. Again a soln of 160 (500 mg, 0.79 mmol) in pyridine (40 mL) was added dropwise over 2 h (syringe pump).

The volatiles were evaporated. Aqueous workup ($CH_2Cl_2$, sat. aq. $NaHCO_3$ soln, $H_2O$, $Na_2SO_4$). Purification by preparative HPLC (method 1d) afforded Ex. 284a.$CF_3CO_2H$ (480 mg) and Ex. 284b.$CF_3CO_2H$ (186 mg, 16%).

Ex. 284a.$CF_3CO_2H$ (480 mg) was dissolved in $CH_2Cl_2$ and washed with sat. aq. $NaHCO_3$ soln. The organic phase was dried ($Na_2SO_4$), filtered and concentrated to afford Ex. 284a (442 mg, 45%).

Data of Ex. 284a: $C_{32}H_{36}N_6O_7$ (616.6). LC-MS (method 1d): $R_t$=2.24 (99), 617.2 ($[M+H]^+$). $^1$H-NMR (DMSO-$d_6$): 8.66 (d, J=2.1, 1H); 8.40 (dd, J=2.1, 8.9, 1H); 7.53-7.49 (m, 2H); 7.36-7.26 (m, 6H); 5.06 (br. d, J=12.6, 1H); 4.92 (s, 2H); 4.37 (br. dd, J ca 2.6, 13.0, 1H); 4.15 (t-like m, 1H); 3.65 (br. t, J ca 8.7, 1H); 3.55 (q-like m, 1H); 3.27 (m, 1H); 3.01 (s, 3H); 2.95-2.82 (m, 2H), 2.61 (s, 3H); 1.97-1.68 (several m, 6H), 1.23-0.90 (br. m, 4H).

Data of Ex. 284b.$CF_3CO_2H$: $C_{32}H_{36}N_6O_7CF_3CO_2H$ (free base 616.6). LC-MS (method 1d): $R_t$=2.14 (99), 617.2 ($[M+H]^+$).

Synthesis of Ex. 285

A soln of Ex. 284a (380 mg, 0.62 mmol) in THF (19 mL) was treated with TBAF (1 M in THF; 0.6 mL, 0.6 mmol) at 75° C. for 7 h. The mixture was cooled to rt and TBAF (1 M in THF; 0.3 mL, 0.3 mmol) was added. Stirring at 75° C. was continued for 8 h. The volatiles were evaporated. FC($CH_2Cl_2$/MeOH 95:5 to 90:10) afforded Ex. 285 (182 mg, ca 60%; containing ca 5% of tetrabutylammonium salts). An analytical sample (15 mg) was further purified by preparative HPLC (method 2a) to afford Ex. 285 (9 mg).

Data of Ex. 285: $C_{24}H_{30}N_6O_5$ (482.5). LC-MS (method 1d): $R_t$=1.47 (95), 483.2 ($[M+H]^+$). $^1$H-NMR (DMSO-$d_6$): 8.66 (d, J=2.2, 1H); 8.41 (dd, J=2.2, 9.0, 1H); 7.51 (s, 1H); 7.47 (d, J=9.1, 1H); 5.17 (d, J=12.5, 1H); 4.30 (dd, J=2.3, 12.7, 1H); 4.14 (t, J=7.0, 1H); 3.51 (m, 1H); ca. 3.2 (m, 1H), 3.02 (s, 3H); 2.97 (m, 1H); 2.81-2.68 (m, 2H); 2.61 (s, 3H); 2.0-1.7 (several m, 8H); 1.4-0.6 (several m, 4H).

Synthesis of Ex. 286

A soln. of Ex. 284a (1.2 g, 1.95 mmol) in MeOH (120 mL) was hydrogenated in the presence of platinum (IV) oxide hydrate (120 mg) for 8 h at rt and normal pressure. More platinum (IV) oxide hydrate (60 mg) was added and the hydrogenation was continued for 6 h. The mixture was filtered through a pad of celite. The solid was washed (MeOH). The combined filtrate and washings were concentrated. FC (hexane/EtOAc 50:50:0 to 0:100 then $CH_2Cl_2$/MeOH 90:10) yielded Ex. 286 (0.75 g, 66%).

Data of Ex. 286: $C_{32}H_{38}N_6O_5$ (586.7). LC-MS (method 1d): $R_t$=1.68 (90), 587.2 ($[M+H]^+$). $^1$H-NMR (DMSO-$d_6$): 7.67 (d, J=2.0, 1H); 7.48-7.43 (m, 2H); 7.39-7.27 (m, 6H); 6.87 (d, J=8.6, 1H); 5.06-4.93 (m, 5H); 4.11 (br. m, not resolved, 1H); 4.00 (br. d, J ca 11.7, 1H); 3.60 (br. t, J ca. 8.4, 1H); 3.49 (q-like m, 1H); 3.15 (m, 1H), 2.99 (s, 3H); 2.96 (m, 1H); 2.78 (m, 1H); 2.54 (s, 3H); 2.21 (m, 1H); 2.15-1.15 (several br. m, 8H); 0.66 (br. m, 1H).

Core 18: Synthesis of Ex. 305 and Ex. 306 (Scheme 21)

Synthesis of the Mitsunobu Product 161

DEAD (40% in toluene; 11.1 mL, 24.3 mmol) was slowly added to a soln of alcohol 122 (5.66 g, 16.2 mmol), 2-iodophenol (111; 5.33 g, 24.3 mmol) and $PPh_3$ (6.36 g, 24.3 mmol) in toluene (345 mL). The mixture was stirred at rt for 4 h. The volatiles were evaporated. FC (hexane/EtOAc gradient) afforded 161 (6.85 g, 77%).

Data of 161: $C_{24}H_{29}IN_2O_5$ (552.4). LC-MS (method 1a): $R_t$=2.71 (99), 553.2 ($[M+H]^+$). $^1$H-NMR (DMSO-$d_6$): 7.76 (d, J=7.7, 1H); 7.60 (d, J=6.5, 1H); 7.40-7.28 (m, 6H); 7.02 (d, J=8.2, 1H); 6.76 (t, J=7.5, 1H); 5.03 (s, 2H); 4.33 (br. m, 1H); 4.17-4.07 (br. m, 3H); 3.59 (br. m, 1H); 3.29 (br. m, 1H); 2.26 (br. m, 1H); 2.02 (br. m, 1H); 1.38 (s, 9H).

Synthesis of the Biphenyl 162

$Pd(dppf)Cl_2.CH_2Cl_2$ (1.0 g, 1.2 mmol) was added to a mixture of 161 (6.8 g, 12.3 mmol), ethyl 2-(4,4,5,5-tetramethyl-1,3,2-dioxaborolan-2-yl)benzoate (113; 3.0 g, 10.8 mmol), 2-(ethoxycarbonyl)phenylboronic acid (112; 2.3 g, 11.8 mmol) in DME (325 mL), EtOH (32 mL) and 1 M aq. $Na_2CO_3$ soln (37 mL). The mixture was heated to 80° C. for 3 h. The mixture was diluted with sat. aq. $NaHCO_3$ soln and repeatedly extracted with $CH_2Cl_2$. The combined organic layer was dried ($Na_2SO_4$), filtered and concentrated. FC (hexane/EtOAc gradient) gave 162 (6.6 g, 94%).

Data of 162: $C_{33}H_{38}N_2O_7$ (574.6). LC-MS (method 4c): $R_t$=2.48 (96), 575.4 ($[M+H]^+$). $^1$H-NMR (DMSO-$d_6$): 7.80 (d, J=7.5, 1H); 7.58 (t, J=7.3, 1H); 7.46-7.25 (m, 9H); 7.12 (m, 1H); 7.03-7.00 (m, 2H); 4.99 (s, 2H); 3.99-3.83 (br. m, 6H); 3.78 (br. not resolved m, 1H); 3.01 (br. not resolved m, 1H); 1.81 (br. not resolved m, 1H); 1.72 (br. not resolved m, 1H); 1.33 (s, 9H); 0.88 (br. t, 3H).

Synthesis of the Carboxylic Acid 164

A soln of 162 (5.2 g, 9.1 mmol) in EtOH (50 mL) was hydrogenated for 3 h at rt and normal pressure in the presence of palladium hydroxide on activated charcoal (moistened with 50% $H_2O$; 0.5 g). The mixture was filtered through a pad of celite. The residue was washed with EtOH. The combined filtrate and washings were concentrated to give crude 163 (4.0 g) which was dissolved in EtOH (84 mL). KOH (10.2 g, 182 mmol) dissolved in $H_2O$ (28 mL) was added and the mixture was stirred at 45° C. for 18 h. The solution was cooled to rt. $NaHCO_3$ (15.2 g, 182 mmol) and $CH_2Cl_2$ (100 mL) followed by CbzOSu (2.7 g, 10.8 mmol) were successively added and the mixture was allowed to stir for 3 h. The mixture was acidified by addn of 3 M aq. HCl soln and extracted with $CH_2Cl_2$. The organic layer was dried ($Na_2SO_4$), filtered and concentrated. FC (EtOAc) afforded 164 (4.87 g, 98%)

Data of 164: $C_{31}H_{34}N_2O_7$ (546.6). LC-MS (method 1c): $R_t$=2.44 (88), 547.1 ($[M+H]^+$).

Synthesis of the Amide 165

EDC.HCl (3.4 g, 17.8 mmol) was added to a soln of 164 (4.8 g, 8.9 mmol) and sarcosine tert.-butylester hydrochloride (132; 3.2 g, 17.8 mmol) in pyridine (150 mL). The mixture was stirred at rt for 3 h. Aqueous workup ($CH_2Cl_2$, aq. 2 M HCl soln, sat. aq. $NaHCO_3$ soln; $Na_2SO_4$) and FC (hexane/EtOAc gradient) afforded 165 (4.9 g, 82%).

Data of 165: $C_{38}H_{47}N_3O_8$ (673.8). LC-MS (method 1a): $R_t$=2.71 (97), 674.2 ($[M+H]^+$).

Synthesis of Ex. 305

A soln of 165 (4.9 g, 7.3 mmol) in $CH_2Cl_2$ (50 mL) was treated with TFA (25 mL) for 4 h at rt. Evaporation of the volatiles afforded the crude amino acid 166-$CF_3CO_2H$ (5.3 g, containing residual solvent) which was used without further purification.

The ring closing reaction was performed in four batches:

A soln of crude 166.$CF_3CO_2H$ (1.3 g) and i-$Pr_2$NEt (1.5 mL, 8.7 mmol) in $CH_2Cl_2$ (40 mL) was added dropwise over 2 h (syringe pump) to a soln of T3P (50% in EtOAc, 2.2 mL, 3.7 mmol) in $CH_2Cl_2$ (1200 mL). The mixture was stirred for 1 h at rt and concentrated.

The four batches were combined and purified by FC (hexane/EtOAc/MeOH gradient) to give Ex. 305 (3.7 g, quant. yield).

Data of Ex. 305: $C_{29}H_{29}N_3O_5$ (499.5). LC-MS (method 1a): $R_t$=2.00 (98), 500.1 ($[M+H]^+$). $^1$H-NMR ($CD_3OD$): Two sets of signals were observed; ratio 7:3; 7.48-7.21 (m, 11H), 7.12-6.96 (m, 1.3H); 6.91 (t, J=7.5, 0.7H); 5.10-5.04 (m, 2H); 4.72 (dd, J=4.2, 9.7, 0.7H); 4.40-4.28 (m, 1.3H); 4.16-4.06 (m, 1.6H); 4.03 (dt, J=4.0, 7.8, 0.7H); 3.93 (br. not resolved m, 0.7H); 3.78 (d, J=14.6, 0.3H); 3.69 (br. d, 0.7H); 3.59-3.50 (m, 1.3H); 3.10, 3.07 (2 s, 3H); 2.99 (br. d, J ca 10.0, 0.7H); 2.10-1.93 (m, 2H).

Synthesis of Ex. 306

A soln of Ex. 305 (3.68 g, 7.3 mmol) in MeOH (50 mL) was hydrogenated for 4 h at rt and normal pressure in the presence of palladium hydroxide on activated charcoal (moistened with 50% $H_2O$; 0.38 g). The mixture was filtered through a pad of celite. The residue was washed (MeOH). The combined filtrate and washings were concentrated. FC (hexane/EtOAc/MeOH gradient) afforded Ex. 306 (2.4 g, 89%).

Data of Ex. 306: $C_{21}H_{23}N_3O_3$ (365.4). LC-MS (method 1a): $R_t$=1.17 (96), 366.0 ($[M+H]^+$).

Core 19: Synthesis of Ex. 327, Ex. 328 and Ex. 329 (Scheme 22)

Synthesis of the Amide 167

At 0° C., i-$Pr_2$NEt (4.5 mL, 26.3 mmol) was added dropwise to a soln of 117 (1.2 g, 4.4 mmol), 125.HCl (1.73 g, 5.2 mmol), HATU (1.67 g, 4.4 mmol) and HOAt (0.60 g, 4.4 mmol) in DMF (30 mL) and THF (45 mL). The mixture was stirred at rt for 1.5 h. Aqueous workup (EtOAc, 0.1 M aq. HCl soln, sat. aq. NaCl soln; $Na_2SO_4$) and FC (hexane/EtOAc 2:1 to 1:1) afforded 167 (1.24 g, 51%).

Data of 167: $C_{26}H_{24}F_3N_3O_7$ (547.5). LC-MS (method 1c): $R_t$=2.37 (89), 548.2 ($[M+H]^+$).

Synthesis of the Mitsunobu Product 168

A soln of phenol 167 (1.23 g, 2.2 mmol), alcohol 16 (0.81 g, 2.7 mmol) and CMBP (1.36 g, 5.6 mmol) in toluene (30 mL) was heated to reflux for 1.5 h. Evaporation of the volatiles and FC($CH_2Cl_2$/EtOAc 3:1 to 1:1) afforded 168 (1.84 g, 99%).

Data of 168: $C_{40}H_{46}F_3N_5O_{11}$ (829.8). LC-MS (method 4a): $R_t$=2.00 (92), 830.4 ($[M+H]^+$).

Synthesis of the Amino Acid 169

A degassed solution of 168 (1.8 g, 2.2 mmol) and 1,3-dimethylbarbituric acid (0.8 g, 5.3 mmol) in $CH_2Cl_2$ (15 mL) and EtOAc (15 mL) was treated with $Pd(PPh_3)_4$ (0.13 g, 0.1 mmol) at rt for 1 h. The volatiles were evaporated. FC($CH_2Cl_2$/MeOH 99:1 to 80:20) afforded 169 (1.32 g, 85%).

Data of 169: $C_{33}H_{38}F_3N_5O_9$ (705.7). LC-MS (method 1a): $R_t$=1.95 (94), 706.3 ($[M+H]^+$).

Synthesis of Ex. 327

A mixture of 169 (1.33 g, 1.9 mmol), i-$Pr_2$NEt (1.6 mL, 9.4 mmol) and $CH_2Cl_2$ (40 mL) was slowly added over 2 h (syringe pump) to a soln of T3P (50% in EtOAc; 3.3 mL, 5.6 mmol) and i-$Pr_2$NEt (1.6 mL, 9.4 mmol) in $CH_2Cl_2$ (1880 mL). The volatiles were partially evaporated. The soln was washed (sat. aq. $NaHCO_3$ soln), dried ($Na_2SO_4$), filtered and concentrated. FC (hexane/EtOAc 25:75 to 0:100) afforded Ex. 327 (0.96 g, 74%).

Data of Ex. 327: $C_{33}H_{36}F_3N_5O_8$ (687.6). LC-MS (method 1f): $R_t$=2.43 (89), 688.3 ($[M+H]^+$). $^1$H-NMR (DMSO-$d_6$): Three sets of signals were observed; ratio 2:1:1; 9.16 (br. s, 0.5H); 8.65 (br. s, 0.25H); 8.50 (br. s, 0.25H); 7.56-7.08 (m, 10H); 5.13-4.92 (several d, 2H); 4.40-2.98 (several br. not resolved m, 12H); 2.43-2.04 (br. not resolved m, 1H); 1.95-1.70 (br. not resolved m, 1H); 1.41, 1.39 (2 s, 9H).

Synthesis of Ex. 328

A soln of Ex. 327 (60 mg, 0.087 mmol) in EtOAc (5 mL) was hydrogenated for 3 h at rt and normal pressure in the presence of palladium hydroxide on activated charcoal (moistened with 50% $H_2O$; 30 mg). The mixture was filtered through a pad of celite. The residue was washed (EtOAc).

The combined filtrate and washings were concentrated. FC($CH_2Cl_2$/MeOH 95:5 to 90:10) afforded Ex. 328 (37 mg, 77%).

Data of Ex. 328: $C_{25}H_{30}F_3N_5O_6$ (553.5). LC-MS (method 1d): $R_t$=1.84 (96), 554.2 ([M+H]$^+$). $^1$H-NMR (DMSO-$d_6$): Two sets of signals were observed; ratio 4:6; 9.19 (t-like m, 0.4H), 8.72 (t-like m, 0.6H); 7.57 (not resolved m, 1H); 7.48-7.30 (m, 2H); 7.23 (d, J=5.1, 1H); 7.04 (not resolved m, 1H); 4.50-4.34 (2 m, 1H); 4.20-4.13 (m, 2H); 4.07-3.94 (m, 2H); 3.84-3.30 (several m, 3H); 3.19-2.66 (several m, 5H); 2.42, 2.26 (2 m, 1H); 1.95, 1.70 (2 m, 1H); 1.40 (s, 9H).

Synthesis of Ex. 329

Ex. 327 (50 mg, 0.073 mmol) was dissolved in $CH_2Cl_2$ (2 mL). At 0° C., TFA (0.03 mL, 0.36 mmol) was added and the soln was stirred for 1.5 h. Aqueous workup (EtOAc, sat. aq. $NaHCO_3$ soln, sat aq. NaCl soln; $Na_2SO_4$) and treatment of the product with HCl in dioxane afforded Ex. 329.HCl (33 mg, 73%).

Data of Ex. 329.HCl: $C_{28}H_{28}F_3N_5O_6$.HCl (free base; 587.5). LC-MS (method 1d): $R_t$=1.69 (97), 588.2 ([M+H]$^+$).

General Procedures

Attachment of Substituents to the Macrocyclic Core Structures:

Synthesis of the Final Products

Acylation, Carbamoylation, Sulfonylation, and Alkylation Reactions

Procedure A

A.1.: Amide Coupling of a Macrocyclic Amine with

A.1.1: Carboxylic Acid and HATU

A soln of an amino macrocycle (free amine or hydrochloride; 0.085 mmol), a carboxylic acid (1.2 equiv.), HATU (1.5 equiv.) and HOAt (1.5 equiv.) in DMF (0.5 mL) was treated at rt with i-$Pr_2$NEt (3.0 equiv.). The mixture was stirred at rt for 2-15 h. The mixture was distributed between $CH_2Cl_2$ and 1 M aq. HCl soln. The organic phase was washed (sat. aq. NaCl soln), dried ($Na_2SO_4$), filtered and concentrated. Purification of the crude product by chromatography (FC, normal phase or reversed phase prep. HPLC) afforded a macrocyclic N-acyl amine.

A.1.2: Acyl Chloride or Carboxylic Acid Anhydride

At 0° C., a soln of an amino macrocycle (free amine or hydrochloride; 0.085 mmol) in $CH_2Cl_2$ (0.5 mL) was successively treated with pyridine (5 equiv.) and carboxylic acid chloride (1.05-2 equiv.) or carboxylic acid anhydride (1.05-2 equiv.). The mixture was stirred at 0° C. to rt for 2-15 h. After the addn of MeOH (0.01 mL) the soln was stirred for 10 min and concentrated. Toluene was added to the crude product and evaporated. Purification of the residue by chromatography (FC, normal phase or reversed phase prep. HPLC) afforded a macrocyclic N-acyl amine.

A.1.2.1: Acyl Chloride

Like A.1.2 and after 15 h at rt more carboxylic acid chloride (2 equiv.) and i-$Pr_2$NEt (3 equiv.) were added. Stirring was continued for 24 h followed by an aq. workup ($CHCl_3$, sat. aq. $Na_2CO_3$ soln; $Na_2SO_4$).

A.1.2.2: Acyl Chloride

At 0° C., a soln of an amino macrocycle (free amine or hydrochloride; 1 mmol) in $CH_2Cl_2$ (7 mL) was successively treated with i-$Pr_2$NEt (5 equiv.) and carboxylic acid chloride (1.05-2 equiv.). The mixture was stirred at 0° C. to rt for 2-15 h. Aq. workup ($CHCl_3$, sat. aq. $Na_2CO_3$ soln; $Na_2SO_4$). Purification of the crude product by chromatography (FC, normal phase or reversed phase prep. HPLC) afforded a macrocyclic N-acyl amine.

A.1.3: Carboxylic Acid and T3P

A soln of a carboxylic acid (2.4 equiv.), T3P (50% in DMF; 3 equiv.) and i-$Pr_2$NEt (4.0 equiv.) in DMF (0.3 mL) was slowly added to a mixture of an amino macrocycle (free amine or hydrochloride; 0.1 mmol) and DMF (0.2 mL). The mixture was stirred at rt for 2-15 h followed by an aq. workup ($CHCl_3$, sat. aq. $Na_2CO_3$ soln; $Na_2SO_4$).

Purification of the crude product by chromatography (FC, normal phase or reversed phase prep. HPLC) afforded a macrocyclic N-acyl amine.

A.2: Amide Coupling of a Macrocyclic Carboxylic Acid with an Amine and HATU

A soln of a macrocyxclic carboxylic acid (0.12 mmol), an amine (1.2 equiv.), HATU (1.5 equiv.) and HOAt (1.5 equiv.) in DMF (0.5 mL) was treated at 4° C. with i-$Pr_2$NEt (3.0 equiv.). The mixture was stirred at 4° C. for 2 h. The mixture was distributed between $CH_2Cl_2$ and 1 M aq. HCl soln. The organic phase was washed (sat. aq. NaCl soln), dried ($Na_2SO_4$), filtered and concentrated.

Purification of the crude product by chromatography (FC, normal phase or reversed phase prep. HPLC) afforded a macrocyclic amide.

Procedure A.3: Urea Formation with Isocyantes or Equivalents of Isocyanates

A soln of an amino macrocycle (free amine or hydrochloride; 0.1 mmol) in $CH_2Cl_2$ (0.5 mL) was treated at rt for 2-15 h with an isocyanate (1.1 equiv.) (or with a succinimidyl carbamate (1.1 equiv.)) and i-$Pr_2$NEt (3 equiv.) followed by aq. workup ($CHCl_3$, sat. aq. $Na_2CO_3$ soln; $Na_2SO_4$). The crude product was purified by chromatography (FC, normal phase or reversed phase prep. HPLC) to afford the targeted macrocyclic urea.

Procedure A.4: Carbamate Formation with Chloroformates

At 0° C. the chloroformate (1.1 equiv.) was added to a stirred mixture of $CH_2Cl_2$ (0.9 mL) and sat. aq. $Na_2CO_3$ soln (0.35 mL). The amino macrocycle (free amine or hydrochloride; 0.085 mmol) and $H_2O$ (0.75 mL) were added. The mixture was stirred at rt for 2-15 h followed by aq. workup (EtOAc, sat. aq. $NaHCO_3$ soln; $Na_2SO_4$). The crude product was purified by chromatography (FC, normal phase or reversed phase prep. HPLC) to afford the targeted macrocyclic carbamate.

Procedure A.5: Sulfonamide Formation with Sulfonyl Chlorides

At 0° C. a soln of an amino macrocycle (free amine or hydrochloride; 0.1 mmol) in $CH_2Cl_2$ (0.5 mL) was successively treated with triethylamine (3.0 equiv.) and the sulfonyl chloride (1.0 equiv.). The mixture was stirred at 0° C. to rt for 2-15 h. (In case of incomplete transformation, more sulfonyl chloride (1.0 equiv.) and auxiliary base (3.0 equiv.) were added and stirring continued.) Aq. workup ($CHCl_3$, sat. aq. $Na_2CO_3$ soln; $Na_2SO_4$) and purification of the crude product by chromatography (FC, normal phase or reversed phase prep. HPLC) afforded the targeted macrocyclic sulfonamide.

Procedure A.6: N-Alkylation by Reductive Amination

A.6.1. N,N-Dimethylamino Macrocycles by Reductive Amination

To a soln. of the amino macrocycle (free amine or hydrochloride; 0.085 mmol) in DCE (1.2 mL) was added formaldehyde soln (36.5% in $H_2O$; 5 equiv.) followed by $NaBH(OAc)_3$ (4 equiv.). The mixture was stirred at rt for 4 h.

Aq. workup (EtOAc, sat. aq. $NaHCO_3$ soln; $Na_2SO_4$) and purification of the crude product by chromatography (FC, normal phase or reversed phase prep. HPLC) afforded a dimethylamino macrocycle.

A.6.2: Synthesis of Tertiary Amines by N-Methylation of Secondary Amines

At 0° C. formaldehyde soln (36.5% in $H_2O$; 5 equiv.), acetic acid (1.2 equiv.) and $NaBH(OAc)_3$ (4.0 equiv.) were added to a soln of the macrocyclic amine (0.25 mmol) in DCE (4 mL). The mixture was stirred at rt for 4 h followed by aqueous workup ($CH_2Cl_2$, sat. aq. $NaHCO_3$ soln; $Na_2SO_4$). Purification of the crude product by chromatography (FC, normal phase or reverse phase prep. HPLC) afforded the desired N-methyl-N,N-dialkylamino macrocycle.

A.6.3: Synthesis of Tertiary Amines by Reductive Amination of Secondary Amines

The aldehyde (1.5 equiv.) was added to a mixture of the macrocyclic amine (0.25 mmol) and THF (1.5 mL). The mixture was stirred at rt for 1 h. Acetic acid (1.2 equiv.) and $NaBH(OAc)_3$ (3 equiv.) were added and stirring was continued for 15 h. (In case of incomplete transformation, more aldehyde (0.5 equiv.) was added and stirring continued.) After aqueous workup ($CH_2Cl_2$, 1 M aq. $Na_2CO_3$ soln; $Na_2SO_4$) the crude product was purified by chromatography (FC, normal phase or reverse phase prep. HPLC) to afford the macrocyclic tertiary amine.

A.6.4: Synthesis of Secondary Amines by Reductive Amination

Activated molecular sieve powder (3 Å; 2 mg per mg of starting material) was added at rt to a soln of an amino macrocycle (0.1 mmol) and an aldehyde (1.1 equiv.) in THF (0.5 mL). The suspension was stirred for 2-4 h at rt, followed by the addition of acetic acid (1.1 equiv.) and $NaBH(OAc)_3$ (3.0 equiv.). The mixture was stirred for 18 h and filtered. Aqueous workup of the filtrate ($CH_2Cl_2$, sat. aq. $Na_2CO_3$ soln; $Na_2SO_4$) and purification of the crude product by chromatography (FC, normal phase or reverse phase prep. HPLC) afforded the alkylamino macrocycle.

Deprotection Reactions

Procedure B

Procedure B.1: Boc Cleavage

A soln of a macrocyclic Boc-amine in dioxane (1 mL per 100 mg) was treated with 4 M HCl in dioxane (1 mL per 100 mg) and stirred at rt for 2-16 h. The volatiles were evaporated. The residue was taken up in $CHCl_3$, concentrated and dried i.v. Solid residues were then washed with $Et_2O/CH_2Cl_2$.

Procedure B.2: Tert.-Butyl Ester Cleavage or Boc Cleavage

Tert.-Butyl Ester Cleavage:

TFA (1 mL per 100 mg) was slowly added to a soln of a macrocyclic tert.-butyl ester in $CH_2Cl_2$ (5 mL per 100 mg). The mixture was stirred for 2 h at rt and concentrated. The residue was twice taken up in toluene and concentrated. The residue was then twice taken up in $CHCl_3$ and concentrated followed by washing with $Et_2O/CH_2Cl_2$.

Boc Cleavage:

TFA (1 mL per 100 mg of starting material) was slowly added to a soln of the macrocyclic Boc-amine in $CH_2Cl_2$ (3 mL per 100 mg). The mixture was stirred at rt for 3 h and concentrated. The residue was dried i.v.

Procedure B.3: Cbz Cleavage

A soln of the macrocyclic benzyl carbamate (500 mg) in MeOH (10 mL) or 2,2,2-trifluoroethanol (10 mL) was hydrogenated for 4 h at rt and at normal pressure in the presence of palladium hydroxide on activated charcoal (moistened with 50% $H_2O$; 15-20% Pd; 0.1 g). The mixture was filtered through a pad of celite. The residue was washed (MeOH). The combined filtrates and washings were concentrated to obtain the macrocyclic amine.

Procedure B.4: Nitro Reduction

A soln of the macrocyclic arylnitro compound (50 mg) in MeOH (5 mL) was hydrogenated for 15 h at rt and at normal pressure in the presence of platinum (IV) oxide hydrate (5 mg). The mixture was filtered through a pad of celite. The residue was washed (MeOH). The combined filtrates and washings were concentrated to obtain the macrocyclic aniline.

B.5: Methyl Ester Cleavage

A soln of the macrocyclic methyl ester (0.07 mmol) in DCE (2 mL) was treated with trimethyltin hydroxide (3 equiv.) at 80° C. for 16 h. Aqueous workup ($CH_2Cl_2$, 1 M aq. HCl soln; $Na_2SO_4$) and purification by reverse phase prep. HPLC afforded the corresponding macrocyclic carboxylic acids.

Procedures for the Synthesis on Solid Support

Procedure C: Description of Examples of Core 10 and Core 11

Procedure D: Description of Examples of Core 01

Synthesis of Final Products

Advanced macrocyclic intermediates and final products depicted in Tables 13-31 (related cores cf. Scheme 23) were prepared starting from the suitable precursor macrocyclic acid, macrocyclic amine, or macrocyclic alcohol applying the general procedures (A.1-A.6; B.1-B.5) or specific procedures described above (as indicated in the corresponding Tables). Deviations from general procedures are indicated in Tables 13a-31a.

Final products of Core 01 prepared on solid support were obtained following the general procedure D (vide supra; Core 01: Synthesis of final products on solid support).

Final products of Cores 10 and 11 were prepared following the general procedure described in the text (vide supra; Procedure C.1: Core 10: Synthesis of Ex. 193a,c-h and Ex. 194b and Procedure C.2: Core 11: Synthesis of Ex. 195a,b, e-h,j; Ex. 196c,i,k and Ex. 197d)

Analytical data of these intermediates and final products are depicted in Tables 13b-31b.

IUPAC names of all examples are listed in Tables 13c-31c.

The generic macrocyclic ring structures (Cores) related to Tables 13-31 are depicted in Scheme 23 in the order of their core numbers Reagents used in the derivatizations are commercially available with the exception of few N-succinimidyl carbamates which were synthesized from amines, anilines or heteroaryl amines according to the procedure of K. Takeda et al. *Tetrahedron Lett.* 1983, 24, 4569-4572.

The synthesis of selected advanced intermediates and final products is described in detail in the text above; cf. corresponding core description.

The generic macrocyclic ring structures (Cores) related to Tables 13-31 are depicted in Scheme 23 in the order of their core numbers.

TABLE 13a

Examples of Core 01 (Ex. 1-Ex. 14 and Ex. 330-Ex. 340;)

| No | $R^A$ | $R^B$ | Starting Material | General Proced. | Reagent | Purification Method | Yield (isolated salt) |
|---|---|---|---|---|---|---|---|
| Ex. 1-Ex. 3 and Ex. 330-Ex. 331: | | cf. experimental description | | | | | |
| Ex. 4 | 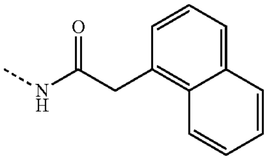 | 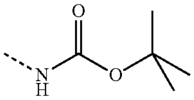 | Ex. 2 | A.1.1; [1)] | 1-Naphthalene-acetic acid | FC (hexane/ EtOAc) | 77% |
| Ex. 5 | 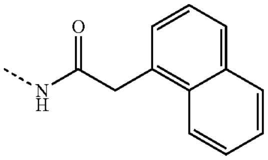 | $NH_2$ | Ex. 4 | B.1; [1)] | HCl-dioxane | crude product | quant. (HCl salt) |
| Ex. 6 | 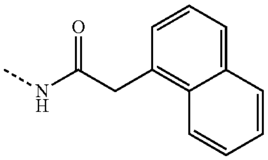 | 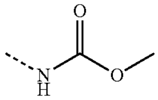 | Ex. 5 | A.4 | Methyl chloroformate | FC ($CH_2Cl_2$/ MeOH) | 82% |
| Ex. 7 | 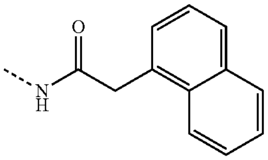 | 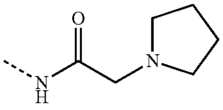 | Ex. 5 | A.1.1; [1)] | 1-Pyrrolidineacetic acid | FC ($CH_2Cl_2$/ MeOH) | 71% |
| Ex. 7 | 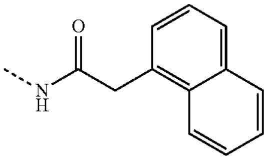 | 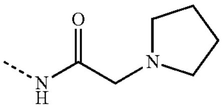 | 133 | D; [1)] | 1.1-Pyrrolidine-acetic acid 2.1-Naphthalene-acetic acid | prep. HPLC method 1a | 15% (TFA salt) |
| Ex. 8 | 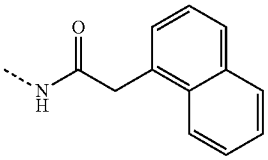 | $N(CH_3)_2$ | Ex. 5 | A.6.1 | Formaldehyde (36.5% in H2O) | FC ($CH_2Cl_2$/ MeOH) | 79% |
| Ex. 9 | $NH_2$ | $NH_2$ | Ex. 2 | B.1 | HCl-dioxane rt, 16 h | crude product | 97% (HCl salt) |
| Ex. 10 | 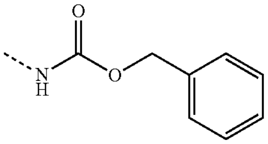 | 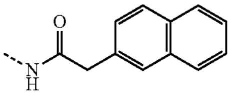 | Ex. 3 | A.1.1 | 2-Naphthalene-acetic acid 4° C., 1 h | FC (hexane/ EtOAc/MeOH 80:20:0 to 0:90:10) | 31% |
| Ex. 11 | $NH_2$ | 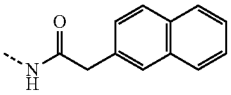 | Ex. 10 | B.3 | H, $Pd(OH)_2$—C 2,2,2-trifluoroethanol | crude product | 90% |

TABLE 13a-continued

Examples of Core 01 (Ex. 1-Ex. 14 and Ex. 330-Ex. 340;)

| No | $R^A$ | $R^B$ | Starting Material | General Proced. | Reagent | Purification Method | Yield (isolated salt) |
|---|---|---|---|---|---|---|---|
| Ex. 12 | 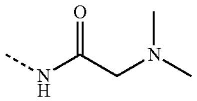 | 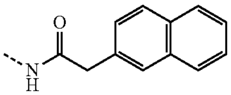 | Ex. 11 | A.1.1 | 2-(Dimethylamino) acetic acid 0° C., 2 h | prep. HPLC method 1b | 48% (TFA salt) |
| Ex. 13 | 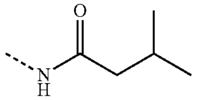 | 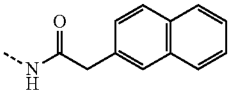 | Ex. 11 | A.1.1 | 3-Methylbutanic acid 0° C., 2 h | prep. HPLC method 1b | 55% |
| Ex. 14 | 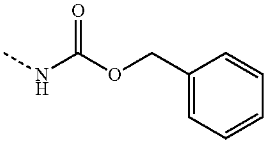 | 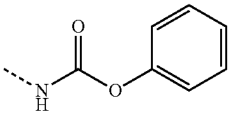 | Ex. 3 | A.4 [1)] | Phenyl chloroformate 0° C., 2 h | FC (EtOAc) | 96% |
| Ex. 332 | 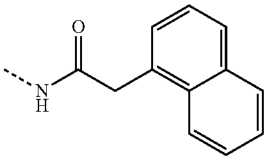 | 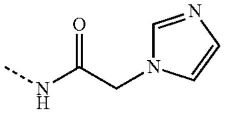 | 133 | D; [1)] | 1. Imidazol-1-yl-acetic acid 2. 1-Naphthalen-acetic acid | prep. HPLC method 1a | 48% (TFA salt) |
| Ex. 333 | 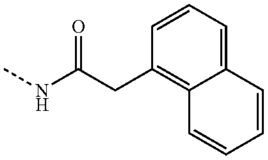 | 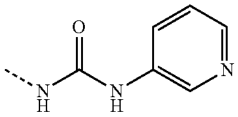 | 133 | D; [1)] | 1. 2,5-Dioxo-pyrrolidin-1-yl pyridin-3-ylcarbamate 2. 1-Naphthalene-acetic acid | prep. HPLC method 1a | 65% (TFA salt) |
| Ex. 334 | 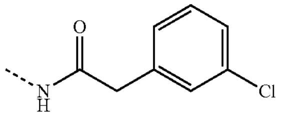 | 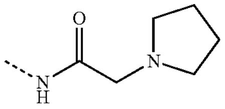 | 133 | D; [1)] | 1. 1-Pyrrolidine-acetic acid 2. 3-Chloro-phenylacetic acid | prep. HPLC method 1a | 38% (TFA salt) |
| Ex. 335 | 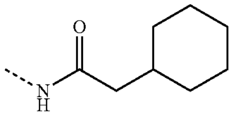 | 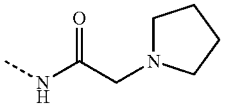 | 133 | D; [1)] | 1. 1-Pyrrolidine-acetic acid 2. Cyclohexylacetic acid | prep. HPLC method 1a | 26% (TFA salt) |
| Ex. 336 | 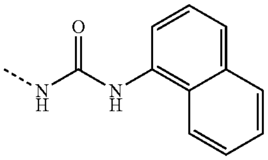 | 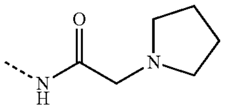 | 133 | D; [1)] | 1. 1-Pyrrolidine-acetic acid 2. 1-Naphthyl isocyanate | prep. HPLC method 1a | 13% (TFA salt) |
| Ex. 337 | 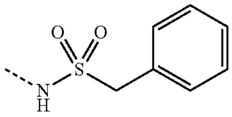 | 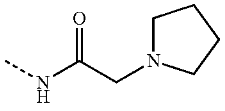 | 133 | D | 1. 1-Pyrrolidine-acetic acid 2. Benzylsulfonyl chloride | prep. HPLC method 1a | 21% (TFA salt) |
| Ex. 338 | 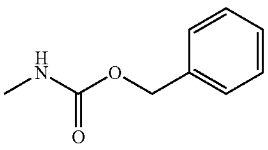 | 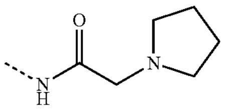 | Ex. 3 | A.1.3 | 1-Pyrrolidineacetic acid $i\text{-}Pr_2NEt$ (5 equiv.) Workup: $CH_2Cl_2$, sat. aq. $NaHCO_3$ soln | FC ($CH_2Cl_2$/MeOH) | 80% |

TABLE 13a-continued

| Examples of Core 01 (Ex. 1-Ex. 14 and Ex. 330-Ex. 340;) | | | | | | | |
|---|---|---|---|---|---|---|---|
| No | $R^A$ | $R^B$ | Starting Material | General Proced. | Reagent | Purification Method | Yield (isolated salt) |
| Ex. 339 | $NH_2$ | 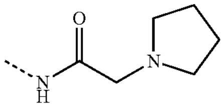 | Ex. 338 | B.3 | $H_2$, $Pd(OH)_2$—C, MeOH | crude product | 98% |
| Ex. 340 | 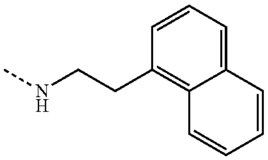 | 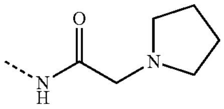 | Ex. 339 | A.6.4 | 1-Naphthalene-acetaldehyde, 3 h; $NaBH(OAc)_3$ (3 eq.) Workup: $CHCl_3$, sat. aq. $NaHCO_3$ soln | FC ($CH_2Cl_2$/MeOH) and prep. HPLC method 1a | 20% (TFA salt) |

[1)] Cf. experimental description for detailed procedure

TABLE 13b

| Examples of Core 01 (Ex. 1-Ex. 14 and Ex. 330-Ex. 340;) | | | | | | | |
|---|---|---|---|---|---|---|---|
| No | $R^A$ | $R^B$ | Formula | Monoisotopic Mass | Rt (purity at 220 nm) | $[M + H]^+$ found | LC-MS-Method |
| Ex. 1-Ex. 3 and Ex. 330-Ex. 331: | | cf. experimental description | | | | | |
| Ex. 4 | 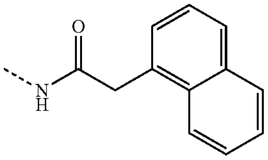 | 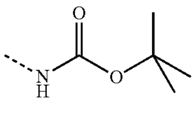 | C39H42N4O6 | 662.3 | 2.27 (86) | 663.2 | method 1a |
| Ex. 5 | 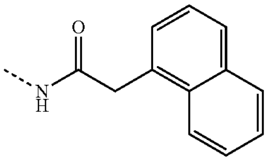 | $NH_2$ | C34H34N4O4 | 562.3 | 1.61 (91) | 563.2 | method 1a |
| Ex. 6 | 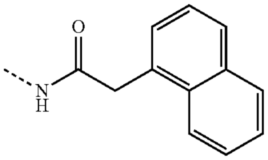 | 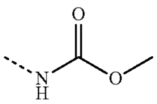 | C36H36N4O6 | 620.3 | 2.01 (90) | 621.0 | method 1a |
| Ex. 7 | 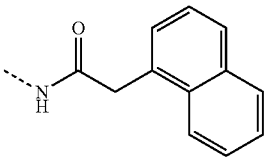 | 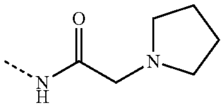 | C40H43N5O5 | 673.3 | 2.13 (99) | 674.3 | method 2c |

TABLE 13b-continued
| No | $R^A$ | $R^B$ | Formula | Mono-isotopic Mass | Rt (purity at 220 nm) | $[M + H]^+$ found | LC-MS-Method |
|---|---|---|---|---|---|---|---|
| Examples of Core 01 (Ex. 1-Ex. 14 and Ex. 330-Ex. 340;) | | | | | | | |
| Ex. 8 | 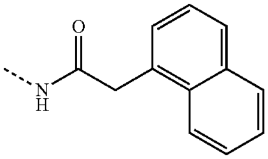 | $N(CH_3)_2$ | C36H38N4O4 | 590.3 | 1.65 (97) | 591.1 | method 1a |
| Ex. 9 | $NH_2$ | $NH_2$ | C22H26N4O3 | 394.2 | 1.01 (96) | 395.2 | method 1a |
| Ex. 10 | 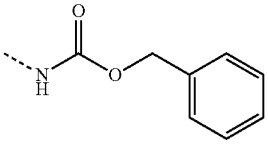 | 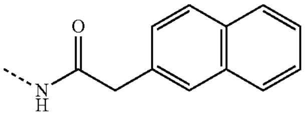 | C42H40N4O6 | 696.3 | 2.25 (91) | 697.1 | method 1a |
| Ex. 11 | $NH_2$ | 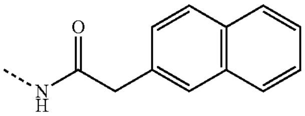 | C34H34N4O4 | 562.3 | 1.73 (91) | 563.1 | method 1a |
| Ex. 12 | 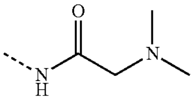 | 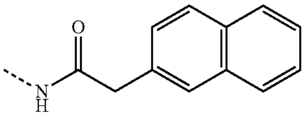 | C38H41N5O5 | 647.3 | 1.71 (96) | 648.1 | method 1a |
| Ex. 13 | 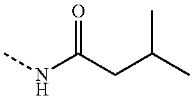 | 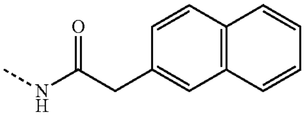 | C39H42N4O5 | 646.3 | 2.09 (89) | 647.2 | method 1a |
| Ex. 14 | 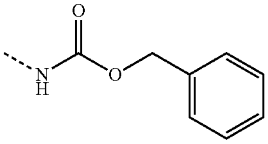 | 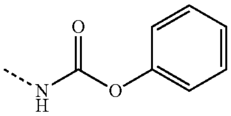 | C37H36N4O7 | 648.3 | 2.22 (97) | 649.1 | method 1a |
| Ex. 332 | 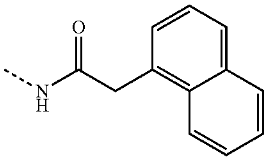 | 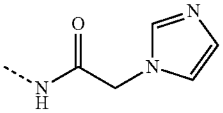 | C39H38N6O5 | 670.3 | 1.84 (99) | 671.3 | method 2c |
| Ex. 333 | 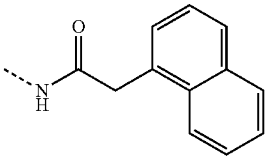 | 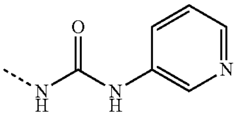 | C40H38N6O5 | 682.3 | 1.94 (99) | 683.2 | method 2c |
| Ex. 334 | 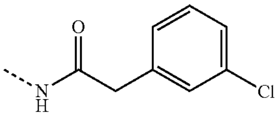 | 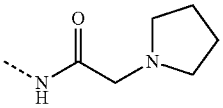 | C36H40ClN5O5 | 657.3 | 2.08 (99) | 658.2 | method 2c |

TABLE 13b-continued

| Examples of Core 01 (Ex. 1-Ex. 14 and Ex. 330-Ex. 340;) | | | | | | | |
|---|---|---|---|---|---|---|---|
| No | $R^A$ | $R^B$ | Formula | Mono-isotopic Mass | Rt (purity at 220 nm) | $[M + H]^+$ found | LC-MS-Method |
| Ex. 335 | 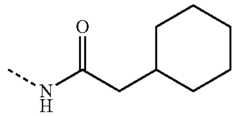 | 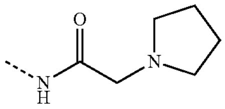 | C36H47N5O5 | 629.4 | 2.10 (99) | 630.3 | method 2c |
| Ex. 336 | 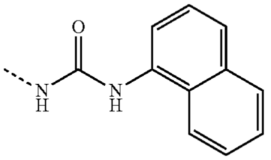 | 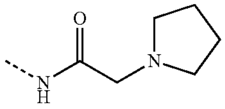 | C39H42N6O5 | 674.3 | 2.09 (98) | 675.3 | method 2c |
| Ex. 337 | 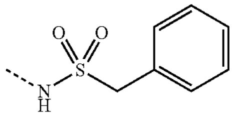 | 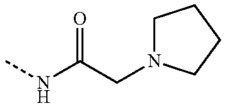 | C35H41N5O6S | 659.3 | 1.59 (99) | 660.3 | method 1a |
| Ex. 338 | 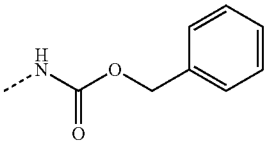 | 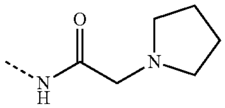 | C36H41N5O6 | 639.3 | 1.63 (99) | 640.2 | method 1a |
| Ex. 339 | $NH_2$ | 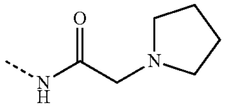 | C28H35N5O4 | 505.3 | 1.15 (97) | 506.2 | method 1c |
| Ex. 340 | 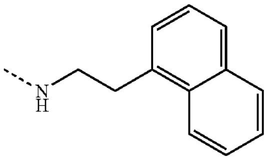 | 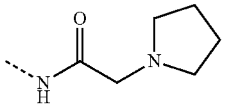 | C40H45N5O4 | 659.3 | 1.60 (87) | 660.3 | method 1a |

TABLE 13c

| Examples of Core 01 (Ex. 1-Ex. 14 and Ex. 330-Ex. 340;) | | | |
|---|---|---|---|
| No | $R^A$ | $R^B$ | IUPAC name |
| Ex. 1 | 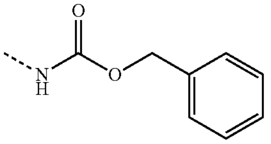 | 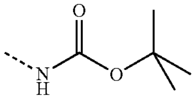 | benzyl N-[(12R,16S,18S)-16-[(tert-butoxycarbonyl)amino]-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 2 | $NH_2$ | 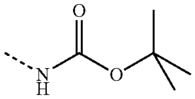 | tert-butyl N-[(12R,16S,18S)-12-amino-8,13-dioxo-20-oxa-9,14-diazatetracyclo[19.3.1.$0^{2,7}$.$0^{14,18}$]pentacosa-1(25),2,4,6,21,23-hexaen-16-yl]carbamate |
| Ex. 3 | 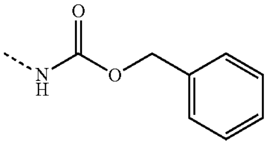 | $NH_2$ | benzyl N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |

TABLE 13c-continued

| Examples of Core 01 (Ex. 1-Ex. 14 and Ex. 330-Ex. 340;) | | | |
|---|---|---|---|
| No | $R^A$ | $R^B$ | IUPAC name |
| Ex. 4 | 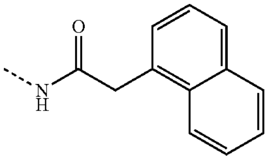 | 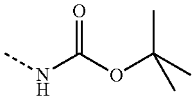 | tert-butyl N-[(12R,16S,18S)-12{[2-(1-naphthyl) acetyl]amino}-8,13-dioxo-20-oxa-9,14-diazatetracyclo[19.3.1.$0^{2,7}$.$0^{14,18}$]pentacosa-1(25)2,4,6,21,23-hexaen-16-yl]carbamate |
| Ex. 5 | 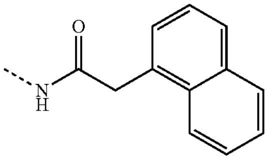 | $NH_2$ | N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 6 | 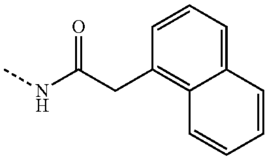 | 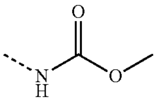 | methyl N-[(12R,16S,18S)-12-{[2-(1-naphthyl) acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]carbamate |
| Ex. 7 | 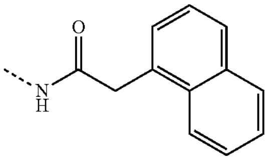 | 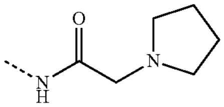 | N-[(12R,16S,18S)-8,13-dioxo-16-{[2-(1-pyrrolidinyl)acetyl]amino}-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 8 | 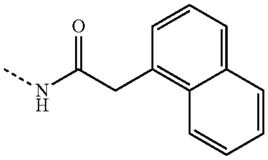 | $N(CH_3)_2$ | N-[(12R,16S,18S)-16-(dimethylamino)-8,13-dioxo-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 9 | $NH_2$ | $NH_2$ | (12R,16S,18S)-12,16-diamino-20-oxa-9,14-diazatetracyclo[19.3.1.$0^{2,7}$.$0^{14,18}$]pentacosa-1(25),2,4,6,21,23-hexaene-8,13-dione |
| Ex. 10 | 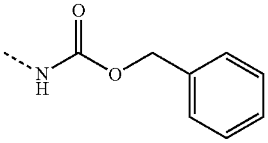 | 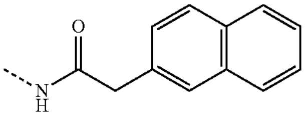 | benzyl N-[(12R,16S,18S)-16-{[2-(2-naphthyl)acetyl] amino}-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 11 | $NH_2$ | 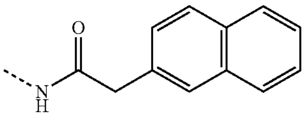 | N-[(12R,16S,18S)-12-amino-8,13-dioxo-20-oxa-9,14-diazatetracyclo[19.3.1.$0^{2,7}$.$0^{14,18}$]pentacosa-1(25),2,4,6,21,23-hexaen-16-yl]-2-(2-naphthyl)acetamide |
| Ex. 12 | 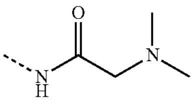 | 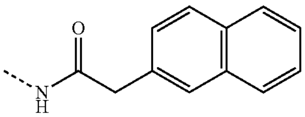 | 2-(dimethylamino)-N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]acetamide |
| Ex. 13 | 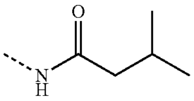 | 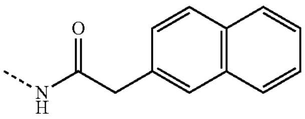 | 3-methyl-N-[(12R,16S,18S)-16-{[2-(2-naphthyl) acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]butanamide |

TABLE 13c-continued

Examples of Core 01 (Ex. 1-Ex. 14 and Ex. 330-Ex. 340;)

| No | $R^A$ | $R^B$ | IUPAC name |
|---|---|---|---|
| Ex. 14 | 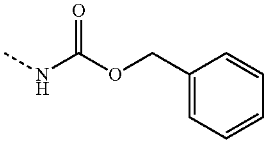 | 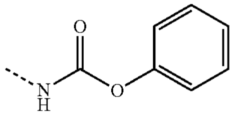 | benzyl N-[(12R,16S,18S)-8,13-dioxo-16-[(phenoxycarbonyl)amino]-20-oxa-9,14-(diazatetracyclo[19.3.1.$0^{2,7}$.$0^{14,18}$]pentacosa-1(25),2,4,6,21,23-hexaen-12-yl]carbamate |
| Ex. 330 | 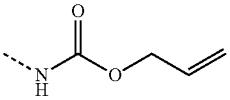 | 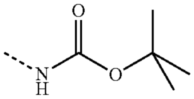 | allyl N-[(12R,16S,18S)-16-[(tert-butoxycarbonyl)amino]-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 331 | 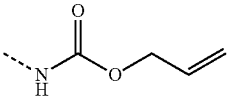 | $NH_2$ | allyl N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]carbamate |
| Ex. 332 | 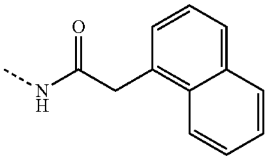 | 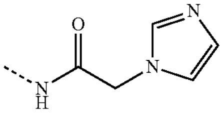 | 2-(1H-imidazol-1-yl)-N-[(12R,16S,18S)-12-{[2-(1-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]acetamide |
| Ex. 333 | 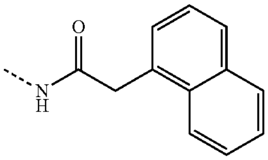 | 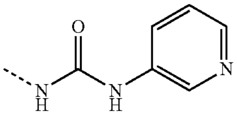 | N-[(12R,16S,18S)-8,13-dioxo-16-{[(3-pyridinylamino)carbonyl]amino}-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide |
| Ex. 334 | 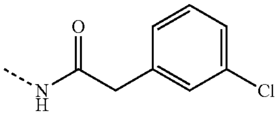 | 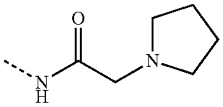 | 2-(3-chlorophenyl)-N-[(12R,16S,18S)-8,13-dioxo-16-{[2-(1-pyrrolidinyl)acetyl]amino}-20-oxa-9,14-diazatetracyclo[19.3.1.$0^{2,7}$.$0^{14,18}$]pentacosa-1(25),2,4,6,21,23-hexaen-12-yl]acetamide |
| Ex. 335 | 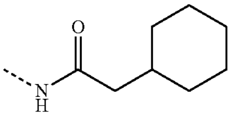 | 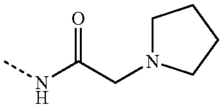 | 2-cyclohexyl-N-[(12R,16S,18S)-8,13-dioxo-16-{[2-(1-pyrrolidinyl)acetyl]amino}-20-oxa-9,14-diazatetracyclo[19.3.1.$0^{2,7}$.$0^{14,18}$]pentacosa-1(25),2,4,6,21,23-hexaen-12-yl]acetamide |
| Ex. 336 | 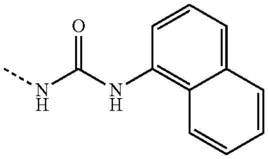 | 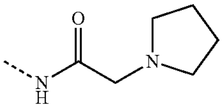 | N-[(12R,16S,18S)-12-{[(1-naphthylamino)carbonyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]-2-(1-pyrrolidinyl)acetamide |
| Ex. 337 | 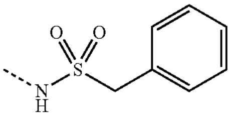 | 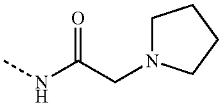 | N-[(12R,16S,18S)-12-[(benzylsulfonyl)amino]-8,13-dioxo-20-oxa-9,14-diazatetracyclo[19.3.1.$0^{2,7}$.$0^{14,18}$]pentacosa-1(25),2,4,6,21,23-hexaen-16-yl]-2-(1-pyrrolidinyl)acetamide |
| Ex. 338 | 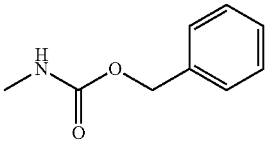 | 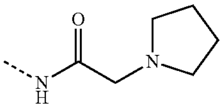 | benzyl N-[(12R,16S,18S)-8,13-dioxo-16-{[2-(1-pyrrolidinyl)acetyl]amino}-20-oxa-9,14-diazatetracyclo[19.3.1.$0^{2,7}$.$0^{14,18}$]pentacosa-1(25),2,4,6,21,23-hexaen-12-yl]carbamate |
| Ex. 339 | $NH_2$ | 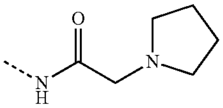 | N-[(12R,16S,18S)-12-amino-8,13-dioxo-20-oxa-9,14-diazatetracyclo[19.3.1.$0^{2,7}$.$0^{14,18}$]pentacosa-1(25),2,4,6,21,23-hexaen-16-yl]-2-(1-pyrrolidinyl)acetamide |

TABLE 13c-continued

| Examples of Core 01 (Ex. 1-Ex. 14 and Ex. 330-Ex. 340;) | | | |
|---|---|---|---|
| No | $R^A$ | $R^B$ | IUPAC name |
| Ex. 340 | 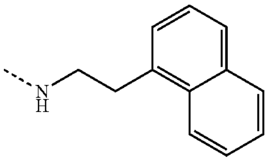 | 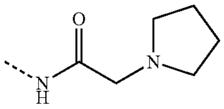 | N-[(12R,16S,18S)-12-{[2-(1-naphthyl)ethyl]amino}-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide |

TABLE 14a

| Examples of Core 02 (Ex. 15-Ex. 40;) | | | | | | | |
|---|---|---|---|---|---|---|---|
| No | $R^A$ | $R^B$ | Starting Material | General Proced. | Reagent | Purification Method | Yield (isolated salt) |
| Ex. 15-Ex. 17: | | cf. experimental description | | | | | |
| Ex. 18 | 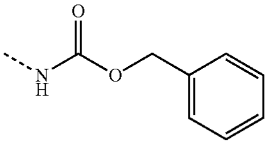 | 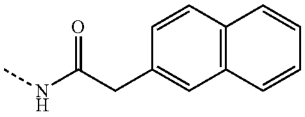 | Ex. 17 | A.1.1; 4) | 2-Naphthaleneacetic acid | FC (EtOAc) | 79% |
| Ex. 19 | $NH_2$ | 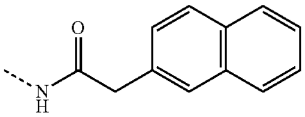 | Ex. 18 | B.3; 4) | $H_2$, $Pd(OH)_2$—C MeOH | crude product | 97% |
| Ex. 20 | 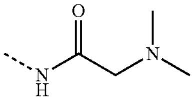 | 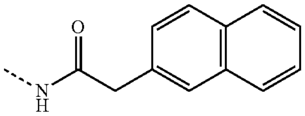 | Ex. 19 | A.1.1; 4) | 2-(Dimethylamino) acetic acid | FC ($CH_2Cl_2$/MeOH) | 30% |
| Ex. 21 | 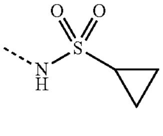 | 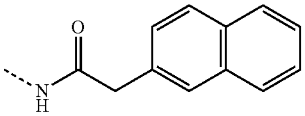 | Ex. 19 | A.5 | Cyclopropanesulfonyl chloride (1.5 equiv.) $Et_3N$ (3 equiv.) DMAP (0.1 equiv) $CHCl_3$ (0.25 mL), 50° C., 15 h Workup: $CH_2Cl_2$, half-sat. aq. $NaHCO_3$ soln.; $Na_2SO_4$ | FC (EtOAc; then $CH_2Cl_2$/MeOH) | 86% |
| Ex. 22 | 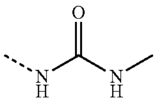 | 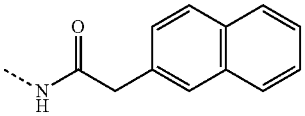 | Ex. 19 | A.3 | N-Succinimidyl N-methylcarbamate (1.3 equiv.) i-$Pr_2NEt$ (3 equiv) THF/$CHCl_3$ 1:1 (1.0 mL) rt, 3 h | FC ($CH_2Cl_2$/MeOH) | 63% |
| Ex. 23 | 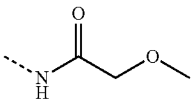 | 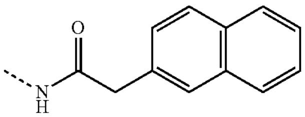 | Ex. 19 | A.1.2 | 2-Methoxyacetyl chloride (1.5 equiv.) rt, 3 h | FC ($CH_2Cl_2$/MeOH) | 51% |

TABLE 14a-continued

Examples of Core 02 (Ex. 15-Ex. 40;)

| No | $R^A$ | $R^B$ | Starting Material | General Proced. | Reagent | Purification Method | Yield (isolated salt) |
|---|---|---|---|---|---|---|---|
| Ex. 24 | 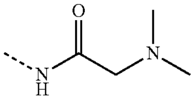 | 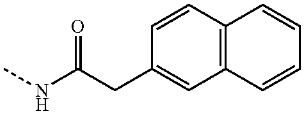 | Ex. 19 | A.1.2 | 3-Methylbutanoyl chloride (1.2 equiv.) 0° C., 2 h (Mixture was concentrated without addn of MeOH.) | prep. HPLC method 1a | 73% |
| Ex. 25 | 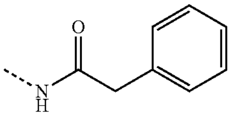 | 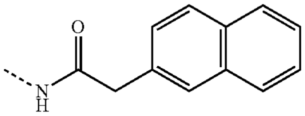 | Ex. 19 | A.1.2; 4) | Phenylacetyl chloride | prep. HPLC method 1a | 60% |
| Ex. 26 | 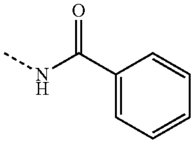 | 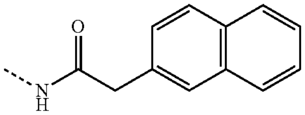 | Ex. 19 | A.1.2; 4) | Benzoyl chloride | prep. HPLC method 1a | 67% |
| Ex. 27 | 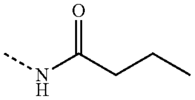 | 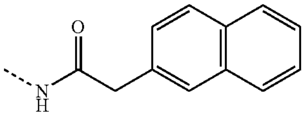 | Ex. 19 | A.1.2 | Butyryl chloride (1.2 equiv.) 0° C., 2 h (Mixture was concentrated without addn of MeOH.) | prep. HPLC method 1a | 67% |
| Ex. 28 | 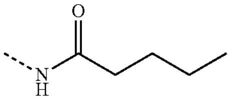 | 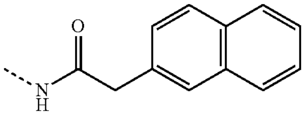 | Ex. 19 | A.1.2 | Pentanoyl chloride (1.2 equiv.) 0° C., 2 h (Mixture was concentrated without addn of MeOH.) | prep. HPLC method 1a | 66% |
| Ex. 29 | 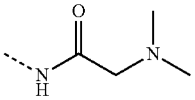 | 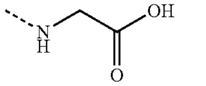 | Ex. 40 | 1) | LiOH 1) | prep. HPLC method 1a | 47% |
| Ex. 30 | 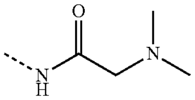 | 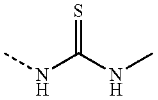 | Ex. 39 | 2) | Methyl isothiocyanate 2) | prep. HPLC method 1a | 48% |
| Ex. 31 | 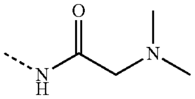 | 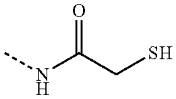 | Ex. 32 | 3) | 3) | FC ($CH_2Cl_2$/MeOH 100:0 to 80:20) | 57% |
| Ex. 32 | 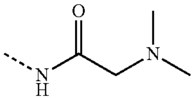 | 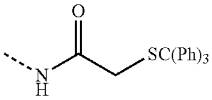 | Ex. 39 | A.1.1 | 2-(Tritylthio)acetic acid i-$Pr_2$NEt (5 equiv.) 0° C., 2 h Workup: $CH_2Cl_2$, sat. aq. $NaHCO_3$ soln | FC ($CH_2Cl_2$/MeOH 90:10) | 85% |
| Ex. 33 | 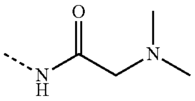 | 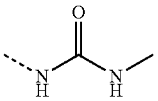 | Ex. 39 | A.3 | N-Succinimidyl N-methylcarbamate (1.4 equiv.) i-$Pr_2$NEt (5.0 equiv.) | prep. HPLC method 1a | 77% (TFA salt) |

TABLE 14a-continued

| Examples of Core 02 (Ex. 15-Ex. 40;) | | | | | | | |
|---|---|---|---|---|---|---|---|
| No | $R^A$ | $R^B$ | Starting Material | General Proced. | Reagent | Purification Method | Yield (isolated salt) |
| Ex. 34 | 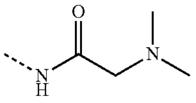 | 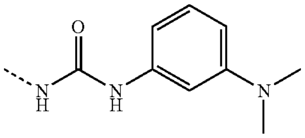 | Ex. 39 | A.3 | 2,5-Dioxo-pyrrolidin-1-yl-3-(dimethylamino) phenyl-carbamate (1.4 equiv.) i-$Pr_2NEt$ (5.0 equiv.) | prep. HPLC method 1a | 77% (TFA salt) |
| Ex. 35 | 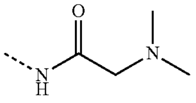 | 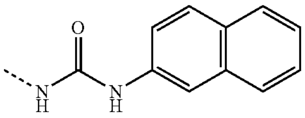 | Ex. 39 | A.3 | 2-Naphthyl isocyanate (1.4 equiv.) i-$Pr_2NEt$ (5.0 equiv.) | prep. HPLC method 1a | 77% (TFA salt) |
| Ex. 36 | 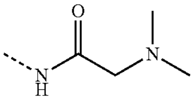 | 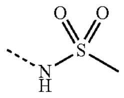 | Ex. 39 | A.5 | Methanesulfonyl chloride (1.3 equiv.) $Et_3N$ (5 equiv.) | prep. HPLC method 1a | 64% (TFA salt) |
| Ex. 37 | 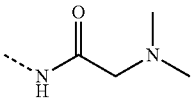 | 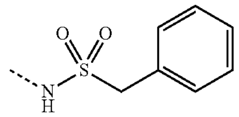 | Ex. 39 | A.5 | Phenylmethane-sulfonyl chloride (1.3 equiv.) $Et_3N$ (5 equiv.) | prep. HPLC method 1a | 43% (TFA salt) |
| Ex. 38 | 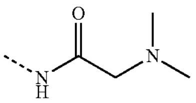 | 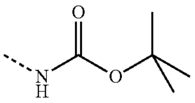 | Ex. 16 | A.1.3 | 2-(Dimethylamino) acetic acid Workup: $CH_2Cl_2$, 1M aq. HCl soln; sat. aq. $NaHCO_3$ soln, sat. aq. NaCl soln; $Na_2SO_4$ | FC ($CH_2Cl_2$/MeOH/ conc. aq. NH3 soln 95:5:2) | 86% |
| Ex. 39 | 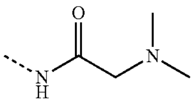 | $NH_2$ | Ex. 38 | B.1 | HCl-dioxane rt, 2 h | crude product | quant. (HCl salt) |
| Ex. 40 | 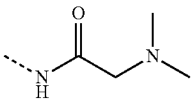 | 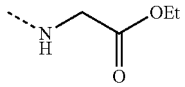 | Ex. 39 | A.6.4 | Ethyl glyoxylate (1.2 equiv.) | FC ($CH_2Cl_2$/MeOH 9:1) | 37% |

[1)] A soln of the macrocyclic ethylester Ex. 40 (63 mg, 0.11 mmol) in THF/MeOH 1:1 (1 mL) was treated at 0° C. for 2 h with 2M aq. LiOH soln (0.16 mL, 0.32 mmol). The mixture was concentrated. The residue was treated with 1M aq. HCl soln and concentrated Purification by reverse phase prep. HPLC afforded Ex. 29 (40 mg, 47%).

[2)] Methyl isothiocyantae (6 mg, 0.11 mmol) was added to a soln of Ex. 39 (50 mg, 0.078 mmol) and i-$Pr_2NEt$ (0.07 mL, 0.39 mmol) in $CH_2Cl_2$ (0.5 mL). The mixture was stired for 16 h at rt. More methyl isothiocyantae (2 mg) was added and stirring continued for 1 h. Aq. Workup ($CHCl_3$, sat. aq. $Na_2CO_3$ soln; $Na_2SO_4$) and purification by prep. HPLC (method 1a) afforded Ex. 30 (26 mg, 48%).

[3)] Triisopropylsilane (0.12 mL, 0.58 mmol) was added to a soln of Ex. 32 (50 mg, 0.115 mmol) in $CH_2Cl_2$ (0.4 mL). The mixture was cooled to 0° C. followed by the addition of TFA (0.4 mL). The mixture was stirred for 30 min at 0° C. and concentrated. FC ($CH_2Cl_2$/MeOH 100:0 to 80:20) afforded Ex. 31 (46 mg, 57%).

[4)] Cf. experimental description for detailed procedure

TABLE 14b
| No | $R^A$ | $R^B$ | Formula | Monoisotopic Mass | Rt (purity at 220 nm) | $[M + H]^+$ found | LC-MS-Method |
|---|---|---|---|---|---|---|---|
| Examples of Core 02 (Ex. 15-Ex. 40;) | | | | | | | |
| cf. experimental description | | | | | | | |
| Ex. 15-Ex. 17: | | | | | | | |
| Ex. 18 | 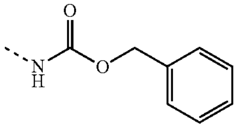 | 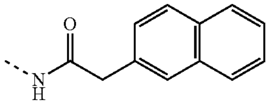 | C44H44N4O6 | 724.3 | 2.36 (98) | 725.2 | method 1a |
| Ex. 19 | $NH_2$ | 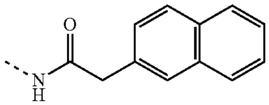 | C36H38N4O4 | 590.3 | 1.76 (97) | 591.2 | method 1a |
| Ex. 20 | 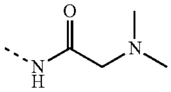 | 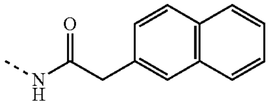 | C40H45N5O5 | 675.3 | 1.82 (95) | 676.3 | method 1a |
| Ex. 21 | 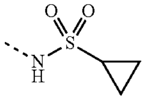 | 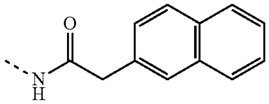 | C39H42N4O6S | 694.3 | 2.10 (97) | 695.2 | method 1a |
| Ex. 22 | 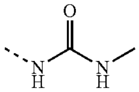 | 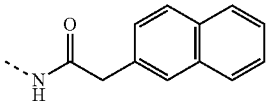 | C38H41N5O5 | 647.3 | 1.96 (98) | 648.2 | method 1a |
| Ex. 23 | 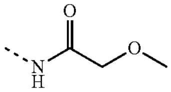 | 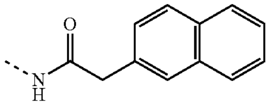 | C39H42N4O6 | 662.3 | 2.04 (99) | 663.2 | method 1a |
| Ex. 24 | 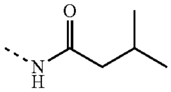 | 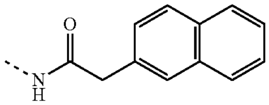 | C41H46N4O5 | 674.3 | 2.20 (98) | 675.2 | method 1a |
| Ex. 25 | 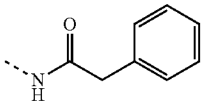 | 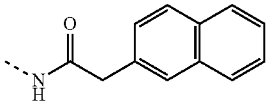 | C44H44N4O5 | 708.3 | 2.27 (99) | 709.2 | method 1a |
| Ex. 26 | 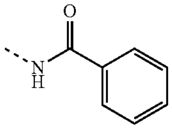 | 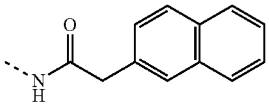 | C43H42N4O5 | 694.3 | 2.26 (99) | 695.2 | method 1a |
| Ex. 27 | 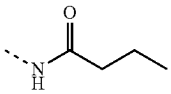 | 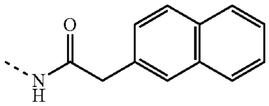 | C40H44N4O5 | 660.3 | 2.15 (99) | 661.2 | method 1a |
| Ex. 28 | 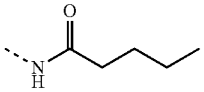 | 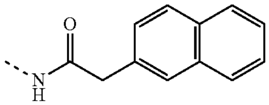 | C41H46N4O5 | 674.3 | 2.24 (99) | 675.3 | method 1a |

TABLE 14b-continued
| Examples of Core 02 (Ex. 15-Ex. 40;) | | | | | | | |
|---|---|---|---|---|---|---|---|
| No | $R^A$ | $R^B$ | Formula | Monoisotopic Mass | Rt (purity at 220 nm) | $[M + H]^+$ found | LC-MS-Method |
| Ex. 29 | 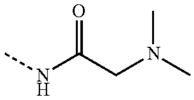 | 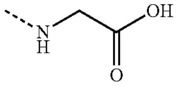 | C30H39N5O6 | 565.3 | 1.25 (99) | 566.2 | method 1a |
| Ex. 30 | 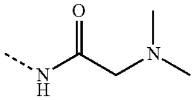 | 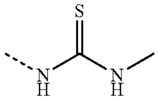 | C30H40N6O4S | 580.3 | 1.38 (95) | 581.2 | method 3a |
| Ex. 31 | 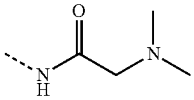 | 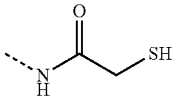 | C30H39N5O5S | 581.3 | 1.49 (90) | 582.0 | method 1a |
| Ex. 32 | 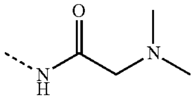 | 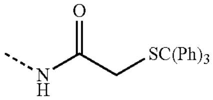 | C49H53N5O5S | 823.4 | 2.18 (90) | 824.3 | method 1a |
| Ex. 33 | 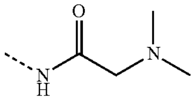 | 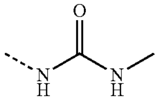 | C30H40N6O5 | 564.3 | 1.40 (99) | 565.1 | method 1a |
| Ex. 34 | 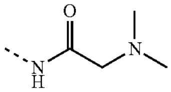 | 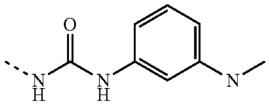 | C37H47N7O5 | 669.4 | 1.37 (97) | 670.2 | method 1a |
| Ex. 35 | 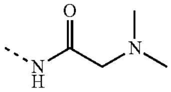 | 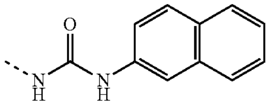 | C39H44N6O5 | 676.3 | 1.84 (98) | 677.3 | method 1a |
| Ex. 36 | 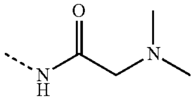 | 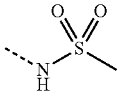 | C29H39N5O6S | 585.3 | 1.44 (99) | 586.0 | method 1a |
| Ex. 37 | 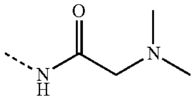 | 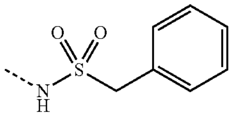 | C35H43N5O6S | 661.3 | 1.68 (97) | 661.8 | method 1e |
| Ex. 38 | 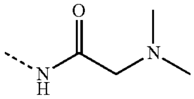 | 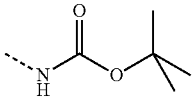 | C33H45N5O6 | 607.3 | 1.73 (93) | 608.1 | method 1a |
| Ex. 39 | 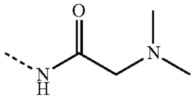 | $NH_2$ | C28H37N5O4 | 507.3 | 1.23 (93) | 508.2 | method 1a |
| Ex. 40 | 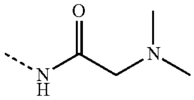 | 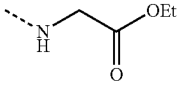 | C32H43N5O6 | 593.3 | 1.38 (96) | 594.1 | method 1a |

TABLE 14c

Examples of Core 02 (Ex. 15-Ex. 40;)

| No | $R^A$ | $R^B$ | IUPAC name |
|---|---|---|---|
| Ex. 15 | 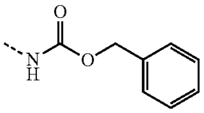 | 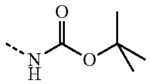 | benzyl N-[(10S,12S,16S)-12-[(tert-butoxycarbonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]carbamate |
| Ex. 16 | $NH_2$ | 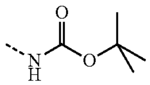 | tert-butyl N-[(10S,12S,16S)-16-amino-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]carbamate |
| Ex. 17 | 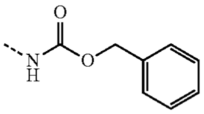 | $NH_2$ | benzyl N-[(10S,12S,16S)-12-amino-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]carbamate |
| Ex. 18 | 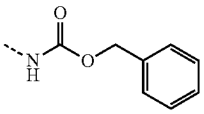 | 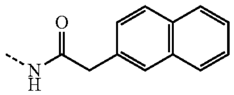 | benzyl N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]carbamate |
| Ex. 19 | $NH_2$ | 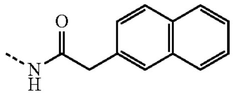 | N-[(10S,12S,16S)-16-amino-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 20 | 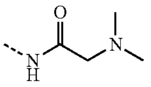 | 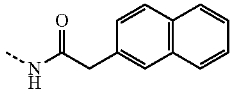 | 2-(dimethylamino)-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 21 | 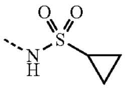 | 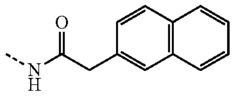 | N-[(10S,12S,16S)-16-[(cyclopropylsulfonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 22 | 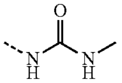 | 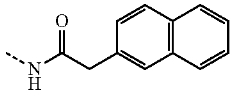 | N-[(10S,12S,16S)-20-methyl-16-{[(methylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 23 | 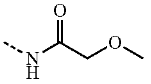 | 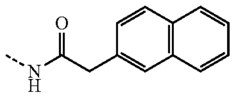 | 2-methoxy-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 24 | 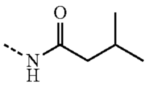 | 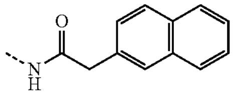 | 3-methyl-N-[(10S,12S,16S)-20-methyl-12-{[2-(2-naphthyl)acetyl]amino}-15,21-dioxo-8-14,20-diazatetracyclo[20.3.1.$0^{2,7}$.$0^{10,14}$]hexacosa-1(26),2,4,6,22,24-hexaen-16-yl]butanamide |
| Ex. 25 | 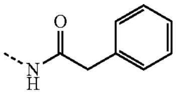 | 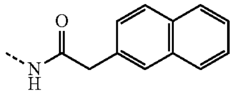 | N-[(10S,12S,16S)-20-methyl-15,21-dioxo-16-[(2-phenylacetyl)amino]-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide |
| Ex. 26 | 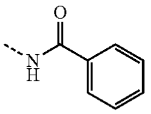 | 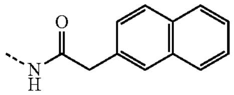 | N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]benzamide |
| Ex. 27 | 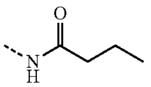 | 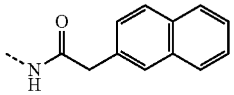 | N-[(10S,12S,16S)-20-methyl-12-{[2-(2-naphthyl)acetyl]amino)-15,21-dioxo-8-oxa-14,20-diazatetracyclo[20.3.1.$0^{2,7}$.$0^{10,14}$]hexacosa-1(26),2,4,6,22,24-hexaen-16-yl]butanamide |

TABLE 14c-continued

Examples of Core 02 (Ex. 15-Ex. 40;)

| No | $R^A$ | $R^B$ | IUPAC name |
|---|---|---|---|
| Ex. 28 | 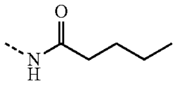 | 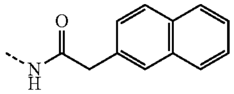 | N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]pentanamide |
| Ex. 29 | 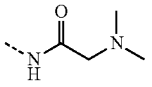 | 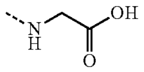 | 2-{[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]amino}acetic acid |
| Ex. 30 | 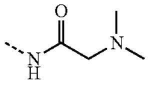 | 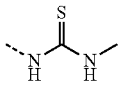 | 2-(dimethylamino)-N-[(10S,12S,16S)-20-methyl-12-{[(methylamino)carbothioyl] amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 31 | 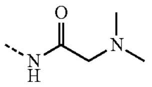 | 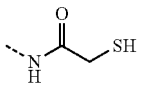 | 2-(dimethylamino)-N-[(10S,12S,16S)-20-methyl-15,21-dioxo-12-[(2-sulfanylacetyl)amino]-8-oxa-14,20-diazatetracyclo[20.3.1.$0^{2,7}$.$0^{10,14}$]hexacosa-1(26),2,4,6,22,24-hexaen-16-yl]acetamide |
| Ex. 32 | 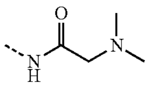 | 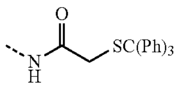 | 2-(dimethylamino)-N-[(10S,12S,16S)-20-methyl-15,21-dioxo-12-{[2-(tritylsulfanyl)acetyl]amino}-8-oxa-14,20-diazatetracyclo[20.3.1.$0^{2,7}$.$0^{10,14}$] hexacosa-1(26),2,4,6,22,24-hexaen-16-yl]acetamide |
| Ex. 33 | 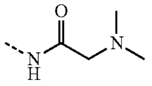 | 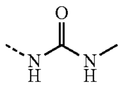 | 2-(dimethylamino)-N-[(10S,12S,16S)-20-methyl-12-{[(methylamino)carbonyl] amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 34 | 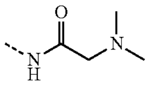 | 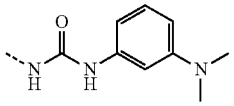 | 2-(dimethylamino)-N-[(10S,12S,16S)-12-({[3-(dimethylamino)anilino]carbonyl} amino)-20-methyl-15,21-dioxo-8-oxa-14,20-diazatetracyclo[20.3.1.$0^{2,7}$.$0^{10,14}$] hexacosa-1(26),2,4,6,22,24-hexaen-16-yl]acetamide |
| Ex. 35 | 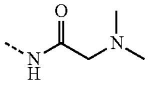 | 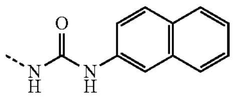 | 2-(dimethylamino)-N-[(10S,12S,16S)-20-methyl-12-{[(2-naphthylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 36 | 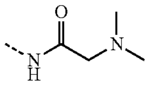 | 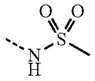 | 2-(dimethylamino)-N-[(10S,12S,16S)-20-methyl-12-[(methylsulfonyl)amino]-15,21-dioxo-8-oxa-14,20-diazatetracyclo[20.3.1.$0^{2,7}$.$0^{10,14}$]hexacosa-1(26),2,4,6,22,24-hexaen-16-yl]acetamide |
| Ex. 37 | 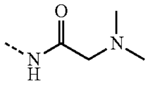 | 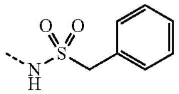 | N-[(10S,12S,16S)-12-[(benzylsulfonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]-2-(dimethylamino)acetamide |
| Ex. 38 | 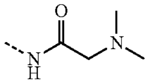 | 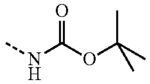 | tert-butyl N-[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]carbamate |
| Ex. 39 | 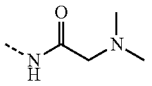 | $NH_2$ | N-[(10S,12S,16S)-12-amino-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]-2-(dimethylamino)acetamide |
| Ex. 40 | 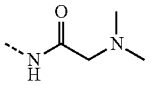 | 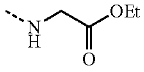 | ethyl 2-{[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]amino}acetate |

TABLE 15a

| No | $R^E$ | Starting Material | General Proced. | Reagent | Purification Method | Yield (isolated salt) |
|---|---|---|---|---|---|---|
| Examples of Core 03 (Ex. 41-Ex. 67;) | | | | | | |
| cf. experimental description | | | | | | |
| Ex. 41-Ex. 42, Ex. 62-Ex. 67: | | | | | | |
| Ex. 43 | $CONH_2$ | Ex. 42 | A.2 | $NH_4Cl$ (4 equiv.)<br>HATU (2.0 equiv.)<br>HOAT (2.0 equiv.)<br>$i\text{-}Pr_2NEt$ (6 equiv.)<br>rt, 2 h<br>Workup: Sat. aq. $Na_2CO_3$, $CH_2Cl_2$ | prep. HPLC method 3 | 64% |
| Ex. 44 | $CONHCH_3$ | Ex. 42 | A.2 | $CH_3NH_3Cl$ (4 equiv.)<br>HATU (2.0 equiv.)<br>HOAT (2.0 equiv.)<br>$i\text{-}Pr_2NEt$ (6 equiv.)<br>4° C., 1 h<br>Workup: Sat. aq. $Na_2CO_3$, $CH_2Cl_2$ | prep. HPLC method 3 | 71% |
| Ex. 45 | CONHPh | Ex. 42 | A.2 | Aniline | prep. HPLC method 3 | 80% |
| Ex. 46 | 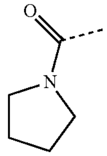 | Ex. 42 | A.2 | Pyrrolidine | prep. HPLC method 3 | 53% |
| Ex. 47 | 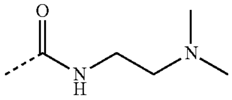 | Ex. 42 | A.2 | N,N-Dimethyl-ethylenediamine (1.0 equiv.)<br>Workup: Sat. aq. $Na_2CO_3$, $CH_2Cl_2$ | prep. HPLC method 1a | 61% (TFA salt) |
| Ex. 48 | 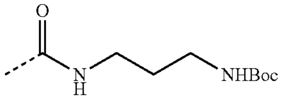 | Ex. 42 | A.2 | tert.-Butyl-3-aminopropylcarbamate | prep. HPLC method 3 | 65% |
| Ex. 49 | 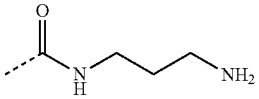 | Ex. 48 | B.1 | HCl-dioxane<br>rt, 2 h | crude product | 74% (HCl salt) |
| Ex. 50 | 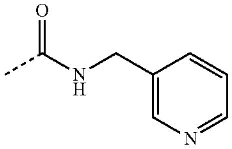 | Ex. 42 | A.2 [1)] | 3-Picolylamine | prep. HPLC method 1c | 37% (TFA salt) |
| Ex. 51 | 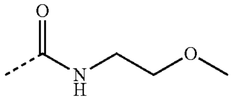 | Ex. 42 | A.2 | 2-Methoxyethylamine | prep. HPLC method 3 | 63% |
| Ex. 52 | 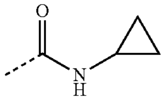 | Ex. 42 | A.2 | Cyclopropylamine | prep. HPLC method 3 | 84% |
| Ex. 53 | 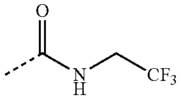 | Ex. 42 | A.2 | 2,2,2-Trifluoroethylamine | prep. HPLC method 3 | 66% |

TABLE 15a-continued

| Examples of Core 03 (Ex. 41-Ex. 67;) | | | | | | |
|---|---|---|---|---|---|---|
| No | $R^E$ | Starting Material | General Proced. | Reagent | Purification Method | Yield (isolated salt) |
| Ex. 54 | 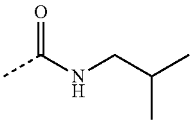 | Ex. 42 | A.2 | Isobutylamine | prep. HPLC method 3 | 66% |
| Ex. 55 | 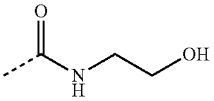 | Ex. 42 | A.2 | 2-Aminoethanol<br>4° C. 2 h and rt 3 h | prep. HPLC method 1c | 82% |
| Ex. 56 | 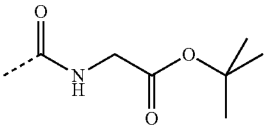 | Ex. 42 | A.2 | Glycine-tert.-butyl ester hydrochloride (1.5 equiv.)<br>HATU 2.0 equiv.)<br>HOAt (2.0 equiv.)<br>i-$Pr_2NEt$ (3.0 equiv.)<br>4° C., 2 h | prep. HPLC method 3 | 76% |
| Ex. 57 | 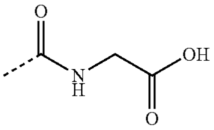 | Ex. 56 | B.2 | TFA, $CH_2Cl_2$ | crude product | 80% |
| Ex. 58 | 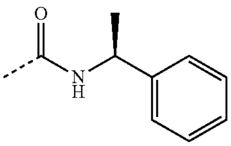 | Ex. 42 | A.2 | (L)-α-Methylbenzylamine<br>4° C. 2 h and rt 2 h | prep. HPLC method 3 | 55% |
| Ex. 59 | 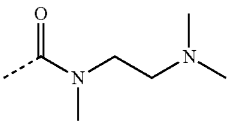 | Ex. 42 | A.2 | N,N,N'-Trimethylethylene-diamine | FC ($CH_2Cl_2$/MeOH/ aq. $NH_3$ soln) | 83% |
| Ex. 60 | 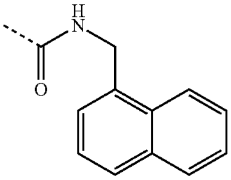 | Ex. 42 | A.2 | Naphthalen-1-ylmethanamine | prep. HPLC method 3 | 57% |
| Ex. 61 | 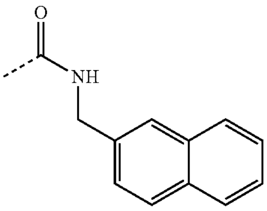 | Ex. 42 | A.2 | Naphthalen-2-ylmethanamine | prep. HPLC method 3 and prep. HPLC method 2a | 29% |

1) Cf. experimental description for detailed procedure

TABLE 15b

| Examples of Core 03 (Ex. 41-Ex. 67;) | | | | | | |
|---|---|---|---|---|---|---|
| No | $R^E$ | Formula | Monoisotopic Mass | Rt (purity at 220 nm) | $[M + H]^+$ found | LC-MS-Method |
| cf. experimental description | | | | | | |
| Ex. 41-Ex. 42, Ex. 62-Ex. 67: | | | | | | |
| Ex. 43 | $CONH_2$ | C23H27N3O5 | 425.2 | 1.47 (95) | 426.1 | method 1a |
| Ex. 44 | $CONHCH_3$ | C24H29N3O5 | 439.2 | 1.49 (99) | 440.1 | method 1a |
| Ex. 45 | CONHPh | C29H31N3O5 | 501.2 | 1.97 (97) | 502.1 | method 1a |
| Ex. 46 | 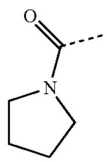 | C27H33N3O5 | 479.2 | 1.74 (98) | 480.1 | method 1a |
| Ex. 47 | 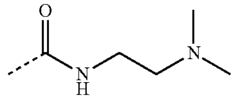 | C27H36N4O5 | 496.3 | 1.32 (99) | 497.2 | method 1a |
| Ex. 48 | 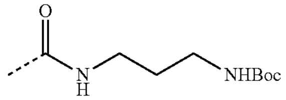 | C31H42N4O7 | 582.3 | 1.91 (99) | 583.1 | method 1a |
| Ex. 49 | 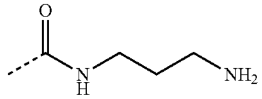 | C26H34N4O5 | 482.2 | 1.32 (95) | 483.1 | method 1a |
| Ex. 50 | 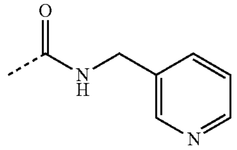 | C29H32N4O5 | 516.2 | 1.32 (99) | 517.1 | method 1a |
| Ex. 51 | 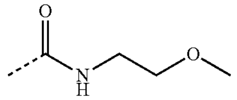 | C26H33N3O6 | 483.2 | 1.57 (95) | 484.1 | method 1a |
| Ex. 52 | 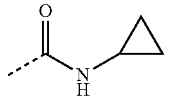 | C26H31N3O5 | 465.2 | 1.67 (99) | 466.1 | method 1a |
| Ex. 53 | 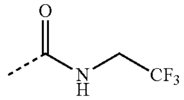 | C25H28F3N3O5 | 507.2 | 1.80 (94) | 508.0 | method 1a |
| Ex. 54 | 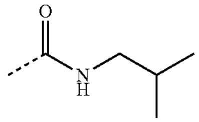 | C27H35N3O5 | 481.2 | 1.85 (95) | 482.1 | method 1a |
| Ex. 55 | 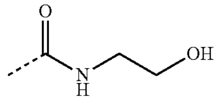 | C25H31N3O6 | 469.2 | 1.40 (94) | 470.1 | method 1a |

TABLE 15b-continued

| Examples of Core 03 (Ex. 41-Ex. 67;) | | | | | | |
|---|---|---|---|---|---|---|
| No | $R^E$ | Formula | Monoisotopic Mass | Rt (purity at 220 nm) | $[M + H]^+$ found | LC-MS-Method |
| Ex. 56 | 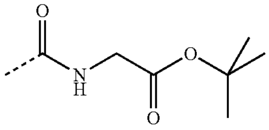 | C29H37N3O7 | 539.3 | 1.91 (93) | 540.0 | method 1a |
| Ex. 57 | 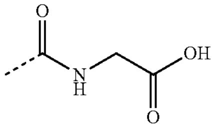 | C25H29N3O7 | 483.2 | 1.47 (85) | 484.1 | method 1a |
| Ex. 58 | 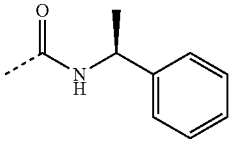 | C31H35N3O5 | 529.2 | 2.00 (93) | 530.1 | method 1a |
| Ex. 59 | 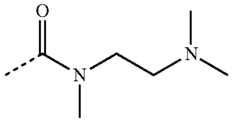 | C28H38N4O5 | 510.3 | 1.37 (97) | 511.2 | method 1a |
| Ex. 60 | 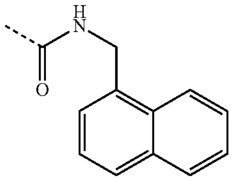 | C34H35N3O5 | 565.2 | 2.09 (97) | 566.1 | method 1a |
| Ex. 61 | 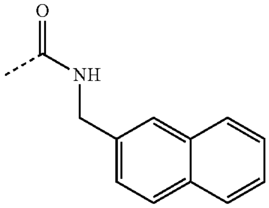 | C34H35N3O5 | 565.2 | 2.12 (100) | 566.1 | method 1a |

TABLE 15c

| Examples of Core 03 (Ex. 41-Ex. 67;) | | |
|---|---|---|
| No | $R^E$ | IUPAC name |
| Ex. 41 | $CO_2CH_2Ph$ | benzyl (10R,15S)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxylate |
| Ex. 42 | $CO_2H$ | (10R,15S)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxylic acid |
| Ex. 43 | $CONH_2$ | (10R,15S)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 44 | $CONHCH_3$ | (10R,15S)-4-methoxy-N,10,16-trimethyl-12,17-dioxo-8-oxa-11,16-diazatricyclo[16.3.1.0$^{2,7}$]docosa-1(22),2,4,6,18,20-hexaene-15-carboxamide |
| Ex. 45 | CONHPh | (10R,15S)-4-methoxy-10,16-dimethyl-12,17-dioxo-N-phenyl-8-oxa-11,16-diazatricyclo[16.3.1.0$^{2,7}$]docosa-1(22),2,4,6,18,20-hexaene-15-carboxamide |

TABLE 15c-continued

Examples of Core 03 (Ex. 41-Ex. 67;)

| No | $R^E$ | IUPAC name |
|---|---|---|
| Ex. 46 | 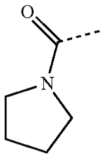 | (10R,15S)-4-methoxy-10,16-dimethyl-15-(1-pyrrolidinylcarbonyl)-8-oxa-11,16-diazatricyclo[16.3.1.0$^{2,7}$]docosa-1(22),2,4,6,18,20-hexaene-12,17-dione |
| Ex. 47 | 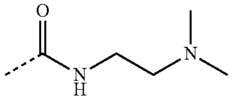 | (10R,15S)-N-[2-(dimethylamino)ethyl]-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 48 | 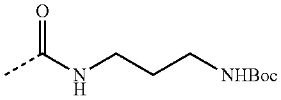 | tert-butyl N-[3-({[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]carbonyl}amino)propyl]carbamate |
| Ex. 49 | 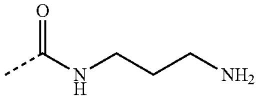 | (10R,15S)-N-(3-aminopropyl)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 50 | 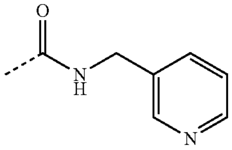 | (10R,15S)-4-methoxy-10,16-dimethyl-12,17-dioxo-N-(3-pyridinylmethyl)-8-oxa-11,16-diazatricyclo[16.3.1.0$^{2,7}$]docosa-1(22),2,4,6,18,20-hexaene-15-carboxamide |
| Ex. 51 | 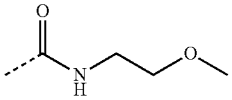 | (10R,15S)-4-methoxy-N-(2-methoxyethyl)-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 52 | 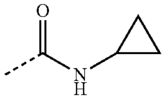 | (10R,15S)-N-cyclopropyl-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 53 | 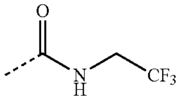 | (10R,15S)-4-methoxy-10,16-dimethyl-12,17-dioxo-N-(2,2,2-trifluoroethyl)-8-oxa-11,16-diazatricyclo[16.3.1.0$^{2,7}$]docosa-1(22),2,4,6,18,20-hexaene-15-carboxamide |
| Ex. 54 | 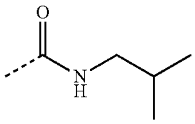 | (10R,15S)-N-isobutyl-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 55 | 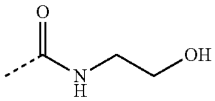 | (10R,15S)-N-(2-hydroxyethyl)-4-methoxy-10,16-dimethyl-12,17-dioxo-8-oxa-11,16-diazatricyclo[16.3.1.0$^{2,7}$]docosa-1(22),2,4,6,18,20-hexaene-15-carboxamide |
| Ex. 56 | 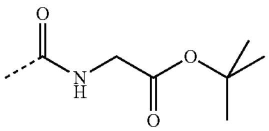 | tert-butyl 2-({[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]carbonyl}amino)acetate |
| Ex. 57 | 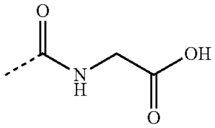 | 2-({[(10R,15S)-4-methoxy-10,16-dimethyl-12,17-dioxo-8-oxa-11,16-diazatricyclo[16.3.1.0$^{2,7}$]docosa-1(22),2,4,6,18,20-hexaen-15-yl]carbonyl}amino)acetic acid |

TABLE 15c-continued

| No | $R^E$ | IUPAC name |
|---|---|---|
| | Examples of Core 03 (Ex. 41-Ex. 67;) | |
| Ex. 58 | 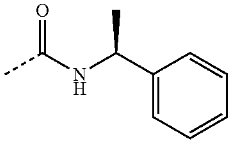 | (10R,15S)-4-methoxy-10,16-dimethyl-12,17-dioxo-N-[(1S)-1-phenylethyl]-8-oxa-11,16-diazatricyclo[16.3.1.$0^{2,7}$]docosa-1(22),2,4,6,18,20-hexaene-15-carboxamide |
| Ex. 59 | 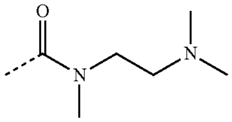 | (10R15S)-N-[2-(dimethylamino)ethyl]-4-methoxy-N,10,16-trimethyl-12,17-dioxo-8-oxa-11,16-diazatricyclo[16.3.1.$0^{2,7}$]docosa-1(22),2,4,6,18,20-hexaene-15-carboxamide |
| Ex. 60 | 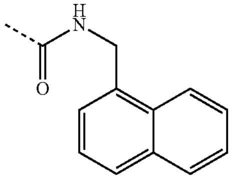 | (10R,15S)-4-methoxy-10,16-dimethyl-N-(1-naphthylmethyl)-12,17-dioxo-8-oxa-11,16-diazatricyclo[16.3.1.$0^{2,7}$]docosa-1(22),2,4,6,18,20-hexaene-15-carboxamide |
| Ex. 61 | 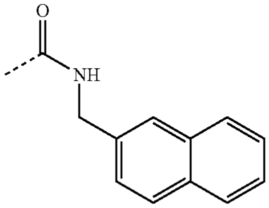 | (10R,15S)-4-methoxy-10,16-dimethyl-N-(2-naphthylmethyl)-12,17-dioxo-8-oxa-11,16-diazatricyclo[16.3.1.$0^{2,7}$]docosa-1(22),2,4,6,18,20-hexaene-15-carboxamide |
| Ex. 62 | $CH_2OH$ | (10R,15S)-15-(hydroxymethyl)-4-methoxy-10,16-dimethyl-8-oxa-11,16-diazatricyclo[16.3.1.$0^{2,7}$]docosa-1(22),2,4,6,18,20-hexaene-12,17-dione |
| Ex. 63 | 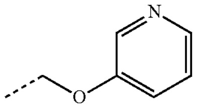 | (10R,15S)-4-methoxy-10,16-dimethyl-15-[(3-pyridinyloxy)methyl]-8-oxa-11,16-diazatricyclo[16.3.1.$0^{2,7}$]docosa-1(22),2,4,6,18,20-hexaene-12,17-dione |
| Ex. 64 | $CH_2N_3$ | (10R,15S)-15-(azidomethyl)-4-methoxy-10,16-dimethyl-8-oxa-11,16-diazatricyclo[16.3.1.$0^{2,7}$]docosa-1(22),2,4,6,18,20-hexaene-12,17-dione |
| Ex. 65 | $CH_2NH_2$ | (10R,15S)-15-(aminomethyl)-4-methoxy-10,16-dimethyl-8-oxa-11,16-diazatricyclo[16.3.1.$0^{2,7}$]docosa-1(22),2,4,6,18,20-hexaene-12,17-dione |
| Ex. 66 | $CH_2NHCOCH_2Ph$ | N-{[(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]methyl}-2-phenylacetamide |
| Ex. 67 | $CH_2OCONHPh$ | [(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]methyl N-phenylcarbamate |

TABLE 16a

| No | $R^c$ | Starting Material | General Proced. | Reagent | Purification Method | Yield (isolated salt) |
|---|---|---|---|---|---|---|
| | | | Examples of Core 04 (Ex. 68-Ex. 89;) | | | |
| | | | cf. experimental description | | | |
| Ex. 68-Ex. 69: | | | | | | |
| Ex. 70 | $NHCH_3$ | Ex. 69 | A.2 | $CH_3NH_3Cl$ (4 equiv.)<br>HATU (2.0 equiv.)<br>HOAT (2.0 equiv.)<br>$i\text{-}Pr_2NEt$ (6 equiv.)<br>rt, 2 h<br>Workup: Sat. aq. $Na_2CO_3$, $CH_2Cl_2$ | FC ($CH_2Cl_2$/MeOH) | 50% |

TABLE 16a-continued

| Examples of Core 04 (Ex. 68-Ex. 89;) | | | | | | |
|---|---|---|---|---|---|---|
| No | $R^c$ | Starting Material | General Proced. | Reagent | Purification Method | Yield (isolated salt) |
| Ex. 71 | $NH_2$ | Ex. 69 | A.2 | $NH_4Cl$ (4 equiv.)<br>HATU (2.0 equiv.)<br>HOAT (2.0 equiv.)<br>i-$Pr_2$NEt (6 equiv.)<br>rt, 2 h<br>Workup: Sat. aq. $Na_2CO_3$, $CH_2Cl_2$ | prep. HPLC method 3 | 95 |
| Ex. 72 | NHPh | Ex. 69 | A.2 | Aniline | prep. HPLC method 3 | 68 |
| Ex. 73 | 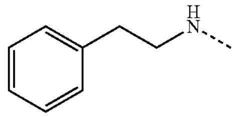 | Ex. 69 | A.2 | 2-Phenylethylamine | prep. HPLC method 3 | 71 |
| Ex. 74 | 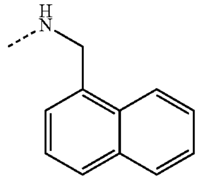 | Ex. 69 | A.2 | Naphthalen-1-ylmethanamine<br>0° C., 1 h | prep. HPLC method 3 and FC (EtOAc) | 70% |
| Ex. 75 | 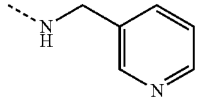 | Ex. 69 | A.2 | 3-Picolylamine<br>4°C, 1 h<br>Workup: Sat. aq. $Na_2CO_3$, $CHCl_3$ | prep. HPLC method 3 | 55% |
| Ex. 76 | 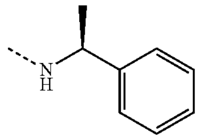 | Ex. 69 | A.2 | (L)-α-Methylbenzylamine | prep. HPLC method 3 | 60% |
| Ex. 77 | 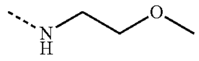 | Ex. 69 | A.2 | 2-Methoxyethylamine | prep. HPLC method 3 | 66% |
| Ex. 78 | 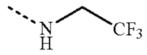 | Ex. 69 | A.2 | 2,2,2-Trifluoroethylamine | prep. HPLC method 3 | 72% |
| Ex. 79 | 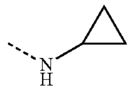 | Ex. 69 | A.2 | Cyclopropylamine | prep. HPLC method 3 then prep. HPLC method 1a | 32% |
| Ex. 80 | 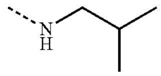 | Ex. 69 | A.2 | Isobutylamine<br>4° C., 1 h | prep. HPLC method 3 | 77% |
| Ex. 81 | 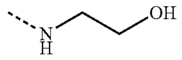 | Ex. 69 | A.2 | 2-Aminoethanol<br>4° C. 2 h and rt 1 h | prep. HPLC method 1a | 56% |
| Ex. 82 | 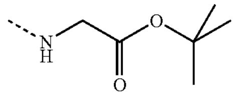 | Ex. 69 | A.2 | Glycine-tert.-butyl ester hydrochloride<br>(2.2 equiv.)<br>HATU (2.5 equiv.)<br>HOAt (2.5 equiv.)<br>i-$Pr_2$NEt (6.0 equiv.)<br>4° C., 3 h | FC (EtOAc) | 78% |
| Ex. 83 | 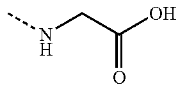 | Ex. 82 | B.2 | TFA, $CH_2Cl_2$,<br>rt, 4 h | prep. HPLC method 1a | 78% |

TABLE 16a-continued

Examples of Core 04 (Ex. 68-Ex. 89;)

| No | $R^c$ | Starting Material | General Proced. | Reagent | Purification Method | Yield (isolated salt) |
|---|---|---|---|---|---|---|
| Ex. 84 | 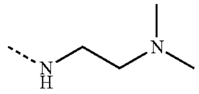 | Ex. 69 | A.2 | N,N-Dimethyl-ethylenediamine 4° C., 1 h Workup: Sat. aq. $Na_2CO_3$, EtOAc | prep. HPLC method 3 | 47% |
| Ex. 85 | 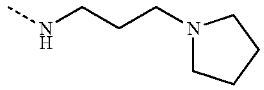 | Ex. 69 | A.2 | 1-(3-Aminopropyl) pyrrolidine | prep. HPLC method 1a | 57% (TFA salt) |
| Ex. 86 | 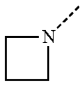 | Ex. 69 | A.2 | Azetidine | prep. HPLC method 3 | 80% |
| Ex. 87 | 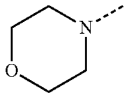 | Ex. 69 | A.2 | Morpholine | prep. HPLC method 3 | 74% |
| Ex. 88 | 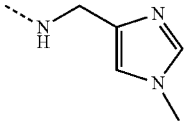 | Ex. 69 | A.2 | (1-Methyl-1H-imidazol-4-yl)methanamine 4° C., 2 h and rt, 1 h | prep. HPLC method 1a | 27% (TFA salt) |
| Ex. 89 | 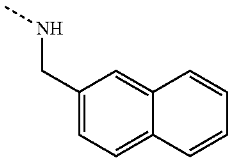 | Ex. 69 | A.2 | Naphthalen-2-ylmethanamine 0° C., 3 h | prep. HPLC method 3 and FC (EtOAc) | 73% |

TABLE 16b

Examples of Core 04 (Ex. 68-Ex. 89;)

| No | $R^c$ | Formula | Monoisotopic Mass | Rt (purity at 220 nm) | $[M + H]^+$ found | LC-MS-Method |
|---|---|---|---|---|---|---|
| | | cf. experimental description | | | | |
| Ex. 68-Ex. 69: | | | | | | |
| Ex.70 | $NHCH_3$ | C23H27N3O4 | 409.2 | 1.57 (96) | 410.1 | method 1a |
| Ex.71 | $NH_2$ | C22H25N3O4 | 395.2 | 1.53 (95) | 396.1 | method 1a |
| Ex.72 | NHPh | C28H29N3O4 | 471.2 | 1.96 (92) | 472.1 | method 1a |
| Ex.73 | 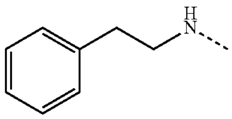 | C30H33N3O4 | 499.2 | 1.97 (99) | 500.1 | method 1a |
| Ex.74 | 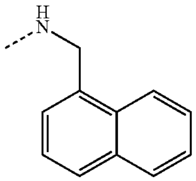 | C33H33N3O4 | 535.2 | 2.11 (96) | 536.2 | method 1a |
| Ex.75 | 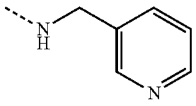 | C28H30N4O4 | 486.2 | 1.40 (93) | 487.1 | method 1a |

TABLE 16b-continued
| Examples of Core 04 (Ex. 68-Ex. 89;) | | | | | | |
|---|---|---|---|---|---|---|
| No | $R^c$ | Formula | Monoisotopic Mass | Rt (purity at 220 nm) | $[M + H]^+$ found | LC-MS-Method |
| Ex.76 | 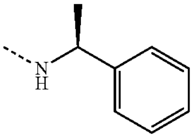 | C30H33N3O4 | 499.2 | 1.99 (96) | 500.1 | method 1a |
| Ex.77 | 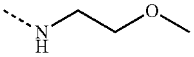 | C25H31N3O5 | 453.2 | 1.60 (99) | 454.1 | method 1a |
| Ex.78 | 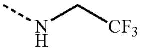 | C24H26F3N3O4 | 477.2 | 1.82 (96) | 478.0 | method 1a |
| Ex.79 | 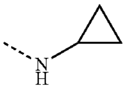 | C25H29N3O4 | 435.2 | 1.71 (98) | 436.1 | method 1a |
| Ex.80 | 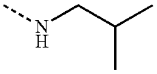 | C26H33N3O4 | 451.2 | 1.90 (98) | 452.1 | method 1a |
| Ex.81 | 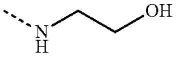 | C24H29N3O5 | 439.2 | 1.50 (91) | 440.1 | method 1a |
| Ex.82 | 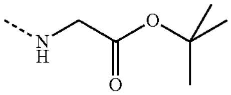 | C28H35N3O6 | 509.2 | 1.97 (95) | 510.1 | method 1a |
| Ex.83 | 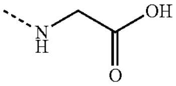 | C24H27N3O6 | 453.2 | 1.50 (98) | 454.1 | method 1a |
| Ex.84 | 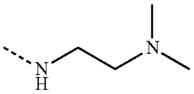 | C26H34N4O4 | 466.2 | 1.40 (99) | 467.1 | method 1a |
| Ex.85 | 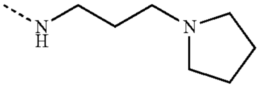 | C29H38N4O4 | 506.3 | 1.46 (99) | 507.2 | method 1a |
| Ex.86 | 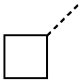 | C25H29N3O4 | 435.2 | 1.63 (92) | 436.1 | method 1a |
| Ex.87 | 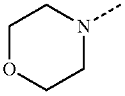 | C26H31N3O5 | 465.2 | 1.64 (92) | 466.1 | method 1a |
| Ex.88 | 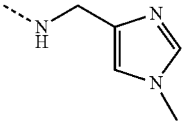 | C27H31N5O4 | 489.2 | 1.43 (99) | 490.1 | method 1a |
| Ex.89 | 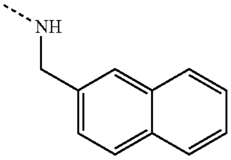 | C33H33N3O4 | 535.2 | 2.14 (93) | 536.1 | method 1a |

TABLE 16c

Examples of Core 04 (Ex. 68-Ex. 89;)

| No | $R^c$ | IUPAC name |
|---|---|---|
| Ex.68 | $OCH_2Ph$ | benzyl (9S,14S)-9,15-dimethyl-11,16-dioxo-7-oxa-10,15-diazatricyclo[15.3.1.1$^{2,6}$]docosa-1(21),2(22),3,5,17,19-hexaene-14-carboxylate |
| Ex.69 | OH | (9S,14S)-9,15-dimethyl-11,16-dioxo-7-oxa-10,15-diazatricyclo[15.3.1.1$^{2,6}$]docosa-1(21),2(22),3,5,17,19-hexaene-14-carboxylic acid |
| Ex.70 | $NHCH_3$ | (9S,14S)-N,9,15-trimethyl-11,16-dioxo-7-oxa-10,15-diazatricyclo[15.3.1.1$^{2,6}$]docosa-1(21),2(22),3,5,17,19-hexaene-14-carboxamide |
| Ex.71 | $NH_2$ | (9S,14S)-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex.72 | NHPh | (9S,14S)-9,15-dimethyl-11,16-dioxo-N-phenyl-7-oxa-10,15-diazatricyclo[15.3.1.1$^{2,6}$]docosa-1(21),2(22),3,5,17,19-hexaene-14-carboxamide |
| Ex.73 | 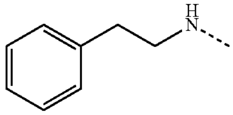 | (9S,14S)-9,15-dimethyl-11,16-dioxo-N-phenethyl-7-oxa-10,15-diazatricyclo[15.3.1.1$^{2,6}$]docosa-1(21),2(22),3,5,17,19-hexaene-14-carboxamide |
| Ex.74 | 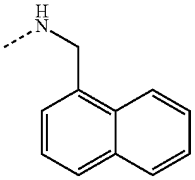 | (9S,14S)-9,15-dimethyl-N-(1-naphthylmethyl)-11,16-dioxo-7-oxa-10,15-diazatricyclo[15.3.1.1$^{2,6}$]docosa-1(21),2(22),3,5,17,19-hexaene-14-carboxamide |
| Ex.75 | 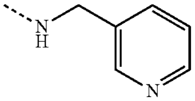 | (9S,14S)-9,15-dimethyl-11,16-dioxo-N-(3-pyridinylmethyl)-7-oxa-10,15-diazatricyclo[15.3.1.1$^{2,6}$]docosa-1(21),2(22),3,5,17,19-hexaene-14-carboxamide |
| Ex.76 | 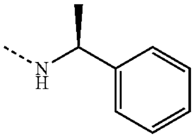 | (9S,14S)-9,15-dimethyl-11,16-dioxo-N-[(1S)-1-phenylethyl]-7-oxa-10,15-diazatricyclo[15.3.1.1$^{2,6}$]docosa-1(21),2(22),3,5,17,19-hexaene-14-carboxamide |
| Ex.77 | 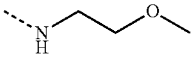 | (9S,14S)-N-(2-methoxyethyl)-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex.78 | 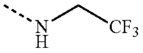 | (9S,14S)-9,15-dimethyl-11,16-dioxo-N-(2,2,2-trifluoroethyl)-7-oxa-10,15-diazatricyclo[15.3.1.1$^{2,6}$]docosa-1(21),2(22),3,5,17,19-hexaene-14-carboxamide |
| Ex.79 | 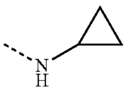 | (9S,14S)-N-cyclopropyl-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex.80 | 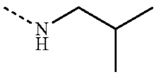 | (9S,14S)-N-isobutyl-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex.81 | 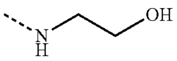 | (9S,14S)-N-(2-hydroxyethyl)-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex.82 | 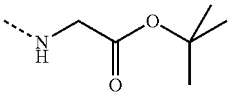 | tert-butyl 2-({[(9S,14S)-9,15-dimethyl-11,16-dioxo-7-oxa-10,15-diazatricyclo[15.3.1.1$^{2,6}$]docosa-1(21),2(22),3,5,17,19-hexaen-14-yl]carbonyl}amino)acetate |

TABLE 16c-continued

| Examples of Core 04 (Ex. 68-Ex. 89;) | | |
|---|---|---|
| No | $R^c$ | IUPAC name |
| Ex.83 | 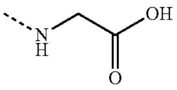 | 2-({[(9S,14S)-9,15-dimethyl-11,16-dioxo-7-oxa-10,15-diazatricyclo[15.3.1.1$^{2,6}$]docosa-1(21),2(22),3,5,17,19-hexaen-14-yl]carbonyl}amino)acetic acid |
| Ex.84 | 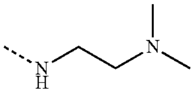 | (9S,14S)-N-[2-(dimethylamino)ethyl]-9,15-dimethyl-11,16-dioxo-7-oxa-10,15-diazatricyclo[15.3.1.1$^{2,6}$]docosa-1(21),2(22),3,5,17,19-hexaene-14-carboxamide |
| Ex.85 | 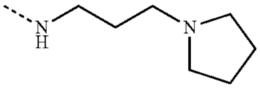 | (9S,14S)-9,15-dimethyl-11,16-dioxo-N-[3-(1-pyrrolidinyl)propyl]-7-oxa-10,15-diazatricyclo[15.3.1.1$^{2,6}$]docosa-1(21),2(22),3,5,17,19-hexaene-14-carboxamide |
| Ex.86 | 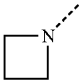 | (9S,14S)-14-(1-azetanylcarbonyl)-9,15-dimethyl-7-oxa-10,15-diazatricyclo[15.3.1.1$^{2,6}$]docosa-1(21),2(22),3,5,17,19-hexaene-11,16-dione |
| Ex.87 | 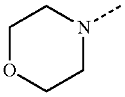 | (9S,14S)-9,15-dimethyl-14-(morpholinocarbonyl)-7-oxa-10,15-diazatricyclo[15.3.1.1$^{2,6}$]docosa-1(21),2(22),3,5,17,19-hexaene-11,16-dione |
| Ex.88 | 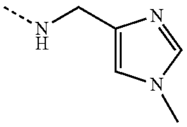 | (9S,14S)-9,15-dimethyl-N-[(1-methyl-1H-imidazol-4-yl)methyl]-11,16-dioxo-7-oxa-10,15-diazatricyclo[15.3.1.1$^{2,6}$]docosa-1(21),2(22),3,5,17,19-hexaene-14-carboxamide |
| Ex.89 | 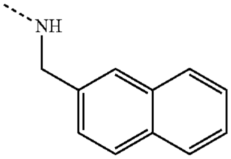 | (9S,14S)-9,15-dimethyl-N-(2-naphthylmethyl)-11,16-dioxo-7-oxa-10,15-diazatricyclo[15.3.1.1$^{2,6}$]docosa-1(21),2(22),3,5,17,19-hexaene-14-carboxamide |

TABLE 17a

| Examples of Core 05 (Ex. 90-Ex. 114 and Ex. 341-Ex. 358;) | | | | | | | |
|---|---|---|---|---|---|---|---|
| No | $R^B$ | $R^D$ | Starting Material | General Procedure | Reagent | Purification Method | Yield (isolated salt) |
| Ex. 90-Ex. 92 | | | cf. experimental description | | | | |
| Ex. 93 | $NH_2$ | H | Ex. 90 | B.1 [1)] | HCl-dioxane rt, 16 h | prep. HPLC method 1c | 17% (TFA salt) |
| Ex. 94 | 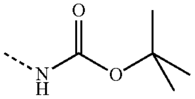 | $CH_3$ | Ex. 91 | A.6.2; [5)] | Formaldehyde (36.5% in $H_2O$) | FC ($CH_2Cl_2$/MeOH) | 84% |
| Ex. 95 | $NH_2$ | $CH_3$ | Ex. 94 | B.1; [5)] | HCl-dioxane rt, 2 h | crude product | quant. (HCl salt) |
| Ex. 96 | 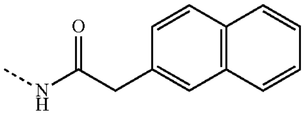 | $CH_3$ | Ex. 95 | A.1.1; [5)] | 2-Naphthaleneacetic acid | FC ($CH_2Cl_2$/MeOH) and prep. HPLC method 1b | 41% (TFA salt) |
| Ex. 97 | 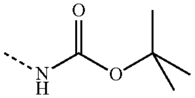 | 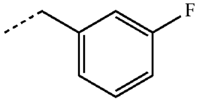 | Ex. 91 | A.6.3; [5)] | 3-Fluorobenzaldehyde | FC ($CH_2Cl_2$/MeOH) | 80% |
| Ex. 98 | $NH_2$ | 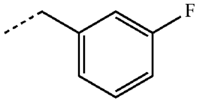 | Ex. 97 | B.1; [5)] | HCl-dioxane rt, 2 h | crude product | 95% (HCl salt) |
| Ex. 99 | $NHCOCH_3$ | $CH_3$ | Ex. 95 | A.1.2.1 | Acetyl chloride (4.0 equiv. in total) | prep. HPLC method 1a | 61% (TFA salt) |
| Ex. 100 | $NHCOCH_3$ | 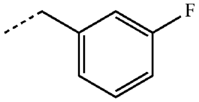 | Ex. 98 | A.1.2.1; [5)] | Acetyl chloride (4.0 equiv. in total) | prep. HPLC method 1a | 64% (TFA salt) |

TABLE 17a-continued

| Examples of Core 05 (Ex. 90-Ex. 114 and Ex. 341-Ex. 358;) | | | | | | | |
|---|---|---|---|---|---|---|---|
| No | $R^B$ | $R^D$ | Starting Material | General Procedure | Reagent | Purification Method | Yield (isolated salt) |
| Ex. 101 | 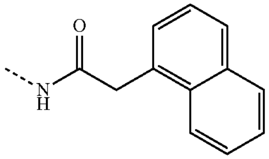 | $CH_3$ | Ex. 95 | A.1.3; [5)] | 1-Naphthaleneacetic acid | prep. HPLC method 1a | 49% (TFA salt) |
| Ex. 102 | 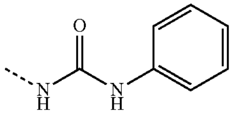 | $CH_3$ | Ex. 95 | A.3 | Phenyl isocyanate rt, 15 h | prep. HPLC method 1a | 57% (TFA salt) |
| Ex. 103 | 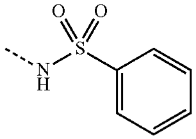 | $CH_3$ | Ex. 95 | A.5; [5)] | Benzenesulfonyl chloride (2.0 equiv.) $Et_3N$ (3.0 equiv.) i-$Pr_2NEt$ (3.0 equiv.) | prep. HPLC method 1a | 44% (TFA salt) |
| Ex. 104 | 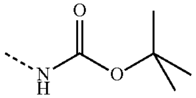 | 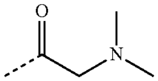 | Ex. 91 | A.1.3 | 2-(Dimethylamino)-acetic acid rt, 2 h | FC ($CH_2Cl_2$/MeOH) | 83% |
| Ex. 105 | $NH_2$ | 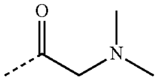 | Ex. 104 | B.1 | HCl-dioxane rt, 2 h | crude product | 90% |
| Ex. 106 | 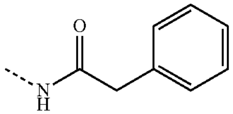 | 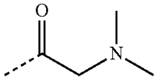 | Ex. 105 | A.1.3 | 2-Phenylacetic acid (4.8 equiv.) rt, 40 h | prep. HPLC method 1a | 41% (TFA salt) |
| Ex. 107 | 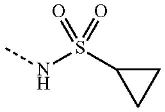 | 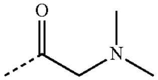 | Ex. 105 | A.5 | Cyclopropanesulfonyl chloride (3.0 equiv.) $Et_3N$ (8.0 equiv.) rt, 16 h | prep. HPLC method 1a | 32% (TFA salt) |

TABLE 17a-continued

Examples of Core 05 (Ex. 90-Ex. 114 and Ex. 341-Ex. 358;)

| No | $R^B$ | $R^D$ | Starting Material | General Procedure | Reagent | Purification Method | Yield (isolated salt) |
|---|---|---|---|---|---|---|---|
| Ex. 108 | 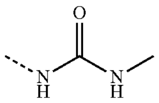 | 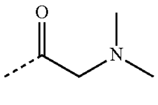 | Ex. 105 | A.3 | N-Succinimidyl N-methylcarbamate (1.4 equiv.) i-$Pr_2NEt$ (5.0 equiv.) rt, 16 h | prep. HPLC method 1a | 55% (TFA salt) |
| Ex. 109 | 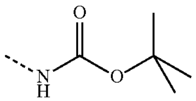 | 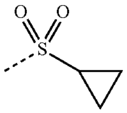 | Ex. 91 | A.5 | Cyclopropanesulfonyl chloride (5.2 equiv.) $Et_3N$ (5.0 equiv.), DMAP (0.1 equiv.) 45° C.,48 h | FC ($CH_2Cl_2$/MeOH) | 64% |
| Ex. 110 | $NH_2$ | 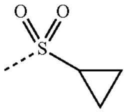 | Ex. 109 | B.1 | HCl-dioxane rt, 3 h | crude product | quant. (HCl salt) |
| Ex. 111 | 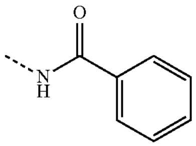 | 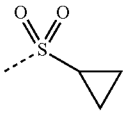 | Ex. 110 | A.1.2.1 | Benzoyl chloride (2.0 equiv) i-$Pr_2NEt$ (5.0 equiv.) rt, 16 h | prep. HPLC method 1a | 19% (TFA salt) |
| Ex. 112 | 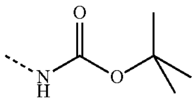 | 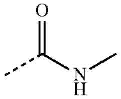 | Ex. 91 | A.3 | N-Succinimidyl N-methylcarbamate (1.4 equiv.) i-$Pr_2NEt$ (5.0 equiv.) rt, 16 h | FC ($CH_2Cl_2$/MeOH) | 82% |
| Ex. 113 | $NH_2$ | 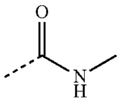 | Ex. 112 | B.1 | HCl-dioxane rt, 4 h | crude product | quant. (HCl salt) |
| Ex. 114 | 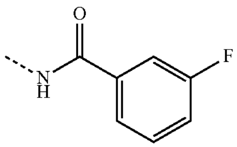 | 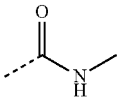 | Ex. 113 | A.1.2.1 | 3-Fluorobenzoyl chloride (4.0 equiv. in total) | prep. HPLC method 1a | 5% (TFA salt) |

TABLE 17a-continued

Examples of Core 05 (Ex. 90-Ex. 114 and Ex. 341-Ex. 358;)

| No | $R^B$ | $R^D$ | Starting Material | General Procedure | Reagent | Purification Method | Yield (isolated salt) |
|---|---|---|---|---|---|---|---|
| Ex. 341 | 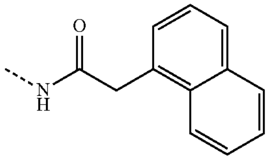 | 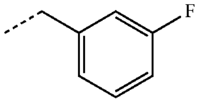 | Ex. 98 | A.1.3 | 1-Naphthaleneacetic acid<br>i-$Pr_2NEt$ (9 equiv.) | prep. HPLC method 1a and FC ($CH_2Cl_2$/MeOH) | 47% |
| Ex. 342 | 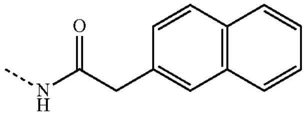 | 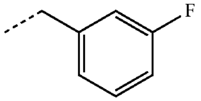 | Ex. 98 | A.1.3 | 2-Naphthaleneacetic acid<br>i-$Pr_2NEt$ (9 equiv.) | prep. HPLC method 1a and FC ($CH_2Cl_2$/MeOH) | 34% |
| Ex. 343 | 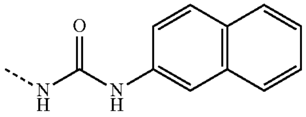 | 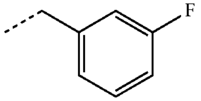 | Ex. 98 | A.3 | 2-Naphthylisocyanate<br>i-$Pr_2NEt$ (5 equiv.) | prep. HPLC method 1a and FC ($CH_2Cl_2$/MeOH) | 63% |
| Ex. 344 | 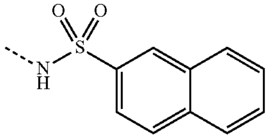 | 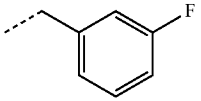 | Ex. 98 | A.5 | Naphthalene-2-sulfonyl chloride<br>i-$Pr_2NEt$ (5 equiv.) | prep. HPLC method 1a | 41% (TFA salt) |
| Ex. 345 | 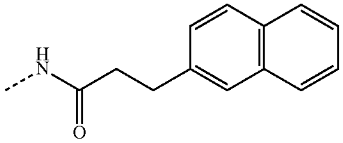 | 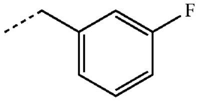 | Ex. 98 | A.1.3 | 2-Naphthalene-propanoic acid<br>i-$Pr_2NEt$ (9 equiv.) | prep. HPLC method 1a | 40% (TFA salt) |
| Ex. 346 | 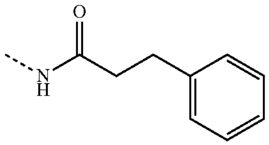 | 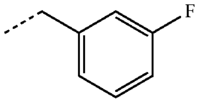 | Ex. 98 | A.1.3 | 3-Phenylpropionic acid<br>i-$Pr_2NEt$ (9 equiv.) | prep. HPLC method 1a | 37% (TFA salt) |

TABLE 17a-continued

Examples of Core 05 (Ex. 90-Ex. 114 and Ex. 341-Ex. 358;)

| No | $R^B$ | $R^D$ | Starting Material | General Procedure | Reagent | Purification Method | Yield (isolated salt) |
|---|---|---|---|---|---|---|---|
| Ex. 347 | 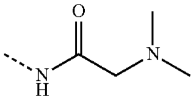 | 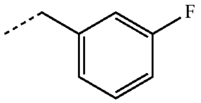 | Ex. 98 | A.1.3 | N,N-Dimethylglycine<br>i-$Pr_2$NEt (9 equiv.) | prep. HPLC method 1a | 9% (TFA salt) |
| Ex. 348 | 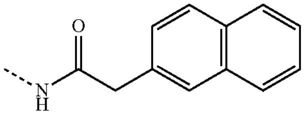 | 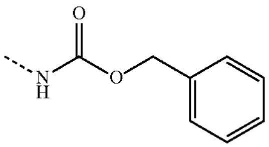 | Ex. 92 | A.1.3 | 2-Naphthaleneacetic acid<br>i-$Pr_2$NEt (6 equiv.) | FC ($CH_2Cl_2$/MeOH) | 80% |
| Ex. 349 | 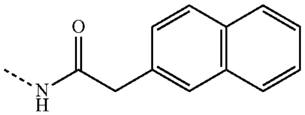 | H | Ex. 348 | B.3 | $H_2$, $Pd(OH)_2$—C, MeOH | crude product | 97% |
| Ex. 350 | 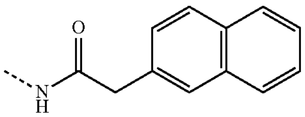 | 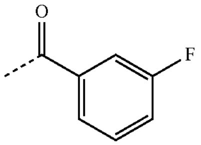 | Ex. 349 | A.1.3 | 3-Fluorobenzoic acid | prep. HPLC method 1a | 55% (TFA salt) |
| Ex. 351 | 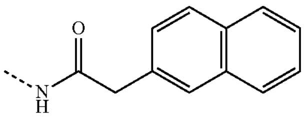 | 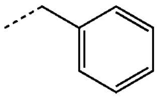 | Ex. 349 | A.6.3 | Benzaldehyde<br>Workup: $CH_2Cl_2$, sat. aq. $Na_2CO_3$ soln | prep. HPLC method 1a | 51% (TFA salt) |
| Ex. 352 | 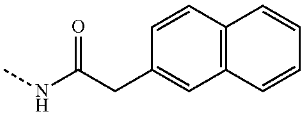 | 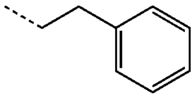 | Ex. 349 | A.6.3 | Phenylacetaldehyde<br>Workup: $CH_2Cl_2$, sat. aq. $Na_2CO_3$ soln | prep. HPLC method 1a | 37% (TFA salt) |
| Ex. 353 | 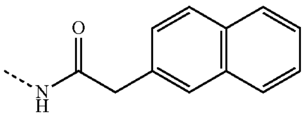 | 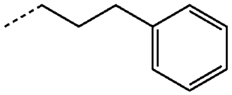 | Ex. 349 | A.6.3 | 3-Phenylpropion-aldehyde<br>Workup: $CH_2Cl_2$, sat. aq. $Na_2CO_3$ soln | prep. HPLC method 1a | 30% (TFA salt) |

TABLE 17a-continued

| Examples of Core 05 (Ex. 90-Ex. 114 and Ex. 341-Ex. 358;) | | | | | | | |
|---|---|---|---|---|---|---|---|
| No | $R^B$ | $R^D$ | Starting Material | General Procedure | Reagent | Purification Method | Yield (isolated salt) |
| Ex. 354 | 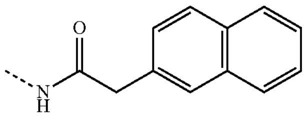 | 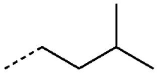 | Ex. 349 | A.6.3 | Isovaleraldehyde (1.7 equiv.) Workup: $CH_2Cl_2$, sat. aq. $Na_2CO_3$ soln | prep. HPLC method 1a | 32% (TFA salt) |
| Ex. 355 | 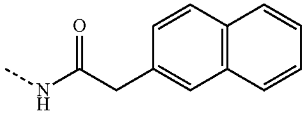 | 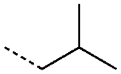 | Ex. 349 | A.6.3 | Isobutyraldehyde Workup: $CH_2Cl_2$, sat. aq. $Na_2CO_3$ soln | prep. HPLC method 1a | 68% (TFA salt) |
| Ex. 356 | 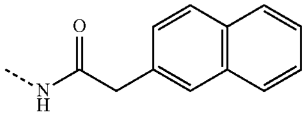 | 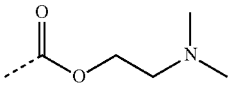 | Ex. 349 | 2) | 2-Dimethylaminoethyl-chlorid hydrochloride | FC ($CH_2Cl_2$/MeOH) | 21% |
| Ex. 357 | 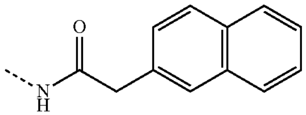 | 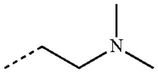 | Ex. 349 | 3) | 2-Dimethylaminoethyl-chlorid hydrochloride | prep. HPLC method 2a and FC ($CH_2Cl_2$/MeOH) | 17% |
| Ex. 358 | 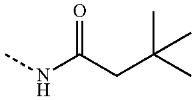 | $CH_3$ | Ex. 95 | 4) | 3,3-Dimethylbutyryl chloride | FC ($CH_2Cl_2$/MeOH) | 83% |

1) Ex. 93 was obtained as a side product upon treatment of Ex. 90 with HCl-dioxane; see description of synthesis of Ex. 92

2) 2-Dimethylaminoethylchloride hydrochloride (13 mg, 0.089 mmol) was added to a mixture of Ex. 349 (50 mg, 0.089 mmol) and dry $K_2CO_3$ (61 mg, 0.44 mmol) in DCE (0.5 mL). The mixture was stirred at 50° C. for 16 h. More 2-dimethylaminoethylchloride hydrochloride (6.4 mg, 0.044 mmol) was added and stirring at 50° C. continued for 2 h. Aqueous workup ($CH_2Cl_2$, sat. aq. $Na_2CO_3$ soln; $Na_2SO_4$) and FC ($CH_2Cl_2$/MeOH 100:0 to 80:20) afforded Ex. 356 (13 mg, 21%).

3) 2-Dimethylaminoethylchloride hydrochloride (64 mg, 0.44 mmol) was added to a mixture of Ex. 349 (60 mg, 0.106 mmol) and i-$Pr_2NEt$ (0.121 mL; 0.71 mmol) in DMF (1 mL). The mixture was stirred at 50° C. for 3 d. More 2-dimethylaminoethylchloride hydrochloride (64 mg, 0.44 mmol) and i-$Pr_2NEt$ (0.121 mL; 0.71 mmol) were added and stirring at 50° C. was continued for 1 d. Aqueous workup (EtOAc, sat. aq. $Na_2CO_3$ soln; $Na_2SO_4$) and FC ($CH_2Cl_2$/MeOH(conc. aq. $NH_3$ soln 100:0:0.1 to 90:10:0.1) afforded Ex. 357 (12 mg, 17%).

4) Synthesis of Ex. 358 3,3-Dimethylbutyryl chloride (0.019 mL, 0.14 mmol) was added at 0° C. to a suspension of Ex. 95 (60 mg, 0.116 mmol) and pyridine (0.047 mL, 0.58 mmol) in $CH_2Cl_2$ (1.2 mL). The mixture was stirred at rt for 1 h and cooled to 0° C. Then i-$Pr_2NEt$ (0.059 mL; 0.35 mmol) and 3,3-dimethylbutyryl chloride (0.019 mL, 0.14 mmol) were added. The resulting clear soln was stirred for 30 min. MeOH (0.01 mL) was added and stirring continued for 10 min. The volatiles were evaporated. FC ($CH_2Cl_2$/MeOH 100:0 to 95:5) afforded Ex. 358 (49 mg, 83%). Data of Ex. 358: cf. Table 17b $^1$H-NMR (DMSO-$d_6$): 9.62 (br. s, 1 H); 9.22 (t, J ca. 1.9, 1 H); 9.18 (d, J = 2.0, 1 H); 8.93 (d, J = 1.9, 1 H); 8.40 (br.s, 1 H); 8.08 (d, J = 6.5, 1 H); 7.59 (d, J = 7.6, 1 H); 7.40 (t, J = 7.9, 1 H); 6.82 (dd; J = 2.0, 8.3, 1 H); 4.53-4.41 (br. not resolved m, 3 H); 3.91 (t, J = 11.2, 1 H); 3.72 (dd; J = 7.0, 9.7, 1 H); 3.46 (d, J = 17.6, 1 H); 3.38-3.24 (m, 3 H, partially superimposed by $H_2O$ signal); 3.13 (dd-like m, 1 H); 2.62 (m, 2 H); 2.37 (s, 3 H); 2.14 (m, 1 H); 1.96 (s, 2 H); 1.93 (m, 1 H); 0.96 (s, 9 H).

5) Cf. experimental description for detailed procedure

TABLE 17b

Examples of Core 05 (Ex. 90-Ex. 114 and Ex. 341-Ex. 358;)

| No | $R^B$ | $R^D$ | Formula | Mono-iso-topic Mass | Rt (purity at 220 nm) | [M + H]+ found | LC-MS-Method |
|---|---|---|---|---|---|---|---|
| Ex. 90-Ex. 92: | | cf experimental description | | | | | |
| Ex. 93 | $NH_2$ | H | C21H25N5O3 | 395.2 | 0.89 (97) | 396.1 | method 1a |
| Ex. 94 | 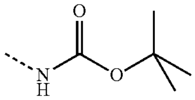 | $CH_3$ | C27H35N5O5 | 509.3 | 1.49 (97) | 510.1 | method 1a |
| Ex. 95 | $NH_2$ | $CH_3$ | C22H27N5O3 | 409.2 | 1.43 (98) | 410.1 | method 2c |
| Ex. 96 | 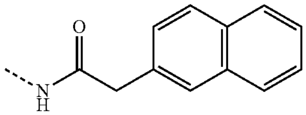 | $CH_3$ | C34H35N5O4 | 577.3 | 1.59 (99) | 578.1 | method 1a |
| Ex. 97 | 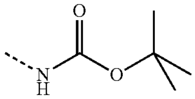 | 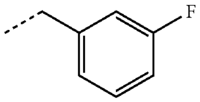 | C33H38FN5O5 | 603.3 | 2.44 (95) | 604.0 | method 2d |
| Ex. 98 | $NH_2$ | 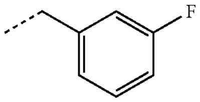 | C28H30FN5O3 | 503.2 | 1.31 (90) | 504.2 | method 1a |
| Ex. 99 | $NHCOCH_3$ | $CH_3$ | C24H29N5O4 | 451.2 | 1.10 (96) | 452.2 | method 1a |
| Ex. 100 | $NHCOCH_3$ | 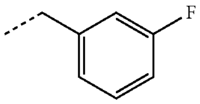 | C30H32FN5O4 | 545.2 | 1.47 (97) | 546.2 | method 1a |
| Ex. 101 | 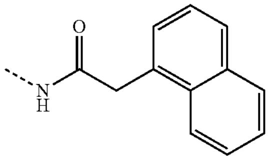 | $CH_3$ | C34H35N5O4 | 577.3 | 1.59 (98) | 578.2 | method 1a |
| Ex. 102 | 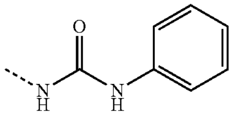 | $CH_3$ | C29H32N6O4 | 528.2 | 1.44 (98) | 529.2 | method 1a |
| Ex. 103 | 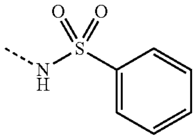 | $CH_3$ | C28H31N5O5S | 549.2 | 1.43 (99) | 550.1 | method 1a |
| Ex. 104 | 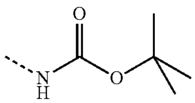 | 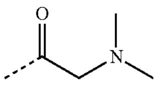 | C30H40N6O6 | 580.3 | 2.02 (96) | 581.2 | method 2d |
| Ex. 105 | $NH_2$ | 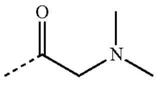 | C25H32N6O4 | 480.2 | 0.97 (95) | 481.1 | method 1a |

TABLE 17b-continued
Examples of Core 05 (Ex. 90-Ex. 114 and Ex. 341-Ex. 358;)
| No | $R^B$ | $R^D$ | Formula | Mono-iso-topic Mass | Rt (purity at 220 nm) | [M + H]+ found | LC-MS-Method |
|---|---|---|---|---|---|---|---|
| Ex. 106 | 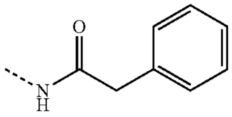 | 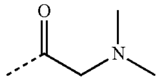 | C33H38N6O5 | 598.3 | 1.45 (98) | 599.2 | method 1a |
| Ex. 107 | 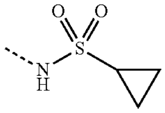 | 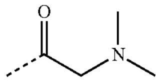 | C28H36N6O6S | 584.2 | 1.30 (95) | 585.1 | method 1a |
| Ex. 108 | 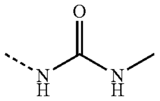 | 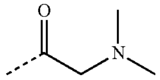 | C27H35N7O5 | 537.3 | 1.17 (97) | 538.2 | method 1a |
| Ex. 109 | 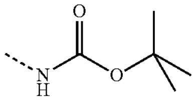 | 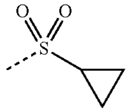 | C29H37N5O7S | 599.2 | 1.87 (93) | 600.1 | method 1a |
| Ex. 110 | $NH_2$ | 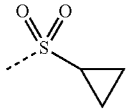 | C24H29N5O5S | 499.2 | 1.20 (91) | 500.1 | method 1a |
| Ex. 111 | 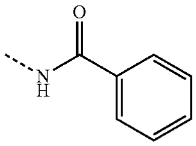 | 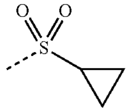 | C31H33N5O6S | 603.2 | 1.73 | 604.0 | method 1a |
| Ex. 112 | 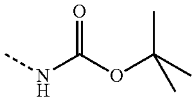 | 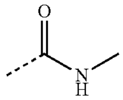 | C28H36N6O6 | 552.3 | 1.67 (94) | 553.1 | method 1a |
| Ex. 113 | $NH_2$ | 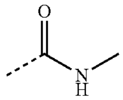 | C23H28N6O4 | 452.2 | 1.04 (89) | 453.1 | method 1a |
| Ex. 114 | 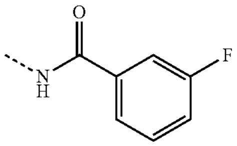 | 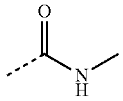 | C30H31FN6O5 | 574.2 | 1.63 (95) | 575.2 | method 1a |
| Ex. 341 | 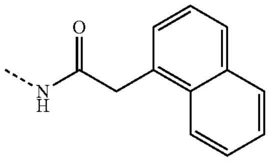 | 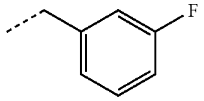 | C40H38FN5O4 | 671.3 | 2.37 (97) | 672.0 | method 2c |
| Ex. 342 | 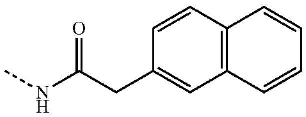 | 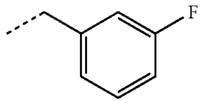 | C40H38FN5O4 | 671.3 | 2.38 (94) | 672.0 | method 2c |

TABLE 17b-continued
Examples of Core 05 (Ex. 90-Ex. 114 and Ex. 341-Ex. 358;)
| No | $R^B$ | $R^D$ | Formula | Mono-iso-topic Mass | Rt (purity at 220 nm) | [M + H]$^+$ found | LC-MS-Method |
|---|---|---|---|---|---|---|---|
| Ex. 343 | 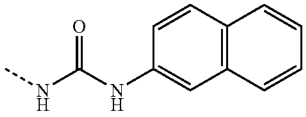 | 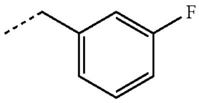 | C39H37FN6O4 | 672.3 | 2.41 (96) | 673.0 | method 2c |
| Ex. 344 | 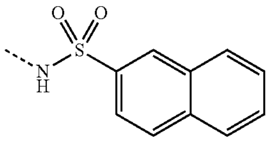 | 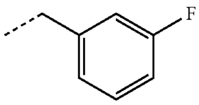 | C38H36FN5O5S | 693.2 | 2.42 (96) | 694.0 | method 2c |
| Ex. 345 | 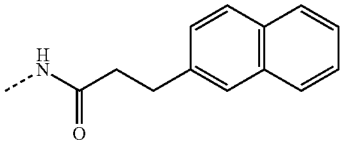 | 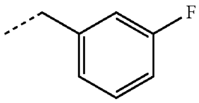 | C41H4OFN5O4 | 685.3 | 2.41 (97) | 686.0 | method 2c |
| Ex. 346 | 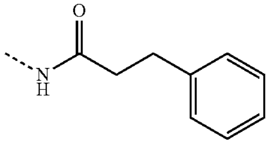 | 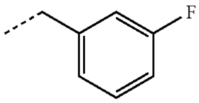 | C37H38FN5O4 | 635.3 | 2.26 (97) | 635.8 | method 2c |
| Ex. 347 | 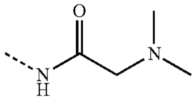 | 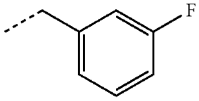 | C32H37FN6O4 | 588.3 | 2.01 (89) | 588.5 | method 2c |
| Ex. 348 | 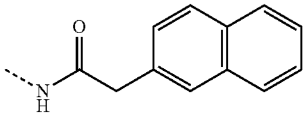 | 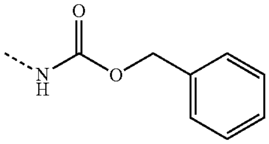 | C41H39N5O6 | 697.3 | 2.06 (97) | 698.0 | method 1a |
| Ex. 349 | 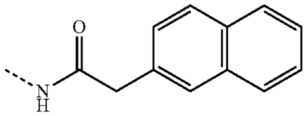 | H | C33H33N5O4 | 563.2 | 1.94 (88) | 563.9 | method 2c |
| Ex. 350 | 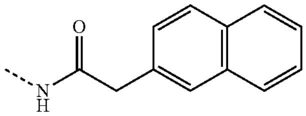 | 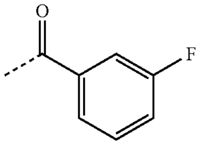 | C40H36FN5O5 | 685.3 | 1.97 (99) | 686.0 | method 1a |
| Ex. 351 | 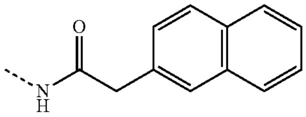 | 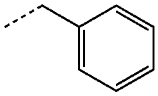 | C40H39N5O4 | 653.3 | 2.38 (98) | 654.0 | method 2c |
| Ex. 352 | 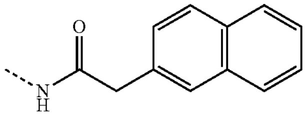 | 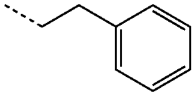 | C41H41N5O4 | 667.3 | 2.40 (94) | 667.9 | method 2c |

TABLE 17b-continued

Examples of Core 05 (Ex. 90-Ex. 114 and Ex. 341-Ex. 358;)

| No | $R^B$ | $R^D$ | Formula | Mono-isotopic Mass | Rt (purity at 220 nm) | [M + H]+ found | LC-MS-Method |
|---|---|---|---|---|---|---|---|
| Ex. 353 | 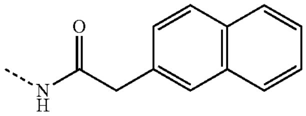 | 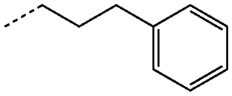 | C42H43N5O4 | 681.3 | 2.51 (97) | 682.1 | method 2c |
| Ex. 354 | 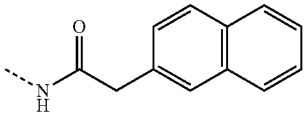 | 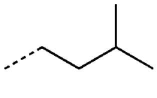 | C38H43N5O4 | 633.3 | 2.47 (98) | 634.0 | method 2c |
| Ex. 355 | 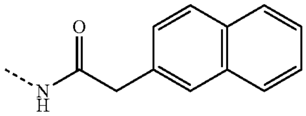 | 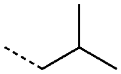 | C37H41N5O4 | 619.3 | 2.41 (96) | 619.9 | method 2c |
| Ex. 356 | 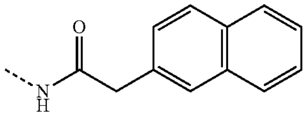 | 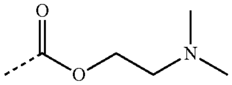 | C38H42N6O6 | 678.3 | 2.05 (96) | 679.3 | method 2e |
| Ex. 357 | 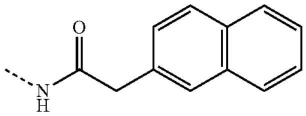 | 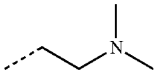 | C37H42N6O4 | 634.3 | 2.20 (96) | 635.3 | method 2e |
| Ex. 358 | 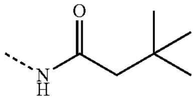 | $CH_3$ | C28H37N5O4 | 507.3 | 1.43 (99) | 508.2 | method 1c |

TABLE 17c

Examples of Core 05 (Ex. 90-Ex. 114 and Ex. 341-Ex. 358;)

| No | $R^B$ | $R^D$ | IUPAC name |
|---|---|---|---|
| Ex. 90 | 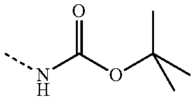 | 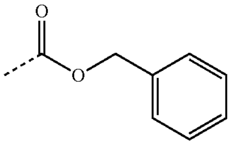 | benzyl (9S,11R)-11-[(tert-butoxycarbonyl)amino]-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxylate |
| Ex. 91 | 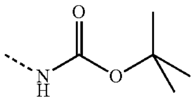 | H | tert-butyl N-[(9S,11R)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate |
| Ex. 92 | $NH_2$ | 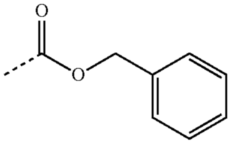 | benzyl (9S,11R)-11-amino-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxylate |
| Ex. 93 | $NH_2$ | H | (9S,11R)-11-amino-7-oxa-13,16,19,23-tetraazatetracyclo[19.3.1.1$^{2,6}$.0$^{9,13}$]hexacosa-1(25),2(26),3,5,21,23-hexaene-14,20-dione |

TABLE 17c-continued

Examples of Core 05 (Ex. 90-Ex. 114 and Ex. 341-Ex. 358;)

| No | $R^B$ | $R^D$ | IUPAC name |
|---|---|---|---|
| Ex. 94 | 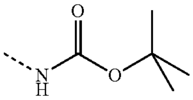 | $CH_3$ | tert-butyl N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate |
| Ex. 95 | $NH_2$ | $CH_3$ | (9S,11R)-11-amino-16-methyl-7-oxa-13,16,19,23-tetraazatetracyclo[19.3.1.1$^{2,6}$.0$^{9,13}$]hexacosa-1(25),2(26),3,5,21,23-hexaene-14,20-dione |
| Ex. 96 | 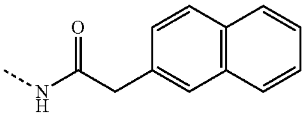 | $CH_3$ | N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl) acetamide |
| Ex. 97 | 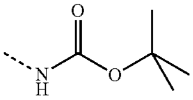 | 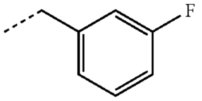 | tert-butyl N-[(9S,11R)-16-(3-fluorobenzyl)-14,20-dioxo-7-oxa-13,16,19,23-tetraazatetracyclo[19.3.1.1$^{2,6}$.0$^{9,13}$] hexacosa-1(25),2(26),3,5,21,23-hexaen-11-yl]carbamate |
| Ex. 98 | $NH_2$ | 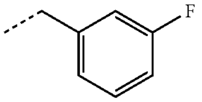 | (9S,11R)-11-amino-16-(3-fluorobenzyl)-7-oxa-13,16,19,23-tetraazatetracyclo[19.3.1.1$^{2,6}$.0$^{9,13}$] hexacosa-1(25),2(26),3,5,21,23-hexaene-14,20-dione |
| Ex. 99 | $NHCOCH_3$ | $CH_3$ | N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]acetamide |
| Ex. 100 | $NHCOCH_3$ | 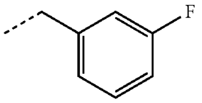 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]acetamide |
| Ex. 101 | 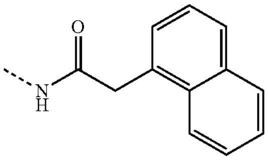 | $CH_3$ | N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(1-naphthyl) acetamide |
| Ex. 102 | 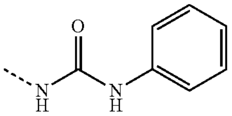 | $CH_3$ | N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-N'-phenylurea |
| Ex. 103 | 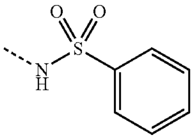 | $CH_3$ | N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]benzenesulfonamide |
| Ex. 104 | 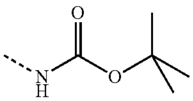 | 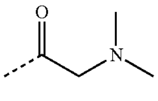 | tert-butyl N-[(9S,11R)-16-[2-(dimethylamino)acetyl]-14,20-dioxo-7-oxa-13,16,19,23-tetraazatetracyclo [19.3.1.1$^{2,6}$.0$^{9,13}$]hexacosa-1(25),2(26),3,5,21,23-hexaen-11-yl]carbamate |
| Ex. 105 | $NH_2$ | 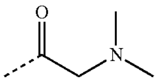 | (9S,11R)-11-amino-16-[2-(dimethylamino)acetyl]-7-oxa-13,16,19,23-tetraazatetracyclo[19.3.1.1$^{2,6}$.0$^{9,13}$] hexacosa-1(25),2(26),3,5,21,23-hexaene-14,20-dione |
| Ex. 106 | 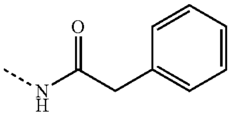 | 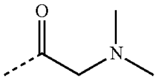 | N-[(9S,11R)-16-[2-(dimethylamino)acetyl]-14,20-dioxo-7-oxa-13,16,19,23-tetraazatetracyclo[19.3.1.1$^{2,6}$.0$^{9,13}$] hexacosa-1(25),2(26),3,5,21,23-hexaene-11-yl]-2-phenylacetamide |

TABLE 17c-continued

| No | $R^B$ | $R^D$ | IUPAC name |
|---|---|---|---|
| | Examples of Core 05 (Ex. 90-Ex. 114 and Ex. 341-Ex. 358;) | | |
| Ex. 107 | 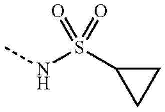 | 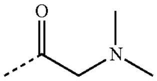 | N-[(9S,11R)-16-[2-(dimethylamino)acetyl]-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl] cyclopropanesulfonamide |
| Ex. 108 | 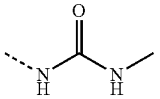 | 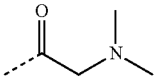 | N-[(9S,11R)-16-[2-(dimethylamino)acetyl]-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl]-N'-methylurea |
| Ex. 109 | 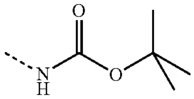 | 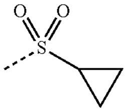 | tert-butyl N-[(9S,11R)-16-(cyclopropylsulfonyl)-14,20-dioxo-7-oxa-13,16,19,23-tetraazatetracyclo [19.3.1.$1^{2,6}$.$0^{9,13}$]hexacosa-1(25),2(26),3,5,21,23-hexaen-11-yl]carbamate |
| Ex. 110 | $NH_2$ | 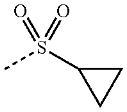 | (9S,11R)-11-amino-16-(cyclopropylsulfonyl)-7-oxa-13,16,19,23-tetraazatetracyclo[19.3.1.$1^{2,6}$.$0^{9,13}$]hexacosa-1(25),2(26),3,5,21,23-hexaene-14,20-dione |
| Ex. 111 | 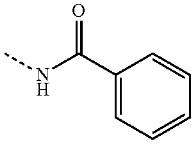 | 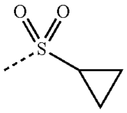 | N-[(9S,11R)-16-(cyclopropylsulfonyl)-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl]benzamide |
| Ex. 112 | 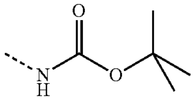 | 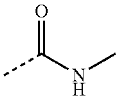 | tert-butyl N-[(9S,11R)-16-[(methylamino)carbonyl]-14,20-dioxo-7-oxa-13,16,19,23-tetraazatetracyclo [19.3.1.$1^{2,6}$.$0^{9,13}$]hexacosa-1(25),2(26),3,5,21,23-hexaen-11-yl]carbamate |
| Ex. 113 | $NH_2$ | 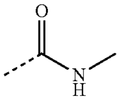 | (9S,11R)-11-amino-N-methyl-14,20-dioxo-7-oxa-13,16,19,23-tetraazatetracyclo[19.3.1.$1^{2,6}$.$0^{9,13}$] hexacosa-1(25),2(26),3,5,21,23-hexaene-16-carboxamide |
| Ex. 114 | 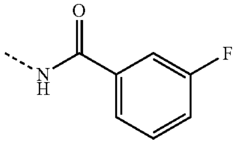 | 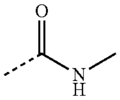 | (9S,11R)-11-[(3-fluorobenzoyl)amino]-N-methyl-14,20-dioxo-7-oxa-13,16,19,23-tetraazatetracyclo [19.3.1.$1^{2,6}$.$0^{9,13}$]hexacosa-1(25),2(26),3,5,21,23-hexaene-16-carboxamide |
| Ex. 341 | 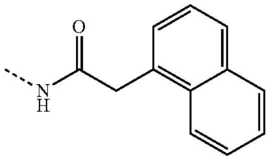 | 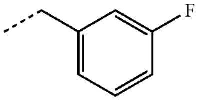 | N-[(9S,11R)-16-(3-fluorobenzyl)-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl]-2-(1-naphthyl)acetamide |
| Ex. 342 | 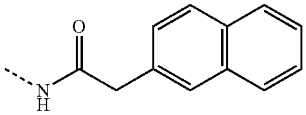 | 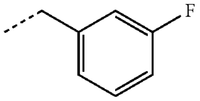 | N-[(9S,11R)-16-(3-fluorobenzyl)-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl]-2-(2-naphthyl)acetamide |
| Ex. 343 | 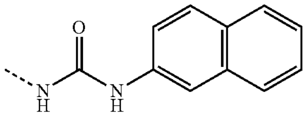 | 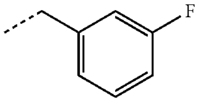 | N-[(9S,11R)-16-(3-fluorobenzyl)-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl]-N'-(2-naphthyl)urea |

TABLE 17c-continued

| Examples of Core 05 (Ex. 90-Ex. 114 and Ex. 341-Ex. 358;) | | | |
|---|---|---|---|
| No | $R^B$ | $R^D$ | IUPAC name |
| Ex. 344 | 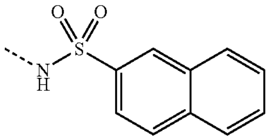 | 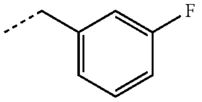 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-naphthalenesulfonamide |
| Ex. 345 | 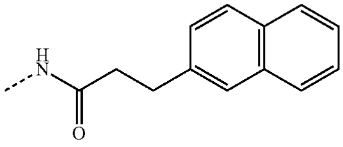 | 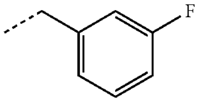 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-3-(2-naphthyl)propanamide |
| Ex. 346 | 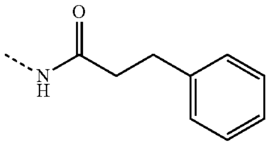 | 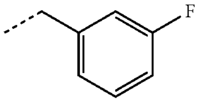 | N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-3-phenylpropanamide |
| Ex. 347 | 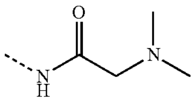 | 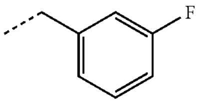 | 2-(dimethylamino)-N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]acetamide |
| Ex. 348 | 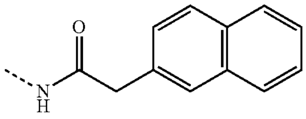 | 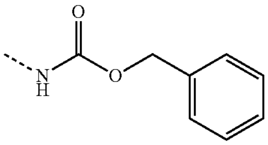 | benzyl (9S,11R)-11-{[2-(2-naphthyl)acetyl]amino}-14,20-dioxo-7-oxa-13,16,19,23-tetraazatetracyclo[19.3.1.1$^{2,6}$.0$^{9,13}$]hexacosa-1(25),2(26),3 ,5,21,23-hexaene-16-carboxylate |
| Ex. 349 | 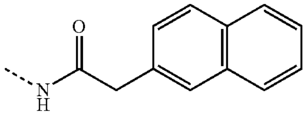 | H | N-[(9S,11R)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl) acetamide |
| Ex. 350 | 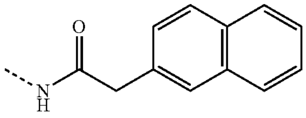 | 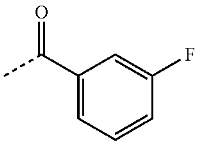 | N-[(9S,11R)-16-(3-fluorobenzoyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 351 | 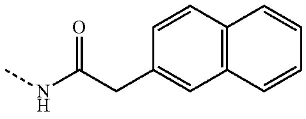 | 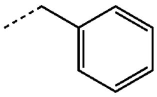 | N-[(9S,11R)-16-benzyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 352 | 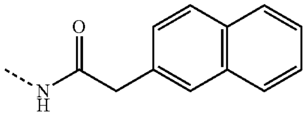 | 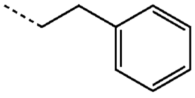 | N-[(9S,11R)-14,20-dioxo-16-phenethyl-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 353 | 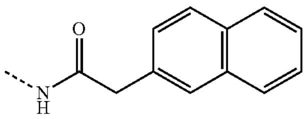 | 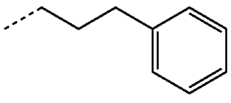 | N-[(9S,11R)-14,20-dioxo-16-(3-phenylpropyl)-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |
| Ex. 354 | 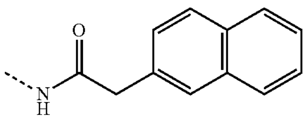 | 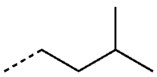 | N-[(9S,11R)-16-isopentyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide |

TABLE 17c-continued

| Examples of Core 05 (Ex. 90-Ex. 114 and Ex. 341-Ex. 358;) | | | |
|---|---|---|---|
| No | $R^B$ | $R^D$ | IUPAC name |
| Ex. 355 | 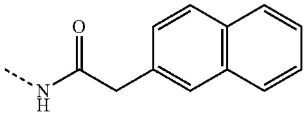 | 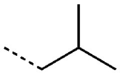 | N-[(9S,11R)-16-isobutyl-14,20-dioxo-7-oxa-13,16,19,23-tetraazatetracyclo[19.3.1.$1^{2,6}$.$0^{9,13}$] hexacosa-1(25),2(26),3,5,21,23-hexaen-11-yl]-2-(2-naphthyl)acetamide |
| Ex. 356 | 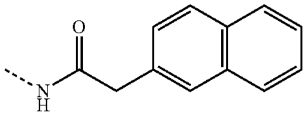 | 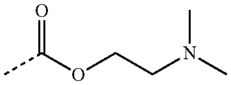 | 2-(dimethylamino)ethyl (9S,11R)-11-{[2-(2-naphthyl)acetyl]amino}-14 ,20-dioxo-7-oxa-13,16,19,23-tetraazatetracyclo[19.3.1.$1^{2,6}$.$0^{9,13}$] hexacosa-1(25),2(26),3,5,21,23-hexaene-16-carboxylate |
| Ex. 357 | 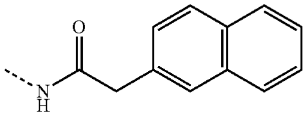 | 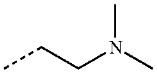 | N-[(9S,11R)-16-[2-(dimethylamino)ethyl]-14,20-dioxo-7-oxa-13,16,19,23-tetraazatetracyclo [19.3.1.$1^{2,6}$.$0^{9,13}$]hexacosa-1(25),2(26),3,5,21,23-hexaen-11-yl]-2-(2-naphthyl)acetamide |
| Ex. 358 | 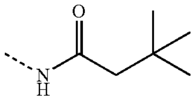 | $CH_3$ | 3,3-dimethyl-N-[(9S,11R)-16-methyl-14,20-dioxo-7-oxa-13,16,19,23-tetraazatetracyclo [19.3.1.$1^{2,6}$.$0^{9,13}$]hexacosa-1(25),2(26),3,5,21,23-hexaen-11-yl]butanamide |

TABLE 18a

| Examples of Core 06 (Ex. 115-Ex. 128;) | | | | | | |
|---|---|---|---|---|---|---|
| No | $R^A$ | Starting Material | General Procedure | Reagent | Purification Method | Yield (isolated salt) |
| Ex. 115-Ex. 116: | | | cf. experimental description | | | |
| Ex. 117 | 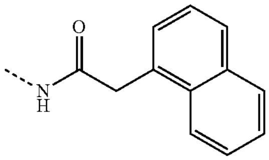 | Ex. 116 | A.1.1 | 1-Naphthaleneacetic acid 0° C., 2 h | prep. HPLC method 3, then washed with $Et_2O$, then FC (hexane/EtOAc) | 66% |
| Ex. 118 | 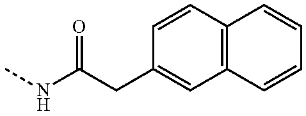 | Ex. 116 | A.1.1 | 2-Naphthaleneacetic acid 0° C., 2 h | prep. HPLC method 3, then washed with $Et_2O$, then FC (hexane/EtOAc) | 60% |
| Ex. 119 | 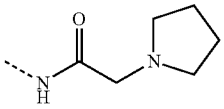 | Ex. 116 | A.1.1 | 1-Pyrrolidineacetic acid 0° C., 2 h aq. workup (EtOAc, sat. aq. $NaHCO_3$ soln, $H_2O$, sat. aq. NaCl soln; $Na_2SO_4$) | prep. HPLC method 3 | 57% |
| Ex. 120 | 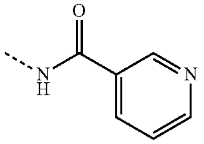 | Ex. 116 | A.1.1 | Nicotinic acid 0° C., 2 h aq. workup (EtOAc, sat. aq. $NaHCO_3$ soln, $H_2O$, sat. aq. NaCl soln; $Na_2SO_4$) | prep. HPLC method 3 | 72% |
| Ex. 121 | 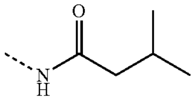 | Ex. 116 | A.1.2 | 3-Methylbutanoyl chloride (1.2 equiv.) 0° C., 2 h | prep. HPLC method 3 | 38% |
| Ex. 122 | 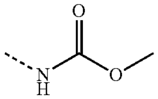 | Ex. 116 | A.4 | Methyl chloroformate 0° C. to rt, 2 h | prep. HPLC method 3 | 83% |

TABLE 18a-continued

Examples of Core 06 (Ex. 115-Ex. 128;)

| No | $R^A$ | Starting Material | General Procedure | Reagent | Purification Method | Yield (isolated salt) |
|---|---|---|---|---|---|---|
| Ex. 123 | 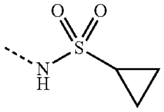 | Ex. 116 | A.5 | Cyclopropanesulfonyl chloride (2.0 equiv.) $Et_3N$ (3 equiv.) DMAP (0.1 equiv) rt, 15 h Workup: $CHCl_3$, half-sat. aq. $NaHCO_3$ soln.; $Na_2SO_4$ | prep. HPLC method 3 | 64% |
| Ex. 124 | 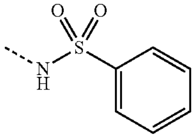 | Ex. 116 | A.5 | Benzenesulfonyl chloride (1.5 equiv.) rt, 1 h | prep. HPLC method 3 | 54% |
| Ex. 125 | 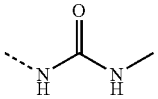 | Ex. 116 | A.3 | N-Succinimidyl N-methylcarbamate (1.8 equiv.) i-$Pr_2NEt$ (4.5 equiv) THF/$CHCl_3$ 1:1 (0.9 mL) rt, 16 h | chromatography; washing of crude product with EtOH and $Et_2O$ | 73% |
| Ex. 126 | 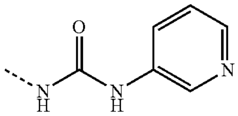 | Ex. 116 | A.3 | 2,5-Dioxopyrrolidin-1-yl pyridin-3-ylcarbamate (1.3 equiv.) i-$Pr_2NEt$ (3 equiv) THF/$CHCl_3$ 1:1 (0.5 mL) rt, 15 h | chromatography; washing of crude product with EtOH and $Et_2O$ | 70% |
| Ex. 127 | 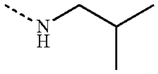 | Ex. 116 | A.6.4 | Isobutyraldehyde (1.05 equiv.) | prep. HPLC method 3 | 52% |
| Ex. 128 | 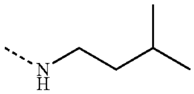 | Ex. 116 | A.6.4 | 3-Methylbutanal (1.05 equiv.) | prep. HPLC method 3 and prep. HPLC method 1a | 8% (TFA salt) |

TABLE 18b

Examples of Core 06 (Ex. 115-Ex. 128;)

| No | $R^A$ | Formula | Monoisotopic Mass | Rt (purity at 220 nm) | $[M + H]^+$ found | LC-MS-Method |
|---|---|---|---|---|---|---|
| Ex. 115-Ex. 116: | | cf. experimental description | | | | |
| Ex. 117 | 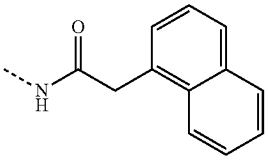 | C33H34N2O3S | 538.2 | 2.55 (95) | 539.2 | method 1a |
| Ex. 118 | 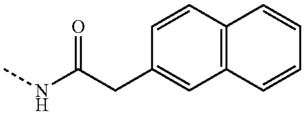 | C33H34N2O3S | 538.2 | 2.54 (95) | 539.2 | method 1a |
| Ex. 119 | 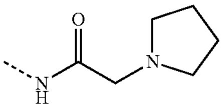 | C27H35N3O3S | 481.2 | 1.82 (97) | 482.2 | method 1a |

TABLE 18b-continued

| Examples of Core 06 (Ex. 115-Ex. 128;) | | | | | | |
|---|---|---|---|---|---|---|
| No | $R^4$ | Formula | Monoisotopic Mass | Rt (purity at 220 nm) | $[M + H]^+$ found | LC-MS-Method |
| Ex. 120 | 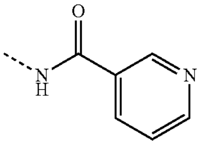 | C27H29N3O3S | 475.2 | 1.90 (92) | 476.1 | method 1a |
| Ex. 121 | 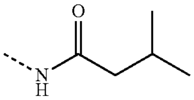 | C26H34N2O3S | 454.2 | 2.32 (90) | 455.2 | method 1a |
| Ex. 122 | 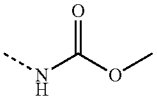 | C23H28N2O4S | 428.2 | 2.15 (97) | 429.2 | method 1a |
| Ex. 123 | 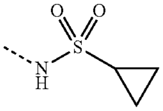 | C24H30N2O4S2 | 474.2 | 2.23 (93) | 475.1 | method 1a |
| Ex. 124 | 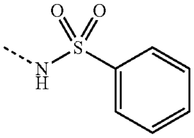 | C27H30N2O4S2 | 510.2 | 2.33 (82) | 511.1 | method 1a |
| Ex. 125 | 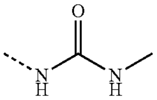 | C23H29N3O3S | 427.2 | 1.97 (88) | 428.2 | method 1a |
| Ex. 126 | 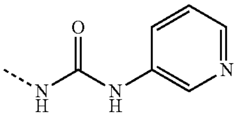 | C27H30N4O3S | 490.2 | 1.80 (95) | 491.2 | method 1a |
| Ex. 127 | 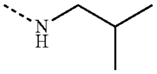 | C25H34N2O2S | 426.2 | 1.97 (97) | 427.2 | method 1a |
| Ex. 128 | 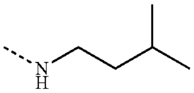 | C26H36N2O2S | 440.2 | 2.05 (98) | 441.2 | method 1a |

TABLE 18C

| Examples of Core 06 (Ex. 115-Ex. 128;) | | |
|---|---|---|
| No | $R^4$ | IUPAC name |
| Ex. 115 | NHAlloc | allyl N-[(13S,16R)-16-methyl-14-oxo-18-oxa-8-thia-15-azatricyclo[17.3.1.0$^{2,7}$]tricosa-1(23),2,4,6,19,21-hexaen-13-yl]carbamate |
| Ex. 116 | $NH_2$ | (13S,16R)-13-amino-16-methyl-18-oxa-8-thia-15-azatricyclo[17.3.1.0$^{2,7}$]tricosa-1(23),2,4,6,19,21-hexaen-14-one |
| Ex. 117 | 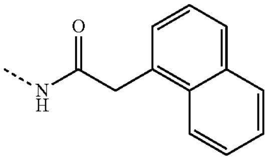 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-naphthyl)acetamide |

TABLE 18C-continued

| Examples of Core 06 (Ex. 115-Ex. 128;) | | |
|---|---|---|
| No | $R^4$ | IUPAC name |
| Ex. 118 | 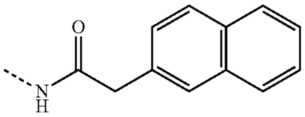 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(2-naphthyl)acetamide |
| Ex. 119 | 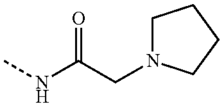 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-pyrrolidinyl)acetamide |
| Ex. 120 | 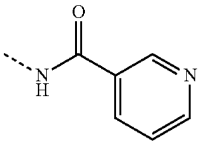 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]nicotinamide |
| Ex. 121 | 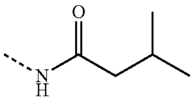 | 3-methyl-N-[(13S,16R)-16-methyl-14-oxo-18-oxa-8-thia-15-azatricyclo[17.3.1.0$^{2,7}$]tricosa-1(23),2,4,6,19,21-hexaen-13-yl]butanamide |
| Ex. 122 | 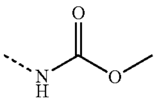 | methyl N-[(13S,16R)-16-methyl-14-oxo-18-oxa-8-thia-15-azatricyclo[17.3.1.0$^{2,7}$]tricosa-1(23),2,4,6,19,21-hexaen-13-yl]carbamate |
| Ex. 123 | 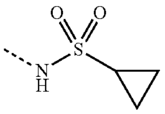 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]cyclopropanesulfonamide |
| Ex. 124 | 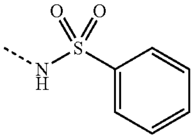 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]benzenesulfonamide |
| Ex. 125 | 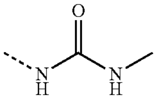 | N-methyl-N'-[(13S,16R)-16-methyl-14-oxo-18-oxa-8-thia-15-azatricyclo[17.3.1.0$^{2,7}$]tricosa-1(23),2,4,6,19,21-hexaen-13-yarea |
| Ex. 126 | 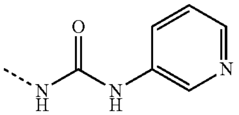 | N-[(13S,16R)-16-methyl-14-oxo-18-oxa-8-thia-15-azatricyclo[17.3.1.0$^{2,7}$]tricosa-1(23),2,4,6,19,21-hexaen-13-yl]-N'-(3-pyridinyl)urea |
| Ex. 127 | 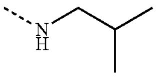 | (13S,16R)-13-(isobutylamino)-16-methyl-18-oxa-8-thia-15-azatricyclo[17.3.1.0$^{2,7}$]tricosa-1(23),2,4,6,19,21-hexaen-14-one |
| Ex. 128 | 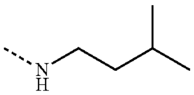 | (13S,16R)-13-(isopentylamino)-16-methyl-18-oxa-8-thia-15-azatricyclo[17.3.1.0$^{2,7}$]tricosa-1(23),2,4,6,19,21-hexaen-14-one |

TABLE 19a

Examples of Core 07 (Ex. 129-Ex. 142):

| No | $R^A$ | Starting Material | General Procedure | Reagent | Purification Method | Yield (isolated salt) |
|---|---|---|---|---|---|---|
| Ex. 129-Ex. 130: | | | cf. experimental description | | | |
| Ex. 131 | 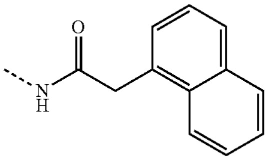 | Ex. 130 | A.1.1 | 1-Naphthaleneacetic acid<br>0° C., 2 h | prep. HPLC method 3 | 71% |
| Ex. 132 | 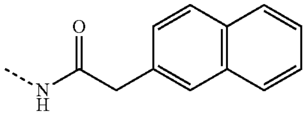 | Ex. 130 | A.1.1 | 2-Naphthaleneacetic acid<br>0° C., 2 h | prep. HPLC method 3 | 73% |
| Ex. 133 | 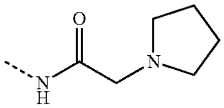 | Ex. 130 | A.1.1 | 1-Pyrrolidineacetic acid<br>0° C., 2 h<br>aq. workup (EtOAc, sat. aq. $NaHCO_3$ soln, $H_2O$, sat. aq. NaCl soln; $Na_2SO_4$) | prep. HPLC method 3 | 46% |
| Ex. 134 | 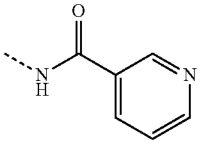 | Ex. 130 | A.1.1 | Nicotinic acid<br>0° C., 2 h<br>aq. workup (EtOAc, sat. aq. $NaHCO_3$ soln, $H_2O$, sat. aq. NaCl soln; $Na_2SO_4$) | prep. HPLC method 3 | 59% |
| Ex. 135 | 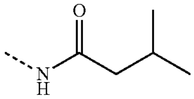 | Ex. 130 | A.1.2 | 3-Methylbutanoyl chloride<br>(1.2 equiv.)<br>0° C., 2 h | prep. HPLC method 3 | 77% |
| Ex. 136 | 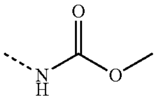 | Ex. 130 | A.4 | Methyl chloroformate<br>0° C., to rt, 2 h | prep. HPLC method 3 | 20% |
| Ex. 137 | 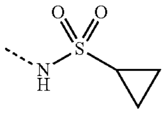 | Ex. 130 | A.5 | Cyclopropanesulfonyl chloride<br>(1.5 equiv.)<br>$Et_3N$ (3 equiv.)<br>DMAP (0.1 equiv)<br>$CHCl_3$ (0.5 mL)<br>rt, 15 h<br>Workup: $CHCl_3$, half-sat. aq. $NaHCO_3$ soln.; $Na_2SO_4$ | prep. HPLC method 3 | 71% |
| Ex. 138 | 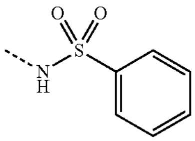 | Ex. 130 | A.5 | Benzenesulfonyl chloride<br>(1.5 equiv.) | prep. HPLC method 3 | 52% |
| Ex. 139 | 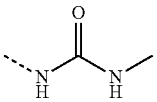 | Ex. 130 | A.3 | N-Succinimidyl-N-methylcarbamate<br>(1.8 equiv.)<br>$i-Pr_2NEt$ (4.5 equiv)<br>$THF/CHCl_3$ 1:1 (0.9 mL)<br>rt, 20 h | prep. HPLC method 3 | 49% |
| Ex. 140 | 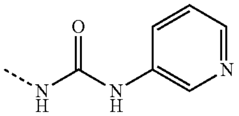 | Ex. 130 | A.3 | 2,5-Dioxopyrrolidin-1-yl pyridin-3-ylcarbamate<br>(1.3 equiv.)<br>$i-Pr_2NEt$ (3 equiv)<br>$THF/CHCl_3$ 1:1 (0.5 mL)<br>rt, 15 h | prep. HPLC method 3 | 64% |

TABLE 19a-continued

Examples of Core 07 (Ex. 129-Ex. 142);

| No | $R^A$ | Starting Material | General Procedure | Reagent | Purification Method | Yield (isolated salt) |
|---|---|---|---|---|---|---|
| Ex. 141 | 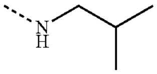 | Ex. 130 | A.6.4 | Isobutyraldedhyde (1.05 equiv.) | prep. HPLC method 3 | 57% |
| Ex. 142 | 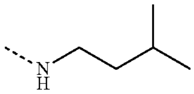 | Ex. 130 | A.6.4 | 3-Methylbutanal (1.05 equiv.) | prep. HPLC method 3 and prep. HPLC method 1a | 11% (TFA salt) |

TABLE 19b

Examples of Core 07 (Ex. 129-Ex. 142);

| No | $R^A$ | Formula | Monoisotopic Mass | Rt (purity at 220 nm) | $[M + H]^+$ found | LC-MS-Method |
|---|---|---|---|---|---|---|
| Ex. 129-Ex. 130: | | cf. experimental description | | | | |
| Ex. 131 | 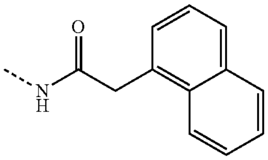 | C33H34N2O5S | 570.2 | 2.28 (91) | 571.2 | method 1a |
| Ex. 132 | 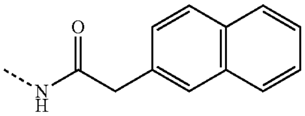 | C33H34N2O5S | 570.2 | 2.20 (97) | 571.2 | method 1a |
| Ex. 133 | 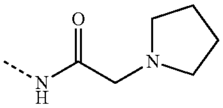 | C27H35N3O5S | 513.2 | 1.55 (93) | 514.2 | method 1a |
| Ex. 134 | 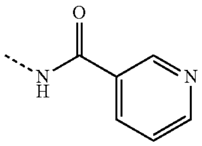 | C27H29N3O5S | 507.2 | 1.59 (99) | 509.0 | method 1a |
| Ex. 135 | 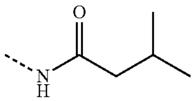 | C26H34N2O5S | 486.2 | 1.92 (99) | 487.2 | method 1a |
| Ex. 136 | 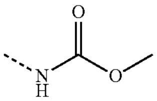 | C23H28N2O6S | 460.2 | 1.74 (99) | 461.0 | method 1a |
| Ex. 137 | 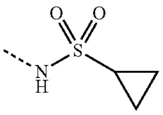 | C24H30N2O6S2 | 506.2 | 1.84 (99) | 507.1 | method 1a |
| Ex. 138 | 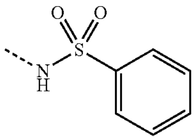 | C27H30N2O6S2 | 542.2 | 2.02 (97) | 543.1 | method 1a |

TABLE 19b-continued

Examples of Core 07 (Ex. 129-Ex. 142);

| No | $R^A$ | Formula | Monoisotopic Mass | Rt (purity at 220 nm) | $[M + H]^+$ found | LC-MS-Method |
|---|---|---|---|---|---|---|
| Ex. 139 | 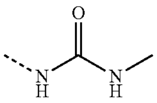 | C23H29N3O5S | 459.2 | 1.61 (99) | 460.1 | method 1a |
| Ex. 140 | 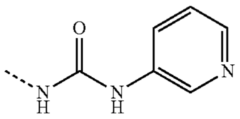 | C27H30N4O5S | 522.2 | 1.53 (98) | 523.2 | method 1a |
| Ex. 141 | 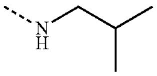 | C25H34N2O4S | 458.2 | 1.70 (99) | 459.2 | method 1a |
| Ex. 142 | 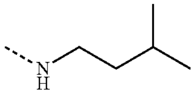 | C26H36N2O4S | 472.3 | 1.78 (85) | 473.2 | method 1a |

TABLE 19c

Examples of Core 07 (Ex. 129-Ex. 142);

| No | $R^A$ | IUPAC name |
|---|---|---|
| Ex. 129 | NHAlloc | allyl N-[(13S,16R)-16-methyl-8,8,14-trioxo-18-oxa-$8\lambda^{6}$-thia-15-azatricyclo[17.3.1.$0^{2,7}$]tricosa-1(23),2,4,6,19,21-hexaen-13-yl]carbamate |
| Ex. 130 | $NH_2$ | (13S,16R)-13-amino-16-methyl-18-oxa-$8\lambda^{6}$-thia-15-azatricyclo[17.3.1.$0^{2,7}$]tricosa-1(23),2,4,6,19,21-hexaene-8,8,14-trione |
| Ex. 131 | 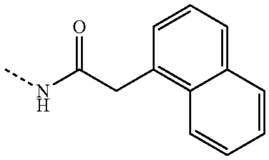 | N-[(13S,16R)-16-methyl-8,8,14-trioxo-18-oxa-$8\lambda^{6}$-thia-15-azatricyclo[17.3.1.$0^{2,7}$]tricosa-1(23),2,4,6,19,21-hexaen-13-yl]-2-(1-naphthyl)acetamide |
| Ex. 132 | 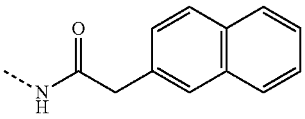 | N-[(13S,16R)-16-methyl-8,8,14-trioxo-18-oxa-$8\lambda^{6}$-thia-15-azatricyclo[17.3.1.$0^{2,7}$]tricosa-1(23),2,4,6,19,21-hexaen-13-yl]-2-(2-naphthyl)acetamide |
| Ex. 133 | 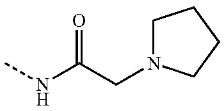 | N-[(13S,16R)-16-methyl-8,8,14-trioxo-18-oxa-$8\lambda^{6}$-thia-15-azatricyclo[17.3.1.$0^{2,7}$]tricosa-1(23),2,4,6,19,21-hexaen-13-yl]-2-(1-pyrrolidinyl)acetamide |
| Ex. 134 | 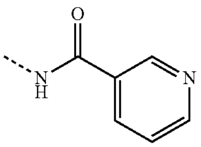 | N-[(13S,16R)-16-methyl-8,8,14-trioxo-18-oxa-$8\lambda^{6}$-thia-15-azatricyclo[17.3.1.$0^{2,7}$]tricosa-1(23),2,4,6,19,21-hexaen-13-yl]nicotinamide |
| Ex. 135 | 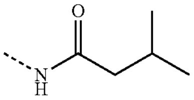 | 3-methyl-N-[(13S,16R)-16-methyl-8,8,14-trioxo-18-oxa-$8\lambda^{6}$-thia-15-azatricyclo[17.3.1.$0^{2,7}$]tricosa-1(23),2,4,6,19,21-hexaen-13-yl]butanamide |

TABLE 19c-continued

Examples of Core 07 (Ex. 129-Ex. 142);

| No | $R^4$ | IUPAC name |
|---|---|---|
| Ex. 136 | 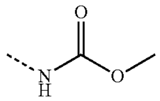 | methyl N-[(13S,16R)-16-methyl-8,8,14-trioxo-18-oxa-8$\lambda^6$-thia-15-azatricyclo[17.3.1.$0^{2,7}$]tricosa-1(23),2,4,6,19,21-hexaen-13-yl]carbamate |
| Ex. 137 | 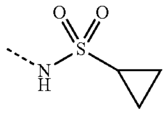 | N-[(13S,16R)-16-methyl-8,8,14-trioxo-18-oxa-8$\lambda^6$-thia-15-azatricyclo[17.3.1.$0^{2,7}$]tricosa-1(23),2,4,6,19,21-hexaen-13-yl]cyclopropanesulfonamide |
| Ex. 138 | 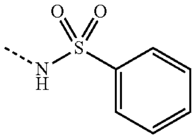 | N-[(13S,16R)-16-methyl-8,8,14-trioxo-18-oxa-8$\lambda^6$-thia-15-azatricyclo[17.3.1.$0^{2,7}$]tricosa-1(23),2,4,6,19,21-hexaen-13-yl]benzenesulfonamide |
| Ex. 139 | 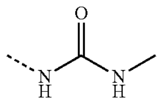 | N-methyl-N'-[(13S,16R)-16-methyl-8,8,14-trioxo-18-oxa-8$\lambda^6$-thia-15-azatricyclo[17.3.1.$0^{2,7}$]tricosa-1(23),2,4,6,19,21-hexaen-13-yl]urea |
| Ex. 140 | 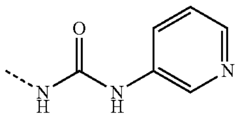 | N-[(13S,16R)-16-methyl-8,8,14-trioxo-18-oxa-8$\lambda^6$-thia-15-azatricyclo[17.3.1.$0^{2,7}$]tricosa-1(23),2,4,6,19,21-hexaen-13-yl]-N'-(3-pyridinyl)urea |
| Ex. 141 | 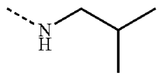 | (13S,16R)-13-(isobutylamino)-16-methyl-18-oxa-8$\lambda^6$-thia-15-azatricyclo[17.3.1.$0^{2,7}$]tricosa-1(23),2,4,6,19,21-hexaene-8,8,14-trione |
| Ex. 142 | 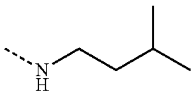 | (13S,16R)-13-(isopentylamino)-16-methyl-18-oxa-8$\lambda^6$-thia-15-azatricyclo[17.3.1.$0^{2,7}$]tricosa-1(23),2,4,6,19,21-hexaene-8,8,14-trione |

TABLE 20a

Examples of Core 08 (Ex. 143-Ex. 167);

| No | $R^4$ | Starting Material | General Procedure | Reagent | Purification Method | Yield (isolated salt) |
|---|---|---|---|---|---|---|
| Ex. 143-Ex. 144: | | cf. experimental description | | | | |
| Ex. 145 | $N(CH_3)_2$ | Ex. 144 | A.6.1 | Formaldehyde (36% in $H_2O$) | prep. HPLC method 3 | 92% |
| Ex. 146 | 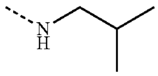 | Ex. 144 | A.6.4 | Isobutyraldehyde | prep. HPLC method 3 | 16% |
| Ex. 147 | 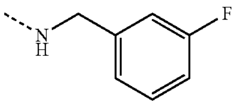 | Ex. 144 | A.6.4 | 3-Fluorobenzaldehyde | prep. HPLC method 3 | 46% |
| Ex. 148 | 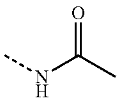 | Ex. 144 | A.1.2 | Acetic anhydrid (2.2 equiv.) Pyridine (7 equiv.); rt | prep. HPLC method 1a | 94% (TFA salt) |
| Ex. 149 | 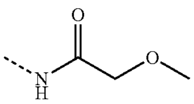 | Ex. 144 | A.1.1[1)] | Methoxyacetic acid i-$Pr_2$NEt (5 equiv.) | prep. HPLC method 3 | 62% |

TABLE 20a-continued

Examples of Core 08 (Ex. 143-Ex. 167);

| No | $R^A$ | Starting Material | General Procedure | Reagent | Purification Method | Yield (isolated salt) |
|---|---|---|---|---|---|---|
| Ex. 150 | 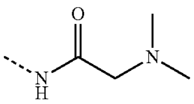 | Ex. 144 | A.1.3 | 2-(Dimethylamino)acetic acid<br>i-$Pr_2$NEt (6 equiv.)<br>Workup: $CHCl_3$,<br>10M aq NaOH soln | prep. HPLC method 3 | 49% |
| Ex. 151 | 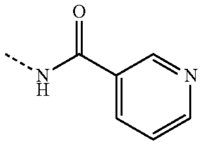 | Ex. 144 | A.1.1 | Nicotinic acid<br>i-$Pr_2$NEt (5 equiv.)<br>Workup: $CHCl_3$,<br>10M aq NaOH soln | prep. HPLC method 3 | 68% |
| Ex. 152 | 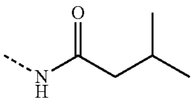 | Ex. 144 | A.1.1[1)] | Isovaleric acid<br>i-$Pr_2$NEt (5 equiv.) | prep. HPLC method 3 | 15% |
| Ex. 153 | 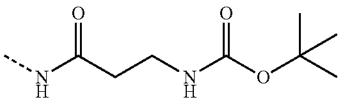 | Ex. 144 | A.1.1[1)] | N-Boc-β-alanine<br>i-$Pr_2$NEt (5 equiv.) | prep. HPLC method 3 | 88% |
| Ex. 154 | 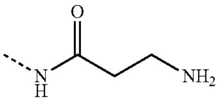 | Ex. 153 | B.2 | TFA, $CH_2Cl_2$<br>rt, 2 h | crude product | 73%<br>(TFA salt) |
| Ex. 155 | 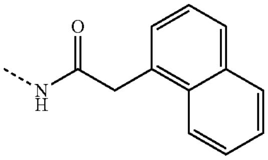 | Ex. 144 | A.1.1[1)] | 1-Naphthaleneacetic acid<br>i-$Pr_2$NEt (5 equiv.) | prep. HPLC method 3 and FC (hexane/EtOAc) | 69% |
| Ex. 156 | 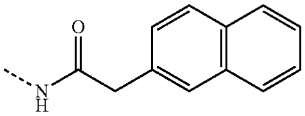 | Ex. 144 | A.1.1[1)] | 2-Naphthaleneacetic acid<br>i-$Pr_2$NEt (5 equiv.) | prep. HPLC method 3 | 66% |
| Ex. 157 | 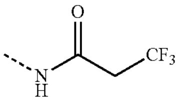 | Ex. 144 | A.1.1[1)] | 3,3,3-Trifluoropropionic acid<br>i-$Pr_2$NEt (5 equiv.) | prep. HPLC method 3 | 45% |
| Ex. 158 | 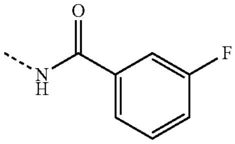 | Ex. 144 | A.1.1[1)] | 3-Fluorobenzoic acid<br>i-$Pr_2$NEt (5 equiv.) | prep. HPLC method 3 and FC (hexane/EtOAc) | 44% |
| Ex. 159 | 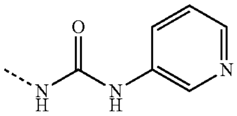 | Ex. 144 | A.3 | 2,5-Dioxopyrrolidin-1-yl pyridin-3-ylcarbamate (1.3 equiv)<br>i-$Pr_2$NEt (5 equiv.) | prep. HPLC method 3 | 78% |
| Ex. 160 | 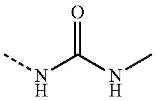 | Ex. 144 | A.3 | N-Succinimidyl-N-methylcarbamamte (1.3 equiv.)<br>i-$Pr_2$NEt (5 equiv.) | prep. HPLC method 3 | 78% |

TABLE 20a-continued

Examples of Core 08 (Ex. 143-Ex. 167):

| No | $R^4$ | Starting Material | General Procedure | Reagent | Purification Method | Yield (isolated salt) |
|---|---|---|---|---|---|---|
| Ex. 161 | 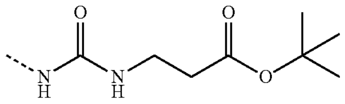 | Ex. 144 | A.3 | tert.-Butyl 3-((2,5-dioxopyrrolidin-1-yloxy)carbonylamino) propanoate (1.3 equiv.) $i\text{-}Pr_2NEt$ (5 equiv.) | prep. HPLC method 3 | 84% |
| Ex. 162 | 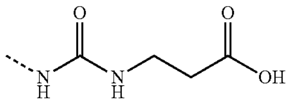 | Ex. 161 | B.2 | TFA, $CH_2Cl_2$ rt, 2 h | crude product | 75% (TFA salt) |
| Ex. 163 | 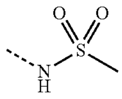 | Ex. 144 | A.5 | Methanesulfonyl chloride (3 equiv.) DMAP (0.1 equiv.) $NEt_3$ (5 equiv.) $CHCl_3$, rt, 2 d | prep. HPLC method 3 | 71% |
| Ex. 164 | 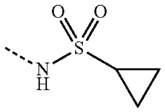 | Ex. 144 | A.5 | Cyclopropanesulfonyl chloride (3 equiv.) DMAP (0.1 equiv.) $NEt_3$ (5 equiv.) $CHCl_3$, rt to 50° C., 3 d | prep. HPLC method 1a | 55% (TFA salt) |
| Ex. 165 | 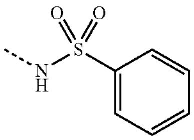 | Ex. 144 | A.5 | Benzenesulfonyl chloride (3 equiv.) $NEt_3$ (5 equiv.) $CHCl_3$, rt, 2 d | prep. HPLC method 3 | 57% |
| Ex. 166 | 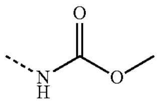 | Ex. 144 | A.4 | Methyl chloroformate (0.89 equiv.); rt 2 h | prep. HPLC method 3 | 66% |
| Ex. 167 | 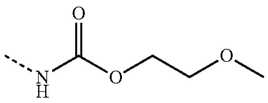 | Ex. 144 | A.4 | 2-Methoxyethyl chloro-formate (0.96 equiv.); rt, 2 h | prep. HPLC method 3 | 52% |

[1)]Method A.1.1; modified aq. workup: The (reaction) mixture was distributed between $CH_2Cl_2$ and 1M aq. HCl soln. The organic phase was dried ($Na_2SO_4$), filtered and concentrated.

TABLE 20b

Examples of Core 08 (Ex. 143-Ex. 167):

| No | $R^4$ | Formula | Mono-isotopic Mass | Rt (purity at 220 nm) | $[M + H]^+$ found | LC-MS-Method |
|---|---|---|---|---|---|---|
| Ex. 143-Ex. 144: | | cf. experimental description | | | | |
| Ex. 145 | $N(CH_3)_2$ | C22H29N3O2S | 399.2 | 1.35 (98) | 400.1 | method 1a |
| Ex. 146 | 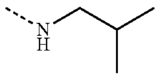 | C24H33N3O2S | 427.2 | 1.46 (95) | 428.2 | method 1a |
| Ex. 147 | 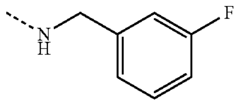 | C27H30FN3O2S | 479.2 | 1.53 (95) | 480.2 | method 1a |
| Ex. 148 | 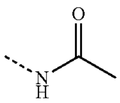 | C22H27N3O3S | 413.2 | 1.40 (99) | 414.1 | method 1a |

TABLE 20b-continued
| Examples of Core 08 (Ex. 143-Ex. 167); | | | | | | |
|---|---|---|---|---|---|---|
| No | $R^A$ | Formula | Mono-isotopic Mass | Rt (purity at 220 nm) | $[M + H]^+$ found | LC-MS-Method |
| Ex. 149 | 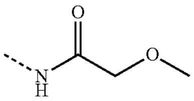 | C23H29N3O4S | 443.2 | 1.49 (94) | 444.2 | method 1a |
| Ex. 150 | 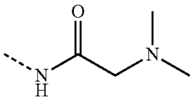 | C24H32N4O3S | 456.2 | 1.94 (96) | 457.2 | method 2c |
| Ex. 151 | 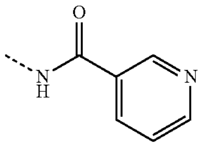 | C26H28N4O3S | 476.2 | 1.86 (92) | 477.0 | method 2c |
| Ex. 152 | 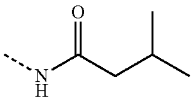 | C25H33N3O3S | 455.2 | 1.66 (90) | 456.2 | method 1a |
| Ex. 153 | 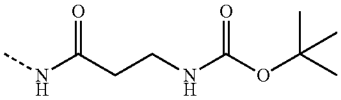 | C28H38N4O5S | 542.3 | 1.70 (90) | 543.2 | method 1a |
| Ex. 154 | 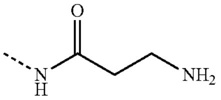 | C23H30N4O3S | 442.2 | 1.30 (87) | 443.2 | method 1c |
| Ex. 155 | 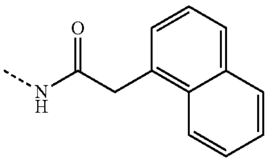 | C32H33N3O3S | 539.2 | 1.91 (93) | 540.1 | method 1a |
| Ex. 156 | 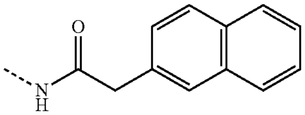 | C32H33N3O3S | 539.2 | 1.90 (97) | 540.1 | method 1a |
| Ex. 157 | 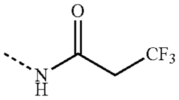 | C23H26F3N3O3S | 481.2 | 1.61 (96) | 482.2 | method 1a |
| Ex. 158 | 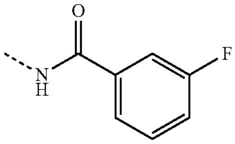 | C27H28FN3O3S | 493.2 | 1.76 (99) | 494.2 | method 1a |
| Ex. 159 | 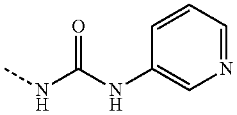 | C26H29N5O3S | 491.2 | 1.86 (90) | 492.1 | method 2c |

TABLE 20b-continued

Examples of Core 08 (Ex. 143-Ex. 167);

| No | $R^A$ | Formula | Mono-isotopic Mass | Rt (purity at 220 nm) | $[M + H]^+$ found | LC-MS-Method |
|---|---|---|---|---|---|---|
| Ex. 160 | 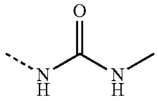 | C22H28N4O3S | 428.2 | 1.39 (99) | 429.1 | method 1a |
| Ex. 161 | 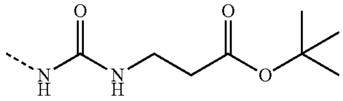 | C28H38N4O5S | 542.3 | 2.13 (99) | 543.1 | method 2c |
| Ex. 162 | 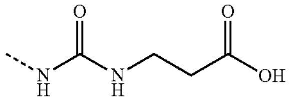 | C24H30N4O5S | 486.2 | 1.38 (98) | 487.2 | method 1a |
| Ex. 163 | 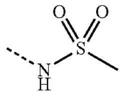 | C21H27N3O4S2 | 449.1 | 1.46 (99) | 450.1 | method 1a |
| Ex. 164 | 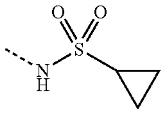 | C23H29N3O4S2 | 475.2 | 1.55 (99) | 476.0 | method 1a |
| Ex. 165 | 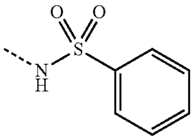 | C26H29N3O4S2 | 511.2 | 1.72 (99) | 512.1 | method 1a |
| Ex. 166 | 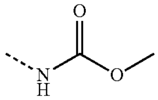 | C22H27N3O4S | 429.2 | 1.49 (99) | 430.1 | method 1a |
| Ex. 167 | 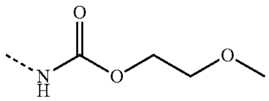 | C24H31N3O5S | 473.2 | 1.52 (99) | 474.2 | method 1a |

TABLE 20c

Examples of Core 08 (Ex. 143-Ex. 167);

| No | $R^A$ | IUPAC name |
|---|---|---|
| Ex. 143 | NHAlloc | allyl N-[(10R,13S)-10-methyl-12-oxa-8-oxa-18-thia-11,21-diazatricyclo[17.3.1.0$^{2,7}$]tricosa-1(23),2,4,6,19,21-hexaen-13-yl]carbamate |
| Ex. 144 | $NH_2$ | (10R,13S)-13-amino-10-methyl-8-oxa-18-thia-11,21-diazatricyclo[17.3.1.0$^{2,7}$]tricosa-1(23),2,4,6,19,21-hexaen-12-one |
| Ex. 145 | $N(CH_3)_2$ | (10R,13S)-13-(dimethylamino)-10-methyl-8-oxa-18-thia-11,21-diazatricyclo[17.3.1.0$^{2,7}$]tricosa-1(23),2,4,6,19,21-hexaen-12-one |
| Ex. 146 | 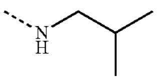 | (10R,13S)-13-(isobutylamino)-10-methyl-8-oxa-18-thia-11,21-diazatricyclo[17.3.1.0$^{2,7}$]tricosa-1(23),2,4,6,19,21-hexaen-12-one |

TABLE 20c-continued

Examples of Core 08 (Ex. 143-Ex. 167);

| No | $R^A$ | IUPAC name |
|---|---|---|
| Ex. 147 | 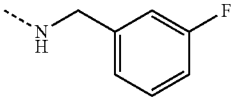 | (10R,13S)-13-[(3-fluorobenzyl)amino]-10-methyl-8-oxa-18-thia-11,21-diazatricyclo[17.3.1.0$^{2,7}$]tricosa-1(23),2,4,6,19,21-hexaen-12-one |
| Ex. 148 | 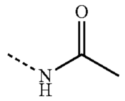 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]acetamide |
| Ex. 149 | 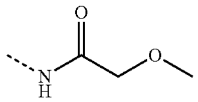 | 2-methoxy-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]acetamide |
| Ex. 150 | 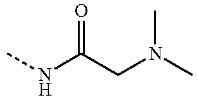 | 2-(dimethylamino)-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]acetamide |
| Ex. 151 | 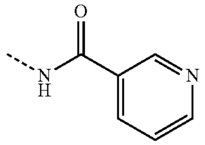 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]nicotinamide |
| Ex. 152 | 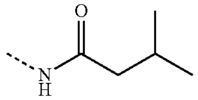 | 3-methyl-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]butanamide |
| Ex. 153 | 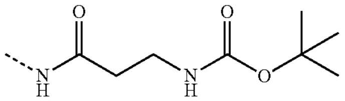 | tert-butyl N-(3-{[(10R,13S)-10-methyl-12-oxo-8-oxa-18-thia-11,21-diazatricyclo[17.3.1.0$^{2,7}$]tricosa-1(23),2,4,6,19,21-hexaen-13-yl]amino}-3-oxopropyl)carbamate |
| Ex. 154 | 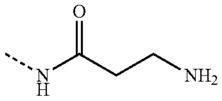 | 3-amino-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]propanamide |
| Ex. 155 | 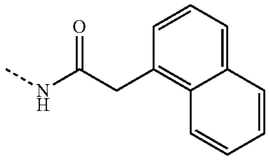 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]-2-(1-naphthyl)acetamide |
| Ex. 156 | 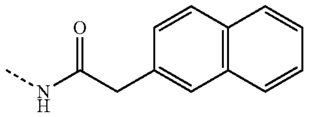 | N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]-2-(2-naphthyl)acetamide |
| Ex. 157 | 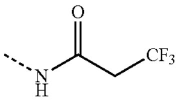 | 3,3,3-trifluoro-N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]propanamide |
| Ex. 158 | 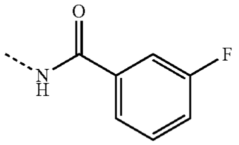 | 3-fluoro-N-[(10R,13S)-10-methyl-12-oxo-8-oxa-18-thia-11,12-diazatricyclo[17.3.1.0$^{2,7}$]tricosa-1(23),2,4,6,19,21-hexaen-13-yl]benzamide |

TABLE 20c-continued

| Examples of Core 08 (Ex. 143-Ex. 167); | | |
|---|---|---|
| No | $R^A$ | IUPAC name |
| Ex. 159 | 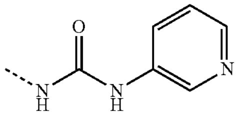 | N-[(10R,13S)-10-methyl-12-oxo-8-oxa-thia-11,21-diazatricyclo[17.3.1.$0^{2,7}$]tricosa-1(23),2,4,6,19,21-hexaen-13-yl]-N'-(3-pyridinyl)urea |
| Ex. 160 | 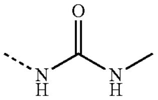 | N-methyl-N'-[(10R,13S)-10-methyl-12-oxo-8-oxa-18-thia-11,21-diazatricyclo[17.3.1.$0^{2,7}$] tricosa-1(23),2,4,6,19,21-hexaen-13-yl]urea |
| Ex. 161 | 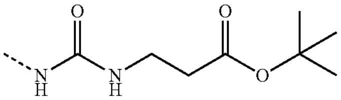 | tert-butyl 3-[({[(10R,13S)-10-methyl-12-oxo-8-oxa-18-thia-11,21-diazatricyclo[17.3.1.$0^{2,7}$]tricosa-1(23),2,4,6,19,21-hexaen-13-yl]amino}carbonyl)amino]propanoate |
| Ex. 162 | 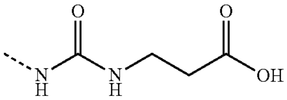 | 3-[({[(10R,13S)-10-methyl-12-oxo-8-oxa-18-thia-11,21-diazatricyclo[17.3.1.$0^{2,7}$]tricosa-1(23),2,4,6,19,21-hexaen-13-yl]amino} carbonyl)amino]propanoic acid |
| Ex. 163 | 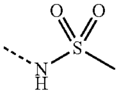 | N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]methanesulfonamide |
| Ex. 164 | 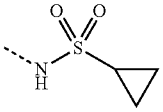 | N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl] cyclopropanesulfonamide |
| Ex. 165 | 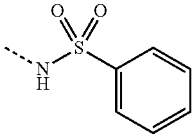 | N-[(10R,13S)-10-methyl-12-oxo-8-oxa-thia-11,21-diazatricyclo[17.3.1.$0^{2,7}$]tricosa-1(23), 2,4,6,19,21-hexaen-13-yl]benzenesulfonamide |
| Ex. 166 | 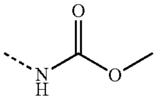 | methyl N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]carbamate |
| Ex. 167 | 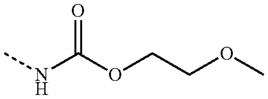 | 2-methoxyethyl N-[(10R,13S)-10-methyl-12-oxo-8-oxa-18-thia-11,21-diazatricyclo [17.3.1.$0^{2,7}$]tricosa-1(23),2,4,6,19,21-hexaen-13-yl]carbamate |

TABLE 21a

| Examples of Core 09 (Ex. 168-Ex. 192; continued on the following pages) | | | | | | |
|---|---|---|---|---|---|---|
| No | $R^A$ | Starting Material | General Procedure | Reagent | Purification Method | Yield (isolated salt) |
| Ex. 168-Ex. 169 cf. experimental description | | | | | | |
| Ex. 170 | $N(CH_3)_2$ | Ex. 169 | A.6.1 | Formaldehyde (36% in $H_2O$) | prep. HPLC method 3 | 67% |
| Ex. 171 | 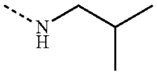 | Ex. 169 | A.6.4 | Isobutyraldehyde | prep. HPLC method 3 | 44% |

TABLE 21a-continued

Examples of Core 09 (Ex. 168-Ex. 192; continued on the following pages)

| No | $R^A$ | Starting Material | General Procedure | Reagent | Purification Method | Yield (isolated salt) |
|---|---|---|---|---|---|---|
| Ex. 172 | 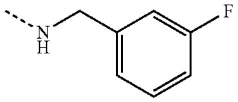 | Ex. 169 | A.6.4 | 3-Fluorobenzaldehyde | prep. HPLC method 3 | 57% |
| Ex. 173 | 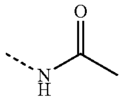 | Ex. 169 | A.1.2 | Acetic anhydride (1.2 equiv.) | prep. HPLC method 3 | 79% |
| Ex. 174 | 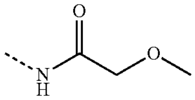 | Ex. 169 | A.1.1[1)] | Methoxyacetic acid | prep. HPLC method 3 | 27% |
| Ex. 175 | 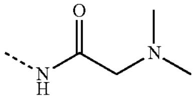 | Ex. 169 | A.1.3 | 2-(Dimethylamino)acetic acid Workup: $CH_2Cl_2$ | prep. HPLC method 3 | 9% |
| Ex. 176 | 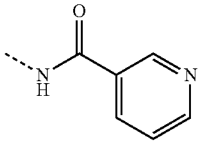 | Ex. 169 | A.1.1 | Nicotinic acid Workup: $CH_2Cl_2$, sat .aq. $Na_2CO_3$ | prep. HPLC method 3 | 26% |
| Ex. 177 | 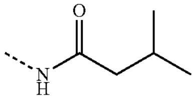 | Ex. 169 | A.1.1[1)] | Isovaleric acid | prep. HPLC method 3 | 18% |
| Ex. 178 | 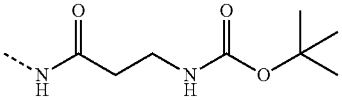 | Ex. 169 | A.1.1[1)] | N-Boc-β-alanine | prep. HPLC method 3 | 57% |
| Ex. 179 | 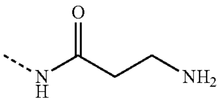 | Ex. 178 | B.2 | TFA, $CH_2Cl_2$ rt, 2 h | crude product | 41% (TFA salt) |
| Ex. 180 | 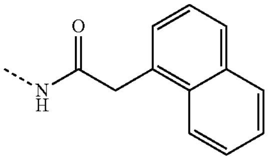 | Ex. 169 | A.1.1[1)] | 1-Naphthaleneacetic acid | prep. HPLC method 3 | 42% |
| Ex. 181 | 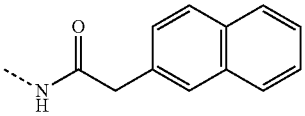 | Ex. 169 | A.1.1[1)] | 2-Naphthaleneacetic acid | prep. HPLC method 3 | 40% |
| Ex. 182 | 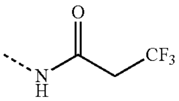 | Ex. 169 | A.1.1[1)] | 3,3,3-Trifluoropropionic acid | prep. HPLC method 3 | 22% |
| Ex. 183 | 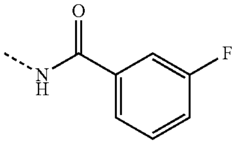 | Ex. 169 | A.1.1[1)] | 3-Fluorobenzoic acid | prep. HPLC method 3 | 58% |

TABLE 21a-continued

Examples of Core 09 (Ex. 168-Ex. 192; continued on the following pages)

| No | $R^A$ | Starting Material | General Procedure | Reagent | Purification Method | Yield (isolated salt) |
|---|---|---|---|---|---|---|
| Ex. 184 | 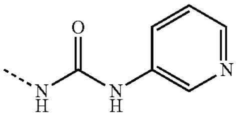 | Ex. 169 | A.3 | 2,5-Dioxopyrrolidin-1-yl pyridin-3-ylcarbamate (1.3 equiv.) | prep. HPLC method 3 | 73% |
| Ex. 185 | 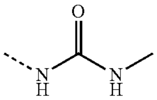 | Ex. 169 | A.3 | N-Succinimidyl N-methylcarbamate (1.3 equiv.) | prep. HPLC method 3 | 76% |
| Ex. 186 | 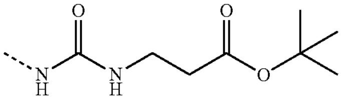 | Ex. 169 | A.3 | tert.-Butyl 3-((2,5-dioxopyrrolidin-1-yloxy)carbonylamino)propanoate (1.3 equiv.) | prep. HPLC method 3 | 77% |
| Ex. 187 | 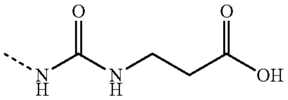 | Ex. 186 | B.2 | TFA, $CH_2Cl_2$ | crude product | 75% |
| Ex. 188 | 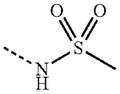 | Ex. 169 | A.5 | Methanesulfonyl chloride (2 equiv.) DMAP (0.1 equiv.) $Et_3N$ (3 equiv.) $CHCl_3$, rt, 2 d | prep. HPLC method 3 | 70% |
| Ex. 189 | 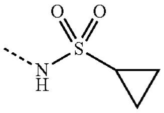 | Ex. 169 | A.5 | Cyclopropanesulfonyl chloride DMAP (0.1 equiv.) $Et_3N$ (3 equiv.) $CHCl_3$, rt, 2 d | prep. HPLC method 3 | 53% |
| Ex. 190 | 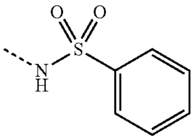 | Ex. 169 | A.5 | Benzenesulfonyl chloride | prep. HPLC method 3 | 51% |
| Ex. 191 | 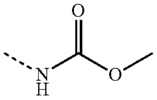 | Ex. 169 | A.4 | Methyl chloroformate (0.86 equiv); rt, 2 h | prep. HPLC method 3 | 52% |
| Ex. 192 | 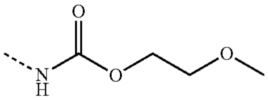 | Ex. 169 | A.4 | 2-Methoxyethyl chloroformate (0.97equiv); rt, 2 h | prep. HPLC method 3 | 55% |

[1)]Method A.1.1; modified aq. workup: The (reaction) mixture was distributed between $CH_2Cl_2$ and 1M aq. HCl soln. The organic phase was dried ($Na_2SO_4$), filtered and concentrated.

TABLE 21b

Examples of Core 09 (Ex. 168-Ex. 192; continued on the following pages)

| No | $R^A$ | Formula | Monoisotopic Mass | Rt (purity at 220 nm) | $[M + H]^+$ found | LC-MS-Method |
|---|---|---|---|---|---|---|
| Ex. 168-Ex. 169 cf. experimental description | | | | | | |
| Ex. 170 | $N(CH_3)_2$ | C22H29N3O4S | 431.2 | 1.39 (97) | 432.1 | method 1a |
| Ex. 171 | 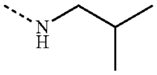 | C24H33N3O4S | 459.2 | 1.53 (95) | 460.1 | method 1a |

TABLE 21b-continued
| Examples of Core 09 (Ex. 168-Ex. 192; continued on the following pages) | | | | | | |
|---|---|---|---|---|---|---|
| No | $R^A$ | Formula | Monoisotopic Mass | Rt (purity at 220 nm) | $[M + H]^+$ found | LC-MS-Method |
| Ex. 172 | 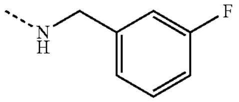 | C27H30FN3O4S | 511.2 | 1.61 (96) | 512.1 | method 1a |
| Ex. 173 | 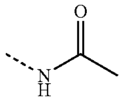 | C22H27N3O5S | 445.2 | 1.50 (100) | 446.1 | method 1a |
| Ex. 174 | 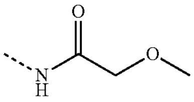 | C23H29N3O6S | 475.2 | 1.57 (96) | 476.0 | method 1a |
| Ex. 175 | 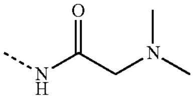 | C24H32N4O5S | 488.2 | 1.38 (92) | 489.1 | method 1a |
| Ex. 176 | 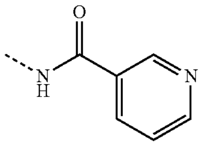 | C26H28N4O5S | 508.2 | 1.43 (98) | 508.9 | method 1a |
| Ex. 177 | 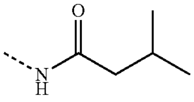 | C25H33N3O5S | 487.2 | 1.77 (97) | 488.2 | method 1a |
| Ex. 178 | 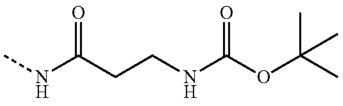 | C28H38N4O7S | 574.2 | 1.83 (98) | 575.1 | method 2c |
| Ex. 179 | 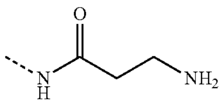 | C23H30N4O5S | 474.2 | 1.35 (99) | 475.2 | method 1a |
| Ex. 180 | 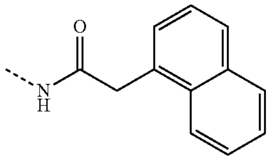 | C32H33N3O5S | 571.2 | 2.03 (97) | 572.0 | method 1a |
| Ex. 181 | 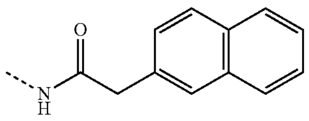 | C32H33N3O5S | 571.2 | 2.05 (100) | 572.1 | method 1a |
| Ex. 182 | 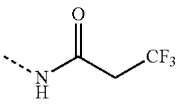 | C23H26F3N3O5S | 513.2 | 1.74 (99) | 514.1 | method 1a |
| Ex. 183 | 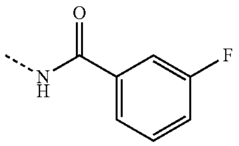 | C27H28FN3O5S | 525.2 | 1.90 (92) | 526.1 | method 1a |

TABLE 21b-continued

Examples of Core 09 (Ex. 168-Ex. 192; continued on the following pages)

| No | $R^A$ | Formula | Monoisotopic Mass | Rt (purity at 220 nm) | $[M + H]^+$ found | LC-MS-Method |
|---|---|---|---|---|---|---|
| Ex. 184 | 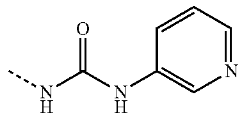 | C26H29N5O5S | 523.2 | 1.42 (99) | 524.0 | method 1a |
| Ex. 185 | 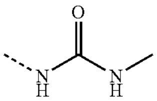 | C22H28N4O5S | 460.2 | 1.48 (99) | 461.0 | method 1a |
| Ex. 186 | 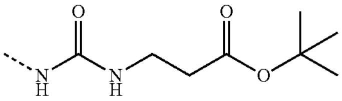 | C28H38N4O7S | 574.2 | 1.88 (98) | 575.1 | method 2c |
| Ex. 187 | 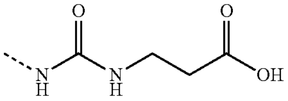 | C24H30N4O7S | 518.2 | 1.45 (97) | 519.1 | method 1a |
| Ex. 188 | 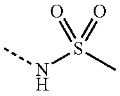 | C21H27N3O6S2 | 481.1 | 1.58 (99) | 482.1 | method 1a |
| Ex. 189 | 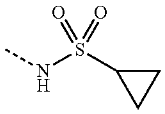 | C23H29N3O6S2 | 507.1 | 1.68 (95) | 508.0 | method 1a |
| Ex. 190 | 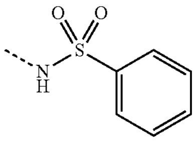 | C26H29N3O6S2 | 543.1 | 1.85 (96) | 544.1 | method 1a |
| Ex. 191 | 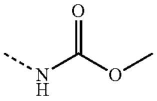 | C22H27N3O6S | 461.2 | 1.60 (98) | 462.1 | method 1a |
| Ex. 192 | 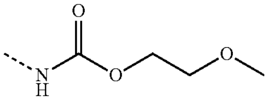 | C24H31N3O7S | 505.2 | 1.63 (99) | 506.2 | method 1a |

TABLE 21c

Examples of Core 09 (Ex. 168-Ex. 192; continued on the following pages)

| No | $R^A$ | IUPAC name |
|---|---|---|
| Ex. 168 | NHAlloc | allyl N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]carbamate |
| Ex. 169 | $NH_2$ | (10R,13S)-13-amino-10-methyl-8-oxa-18λ$^6$-thia-11,21-diazatricyclo[17.3.1.0$^{2,7}$]tricosa-1(23),2,4,6,19,21-hexaene-12,18,18-trione |
| Ex. 170 | $N(CH_3)_2$ | (10R,13S)-13-(dimethylamino)-10-methyl-8-oxa-18λ$^6$-thia-11,21-diazatricyclo[17.3.1.0$^{2,7}$]tricosa-1(23),2,4,6,19,21-hexaene-12,18,18-trione |

TABLE 21c-continued

Examples of Core 09 (Ex. 168-Ex. 192; continued on the following pages)

| No | $R^A$ | IUPAC name |
|---|---|---|
| Ex. 171 | 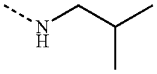 | (10R,13S)-13-(isobutylamino)-10-methyl-8-oxa-18λ$^6$-thia-11,21-diazatricyclo[17.3.1.0$^{2,7}$]tricosa-1(23),2,4,6,19,21-hexaene-12,18,18-trione |
| Ex. 172 | 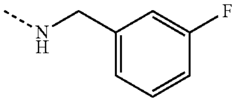 | (10R,13S)-13-[(3-fluorobenzyl)amino]-10-methyl-8-oxa-18λ$^6$-thia-11,21-diazatricyclo[17.3.1.0$^{2,7}$]tricosa-1(23),2,4,6,19,21-hexaene-12,18,18-trione |
| Ex. 173 | 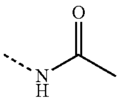 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]acetamide |
| Ex. 174 | 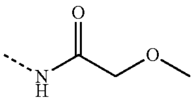 | 2-methoxy-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]acetamide |
| Ex. 175 | 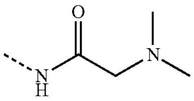 | 2-(dimethylamino)-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]acetamide |
| Ex. 176 | 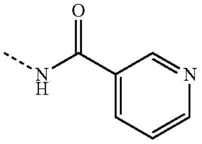 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]nicotinamide |
| Ex. 177 | 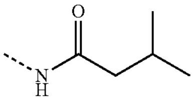 | 3-methyl-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]butanamide |
| Ex. 178 | 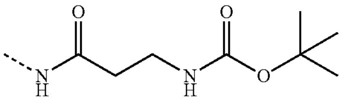 | tert-butyl N-(3-{[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]amino}-3-oxopropyl)carbamate |
| Ex. 179 | 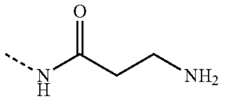 | 3-amino-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]propanamide |
| Ex. 180 | 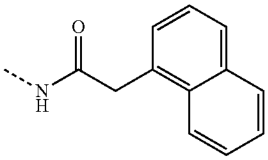 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]-2-(1-naphthyl)acetamide |
| Ex. 181 | 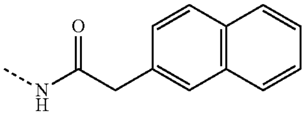 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]-2-(2-naphthyl)acetamide |
| Ex. 182 | 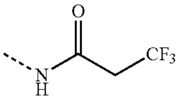 | 3,3,3-trifluoro-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]propanamide |

TABLE 21c-continued

| Examples of Core 09 (Ex. 168-Ex. 192; continued on the following pages) | | |
|---|---|---|
| No | $R^A$ | IUPAC name |
| Ex. 183 | 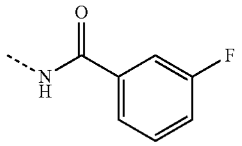 | 3-fluoro-N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]benzamide |
| Ex. 184 | 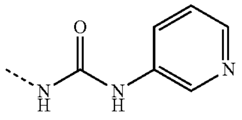 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]-N'-(3-pyridinyl)urea |
| Ex. 185 | 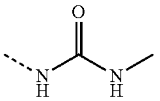 | N-methyl-N'-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]urea |
| Ex. 186 | 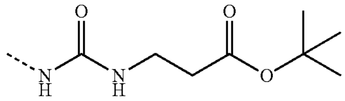 | tert-butyl 3[({[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]amino}carbonyl)amino]propanoate |
| Ex. 187 | 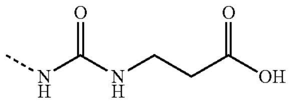 | 3-[({[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]amino}carbonyl)amino]propanoic acid |
| Ex. 188 | 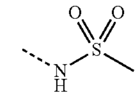 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]methanesulfonamide |
| Ex. 189 | 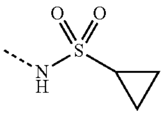 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]cyclopropanesulfonamide |
| Ex. 190 | 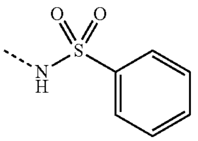 | N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]benzenesulfonamide |
| Ex. 191 | 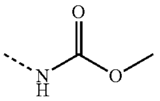 | methyl N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]carbamate |
| Ex. 192 | 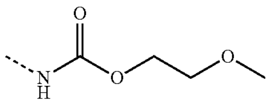 | 2-methoxyethyl N-[(10R,13S)-10-methyl-12,18,18-trioxo-8-oxa-18λ$^6$-thia-11,21-diazatricyclo[17.3.1.0$^{2,7}$]tricosa-1(23),2,4,6,19,21-hexaen-13-yl]carbamate |

TABLE 22a

| Examples of Core 10 (Ex. 193a, c-h and Ex. 194b; continued on the following page) | | | | | |
|---|---|---|---|---|---|
| No | General Procedure | Fmoc-AA1-OH | Fmoc-AA2-OH | Purification Method | Yield (isolated salt) |
| Ex. 193a | C.1 | Fmoc-β$^3$-homoPhe-OH | Fmoc-NMe-DAla-OH | prep. HPLC method 2b | 20 mg/53% |

TABLE 22a-continued

Examples of Core 10 (Ex. 193a, c-h and Ex. 194b; continued on the following page)

| No | General Procedure | Fmoc-AA1-OH | Fmoc-AA2-OH | Purification Method | Yield (isolated salt) |
|---|---|---|---|---|---|
| Ex. 193c | C.1 | Fmoc-β-Ala-OH | Fmoc-NMePhe-OH | prep. HPLC method 2b | 7 mg/19% |
| Ex. 193d | C.1 | Fmoc-β-Ala-OH | Fmoc-Phe-OH | prep. HPLC method 2b | 2 mg/6% |
| Ex. 193e | C.1 | Fmoc-NMe-β$^3$-homoDAla-OH | Fmoc-NMePhe-OH | prep. HPLC method 2b | 7 mg/18% |
| Ex. 193f | C.1 | Fmoc-NMe-β$^3$-homoDAla-OH | Fmoc-Sar-OH | prep. HPLC method 2b | 9 mg/27% |
| Ex. 193g | C.1 | Fmoc-NMe-β$^3$-homoDAla-OH | Fmoc-Phe-OH | prep. HPLC method 2b | 8 mg/22% |
| Ex. 193h | C.1 | Fmoc-β$^3$-homoPhe-OH | Fmoc-NMe-β-Ala-OH | prep. HPLC method 2b | 13 mg/33% |
| Ex. 194b | C.1 | Fmoc-NMe-β$^3$-homoDAla-OH | Fmoc-NMe-Glu(OtBu)-OH | prep. HPLC method 1a | 14 mg/31% |

TABLE 22b

Examples of Core 10 (Ex. 193a, c-h and Ex. 194b; continued on the following page)

| No | Formula | Monoisotopic Mass | Rt (purity at 220 nm) | [M + H]$^+$ found | LC-MS-Method |
|---|---|---|---|---|---|
| Ex. 193a | C31H34N4O4 | 526.2 | 2.03 (99) | 527.2 | method 1d |
| Ex. 193c | C30H32N4O4 | 512.2 | 1.94 (94) | 513.0 | method 1d |
| Ex. 193d | C29H30N4O4 | 498.2 | 1.80 (93) | 499.2 | method 1d |
| Ex. 193e | C32H36N4O4 | 540.2 | 2.07 (86) | 541.2 | method 1d |
| Ex. 193f | C25H30N4O4 | 450.2 | 1.50 (99) | 451.2 | method 1d |
| Ex. 193g | C31H34N4O4 | 526.2 | 1.94 (98) | 527.2 | method 1d |
| Ex. 193h | C31H34N4O4 | 526.2 | 1.78 (98) | 527.2 | method 1d |
| Ex. 194b | C28H34N4O6 | 522.2 | 1.68 (97) | 523.2 | method 1d |

TABLE 22c

Examples of Core 10 (Ex. 193a, c-h and Ex. 194b) (continued on the following page)

| No | IUPAC name |
|---|---|
| Ex. 193a | (9S,16S,19R)-16-benzyl-19,20-dimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193c | (9S,19S)-19-benzyl-20-methyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193d | (9S,19S)-19-benzyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193e | (9S,16R,19S)-19-benzyl-16,17,20-trimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193f | (9S,16R)-16,17,20-trimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193g | (9S,16R,19S)-19-benzyl-16,17-dimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione |
| Ex. 193h | (9S,16S)-16-benzyl-21-methyl-7-oxa-13,17,21,25-tetraazatetracyclo[21.3.1.1$^{2,6}$.0$^{9,13}$]octacosa-1(27),2(28),3,5,23,25-hexaene-14,18,22-trione |
| Ex. 194b | 3-[(9S,16R,19S)-16,17,20-trimethyl-14,18,21-trioxo-7-oxa-13,17,20,24-tetraazatetracyclo[20.3.1.1$^{2,6}$.0$^{9,13}$]heptacosa-1(26),2(27),3,5,22,24-hexaen-19-yl]propanoic acid |

TABLE 23a

Examples of Core 11 (Ex. 195a, b, e-h, j; Ex. 196c, i, k and Ex. 197d; continued on the following page)

| No | General Procedure | Fmoc-AA1-OH | Fmoc-AA2-OH | Fmoc-AA3-OH | Purification Method | Yield (isolated salt) |
|---|---|---|---|---|---|---|
| Ex. 195a | C.2 | Fmoc-NMe-β$^3$-homoDAla-OH | Fmoc-Sar-OH | Fmoc-NMeAla-OH | prep. HPLC method 2a | 31% |
| Ex. 195b | C.2 | Fmoc-NMe-β$^3$-homoDAla-OH | Fmoc-Gly-OH | Fmoc-Ala-OH | prep. HPLC method 2a | 18% |
| Ex. 196c | C.2 | Fmoc-NMe-β$^3$-homoDAla-OH | Fmoc-Ala-OH | Fmoc-NMeGlu(OtBu)-OH | prep. HPLC method 1a | 33% (TFA salt) |

TABLE 23a-continued

Examples of Core 11 (Ex. 195a, b, e-h, j; Ex. 196c, i, k and Ex. 197d; continued on the following page)

| No | General Procedure | Fmoc-AA1-OH | Fmoc-AA2-OH | Fmoc-AA3-OH | Purification Method | Yield (isolated salt) |
|---|---|---|---|---|---|---|
| Ex. 197d | C.2 | Fmoc-NMe-$\beta^3$-homoDAla-OH | Fmoc-Lys(Boc)-OH | Fmoc-DAla-OH | prep. HPLC method 2a | 24% |
| Ex. 195e | C.2 | Fmoc-Sar-OH | Fmoc-NMe-$\beta^3$-homoDAla-OH | Fmoc-NMeAla-OH | prep. HPLC method 2a | 33% |
| Ex. 195f | C.2 | Fmoc-Sar-OH | Fmoc-NMeAla-OH | Fmoc-NMe-$\beta^3$-homoDAla-OH | prep. HPLC method 2a | 22% |
| Ex. 195g | C.2 | Fmoc-Gly-OH | Fmoc-Phe-OH | Fmoc-NMeDAla-OH | prep. HPLC method 2a | 17% |
| Ex. 195h | C.2 | Fmoc-Sar-OH | Fmoc-Phe-OH | Fmoc-DAla-OH | prep. HPLC method 2a | 13% |
| Ex. 196i | C.2 | Fmoc-Ala-OH | Fmoc-DPhe-OH | Fmoc-NMeGlu(OtBu)-OH | prep. HPLC method 1a | 12% (TFA salt) |
| Ex. 195j | C.2 | Fmoc-Sar-OH | Fmoc-Phe-OH | Fmoc-NMeDAla-OH | prep. HPLC method 2a | 13% |
| Ex. 196k | C.2 | Fmoc-DAla-OH | Fmoc-Phe-OH | Fmoc-NMeGlu(OtBu)-OH | prep. HPLC method 1a | 10% (TFA salt) |

TABLE 23b

Examples of Core 11 (Ex. 195a,b,e-h,j; Ex. 196c,i,k and Ex. 197d)

| No | Formula | Monoisotopic Mass | Rt (purity at 220 nm) | $[M + H]^+$ found | LC-MS-Method |
|---|---|---|---|---|---|
| Ex. 195a | C29H37N5O5 | 535.3 | 1.50 (98) | 536.2 | method 1d |
| Ex. 195b | C27H33N5O5 | 507.3 | 1.44 (98) | 508.2 | method 1d |
| Ex. 196c | C31H39N5O7 | 593.3 | 1.47 (98) | 594.2 | method 1d |
| Ex. 197d | C31H42N6O5 | 578.3 | 2.10 (92) | 579.2 | method 2f |
| Ex. 195e | C29H37N5O5 | 535.3 | 1.53 (98) | 536.3 | method 1d |
| Ex. 195f | C29H37N5O5 | 535.2 | 1.40 (98) | 536.2 | method 1d |
| Ex. 195g | C32H35N5O5 | 569.3 | 1.71 (97) | 569.9 | method 1d |
| Ex. 195h | C32H35N5O5 | 569.3 | 1.67 (97) | 570.2 | method 1d |
| Ex. 196i | C35H39N5O7 | 641.3 | 1.41 (90) | 642.3 | method 2f |
| Ex. 195j | C33H37N5O5 | 583.3 | 1.72 (93) | 584.0 | method 1d |
| Ex. 196k | C35H39N5O7 | 641.3 | 1.71 (99) | 642.2 | method 1d |

TABLE 23c

Examples of Core 11 (Ex. 195a,b,e-h,j; Ex. 196c,i,k and Ex. 197d) (continued on the following page)

| No | IUPAC name |
|---|---|
| Ex. 195a | (9S,16R,22S)-16,17,20,22,23-pentamethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone |
| Ex. 195b | (9S,16R,22S)-16,17,22-trimethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone |
| Ex. 196c | 3-[(9S,16R,19S,22S)-16,17,19,23-tetramethyl-14,18,21,24-tetraoxo-7-oxa-13,17,20,23,27-pentaazatetracyclo[23.3.1.1$^{2,6}$.0$^{9,13}$]triaconta-1(29),2(30),3,5,25,27-hexaen-22-yl]propanoic acid |
| Ex. 197d | (9S,16R,19S,22R)-19-(4-aminobutyl)-16,17,22-trimethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone |
| Ex. 195e | (9S,19R,22S)-16,19,20,22,23-pentamethyl-7-oxa-13,16,20,23,27-pentaazatetracyclo[23.3.1.1$^{2,6}$.0$^{9,13}$]triaconta-1(29),2(30),3,5,25,27-hexaene-14,17,21,24-tetrone |
| Ex. 195f | (9S,18S,22R)-16,18,19,22,23-pentamethyl-7-oxa-13,16,19,23,27-pentaazatetracyclo[23.3.1.1$^{2,6}$.0$^{9,13}$]triaconta-1(29),2(30),3,5,25,27-hexaene-14,17,20,24-tetrone |
| Ex. 195g | (9S,18S,21R)-18-benzyl-21,22-dimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone |
| Ex. 195h | (9S,18S,21R)-18-benzyl-16,21-dimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone |
| Ex. 196i | 3-[(9S,15S,18R,21S)-18-benzyl-15,22-dimethyl-14,17,20,23-tetraoxo-7-oxa-13,16,19,22,26-pentaazatetracyclo[22.3.1.1$^{2,6}$.0$^{9,13}$]nonacosa-1(28),2(29),3,5,24,26-hexaen-21-yl]propanoic acid |
| Ex. 195j | (9S,18S,21R)-18-benzyl-16,21,22-trimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone |
| Ex. 196k | 3-[(9S,15R,18S,21S)-18-benzyl-15,22-dimethyl-14,17,20,23-tetraoxo-7-oxa-13,16,19,22,26-pentaazatetracyclo[22.3.1.1$^{2,6}$.0$^{9,13}$]nonacosa-1(28),2(29),3,5,24,26-hexaen-21-yl]propanoic acid |

TABLE 24a

Examples of Core 12 (Ex. 198-Ex. 219; continued on the following pages)

| No | RB | $R^D$ | Starting Material | General Proced. | Reagent | Purification Method | Yield (isolated salt) |
|---|---|---|---|---|---|---|---|
| Ex. 198-Ex. 200: cf. experimental description | | | | | | | |
| Ex. 201 | 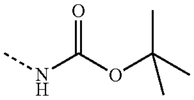 | $CH_3$ | Ex. 200 | (A.6.2)[1)] | Formaldehyde (36.5% in $H_2O$); details cf. [1)] | FC ($CH_2Cl_2$/MeOH) | 89% |
| Ex. 202 | $NH_2$ | $CH_3$ | Ex. 201 | B.1 | HCl-dioxane | crude product | 93% (HCl salt) |
| Ex. 203 | 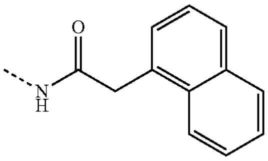 | CH 3 | Ex. 202 | A.1.3 | 2-Naphthaleneacetic acid T3P 50% in EtOAc i-$Pr_2$NEt (7 equiv.) | prep. HPLC method 2a | 6% |
| Ex. 204 | 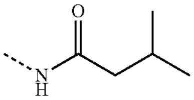 | $CH_3$ | Ex. 202 | A.1.3 | 3-Methylbutanoic acid T3P 50% in EtOAc i-$Pr_2$NEt (7 equiv.) | prep. HPLC method 1a and prep. HPLC method 2a | 7% |
| Ex. 205 | 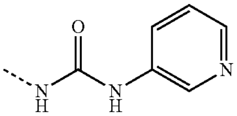 | $CH_3$ | Ex. 202 | A.3 | 3-Pyridinyl isocyanate i-$Pr_2$NEt (5 equiv.) | prep. HPLC method 1a and prep. HPLC method 2a | 24% |
| Ex. 206 | 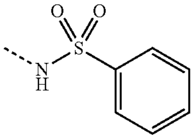 | $CH_3$ | Ex. 202 | A.5 | Benzenesulfonyl chloride (1.1 equiv.) $NEt_3$ (5 equiv.) | prep. HPLC method 2a | 68% |
| Ex. 207 | 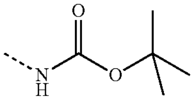 | 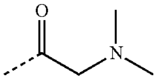 | Ex. 200 | A.1.3 | 2-(Dimethylamino) acetic acid Workup: $CH_2Cl_2$, sat. aq. $NaHCO_3$ soln | prep. HPLC method 2a | 49% |
| Ex. 208 | $NH_2$ | 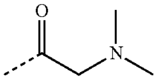 | Ex. 207 | B.1 | HCl-dioxane | crude product | 85% (HCl salt) |
| Ex. 209 | 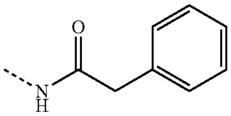 | 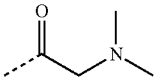 | Ex. 208 | A.1.3 | 2-Phenylacetic acid (3.4 equiv.) i-$Pr_2$NEt (8 equiv.) | prep. HPLC method 1a and prep. HPLC method 2a | 22% |
| Ex. 210 | 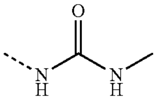 | 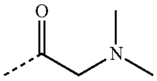 | Ex. 208 | A.3 | N-Succinimidyl N-methylcarbamate i-$Pr_2$NEt (5 equiv.) | prep. HPLC method 1a and prep. HPLC method 2a | 38% |
| Ex. 211 | 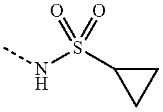 | 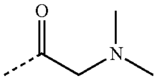 | Ex. 208 | A.5 | Cyclopropane-sulfonyl chloride $NEt_3$ (5 equiv.) | prep. HPLC method 1a and prep. HPLC method 2a | 30% |

TABLE 24a-continued

Examples of Core 12 (Ex. 198-Ex. 219; continued on the following pages)

| No | RB | $R^D$ | Starting Material | General Proced. | Reagent | Purification Method | Yield (isolated salt) |
|---|---|---|---|---|---|---|---|
| Ex. 212 | 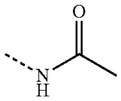 | 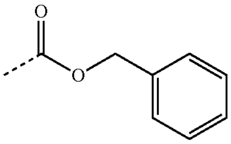 | Ex. 199 | A.1.2.2 | Acetyl chloride (2 equiv.); 0° C., 2 h | FC ($CH_2Cl_2$/MeOH) | 68% |
| Ex. 213 | 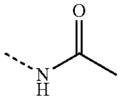 | H | Ex. 212 | B.3 | $H_2$, $Pd(OH)_2$—C, MeOH | crude product | 86% |
| Ex. 214 | 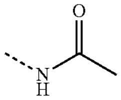 | 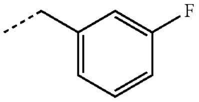 | Ex. 213 | A.6.3 | 3-Fluorobenz-aldehyde (1.8 equiv.) Acetic acid (1.5 equiv.) $NaBH(OAc)_3$ (4 equiv.) Workup: $CHCl_3$, sat. aq. $Na_2CO_3$ soln | prep. HPLC method 1a and prep. HPLC method 2a | 8% |
| Ex. 215 | 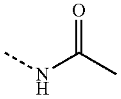 | 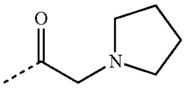 | Ex. 213 | A.1.3 | 1-Pyrrolidineacetic acid | prep. HPLC method 1a and prep. HPLC method 2a | 14% |
| Ex. 216 | 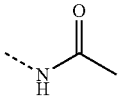 | 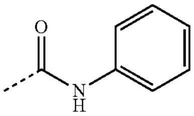 | Ex. 213 | A.3 | Phenyl isocyanate (1.4 equiv.) | prep. HPLC method 1a and prep. HPLC method 2a | 28% |
| Ex. 217 | 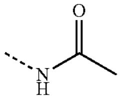 | 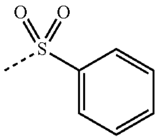 | Ex. 213 | A.5 | Benzenesulfonyl chlorid | prep. HPLC method 1a and prep. HPLC method 2a | 18% |
| Ex. 218 | 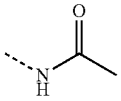 | 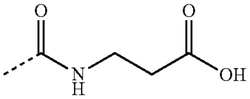 | Ex. 219 | B.2 | TFA, $CH_2Cl_2$ rt, 2 h | crude product | 87% (TFA salt) |
| Ex. 219 | 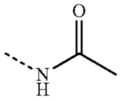 | 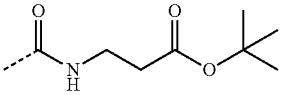 | Ex. 213 | A.3 | tert.-Butyl 3-((2,5-dioxopyrrolidin-1-yloxy) carbonylamino) propanoate | prep. HPLC method 1a and prep. HPLC method 2a | 49% |

[1)]At 0° C., formadehyde (36.5% in $H_2O$; 0.48 mL, 6.4 mmol), acetic acid (0.088 mL, 1.5 mmol) and $NaBH(OAc)_3$ (1.09 g, 5.1 mmol) were added to a soln of Ex. 200 (0.635 g, 1.3 mmol) in DCE (20 mL). The mixture was stirred for 2 h at 0° C., followed by an aqueous workup ($CH_2Cl_2$, sat. aq. $NaHCO_3$ soln; $Na_2SO_4$). The crude product was dissolved in MeCN (3 mL) and treated with 25% aq. $NH_3$ soln (1 mL) for 3 h at rt. More 25% aq. $NH_3$ soln (1 mL) was added and stirrig was continued for 2 h. Aqueous workup (EtOAc, sat. aq. $Na_2CO_3$ soln, sat. aq. NaCl soln; $Na_2SO_4$) and FC ($CH_2Cl_2$/MeOH 9:1) afforded Ex. 201 (0.587g, 89%).

TABLE 24b

| No | $R^B$ | $R^D$ | Formula | Mono-isotopic Mass | Rt (purity at 220 nm) | $[M + H]^+$ found | LC-MS-Method |
|---|---|---|---|---|---|---|---|
| Examples of Core 12 (Ex. 198-Ex. 219; continued on the following page) | | | | | | | |
| Ex. 198-Ex. 200: cf. experimental description | | | | | | | |
| Ex. 201 | 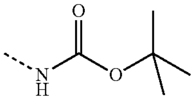 | $CH_3$ | C27H35N5O5 | 509.3 | 1.58 (97) | 510.3 | method 2f |
| Ex. 202 | $NH_2$ | $CH_3$ | C22H27N5O3 | 409.2 | 1.05 (95) | 410.0 | method 2f |
| Ex. 203 | 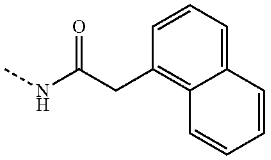 | $CH_3$ | C34H35N5O4 | 577.3 | 1.58 (97) | 578.1 | method 2c |
| Ex. 204 | 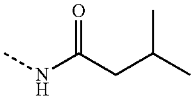 | $CH_3$ | C27H35N5O4 | 493.3 | 1.38 (99) | 494.2 | method 2c |
| Ex. 205 | 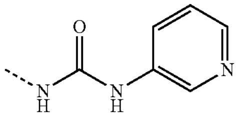 | $CH_3$ | C28H31N7O4 | 529.2 | 1.20 (99) | 530.2 | method 2c |
| Ex. 206 | 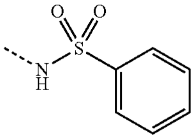 | $CH_3$ | C28H31N5O5S | 549.2 | 1.48 (99) | 550.1 | method 2c |
| Ex. 207 | 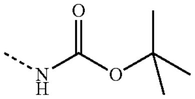 | 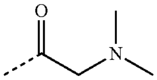 | C30H40N6O6 | 580.3 | 1.18 (98) | 581.2 | method 1d |
| Ex. 208 | $NH_2$ | 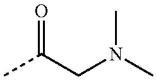 | C25H32N6O4 | 480.2 | 1.09 (95) | 481.3 | method 2f |
| Ex. 209 | 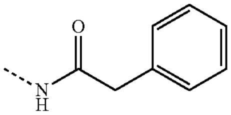 | 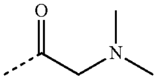 | C33H38N6O5 | 598.3 | 1.44 (98) | 599.1 | method 2c |
| Ex. 210 | 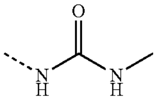 | 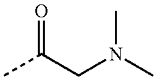 | C27H35N7O5 | 537.3 | 1.12 (99) | 538.2 | method 2c |
| Ex. 211 | 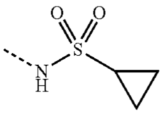 | 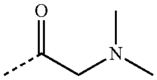 | C28H36N6O6S | 584.2 | 1.28 (99) | 585.1 | method 2c |
| Ex. 212 | 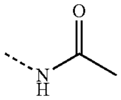 | 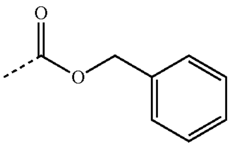 | C31H33N5O6 | 571.2 | 1.18 (97) | 572.0 | method 1a |

TABLE 24b-continued

Examples of Core 12 (Ex. 198-Ex. 219; continued on the following page)

| No | $R^B$ | $R^D$ | Formula | Mono-isotopic Mass | Rt (purity at 220 nm) | $[M + H]^+$ found | LC-MS-Method |
|---|---|---|---|---|---|---|---|
| Ex. 213 | 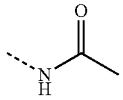 | H | C23H27N5O4 | 437.2 | 1.32 (96) | 438.1 | method 5a |
| Ex. 214 | 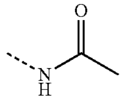 | 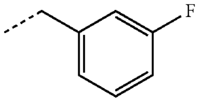 | C30H32FN5O4 | 545.2 | 1.51 (99) | 546.1 | method 2c |
| Ex. 215 | 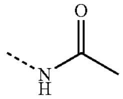 | 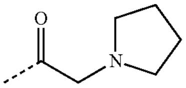 | C29H36N6O5 | 548.3 | 1.20 (99) | 549.2 | method 2c |
| Ex. 216 | 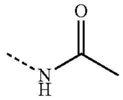 | 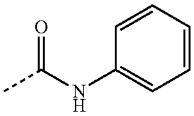 | C30H32N6O5 | 556.2 | 1.32 (97) | 556.9 | method 2c |
| Ex. 217 | 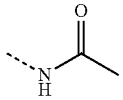 | 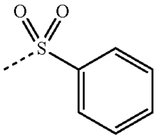 | C29H31N5O6S | 577.2 | 1.37 (100) | 578.1 | method 2c |
| Ex. 218 | 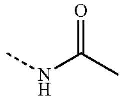 | 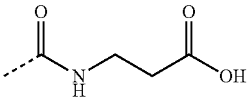 | C27H32N6O7 | 552.2 | 1.50 (92) | 553.1 | method 5a |
| Ex. 219 | 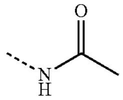 | 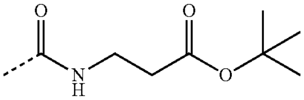 | C31H40N6O7 | 608.3 | 1.42 (98) | 609.2 | method 2c |

TABLE 24c

Examples of Core 12 (Ex. 198-Ex. 219; continued on the following pages)

| No | $R^B$ | $R^D$ | IUPAC name |
|---|---|---|---|
| Ex. 198 | 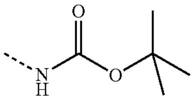 | 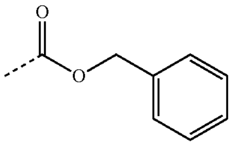 | benzyl (10S,12S)-12-[(tert-butoxycarbonyl)amino]-15,21-dioxo-8-oxa-3,14,17,20-tetraazatetracyclo[20.2.2.$0^{2,7}$.$0^{10,14}$]hexacosa-1(24),2,4,6,22,25-hexaene-17-carboxylate |
| Ex. 199 | $NH_2$ | 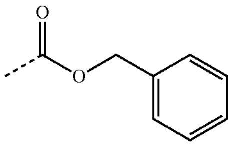 | benzyl (10S,12S)-12-amino-15,21-dioxo-8-oxa-3,14,17,20-tetraazatetracyclo[20.2.2.$0^{2,7}$.$0^{10,14}$]hexacosa-1(24),2,4,6,22,25-hexaene-17-carboxylate |
| Ex. 200 | 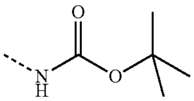 | H | tert-butyl N-[(10S,12S)-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]carbamate |

TABLE 24c-continued

Examples of Core 12 (Ex. 198-Ex. 219; continued on the following pages)

| No | $R^B$ | $R^D$ | IUPAC name |
|---|---|---|---|
| Ex. 201 | 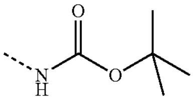 | $CH_3$ | tert-butyl N-[(10S,12S)-17-methyl-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]carbamate |
| Ex. 202 | $NH_2$ | $CH_3$ | (10S,12S)-12-amino-17-methyl-8-oxa-3,14,17,20-tetraazatetracyclo[20.2.2.$0^{2,7}$.$0^{10,14}$]hexacosa-1(24),2,4,6,22,25-hexaene-15,21-dione |
| Ex. 203 | 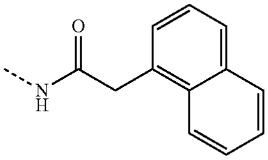 | $CH_3$ | N-[(10S,12S)-17-methyl-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]-2-(1-naphthyl)acetamide |
| Ex. 204 | 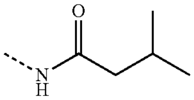 | $CH_3$ | 3-methyl-N-[(10S,12S)-17-methyl-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]butanamide |
| Ex. 205 | 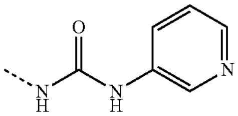 | $CH_3$ | N-[(10S,12S)-17-methyl-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]-N-(3-pyridinyl)urea |
| Ex. 206 | 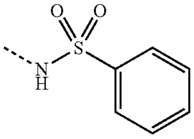 | $CH_3$ | N-[(10S,12S)-17-methyl-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]benzenesulfonamide |
| Ex. 207 | 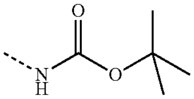 | 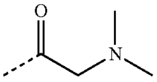 | tert-butyl N-[(10S,12S)-17-[2-(dimethylamino)acetyl]-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]carbamate |
| Ex. 208 | $NH_2$ | 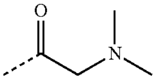 | (10S,12S)-12-amino-17-[2-(dimethylamino)acetyl]-8-oxa-3,14,17,20-tetraazatetracyclo[20.2.2.$0^{2,7}$.$0^{10,14}$]hexacosa-1(24),2,4,6,22,25-hexaene-15,21-dione |
| Ex. 209 | 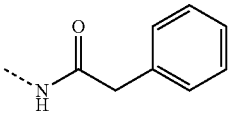 | 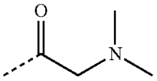 | N-[(10S,12S)-17-[2-(dimethylamino)acetyl]-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]-2-phenylacetamide |
| Ex. 210 | 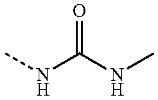 | 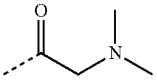 | N-[(10S,12S)-17-[2-(dimethylamino)acetyl]-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]-N'-methylurea |
| Ex. 211 | 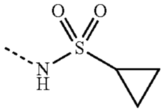 | 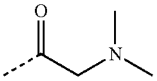 | N-[(10S,12S)-17-[2-(dimethylamino)acetyl]-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]cyclopropanesulfonamide |
| Ex. 212 | 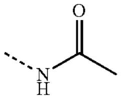 | 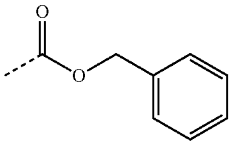 | benzyl (10S,12S)-12-(acetylamine)-15,21-dioxo-8-oxa-3,14,17,20-tetraazatetracyclo[20.2.2.$0^{2,7}$.$0^{10,14}$]hexacosa-1(24),2,4,6,22,25-hexaene-17-carboxylate |

TABLE 24c-continued

| Examples of Core 12 (Ex. 198-Ex. 219; continued on the following pages) | | | |
|---|---|---|---|
| No | $R^B$ | $R^D$ | IUPAC name |
| Ex. 213 | 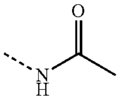 | H | N-[(10S,12S)-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 214 | 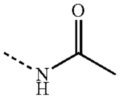 | 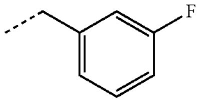 | N-[(10S,12S)-17-(3-fluorobenzyl)-15,21-dioxo-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 215 | 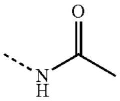 | 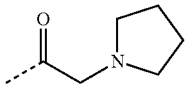 | N-[(10S,12S)-15,21-dioxo-17-[2-(1-pyrrolidinyl)acetyl]-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 216 | 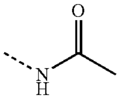 | 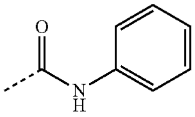 | (10S,12S)-12-(acetylamino)-15,21-dioxo-N-phenyl-8-oxa-3,14,17,20-tetraazatetracyclo[20.2.2.$0^{2,7}$.$0^{10,14}$]hexacosa-1(24),2,4,6,22,25-hexaene-17-carboxamide |
| Ex. 217 | 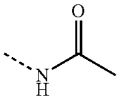 | 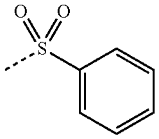 | N-[(10S,12S)-15,21-dioxo-17-(phenylsulfonyl)-8-oxa-3,14,17,20-tetraazatetracyclo[20.2.2.$0^{2,7}$.$0^{10,14}$]hexacosa-1(24),2,4,6,22,25-hexaen-12-yl]acetamide |
| Ex. 218 | 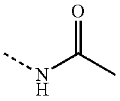 | 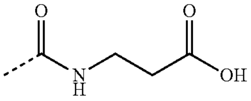 | 3-({[(10S,12S)-12-(acetylamino)-15,21-dioxo-8-oxa-3,14,17,20-tetraazatetracyclo[20.2.2.$0^{2,7}$.$0^{10,14}$]hexacosa-1(24),2,4,6,22,25-hexaen-17-yl]carbonyl}amino)propanoic acid |
| Ex. 219 | 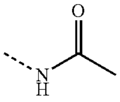 | 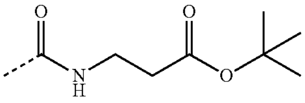 | tert-butyl 3-({[(10S,12S)-12-(acetylamino)-15,21-dioxo-8-oxa-3,14,17,20-tetraazatetracyclo[20.2.2.$0^{2,7}$.$0^{10,14}$]hexacosa-1(24),2,4,6,22,25-hexaen-17-yl]carbonyl}amino)propanoate |

TABLE 25a

| Examples of Core 13 (Ex. 220-Ex. 226; continued on the following pages) | | | | | | | |
|---|---|---|---|---|---|---|---|
| No | $R^B$ | $R^E$ | Starting Material | General Proced. | Reagent | Purification Method | Yield (isolated salt) |
| Ex. 220-Ex. 222 cf. experimental description | | | | | | | |
| Ex. 223 | 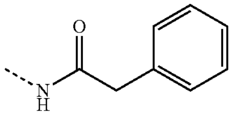 | $CO_2CH_3$ | Ex. 222 | A.1.1 | 2-Phenylacetic acid i-$Pr_2$NEt added at 0° C. 0° C. to rt, 2 h Workup: EtOAc, 1M aq. HCl soln, $H_2O$, sat. aq. $NaHCO_3$ soln | FC ($CH_2Cl_2$/MeOH) | 93% |
| Ex. 224 | 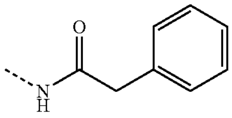 | $CO_2H$ | Ex. 223 | B.5 | Trimethyltin hydroxide | FC ($CH_2Cl_2$/MeOH) and prep. HPLC method 1a | 80% |
| Ex. 225 | 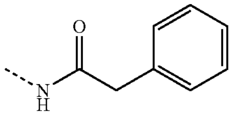 | $CONH_2$ | Ex. 224 | A.2 | Ammoniun chloride (5.2 equiv.) HATU (3.2 equiv.) HOAt (3.2 equiv.) i-$Pr_2$NEt (8.4 equiv.) Workup: EtOAc, 1M aq. HCl soln, $H_2O$, sat. aq. $NaHCO_3$ soln, sat. aq. NaCl soln | FC ($CH_2Cl_2$/MeOH) | 64% |

TABLE 25a-continued

Examples of Core 13 (Ex. 220-Ex. 226; continued on the following pages)

| No | $R^B$ | $R^E$ | Starting Material | General Proced. | Reagent | Purification Method | Yield (isolated salt) |
|---|---|---|---|---|---|---|---|
| Ex. 226 | 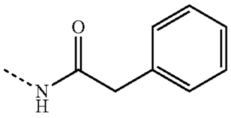 | 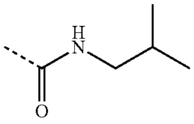 | Ex. 224 | A.2 | Isobutylamine Workup: EtOAc, 1M aq. HCl soln, $H_2O$, sat. aq. $NaHCO_3$ soln, sat. aq. NaCl soln | FC ($CH_2Cl_2$/MeOH) | 80% |

TABLE 25b

Examples of Core 13 (Ex. 220-Ex. 226)

| No | $R^B$ | $R^E$ | Formula | Monoisotopic Mass | Rt (purity at 220 nm) | $[M + H]^+$ found | LC-MS-Method |
|---|---|---|---|---|---|---|---|
| Ex. 220-Ex. 222.: cf. experimental description | | | | | | | |
| Ex. 223 | 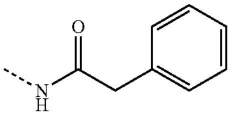 | $CO_2CH_3$ | C32H34FN3O7S | 623.2 | 2.31 (99) | 624.3 | method 1d |
| Ex. 224 | 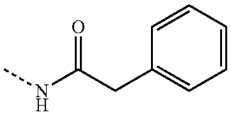 | $CO_2H$ | C31H32FN3O7S | 609.2 | 2.05 (99) | 610.2 | method 1d |
| Ex. 225 | 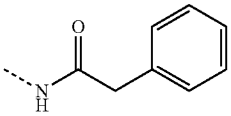 | $CONH_2$ | C31H33FN4O6S | 608.2 | 1.93 (99) | 609.2 | method 1d |
| Ex. 226 | 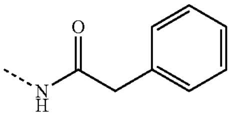 | 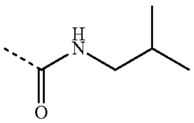 | C35H41FN4O6S | 664.3 | 2.22 (89) | 665.3 | method 1d |

TABLE 25c

Examples of Core 13 (Ex. 220-Ex. 226)

| No | $R^B$ | $R^E$ | IUPAC name |
|---|---|---|---|
| Ex. 220 | 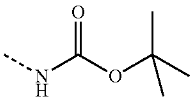 | $CO_2CH_3$ | methyl (8S,17S,19S)-17-[(tert-butoxycarbonyl)amino]-24-fluoro-6,14-dioxo-10,21-dioxa-4-thia-7,15-diazatetracyclo[20.3.1.$1^{2,5}$.$0^{15,19}$]heptacosa-1(26),2,5(27),12,22,24-hexaene-8-carboxylate |
| Ex. 221 | 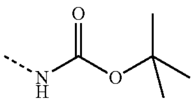 | $CO_2CH_3$ | methyl (8S,17S,19S)-17-[(tert-butoxycarbonyl)amino]-24-fluoro-6,14-dioxo-10,21-dioxa-4-thia-7,15-diazatetracyclo[20.3.1.$1^{2,5}$.$0^{15,19}$]heptacosa-1(26),2,5(27),22,24-pentaene-8-carboxylate |
| Ex. 222 | $NH_2$ | $CO_2CH_3$ | methyl (8S,17S,19S)-17-amino-24-fluoro-6,14-dioxo-10,21-dioxa-4-thia-7,15-diazatetracyclo[20.3.1.$1^{2,5}$.$0^{15,19}$]heptacosa-1(26),2,5(27),22,24-pentaene-8-carboxylate |
| Ex. 223 | 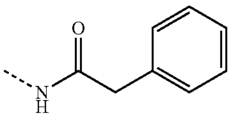 | $CO_2CH_3$ | methyl (8S,17S,19S)-24-fluoro-6,14-dioxo-17-[(2-phenylacetypamino]-10,21-dioxa-4-thia-7,15-diazatetracyclo[20.3.1.$1^{2,5}$.$0^{15,19}$]heptacosa-1(26),2,5(27),22,24-pentaene-8-carboxylate |

TABLE 25c-continued

| Examples of Core 13 (Ex. 220-Ex. 226) | | | |
|---|---|---|---|
| No | $R^B$ | $R^E$ | IUPAC name |
| Ex. 224 | 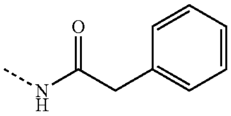 | $CO_2H$ | (8S,17S,19S)-24-fluoro-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxylic acid |
| Ex. 225 | 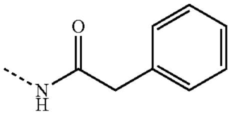 | $CONH_2$ | (8S,17S,19S)-24-fluoro-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxamide |
| Ex. 226 | 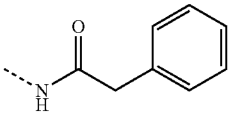 | 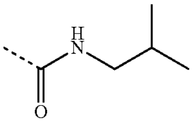 | (8S,17S,19S)-24-fluoro-N-isobutyl-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxamide |

TABLE 26a

| Examples of Core 14 (Ex. 227-Ex. 241; continued on the following page) | | | | | | | |
|---|---|---|---|---|---|---|---|
| No | $R^B$ | $R^E$ | Starting Material | General Proced. | Reagent | Purification Method | Yield (isolated salt) |
| Ex. 227-Ex. 229: cf. experimental description | | | | | | | |
| Ex. 230 | 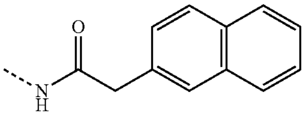 | $CO_2CH_3$ | Ex. 229 | A.1.2 | 2-Naphthalene-acetyl chloride (1.1 equiv.) | prep. HPLC method 3 | 57% |
| Ex. 231 | 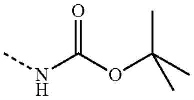 | 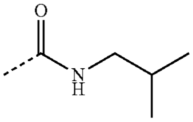 | Ex. 228 | A.2 | Isobutylamine | FC (hexane/EtOAc/MeOH) | 40% |
| Ex. 232 | $NH_2$ | 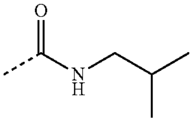 | Ex. 231 | B.1 | HCl-dioxane | crude product | 93% (HCl salt) |
| Ex. 233 | 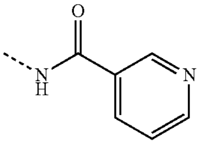 | 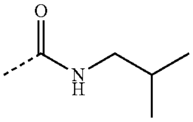 | Ex. 232 | A.1.1 | Nicotinic acid (1.3 equiv.), 0° C., 2 h Workup: EtOAc, 1M aq. HCl soln, sat. aq. $Na_2CO_3$ soln, sat. aq. NaCl soln | FC ($CH_2Cl_2$/MeOH) | 14% |
| Ex. 234 | 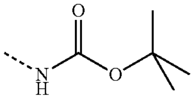 | 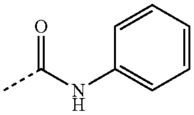 | Ex. 228 | A.2 | Aniline | FC (hexane/EtOAc) | 4% |
| Ex. 235 | $NH_2$ | 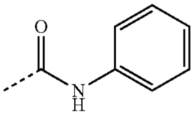 | Ex. 234 | B.1 | HCl-dioxane | prep. HPLC method 1a | 44% (TFA salt) |

TABLE 26a-continued

Examples of Core 14 (Ex. 227-Ex. 241; continued on the following page)

| No | $R^B$ | $R^E$ | Starting Material | General Proced. | Reagent | Purification Method | Yield (isolated salt) |
|---|---|---|---|---|---|---|---|
| Ex. 236 | 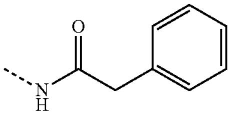 | $CO_2CH_3$ | Ex. 229 | A.1.2 | Phenylacetyl chloride (1.1 equiv.) | prep. HPLC method 3 | 75% |
| Ex. 237 | 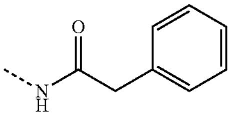 | $CO_2H$ | Ex. 236 | B.5 | Trimethylthin hydroxide | prep. HPLC method 1a | 78% |
| Ex. 238 | 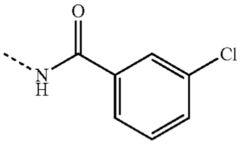 | $CO_2CH_3$ | Ex. 229 | A.1.2 | 3-Chlorobenzoyl chloride (1.1 equiv.) | prep. HPLC method 3 | 62% |
| Ex. 239 | 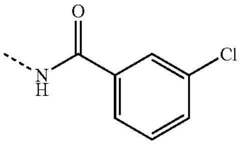 | $CO_2H$ | Ex. 238 | B.5 | Trimethyltin hydroxide | prep. HPLC method 1a | 70% |
| Ex. 240 | 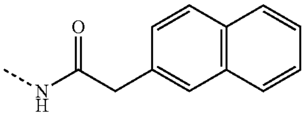 | 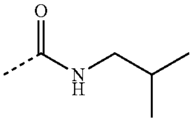 | Ex. 241 | A.2 | Isobutylamine | FC (hexane/EtOAc/MeOH) | 78% |
| Ex. 241 | 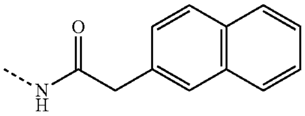 | $CO_2H$ | Ex. 230 | B.5 | Trimethyltin hydroxide | FC ($CH_2Cl_2$/MeOH) | 84% |

TABLE 26b

Examples of Core 14 (Ex. 227-Ex. 241;)

| No | $R^B$ | $R^E$ | Formula | Mono-isotopic Mass | Rt (purity at 220 nm) | $[M + H]^+$ found | LC-MS-Method |
|---|---|---|---|---|---|---|---|
| Ex. 227-Ex. 229: | | cf. experimental description | | | | | |
| Ex. 230 | 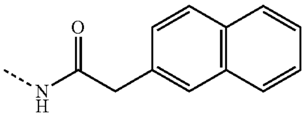 | $CO_2CH_3$ | C37H36FN3O7S | 685.2 | 2.28 (96) | 686.2 | method 1a |
| Ex. 231 | 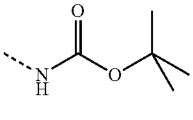 | 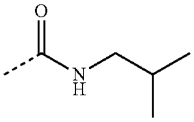 | C33H43FN4O7S | 658.3 | 2.37 (95) | 659.3 | method 1a |
| Ex. 232 | $NH_2$ | 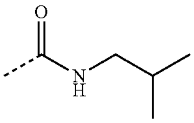 | C28H35FN4O5S | 558.2 | 1.59 (93) | 559.2 | method 1a |

TABLE 26b-continued
| Examples of Core 14 (Ex. 227-Ex. 241;) | | | | | | | | |
|---|---|---|---|---|---|---|---|---|
| No | $R^B$ | $R^E$ | Formula | Mono-isotopic Mass | Rt (purity at 220 nm) | $[M + H]^+$ found | LC-MS-Method |
| Ex. 233 | 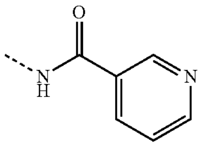 | 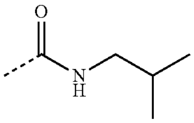 | C34H38FN5O6S | 663.3 | 1.95 (87) | 664.3 | method 2c |
| Ex. 234 | 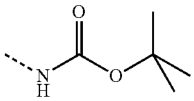 | 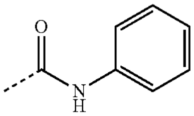 | C35H39FN4O7S | 678.3 | 2.43 (77) | 679.2 | method 1a |
| Ex. 235 | $NH_2$ | 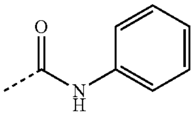 | C30H31FN4O5S | 578.2 | 1.66 (95) | 579.2 | method 1a |
| Ex. 236 | 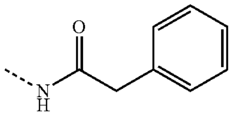 | $CO_2CH_3$ | C33H34FN3O7S | 635.2 | 2.15 (91) | 636.0 | method 1a |
| Ex. 237 | 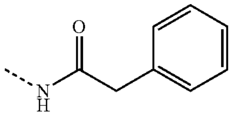 | $CO_2H$ | C32H32FN3O7S | 621.2 | 1.98 (96) | 622.1 | method 1c |
| Ex. 238 | 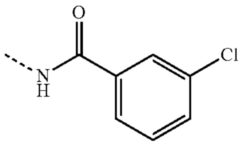 | $CO_2CH_3$ | C32H31ClFN3O7S | 655.2 | 2.31 (97) | 656.1 | method 1a |
| Ex. 239 | 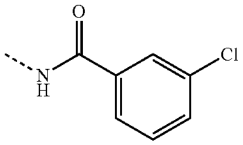 | $CO_2H$ | C31H29ClFN3O7S | 641.1 | 2.14 (97) | 642.1 | method 1a |
| Ex. 240 | 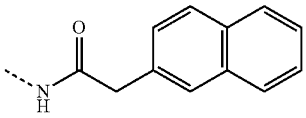 | 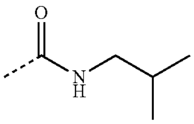 | C40H43FN4O6S | 726.3 | 2.32 (79) | 727.3 | method 1a |
| Ex. 241 | 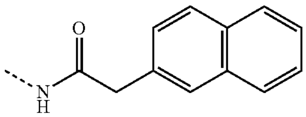 | $CO_2H$ | C36H34FN3O7S | 671.2 | 2.15 (88) | 672.1 | method 1a |

TABLE 26c

| Examples of Core 14 (Ex. 227-Ex. 241;) | | | |
|---|---|---|---|
| No | $R^B$ | $R^E$ | IUPAC name |
| Ex. 227 | 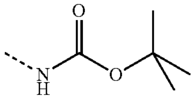 | $CO_2CH_3$ | methyl (8S,12E,18S,20S)-18-[(tert-butoxycarbonyl)amino]-25-fluoro-6,15-dioxo-10,22-dioxa-4-thia-7,16-diazatetracyclo $[21.3.1.1^{2,5}.0^{16,20}]$octacosa-1(27),2,5(28),12,23,25-hexaene-8-carboxylate |
| Ex. 228 | 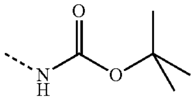 | $CO_2H$ | (8S,12E,18S,20S)-18-[(tert-butoxycarbonyl)amino]-25-fluoro-6,15-dioxo-10,22-dioxa-4-thia-7,16-diazatetracyclo$[21.3.1.1^{2,5}.0^{16,20}]$ octacosa-1(27),2,5(28),12,23,25-hexaene-8-carboxylic acid |
| Ex. 229 | $NH_2$ | $CO_2CH_3$ | methyl (8S,12E, 18S,20S)-18-amino-25-fluoro-6,15-dioxo-10,22-dioxa-4-thia-7,16-diazatetracyclo$[21.3.1.1^{2,5}.0^{16,20}]$octacosa-1(27),2,5(28),12,23,25-hexaene-8-carboxylate |
| Ex. 230 | 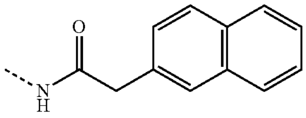 | $CO_2CH_3$ | methyl (8S,12E, 18S,20S)-25-fluoro-1842-(2-naphthyl)acetyl] amino-6,15-dioxo-10,22-dioxa-4-thia-7,16-diazatetracyclo $[21.3.1.1^{2,5}.0^{16,20}]$octacosa-1(27),2,5(28),12,23,25-hexaene-8-carboxylate |
| Ex. 231 | 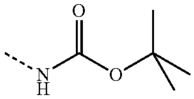 | 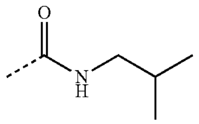 | tert-butyl N-[(8S,12E, 18S,20S)-25-fluoro-8-[8 (isobutylamino) carbonyl]-6,15-dioxo-10,22-dioxa-4-thia-7,16-diazatetracyclo $[21.3.1.1^{2,5}.0^{16,20}]$octacosa-1(27),2,5(28),12,23,25-hexaen-18-yl]carbamate |
| Ex. 232 | $NH_2$ | 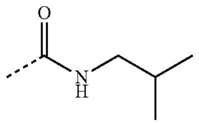 | (8S,12E,18S,20S)-18-amino-25-fluoro-N-isobutyl-6,15-dioxo-10,22-dioxa-4-thia-7,16-diazatetracyclo$[21.3.1.1^{2,5}.0^{16,20}]$octacosa-1(27),2,5(28),12,23,25-hexaene-8-carboxamide |
| Ex. 233 | 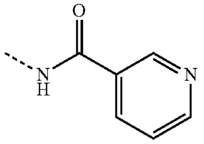 | 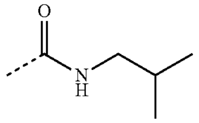 | (8S,12E,18S,20S)-25-fluoro-N-isobutyl-6,15-dioxo-18-[(3-pyridinylcarbonyl)amino]-10,22-dioxa-4-thia-7,16-diazatetracyclo$[21.3.1.1^{2,5}.0^{16,20}]$octacosa-1(27),2,5(28),12,23,25-hexaene-8-carboxamide |
| Ex. 234 | 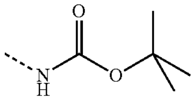 | 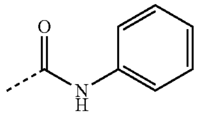 | tert-butyl N-[(8S,12E,18S,20S)-8-(anilinocarbonyl)-25-fluoro-6,15-dioxo-10,22-dioxa-4-thia-7,16-diazatetracyclo $[21.3.1.1^{2,5}.0^{16,20}]$octacosa-1(27),2,5(28),12,23,25-hexaen-18-yl]carbamate |
| Ex. 235 | $NH_2$ | 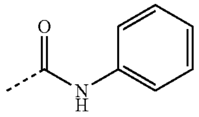 | (8S,12E,18S,20S)-18-amino-25-fluoro-6,15-dioxo-N-phenyl-10,22-dioxa-4-thia-7,16-diazatetracyclo$[21.3.1.1^{2,5}.0^{16,20}]$ octacosa-1(27),2,5(28),12,23,25-hexaene-8-carboxamide |
| Ex. 236 | 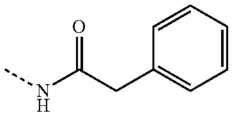 | $CO_2CH_3$ | methyl (8S,12E,18S,20S)-25-fluoro-6,15-dioxo-18-[(2-phenylacetyl)amino]-10,22-dioxa-4-thia-7,16-diazatetracyclo $[21.3.1.1^{2,5}.0^{16,20}]$octacosa-1(27),2,5(28),12,23,25-hexaene-8-carboxylate |
| Ex. 237 | 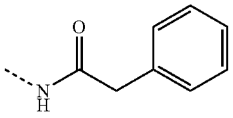 | $CO_2H$ | (8S,12E,18S,20S)-25-fluoro-6,15-dioxo-18-[(2-phenylacetyl) amino]-10,22-dioxa-4-thia-7,16-diazatetracyclo$[21.3.1.1^{2,5}.0^{16,20}]$ octacosa-1(27),2,5(28),12,23 ,25-hexaene-8-carboxylic acid |
| Ex. 238 | 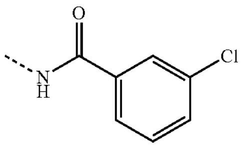 | $CO_2CH_3$ | methyl (8S,12E,18S,20S)-18-[(3-chlorobenzoyl)amino]-25-fluoro-6,15-dioxo-10,22-dioxa-4-thia-7,16-diazatetracyclo $[21.3.1.1^{2,5}.0^{16,20}]$octacosa-1(27),2,5(28),12,23,25-hexaene-8-carboxylate |

TABLE 26c-continued

| Examples of Core 14 (Ex. 227-Ex. 241;) | | | |
|---|---|---|---|
| No | $R^B$ | $R^E$ | IUPAC name |
| Ex. 239 | 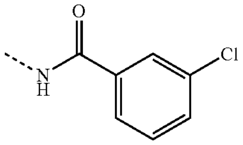 | $CO_2H$ | (8S,12E,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid |
| Ex. 240 | 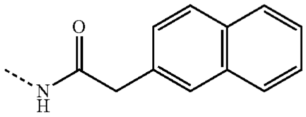 | 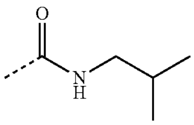 | (8S,12E,18S,20S)-25-fluoro-N-isobutyl-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxamide |
| Ex. 241 | 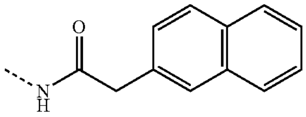 | $CO_2H$ | (8S,12E,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid |

TABLE 27a

| Examples of Core 15 (Ex. 242-Ex. 261;) | | | | | | | |
|---|---|---|---|---|---|---|---|
| No | $R^B$ | $R^E$ | Starting Material | General Proced. | Reagent | Purification Method | Yield (isolated salt) |
| Ex. 242-Ex. 244: | | cf. experimental description | | | | | |
| Ex. 245 | 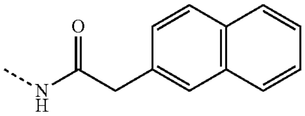 | $CO_2CH_3$ | Ex. 244 | 1) | 2-Naphthaleneacetyl chloride | FC (EtOAc) and FC ($CH_2Cl_2$/MeOH) | 52% |
| Ex. 246 | 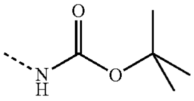 | 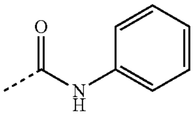 | Ex. 243 | 2) | Aniline (5 equiv.) | FC (hexane/EtOAc) | 62% |
| Ex. 247 | $NH_2$ | 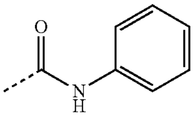 | Ex. 246 | 2) | HCl-dioxane then TFA, $CH_2Cl_2$ | FC ($CH_2Cl_2$/MeOH) | 60% (HCl salt) |
| Ex. 248 | 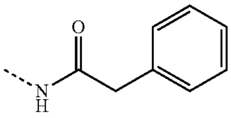 | $CO_2CH_3$ | Ex. 244 | A.1.2 | Phenylacetyl chloride (1.6 equiv.) | FC (hexane/EtOAc/MeOH) | 90% |
| Ex. 249 | 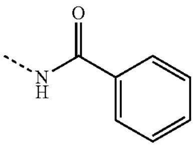 | $CO_2H$ | Ex. 250 | B.5 | Trimethyltin hydroxide | prep. HPLC method 1a | 65% |
| Ex. 250 | 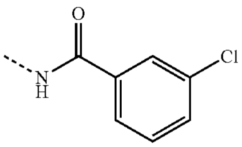 | $CO_2CH_3$ | Ex. 244 | A.1.2 | 3-Chlorobenzoyl chloride (1.6 equiv.) | FC (hexane/EtOAc) | 87% |

TABLE 27a-continued

Examples of Core 15 (Ex. 242-Ex. 261;)

| No | $R^B$ | $R^E$ | Starting Material | General Proced. | Reagent | Purification Method | Yield (isolated salt) |
|---|---|---|---|---|---|---|---|
| Ex. 251 | 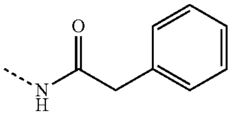 | $CO_2H$ | Ex. 248 | B.5 | Trimethyltin hydroxide | prep. HPLC method 1a | 70% |
| Ex. 252 | 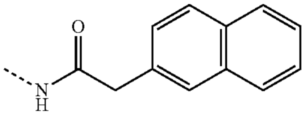 | $CO_2H$ | Ex. 245 | B.5 | Trimethyltin hydroxide | prep. HPLC method 1a | 45% |
| Ex. 253 | 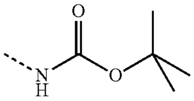 | 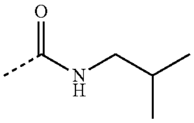 | Ex. 243 | A.2 | Isobutylamine (1.5 equiv.) Workup: $CH_2Cl_2$, sat. aq. $NaHCO_3$ soln, $H_2O$, sat. aq. NaCl soln | FC (hexane, EtOAc) | 73% |
| Ex. 254 | $NH_2$ | 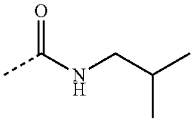 | Ex. 253 | B.1 | HCl-dioxane | crude product | quant. (HCl salt) |
| Ex. 255 | 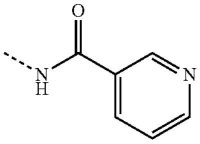 | 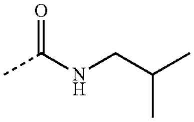 | Ex. 254 | A.1.1 | Nicotinic acid (1.3 equiv.) 0° C., 2 h Workup: EtOAc, sat. aq. $NaHCO_3$ soln, $H_2O$, sat. aq. NaCl soln, | FC ($CH_2Cl_2$/MeOH) | 50% |
| Ex. 256 | 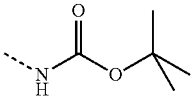 | 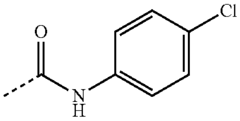 | Ex. 243 | 2) | 4-Chloroaniline (5 equiv.) | FC (hexane/EtOAc) | 14% |
| Ex. 257 | $NH_2$ | 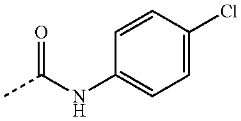 | Ex. 256 | 2) | HCl-dioxane then TFA, $CH_2Cl_2$ | FC ($CH_2Cl_2$/MeOH) | 66% (HCl salt) |
| Ex. 258 | 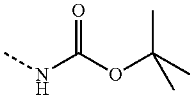 | 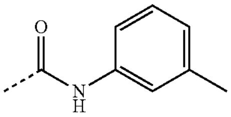 | Ex. 243 | 2) | m-Toluidine (5 equiv.) | FC (hexane/EtOAc) | 43% |
| Ex. 259 | $NH_2$ | 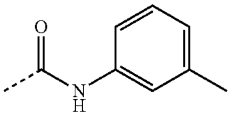 | Ex. 258 | 2) | HCl-dioxane then TFA, $CH_2Cl_2$ | FC ($CH_2Cl_2$/MeOH) | 66% (HCl salt) |
| Ex. 260 | 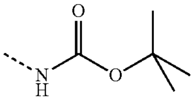 | 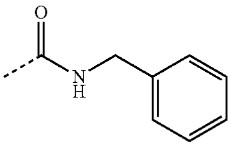 | Ex. 243 | 3) | Benzylamine (5 equiv.) | FC (hexane/EtOAc) | 57% |

TABLE 27a-continued

Examples of Core 15 (Ex. 242-Ex. 261;)

| No | $R^B$ | $R^E$ | Starting Material | General Proced. | Reagent | Purification Method | Yield (isolated salt) |
|---|---|---|---|---|---|---|---|
| Ex. 261 | $NH_2$ | 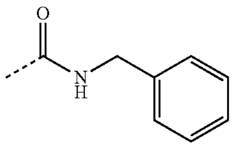 | Ex. 260 | [3)] | HCl-dioxane then TFA, $CH_2Cl_2$ | FC ($CH_2Cl_2$/ MeOH) | 74% (HCl salt) |

[1)] 2-Naphthaleneacetic acid (41 mg, 0.22 mmol) in $CH_2Cl_2$ (3 mL) was treated at 0° C. for 1 h with oxalyl chloride (0.08 mL, 0.93 mmol) and DMF (0.007 mL). The volatiles were evaporated. The residue was dissolved in $CH_2Cl_2$ (3 mL) and added dropwise to a mixture of Ex. 244·HCl (103 mg, 0.19 mmol) and i-$Pr_2NEt$ (0.2 mL; 0.93 mmol) in $CH_2Cl_2$ (3 mL). The solution was stirred at 0° C. for 1 h, followed by an aqueous workup ($CH_2Cl_2$, sat. aq. $NaHCO_3$ soln; $Na_2SO_4$), FC (EtOAc) and FC ($CH_2Cl_2$/MeOH 99:1 to 97:3) to afford Ex. 245 (67 mg, 52%).

[2)] Cf. experimental description for detailed procedure

[3)] Ex. 260 was obtained by applying the method described for the saynthesis of Ex. 246; Ex. 261 was obtained by applying the method described for the saynthesis of Ex. 247.

TABLE 27b

Examples of Core 15 (Ex. 242-Ex. 261;)

| No | $R^B$ | $R^E$ | Formula | Mono-iso-topic Mass | Rt (purity at 220 nm) | $[M + H]^+$ found | LC-MS-Method |
|---|---|---|---|---|---|---|---|
| Ex. 242-Ex. 244.: | | cf. experimental description | | | | | |
| Ex. 245 | 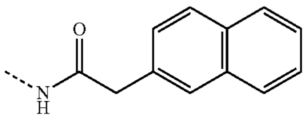 | $CO_2CH_3$ | C37H38FN3O7S | 687.2 | 1.62 (91) | 688.2 | method 4a |
| Ex. 246 | 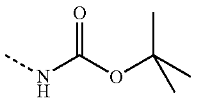 | 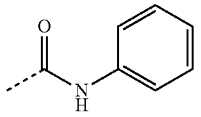 | C35H41FN4O7S | 680.3 | 2.48 (86) | 681.3 | method 1a |
| Ex. 247 | $NH_2$ | 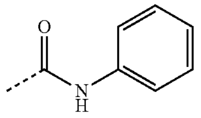 | C30H33FN4O5S | 580.2 | 1.66 (96) | 581.2 | method 1a |
| Ex. 248 | 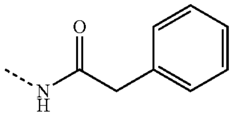 | $CO_2CH_3$ | C33H36FN3O7S | 637.2 | 2.21 (91) | 638.2 | method 1a |
| Ex. 249 | 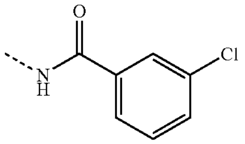 | $CO_2H$ | C31H31ClFN3O7S | 643.2 | 2.22 (97) | 644.1 | method 1a |
| Ex. 250 | 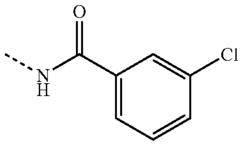 | $CO_2CH_3$ | C32H33ClFN3O7S | 657.2 | 2.40 (94) | 658.1 | method 1c |
| Ex. 251 | 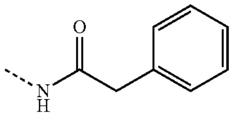 | $CO_2H$ | C32H34FN3O7S | 623.2 | 2.06 (97) | 624.1 | method 1a |

TABLE 27b-continued
| Examples of Core 15 (Ex. 242-Ex. 261;) | | | | | | | |
|---|---|---|---|---|---|---|---|
| No | $R^B$ | $R^E$ | Formula | Mono-iso-topic Mass | Rt (purity at 220 nm) | $[M + H]^+$ found | LC-MS-Method |
| Ex. 252 | 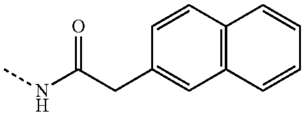 | $CO_2H$ | C36H36FN3O7S | 673.2 | 2.23 (89) | 674.2 | method 1g |
| Ex. 253 | 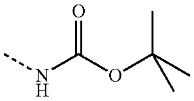 | 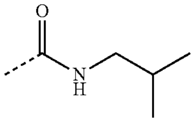 | C33H45FN4O7S | 660.3 | 2.45 (93) | 661.2 | method 1a |
| Ex. 254 | $NH_2$ | 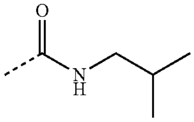 | C28H37FN4O5S | 560.2 | 1.60 (97) | 561.2 | method 1a |
| Ex. 255 | 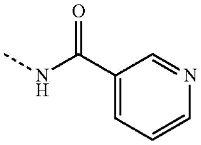 | 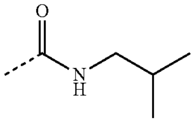 | C34H40FN5O6S | 665.3 | 2.00 (95) | 666.2 | method 2c |
| Ex. 256 | 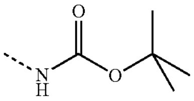 | 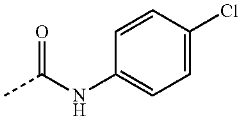 | C35H4OClFN4O7S | 714.2 | 2.59 (89) | 715.4 | method 1a |
| Ex. 257 | $NH_2$ | 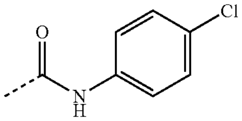 | C30H32ClFN4O5S | 614.2 | 1.80 (87) | 615.2 | method 1a |
| Ex. 258 | 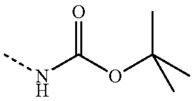 | 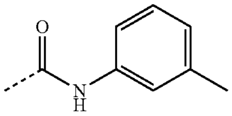 | C36H43FN4O7S | 694.3 | 2.55 (91) | 695.4 | method 1a |
| Ex. 259 | $NH_2$ | 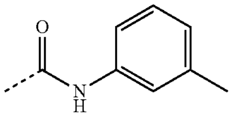 | C31H35FN4O5S | 594.2 | 1.74 (90) | 595.3 | method 1a |
| Ex. 260 | 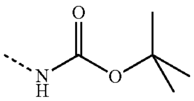 | 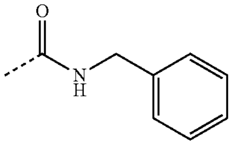 | C36H43FN4O7S | 694.3 | 2.44 (92) | 695.3 | method 1a |
| Ex. 261 | $NH_2$ | 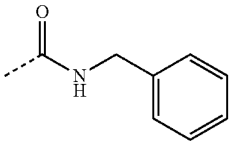 | C31H35FN4O5S | 594.2 | 1.63 (92) | 595.2 | method 1a |

TABLE 27c

Examples of Core 15 (Ex. 242-Ex. 261;)

| No | $R^B$ | $R^E$ | IUPAC name |
|---|---|---|---|
| Ex. 242 | 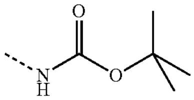 | $CO_2CH_3$ | methyl (8S,18S,20S)-18-[(tert-butoxycarbonyl)amino]-25-fluoro-6,15-dioxo-10,22-dioxa-4-thia-7,16-diazatetracyclo [21.3.1.1$^{2,5}$.0$^{16,20}$]octacosa-1(27),2,5(28),23,25-pentaene-8-carboxylate |
| Ex. 243 | 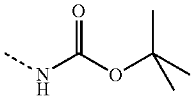 | $CO_2H$ | (8S,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$] octacosa-1(27),2,5(28),23,25-pentaene-8-carboxylic acid |
| Ex. 244 | $NH_2$ | $CO_2CH_3$ | methyl (8S,18S,20S)-18-amino-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate |
| Ex. 245 | 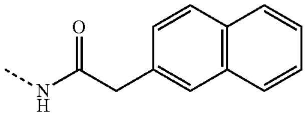 | $CO_2CH_3$ | methyl (8S,18S,20S)-25-fluoro-18-{[2-(2-naphthyl)acetyl] amino}-6,15-dioxo-10,22-dioxa-4-thia-7,16-diazatetracyclo [21.3.1.1$^{2,5}$.0$^{16,20}$]octacosa-1(27),2,5(28),23,25-pentaene-8-carboxylate |
| Ex. 246 | 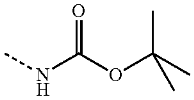 | 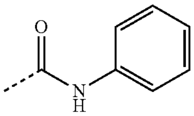 | tert-butyl N-[(8S,18S,20S)-8-(anilinocarbonyl)-25-fluoro-6,15-dioxo-10,22-dioxa-4-thia-7,16-diazatetracyclo[21.3.1.1$^{2,5}$.0$^{16,20}$] octacosa-1(27),2,5(28),23,25-pentaen-18-yl]carbamate |
| Ex. 247 | $NH_2$ | 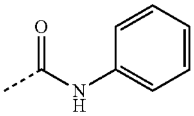 | (8S,18S,20S)-18-amino-25-fluoro-6,15-dioxo-N-phenyl-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 248 | 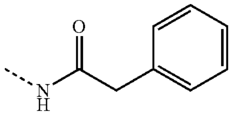 | $CO_2CH_3$ | methyl (8S,18S,20S)-25-fluoro-6,15-dioxo-18-[(2-phenylacetyl) amino]-10,22-dioxa-4-thia-7,16-diazatetracyclo[21.3.1.1$^{2,5}$.0$^{16,20}$] octacosa-1(27),2,5(28),23,25-pentaene-8-carboxylate |
| Ex. 249 | 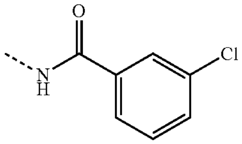 | $CO_2H$ | (8S,18S,20S)-18-[(3-chlorobenzoyl)amino]-25-fluoro-6,15-dioxo-10,22-dioxa-4-thia-7,16-diazatetracyclo [21.3.1.1$^{2,5}$.0$^{16,20}$]octacosa-1(27),2,5(28),23,25-pentaene-8-carboxylic acid |
| Ex. 250 | 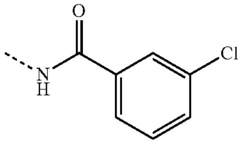 | $CO_2CH_3$ | methyl (8S,18S,20S)-18-[(3-chlorobenzoyl)amino]-25-fluoro-6,15-dioxo-10,22-dioxa-4-thia-7,16-diazatetracyclo [21.3.1.1$^{2,5}$.0$^{16,20}$]octacosa-1(27),2,5(28),23,25-pentaene-8-carboxylate |
| Ex. 251 | 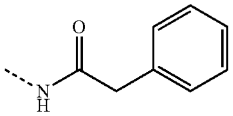 | $CO_2H$ | (8S,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$] octacosa-1(27),2,5(28),23,25-pentaene-8-carboxylic acid |
| Ex. 252 | 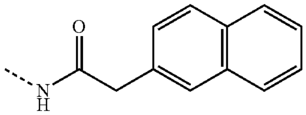 | $CO_2H$ | (8S,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$] octacosa-1(27),2,5(28),23,25-pentaene-8-carboxylic acid |
| Ex. 253 | 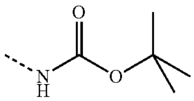 | 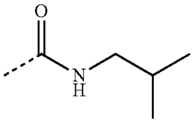 | tert-butyl N-[(8S,18S,20S)-25-fluoro-8-[(isobutylamino) carbonyl]-6,15-dioxo-10,22-dioxa-4-thia-7,16-diazatetracyclo [21.3.1.1$^{2,5}$.0$^{16,20}$]octacosa-1(27),2,5(28),23,25-pentaen-18-yl]carbamate |

TABLE 27c-continued

| No | $R^B$ | $R^E$ | IUPAC name |
|---|---|---|---|
| Examples of Core 15 (Ex. 242-Ex. 261;) | | | |
| Ex. 254 | $NH_2$ | 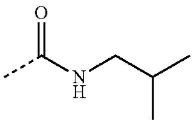 | (8S,18S,20S)-18-amino-25-fluoro-N-isobutyl-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide |
| Ex. 255 | 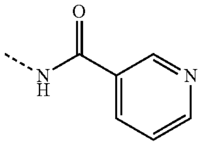 | 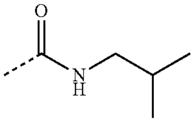 | (8S,18S,20S)-25-fluoro-N-isobutyl-6,15-dioxo-18-[(3-pyridinyl-carbonyl)amino]-10,22-dioxa-4-thia-7,16-diazatetracyclo [21.3.1.1$^{2,5}$.0$^{16,20}$]octacosa-1(27),2,5(28),23,25-pentaene-8-carboxamide |
| Ex. 256 | 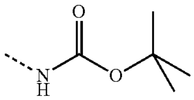 | 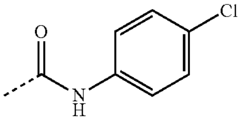 | tert-butyl N-[(8S,18S,20S)-8-[(4-chloroanilino)carbonyl]-25-fluoro-6,15-dioxo-10,22-dioxa-4-thia-7,16-diazatetracyclo [21.3.1.1$^{2,5}$.0$^{16,20}$]octacosa-1(27),2,5(28),23,25-pentaen-18-yl]carbamate |
| Ex. 257 | $NH_2$ | 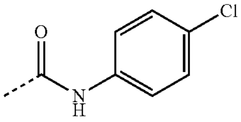 | (8S,18S,20S)-18-amino-N-(4-chlorophenyl)-25-fluoro-6,15-dioxo-10,22-dioxa-4-thia-7,16-diazatetracyclo[21.3.1.1$^{2,5}$.0$^{16,20}$] octacosa-1(27),2,5(28),23,25-pentaene-8-carboxamide |
| Ex. 258 | 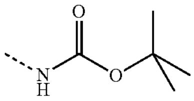 | 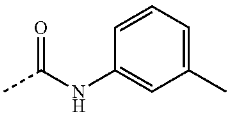 | tert-butyl N-[(8S,18S,20S)-25-fluoro-6,15-dioxo-8-(3-toluidino-carbonyl)-10,22-dioxa-4-thia-7,16-diazatetracyclo [21.3.1.1$^{2,5}$.0$^{16,20}$]octacosa-1(27),2,5(28),23,25-pentaen-18-yl]carbamate |
| Ex. 259 | $NH_2$ | 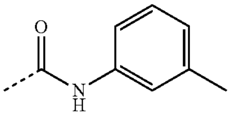 | (8S,18S,20S)-18-amino-25-fluoro-N-(3-methylphenyl)-6,15-dioxo-10,22-dioxa-4-thia-7,16-diazatetracyclo[21.3.1.1$^{2,5}$.0$^{16,20}$] octacosa-1(27),2,5(28),23,25-pentaene-8-carboxamide |
| Ex. 260 | 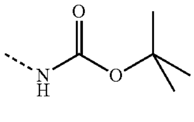 | 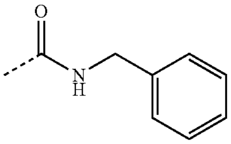 | tert-butyl N-[(8S,18S,20S)-8-[(benzylamino)carbonyl]-25-fluoro-6,15-dioxo-10,22-dioxa-4-thia-7,16-diazatetracyclo [21.3.1.1$^{2,5}$.0$^{16,20}$]octacosa-1(27),2,5(28),23,25-pentaen-18-yl]carbamate |
| Ex. 261 | $NH_2$ | 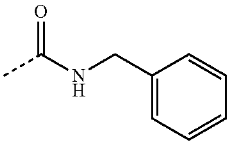 | (8S,18S,20S)-18-amino-N-benzyl-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide |

TABLE 28a

| No | $R^A$ | $R^F$ | Starting Material | General Proced. | Reagent | Purification Method | Yield (isolated salt) |
|---|---|---|---|---|---|---|---|
| Examples of Core 16 (Ex. 262-Ex. 283;) | | | | | | | |
| Ex. 262-Ex. 264: | | | cf. experimental description | | | | |
| Ex. 265 | 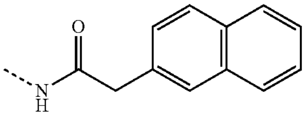 | H | Ex. 263 | 1) | 2-Naphthaleneacetyl chloride | FC ($CH_2Cl_2$/i-PrOH) | 78% |

TABLE 28a-continued

Examples of Core 16 (Ex. 262-Ex. 283;)

| No | $R^A$ | $R^F$ | Starting Material | General Proced. | Reagent | Purification Method | Yield (isolated salt) |
|---|---|---|---|---|---|---|---|
| Ex. 266 | 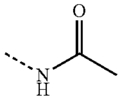 | 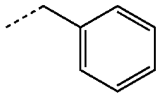 | Ex. 264 | A.1.2 | Acetic anhydride (1.3 equiv.) | prep. HPLC method 1a | 58% (TFA salt) |
| Ex. 267 | 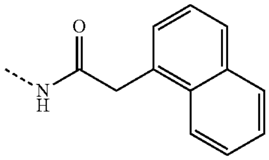 | H | Ex. 263 | 2) | 1-Naphthaleneacetyl chloride | prep. HPLC method 3 | 58% |
| Ex. 268 | 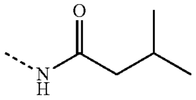 | H | Ex. 263 | A.1.2 | Isovaleryl chloride (1.6 equiv.) 0° C. to rt, 16 h | prep. HPLC method 3 | 69% |
| Ex. 269 | 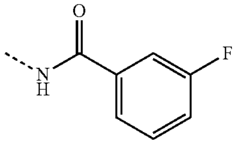 | H | Ex. 263 | A.1.2 | 3-Fluorobenzoyl chloride (1.1 equiv.) | prep. HPLC method 3 | 52% |
| Ex. 270 | 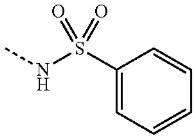 | H | Ex. 263 | A.5 | Benzenesulfonyl chloride | prep. HPLC method 3 | 49% |
| Ex. 271 | 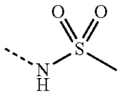 | H | Ex. 263 | A.5 | Methanesulfonyl chloride | prep. HPLC method 3 | 39% |
| Ex. 272 | 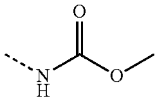 | H | Ex. 263 | A.4 | Methyl chloroformate | prep. HPLC method 3 | 69% |
| Ex. 273 | 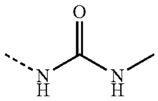 | H | Ex. 263 | A.3 | N-Succinimidyl N-methylcarbamate | prep. HPLC method 3 | 65% |
| Ex. 274 | 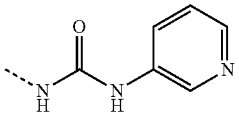 | H | Ex. 263 | A.3 | 2,5-Dioxopyrrolidin-1-ylpyridin-3-ylcarbamate 0° C. to rt, 1 h | prep. HPLC method 3 | 64% |
| Ex. 275 | 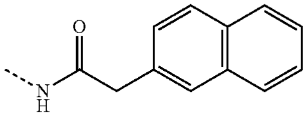 | $CH_3$ | Ex. 265 | 1) | Trimethyloxonium tetrafluoroborate | prep. HPLC method 1a | 12% |
| Ex. 276 | 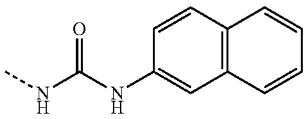 | H | Ex. 263 | 1) | 2-Naphthylisocyanate | prep. HPLC method 3 | 71% |

TABLE 28a-continued

Examples of Core 16 (Ex. 262-Ex. 283;)

| No | $R^A$ | $R^F$ | Starting Material | General Proced. | Reagent | Purification Method | Yield (isolated salt) |
|---|---|---|---|---|---|---|---|
| Ex. 277 | 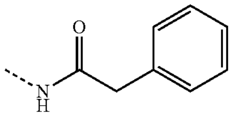 | H | Ex. 263 | A.1.1 | Phenylacetic acid | prep. HPLC method 3 | 58% |
| Ex. 278 | 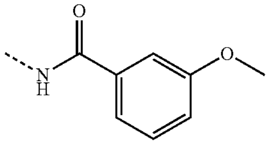 | H | Ex. 263 | A.1.2 | m-Anisoyl chloride (1.1 equiv.) | prep. HPLC method 3 | 75% |
| Ex. 279 | 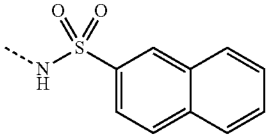 | H | Ex. 263 | A.5 | 2-Naphthalenesulfonyl chloride | prep. HPLC method 3 | 76% |
| Ex. 280 | 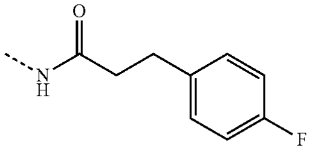 | H | Ex. 263 | A.1.1 | 3-(4-Fluorophenyl) propionic acid | prep. HPLC method 3 | 42% |
| Ex. 281 | 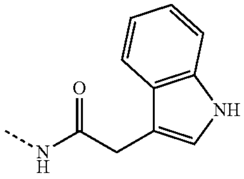 | H | Ex. 263 | A.1.1 | 1H-indole-3-acetic acid | prep. HPLC method 3 and prep. HPLC method 2a | 38% |
| Ex. 282 | 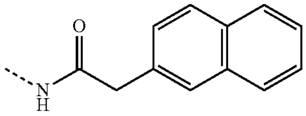 | H | Ex. 263 | A.6.4 | 2-Naphthylacetaldehyde (1.3 equiv.) | prep. HPLC method 2a | 26% |
| Ex. 283 | 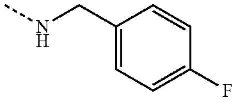 | H | Ex. 263 | A.6.4 | 4-Fluorobenzaldehyde | prep. HPLC method 3 | 52% |

1) Cf. experimental description for detailed procedure

2) Ex. 267 was prepared applying the protocol described for the synthesis of Ex. 265.

TABLE 28b

Examples of Core 16 (Ex. 262-Ex. 283;)

| No | $R^A$ | $R^F$ | Formula | Monoisotopic Mass | Rt (purity at 220 nm) | $[M + H]^+$ found | LC-MS-Method |
|---|---|---|---|---|---|---|---|
| Ex. 262-Ex. 264: | | cf. experimental description | | | | | |
| Ex. 265 | 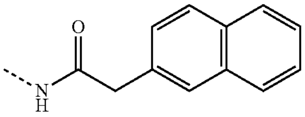 | H | C31H33N5O5S | 587.2 | 1.86 (93) | 587.9 | method 1a |

TABLE 28b-continued
| Examples of Core 16 (Ex. 262-Ex. 283;) | | | | | | | |
|---|---|---|---|---|---|---|---|
| No | $R^A$ | $R^F$ | Formula | Mono-isotopic Mass | Rt (purity at 220 nm) | $[M + H]^+$ found | LC-MS-Method |
| Ex. 266 | 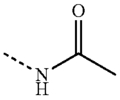 | 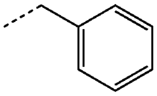 | C28H33N5O5S | 551.2 | 1.86 (96) | 552.2 | method 1d |
| Ex. 267 | 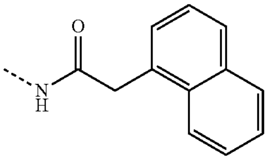 | H | C31H33N5O5S | 587.2 | 1.85 (87) | 588.0 | method 1a |
| Ex. 268 | 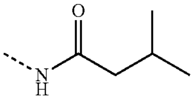 | H | C24H33N5O5S | 503.2 | 1.54 (98) | 504.2 | method 1a |
| Ex. 269 | 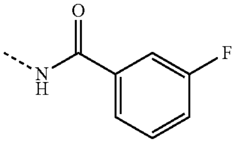 | H | C26H28FN5O5S | 541.2 | 1.66 (98) | 542.1 | method 1a |
| Ex. 270 | 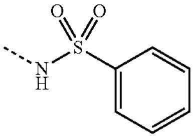 | H | C25H29N5O6S2 | 559.2 | 1.58 (97) | 560.0 | method 1a |
| Ex. 271 | 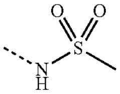 | H | C2OH27N5O6S2 | 497.1 | 1.30 (98) | 498.0 | method 1a |
| Ex. 272 | 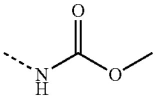 | H | C21H27N5O6S | 477.2 | 1.34 (99) | 478.1 | method 1a |
| Ex. 273 | 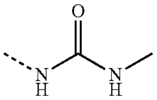 | H | C21H28N6O5S | 476.2 | 1.23 (97) | 476.9 | method 1a |
| Ex. 274 | 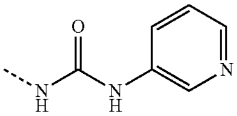 | H | C25H29N7O5S | 539.2 | 1.19 (99) | 540.0 | method 1a |
| Ex. 275 | 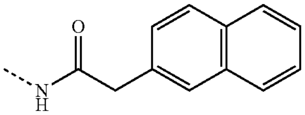 | $CH_3$ | C32H35N5O5S | 601.2 | 2.05 (97) | 602.2 | method 1d |
| Ex. 276 | 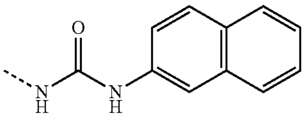 | H | C30H32N6O5S | 588.2 | 1.86 (99) | 589.0 | method 1a |

TABLE 28b-continued

| Examples of Core 16 (Ex. 262-Ex. 283;) | | | | | | | |
|---|---|---|---|---|---|---|---|
| No | $R^A$ | $R^F$ | Formula | Mono-isotopic Mass | Rt (purity at 220 nm) | [M + H]$^+$ found | LC-MS-Method |
| Ex. 277 | 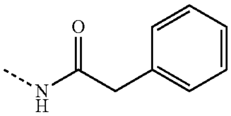 | H | C27H31N5O5S | 537.2 | 1.62 (96) | 538.2 | method 1a |
| Ex. 278 | 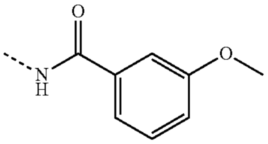 | H | C27H31N5O6S | 553.2 | 1.65 (96) | 554.1 | method 1a |
| Ex. 279 | 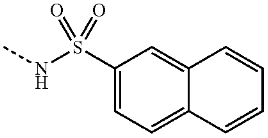 | H | C29H31N5O6S2 | 609.2 | 1.82 (96) | 610.1 | method 1a |
| Ex. 280 | 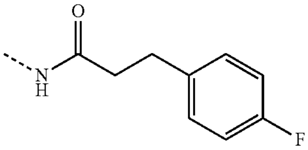 | H | C28H32FN5O5S | 569.2 | 1.72 (92) | 570.2 | method 1a |
| Ex. 281 | 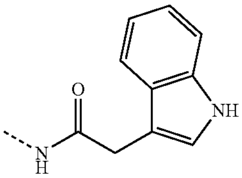 | H | C29H32N6O5S | 576.2 | 1.61 (78) | 577.1 | method 1a |
| Ex. 282 | 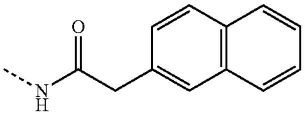 | H | C31H35N5O4S | 573.2 | 1.63 (89) | 574.2 | method 1d |
| Ex. 283 | 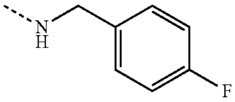 | H | C26H30FN5O4S | 527.2 | 1.37 (97) | 528.2 | method 1a |

TABLE 28c

| Examples of Core 16 (Ex. 262-Ex. 283;) | | | |
|---|---|---|---|
| No | $R^A$ | $R^F$ | IUPAC name |
| Ex. 262 | 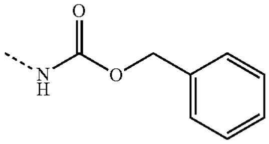 | 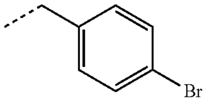 | benzyl N-[(9S,11S,15S)-11-[(4-bromobenzyl)oxy]-18,21-dimethyl-14,19-dioxo-7-oxa-3-thia-13,18,21,22-tetraazatetracyclo [18.2.1.0$^{2,6}$.0$^{9,13}$]tricosa-1(22),2(6),4,20(23)-tetraen-15-yl]carbamate |
| Ex. 263 | $NH_2$ | H | (9S,11S,15S)-15-amino-11-hydroxy-18,21-dimethyl-7-oxa-3-thia-13,18,21,22-tetraazatetracyclo[18.2.1.0$^{2,6}$.0$^{9,13}$]tricosa-1(22),2(6),4,20(23)-tetraene-14,19-dione |

TABLE 28c-continued

Examples of Core 16 (Ex. 262-Ex. 283;)

| No | $R^A$ | $R^F$ | IUPAC name |
|---|---|---|---|
| Ex. 264 | $NH_2$ | 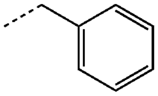 | (9S,11S,15S)-15-amino-11-(benzyloxy)-18,21-dimethyl-7-oxa-3-thia-13,18,21,22-tetraazatetracyclo[18.2.1.$0^{2,6}$.$0^{9,13}$]tricosa-1(22),2(6),4,20(23)-tetraene-14,19-dione |
| Ex. 265 | 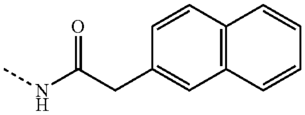 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-2-(2-naphthyl)acetamide |
| Ex. 266 | 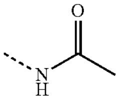 | 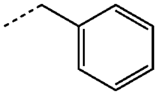 | N-[(9S,11S,15S)-11-(benzyloxy)-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]acetamide |
| Ex. 267 | 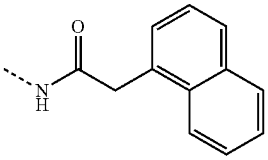 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-2-(1-naphthyl)acetamide |
| Ex. 268 | 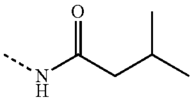 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-3-methylbutanamide |
| Ex. 269 | 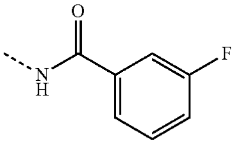 | H | 3-fluoro-N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]benzamide |
| Ex. 270 | 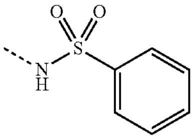 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]benzenesulfonamide |
| Ex. 271 | 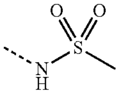 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]methanesulfonamide |
| Ex. 272 | 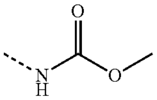 | H | methyl N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]carbamate |
| Ex. 273 | 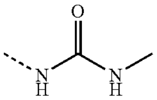 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-N-methylurea |
| Ex. 274 | 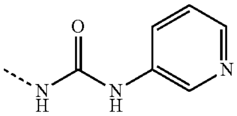 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4 ,20(23)-tetraen-15-yl]-N-(3-pyridinyl)urea |
| Ex. 275 | 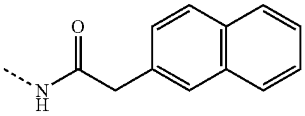 | $CH_3$ | N-[(9S,11S,15S)-11-methoxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-2-(2-naphthyl)acetamide |

TABLE 28c-continued

Examples of Core 16 (Ex. 262-Ex. 283;)

| No | $R^A$ | $R^F$ | IUPAC name |
|---|---|---|---|
| Ex. 276 | 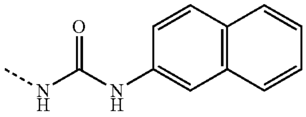 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-N-(2-naphthyl)urea |
| Ex. 277 | 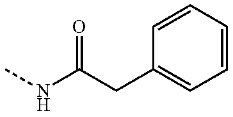 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-2-phenylacetamide |
| Ex. 278 | 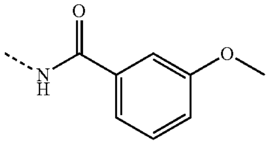 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-3-methoxybenzamide |
| Ex. 279 | 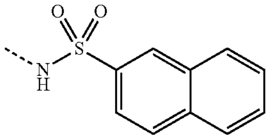 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-2-naphthalenesulfonamide |
| Ex. 280 | 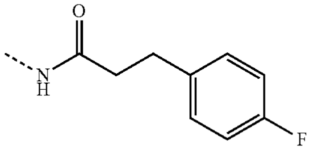 | H | 3-(4-fluorophenyl)-N-[(9S,11S,15S)-11-hydroxy-18,21-dimethyl-14,19-dioxo-7-oxa-3-thia-13,18,21,22-tetraazatetracyclo [18.2.1.$0^{2,6}$.$0^{9,13}$]tricosa-1(22),2(6),4,20(23)-tetraen-15-yl]propanamide |
| Ex. 281 | 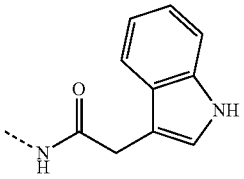 | H | N-[(9S,11S,15S)-11-hydroxy-18,21-dimethyl-14,19-dioxo-7-oxa-3-thia-13,18,21,22-tetraazatetracyclo[18.2.1.$0^{2,6}$.$0^{9,13}$]tricosa-1(22),2(6),4,20(23)-tetraen-15-yl]-2-(1H-indol-3-yl)acetamide |
| Ex. 282 | 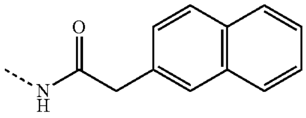 | H | (9S,11S,15S)-11-hydroxy-18,21-dimethyl-15-{[2-(2-naphthyl)ethyl] amino}-7-oxa-3-thia-13,18,21,22-tetraazatetracyclo[18.2.1.$0^{2,6}$.$0^{9,13}$] tricosa-1(22),2(6),4,20(23)-tetraene-14,19-dione |
| Ex. 283 | 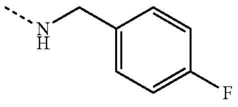 | H | (9S,11S,15S)-15-[(4-fluorobenzyl)amino]-11-hydroxy-18,21-dimethyl-7-oxa-3-thia-13,18,21,22-tetraazatetracyclo [18.2.1.$0^{2,6}$.$0^{9,13}$]tricosa-1(22),2(6),4,20(23)-tetraene-14,19-dione |

TABLE 29a

Examples of Core 17 (Ex.284a-Ex.304; continued on the following pages)

| No | $R^A$ | $R^G$ | Starting Material | General Proced. | Reagent | Purification Method | Yield (isolated salt) |
|---|---|---|---|---|---|---|---|
| Ex. 284a-Ex. 286: cf. experimental description | | | | | | | |
| Ex. 287 | 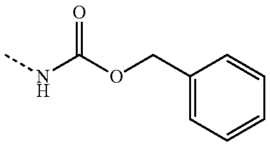 | 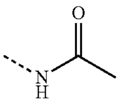 | Ex. 286 | 1) | Acetyl chloride | FC (hexane, EtOAc, MeOH) | 77% |

TABLE 29a-continued

Examples of Core 17 (Ex.284a-Ex.304; continued on the following pages)

| No | $R^A$ | $R^G$ | Starting Material | General Proced. | Reagent | Purification Method | Yield (isolated salt) |
|---|---|---|---|---|---|---|---|
| Ex. 288 | $NH_2$ | 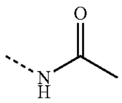 | Ex 287 | B.3 | $H_2$, $Pd(OH)_2$—C, MeOH | crude product | 78% |
| Ex. 289 | 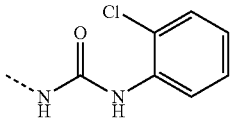 | $NO_2$ | Ex. 285 | A.3 | 1-Chloro-2-isocyanatobenzene | FC (hexane, EtOAc, MeOH) | 90% |
| Ex. 290 | 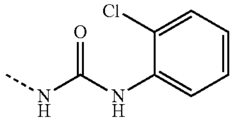 | $NH_2$ | Ex. 289 | B.4 | $H_2$, $PtO_2$ | crude product | 96% |
| Ex. 291 | 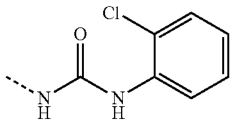 | 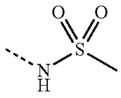 | Ex. 290 | A.5 | Methanesulfonyl chloride (1.2 equiv.) | prep. HPLC method 1a | 49% (TFA salt) |
| Ex. 292 | 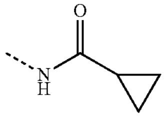 | $NO_2$ | Ex. 285 | A.1.1 | Cyclopropanecarboxylic acid, 0° C., 2 h Workup: EtOAc, 1M aq. HCl soln, sat. aq. $NaHCO_3$ soln, sat. aq. NaCl soln | FC (hexane, EtOAc, MeOH) | 70% |
| Ex. 293 | 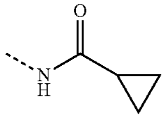 | $NH_2$ | Ex. 292 | B.4 | H2, PtO2 | crude product | 95% |
| Ex. 294 | 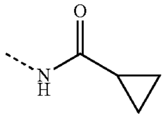 | 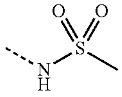 | Ex. 293 | A.5 | Methanesulfonyl chloride (1.2 equiv.) | prep. HPLC method 1a | 45% |
| Ex. 295 | $NH_2$ | 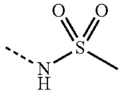 | Ex. 296 | B.3 | $H_2$, $Pd(OH)_2$—C, MeOH | crude product | 86% |
| Ex. 296 | 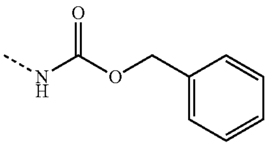 | 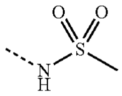 | Ex. 286 | A.5 | Methanesulfonyl chloride (1.2 equiv.) | FC (hexane/ EtOAc) and prep. HPLC method 3 | 54% |
| Ex. 297 | 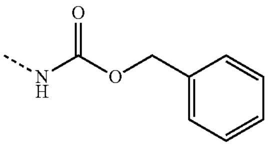 | 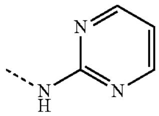 | Ex. 286 | 2) | 2-Chloropyrimidine | FC (EtOAc) | 38% |
| Ex. 298 | $NH_2$ | 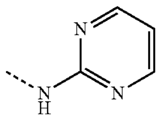 | Ex. 297 | B.3 | $H_2$, $Pd(OH)_2$—C, MeOH | crude product | 100% |

TABLE 29a-continued

Examples of Core 17 (Ex.284a-Ex.304; continued on the following pages)

| No | $R^A$ | $R^G$ | Starting Material | General Proced. | Reagent | Purification Method | Yield (isolated salt) |
|---|---|---|---|---|---|---|---|
| Ex. 299 | 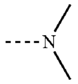 | 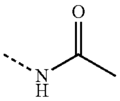 | Ex. 288 | A.6.1 | Formaldehyde (36.5% in $H_2O$) | prep. HPLC method 1a | 50% (TFA salt) |
| Ex. 300 | 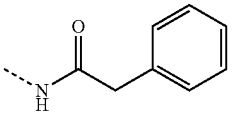 | 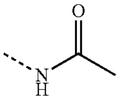 | Ex. 288 | A.1.1 | 2-Phenylacetic acid (2.2 equiv.) HATU (2.5 equiv.) HOAt (2.5 equiv.) i-$Pr_2$NEt (6 equiv.) Workup: EtOAc, 1M aq. HCl soln, sat. aq. $Na_2CO_3$ soln | prep. HPLC method 1a | 17% (TFA salt) |
| Ex. 301 | 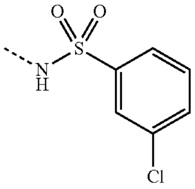 | 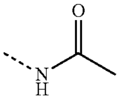 | Ex. 288 | A.5 | 3-Chlorobenzene-sulfonyl chloride | prep. HPLC method 1a | 60% (TFA salt) |
| Ex. 302 | 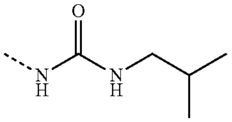 | 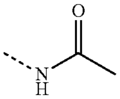 | Ex. 288 | A.3 | 2.5-dioxopyrrolidin-1-yl isobutylcarbamate | prep. HPLC method 1a | 70% (TFA salt) |
| Ex. 303 | 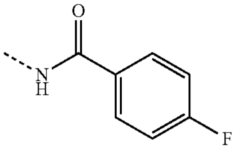 | 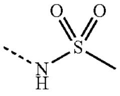 | Ex. 295 | A.1.1 | 4-Fluorobenzoic acid (2.2 equiv.) HATU (2.5 equiv.) HOAt (2.5 equiv.) i-$Pr_2$NEt (6 equiv.) Workup: EtOAc, 1M aq. HCl soln, sat. aq. $Na_2CO_3$soln, $H_2O$ | prep. HPLC method 1a | 11% (TFA salt) |
| Ex. 304 | 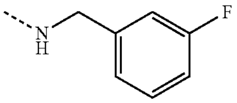 | 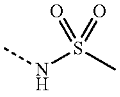 | Ex. 295 | A.6.4 | 3-Fluorobenzaldehyde | prep. HPLC method 1a | 55% (TFA salt) |

1) Acetyl chloride (0.109 mL, 1.5 mmol) was added at 0° C. to a soln of Ex. 286 (450 mg, 0.77 mmol) and i-$Pr_2$NEt (0.394 mL, 2.3 mmol) in $CH_2Cl_2$ (16 mL). The soln was stirred at 0° C. to rt for 2.5 h. MeOH (0.1 mL) was added and stirring continued for 10 min, followed by evaporation of the volatiles and FC (hexane/EtOAc/MeOH gradient) to afford Ex. 287 (371 mg, 77%).

2) A soln of Ex. 286 (115 mg, 0.196 mmol), 2-chloropyrimidine (27 mg, 0.235 mmol) and pTsOH·$H_2O$ (45 mg, 0.235 mmol) in dioxane (3 mL) was heated to reflux for 8 h. More 2-chloropyrimidine (13 mg, 0.118 mmol) and pTsOH·$H_2O$ (22 mg, 0.118 mmol) were added and refluxing was continued for 6 h. The volatiles were evaporated. Aqueous workup ($CH_2Cl_2$, sat. aq. $NaHCO_3$ soln; $Na_2SO_4$) and FC (EtOAc) afforded Ex. 297 (50 mg, 38%).

TABLE 29b

Examples of Core 17 (Ex. 284a-Ex. 304; continued on the following page)

| No | $R^A$ | $R^G$ | Formula | Monoisotopic Mass | Rt (purity at 220 nm) | $[M + H]^+$ found | LC-MS-Method |
|---|---|---|---|---|---|---|---|
| Ex. 284a-Ex. 286: cf. experimental description | | | | | | | |
| Ex. 287 | 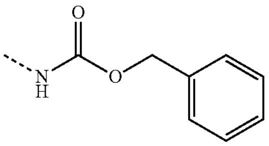 | 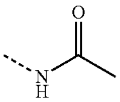 | C34H40N6O6 | 628.3 | 1.89 (97) | 629.3 | method 1a |
| Ex. 288 | $NH_2$ | 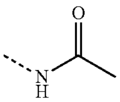 | C26H34N6O4 | 494.3 | 1.20 (92) | 495.3 | method 1a |

TABLE 29b-continued

| Examples of Core 17 (Ex. 284a-Ex. 304; continued on the following page) | | | | | | | |
|---|---|---|---|---|---|---|---|
| No | $R^A$ | $R^G$ | Formula | Monoisotopic Mass | Rt (purity at 220 nm) | $[M + H]^+$ found | LC-MS-Method |
| Ex. 289 | 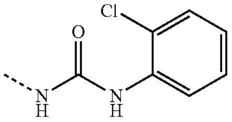 | $NO_2$ | C31H34ClN7O6 | 635.2 | 2.26 (98) | 636.2 | method 1d |
| Ex. 290 | 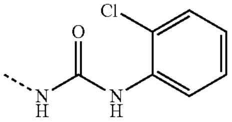 | $NH_2$ | C31H36ClN7O4 | 605.3 | 1.66 (95) | 606.2 | method 1a |
| Ex. 291 | 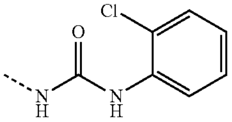 | 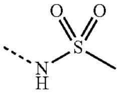 | C32H38ClN7O6S | 683.2 | 1.98 (99) | 684.3 | method 1d |
| Ex. 292 | 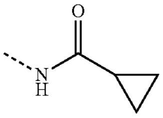 | $NO_2$ | C28H34N6O6 | 550.3 | 1.87 (96) | 551.2 | method 1a |
| Ex. 293 | 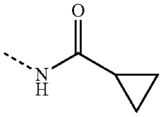 | $NH_2$ | C28H36N6O4 | 520.3 | 1.32 (99) | 521.3 | method 1a |
| Ex. 294 | 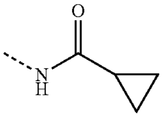 | 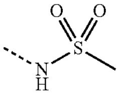 | C29H38N6O6S | 598.3 | 1.60 (99) | 599.3 | method 1d |
| Ex. 295 | $NH_2$ | 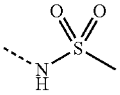 | C25H34N6O5S | 530.2 | 1.24 (90) | 531.2 | method 1a |
| Ex. 296 | 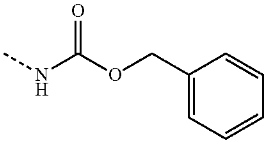 | 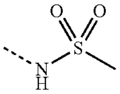 | C33H40N6O7S | 664.3 | 1.97 (91) | 665.3 | method 1a |
| Ex. 297 | 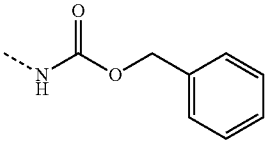 | 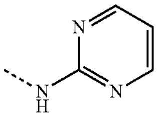 | C36H40N8O5 | 664.3 | 1.96 (86) | 665.4 | method 1d |
| Ex. 298 | $NH_2$ | 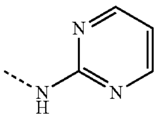 | C28H34N8O3 | 530.3 | 1.31 (87) | 531.3 | method 1d |
| Ex. 299 | 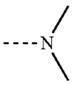 | 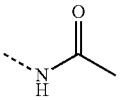 | C28H38N6O4 | 522.3 | 1.33 (100) | 523.3 | method 1d |

TABLE 29b-continued

Examples of Core 17 (Ex. 284a-Ex. 304; continued on the following page)

| No | $R^A$ | $R^G$ | Formula | Monoisotopic Mass | Rt (purity at 220 nm) | $[M + H]^+$ found | LC-MS-Method |
|---|---|---|---|---|---|---|---|
| Ex. 300 | 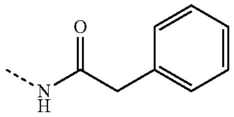 | 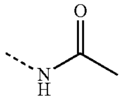 | C34H40N6O5 | 612.3 | 1.82 (97) | 613.3 | method 1d |
| Ex. 301 | 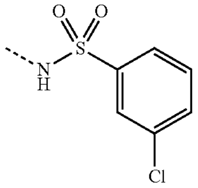 | 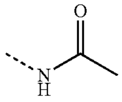 | C32H37ClN6O6S | 668.2 | 2.03 (96) | 669.3 | method 1d |
| Ex. 302 | 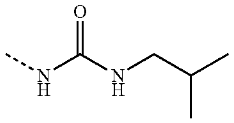 | 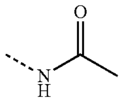 | C31H43N7O5 | 593.3 | 1.24 (94) | 594.0 | method 3b |
| Ex. 303 | 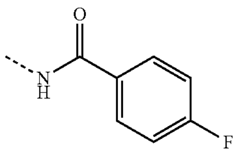 | 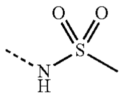 | C32H37FN6O6S | 652.2 | 1.95 (97) | 653.3 | method 1d |
| Ex. 304 | 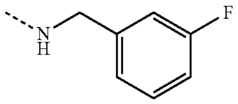 | 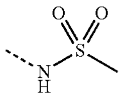 | C32H39FN6O5S | 638.3 | 1.51 (97) | 639.3 | method 1d |

TABLE 29c

Examples of Core 17 (Ex. 284a-Ex. 304; continued on the following pages)

| No | $R^A$ | $R^G$ | IUPAC name |
|---|---|---|---|
| Ex. 284a | 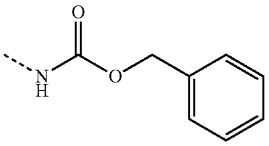 | $NO_2$ | benzyl N-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex.284b | 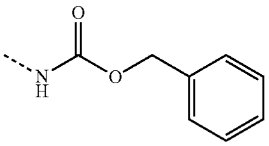 | $NO_2$ | benzyl N-[(13R,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 285 | $NH_2$ | $NO_2$ | (13S,19S)-13-amino-4,8-dimethyl-23-nitro-21-oxa-3,8,15,27-tetraazatetracyclo[20.2.2.1$^{2,6}$.0$^{15,19}$]heptacosa-1(24),2(27),3,5,22,25-hexaene-7,14-dione |
| Ex. 286 | 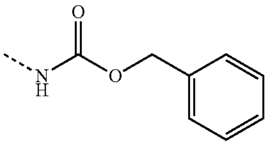 | $NH_2$ | benzyl N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |

TABLE 29c-continued

Examples of Core 17 (Ex. 284a-Ex. 304; continued on the following pages)

| No | $R^A$ | $R^G$ | IUPAC name |
| --- | --- | --- | --- |
| Ex. 287 | 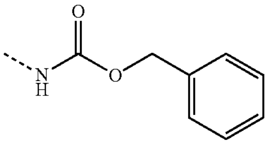 | 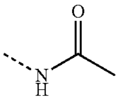 | benzyl N-[(13S,19S)-23-(acetylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 288 | $NH_2$ | 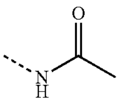 | N-[(13S,19S)-13-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 289 | 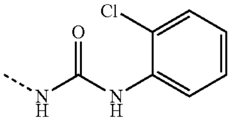 | $NO_2$ | N-(2-chlorophenyl)-N'-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]urea |
| Ex. 290 | 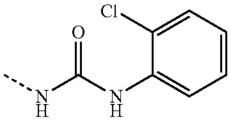 | $NH_2$ | N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-N'-(2-chlorophenyl)urea |
| Ex. 291 | 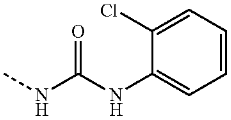 | 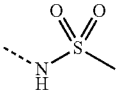 | N-[(13S,19S)-13-{[(2-chloroanilino)carbonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide |
| Ex. 292 | 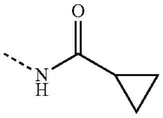 | $NO_2$ | N-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide |
| Ex. 293 | 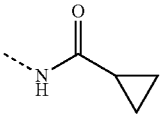 | $NH_2$ | N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide |
| Ex. 294 | 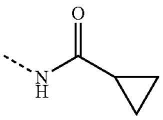 | 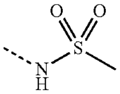 | N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide |
| Ex. 295 | $NH_2$ | 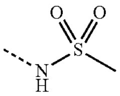 | N-[(13S,19S)-13-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide |
| Ex. 296 | 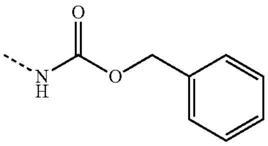 | 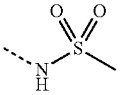 | benzyl N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate |
| Ex. 297 | 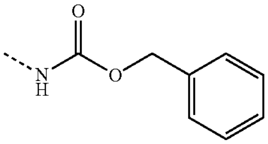 | 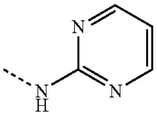 | benzyl N-[(13S,19S)-4,8-dimethyl-7,14-dioxo-23-(2-pyrimidinylamino)-21-oxa-3,8,15,27-tetraazatetracyclo[20.2.2.1$^{2,6}$.0$^{15,19}$]heptacosa-1(24),2(27),3,5,22,25-hexaen-13-yl]carbamate |

TABLE 29c-continued

Examples of Core 17 (Ex. 284a-Ex. 304; continued on the following pages)

| No | $R^A$ | $R^G$ | IUPAC name |
|---|---|---|---|
| Ex. 298 | $NH_2$ | 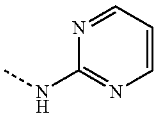 | (13S,19S)-13-amino-4,8-dimethyl-23-(2-pyrimidinylamino)-21-oxa-3,8,15,27-tetraazatetracyclo[20.2.2.1$^{2,6}$.0$^{15,19}$]heptacosa-1(24),2(27),3,5,22,25-hexaene-7,14-dione |
| Ex. 299 | 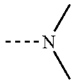 | 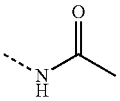 | N-[(13S,19S)-13-(dimethylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 300 | 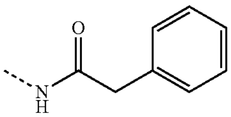 | 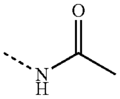 | N-[(13S,19S)-23-(acetylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-2-phenylacetamide |
| Ex. 301 | 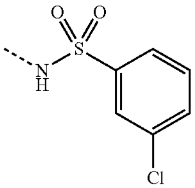 | 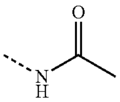 | N-[(13S,19S)-13-{[(3-chlorophenyl)sulfonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide |
| Ex. 302 | 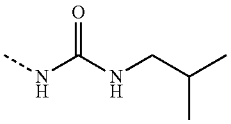 | 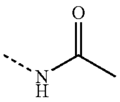 | N-[(13S,19S)-13-{[(isobutylamino)carbonyl]amino}-4,8-dimethyl-7,14-dioxo-21-oxa-3,8,15,27-tetraazatetracyclo[20.2.2.1$^{2,6}$0$^{15,19}$]heptacosa-1(24),2(27),3,5,22,25-hexaen-23-yl]acetamide |
| Ex. 303 | 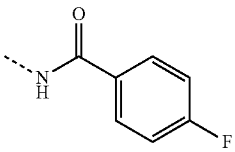 | 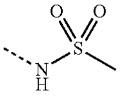 | N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-4-fluorobenzamide |
| Ex. 304 | 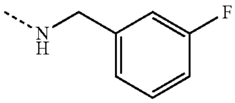 | 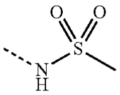 | N-[(13S,19S)-13-[(3-fluorobenzyl)amino]-4-8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide |

TABLE 30a

Examples of Core 18 (Ex. 305-Ex. 326; continued on the following pages)

| No | $R^B$ | Starting Material | General Proced. | Reagent | Purification Method | Yield (isolated salt) |
|---|---|---|---|---|---|---|
| Ex. 305-Ex. 306: cf. experimental description | | | | | | |
| Ex. 307 | $N(CH_3)_2$ | Ex. 306 | A.6.1 | Formaldehyde (36.5% in $H_2O$) | prep. HPLC method 2a | 72% |
| Ex. 308 | 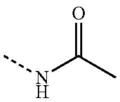 | Ex. 306 | A.1.2 | Acetyl chloride (2.0 equiv.) | prep. HPLC method 3 | 71% |
| Ex. 309 | 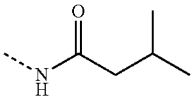 | Ex. 306 | A.1.1 | 3-Methylbutanoic acid | prep. HPLC method 3 | 65% |

TABLE 30a-continued

Examples of Core 18 (Ex. 305-Ex. 326; continued on the following pages)

| No | $R^B$ | Starting Material | General Proced. | Reagent | Purification Method | Yield (isolated salt) |
|---|---|---|---|---|---|---|
| Ex. 310 | 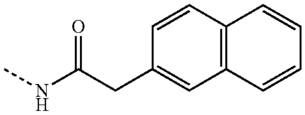 | Ex. 306 | A.1.1 | 2-Naphthaleneacetic acid | prep. HPLC method 3 | 56% |
| Ex. 311 | 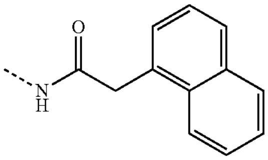 | Ex. 306 | A.1.1 | 1-Naphthaleneacetic acid | prep. HPLC method 3 | 70% |
| Ex. 312 | 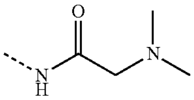 | Ex. 306 | A.1.3 | 2-(Dimethylamino) acetic | prep. HPLC method 2a | 56% |
| Ex. 313 | 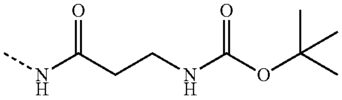 | Ex. 306 | A.1.1 | N-Boc-β-alanine | FC (hexane/ EtOAc/MeOH) | 80% |
| Ex. 314 | 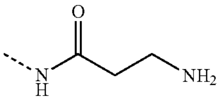 | Ex. 313 | B.1 | HCl-dioxane | prep. HPLC method 2a | 43% |
| Ex. 315 | 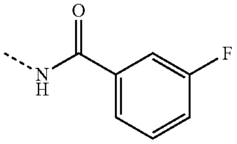 | Ex. 306 | A.1.1 | 3-Fluorobenzoic acid | prep. HPLC method 3 | 43% |
| Ex. 316 | 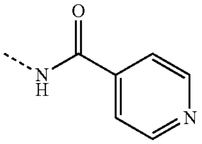 | Ex. 306 | A.1.2 | Isonicotinoyl chloride hydrochloride (2.5 equiv.) Pyridine (6.5 equiv.) | prep. HPLC method 2a | 58% |
| Ex. 317 | 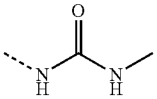 | Ex. 306 | A.3 | N-Succinimidyl N-methylcarbamate | prep. HPLC method 3 | 67% |
| Ex. 318 | 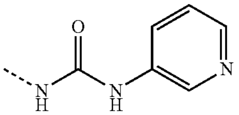 | Ex. 306 | A.4 | 2,5-Dioxopyrrolidin-1-yl pyridin-3-ylcarbamate | prep. HPLC method 3 | 62% |
| Ex. 319 | 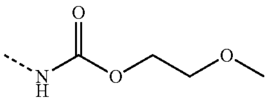 | Ex. 306 | A.4 | 2-Methoxyethyl chloro-formate | prep. HPLC method 3 | 70% |
| Ex. 320 | 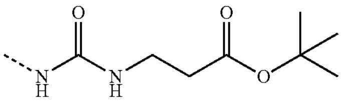 | Ex. 306 | A.3 | tert-Butyl 3-((2,5-dioxopyrrolidin-1-yloxy)carbonylamino) propanoate | FC (hexane/ EtOAc/MeOH) | 82% |
| Ex. 321 | 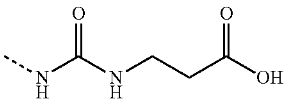 | Ex. 320 | [1)] | HCl-dioxane | crude product | 83% |

TABLE 30a-continued

| Examples of Core 18 (Ex. 305-Ex. 326; continued on the following pages) | | | | | | |
|---|---|---|---|---|---|---|
| No | $R^B$ | Starting Material | General Proced. | Reagent | Purification Method | Yield (isolated salt) |
| Ex. 322 | 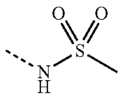 | Ex. 306 | A.5 | Methanesulfonyl chloride | prep. HPLC method 3 | 75% |
| Ex. 323 | 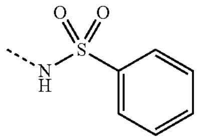 | Ex. 306 | A.5 | Benzenesulfonyl chloride | prep. HPLC method 3 | 61% |
| Ex. 324 | 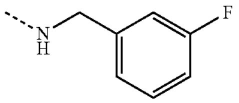 | Ex. 306 | A.6.4 | 3-Fluorobenzaldehyde | prep. HPLC method 3 | 69% |
| Ex. 325 | 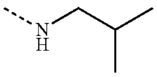 | Ex. 306 | A.6.4 | Isobutyraldehyde | FC (hexane/EtOAc/ MeOH) | 60% |
| Ex. 326 | 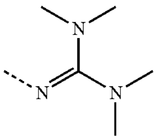 | Ex. 306 | A.1.1 | Side product from HATU coupling | prep. HPLC method 1a | — |

1) A soln of Ex. 320 (82 mg, 0.15 mmol) in dioxane (0.8 mL) was treated with 4M HCl-dioxane (0.8 mL) for 2 h at rt. Evaporation of the solvents and washing of the solid crude product with $CH_2Cl_2/Et_2O$ yielded Ex. 321 (61 mg, 83%).

TABLE 30b

| Examples of Core 18 (Ex. 305-Ex. 326; continued on the following pages) | | | | | | |
|---|---|---|---|---|---|---|
| No | $R^B$ | Formula | Monoisotopic Mass | Rt (purity at 220 nm) | $[M + H]^+$ found | LC-MS-Method |
| Ex. 305-Ex. 306: cf. experimental description | | | | | | |
| Ex. 307 | $N(CH_3)_2$ | C23H27N3O3 | 393.2 | 1.57 (98) | 394.2 | method 2c |
| Ex. 308 | 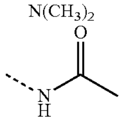 | C23H25N3O4 | 407.2 | 1.38 (97) | 408.1 | method 1a |
| Ex. 309 | 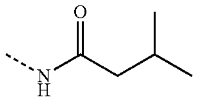 | C26H31N3O4 | 449.2 | 1.68 (98) | 450.2 | method 1a |
| Ex. 310 | 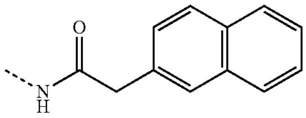 | C33H31N3O4 | 533.2 | 1.99 (93) | 534.2 | method 1a |
| Ex. 311 | 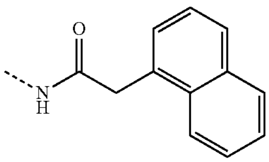 | C33H31N3O4 | 533.2 | 1.97 (95) | 534.2 | method 1a |
| Ex.312 | 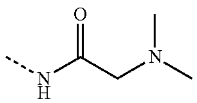 | C25H30N4O4 | 450.2 | 1.48 (98) | 451.2 | method 2c |

TABLE 30b-continued
| Examples of Core 18 (Ex. 305-Ex. 326; continued on the following pages) | | | | | | |
|---|---|---|---|---|---|---|
| No | $R^B$ | Formula | Monoisotopic Mass | Rt (purity at 220 nm) | $[M + H]^+$ found | LC-MS-Method |
| Ex. 313 | 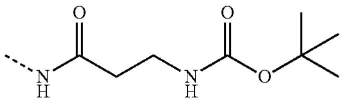 | C29H36N4O6 | 536.3 | 1.74 (91) | 537.2 | method 1a |
| Ex. 314 | 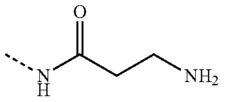 | C24H28N4O4 | 436.2 | 1.23 (99) | 437.2 | method 1a |
| Ex. 315 | 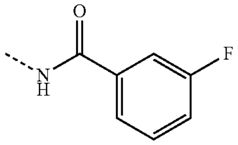 | C28H26FN3O4 | 487.2 | 1.83 (96) | 488.2 | method 1a |
| Ex. 316 | 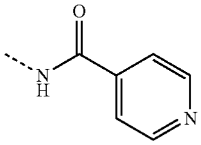 | C27H26N4O4 | 470.2 | 1.51 (99) | 471.2 | method 2c |
| Ex. 317 | 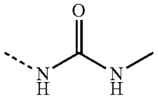 | C23H26N4O4 | 422.2 | 1.37 (96) | 423.2 | method 1a |
| Ex. 318 | 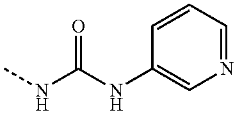 | C27H27N5O4 | 485.2 | 1.33 (98) | 486.2 | method 1a |
| Ex. 319 | 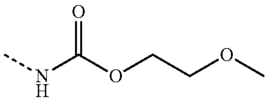 | C25H29N3O6 | 467.2 | 1.58 (96) | 468.2 | method 1a |
| Ex. 320 | 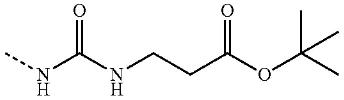 | C29H36N4O6 | 536.3 | 1.79 (98) | 537.2 | method 1a |
| Ex. 321 | 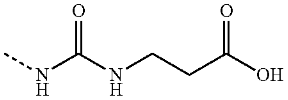 | C25H28N4O6 | 480.2 | 0.99 (87) | 481.2 | method 2c |
| Ex. 322 | 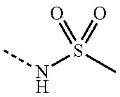 | C22H25N3O5S | 443.2 | 1.46 (97) | 444.1 | method 1a |
| Ex. 323 | 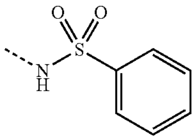 | C27H27N3O5S | 505.2 | 1.82 (97) | 506.1 | method 1a |
| Ex. 324 | 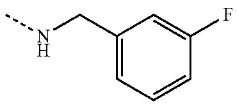 | C28H28FN3O3 | 473.2 | 1.46 (98) | 474.2 | method 1a |

TABLE 30b-continued

| Examples of Core 18 (Ex. 305-Ex. 326; continued on the following pages) | | | | | | |
|---|---|---|---|---|---|---|
| No | $R^B$ | Formula | Monoisotopic Mass | Rt (purity at 220 nm) | $[M + H]^+$ found | LC-MS-Method |
| Ex. 325 | 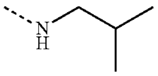 | C25H31N3O3 | 421.2 | 1.35 (98) | 422.1 | method 1a |
| Ex. 326 | 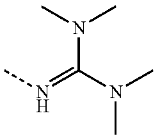 | C26H33N5O3 | 463.3 | 1.35 (95) | 464.2 | method 1a |

TABLE 30c

| Examples of Core 18 (Ex. 305-Ex. 326; continued on the following pages) | | |
|---|---|---|
| No | $R^B$ | IUPAC name |
| Ex. 305 | 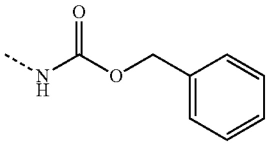 | benzyl N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]carbamate |
| Ex. 306 | $NH_2$ | (15R,16aS)-15-amino-10-methyl-10,11,15,16,16a,17-hexahydro-14H-dibenzo[i,k]pyrrolo[2,1-c][1,4,7]oxadiazacyclododecine-9,12-dione |
| Ex. 307 | $N(CH_3)_2$ | (15R,16aS)-15-(dimethylamino)-10-methyl-10,11,15,16,16a,17-hexahydro-14H-dibenzo[i, k]pyrrolo[2,1-c][1,4,7]oxadiazacyclododecine-9,12-dione |
| Ex. 308 | 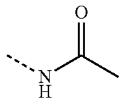 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]acetamide |
| Ex. 309 | 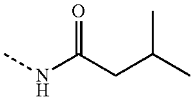 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-methylbutanamide |
| Ex. 310 | 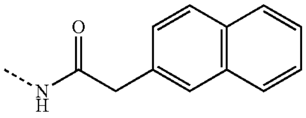 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(2-naphthyl)acetamide |
| Ex. 311 | 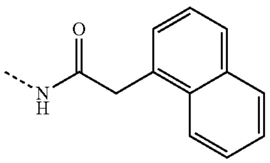 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(1-naphthyl)acetamide |
| Ex. 312 | 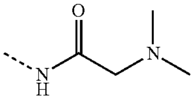 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(dimethylamino)acetamide |
| Ex. 313 | 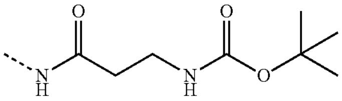 | tert-butyl N-(3-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino-3-oxopropyl)carbamate |
| Ex. 314 | 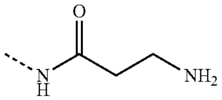 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-aminopropanamide |

TABLE 30c-continued

| Examples of Core 18 (Ex. 305-Ex. 326; continued on the following pages) | | |
|---|---|---|
| No | $R^B$ | IUPAC name |
| Ex. 315 | 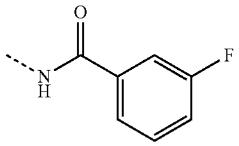 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-fluorobenzamide |
| Ex. 316 | 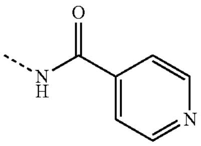 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]isonicotinamide |
| Ex. 317 | 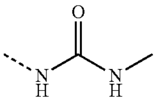 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N'-methylurea |
| Ex. 318 | 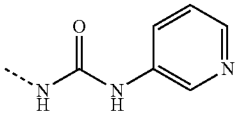 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N-(3-pyridinyl)urea |
| Ex. 319 | 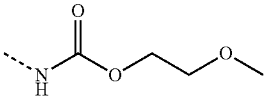 | 2-methoxyethyl N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]carbamate |
| Ex. 320 | 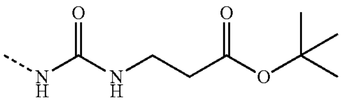 | tert-butyl 3-[({[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino}carbonyl)amino]propanoate |
| Ex. 321 | 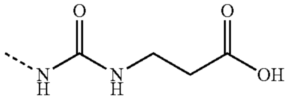 | 3-[({[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino}carbonyl)amino]propanoic acid |
| Ex. 322 | 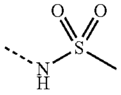 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]methanesulfonamide |
| Ex. 323 | 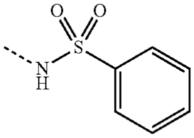 | N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]benzenesulfonamide |
| Ex. 324 | 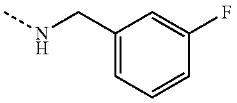 | (15R,16aS)-15-[(3-fluorobenzyl)amino]-10-methyl-10,11,15,16,16a,17-hexahydro-14H-dibenzo[i,k]pyrrolo[2,1-c][1,4,7]oxadiazacyclododecine-9,12-dione |

TABLE 30c-continued

| Examples of Core 18 (Ex. 305-Ex. 326; continued on the following pages) | | |
|---|---|---|
| No | $R^B$ | IUPAC name |
| Ex. 325 | 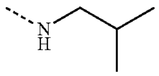 | (15R,16aS)-15-(isobutylamino)-10-methyl-10,11,15,16,16a,17-hexahydro-14H-dibenzo[i,k]pyrrolo[2,1-c][81,4,7]oxadiazacyclododecine-9,12-dione |
| Ex. 326 | 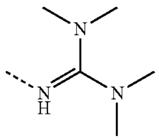 | N''-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N,N,N',N'-tetramethylguanidine |

TABLE 31a

| Examples of Core 19 (Ex. 327-Ex. 329) | | | | | | | | |
|---|---|---|---|---|---|---|---|---|
| No | $R^B$ | $R^D$ | Starting material | General Proced. | Reagent | Purification Method | Yield (isolated salt) |
| Ex. 327-Ex. 329: | cf. experimental description | | | | | | |

TABLE 31b

| Examples of Core 19 (Ex. 327-Ex. 329) | | | | | | | |
|---|---|---|---|---|---|---|---|
| No | $R^B$ | $R^D$ | Formula | Mono-isotopic Mass | Rt (purity at 220 nm) | $[M + H]^+$ found | LC-MS-Method |
| Ex. 327-Ex. 329: | cf. experimental description | | | | | | |

TABLE 31c

| Examples of Core 19 (Ex. 327-Ex. 329) | | | |
|---|---|---|---|
| No | $R^B$ | $R^D$ | IUPAC name |
| Ex. 327 | 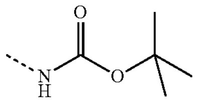 | 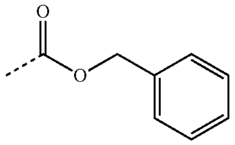 | benzyl (16S,18S)-16-[(tert-butoxycarbonyl)amino]-7,13-dioxo-4-(trifluoromethyl)-5,20-dioxa-3,8,11,14-tetraazatetracyclo[19.3.1.$0^{2,6}$.$0^{14,18}$]pentacosa-1(25),2(6),3,21,23-pentaene-11-carboxylate |
| Ex. 328 | 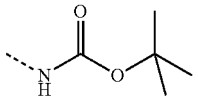 | H | tert-butyl N-[(16S,18S)-7,13-dioxo-4-(trifluoromethyl)-5,20-dioxa-3,8,11,14-tetraazatetracyclo[19.3.1.$0^{2,6}$.$0^{14,18}$]pentacosa-1(25),2(6),3,21,23-pentaen-16-yl] carbamate |
| Ex. 329 | $NH_2$ | 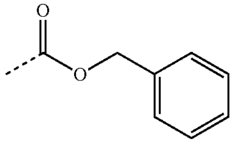 | benzyl (16S,18S)-16-amino-7,13-dioxo-4-(trifluoromethyl)-5,20-dioxa-3,8,11,14-tetraazatetracyclo[19.3.1.$0^{2,6}$.$0^{14,18}$]pentacosa-1(25),2(6),3,21,23-pentaene-11-carboxylate |

Scheme 5
Building Blocks Type A
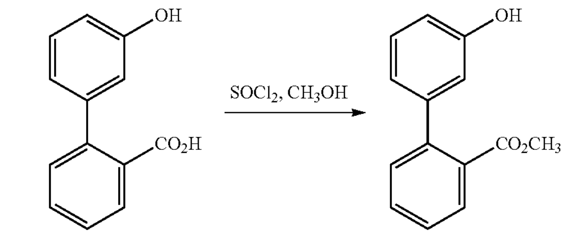
1 2
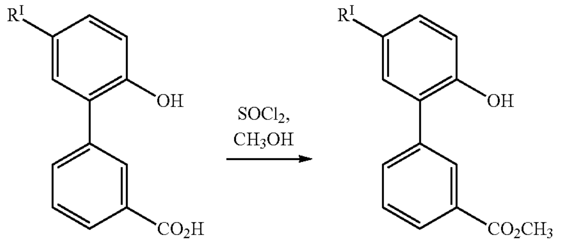
3 $R^I$ = H
5 $R^I$ = OCH$_3$
4 $R^I$ = H
6 $R^I$ = OCH$_3$
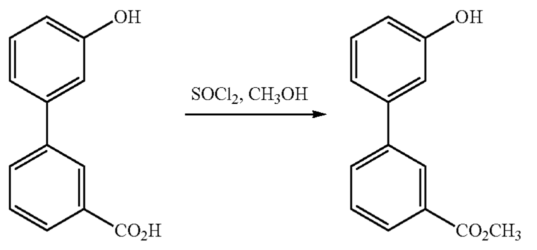
7 8
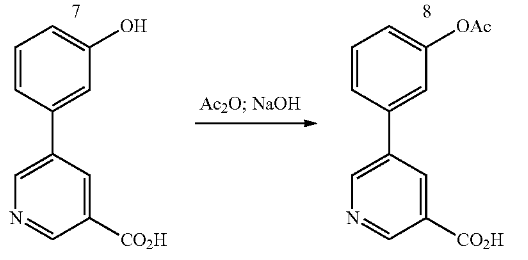
9 10
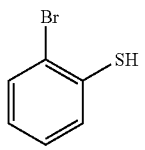
11
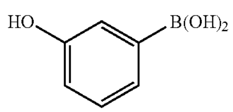
12
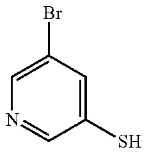
13
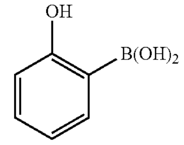
14
-continued
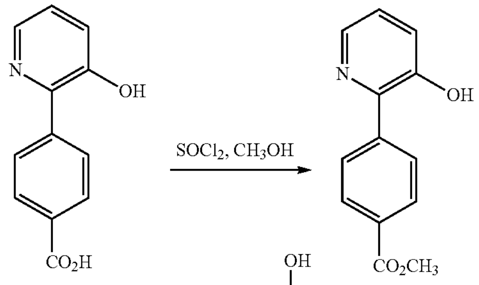
92 93
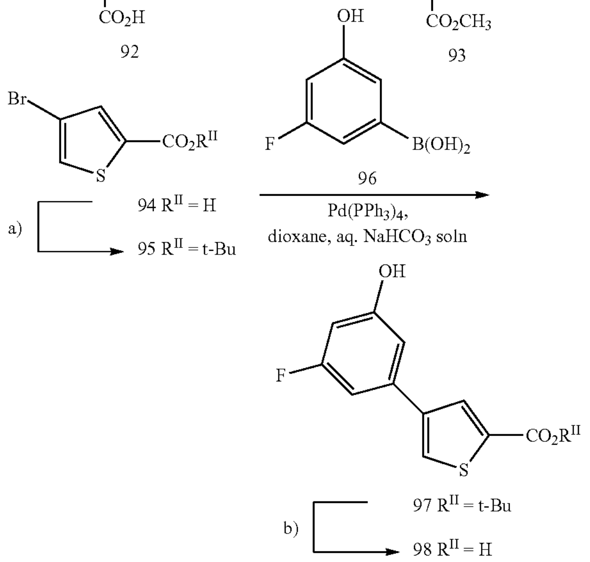
94 $R^{II}$ = H
95 $R^{II}$ = t-Bu
96
97 $R^{II}$ = t-Bu
98 $R^{II}$ = H
a) tert-Butyl-2,2,2-trichloroacetimidate, CH$_2$Cl$_2$;
b) TFA, CH$_2$Cl$_2$
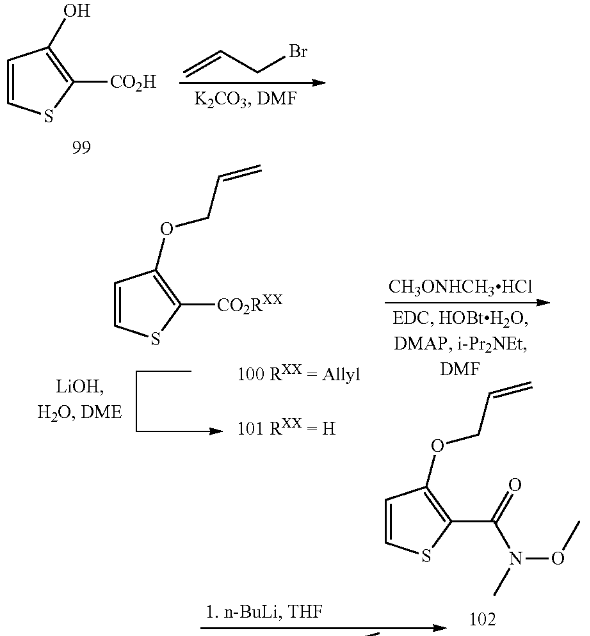
99
100 $R^{XX}$ = Allyl
101 $R^{XX}$ = H
102
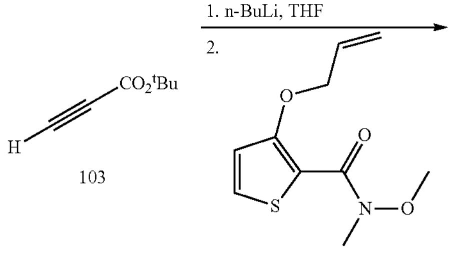
103
102
102

-continued
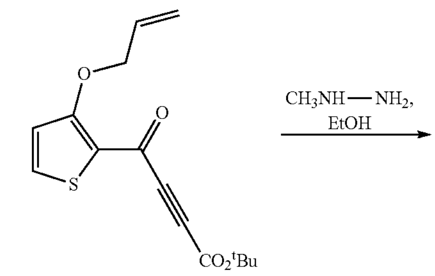
104
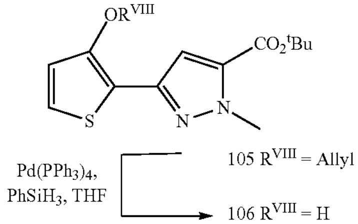
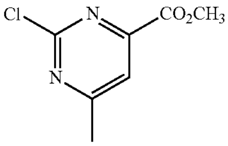
107
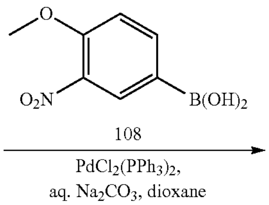
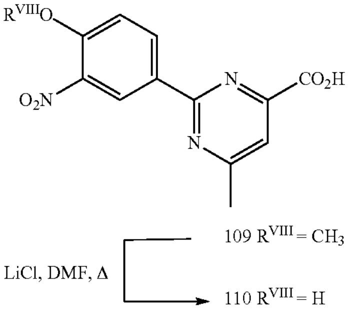
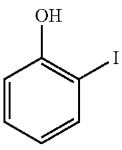
111
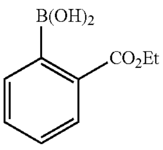
112
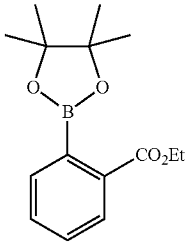
113
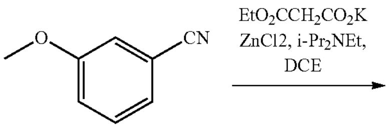
114
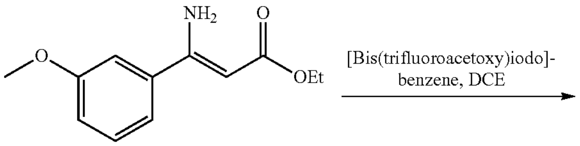
115
-continued
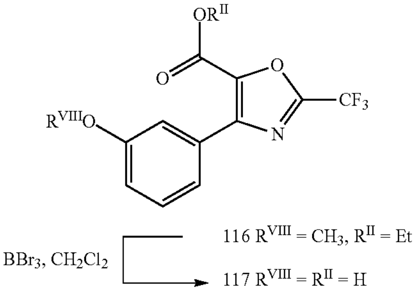
Scheme 6
Building Blocks Type B
15
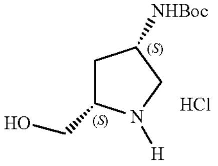
16
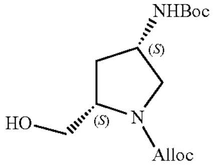
17
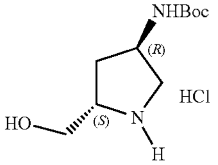
18
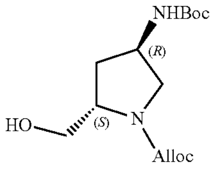
19
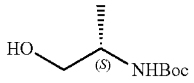
20
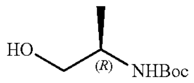

-continued
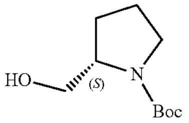
21
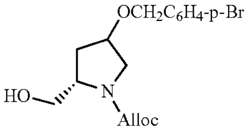
118
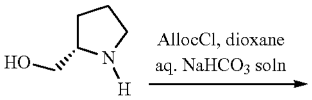
119
-continued
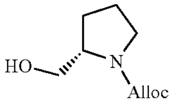
120
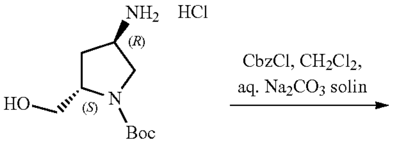
121
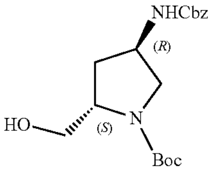
122
Scheme 7
Building Blocks Type C
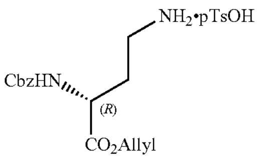
22
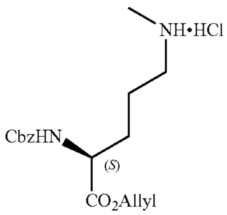
23
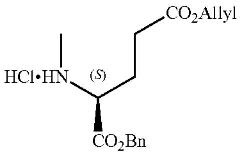
24
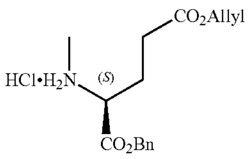
25
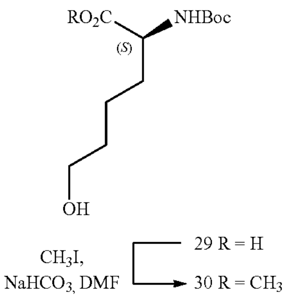

-continued
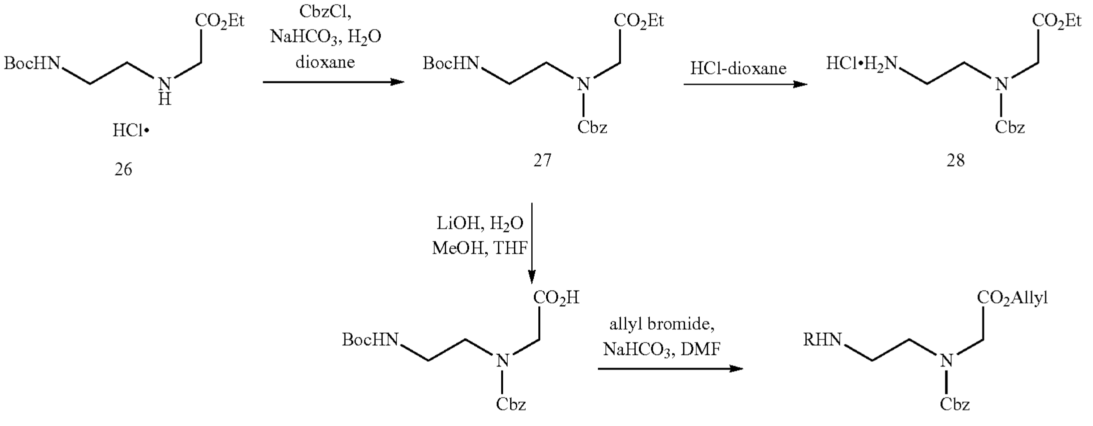
26 27 28
123
124 R = Boc
125 R = H (HCl salt)
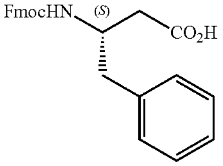
31
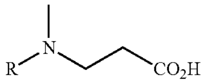
32 R = H
33 R = Fmoc
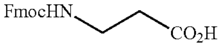
34
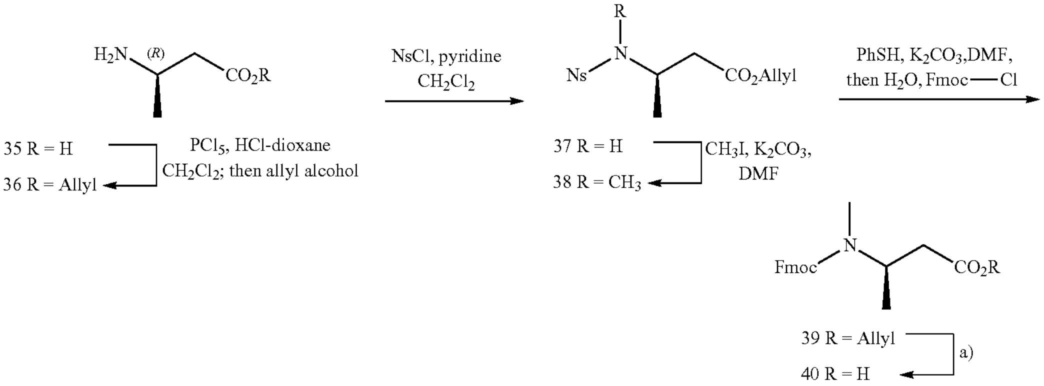
35 R = H
36 R = Allyl
37 R = H
38 R = $CH_3$
39 R = Allyl
40 R = H
a) $Pd(PPh_3)_4$, 1,3-dimethylbrbituric acid, $CH_2Cl_2$, EtOAc
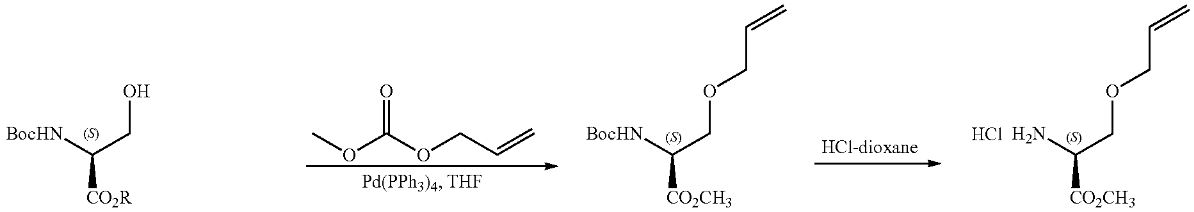
126 R = H
127 R = $CH_2$
128
129
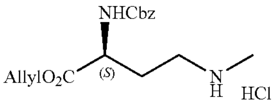
130
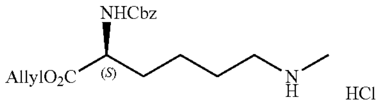
131
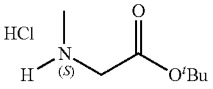
132

Scheme 8
Core 01
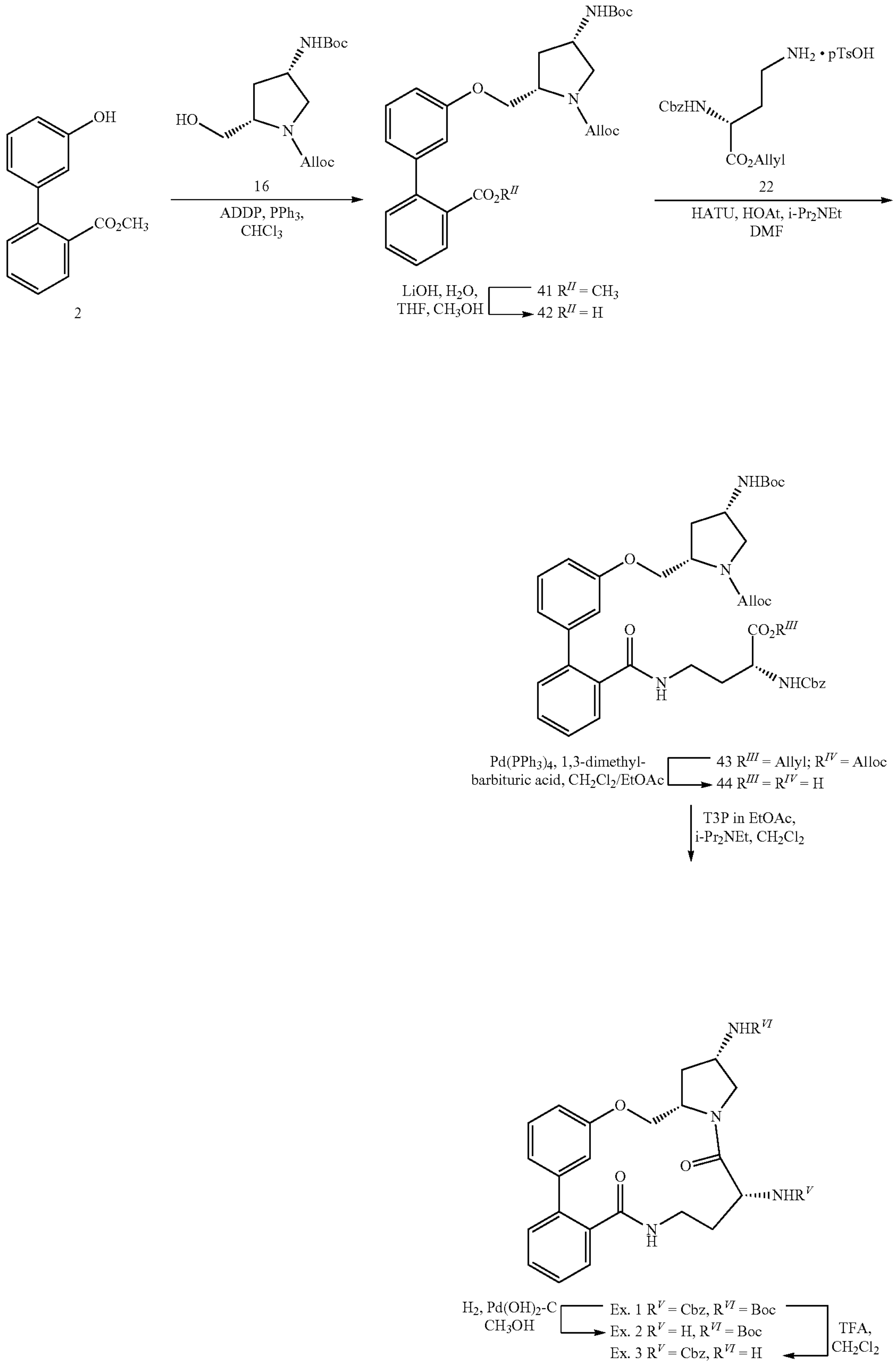

-continued
Selected examples
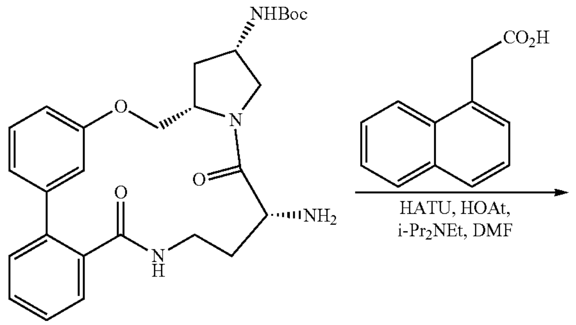
Ex. 2
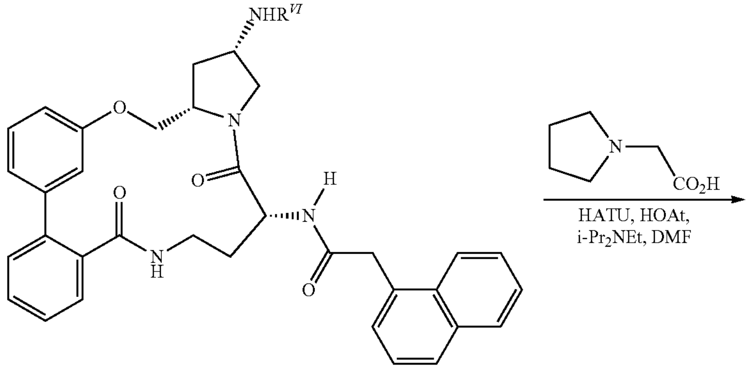
HCl-dioxane Ex. 4 $R^{VI}$ = Boc
Ex. 5 $R^{VI}$ = H
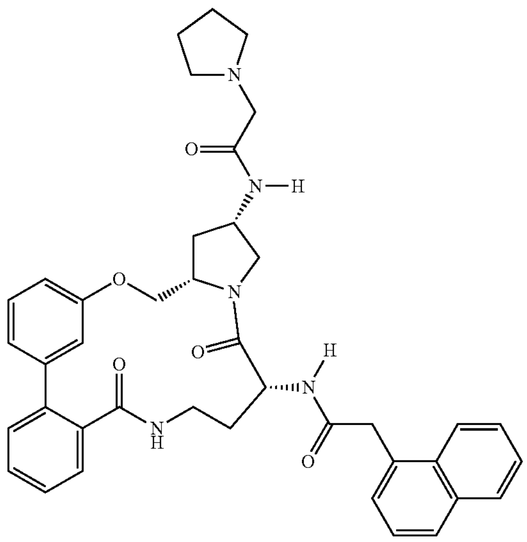
Ex. 7

-continued
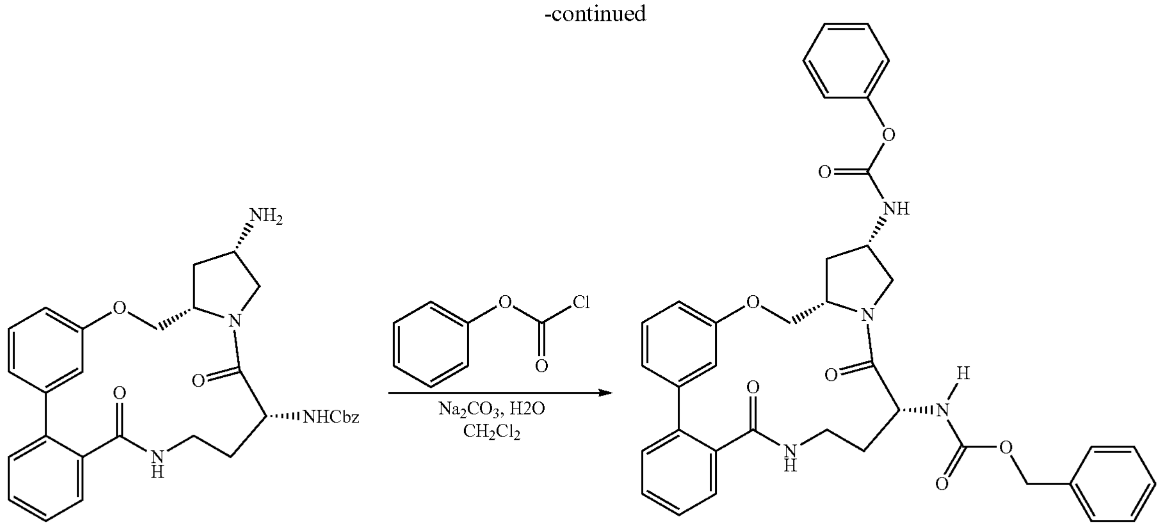
Ex. 3 Ex. 14
Core 01;
Derivatization on Solid Support
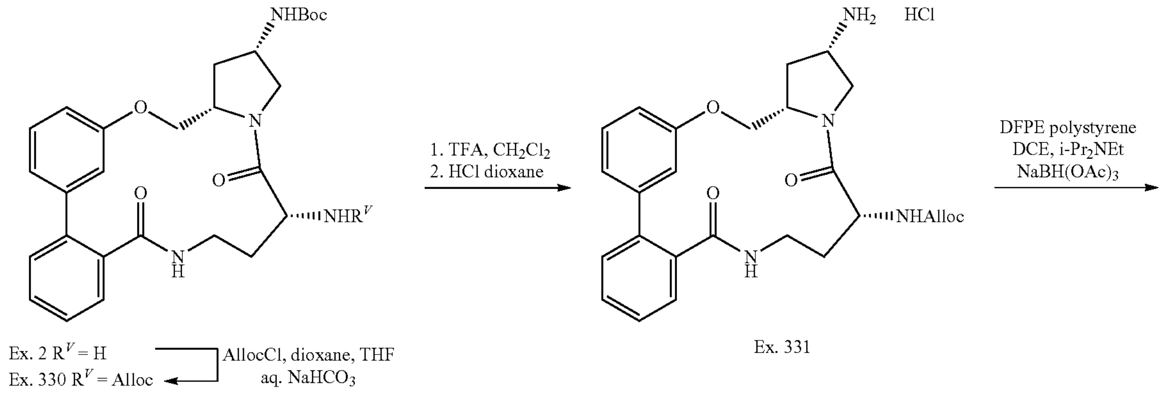
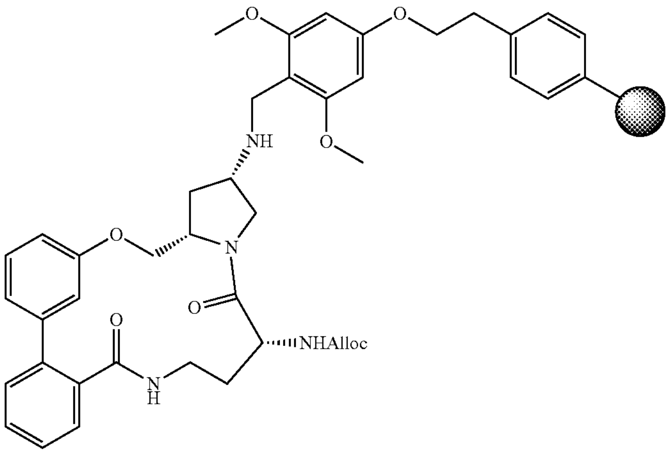

-continued
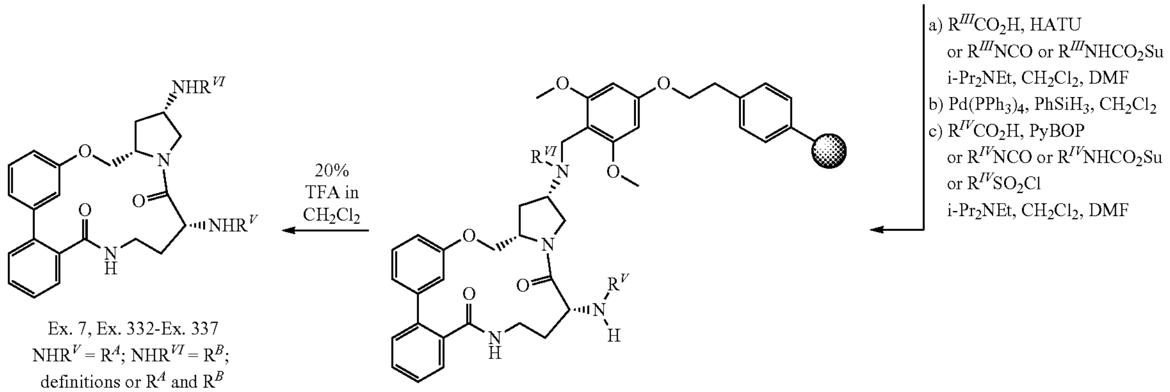
Ex. 7, Ex. 332-Ex. 337
$NHR^V = R^A$; $NHR^{VI} = R^B$;
definitions or $R^A$ and $R^B$
cf. Tab. 13
134
$R^V = R^{IV}CO$,
$R^{IV}NHCO$, $R^{IV}SO_2$
$R^{VI} = R^{III}CO$, $R^{III}NHCO$
Scheme 9
Core 02
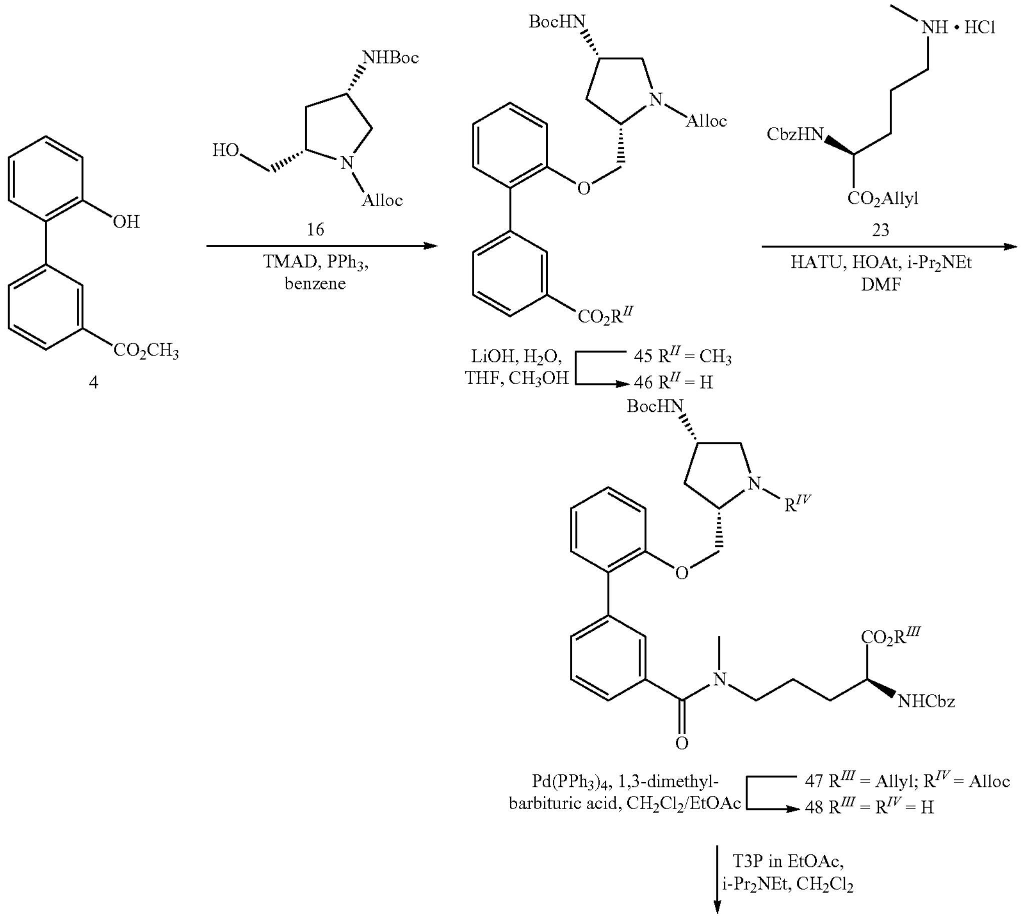
4
16
23
45 $R^{II} = CH_3$
46 $R^{II} = H$
47 $R^{III}$ = Allyl; $R^{IV}$ = Alloc
48 $R^{III} = R^{IV} = H$ -continued
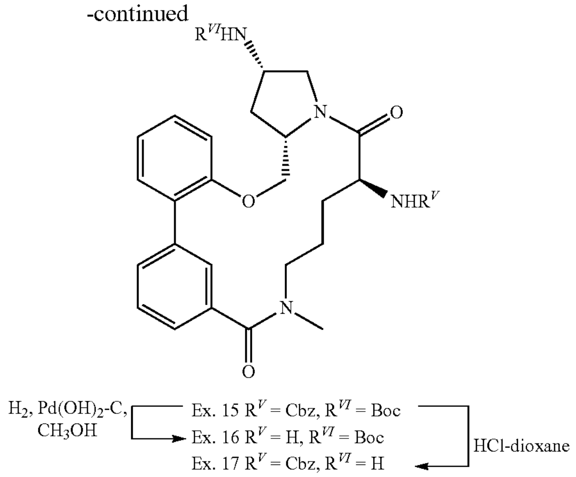
Selected examples:
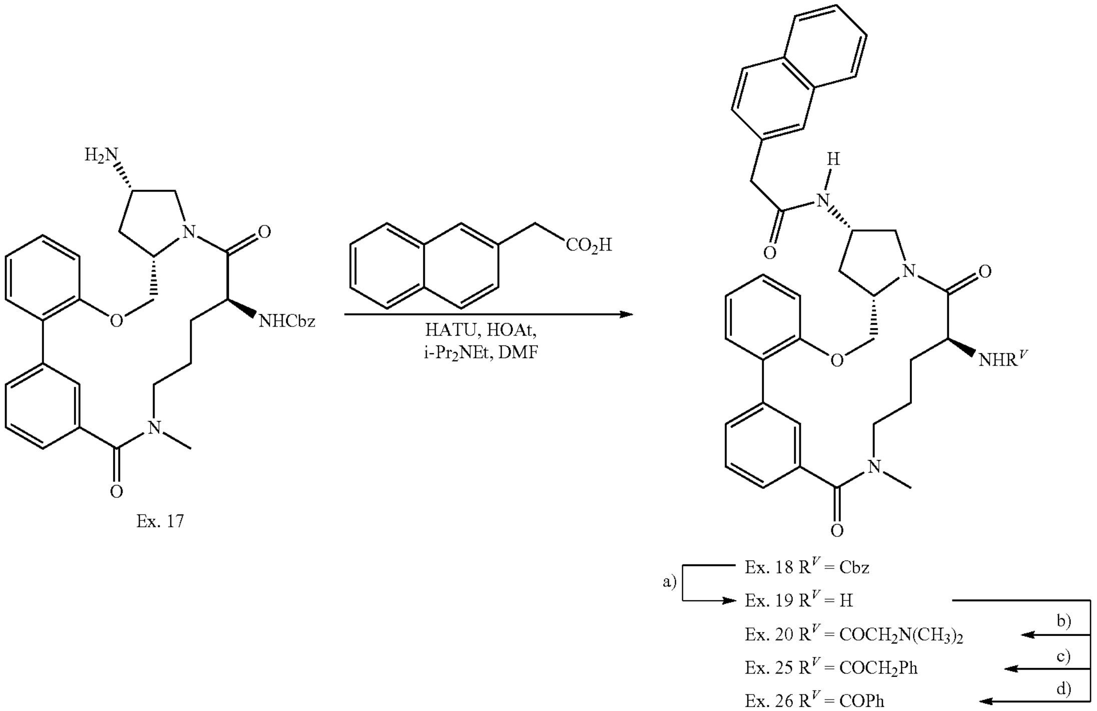
a) $H_2$, $Pd(OH)_2-C$, MeOH
b) $(CH_3)_2NCH_2CO_2H$, HATU, HOAt, i-$Pr_2NEt$, DMF
c) $PhCH_2COCl$, pyridine, $CH_2Cl_2$
d) PhCOCl, pyridine, $CH_2Cl_2$ Scheme 10
Core 03
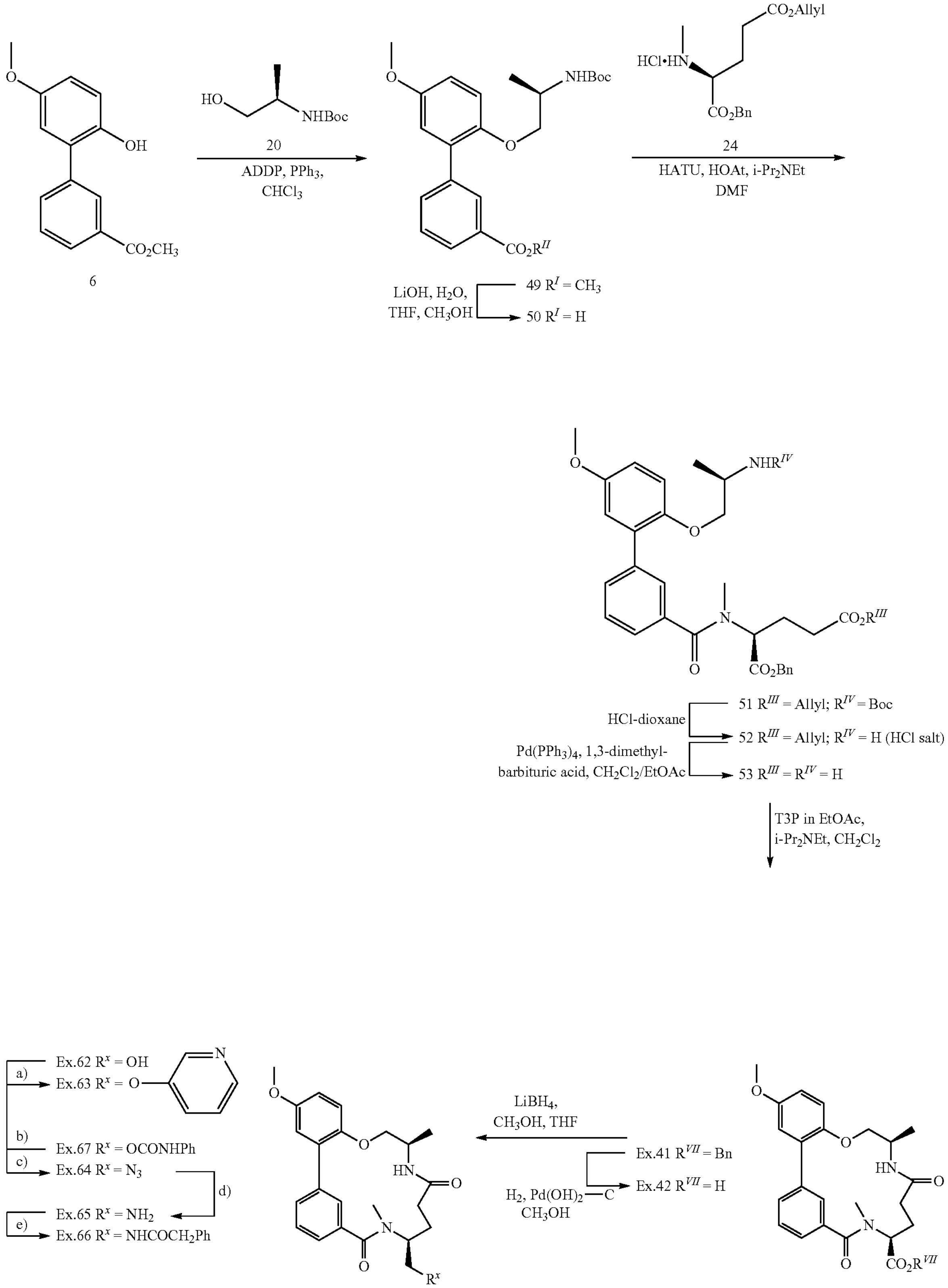
a) 3-Hydroxypyrdine, $PPh_3$, DEAD, benzene; b) PhNCO, i-$Pr_2NEt$, DMF, THF, c) DPPA, $PPh_3$, DEAD, benzene; d) $H_2$, $Pd(OH)_2$—C, $CH_3OH/CH_2Cl_2$; e) $PhCH_2CO_2H$, HATU, HOAt, i-$Pr_2NEt$ -continued
Selected examples
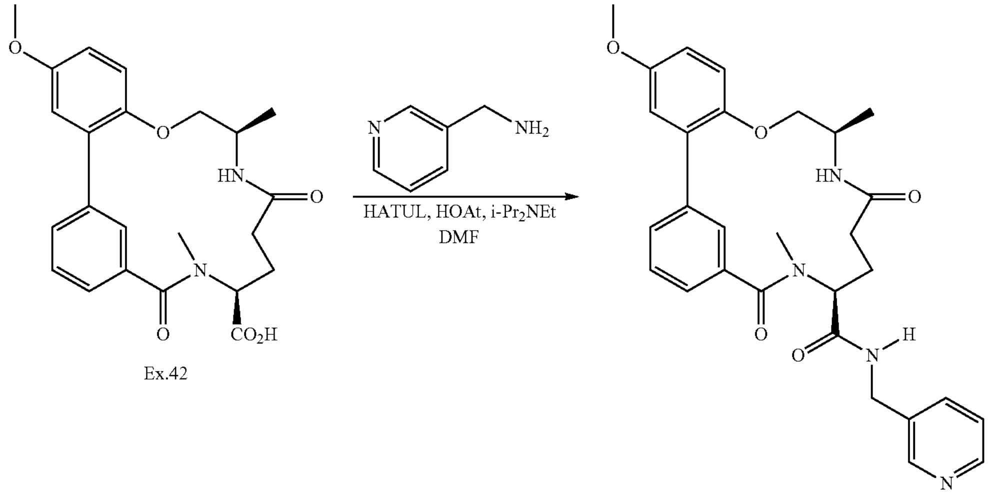
Ex.42
Ex.50
Scheme 11
Core 04
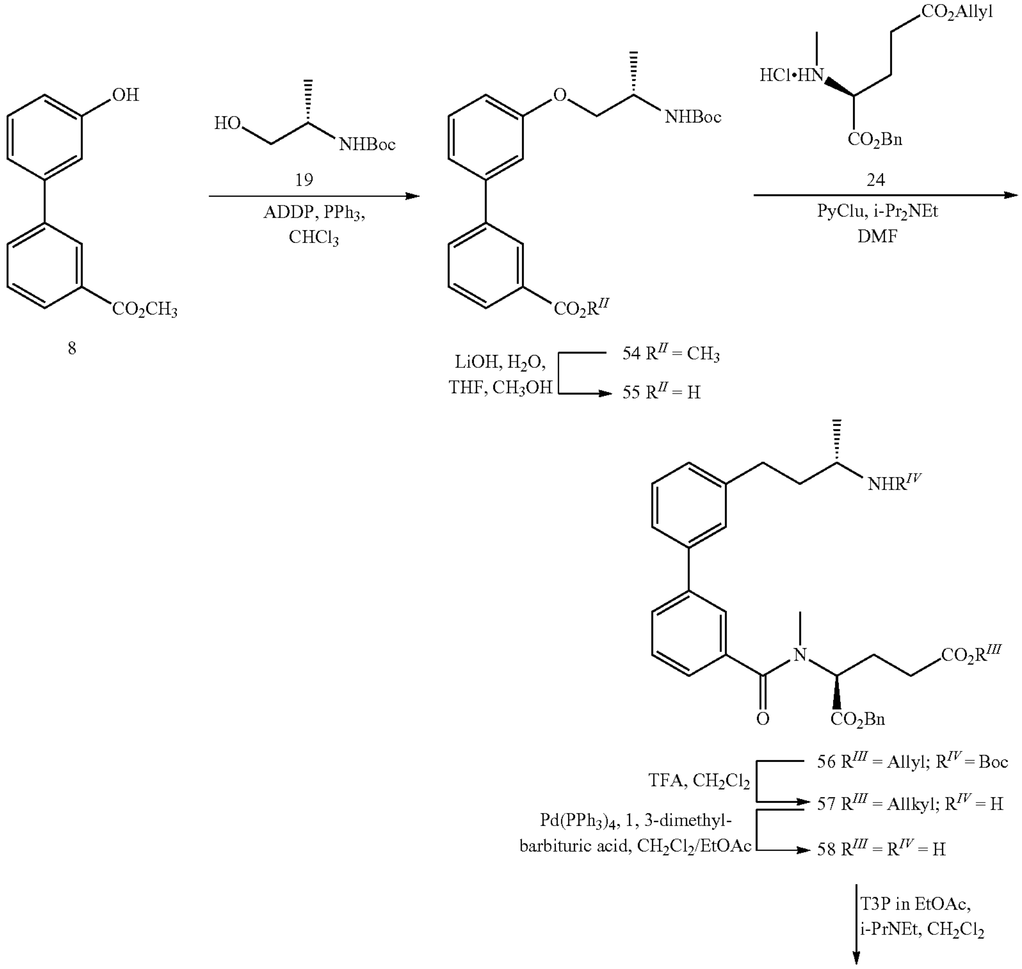
8

-continued
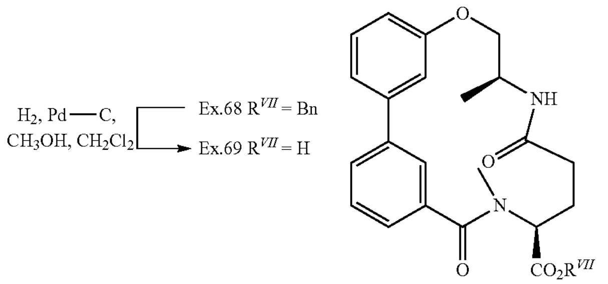
Scheme 12
Core 05
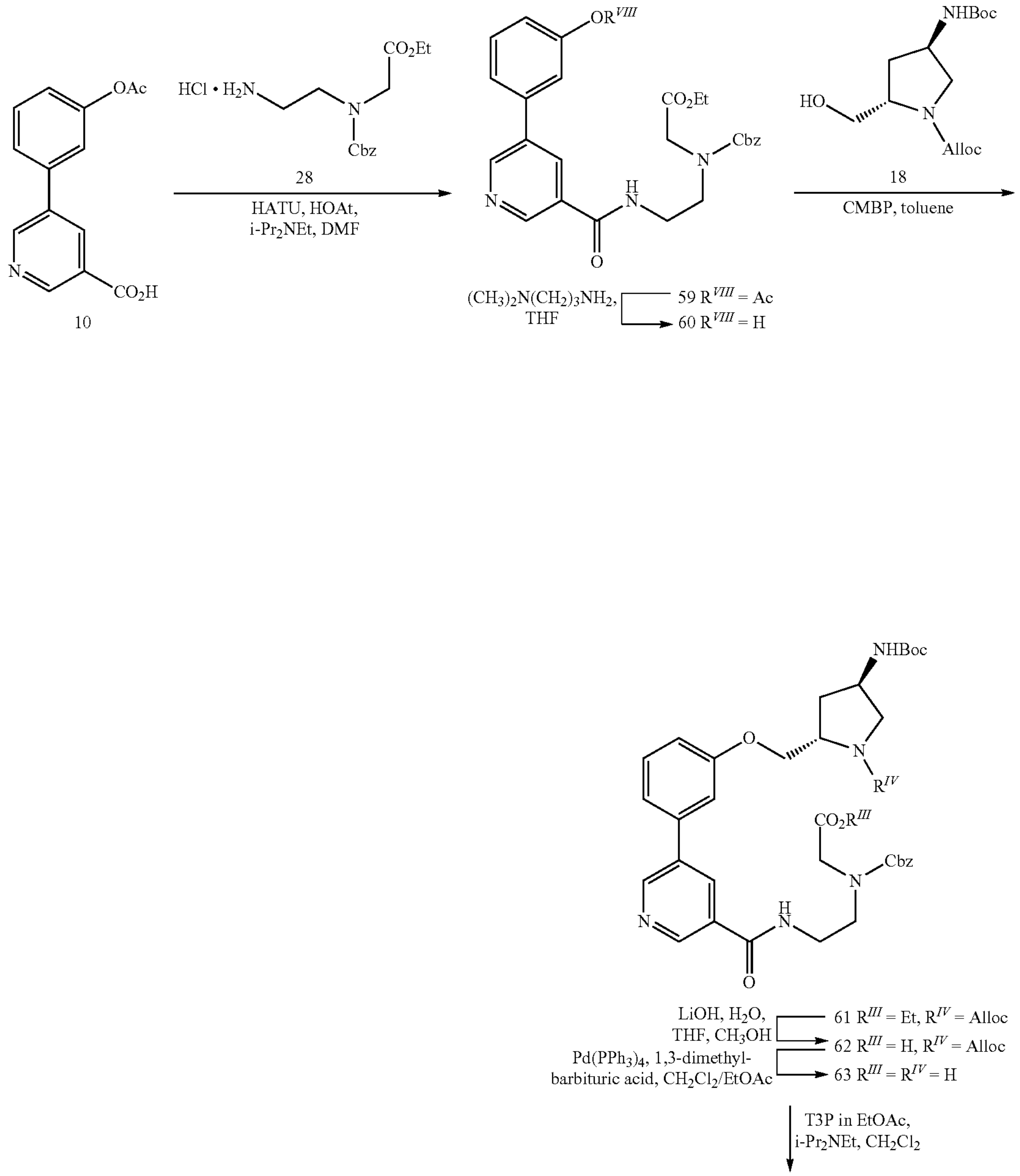

-continued
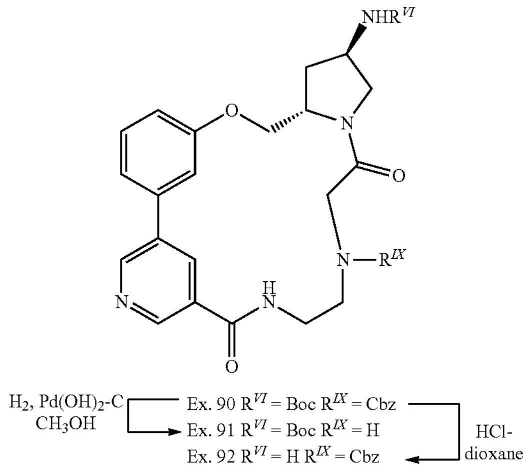
Selected examples
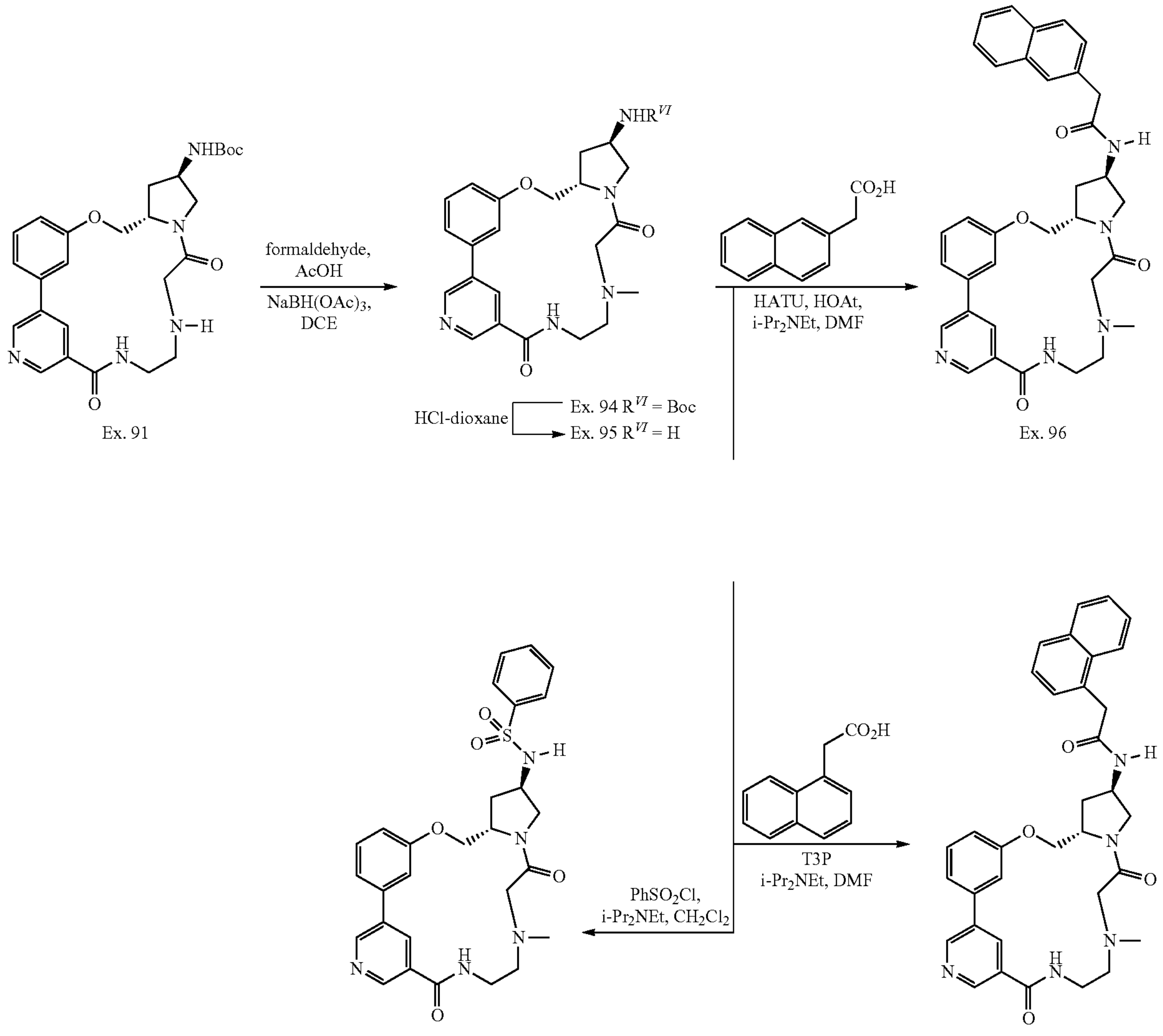

-continued
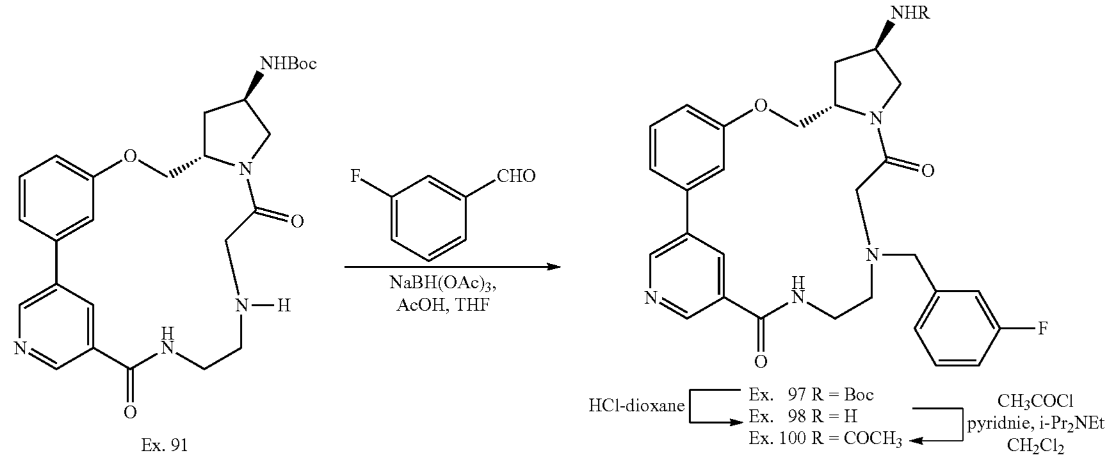
Scheme 13
Core 06/07
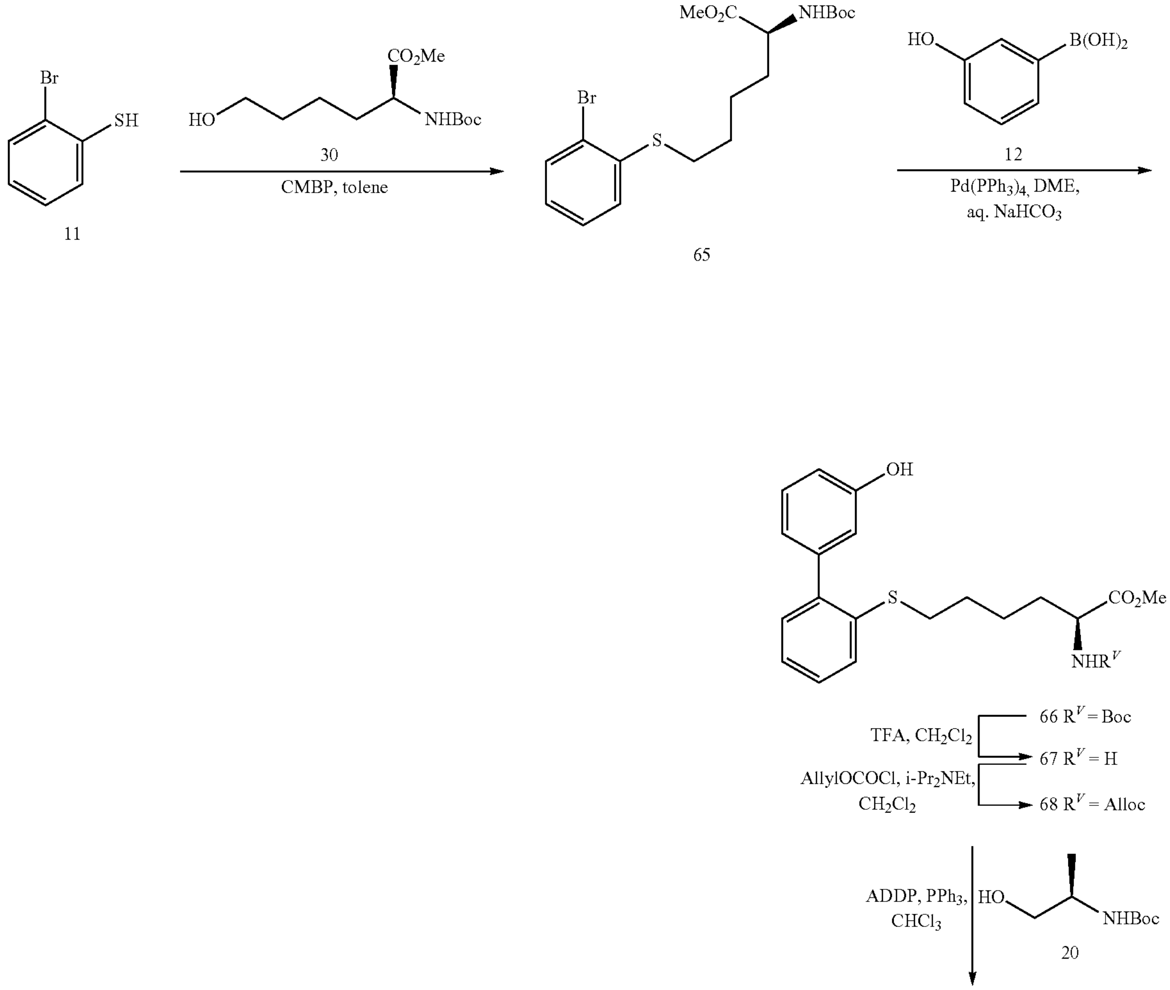

-continued
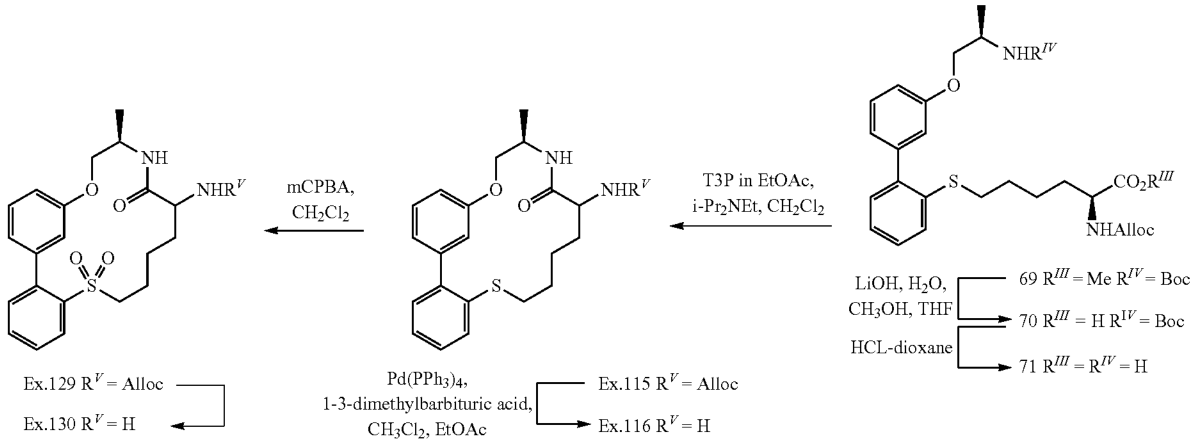
69 $R^{III}$ = Me $R^{IV}$ = Boc
70 $R^{III}$ = H $R^{IV}$ = Boc
71 $R^{III}$ = $R^{IV}$ = H
Ex.115 $R^{V}$ = Alloc
Ex.116 $R^{V}$ = H
Ex.129 $R^{V}$ = Alloc
Ex.130 $R^{V}$ = H
Selected examples
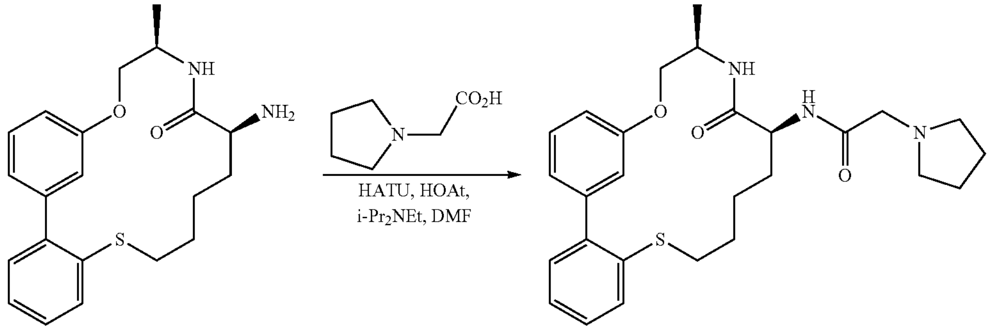
Ex.116 Ex.119
Scheme 14
Core 08/09
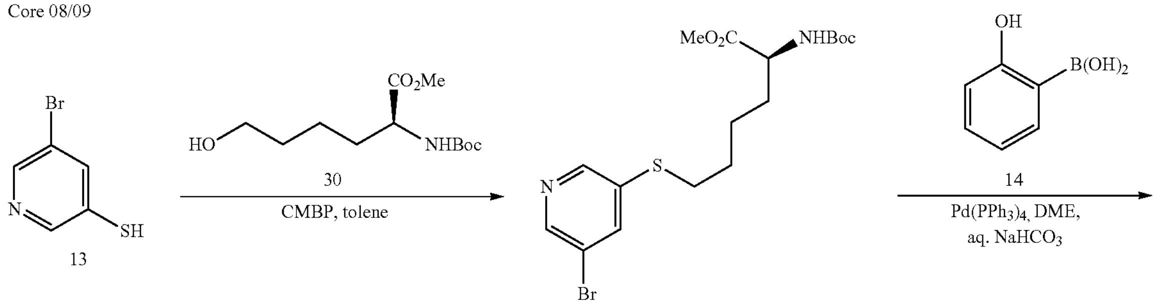
13 30 14

-continued
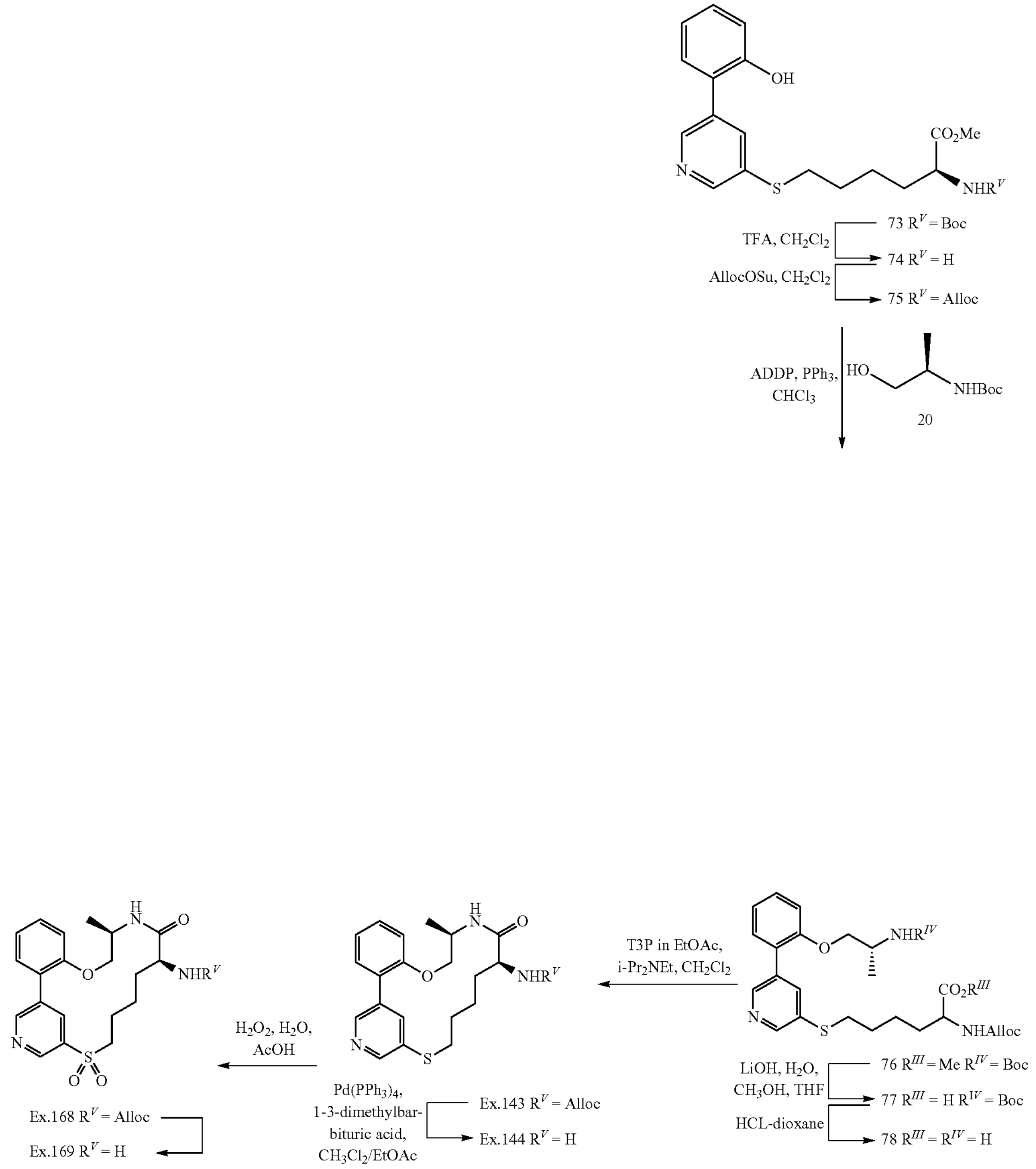

Scheme 15
Core 10
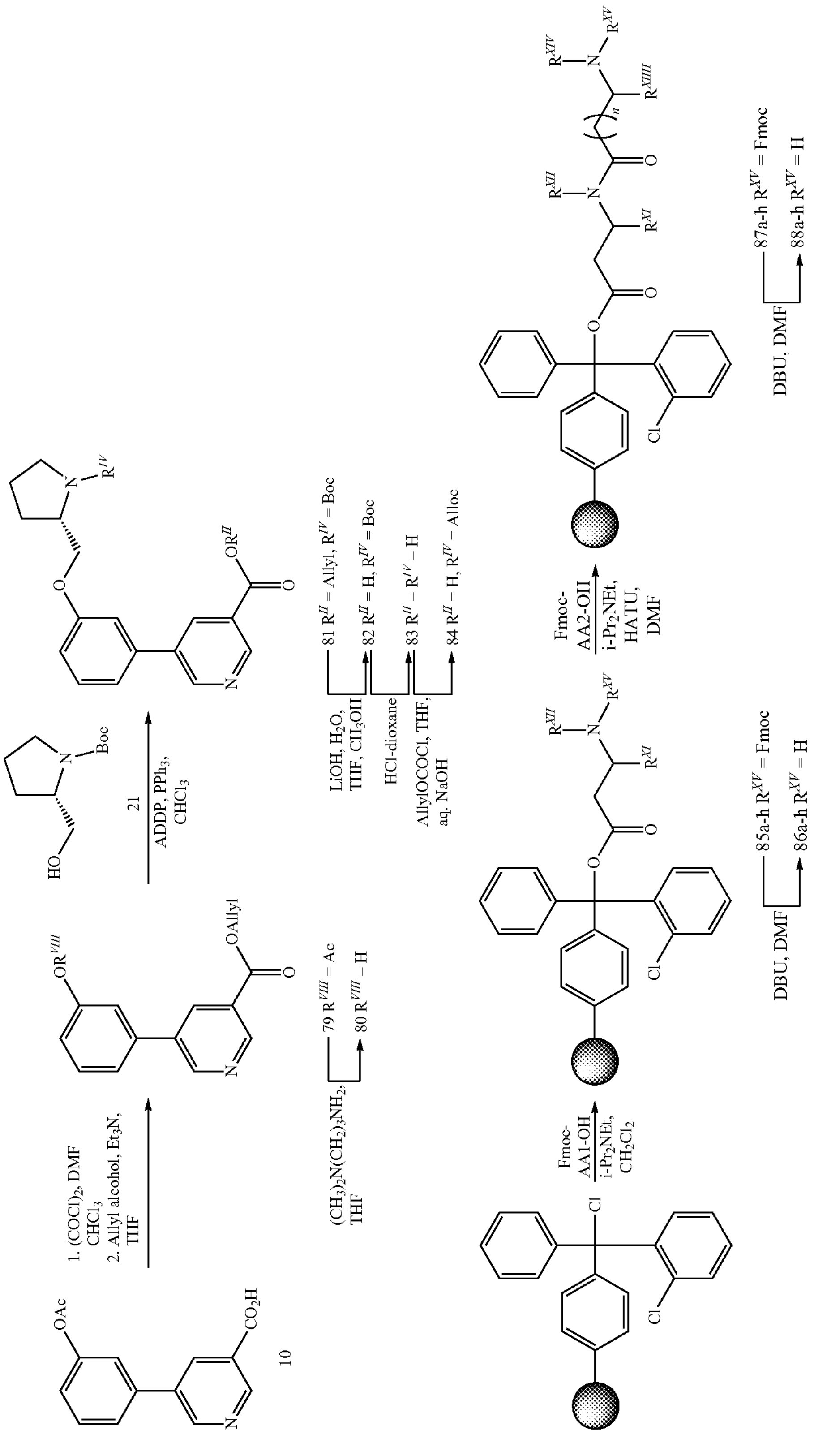

-continued

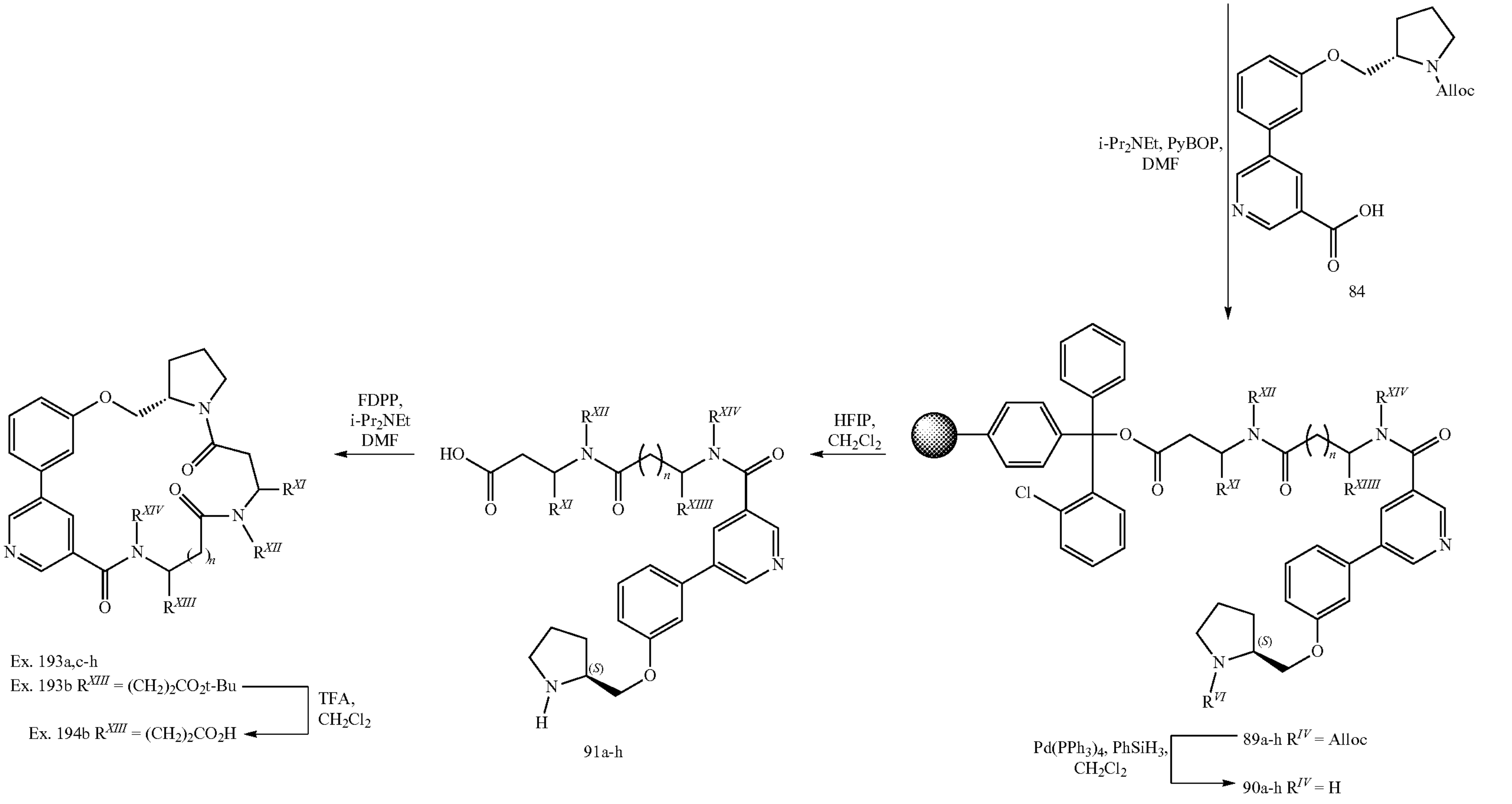

84

89a-h $R^{IV}$ = Alloc 90a-h $R^{IV}$ = H 91a-h

Ex. 193a,c-h

Ex. 193b $R^{XIII}$ = $(CH_2)_2CO_2$t-Bu

Ex. 194b $R^{XIII}$ = $(CH_2)_2CO_2H$

| Cpd No | n | $R^{XI}$ | $R^{XII}$ | $R^{XIII}$ | $R^{XIV}$ | Fmoc-AA1-OH | Fmoc-AA2-OH |
|---|---|---|---|---|---|---|---|
| 85a-Ex. 193a | 0 | $CH_2Ph$ | H | $CH_3$ | $CH_3$ | Fmoc-β$^3$-homoPhe-OH | Fmoc-NMeDAla-OH |
| 85b-Ex. 193b | 0 | $CH_3$ | $CH_3$ | $(CH_2)_2CO_2tBu$ | $CH_3$ | Fmoc-NMe-β$^3$-homoDAla-OH | Fmoc-NMeDGlu(OtBu)-OH |
| 85c-Ex. 193c | 0 | H | H | $CH_2Ph$ | $CH_3$ | Fmoc-β-Ala-OH | Fmoc-NMePhe-OH |
| 85d-Ex. 193d | 0 | H | H | $CH_2Ph$ | H | Fmoc-β-Ala-OH | Fmoc-Phe-OH |
| 85e-Ex. 193e | 0 | $CH_3$ | $CH_3$ | $CH_2Ph$ | $CH_3$ | Fmoc-NMe-β$^3$-homoDAla-OH | Fmoc-NMePhe-OH |
| 85f-Ex. 193f | 0 | $CH_3$ | $CH_3$ | H | $CH_3$ | Fmoc-NMe-β$^3$-homoDAla-OH | Fmoc-Sar-OH |
| 85g-Ex. 193g | 0 | $CH_3$ | $CH_3$ | $CH_2Ph$ | H | Fmoc-NMe-β$^3$-homoDAla-OH | Fmoc-Phe-OH |
| 85h-Ex. 193h | 1 | $CH_2Ph$ | H | H | $CH_3$ | Fmoc-β$^3$-homoPhe-OH | Fmoc-NMe-β-Ala-OH |

Scheme 16
Core 11
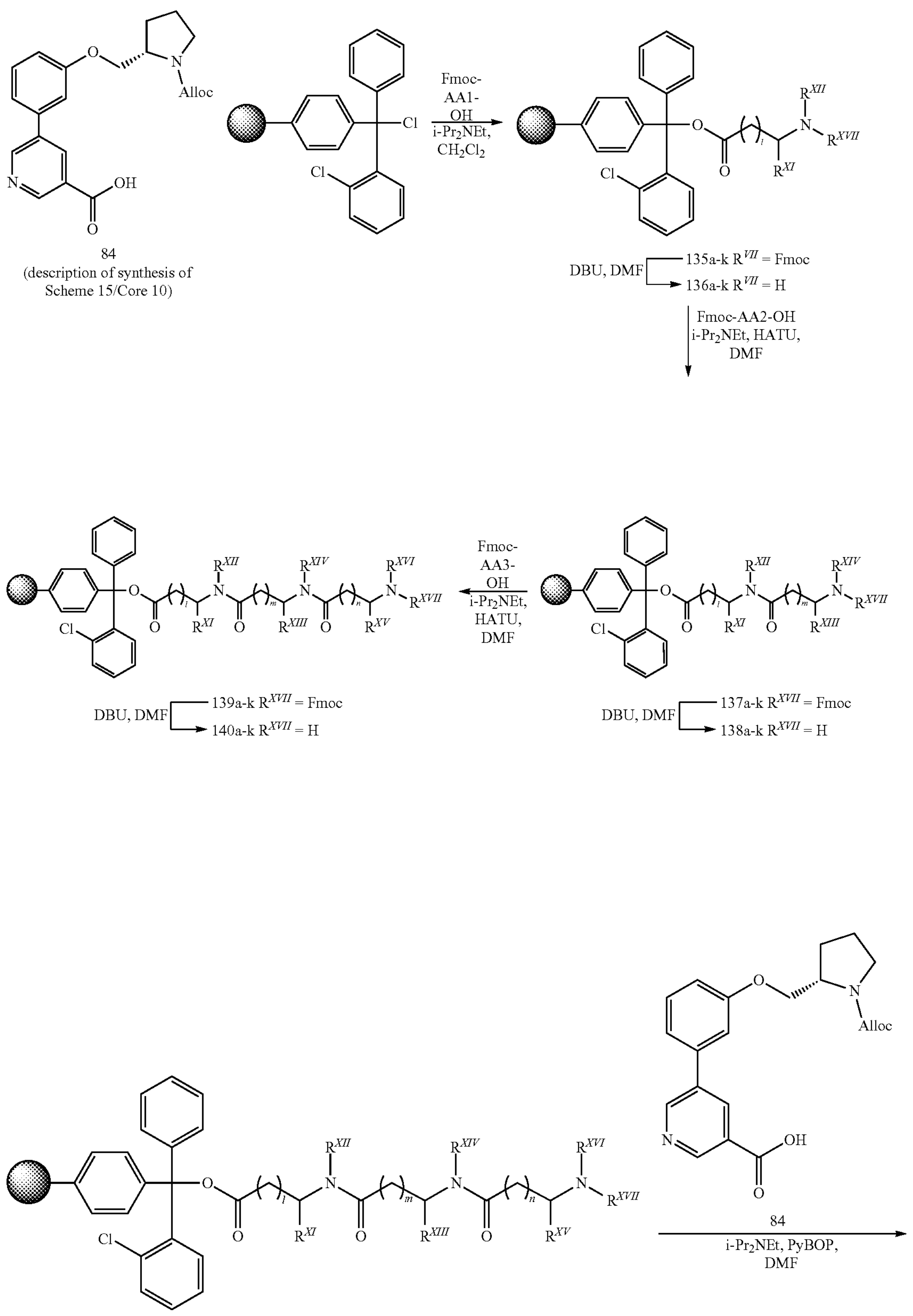
140a-k

-continued
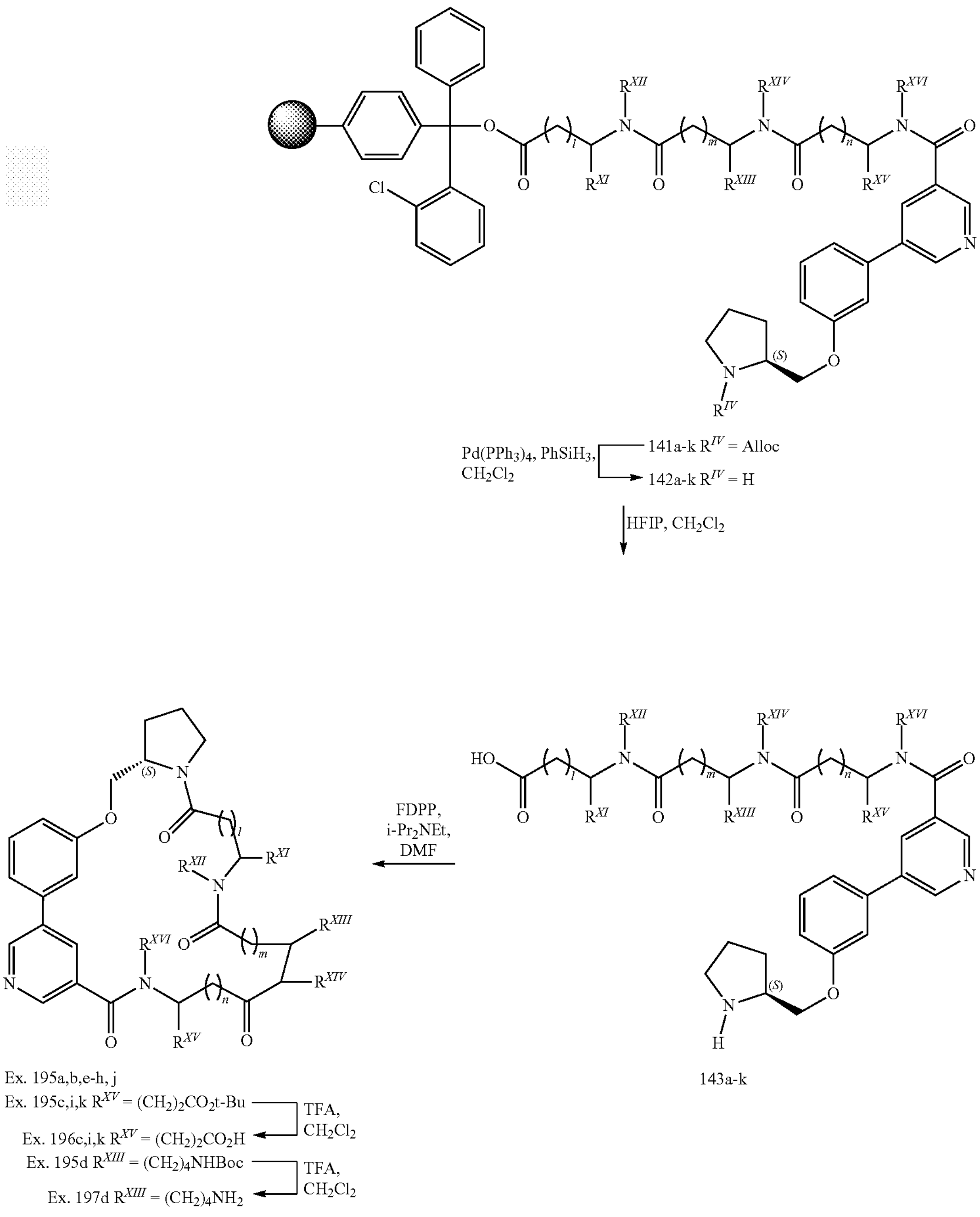
| Cpd No | l | m | n | $R^{XI}$ | $R^{XII}$ | $R^{XIII}$ | $R^{XIV}$ | $R^{XV}$ | $R^{XVI}$ |
|---|---|---|---|---|---|---|---|---|---|
| 135a-Ex. 195a | 1 | 0 | 0 | $CH_3$ | $CH_3$ | H | $CH_3$ | $CH_3$ | $CH_3$ |
| 135b-Ex. 195b | 1 | 0 | 0 | $CH_3$ | $CH_3$ | H | H | $CH_3$ | H |
| 135c-Ex. 195c | 1 | 0 | 0 | $CH_3$ | $CH_3$ | $CH_3$ | H | $(CH_2)_2CO_2tBu$ | $CH_3$ |
| 135d-Ex. 195d | 1 | 0 | 0 | $CH_3$ | $CH_3$ | $(CH_2)_4NHBoc$ | H | $CH_3$ | H |
| 135e-Ex. 195e | 0 | 1 | 0 | H | $CH_3$ | $CH_3$ | $CH_3$ | $CH_3$ | $CH_3$ |
| 135f-Ex. 195f | 0 | 0 | 1 | H | $CH_3$ | $CH_3$ | $CH_3$ | $CH_3$ | $CH_3$ |
| 135g-Ex. 195g | 0 | 0 | 0 | H | H | $CH_2Ph$ | H | $CH_3$ | $CH_3$ |
| 135h-Ex. 195h | 0 | 0 | 0 | H | $CH_3$ | $CH_2Ph$ | H | $CH_3$ | H |
| 135i-Ex. 195i | 0 | 0 | 0 | $CH_3$ | H | $CH_2Ph$ | H | $(CH_2)_2CO_2tBu$ | $CH_3$ |

-continued

| | | | | | | | | | |
|---|---|---|---|---|---|---|---|---|---|
| 135j-Ex. 195j | 0 | 0 | 0 | H | $CH_3$ | $CH_2Ph$ | H | $CH_3$ | $CH_3$ |
| 135k-Ex. 195k | 0 | 0 | 0 | $CH_3$ | H | $CH_2Ph$ | H | $(CH_2)_2CO_2tBu$ | $CH_3$ |

| Cpd No | Fmoc-AA1-OH | Fmoc-AA2-OH | Fmoc-AA3-OH |
|---|---|---|---|
| 135a-Ex. 195a | Fmoc-NMe-$\beta^3$-homoDAla-OH | Fmoc-Sar-OH | Fmoc-NMeAla-OH |
| 135b-Ex. 195b | Fmoc-NMe-$\beta^3$-homoDAla-OH | Fmoc-Gly-OH | Fmoc-Ala-OH |
| 135c-Ex. 195c | Fmoc-NMe-$\beta^3$-homoDAla-OH | Fmoc-Ala-OH | Fmoc-NMeGlu(OtBu)-OH |
| 135d-Ex. 195d | Fmoc-NMe-$\beta^3$-homoDAla-OH | Fmoc-Lys(Boc)-OH | Fmoc-DAla-OH |
| 135e-Ex. 195e | Fmoc-Sar-OH | Fmoc-NMe-$\beta^3$-homoDAla-OH | Fmoc-NMeAla-OH |
| 135f-Ex. 195f | Fmoc-Sar-OH | Fmoc-NMeAla-OH | Fmoc-NMe-$\beta^3$-homoDAla-OH |
| 135g-Ex. 195g | Fmoc-Gly-OH | Fmoc-Phe-OH | Fmoc-NMeDAla-OH |
| 135h-Ex. 195h | Fmoc-Sar-OH | Fmoc-Phe-OH | Fmoc-DAla-OH |
| 135i-Ex. 195i | Fmoc-Ala-OH | Fmoc-DPhe-OH | Fmoc-NMeGlu(OtBu)-OH |
| 135j-Ex. 195j | Fmoc-Sar-OH | Fmoc-Phe-OH | Fmoc-NMeDAla-OH |
| 135k-Ex. 195k | Fmoc-DAla-OH | Fmoc-Phe-OH | Fmoc-NMeGlu(OtBu)-OH |

Scheme 17

Core 12

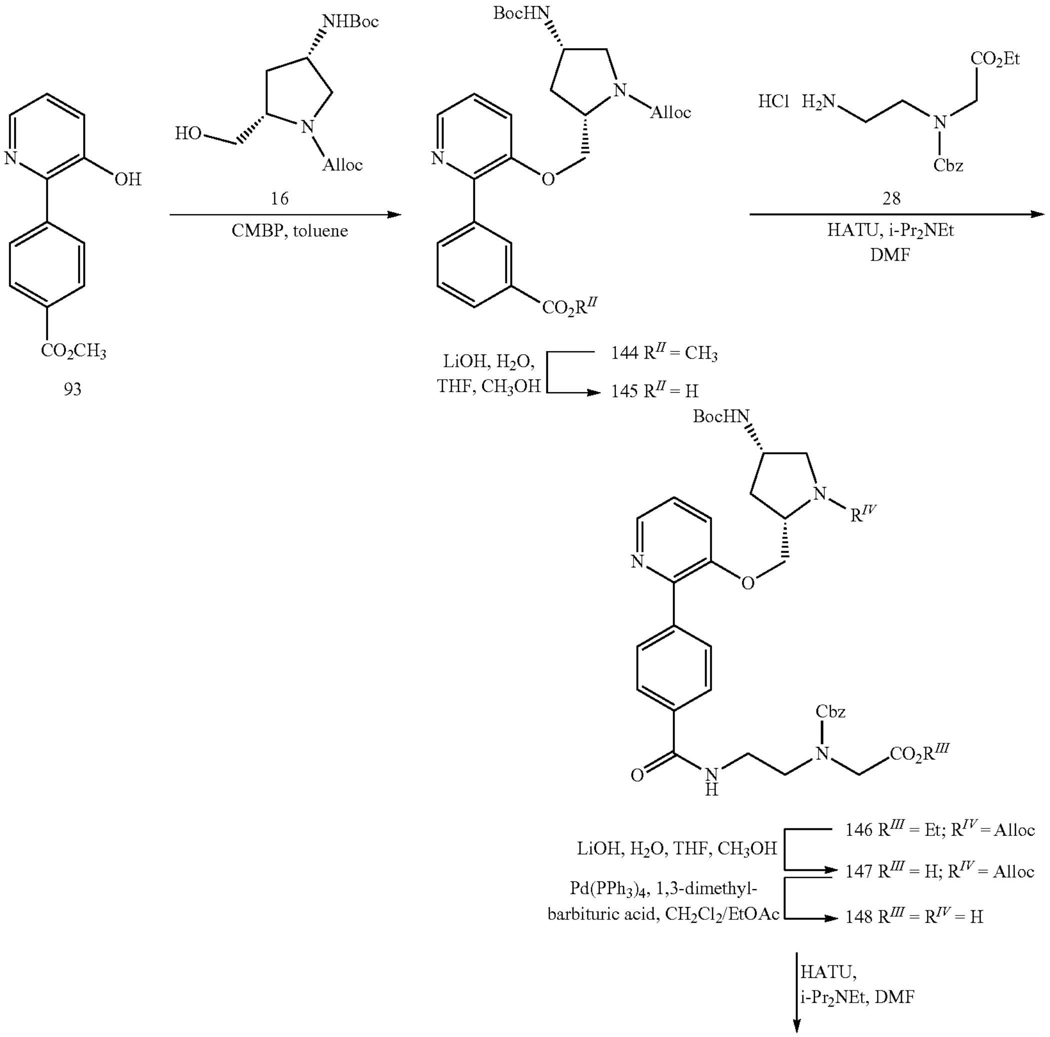

-continued
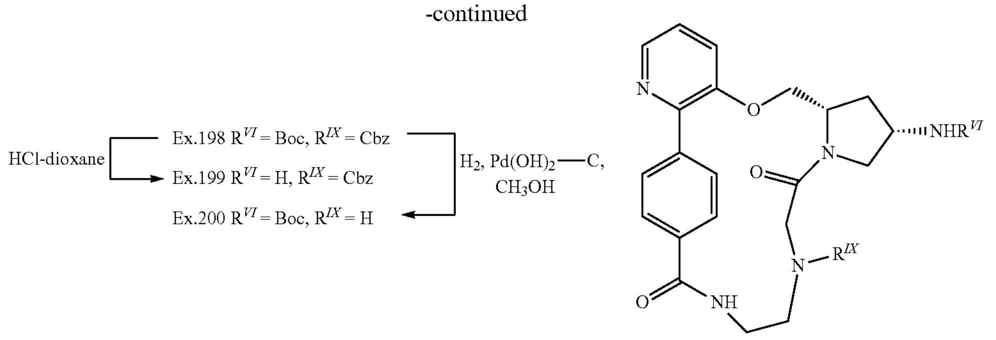
Scheme 18
Cores 13 - 15
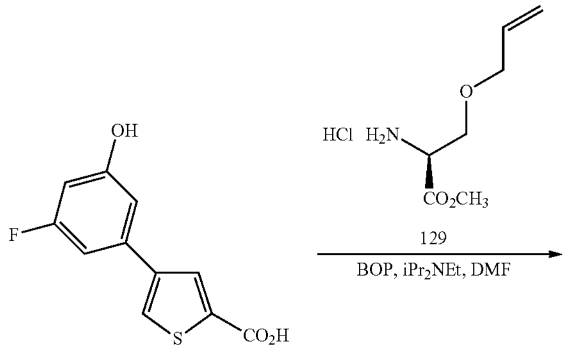
98
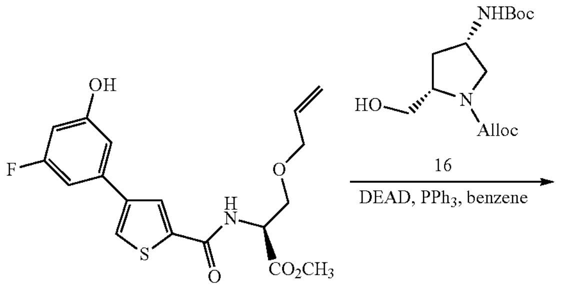
149
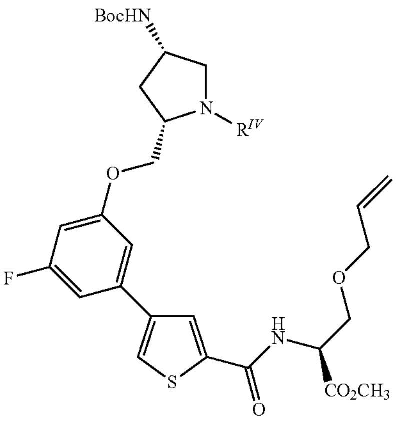
Pd($PPh_3)_4$, 1,3-dimethyl-barbituric acid, $CH_2Cl_2$ EtOAc
150 $R^{IV}$ = Alloc
151 $R^{IV}$ = H
-continued
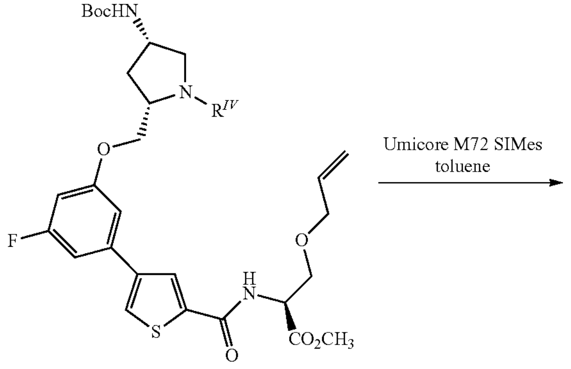
151 $R^{IV}$ = H
152 $R^{IV}$ = $COCH{=}CH_2$
Acryloyl chloride, i-$Pr_2NEt$, $CH_2Cl_2$
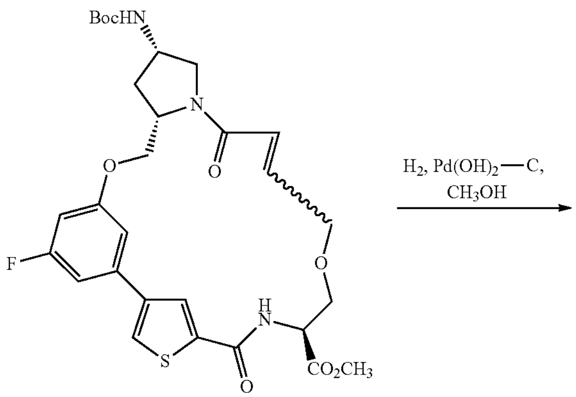
Ex.220

-continued

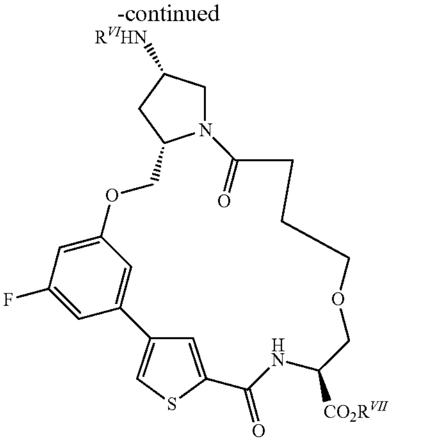

Ex.221 $R^{VII} = CH_3$, $R^{VI}$ = Boc

HCl-dioxane

Ex. 222 $R^{VII} = CH_3$, $R^{VI}$ = H

-continued

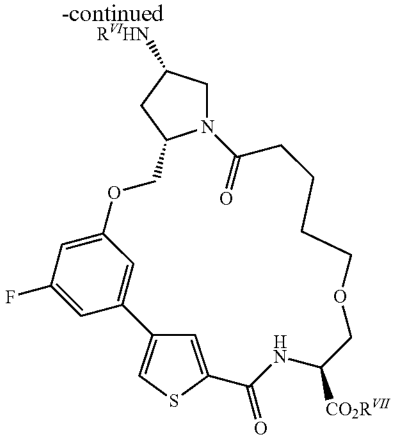

Ex.242 $R^{VII} = CH_3$, $R^{VI}$ = Boc b)

Ex.243 $R^{VII}$ = H, $R^{VI}$ = Boc c)

Ex.244 $R^{VII} = CH_3$, $R^{VI}$ = H a) But-3-enoic acid, HATU, HOAt, i-$Pr_2NEt$, DMF;
b) $(CH_3)_3SnOH$, DCE; c) HCl-dioxane Selected examples:

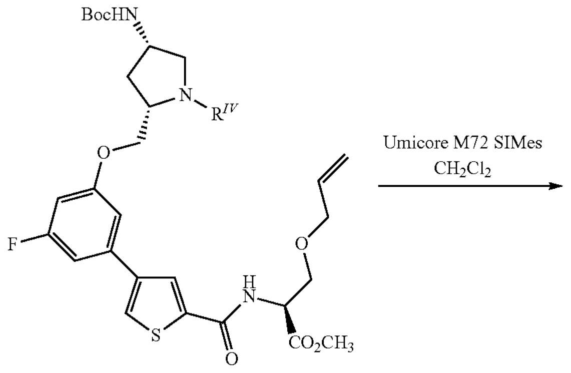

151 $R^{IV}$ = H a)

152 $R^{IV}$ = $COCH_2CH{=}CH_2$

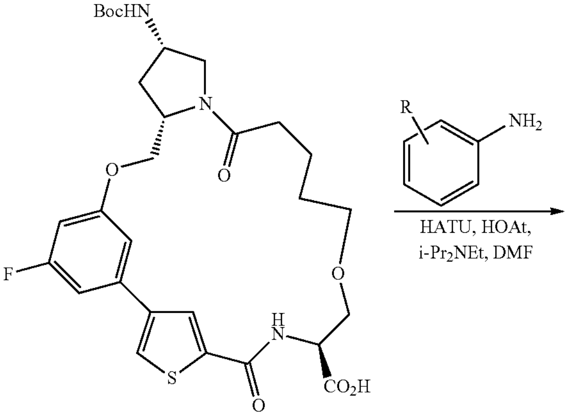

Ex.243

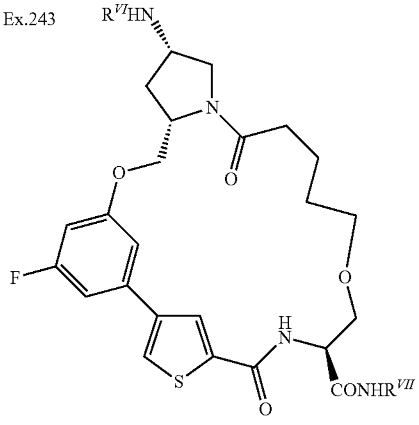

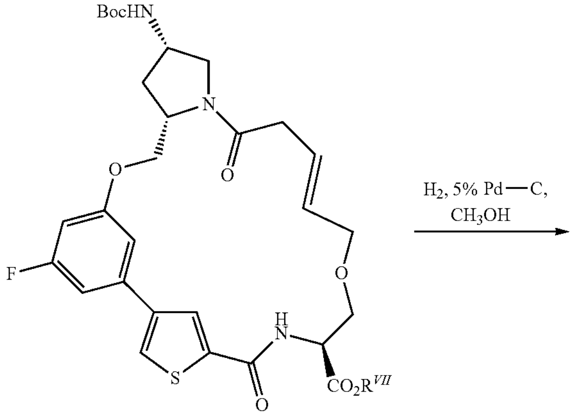

Ex.227 $R^{VII} = CH_3$, $R^{VI}$ = Boc b)

Ex.228 $R^{VII}$ = H, $R^{VI}$ = Boc c)

Ex.229 $R^{VII} = CH_3$, $R^{VI}$ = H a)

Ex.246 $R^{VI}$ = Boc, $R^{VII} = C_6H_5$

Ex.247 $R^{VI}$ = H, $R^{VII} = C_6H_5$ a)

Ex.256 $R^{VI}$ = Boc, $R^{VII} = C_6H_4$-p-Cl

Ex.257 $R^{VI}$ = H, $R^{VII} = C_6H_4$-p-Cl a)

Ex.258 $R^{VI}$ = Boc, $R^{VII} = C_6H_4$-m-Cl

Ex.259 $R^{VI}$ = H, $R^{VII} = C_6H_4$-m-Cl a) HCl-dioxane, then TFA, $CH_2Cl_2$ Scheme 19
Core 16
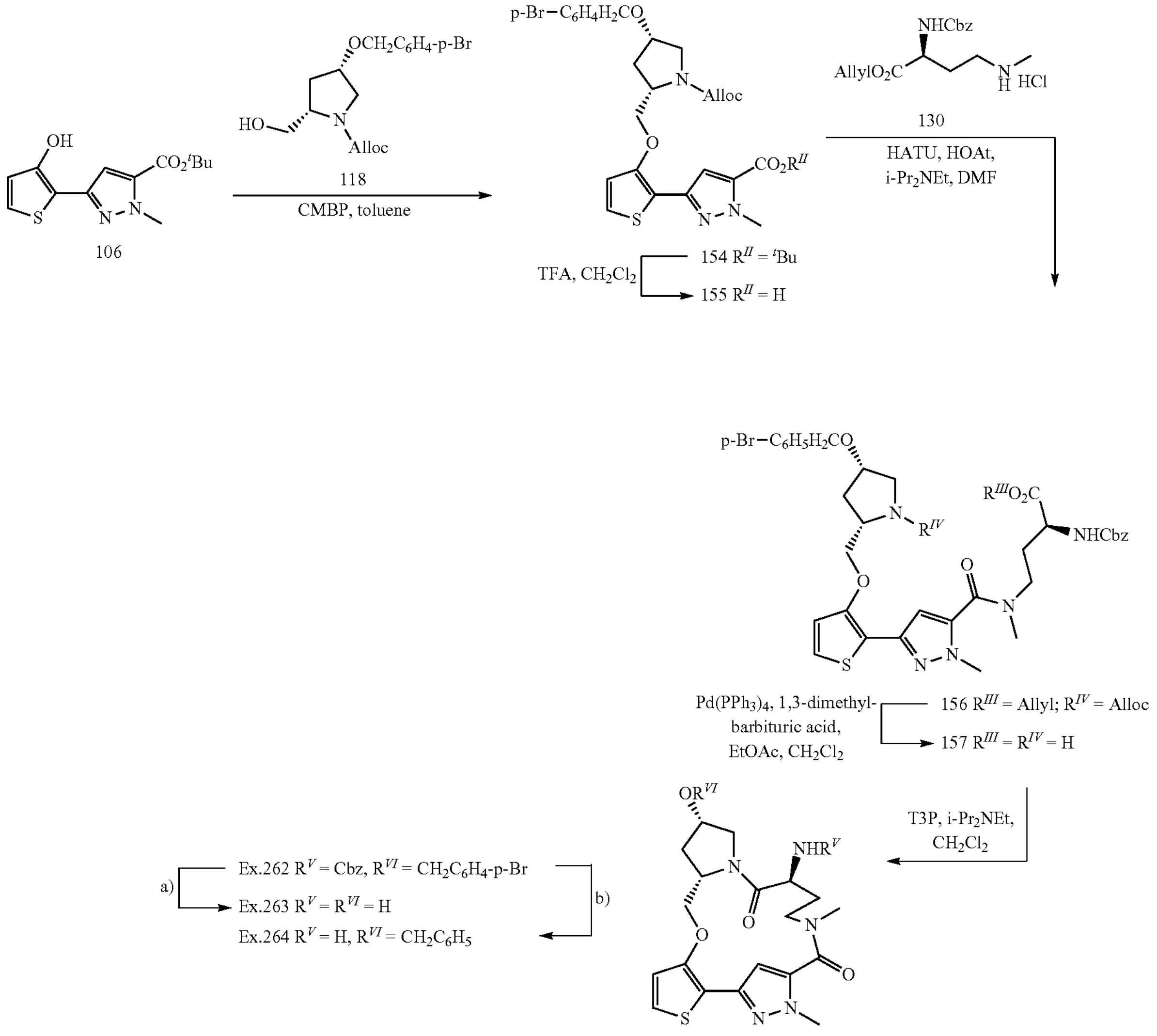
a) $BCl_3$, $CH_2Cl_2$
b) 1. TBAF, THF; 2. $H_2$, $Pd(OH)_2$—C, DMF
Selected examples
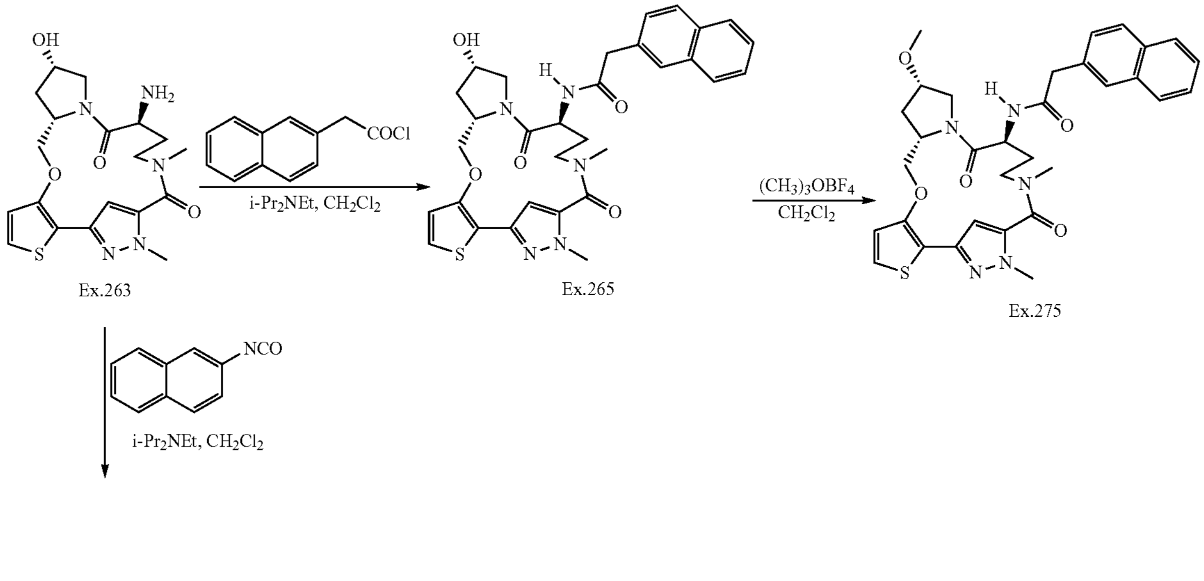

-continued
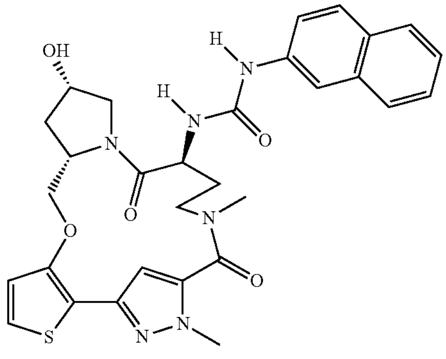
Ex.276
Scheme 20
Core 17
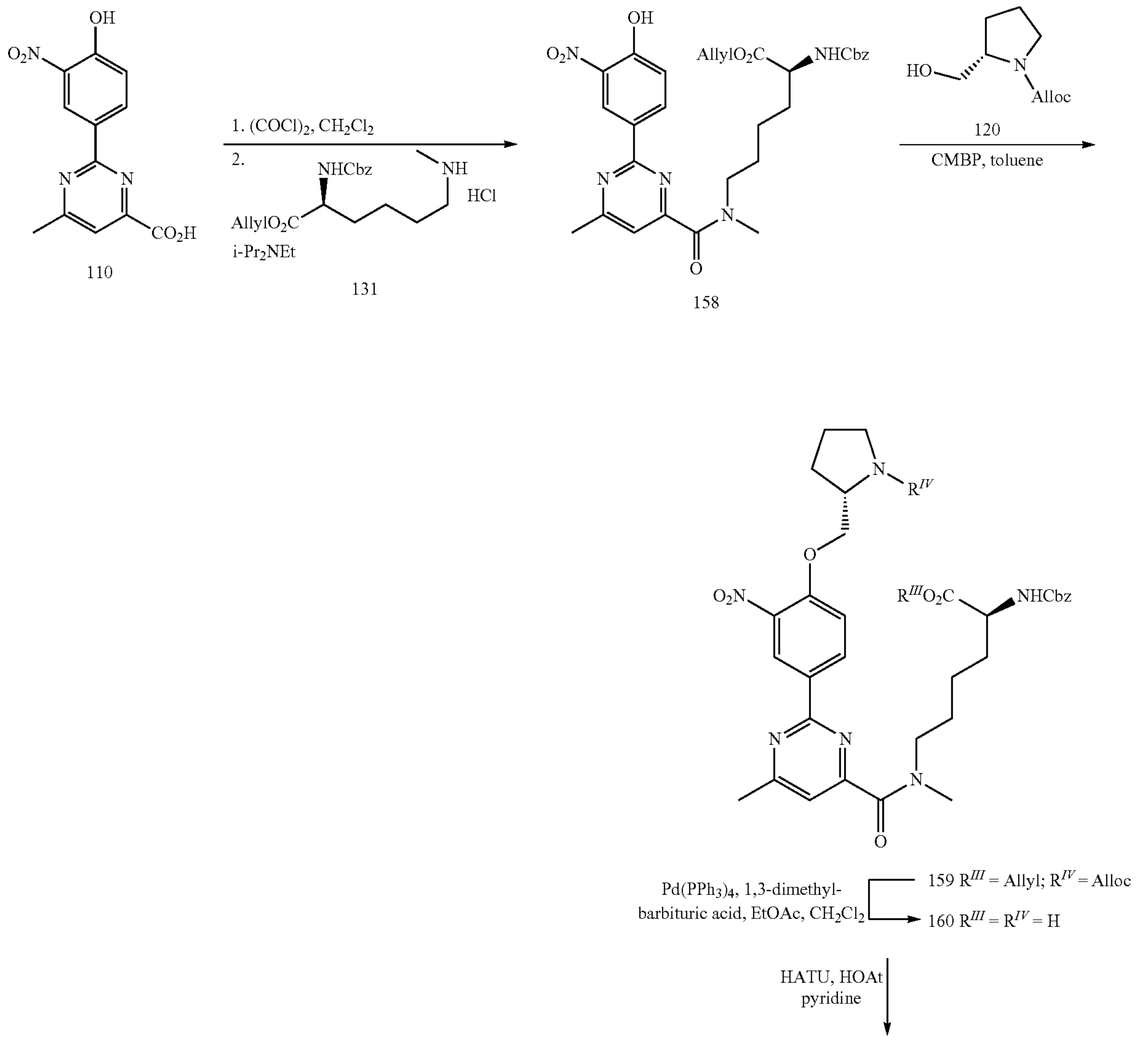
110
131
158
120
159 $R^{III}$ = Allyl; $R^{IV}$ = Alloc
160 $R^{III}$ = $R^{IV}$ = H -continued
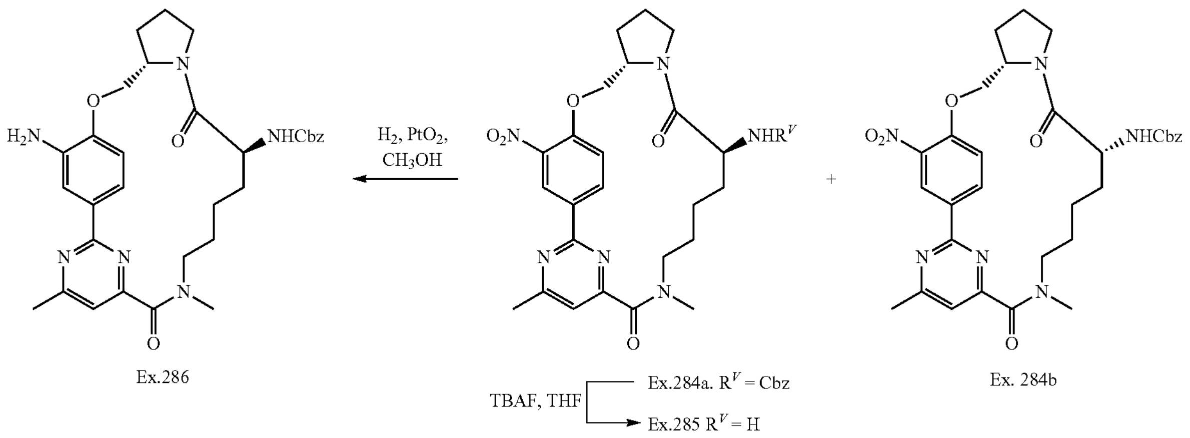
Ex.286
Ex.284a. $R^V$ = Cbz
Ex.285 $R^V$ = H
Ex. 284b
Scheme 21
Core 18
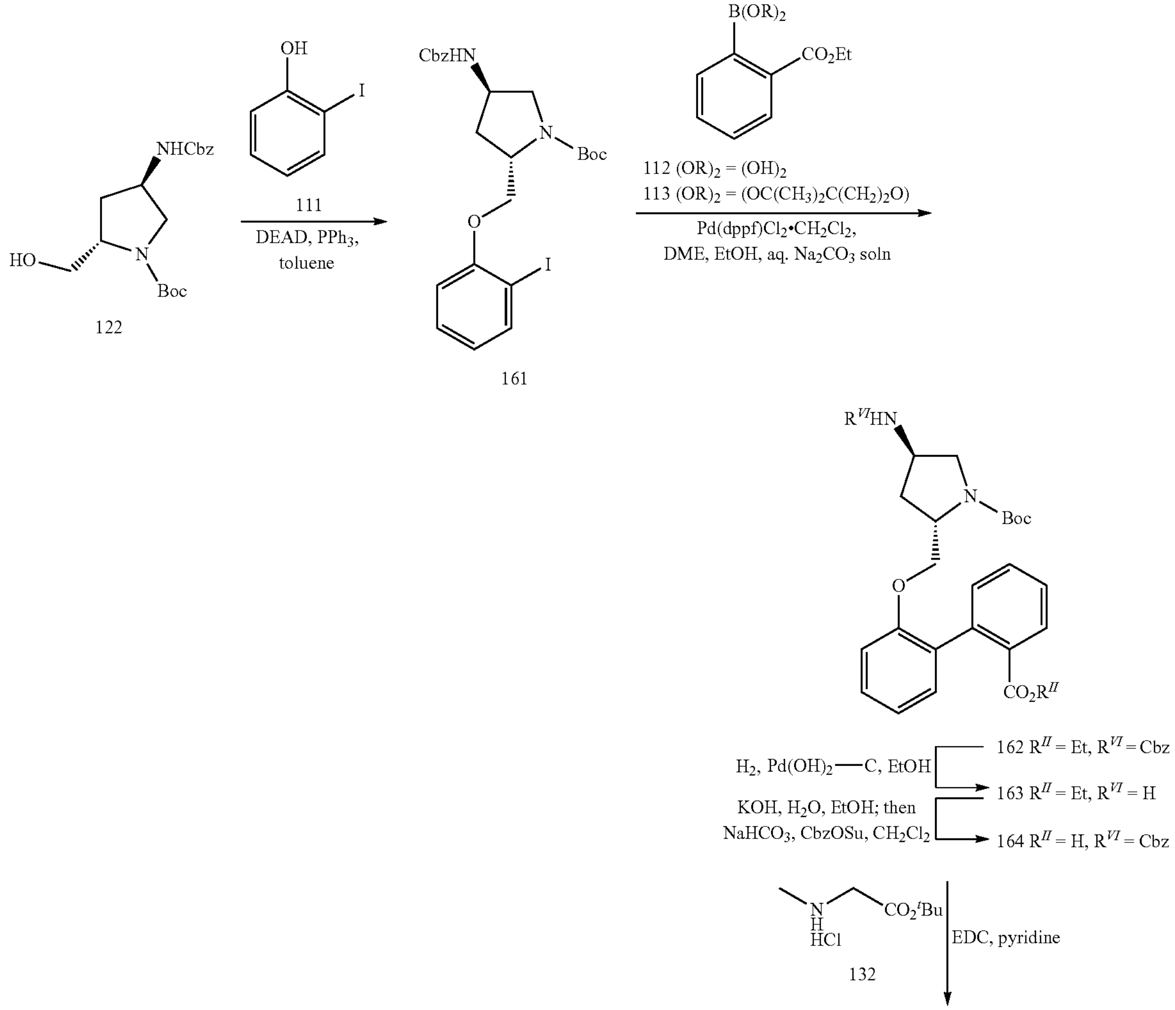
122
111
161
162 $R^{II}$ = Et, $R^{VI}$ = Cbz
163 $R^{II}$ = Et, $R^{VI}$ = H
164 $R^{II}$ = H, $R^{VI}$ = Cbz
132

-continued
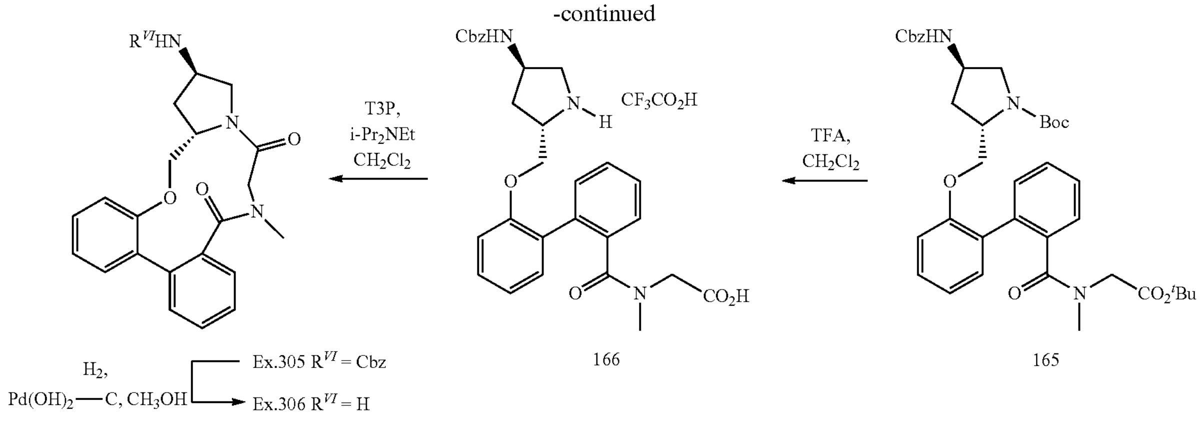
166
165
Scheme 22
Core 19
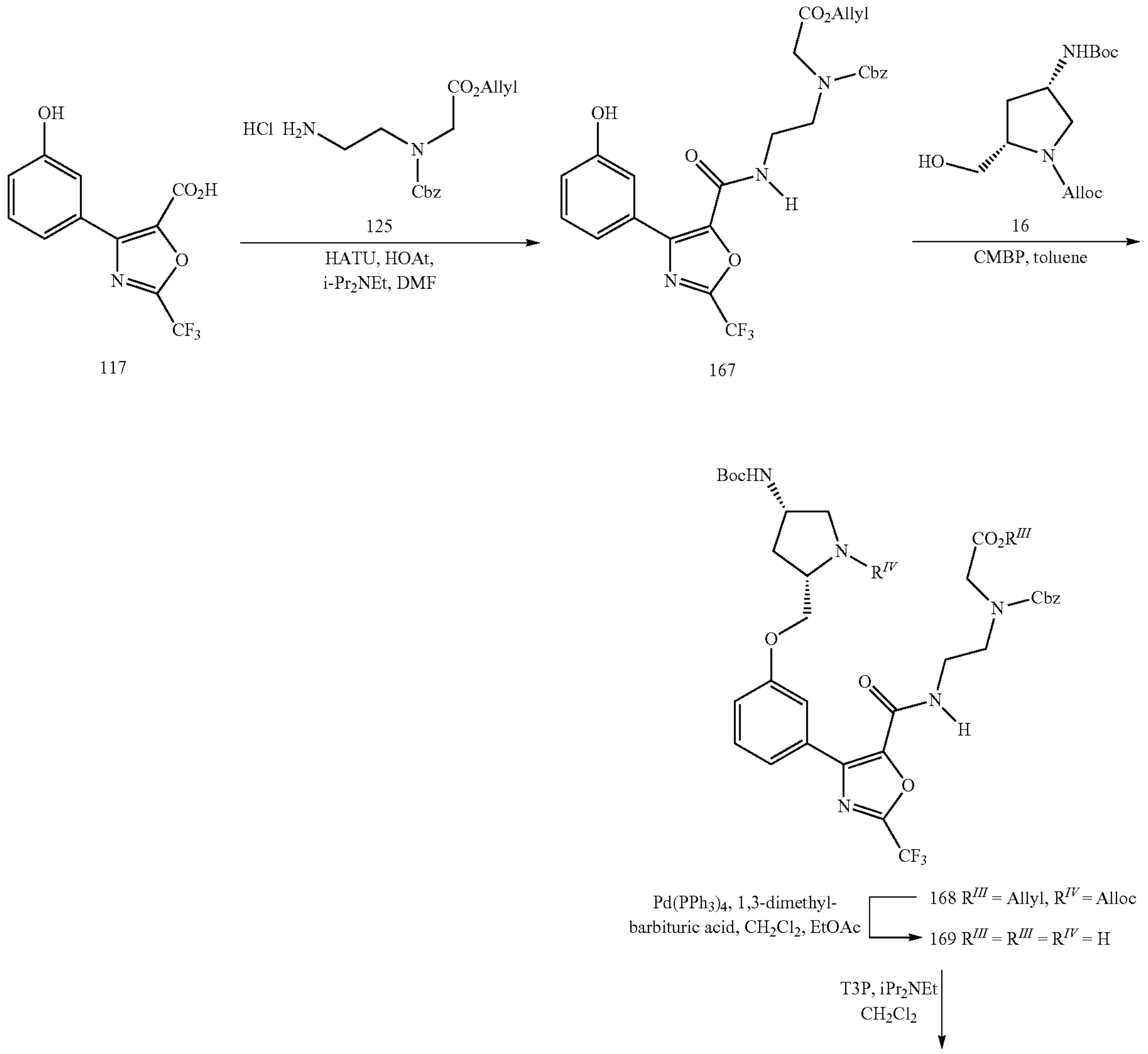
117
125
167
16

-continued
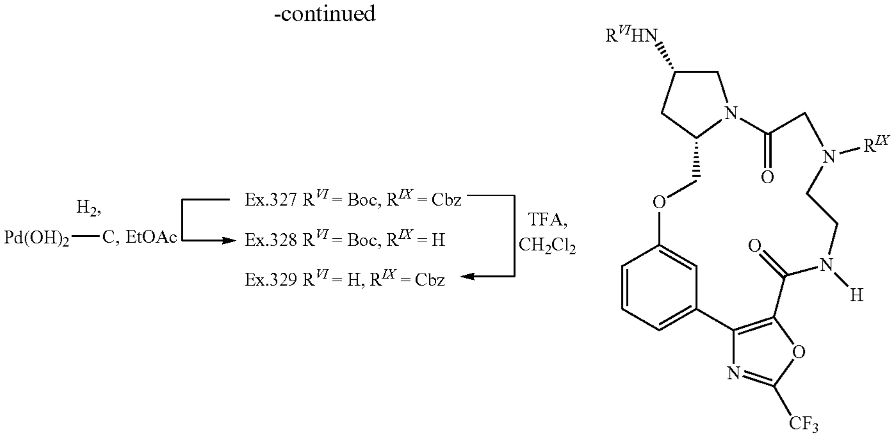
Scheme 23
Structure of Examples
Core 01
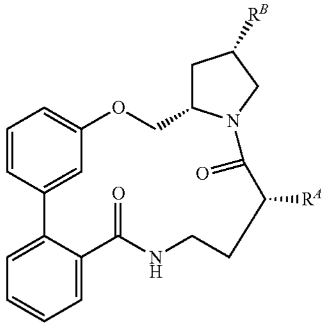
Ex.1 - Ex.#14
and Ex.330 - Ex.340
definition of R-groups
cf. Table 13
Core 02
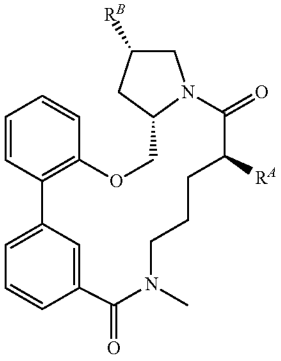
Ex.15 - Ex.40
definition of R-groups
cf. Table 14
-continued
Core 03
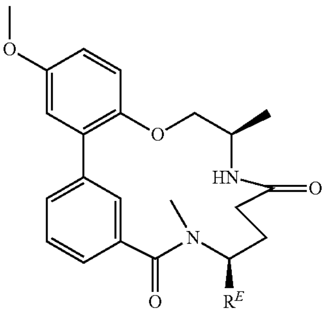
Ex.41 - Ex.67
definition of R-groups
cf. Table 15
Core 04
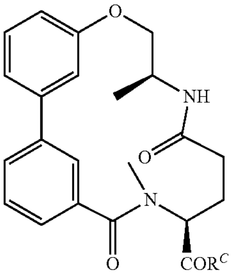
Ex.68 - Ex.89
definition of R-groups
cf. Table 16

-continued
Core 05
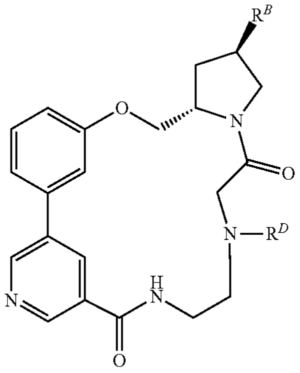
Ex.90 - Ex.114
and Ex.341 - Ex.358
definition of R-groups
cf. Table 17
Core 06
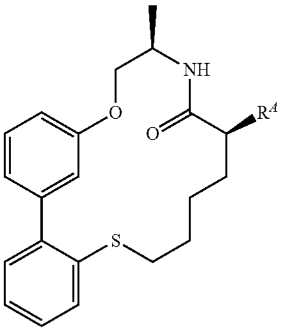
Ex.115 - Ex.128
definition of R-groups
cf. Table 18
Core 07
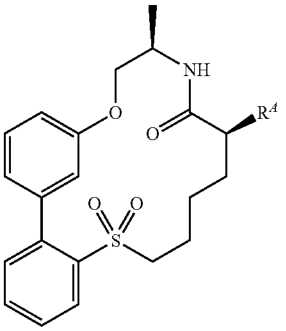
Ex.129 - Ex.142
definition of R-groups
cf. Table 19
Core 08
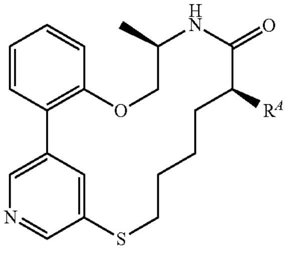
Ex.143 - Ex.167
definition of R-groups
cf. Table 20
-continued
Core 09
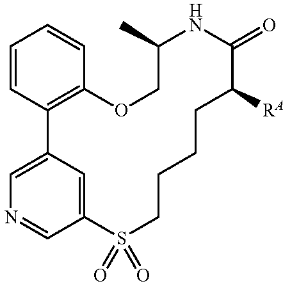
Ex.168 - Ex.192
definition of R-groups
cf. Table 21
Core 10
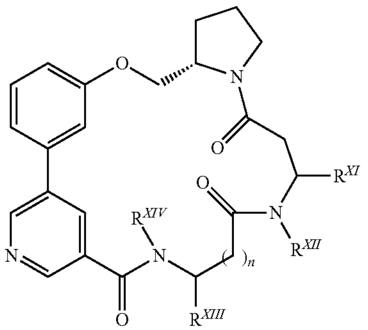
Ex.193a, c-h; Ex.194b
definition of R-groups
cf. Table 22 and Scheme 15
Core 11
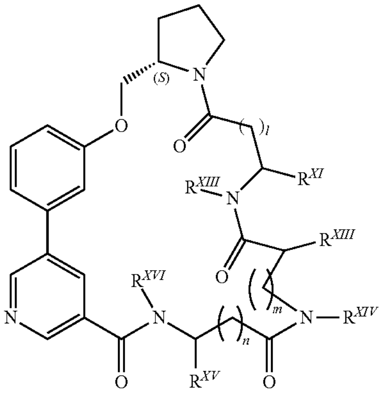
Ex.195a,b,e-h j,
Ex.196c,i,k and Ex.197d
definition of R-groups
cf. Table 23 and Scheme 16

-continued
Core 12
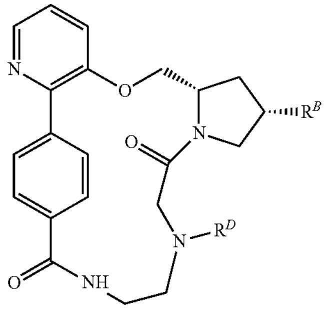
Ex.198 - Ex.219
definition of R-groups
cf. Table 24
Core 13
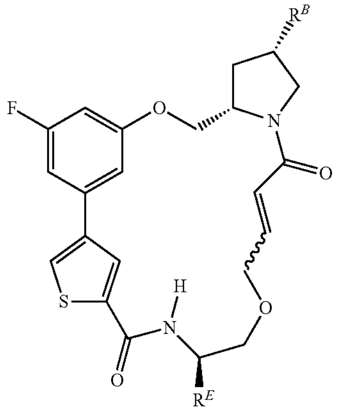
Ex.220
definition of R-groups
cf. Table 25
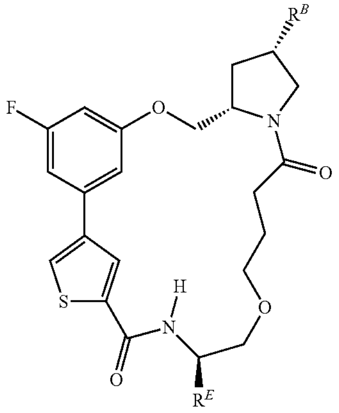
Ex.221 - Ex.226
definition of R-groups
cf. Table 25
-continued
Core 14
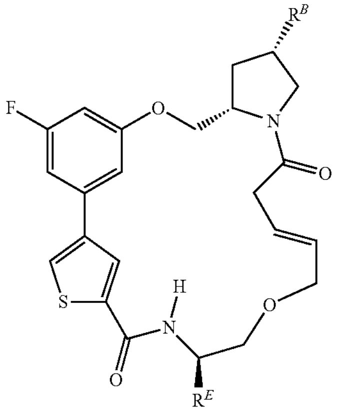
Ex.227 - Ex.241
definition of R-groups
cf. Table 26
Core 15
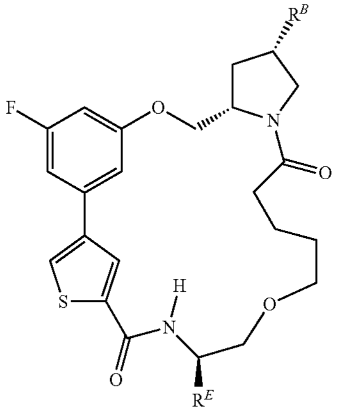
Ex.242 - Ex.261
definition of R-groups
cf. Table 27
Core 16
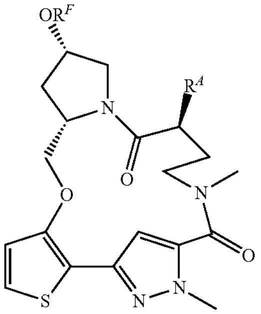
Ex.262 - Ex.283
definition of R-groups
cf. Table 28

-continued

Core 17

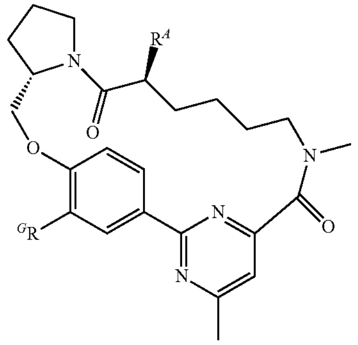

Ex.284a - Ex.304
definition of R-groups
cf. Table 29

Core 18

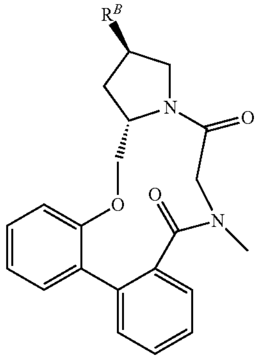

Ex.305 - Ex.326
definition of R-groups
cf. Table 30

Corre 19

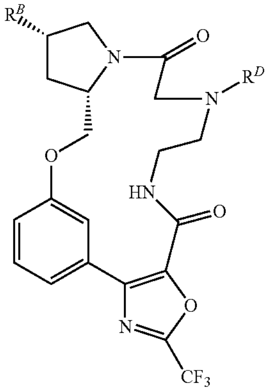

Ex.327 - Ex.329
definition of R-groups
cf. Table 31

Biological and Pharmacological Methods

1. $Ca^{2+}$ Flux Assays for the GPCRs Oxytocin Receptor (OT Receptor), Thyrotropin-Releasing Hormone Receptor (TRH Receptor) and Bombesin Receptor Subtype 3 (BB3 Receptor)

Assays were performed on a FLIPR$^{TETRA}$ fluorometric imaging plate reader (Molecular Devices) with ScreenWorks Version 2 (Molecular Devices) as device operating and data analysis software.

Dose dependent agonist and antagonist activities were determined. Percentage activation and percentage inhibition values were determined.

Percentage activation was determined upon initial addition of the sample compounds followed by 10 minutes' incubation at 25° C. Following compound incubation, reference agonists were added at $EC_{80}$ to determine percentage inhibition.

Reference agonists were purchased from reputable commercial vendors and prepared according to each ligand's specifications. All handling of ligands were done to ensure proper control throughout the experiments.

Example compounds were weighed on a Microbalance (Mettler MX5) and dissolved in 100% DMSO to a final concentration of 2.5 mM and subsequently diluted into the assay buffer.

The assay buffer was a supplemented HBSS (Hank's Balanced Salt Solution). HBSS was supplemented with 20 mM HEPES (4-(2-hydroxyethyl)-piperazin-1-ethansulfonic acid) and 2.5 mM Probenecid (Sigma P8761).

Assay Plate Seeding:

GPCR assays were performed using $Ca^{2+}$ optimized hematopoietic cell lines (rat) with cultures never exceeding 90% confluency. Cells were harvested and seeded (from cultures at less than 90% confluency) at 50000 cells/well for a 96-well plate (12500 cells/well for 384). After seeding, the assay plates were incubated for 45 minutes at room temperature. After room temperature incubation, the assay plates were incubated at 37° C. 5% $CO_2$ for 24 hours prior to assaying.

Calcium Dye Loading:

All GPCR assays were performed using Fluo-8 $Ca^{2+}$ dye. $Ca^{2+}$ dye was prepared at 1× dye concentration in GPCR assay buffer. After 24 hours of incubation, cells were washed with GPCR assay buffer, and then $Ca^{2+}$-dye (100 μL/well) was added.

The plates were incubated for 90 minutes at 30° C. 5% $CO_2$ prior to FLIPR assay.

Agonist Assay:

Compound plates were prepared to add 50 μL/well during the agonist assay mode. During the FLIPR assay, 50 μL/well from the compound plate was diluted 3-fold into the existing 100 μL/well from the dye loading step. Therefore all compounds were prepared as 3× the final concentration desired in the assay.

Antagonist Assay:

After completion of the first single addition assay run, assay plate was removed from the FLIPR Tetra and placed at 25° C. for 7 minutes before antagonist assay.

Using the $EC_{80}$ values determined during the agonist assay, all pre-incubated sample compound and reference antagonist (if applicable) wells were stimulated at the $EC_{80}$ of the reference agonist. As reference ligands for these assays their obvious natural ligands oxytocin (OT), thyrotropin-releasing hormone (TRH) and bombesin (6-14) [BN(6-14)] were used.

After the addition of the reference agonist fluorescence was monitored for 180 sec using FLIPR Tetra.

Data Analysis and Results:

From the FLIPR data, with negative control correction enabled, the maximum statistic for each well was exported and percentage activation relative to $E_{max}$ control was calculated.

The results of the GPCR assays are summarized in Table 32.3 to Table 32.5.

2. Enzyme Assays for the Peptidase Endothelin Converting Enzyme-1 (ECE-1) and for the Cysteine Protease Cathepsin S (CatS)

The assays were performed according to provider's (Ricerca Biosciences, LLC) protocols which in turn are based on literature procedures (for ECE-1 cf.: O. Valdenaire et al., *Eur. J. Biochem.* 1999, 264, 341-349; F. D. Russell, A. P. Davenport, *Circ. Res.* 1999, 84, 891-896; and for CatS: G P Shi et al., *J. Biol. Chem.* 1992, 267, 7258-62; D Brömme et al., *J. Biol. Chem.* 1993 268, 4832-4838.).

Procedures:

i) ECE-1 Assay:

Human recombinant ECE-1 expressed in murine myeloma cells NS0 is used. Test compound and/or vehicle is preincubated with 20 ng/ml enzyme in modified MES buffer pH 6.0 for 15 minutes at 25° C. The reaction is initiated by addition of 10 mM Mca-Arg-Pro-Pro-Gly-Phe-Ser-Ala-Phe-Lys(Dnp) for another 60 minutes' incubation period. Determination of the amount of Mca-Arg-Pro-Pro-Gly-Phe-Ser-Ala formed is read spectrophotometrically at 320 nm/405 nm. Compounds are screened at 10 mM.

Reference Compound: Phosphoramidon ($IC_{50}$ 0.0049 μM)

ii) CatS Assay:

Human recombinant cathepsin S expressed in a murine myeloma NS0 cells is used. Test compound and/or vehicle is preincubated with 0.1 μg/ml enzyme in modified acetate buffer pH 4.5 for 15 minutes at 25° C. The reaction is initiated by addition of 10 mM Z-Leu-Arg-AMC for another 30 minutes' incubation period. Determination of the amount of AMC formed is read spectrofluorimetrically at 360 nm/465 nm. Compounds are screened at 10 mM.

Reference Compound: E-64 ($IC_{50}$ 0.0014 μM)

Data Analysis:

$IC_{50}$ values were determined by a non-linear, least squares regression analysis using MathIQ™ (ID Business Solutions Ltd., UK). Inhibition constants K were calculated according to the equation of Cheng and Prusoff (Y. Cheng, W. H. Prusoff, *Biochem. Pharmacol.* 1973, 22, 3099-3108) using the observed $IC_{50}$ of the tested compound, the concentration of radioligand employed in the assay, and the historical values for the $K_D$ of the ligand. The Hill coefficient (nH), defining the slope of the competitive binding curve, was calculated using MathIQ™.

The results of the assays are summarized in Table 32.1 and Table 32.2.

3. Human LTB4 Receptor Cell-Based Assay

CHO mito-i-Photina® cells (Axxam SpA) stably expressing the human leukotriene B4 receptor (LTB4R) were used for monitoring activation of the target LTB4R, a GPCR (Gαq), by measuring the flash luminescence of $Ca^{2+}$ sensitive photoprotein as reporter system with $FLIPR^{TETRA}$ screening instrumentation (Molecular Devices) upgraded with an ICCD Camera (MDC). For data quality check and data analysis a Genedata Screener 10.0.3 was used, and for curve fitting of reference agonist and antagonist GraphPad Prism Software.

The reference agonist LTB4 and antagonist U-75302 were purchased from reputable commercial vendors and prepared according to each ligand's specifications. All handling of ligands were done to ensure proper control throughout the experiments.

The steps of the implemented workflow and data analysis are mainly as follows:

Assay Plate Seeding:

mito-1-Photina cells are seeded (10000 c/w in 384 MTP; in complete medium 25 μL/well) for 24 hours, removed from the incubator, equilibrated at room temperature for 1 h, freed from the growth medium, loaded with 30 μL/well of Tyrode's buffer containing 10 μM coelenterazine, and incubated for 3 hours at rt.

Agonist/Antagonist Assay:

All compounds were tested at 10 μM with triplicate data points.

After incubation, the volume in all the wells is flattened to 20 μL by aspiration with CyBi®-Vario pipettor. The First Injection (10 μL of test compounds or reference antagonist U-75302 in Tyrode's buffer+DMSO 0.5%) is performed by the $FLIPR^{TETRA}$ and the kinetic response is monitored over a period of 120 seconds. Incubation at rt for 10 min. is followed by the Second Injection (15 μL of LTB4 at $EC_{80}$ in Tyrode's buffer) and monitoring of the kinetic response over a period of 120 seconds.

Data Analysis and Results:

The possible kinetic response is divided into two distinct phases: Monitoring the kinetic response after the First Injection is indicated as Compound Addition (CA) and measures the agonistic activity of compounds; monitoring the kinetic response after the Second Injection is indicated as Target Activation (TA) and measures the antagonistic activity of a compound.

The activity determination ($IC_{50}$ determination) experiment is performed using LTB4 as agonist (100 nM corresponding to $EC_{80}$). Selected compound are tested in 8 doses intraplate dose response with quadruplicate data points.

The results of the LTB4R assays are summarized in Table 32.6.

4. Antimicrobial Assays

The antimicrobial activities of the compounds were determined in 96-well plates (Greiner, polystyrene) by the standard NCCLS broth microdilution method (National Committee for Clinical Laboratory Standards 1993. Methods for dilution antimicrobial susceptibility tests for bacteria that grow aerobically, 3rd ed. Approved standard M7-A6. National Committee for Clinical laboratory standards, Wayne, Pa.) with slight modifications. Inocula of the microorganisms were diluted into Mueller-Hinton II (MH, cation adjusted) broth+0.002% P-80 and compared with a 0.5 McFarland standard to give appr. $10^6$ colony forming units (CFU)/mL. Aliquots (50 μl) of inoculate were added to 50 μl of MH broth+0.002% P-80 containing the compounds in serial two-fold dilutions. The following microorganisms were used to determine antibiotic selectivity of the compounds: *S. pneumoniae* DSM 20566 11A11, 3313A6, 704CG4B21, 82BERG72; *S. aureus* ATCC 29213, ATCC 25923, DSM 11729, DSM 46320, *S. aureus* 39. Antimicrobial activities of the compounds were expressed as the minimal inhibitory concentration (MIC) in μg/mL at which no visible growth was observed after 18-20 hours of incubation at 36° C.

The results of the antimicrobial assays are summarized in Table 32.7 and Table 32.8.

5. Plasma and Metabolic Stability Assays

Example compounds were dissolved in DMSO/$H_2O$ 90:10 to a final concentration of 10 mM for plasma stability determination and metabolic stability determination.

The assays were conducted according to literature precedents (F. P. Guengerich, *Analysis and Characterization of Enzymes*; in: *Principles and Methods of Toxicology*, A. W. Hayes (Ed.) Raven Press: New York, 1989, 777-813; R. Singh et al., *In vitro metabolism of a potent HIV-protease inhibitor* (141*W*94) *using rat, monkey and human liver S9, Rapid Commun. Mass Spectrom.* 1996, 10, 1019-1026).

Results of the stability assays are listed in Table 33 below.

Plasma Stability Assay

Human plasma (Blutspendedienst SRK, Basel) and CD-1 mouse plasma (mixed gender pool >50 animals, Innovative Research, Calif., USA) are both sodium citrate stabilized.

The assay is performed in triplicates at 10 μM compound concentration and 37° C. Samples are taken at 0, 15, 30, 60, 120 and 240 minutes and stopped by precipitation with 3 volumes of acetonitrile/formic acid 98:2 and shaking (2 minutes, 600 rpm) followed by filtration (−20 mm Hg). The filtrate is collected. The filtrate (100 μL) is evaporated and reconstituted in the suitable solvent (cf. Table 33) to be analyzed by HPLC/MS/MS. The resulting peak area counts are expressed in percent of the 0 value and used to determine the endpoint stability in % and the half life T in minutes. In order to monitor assay integrity the degradation of propantheline is assayed with every experimental set.

Metabolic Stability Assay

Microsomes from a human 50 donor mixed gender pool and 1:1 mixtures of microsomes from CD-1 mouse single-gender pools are purchased from Celsis (Belgium). The enzymatic reaction is performed in a buffer containing an NADPH regeneration system and microsomes with the following end concentrations: 100 mM potassium phosphate buffer (all from Sigma), 1 mg/mL glucose-6-phosphate, 1 mg/mL β-nicotinamide adenine dinucleotide phosphate (NADP), 0.65 mg/mL magnesium chloride, 0.8 units/mL of glucose-6-phosphate dehydrogenase (prediluted with 5 mM citrate buffer), 10 μM compound and 1 mg/ml microsomal protein. Compounds are incubated at 37° C. in duplicates and samples are taken after 0, 5, 10, 20 and 60 minutes. After acetonitrile precipitation (3 volumes), shaking (2 minutes, 600 rpm) followed by centrifugation (10 minutes, 3200 g), the supernatant is dried reconstituted in the suitable solvent (cf. Table 33) and analyzed by HPLC/MS/MS. Metabolic turnover is expressed in % of the initial 0 minutes value and half life T½ (min) is calculated. Verapamil for human and propranolol for mouse are used as reference and are assayed with every experimental set.

TABLE 32.1

| Endothelin Converting Enzyme-1 Assay | | |
|---|---|---|
| No | [% Inhibition at 10 μM] | IC50 [μM] |
| Ex. 18 | 98 | 3.01 |
| Ex. 25 | 97 | 4.28 |
| Ex. 26 | 98 | 4.07 |

TABLE 32.2

| Cathepsin S Assay | | |
|---|---|---|
| No | [% Inhibition at 10 μM] | IC50 [μM] |
| Ex. 18 | 82 | 3.65 |
| Ex. 20 | 45 | 14.7 |
| Ex. 21 | 75 | n.d. |
| Ex. 24 | 55 | n.d. |
| Ex. 25 | 87 | 3.18 |
| Ex. 26 | 81 | 3.83 |
| Ex. 27 | 50 | n.d. |
| Ex. 28 | 57 | n.d. |

TABLE 32.3

| TRH (Thyrotropin-releasing hormone) receptor Assay | | |
|---|---|---|
| No | Antagonist activity [% Inhibition at 10 μM] | Antagonist activity IC50 [μM] |
| Ex. 7 | 91 | 1.4 |
| Ex. 332 | 29 | n.d. |

TABLE 32.3-continued

| TRH (Thyrotropin-releasing hormone) receptor Assay | | |
|---|---|---|
| No | Antagonist activity [% Inhibition at 10 μM] | Antagonist activity IC50 [μM] |
| Ex. 333 | 35 | n.d. |
| Ex. 334 | 40 | n.d. |
| Ex. 335 | 34 | n.d. |
| Ex. 336 | 48 | 8.2 |

TABLE 32.4

| OT (Oxytocin) receptor Assay | | |
|---|---|---|
| No | Antagonist activity [% Inhibition at 10 μM] | Antagonist activity IC50 [μM] |
| Ex. 94 | 58 | 3.0 |
| Ex. 96 | 60 | 1.2 |
| Ex. 100 | 57 | 4.6 |
| Ex. 101 | 69 | 2.6 |
| Ex. 103 | 77 | 6.9 |

TABLE 32.5

| BB3 (Bombesin) receptor Assay | | |
|---|---|---|
| No | Agonist activity [% activation at 12.5 μM] | Agonist activity EC50 [nM] |
| Ex. 265 | 84 | 630 |
| Ex. 267 | 61 | >50'000 |
| Ex. 275 | 60 | 780 |
| Ex. 276 | 75 | 480 *) |
| Ex. 282 | 39 | >50'000 |

*) Ca 75% of Bombesin efficacy

TABLE 32.6

| LTB4 (Leukotriene B4) receptor Assay | | |
|---|---|---|
| No | Antagonist activity [% inhibition at 10 μM] | Antagonist activity IC50 [μM] |
| Ex. 14 | 46 | 39.4 |
| Ex. 50 | 100 | 1.97 |
| Ex. 116 | 49 | 15.4 |
| Ex. 119 | 47 | 14.2 |
| Ex. 144 | 41 | 40.9 |

TABLE 32.7

| Antimicrobial activity | | | | | | |
|---|---|---|---|---|---|---|
| No | *S. aureus* ATCC 29213 MIC [μg/mL] | *S. aureus* 39 MIC [μg/mL] | *S. aureus* ATCC 25923 MIC [μg/mL] | *S. aureus* DSM 11729 MIC [μg/mL] | *S. aureus* DSM 46320 MIC [μg/mL] | *S. pneumoniae* DSM 20566 MIC [μg/mL] |
| Ex. 2 | 8-16 | 4 | 16 | 8-16 | 16->16 | 8 |
| Ex. 91 | 2-4 | 8 | 4 | 2 | 4 | >16 |
| Ex. 94 | 4 | 8 | 8 | 4 | 8 | >16 |

*S. aureus*: *Staphylococcus aureus*;

*S. pneumoniae*: *Streptococcus pneumoniae*

TABLE 32.8

| Antimicrobial activity | | | | | |
|---|---|---|---|---|---|
| No | *S. pneumoniae* DSM 20566 MIC [μg/mL] | *S. pneumoniae* 11A11 MIC [μg/mL] | *S. pneumoniae* 3313A6 MIC [μg/mL] | *S. pneumoniae* 704CG4B21 MIC [μg/mL] | *S. pneumoniae* 82BERG72 MIC [μg/mL] |
| Ex. 247 | 16 | 16 | 16 | 16 | 8 |
| Ex. 257 | 8 | 8 | 8 | 8 | 2 |
| Ex. 259 | 8 | 16 | 8 | 8 | 4 |

*S. pneumoniae*: *Streptococcus pneumonia*

TABLE 33

Plasma Stability and Metabolic Stability Assays of Selected Examples (continued on the following pages)

| | | Plasma Stability | | | | Metabolic Stability | | | |
|---|---|---|---|---|---|---|---|---|---|
| No | Solvent for reconstitution | T ½ [min] hum | 240 min hum [% remain.] | T ½ [min] mouse/ (rat) | 240 min mouse/ (rat) [% remain.] | T ½ [min] hum | 60 min hum [% remain.] | T ½ [min] mouse/ (rat) | 60 min mouse/ (rat) [% remain.] |
| Ex. 42 | B | >240 | 91 | >240 | 100 | >60 | 100 | >60 | 100 |
| Ex. 43 | B | >240 | 97 | >240 | 63 | >60 | 100 | >60 | 83 |
| Ex. 44 | B | >240 | 100 | >240 | 83 | >60 | 68 | >60 | 77 |
| Ex. 45 | C | >240 | 76 | 190 | 46 | >60 | 66 | >60 | 73 |
| Ex. 46 | B | >240 | 100 | >240 | 78 | 32 | 26 | >60 | 71 |
| Ex. 47 | B | >240 | 99 | >240 | 86 | >60 | 83 | >60 | 100 |
| Ex. 49 | B | >240 | 95 | >240 | 76 | >60 | 100 | >60 | 92 |
| Ex. 50 | B | >240 | 100 | n.d. | n.d. | >60 | 53 | 40 | 34 |
| Ex. 51 | B | >240 | 100 | >240 | 80 | >60 | 71 | >60 | 69 |
| Ex. 52 | B | >240 | 99 | >240 | 95 | >60 | 100 | >60 | 78 |
| Ex. 53 | 1) | n.d. | n.d. | >240 | 86 | >60 | 100 | >60 | 92 |
| Ex. 54 | B | >240 | 100 | >240 | 100 | >60 | 60 | >60 | 82 |
| Ex. 55 | B | n.d. | n.d. | >240 | 80 | >60 | 97 | >60 | 98 |
| Ex. 57 | B | >240 | 100 | >240 | 74 | >60 | 100 | >60 | 100 |
| Ex. 58 | D | >240 | 95 | n.d. | n.d. | >60 | 87 | >60 | 70 |
| Ex. 59 | B | >240 | 74 | >240 | 67 | >60 | 94 | >60 | 81 |
| Ex. 60 | C | >240 | 97 | n.d. | n.d. | 8 | 0 | 25 | 19 |
| Ex. 69 | 1) | >240 | 91 | 200 | 45 | >60 | 100 | >60 | 100 |
| Ex. 70 | 1) | >240 | 99 | >240 | 61 | >60 | 100 | >60 | 77 |
| Ex. 71 | B | >240 | 100 | >240 | 92 | >60 | 100 | >60 | 89 |
| Ex. 72 | B | >240 | 100 | >240 | 65 | 22 | 14 | 35 | 30 |
| Ex. 73 | B | >240 | 89 | n.d. | n.d. | 2 | 0 | 1 | 0 |
| Ex. 74 | C | >240 | 100 | >240 | 67 | 7 | 1 | 3 | 0 |
| Ex. 75 | B | >240 | 93 | >240 | 55 | 21 | 12 | 53 | 48 |
| Ex. 76 | D | >240 | 88 | n.d. | n.d. | 16 | 4 | 15 | 9 |
| Ex. 77 | B | >240 | 96 | >240 | 85 | 44 | 41 | >60 | 75 |
| Ex. 78 | B | >240 | 100 | >240 | 86 | >60 | 99 | >60 | 92 |
| Ex. 79 | B | >240 | 100 | >240 | 60 | >60 | 95 | >60 | 73 |
| Ex. 80 | 1) | >240 | 90 | >240 | 84 | 19 | 6 | 24 | 19 |
| Ex. 81 | 2) | >240 | 88 | >240 | 100 | >60 | 100 | >60 | 97 |
| Ex. 83 | 3) | >240 | 85 | >240 | 93 | >60 | 85 | >60 | 96 |
| Ex. 84 | B | >240 | 99 | >240 | 56 | >60 | 97 | >60 | 71 |
| Ex. 85 | D | >240 | 100 | >240 | 88 | >60 | 100 | >60 | 80 |
| Ex. 86 | B | n.d. | n.d. | >240 | 60 | n.d. | n.d. | >60 | 71 |
| Ex. 87 | B | >240 | 100 | >240 | 90 | 27 | 17 | 60 | 63 |

TABLE 33-continued

Plasma Stability and Metabolic Stability Assays of Selected Examples (continued on the following pages)

| | | Plasma Stability | | | | Metabolic Stability | | | |
|---|---|---|---|---|---|---|---|---|---|
| No | Solvent for reconstitution | T ½ [min] hum | 240 min hum [% remain.] | T ½ [min] mouse/ (rat) | 240 min mouse/ (rat) [% remain.] | T ½ [min] hum | 60 min hum [% remain.] | T ½ [min] mouse/ (rat) | 60 min mouse/ (rat) [% remain.] |
| Ex. 88 | 1) | n.d. | n.d. | >240 | 81 | 56 | 49 | >60 | 62 |
| Ex. 89 | C | >240 | 100 | >240 | 76 | 13 | 8 | 10 | 2 |

1) Reconstitution solvent for plasma stabilty determination B; reconstitution solvent for metabolic stability determination: C 2) Reconstitution solvent for plasma stabilty determination; human: D; mouse B; reconstitution solvent for metabolic stability determination: D 3) Reconstitution solvent for plasma stability determination: B; reconstitution solvent for metabolic stability determination; human D; mouse B.

Reconstitution solvents:

Solvent A: DPBS (100 mg $CaCl_2$, 100 mg $MgCl_2$•$6H_2O$, 200 mg KCl, 200 mg $KH_2PO_4$, 8000 mg NaCl and 2160 mg $Na_2HPO_4$•$7H_2O$ to be made up to 1000 mL by addition of $H_2O$);

Solvent B: $H_2O/CH_3CN$ 95:5 (v/v) + 0.2% formic acid;

Solvent C: DMSO/($H_2O/CH_3CN$ 95:5)/DPBS 50:45:5 + 2% formic acid;

Solvent D: $H_2O/CH_3CN$ 1:1 (v/v) + 5% DPBS + 0.2% formic acid

The invention claimed is:

1. A compound consisting of a cyclic arrangement of the building blocks A, B and C and represented by the general formula I

I

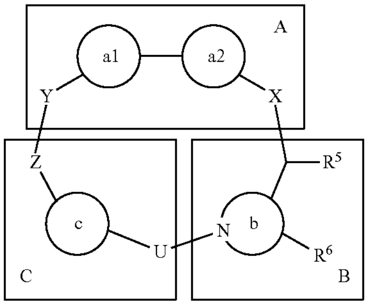

wherein building block A ("Template") is represented by

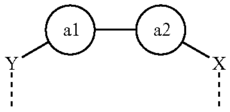

building block B ("Modulator") is represented by

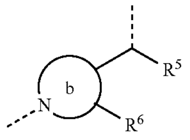

building block C ("Bridge") is represented by

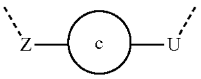

which in turn consists of

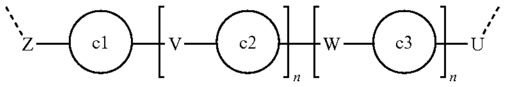

and wherein

X represents a divalent radical selected from the group of

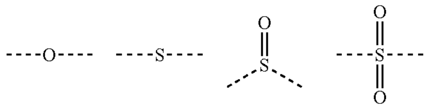

Z represents a divalent or trivalent radical selected from the group of

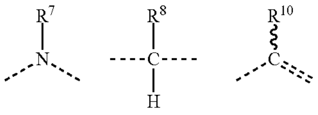

forming an integral part of the

Y-Z connectivity which in turn represents a divalent radical selected from the group of

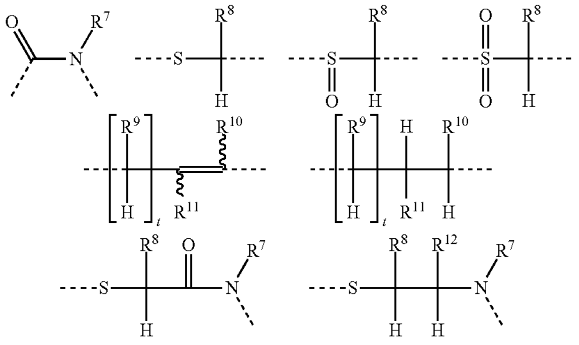

-continued

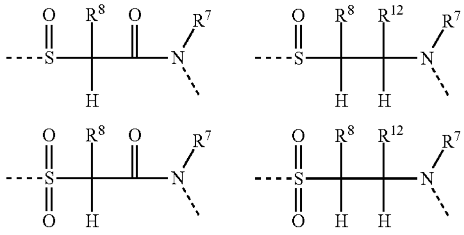

U represents a divalent radical selected from the group of

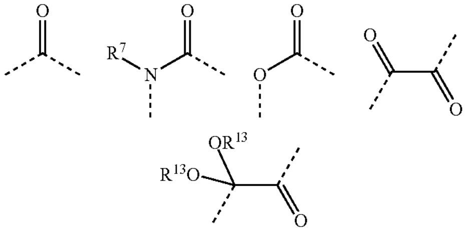

V and W are representing independently a divalent radical selected from the group of

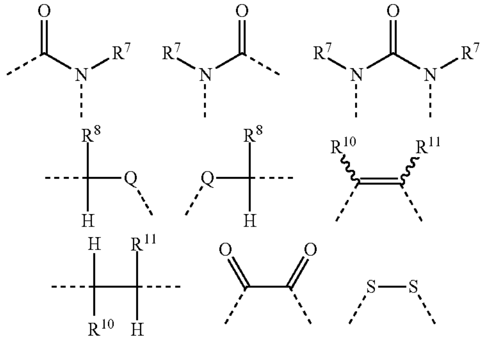

and wherein said Template A is a bivalent radical consisting of all possible combinations of structure $A_BA_C$ of which $A_B$ is selected from the group of $A_B1$

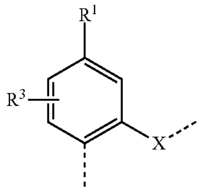

$A_B2$

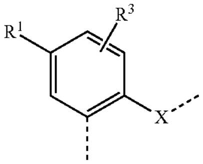

-continued $A_B3$

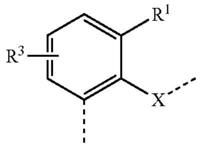

$A_B4$

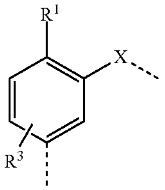

$A_B5$

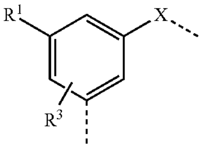

$A_B6$

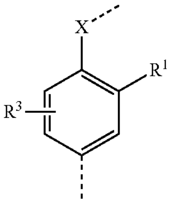

$A_B7$

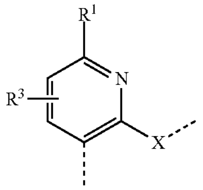

$A_B8$

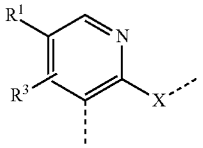

$A_B9$

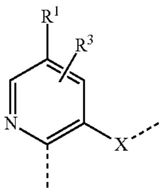

$A_B10$

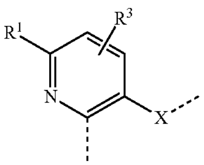

-continued
$A_B11$
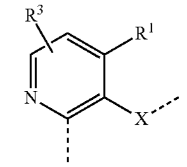
$A_B12$
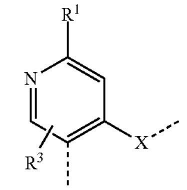
$A_B13$
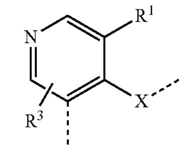
$A_B14$
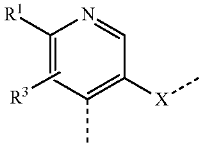
$A_B15$
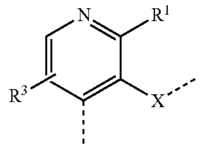
$A_B16$
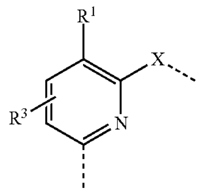
$A_B17$
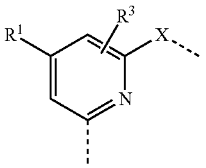
$A_B18$
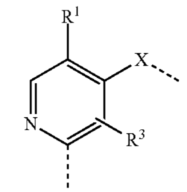
$A_B19$
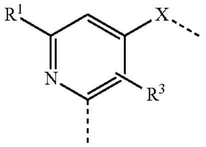
-continued
$A_B20$
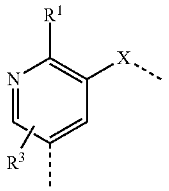
$A_B21$
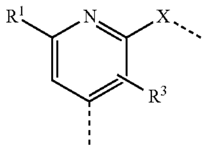
$A_B22$
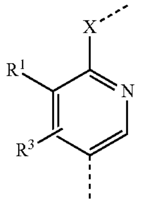
$A_B23$
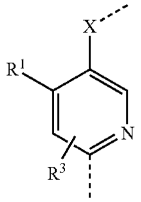
$A_B24$
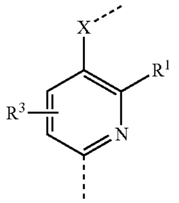
$A_B25$
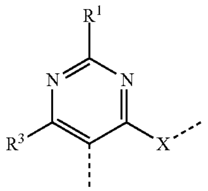
$A_B26$
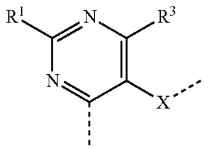
$A_B27$
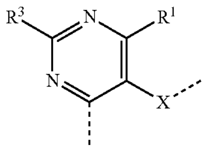

-continued
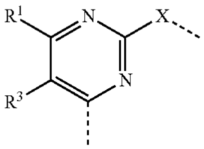
$A_B$28
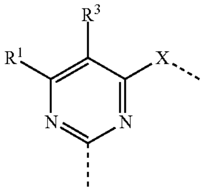
$A_B$29
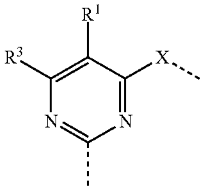
$A_B$30
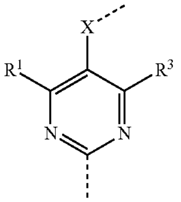
$A_B$31
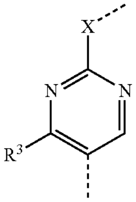
$A_B$32
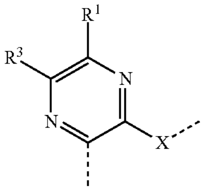
$A_B$33
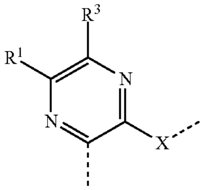
$A_B$34
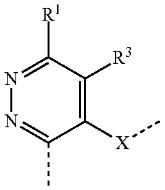
$A_B$35
-continued
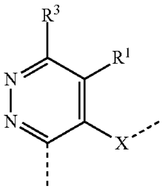
$A_B$36
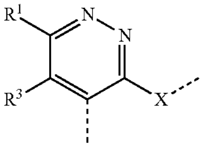
$A_B$37
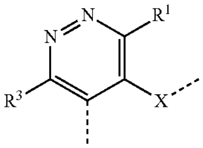
$A_B$38
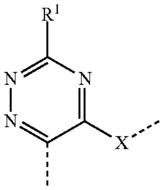
$A_B$39
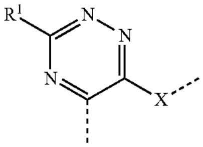
$A_B$40
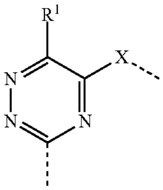
$A_B$41
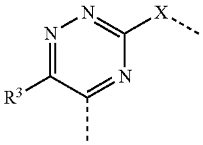
$A_B$42
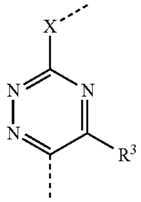
$A_B$43

-continued
$A_B$44
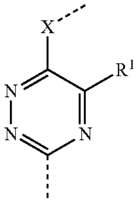
$A_B$45
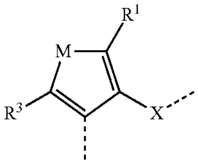
$A_B$46
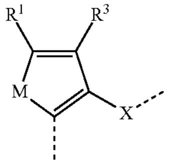
$A_B$47
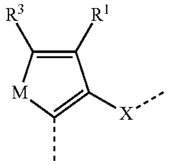
$A_B$48
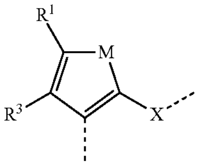
$A_B$49
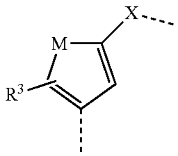
$A_B$50
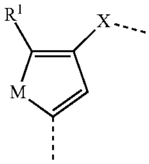
$A_B$51
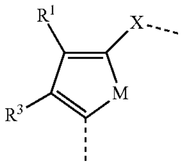
$A_B$52
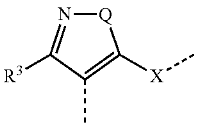
-continued
$A_B$53
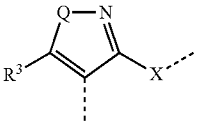
$A_B$54
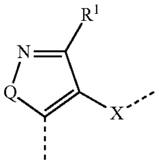
$A_B$55
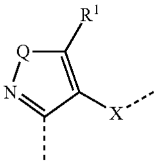
$A_B$56
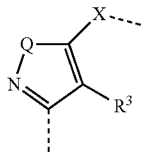
$A_B$57
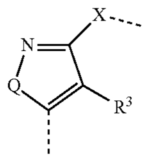
$A_B$58
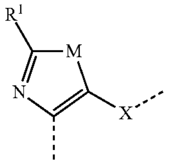
$A_B$59
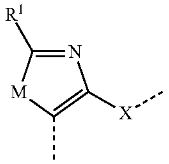
$A_B$60
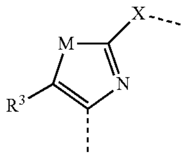
$A_B$61
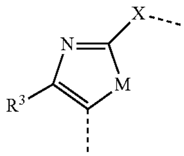

-continued
$A_B62$
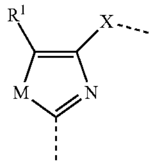
$A_B63$
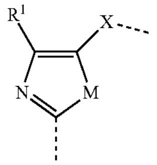
$A_B64$
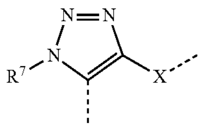
$A_B65$
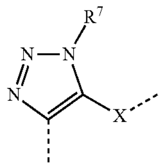
and $A_C$ is selected from the group of
$A_C1$
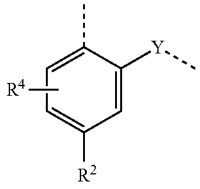
$A_C2$
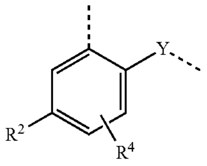
$A_C3$
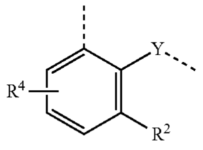
$A_C4$
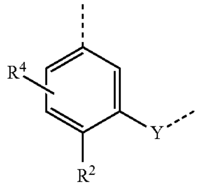
-continued
$A_C5$
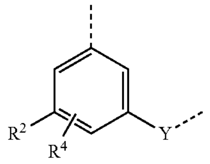
$A_C6$
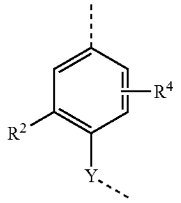
$A_C7$
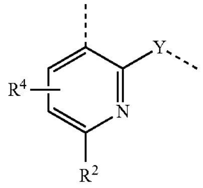
$A_C8$
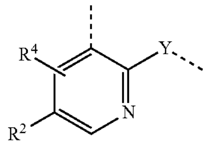
$A_C9$
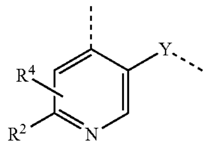
$A_C10$
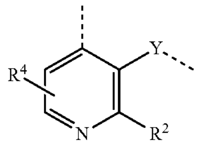
$A_C11$
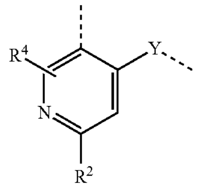
$A_C12$
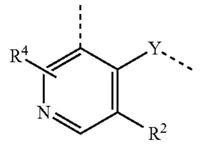
$A_C13$
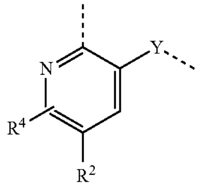

$A_C$14
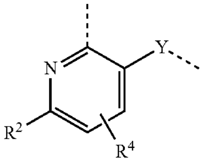
$A_C$15
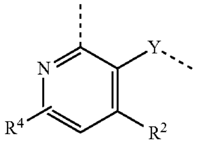
$A_C$16
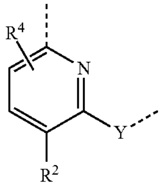
$A_C$17
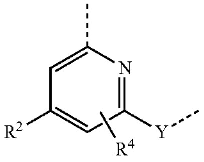
$A_C$18
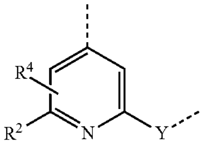
$A_C$19
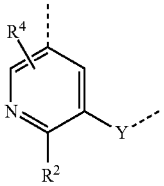
$A_C$20
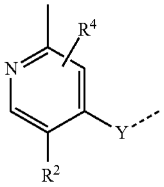
$A_C$21
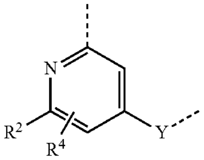
$A_C$22
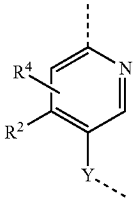
$A_C$23
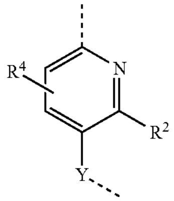
$A_C$24
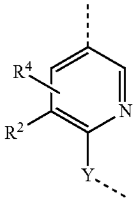
$A_C$25
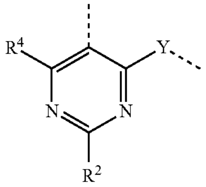
$A_C$26
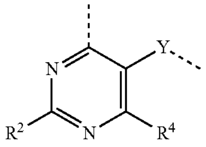
$A_C$27
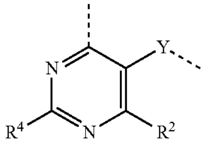
$A_C$28
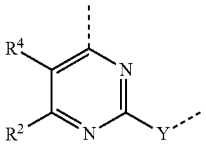
$A_C$29
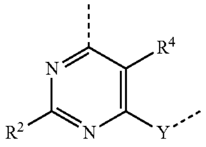

-continued
$A_C$30
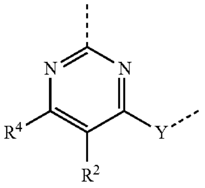
$A_C$31
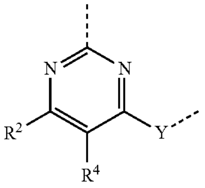
$A_C$32
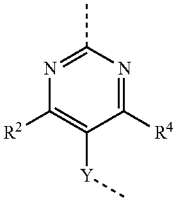
$A_C$33
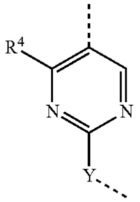
$A_C$34
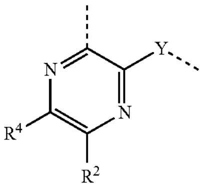
$A_C$35
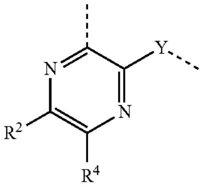
$A_C$36
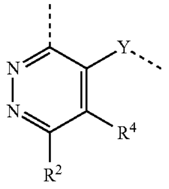
$A_C$37
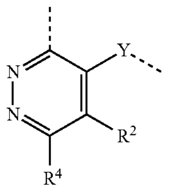
-continued
$A_C$38
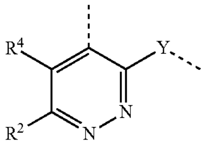
$A_C$39
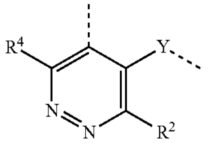
$A_C$40
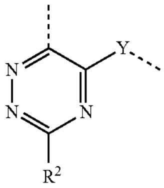
$A_C$41
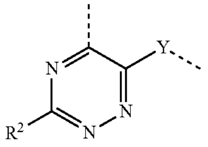
$A_C$42
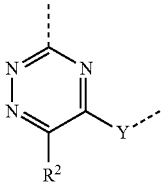
$A_C$43
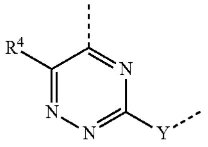
$A_C$44
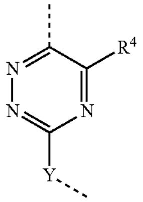
$A_C$45
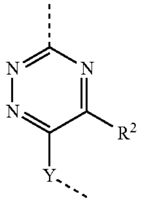
$A_C$46
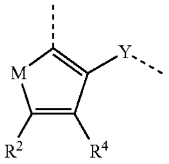

-continued
$A_{C}47$
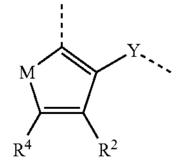
$A_{C}48$
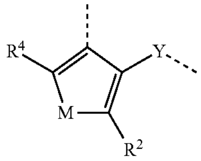
$A_{C}49$
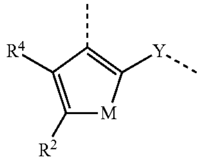
$A_{C}50$
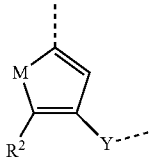
$A_{C}51$
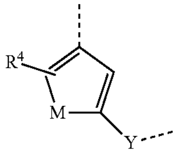
$A_{C}52$
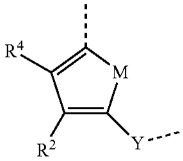
$A_{C}53$
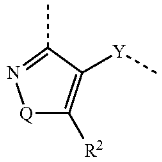
$A_{C}54$
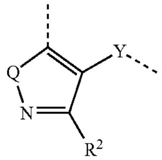
$A_{C}55$
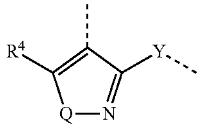
-continued
$A_{C}56$
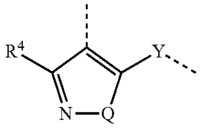
$A_{C}57$
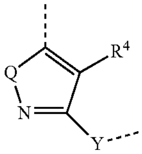
$A_{C}58$
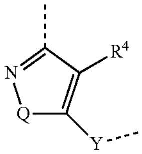
$A_{C}59$
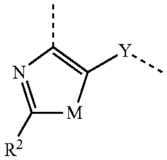
$A_{C}60$
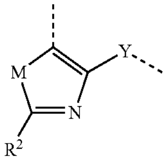
$A_{C}61$
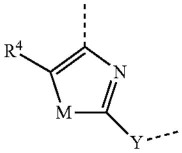
$A_{C}62$
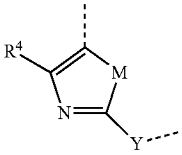
$A_{C}63$
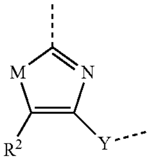
$A_{C}64$
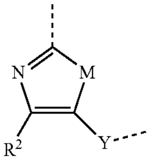

-continued
Ac65
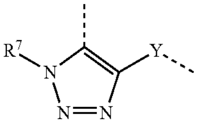
Ac66
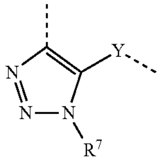
wherein Modulator B is a bivalent radical selected from the group of
B1
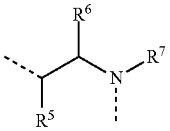
B2
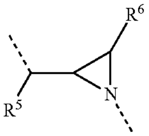
B3
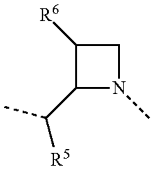
B4
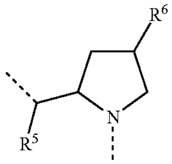
-continued
B5
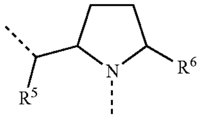
B6
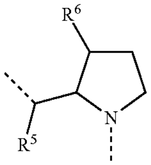
B7
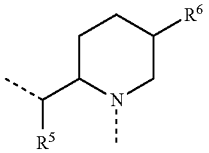
B8
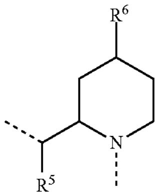
B9
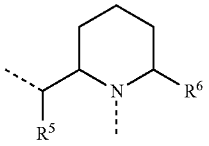
B10
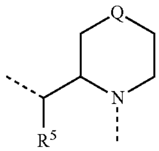
and Bridge C is a bivalent radical selected from the group of
C1
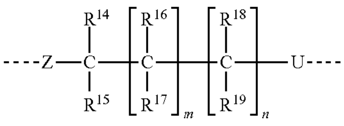
C2
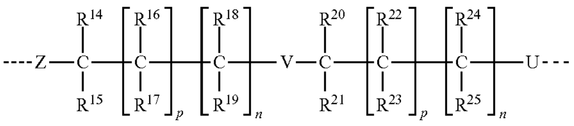
C3
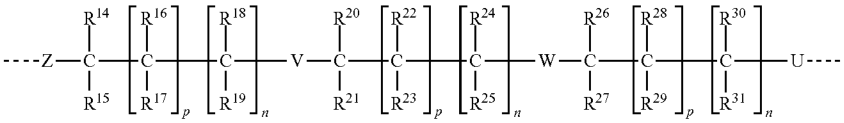

and wherein further $R^1$ and $R^2$ are independently defined as H; F; Cl; Br; I; $CF_3$; $OCF_3$; $OCHF_2$; $NO_2$; CN; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_q R^{40}$; $—(CR^{32}R^{33})_qR^{41}$; or $—(CR^{32}R^{33})_q R^{44}$;

$R^3$ and $R^4$ are independently defined as H; F; Cl; $CF_3$; $OCF_3$; $OCHF_2$; $NO_2$; CN; $C_{1-24}$-alkyl; cycloalkyl; heterocycloalkyl; aryl; heteroaryl; aryl-$C_{1-12}$-alkyl; heteroaryl-$C_{1-12}$-alkyl; $C_{1-12}$-alkoxy or aryloxy;

$R^5$ is H; $CF_3$; $C_{1-24}$-alkyl; cycloalkyl; heterocycloalkyl; aryl; heteroaryl; aryl-$C_{1-12}$-alkyl; or heteroaryl-$C_{1-12}$-alkyl;

$R^6$ is H; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_sR^{40}$; or $—(CR^{32}R^{33})_qR^{41}$; or $—(CR^{32}R^{33})_rR^{44}$;

$R^7$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; or an N-protecting group;

$R^8$ and $R^9$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{10}$, $R^{11}$ and $R^{12}$ are independently defined as H; $C_{1-24}$-alkyl; or cycloalkyl;

$R^{13}$ is $C_{1-24}$-alkyl or cycloalkyl;

$R^{14}$, $R^{20}$ and $R^{26}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_s R^{40}$; $—(CR^{32}R^{33})_qR^{41}$; or $—(CR^{32}R^{33})_q R^{44}$;

$R^{15}$, $R^{17}$, $R^{19}$, $R^{21}$, $R^{23}$, $R^{25}$, $R^{27}$, $R^{29}$ and $R^{31}$ are independently defined as H; $C_{1-24}$-alkyl; cycloalkyl; or heterocycloalkyl;

$R^{16}$, $R^{22}$ and $R^{28}$ are independently defined as H; $CF_3$; $C_{1-24}$-alkyl; cycloalkyl; heterocycloalkyl; aryl; heteroaryl; aryl-$C_{1-12}$-alkyl; or heteroaryl-$C_{1-12}$-alkyl;

$R^{18}$, $R^{24}$ and $R^{30}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{32}R^{33})_qOR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_q NR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_q COOR^{36}$; $—(CR^{32}R^{33})_qCONR^7R^{35}$; $—(CR^{32}R^{33})_q SO_2NR^7R^{35}$; $—(CR^{32}R^{33})_qCOR^{37}$; or $—(CR^{32}R^{33})_qR^{44}$;

$R^{32}$ is H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{51}R^{53})_qOR^{45}$; $—(CR^{51}R^{53})_qSR^{45}$; $—(CR^{51}R^{53})_qNR^7R^{45}$; $—(CR^{51}R^{53})_qOCONR^7R^{45}$; $—(CR^{51}R^{53})_qNR^{74}COOR^{36}$; $—(CR^{51}R^{53})_qNR^7COR^{37}$; $—(CR^{51}R^{53})_qNR^7CONR^7R^{45}$; $—(CR^{51}R^{53})_qNR^7SO_2R^{38}$; $—(CR^{51}R^{53})_qNR^7SO_2NR^7R^{45}$; $—(CR^{51}R^{53})_qCOOR^{36}$; $—(CR^{51}R^{53})_qCONR^7R^{45}$; $—(CR^{51}R^{53})_qSO_2NR^7R^{45}$; $—(CR^{51}R^{53})_qCOR^{37}$; $—(CR^{51}R^{53})_qSO_2R^{38}$; $—(CR^{51}R^{53})_qR^{39}$; $—(CR^{51}R^{53})_s R^{40}$; $—(CR^{51}R^{53})_qR^{41}$; or $—(CR^{51}R^{53})_q R^{44}$;

$R^{33}$ is H; $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{34}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{51}R^{53})_rOR^{45}$; $—(CR^{51}R^{53})_rNR^7R^{45}$; $—(CR^{51}R^{53})_rOCONR^7R^{35}$; $—(CR^{51}R^{53})_rNR^7COOR^{36}$; $—(CR^{51}R^{53})_rNR^7COR^{38}$; $—(CR^{51}R^{53})_rNR^7CONR^7R^{45}$; $—(CR^{51}R^{53})_rNR^7SO_2R^{38}$; $—(CR^{51}R^{53})_qCOOR^{36}$; $—(CR^{51}R^{53})_qCONR^7R^{45}$; $—(CR^{51}R^{53})_qSO_2NR^7R^{45}$; $—(CR^{51}R^{53})_qCOR^{38}$; $—(CR^{51}R^{53})_qSO_2R^{38}$; $—(CR^{51}R^{53})_qR^{39}$; $—(CR^{51}R^{53})_s R^{40}$; $—(CR^{51}R^{53})_qR^{41}$; or $—(CR^{51}R^{53})_q R^{44}$;

$R^{35}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; an N-protecting group; $—(CR^{32}R^{33})_rOR^{45}$; $—(CR^{32}R^{33})_rNR^7R^{45}$; $—(CR^{32}R^{33})_rOCONR^7R^{45}$; $—(CR^{32}R^{33})_rNR^7COOR^{36}$; $—(CR^{32}R^{33})_rNR^7CONR^7R^{50}$; $—(CR^{32}R^{33})_rNR^7SO_2R^{38}$; $—(CR^{32}R^{33})_rNR^7SO_2NR^7R^{50}$; $—(CR^{32}R^{33})_qCOOR^{36}$; $—(CR^{32}R^{33})_rNR^7COR^{37}$; $—(CR^{32}R^{33})_qCONR^7R^{50}$; $—(CR^{32}R^{33})_qCOR^{37}$; $—(CR^{32}R^{33})_qSO_2R^{38}$; $—(CR^{32}R^{33})_qSO_2NR^7R^{50}$; $—(CR^{32}R^{33})_qR^{39}$; $—(CR^{32}R^{33})_sR^{40}$; $—(CR^{32}R^{33})_qR^{41}$; or $—(CR^{32}R^{33})_q R^{44}$;

$R^{36}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; or an O/S-protecting group;

$R^{37}$ is $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{51}R^{53})_qOR^{45}$; $—(CR^{51}R^{53})_qSR^{45}$; $—(CR^{51}R^{53})_qNR^7R^{45}$; $—(CR^{51}R^{53})_qOCONR^7R^{45}$; $—(CR^{51}R^{53})_qNR^7COOR^{36}$; $—(CR^{51}R^{53})_qNR^7COR^{38}$; $—(CR^{51}R^{53})_qNR^7CONR^7R^{45}$; $—(CR^{51}R^{53})_qNR^7SO_2R^{38}$; $—(CR^{51}R^{53})_qNR^7SO_2NR^7R^{45}$; $—(CR^{51}R^{53})_qCOOR^{36}$; $—(CR^{51}R^{53})_qCONR^7R^{45}$; $—(CR^{51}R^{53})_qSO_2NR^7R^{45}$; $—(CR^{51}R^{53})_tCOR^{44}$; $—(CR^{51}R^{53})_qSO_2R^{38}$; $—(CR^{51}R^{53})_tR^{39}$; $—(CR^{51}R^{53})_u R^{40}$; $—(CR^{51}R^{53})_tR^{41}$; or $—(CR^{51}R^{53})_t R^{44}$;

$R^{38}$ is $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{39}$ is aryl; heteroaryl; $—C_6H_2R^3R^4R^{46}$; or a group of one of the formulae H1
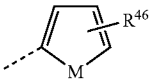
H2
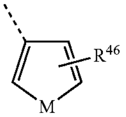
H3
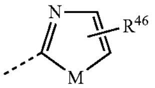
H4
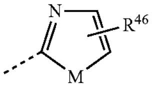
H5
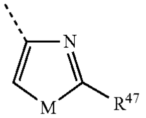
H6
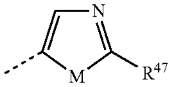
H7
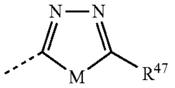
H8
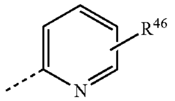
H9
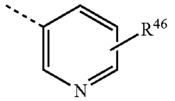
H10
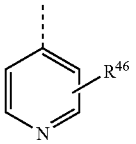
H11
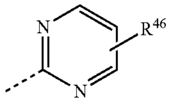
H12
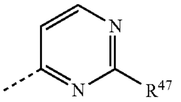
H13
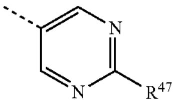
H14
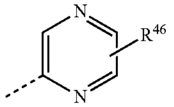
-continued
H15
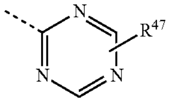
H16
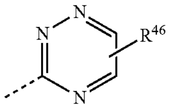
H17
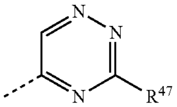
H18
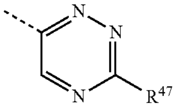
H19
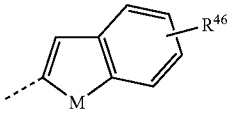
H20
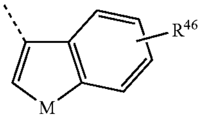
H21
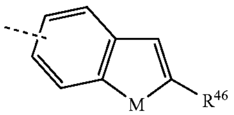
H22
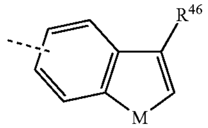
H23
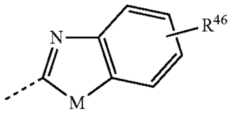
H24
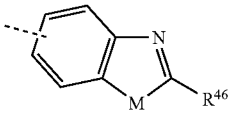
H25
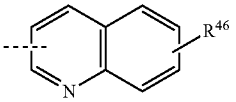
H26
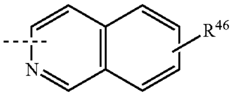
H27
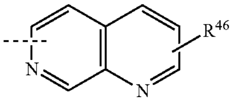

-continued
H28
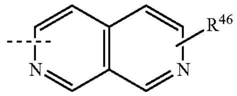
H29
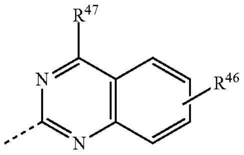
H30
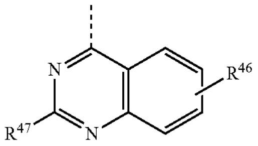
H31
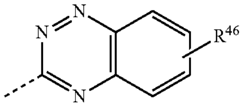
H32
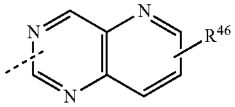
H33
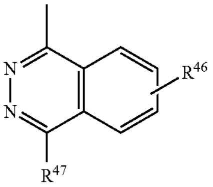
H34
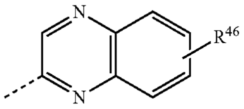
$R^{40}$ is a group of one of the formulae
H35
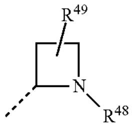
H36
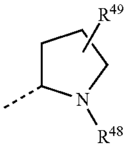
H37
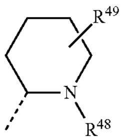
-continued
H38
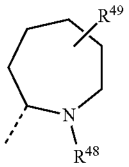
H39
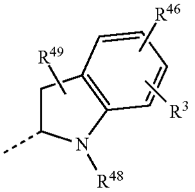
H40
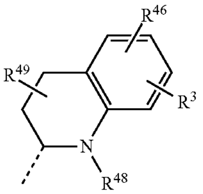
H41
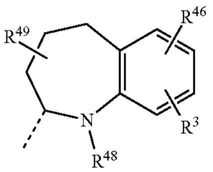
$R^{41}$ is a group of one of the formulae
H42
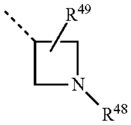
H43
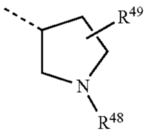
H44
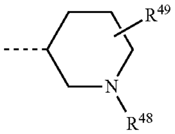
H45
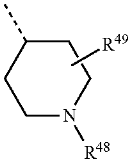

-continued

H46

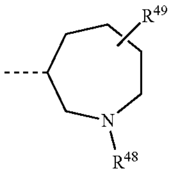

H47

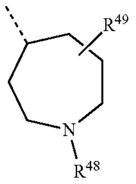

H48

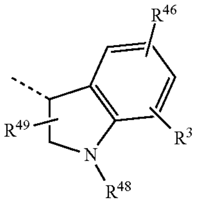

H49

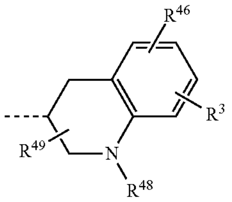

H50

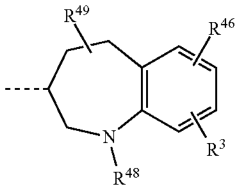

$R^{42}$ and $R^{43}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; or heteroaryl-$C_{1-12}$-alkyl;

$R^{44}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; or a group of one of the formulae

H51

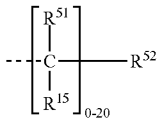

H52

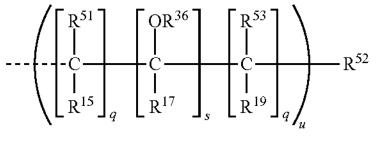

-continued

H53

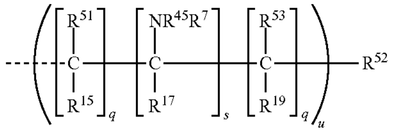

H54

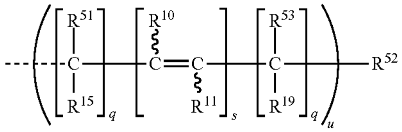

H55

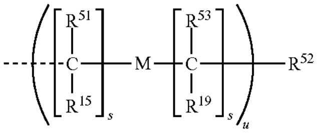

$R^{45}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; an N-protecting group; $—(CR^{51}R^{53})_rOR^{36}$; $—(CR^{51}R^{53})_rNR^7R^{57}$; $—(CR^{51}R^{53})_rOCONR^7R^{57}$; $—(CR^{51}R^{53})_rNR^7CONR^7R^{57}$; $—(CR^{51}R^{53})_rNR^7COR^{38}$; $—(CR^{51}R^{53})_rNR^7SO_2NR^7R^{57}$; $—(CR^{51}R^{53})_rNR^7SO_2R^{38}$; $—(CR^{51}R^{53})_qCOOR^{36}$; $—(CR^{51}R^{53})_qCOR^{38}$; $—(CR^{51}R^{53})_qSO_2R^{38}$; $—(CR^{51}R^{53})_qR^{39}$; $—(CR^{51}R^{53})_sR^{40}$; $—(CR^{51}R^{53})_qR^{41}$; or $—(CR^{51}R^{53})R^{44}$;

$R^{46}$ is H; F; Cl; $CF_3$; $OCF_3$; $OCHF_2$; $NO_2$; CN; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; $—(CR^{51}R^{53})_qOR^{36}$; $—(CR^{51}R^{53})_qSR^{36}$; $—(CR^{51}R^{53})_q(NR^7R^{57}$; $—(CR^{51}R^{53})_qOCONR^7R^{57}$; $—(CR^{51}R^{53})_q(NR^7COOR^{36}$; $—(CR^{51}R^{53})_q(NR^7COR^{38}$; $—(CR^{51}R^{53})_q(NR^7CONR^7R^{45}$; $—(CR^{51}R^{53})_q(NR^7SO_2R^{38}$; $—(CR^{51}R^{53})_q(NR^7SO_2NR^7R^{45}$; $—(CR^{51}R^{53})_qCOOR^{36}$; $—(CR^{51}R^{53})_qCONR^7R^{45}$; $—(CR^{51}R^{53})_qSO_2NR^7R^{45}$; $—(CR^{51}R^{53})_qCOR^{38}$; $—(CR^{51}R^{53})_qSO_2R^{38}$; or $—(CR^{51}R^{53})_qR^{44}$;

$R^{47}$ is H; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; or $—NR^7R^{45}$;

$R^{48}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; an N-protecting group; $—(CR^{51}R^{53})_rOR^{45}$; $—(CR^{51}R^{53})_rSR^{45}$; $—(CR^{51}R^{53})_rNR^7R^{45}$; $—(CR^{51}R^{53})_rOCONR^7R^{45}$; $—(CR^{51}R^{53})_rNR^7COOR^{36}$; $—(CR^{51}R^{53})_rNR^7COR^{38}$; $—(CR^{51}R^{53})_rNR^7CONR^7R^{45}$; $—(CR^{51}R^{53})_rNR^7SO_2R^{38}$; $—(CR^{51}R^{53})_rNR^7SO_2NR^7R^{45}$; $—(CR^{51}R^{53})_qCOOR^{36}$; $—(CR^{51}R^{53})_qCONR^7R^{45}$; $—(CR^{51}R^{53})_rSO_2NR^7R^{45}$; $—(CR^{51}R^{53})_qCOR^{38}$; $—(CR^{51}R^{53})_qSO_2R^{38}$; or $—(CR^{51}R^{53})_sR^{44}$;

$R^{49}$ is H; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; $—(CR^{51}R^{53})_qOR^{36}$; $—(CR^{51}R^{53})_qSR^{36}$; $—(CR^{51}R^{53})_qNR^7R^{45}$; $—(CR^{51}R^{53})_qNR^7COOR^{36}$; $—(CR^{51}R^{53})_qNR^7COR^{38}$; $—(CR^{51}R^{53})_q NR^7SO_2R^{38}$; $—(CR^{51}R^{53})_qNR^7CONR^7R^{45}$; $—(CR^{51}R^{53})_qCOOR^{36}$; $—(CR^{51}R^{53})_q CONR^7R^{45}$; $—(CR^{51}R^{53})_qCOR^{38}$; or $—(CR^{51}R^{53})_q R^{44}$;

$R^{50}$ is H; $C_{1-24}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{42}R^{43})_tOR^{36}$; —$(CR^{42}R^{43})_tNR^7R^{57}$; —$(CR^{42}R^{43})_tCOOR^{36}$; or —$(CR^{42}R^{43})_tCONR^7R^{57}$;

$R^{52}$ is H; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$OR^{36}$; —$NR^7R^{57}$; —$NR^7COR^{38}$; —$NR^7COOR^{36}$; —$NR^7SO_2R^{38}$; —$NR^7CONR^7R^{57}$; —$COOR^{36}$; —$CONR^7R^{57}$; —$C(=NR^7)NR^7R^{57}$; —$NR^7C(=NR^7)NR^7R^{57}$; or a group of one of the formulae

H56

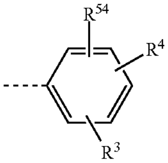

H57

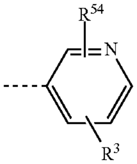

H58

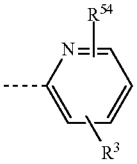

H59

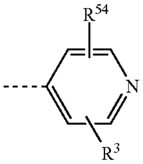

H60

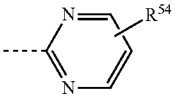

H61

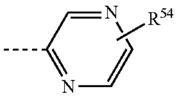

H62

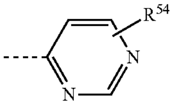

H63

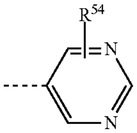

-continued

H64

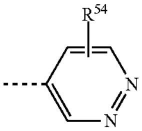

H65

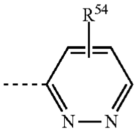

H66

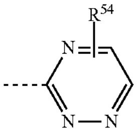

H67

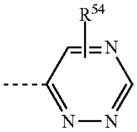

H68

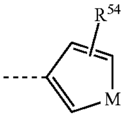

H69

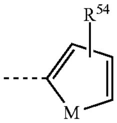

H70

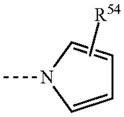

H71

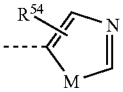

H72

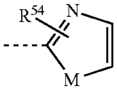

H73

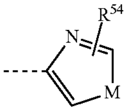

H74

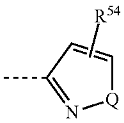

H75

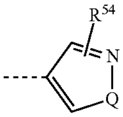

-continued
H76
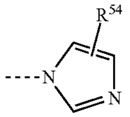
H77
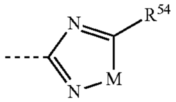
H78
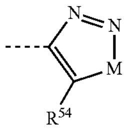
H79
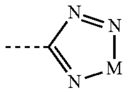
H80
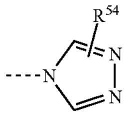
H81
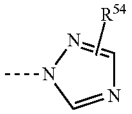
H82
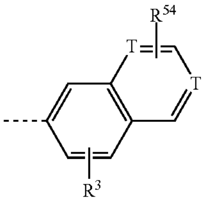
H83
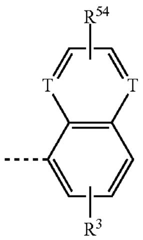
H84
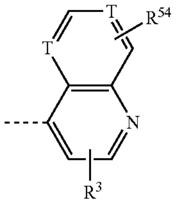
H85
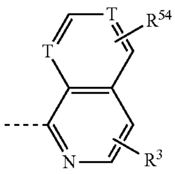
-continued
H86
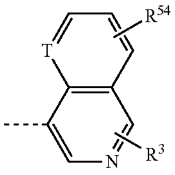
H87
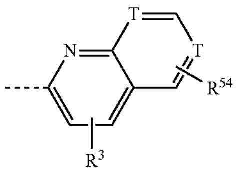
H88
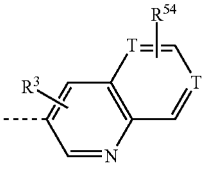
H89
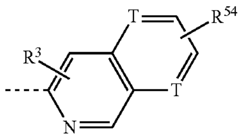
H90
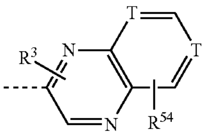
H91
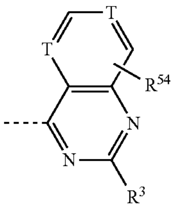
H92
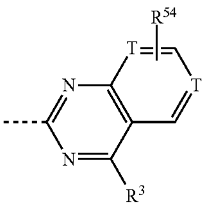
H93
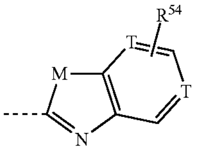
H94
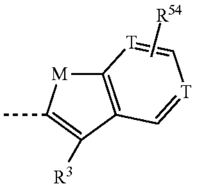

-continued

H95

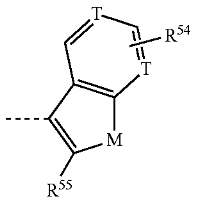

H96

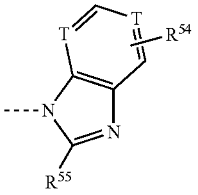

H97

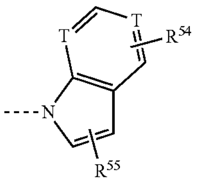

H98

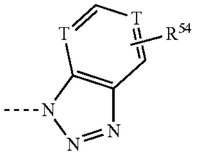

H99

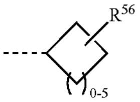

H100

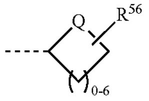

H101

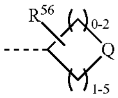

H102

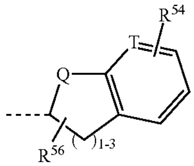

H103

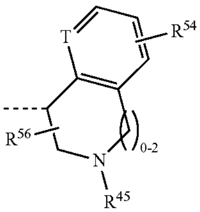

-continued

H104

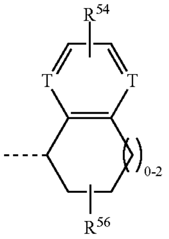

H105

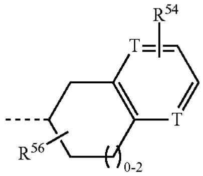

H106

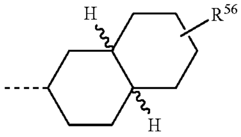

H107

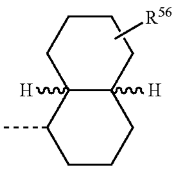

H108

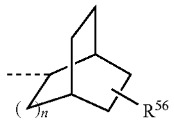

H109

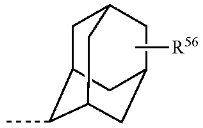

H110

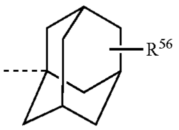

$R^{54}$ is H; F; $CF_3$; $OCF_3$; $OCHF_2$; $NO_2$; CN; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; —$OR^{36}$; —$NR^7R^{57}$; —$NR^7COR^{38}$; —$NR^7SO_2R^{38}$; —$NR^7CONR^7R^{57}$; —$COR^{38}$; or —$SO_2R^{38}$;

$R^{55}$ is H; $CF_3$; $C_{1-24}$-alkyl; $C_{2-24}$-alkenyl; $C_{2-10}$-alkynyl; cycloalkyl; heterocycloalkyl; aryl; heteroaryl; aryl-$C_{1-12}$-alkyl; heteroaryl-$C_{1-12}$-alkyl; —$COOR^{36}$; or —$CONR^7R^{45}$;

$R^{56}$ is H; F; $CF_3$; $C_{1-24}$-alkyl; $C_{2-24}$-alkenyl; cycloalkyl; heterocycloalkyl; aryl; heteroaryl; aryl-$C_{1-12}$-alkyl; heteroaryl-$C_{1-12}$-alkyl; —$(CR^{42}R^{43})_sOR^{36}$; —$(CR^{42}R^{43})_sNR^7R^{45}$; —$(CR^{42}R^{43})_qCOOR^{36}$; or —$(CR^{42}R^{43})_qCONR^7R^{45}$;

$R^{57}$ is H; $C_{1-24}$-alkyl; $C_{2-24}$-alkenyl; cycloalkyl; aryl; aryl-$C_{1-12}$-alkyl; or an N-protecting group;

taken together ($R^5$ and $R^6$); ($R^7$ and $R^{14}$); ($R^7$ and $R^{16}$); ($R^7$ and $R^{18}$); ($R^7$ and $R^{20}$); ($R^7$ and $R^{22}$); ($R^7$ and $R^{24}$); ($R^7$ and $R^{26}$); ($R^7$ and $R^{28}$); ($R^7$ and $R^{30}$); ($R^7$ and $R^{35}$); ($R^7$ and $R^{45}$); ($R^7$ and $R^{57}$); ($R^{13}$ and $R^{13}$); ($R^{14}$ and $R^{16}$); ($R^{14}$ and $R^{18}$); ($R^{15}$ and $R^{51}$); ($R^{19}$ and $R^{51}$); ($R^{20}$ and $R^{22}$); ($R^{20}$ and $R^{24}$); ($R^{26}$ and $R^{28}$); ($R^{26}$ and $R^{30}$); ($R^{32}$ and $R^{33}$); ($R^{42}$ and $R^{43}$); or ($R^{51}$ and $R^{53}$) can form optionally substituted cycloalkyl or heterocycloalkyl moieties;

and the structural elements $—NR^7R^{35}$; or $—NR^{44}R^{45}$ can form one of the groups of the formulae

H111

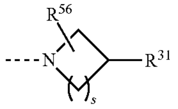

H112

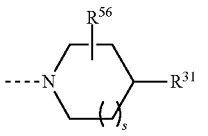

H113

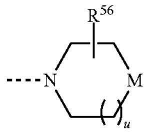

H114

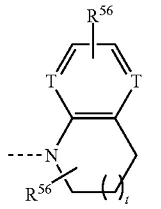

H115

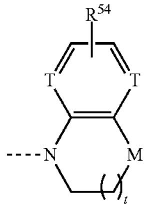

H116

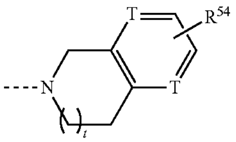

H117

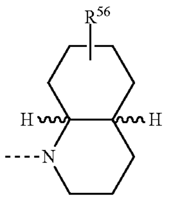

-continued

H118

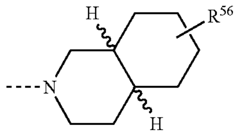

T is $CR^{54}$ or N;
Q is O; S; or $NR^{35}$;
M is O; S; or NR';
m is an integer of 0-8;
n is an integer of 0-1;
p is an integer of 0-4;
q is an integer of 0-4;
r is an integer of 2-4;
s is an integer of 1-4;
t is an integer of 0-2;
u is an integer of 1-2;

or a stereoisomer of such a compound; or a salt, solvate, clathrate, N-oxide, isotopically enriched or enantiomerically enriched version thereof.

2. A compound according to claim 1 wherein the Template A is selected from $A_B1$-$A_C1$; $A_B1$-$A_C2$; $A_B1$-$A_C3$; $A_B1$-$A_C4$; $A_B1$-$A_C5$; $A_B1$-$A_C6$; $A_B1$-$A_C8$; $A_B1$-$A_C9$; $A_B1$-$A_C11$; $A_B1$-$A_C12$; $A_B1$-$A_C13$; $A_B1$-$A_C19$; $A_B1$-$A_C22$; $A_B1$-$A_C24$; $A_B1$-$A_C49$; $A_B1$-$A_C51$; $A_B2$-$A_C1$; $A_B2$-$A_C2$; $A_B2$-$A_C3$; $A_B2$-$A_C4$; $A_B2$-$A_C5$; $A_B2$-$A_C11$; $A_B2$-$A_C12$; $A_B2$-$A_C51$; $A_B3$-$A_C1$; $A_B3$-$A_C2$; $A_B3$-$A_C3$; $A_B3$-$A_C4$; $A_B3$-$A_C5$; $A_B3$-$A_C11$; $A_B3$-$A_C12$; $A_B4$-$A_C1$; $A_B4$-$A_C2$; $A_B4$-$A_C3$; $A_B4$-$A_C4$; $A_B4$-$A_C5$; $A_B4$-$A_C6$; $A_B4$-$A_C11$; $A_B4$-$A_C12$; $A_B4$-$A_C19$; $A_B4$-$A_C22$; $A_B4$-$A_C24$; $A_B4$-$A_C49$; $A_B4$-$A_C51$; $A_B4$-$A_C59$; $A_B5$-$A_C1$; $A_B5$-$A_C2$; $A_B5$-$A_C3$; $A_B5$-$A_C4$; $A_B5$-$A_C5$; $A_B5$-$A_C11$; $A_B5$-$A_C12$; $A_B5$-$A_C51$; $A_B5$-$A_C59$; $A_B6$-$A_C1$; $A_B6$-$A_C4$; $A_B6$-$A_C8$; $A_B6$-$A_C9$; $A_B6$-$A_C11$; $A_B6$-$A_C13$; $A_B6$-$A_C16$; $A_B6$-$A_C18$; $A_B6$-$A_C19$; $A_B6$-$A_C20$; $A_B6$-$A_C30$; $A_B6$-$A_C31$; $A_B6$-$A_C49$; $A_B6$-$A_C51$; $A_B9$-$A_C6$; $A_B9$-$A_C49$; $A_B10$-$A_C6$; $A_B11$-$A_C6$; $A_B12$-$A_C2$; $A_B12$-$A_C5$; $A_B12$-$A_C11$; $A_B12$-$A_C12$; $A_B13$-$A_C2$; $A_B13$-$A_C5$; $A_B13$-$A_C11$; $A_B13$-$A_C12$; $A_B13$-$A_C5$; $A_B13$-$A_C11$; $A_B13$-$A_C12$; $A_B14$-$A_C49$; $A_B20$-$A_C2$; $A_B20$-$A_C6$; $A_B20$-$A_C49$; $A_B23$-$A_C4$; $A_B23$-$A_C49$; $A_B26$-$A_C2$; $A_B26$-$A_C5$; $A_B26$-$A_C11$; $A_B26$-$A_C12$; $A_B40$-$A_C2$; $A_B40$-$A_C5$; $A_B40$-$A_C11$; $A_B40$-$A_C12$; $A_B45$-$A_C49$; $A_B45$-$A_C52$; $A_B45$-$A_C57$; $A_B45$-$A_C58$; $A_B45$-$A_C65$; $A_B45$-$A_C66$; $A_B46$-$A_C57$; $A_B46$-$A_C58$; $A_B47$-$A_C58$; $A_B49$-$A_C49$; $A_B50$-$A_C57$; $A_B50$-$A_C58$; $A_B50$-$A_C61$; $A_B51$-$A_C49$; $A_B51$-$A_C61$; $A_B53$-$A_C2$; $A_B53$-$A_C5$; $A_B53$-$A_C11$; $A_B53$-$A_C12$; $A_B58$-$A_C2$; $A_B58$-$A_C5$; $A_B58$-$A_C11$; $A_B58$-$A_C12$; $A_B59$-$A_C2$; $A_B59$-$A_C5$; $A_B59$-$A_C11$; $A_B59$-$A_C12$; or $A_B59$-$A_C61$;

the Modulator B is selected from

B1; B4; B5; B6; B7; B8; B9 or B10;

the Bridge C is selected from

C1; C2; or C3;

and wherein the Y-Z connectivity representing a divalent radical is selected from the group of

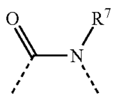 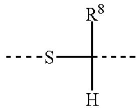 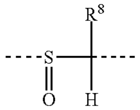 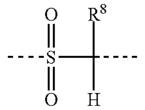

-continued

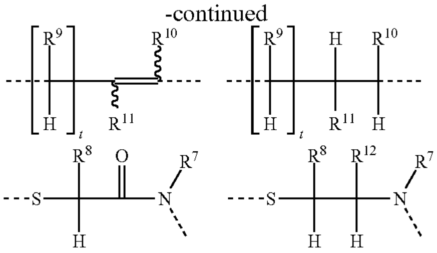

V and W are representing independently a divalent radical selected from the group of

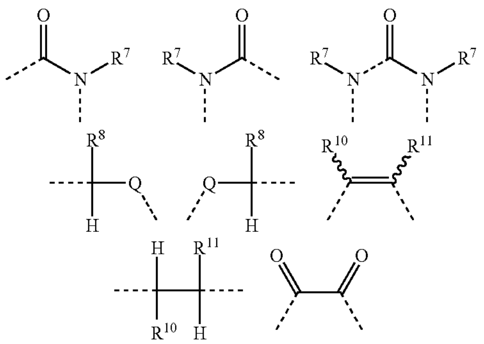

or a stereoisomer of such a compound; or a salt, solvate, clathrate, N-oxide, isotopically enriched or enantiomerically enriched version thereof.

3. A compound according to claim 1 wherein $R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_qR^{40}$; $—(CR^{32}R^{33})_qR^{41}$; or $—(CR^{32}R^{33})_qR^{44}$;

$R^3$ and $R^4$ are independently defined as H; F; Cl; $CF_3$; $OCF_3$; $OCHF_2$; $NO_2$; CN; $C_{1-6}$-alkyl; cycloalkyl; $C_{1-6}$-alkoxy or aryloxy;

$R^5$ is H; $CF_3$; $C_{1-6}$-alkyl; or cycloalkyl;

$R^6$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^7$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^8$ and $R^9$ are independently defined as H; $CF_3$; $C_{1-6}$-alkyl; cycloalkyl; heterocycloalkyl;

$R^{10}$, $R^{11}$ and $R^{12}$ are independently defined as H; $C_{1-6}$-alkyl; or cycloalkyl;

$R^{13}$ is $C_{1-6}$-alkyl;

$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{15}$, $R^{17}$, $R^{19}$, $R^{21}$, $R^{23}$, $R^{25}$, $R^{27}$, $R^{29}$ and $R^{31}$ are independently defined as H; or $C_{1-6}$-alkyl;

$R^{16}$, $R^{22}$ and $R^{28}$ are independently defined as H; $CF_3$; or $C_{1-6}$-alkyl;

$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; $—(CR^{32}R^{33})_qOR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; or $—(CR^{32}R^{33})_qR^{44}$;

$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{51})_qOR^{45}$; $—(CR^{42}R^{51})_qSR^{45}$; $—(CR^{42}R^{51})_qNR^7R^{45}$; $—(CR^{42}R^{51})_qOCONR^7R^{45}$; $—(CR^{42}R^{51})_qNR^7COOR^{36}$; $—(CR^{42}R^{51})_qNR^7COR^{38}$; $—(CR^{42}R^{51})_qNR^7CONR^7R^{45}$; $—(CR^{42}R^{51})_qNR^7SO_2R^{38}$; $—(CR^{42}R^{51})_qNR^7SO_2NR^7R^{45}$; $—(CR^{42}R^{51})_qCOOR^{36}$; $—(CR^{42}R^{51})_qCONR^7R^{45}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_qCOR^{38}$; $—(CR^{42}R^{51})_qSO_2R^{38}$; $—(CR^{42}R^{51})_qR^{39}$; $—(CR^{42}R^{51})_sR^{40}$; $—(CR^{42}R^{51})_qR^{41}$; or $—(CR^{42}R^{51})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; heteroaryl-$C_{1-6}$-alkyl; $—(CR^{42}R^{51})_rOR^{45}$; $—(CR^{42}R^{51})_rNR^7R^{45}$; $—(CR^{42}R^{51})_rOCONR^7R^{35}$; $—(CR^{42}R^{51})_rNR^7COOR^{36}$; $—(CR^{42}R^{51})_rNR^7COR^{38}$; $—(CR^{42}R^{51})_rNR^7CONR^7R^{45}$; $—(CR^{42}R^{51})_rNR^7SO_2R^{38}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_qCOR^{38}$; $—(CR^{42}R^{51})_qSO_2R^{38}$; $—(CR^{42}R^{51})_qR^{39}$; $—(CR^{42}R^{51})_sR^{40}$; $(CR^{42}R^{51})_qR^{41}$; or $(CR^{42}R^{51})_qR^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{32}R^{33})_rOR^{45}$; $—(CR^{32}R^{33})_rNR^7R^{45}$; $—(CR^{32}R^{33})_rOCONR^7R^{45}$; $—(CR^{32}R^{33})_rNR^7COOR^{36}$; $—(CR^{32}R^{33})_rNR^7COR^{37}$; $—(CR^{32}R^{33})_rNR^7CONR^7R^{45}$; $—(CR^{32}R^{33})_rNR^7SO_2R^{38}$; $—(CR^{32}R^{33})_rNR^7SO_2NR^7R^{45}$; $—(CR^{32}R^{33})_qCOOR^{36}$; $—(CR^{32}R^{33})_qCONR^7R^{45}$; $—(CR^{32}R^{33})_qCOR^{37}$; $—(CR^{32}R^{33})_qSO_2R^{38}$;

$—(CR^{32}R^{33})_qSO_2NR^7R^{50}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{36}$ is H; $C_{1-6}$-alkyl; cycloalkyl; aryl; aryl-$C_{1-6}$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; $—(CR^{42}R^{51})_qOR^{45}$; $—(CR^{42}R^{51})_qSR^{45}$; $—(CR^{42}R^{51})_rNR^7R^{45}$; $—(CR^{42}R^{51})_rOCONR^7R^{45}$; $—(CR^{42}R^{51})_rNR^7COOR^{36}$; $—(CR^{42}R^{51})_rNR^7COR^{44}$; $—(CR^{42}R^{51})_rNR^7CONR^7R^{45}$; $—(CR^{42}R^{51})_rNR^7SO_2R^{38}$; $—(CR^{42}R^{51})_rNR^7SO_2NR^7R^{45}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_tCOR^{38}$; $—(CR^{42}R^{51})_qSO_2R^{38}$; $—(CR^{42}R^{51})_tR^{39}$; $—(CR^{42}R^{51})_uR^{40}$; $—(CR^{42}R^{51})_tR^{41}$; or $—(CR^{42}R^{51})_tR^{44}$;

$R^{38}$ is $C_{1-6}$-alkyl; $C_{2-6}$-alkenyl; cycloalkyl; heterocycloalkyl; aryl; heteroaryl; aryl-$C_{1-6}$-alkyl; or heteroaryl-$C_{1-6}$-alkyl;

$R^{42}$ and $R^{43}$ are independently defined as H; F; $CF_3$; $C_{1-6}$-alkyl; $C_{2-6}$-alkenyl; cycloalkyl; heterocycloalkyl; aryl-$C_{1-6}$-alkyl; or heteroaryl-$C_{1-6}$-alkyl;

$R^{44}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or a group of one of the formulae

H51

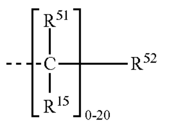

H52

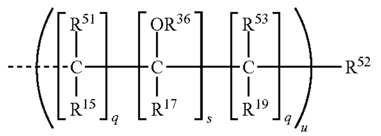

H53

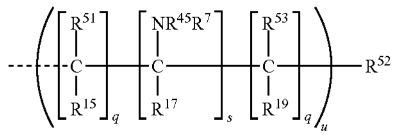

H54

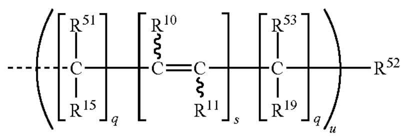

H55

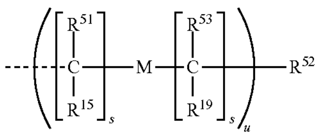

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{42}R^{51})_rOR^{36}$; $—(CR^{42}R^{51})_rNR^7R^{57}$; $—(CR^{42}R^{51})_rOCONR^7R^{57}$; $—(CR^{42}R^{51})_rNR^7CONR^7R^{57}$; $—(CR^{42}R^{51})_rNR^7COR^{38}$; $—(CR^{42}R^{51})_rNR^7SO_2R^{38}$; $—(CR^{42}R^{51})_rNR^7SO_2NR^7R^{57}$; $—(CR^{42}R^{51})_qCOOR^{36}$; $—(CR^{42}R^{51})_q(COR^{38}$; $—(CR^{42}R^{51})_qSO_2R^{33}$; $—(CR^{42}R^{51})_qR^{39}$; $—(CR^{42}R^{51})_sR^{40}$; $—(CR^{42}R^{51})_qR^{41}$; or $—(CR^{42}R^{51})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—(CR^{42}R^{51})_qOR^{36}$; $—(CR^{42}R^{51})_qSR^{36}$; $—(CR^{42}R^{51})_q(NR^7R^{57}$; $—(CR^{42}R^{51})_qOCONR^7R^{57}$; $—(CR^{42}R^{51})_q(NR^{44}COOR^{36}$; $—(CR^{42}R^{51})_q(NR^7COR^{38}$; $—(CR^{42}R^{51})_q(NR^7CONR^7R^{45}$; $—(CR^{42}R^{51})_q(NR^7SO_2R^{38}$; $—(CR^{42}R^{51})_q(NR^7SO_2NR^7R^{45}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_qCOR^{38}$; $—(CR^{42}R^{51})_qSO_2R^{38}$; or $—(CR^{42}R^{51})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $—NR^7R^{45}$;

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{42}R^{51})_rOR^{45}$; $—(CR^{42}R^{51})_rSR^{45}$; $—(CR^{42}R^{51})_rNR^7R^{45}$; $—(CR^{42}R^{51})_rOCONR^7R^{45}$; $—(CR^{42}R^{51})_rNR^7COOR^{36}$; $—(CR^{42}R^{51})_rNR^7COR^{38}$; $—(CR^{42}R^{51})_rNR^7CONR^7R^{45}$; $—(CR^{42}R^{51})_rNR^7SO_2R^{38}$; $—(CR^{42}R^{51})_rNR^7SO_2NR^7R^{45}$; $—(CR^{42}R^{51})_qCOOR^{36}$; $—(CR^{42}R^{51})_qCONR^7R^{45}$; $—(CR^{42}R^{51})_rSO_2NR^7R^{45}$; $—(CR^{42}R^{51})_qCOR^{38}$; $—(CR^{42}R^{51})_qSO_2R^{38}$; or $—(CR^{42}R^{51})_sR^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{51})_qOR^{36}$; $—(CR^{42}R^{51})_qSR^{36}$; $—(CR^{42}R^{51})_q(NR^7R^{45}$; $—(CR^{42}R^{51})_q(NR^7COOR^{36}$; $—(CR^{42}R^{51})_q(NR^7COR^{38}$; $—(CR^{42}R^{51})_q(NR^7SO_2R^{38}$; $—(CR^{42}R^{51})_q(NR^7CONR^7R^{45}$; $—(CR^{42}R^{51})_qCOOR^{36}$; $—(CR^{42}R^{51})_qCONR^7R^{45}$; $—(CR^{42}R^{51})_qCOR^{38}$; or $—(CR^{42}R^{51})_qR^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_rOR^{36}$; $—(CR^{42}R^{43})_rNR^7R^{57}$; $—(CR^{42}R^{43})_rCOOR^{36}$; or $—(CR^{42}R^{43})_rCONR^7R^{57}$;

$R^{52}$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—OR^{36}$; $—NR^7R^{57}$; $—NR^7COR^{38}$; $—NR^7COOR^{36}$; $—NR^7SO_2R^{38}$; $—NR^7CONR^7R^{57}$; $—COOR^{36}$; $—CONR^7R^{57}$; $—C(=NR^7)NR^7R^{57}$; $—NR^7C(=NR^7)NR^7R^{57}$; or a group of one of the formulae

H56

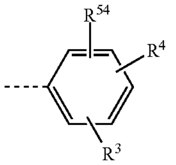

H57

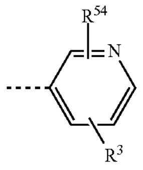

-continued
H58
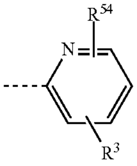
H59
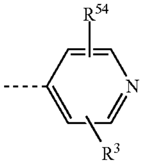
H60
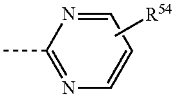
H61
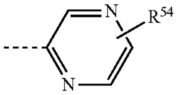
H62
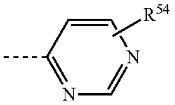
H63
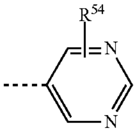
H64
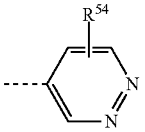
H65
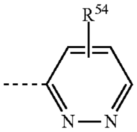
H66
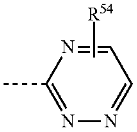
H67
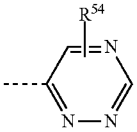
H68
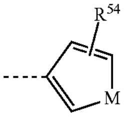
-continued
H69
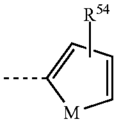
H70
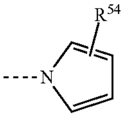
H71
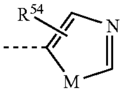
H72
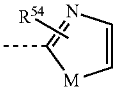
H73
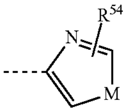
H74
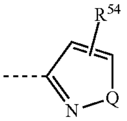
H75
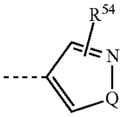
H76
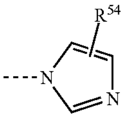
H77
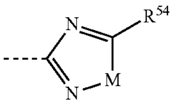
H78
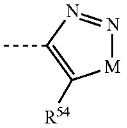
H79
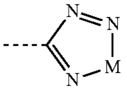
H80
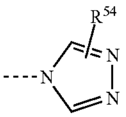
H81
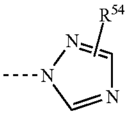

-continued
H82
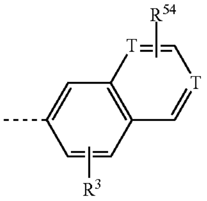
H83
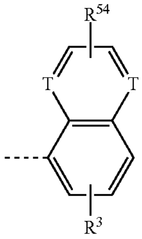
H84
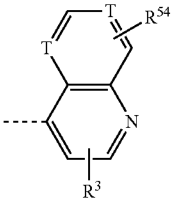
H85
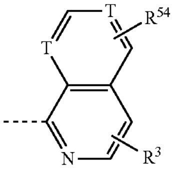
H86
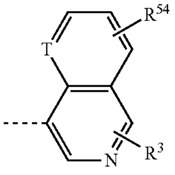
H87
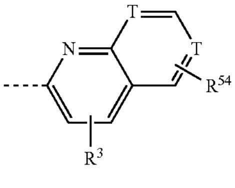
H88
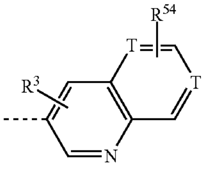
H89
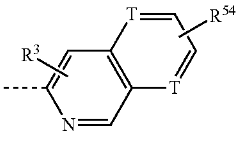
-continued
H90
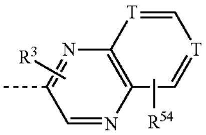
H91
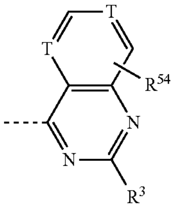
H92
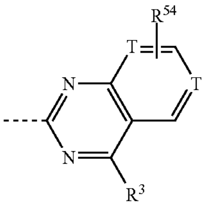
H93
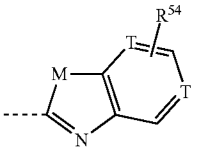
H94
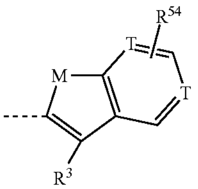
H95
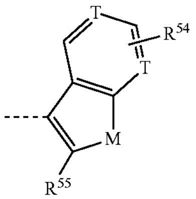
H96
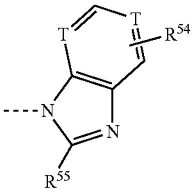
H97
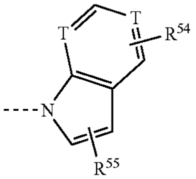

-continued

H98

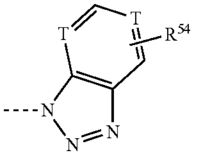

H99

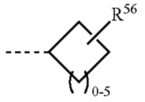

H100

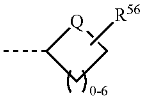

H101

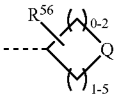

H102

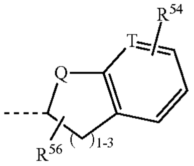

H103

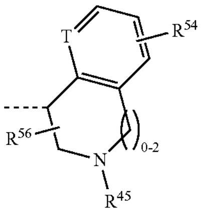

H104

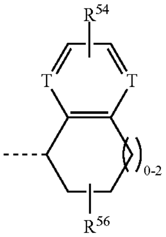

H105

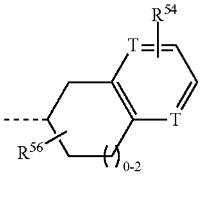

H106

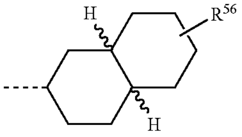

-continued

H107

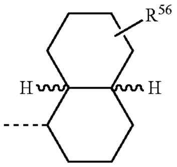

H108

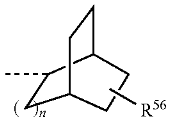

H109

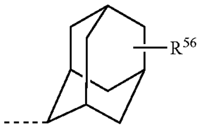

H110

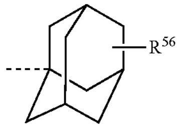

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$OR^{36}$; —$NR^7R^{57}$; —$NR^7COR^{38}$; —$NR^7SO_2R^{38}$; —$NR^7CONR^7R^{57}$; —$COR^{38}$; or —$SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; —$COOR^{36}$; or —$CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_rOR^{36}$; —$(CR^{42}R^{43})_rNR^7R^{45}$; —$(CR^{42}R^{43})_qCOOR^{36}$; or —$(CR^{42}R^{43})_qCONR^7R^{45}$;

$R^{57}$ is H; $C_{1-6}$-alkyl; $C_{2-6}$-alkenyl; cycloalkyl; aryl-$C_{1-6}$-alkyl; or an N-protecting group;

or a stereoisomer of such a compound; or a salt, solvate, clathrate, N-oxide, isotopically enriched or enantiomerically enriched version thereof.

4. A compound according to claim 1 wherein the Template A is selected from $A_B$1-$A_C$1; $A_B$1-$A_C$4; $A_B$1-$A_C$6; $A_B$1-$A_C$8; $A_B$1-$A_C$9; $A_B$1-$A_C$11; $A_B$1-$A_C$13; $A_B$1-$A_C$19; $A_B$1-$A_C$22; $A_B$1-$A_C$24; $A_B$1-$A_C$49; $A_B$1-$A_C$51; $A_B$2-$A_C$4; $A_B$2-$A_C$51; $A_B$4-$A_C$1; $A_B$4-$A_C$4; $A_B$4-$A_C$6; $A_B$4-$A_C$19; $A_B$4-$A_C$22; $A_B$4-$A_C$24; $A_B$4-$A_C$49; $A_B$4-$A_C$51; $A_B$4-$A_C$59; $A_B$5-$A_C$51; $A_B$5-$A_C$59; $A_B$6-$A_C$1; $A_B$6-$A_C$4; $A_B$6-$A_C$8; $A_B$6-$A_C$9; $A_B$6-$A_C$11; $A_B$6-$A_C$13; $A_B$6-$A_C$16; $A_B$6-$A_C$18; $A_B$6-$A_C$19; $A_B$6-$A_C$20; $A_B$6-$A_C$30; $A_B$6-$A_C$31; $A_B$6-$A_C$49; $A_B$6-$A_C$51; $A_B$9-$A_C$6; $A_B$9-$A_C$49; $A_B$14-$A_C$49; $A_B$20-$A_C$6; $A_B$20-$A_C$49; $A_B$23-$A_C$4; $A_B$23-$A_C$49; $A_B$45-$A_C$49; $A_B$45-$A_C$52; $A_B$45-$A_C$57; $A_B$45-$A_C$58; $A_B$45-$A_C$65; $A_B$45-$A_C$66; $A_B$46-$A_C$57; $A_B$46-$A_C$58; $A_B$49-$A_C$49; $A_B$50-$A_C$57; $A_B$50-$A_C$58; $A_B$50-$A_C$61; $A_B$51-$A_C$49; $A_B$51-$A_C$61; $A_B$59-$A_C$61;

the Modulator B is selected from

B1; B4; B5; B6; or B7;

and wherein $R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-C kyl; heteroaryl alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_q NR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qR^{39}$; $—(CR^{32}R^{33})_qR^{40}$; $—(CR^{32}R^{33})_q R^{41}$; or $—(CR^{32}R^{33})_qR^{44}$;

$R^3$ and $R^4$ are independently defined as H; F; Cl; $CF_3$; $OCF_3$; $OCHF_2$; $NO_2$; CN; $C_{1-6}$-alkyl; or $C_{1-6}$-alkoxy;

$R^5$ is H; $CF_3$; or $C_{1-6}$-alkyl;

$R^6$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_q NR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qR^{39}$; $—(CR^{32}R^{33})_sR^{40}$; $—(CR^{32}R^{33})_q R^{41}$; or $—(CR^{32}R^{33})_qR^{44}$;

$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; $—(CR^{32}R^{33})_qOR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_rNR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qCOR^{37}$; or $—(CR^{32}R^{33})_qR^{44}$;

$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_qOR^{45}$; $—(CR^{42}R^{43})_qSR^{45}$; $—(CR^{42}R^{43})_rNR^7R^{45}$; $—(CR^{42}R^{43})_rNR^7COOR^{36}$; $—(CR^{42}R^{43})_rNR^7COR^{38}$; $—(CR^{42}R^{43})_q COOR^{36}$; $—(CR^{42}R^{43})_qCONR^7R^{45}$; $—(CR^{42}R^{43})_q COR^{38}$; $—(CR^{42}R^{43})_qR^{39}$; $—(CR^{42}R^{43})_s R^{40}$; $—(CR^{42}R^{43})_qR^{41}$; or $—(CR^{42}R^{43})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; $—(CR^{42}R^{43})_rOR^{45}$; $—(CR^{42}R^{43})_rNR^7R^{45}$; $—(CR^{42}R^{43})_rOCONR^7R^{35}$; $—(CR^{42}R^{43})_rNR^7COOR^{36}$; $—(CR^{42}R^{43})_rNR^7COR^{38}$; $—(CR^{42}R^{43})_rNR^7CONR^7R^{45}$; $—(CR^{42}R^{43})_rNR^7SO_2R^{38}$; $—(CR^{42}R^{43})_qCOOR^{36}$; $—(CR^{42}R^{43})_qCONR^7R^{45}$; $—(CR^{42}R^{43})_qCOR^{38}$; $—(CR^{42}R^{43})_qR^{39}$; $—(CR^{42}R^{43})_sR^{40}$; $—(CR^{42}R^{43})_qR^{41}$; or $—(CR^{42}R^{43})_qR^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{32}R^{33})_rOR^{45}$; $(CR^{32}R^{33})_rNR^7R^{45}$; $—(CR^{32}R^{33})_rOCONR^7R^{45}$; $—(CR^{32}R^{33})_rNR^7COOR^{36}$; $—(CR^{32}R^{33})_rNR^7COR^{37}$; $—(CR^{32}R^{33})_rNR^7CONR^7R^{50}$; $—(CR^{32}R^{33})_rNR^7SO_2R^{38}$; $—(CR^{32}R^{33})_qCOOR^{36}$; $—(CR^{32}R^{33})_qCONR^7R^{45}$; $—(CR^{32}R^{33})_qCOR^{38}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{36}$ is H; $C_{1-6}$-alkyl; cycloalkyl; aryl; aryl-$C_{1-6}$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; $—(CR^{42}R^{43})_qOR^{45}$; $—(CR^{42}R^{43})_qSR^{45}$; $—(CR^{42}R^{43})_rNR^7R^{45}$; $—(CR^{42}R^{43})_sOCONR^7R^{45}$; $—(CR^{42}R^{43})_rNR^7COOR^{36}$; $—(CR^{42}R^{43})_rNR^7COR^{44}$; $—(CR^{42}R^{43})_rNR^7CONR^7R^{45}$; $—(CR^{42}R^{43})_rNR^7SO_2R^{38}$; $—(CR^{42}R^{43})_qCOOR^{36}$; $—(CR^{42}R^{43})_qCONR^7R^{45}$; $—(CR^{42}R^{43})_tCOR^{38}$; $—(CR^{42}R^{43})_tR^{39}$; $—(CR^{42}R^{43})_uR^{40}$; $—(CR^{42}R^{43})_tR^{41}$; or $—(CR^{42}R^{43})_tR^{44}$;

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{42}R^{43})_rOR^{36}$; $—(CR^{42}R^{43})_rNR^7R^{57}$; $—(CR^{42}R^{43})_rOCONR^7R^{57}$; $—(CR^{42}R^{43})_rNR^7CONR^7R^{57}$; $—(CR^{42}R^{43})_rNR^7COR^{38}$; $—(CR^{42}R^{43})_rNR^7SO_2R^{38}$; $—(CR^{42}R^{43})_qCOOR^{36}$; $—(CR^{42}R^{43})_qCOR^{38}$; $—(CR^{42}R^{43})_qR^{39}$; $—(CR^{42}R^{43})_sR^{40}$; $(CR^{42}R^{43})^{41}$; or $—(CR^{42}R^{43})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—(CR^{42}R^{43})_qOR^{36}$; $—(CR^{42}R^{43})_qNR^7R^{57}$; $—(CR^{42}R^{43})_qNR^7COR^{38}$; $—(CR^{42}R^{43})_qCOOR^{36}$; $—(CR^{42}R^{43})_qCONR^7R^{45}$; $—(CR^{42}R^{43})_qSO_2NR^7R^{45}$; $—(CR^{42}R^{43})_qCOR^{38}$; or $—(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $—NR^7R^{45}$;

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{42}R^{43})_rOR^{45}$; $—(CR^{42}R^{43})_rSR^{45}$; $—(CR^{42}R^{43})_rNR^7R^{45}$; $—(CR^{42}R^{43})_rOCONR^7R^{45}$; $—(CR^{42}R^{43})_rNR^7COOR^{36}$; $—(CR^{42}R^{43})_rNR^7COR^{38}$; $—(CR^{42}R^{43})_rNR^7CONR^7R^{45}$; $—(CR^{42}R^{43})_rNR^7SO_2R^{38}$; $—(CR^{42}R^{43})_qCOOR^{36}$; $—(CR^{42}R^{43})_qCONR^7R^{45}$; $—(CR^{42}R^{43})_qCOR^{38}$; or $—(CR^{42}R^{43})_sR^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_qOR^{36}$; $—(CR^{42}R^{43})_qNR^7R^{45}$; $—(CR^{42}R^{43})_qNR^7COR^{38}$; $—(CR^{42}R^{43})_qNR^7SO_2R^{38}$; $—(CR^{42}R^{43})_qCOOR^{36}$; $—(CR^{42}R^{43})_qCONR^7R^{45}$; $—(CR^{42}R^{43})_qCOR^{38}$; or $—(CR^{42}R^{43})_qR^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_tOR^{36}$; $—(CR^{42}R^{43})_tNR^7R^{57}$; $—(CR^{42}R^{43})_tCOOR^{36}$; or $—(CR^{42}R^{43})_tCONR^7R^{57}$;

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—OR^{36}$; $—NR^7R^{57}$; $—NR^7COR^{38}$; $—NR^7SO_2R^{38}$; $—NR^7CONR^7R^{57}$; $—COR^{38}$; or $—SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; $—COOR^{36}$; or $—CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_rOR^{36}$; —$(CR^{42}R^{43})_rNR^7R^{45}$; —$(CR^{42}R^{43})_qCOOR^{36}$; or —$(CR^{42}R^{43})_qCONR^7R^{45}$;

or a stereoisomer of such a compound; or a salt, solvate, clathrate, N-oxide, isotopically enriched or enantiomerically enriched version thereof.

5. A compound according to claim 1 wherein the Template A is selected from $A_B1$-$A_C1$; $A_B1$-$A_C4$; $A_B1$-$A_C19$; $A_B2$-$A_C4$; $A_B4$-$A_C1$; $A_B4$-$A_C4$; $A_B4$-$A_C19$; $A_B4$-$A_C59$; $A_B5$-$A_C51$; $A_B5$-$A_C59$; $A_B6$-$A_C31$; $A_B9$-$A_C6$; or $A_B46$-$A_C58$;

and wherein $R^3$ and $R^4$ are independently defined as H; F; $CF_3$; $OCF_3$; $OCHF_2$; CN; or $C_{1-6}$-alkoxyl;

$R^5$ is H; $CF_3$; or $C_{1-6}$-alkyl;

$R^{33}$ is H; or $C_{1-6}$-alkyl;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or —$(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or —$NR^7R^{45}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or —$(CR^{42}R^{43})_qR^{44}$;

$R^{51}$ and $R^{53}$ are independently defined as H; F; $CF_3$; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_tOR^{36}$; —$(CR^{42}R^{43})NR^7R^{57}$; —$(CR^{42}R^{43})_tCOOR^{36}$; or —$(CR^{42}R^{43})_tCONR^7R^{57}$;

$R^{54}$ is H; F; $CF_3$; $OCF_3$; $OCHF_2$; $NO_2$; CN; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$OR^{36}$; —$NR^7R^{57}$; —$NR^7COR^{38}$; —$NR^7SO_2R^{38}$; —$NR^7CONR^7R^{57}$; —$COR^{38}$; or —$SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; —$COOR^{36}$; or —$CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_rOR^{36}$; —$(CR^{42}R^{43})_rNR^7R^{45}$; —$(CR^{42}R^{43})_qCOOR^{36}$; or —$(CR^{42}R^{43})_qCONR^7R^{45}$;

or a stereoisomer of such a compound; or a salt, solvate, clathrate, N-oxide, isotopically enriched or enantiomerically enriched version thereof.

6. A compound according to claim 1 wherein the Bridge C is represented by $$---[C_{AA}]_{1-3}---$$

and wherein $C_{AA}$ is an amino acid selected from

Ala L-Alanine;
Arg L-Arginine;
Asn L-Asparagine;
Asp L-Aspartic acid;
Cys L-Cysteine;
Glu L-Glutamic acid;
Gln L-Glutamine;
Gly Glycine;
His L-Histidine;
Ile L-Isoleucine;
Leu L-Leucine;
Lys L-Lysine;
Met L-Methionine;
Phe L-Phenylalanine;
Pro L-Proline;
Ser L-Serine;
Thr L-Threonine;
Trp L-Tryptophan;
Tyr L-Tyrosine;
Val L-Valine;
Apa 3-Amino-propanoic acid;
H-β[3]-HAla-OH (3S)-3-Amino-butyric acid;
H-β[3]-HVal-OH (3R)-3-Amino-4-methyl-valeric acid;
H-β[3]-HIle-OH (3R,4S)-3-Amino-4-methyl-hexanoic acid;
H-β[3]-HLeu-OH (3 S)-3-Amino-5-methyl-hexanoic acid;
H-β[3]-HMet-OH (3S)-3-Amino-5-methylthio pentanoic acid;
H-β[3]-HTyr-OH (3S)-3-Amino-4-(4'-hydroxyphenyl)-butyric acid;
H-β[3]-HHis-OH (3 S)-3-Amino-4-(imidazole-4'-yl)-butyric acid;
H-β[3]-HPhe-OH (3S)-3-Amino-4-phenyl butyric acid;
H-β[3]-HTrp-OH (3 S)-3-Amino-4-(indol-3'-yl)-butyric acid;
H-β[3]-HSer-OH (3R)-3-Amino-4-hydroxy-butyric acid;
H-β[3]-HAsp-OH 3-Amino-pentanedioic acid;
H-β[3]-HGlu-OH (3 S)-3-Amino-hexanedioic acid;
H-β[3]-HLys-OH (3 S)-3,7-Diamino-heptanoic acid;
H-β[3]-HArg-OH (3 S)-3-Amino-6-guanidino-hexanoic-acid;
H-β[3]-HCys-OH (3R)-3-Amino-4-mercapto-butyric acid;
H-β[3]-HAsn-OH (3S)-3-Amino-4-carbamoyl-butyric acid;
H-β[3]-HGln-OH (3S)-3-Amino-5-carbamoyl-pentanoic acid;
H-β[3]-HThr-OH (3R,4R)-3-Amino-4-hydroxy-pentanoic acid;
Gaba 4-Amino-butyric acid;
H-γ[4]-DiHAla-OH (4S)-4-Amino-pentanoic acid;
H-γ[4]-DiHVal-OH (4R)-4-Amino-5-methyl-hexanoic acid;
H-γ[4]-DiHIle-OH (4R,5S)-4-Amino-5-methyl-heptanoic acid;
H-γ[4]-DiHLeu-OH (4R)-4-Amino-6-methyl-heptanoic acid;
H-γ[4]-DiHMet-OH (4R)-4-Amino-6-methylthio-hexanoic acid;
H-γ[4]-DiHTyr-OH (4R)-4-Amino-5-(4'-hydroxyphenyl)-pentanoic acid;
H-γ[4]-DiHHis-OH (4R)-4-Amino-5-(imidazole-4'-yl)-pentanoic acid;
H-γ[4]-DiHPhe-OH (4R)-4-Amino-5-phenyl-pentanoic acid;
H-γ[4]-DiHTrp-OH (4R)-4-Amino-5-(indol-3'-yl)-pentanoic acid;
H-γ[4]-DiHSer-OH (4R)-4-Amino-5-hydroxy-pentanoic acid;
H-γ[4]-DiHAsp-OH (4R)-4-Amino-hexanedioic acid;
H-γ[4]-DiHGlu-OH 4-Amino-heptanedioic acid;
H-γ[4]-DiHLys-OH (4S)-4,8-Diamino-octanoic acid;
H-γ[4]-DiHArg-OH (4S)-4-Amino-7-guanidino-heptanoic-acid;
H-γ[4]-DiHCys-OH (4R)-4-Amino-5-mercapto-pentanoic acid;

H-$\gamma^4$-DiHAsn-OH (4R)-4-Amino-5-carbamoyl-pentanoic acid;
H-$\gamma^4$-DiHGln-OH (3 S)-3-Amino-5-carbamoyl-hexanoic acid;
H-$\gamma^4$-DiHThr-OH (4R,5R)-4-Amino-5-hydroxy-hexanoic acid;
Cit L-Citrulline;
Orn L-Ornithine;
tBuA L-t-Butylalanine;
Sar Sarcosine;
Pen L-Penicillamine;
tBuG L-tert.-Butylglycine;
4AmPhe L-para-Aminophenylalanine;
3AmPhe L-meta-Aminophenylalanine;
2AmPhe L-ortho-Aminophenylalanine;
Phe(mC($NH_2$)═NH) L-meta-Amidinophenylalanine;
Phe(pC($NH_2$)═NH) L-para-Amidinophenylalanine;
Phe(mNHC($NH_2$)═NH) L-meta-Guanidinophenylalanine;
Phe(pNHC($NH_2$)═NH) L-para-Guanidinophenylalanine;
2Pal (2S)-2-Amino-3-(pyridine-2'-yl)-propionic acid;
4Pal (2S)-2-Amino-3-(pyridine-4'-yl)-propionic acid;
Phg L-Phenylglycine;
Cha L-Cyclohexylalanine;
$C_4$al L-3-Cyclobutylalanine;
$C_5$al L-3-Cyclopentylalanine;
Nle L-Norleucine;
2-Nal L-2-Naphthylalanine;
1-Nal L-1-Naphthylalanine;
4ClPhe L-4-Chlorophenylalanine;
3 ClPhe L-3-Chlorophenylalanine;
2ClPhe L-2-Chlorophenylalanine;
3,4$Cl_2$Phe L-3,4-Dichlorophenylalanine;
4FPhe L-4-Fluorophenylalanine;
3FPhe L-3-Fluorophenylalanine;
2FPhe L-2-Fluorophenylalanine;
Thi L-β-2-Thienylalanine;
Tza L-2-Thiazolylalanine;
Mso L-Methionine sulfoxide;
AcLys N-Acetyllysine;
Dap 2,3-Diaminopropionic acid;
Dab 2,4-Diaminobutyric acid;
Dbu (2S)-2,3-Diamino-butyric acid;
Abu γ-Aminobutyric acid (GABA);
Aha ε-Aminohexanoic acid;
Aib α-Aminoisobutyric acid;
ACC 1-Amino cyclopropane carboxylic acid;
ACBC 1-Amino cyclobutane carboxylic acid;
ACPC 1-Amino cyclopentane carboxylic acid;
1-ACHC 1-Amino cyclohexane carboxylic acid;
2-ACHC 2-Amino cyclohexane carboxylic acid;
3-ACHC 3-Amino cyclohexane carboxylic acid;
4-ACHC 4-Amino cyclohexane carboxylic acid;
Y(Bzl) L-O-Benzyltyrosine;
H(Bzl) (3 S)-2-Amino-3-(1'-benzylimidazole-4'-yl)-propionic acid;
Bip L-(4-phenyl)phenylalanine;
S(Bzl) L-O-Benzylserine;
T(Bzl) L-O-Benzylthreonine;
alloT (2S,3S)-2-Amino-3-hydroxy-butyric acid;
Leu3 OH (2S,3R)-2-Amino-3-hydroxy-4-methyl-pentanoic acid;
hAla L-Homo-alanine;
hArg L-Homo-arginine;
hCys L-Homo-cysteine;
hGlu L-Homo-glutamic acid;
hGln L-Homo-glutamine;
hHis L-Homo-histidine;
hIle L-Homo-isoleucine;
hLeu L-Homo-leucine;
hNle L-Homo-norleucine;
hLys L-Homo-lysine;
hMet L-Homo-Methionine;
hPhe L-Homo-phenylalanine;
hSer L-Homo-serine;
hThr L-Homo-threonine;
hTrp L-Homo-tryptophan;
hTyr L-Homo-tyrosine;
hVal L-Homo-valine;
hCha L-Homo-cyclohexylalanine;
Bpa L-4-Benzoylphenylalanine;
OctG L-Octylglycine;
Tic (3 S)-1,2,3,4-Tetrahydroisoquinoline-3-carboxylic acid;
Tiq (1S)-1,2,3,4-Tetrahydroisoquinoline-1-carboxylic acid;
Oic (2S,3aS,7aS)-1-Octahydro-1H-indole-2-carboxylic acid;
4AmPyrr1 (2S,4S)-4-Amino-pyrrolidine-2-carboxylic acid;
4AmPyrr2 (2S,4R)-4-Amino-pyrrolidine-2-carboxylic acid;
4PhePyrr1 (2S,4R)-4-Phenyl-pyrrolidine-2-carboxylic acid;
4PhePyrr2 (2S,4S)-4-Phenyl-pyrrolidine-2-carboxylic acid;
5PhePyrr1 (2S,5R)-5-Phenyl-pyrrolidine-2-carboxylic acid;
5PhePyrr2 (2S,5S)-5-Phenyl-pyrrolidine-2-carboxylic acid;
4Hyp1 (4S)-L-Hydroxyproline;
4Hyp2 (4R)-L-Hydroxyproline;
4Mp1 (4S)-L-Mercaptoproline;
4Mp2 (4R)-L-Mercaptoproline;
Pip L-Pipecolic acid;
H-$\beta^3$-HCit-OH (3S)-3-Amino-6-carbamidyl-hexanoic acid;
H-$\beta^3$-HOrn-OH (3 S)-3,6-Diamino-hexanoic acid;
H-$\beta^3$-HtBuA-OH (3 S)-3-Amino-5,5-dimethyl-hexanoic acid;
H-$\beta^3$-HSar-OH N-Methyl-3-amino-propionic acid;
H-$\beta^3$-HPen-OH (3R)-3-Amino-4-methyl-4-mercapto-pentanoic acid;
H-$\beta^3$-HtBuG-OH (3R)-3-Amino-4,4-dimethyl-pentanoic acid;
H-$\beta^3$-H4AmPhe-OH (3 S)-3-Amino-4-(4'-aminophenyl)-butyric acid;
H-$\beta^3$-H3AmPhe-OH (3 S)-3-Amino-4-(3'-aminophenyl)-butyric acid;
H-$\beta^3$-H2AmPhe-OH (3 S)-3-Amino-4-(2'-aminophenyl)-butyric acid;
H-$\beta^3$-HPhe(mC($NH_2$)=NH)—OH (3 S)-3-Amino-4-(3'-amidinophenyl)-butyric acid;
H-$\beta^3$-HPhe(pC($NH_2$)=NH)—OH (3 S)-3-Amino-4-(4'-amidinophenyl)-butyric acid;
H-$\beta^3$—OH (3 S)-3-Amino-4-(3'-guanidinophenyl)-butyric acid;
HPhe(mNHC($NH_2$)═NH)—OH
H-$\beta^3$—OH (3 S)-3-Amino-4-(4'-guanidino-phenyl)-butyric acid;
HPhe(pNHC($NH_2$)═NH)—OH
H-$\beta^3$-H2Pal-OH (3 S)-3-Amino-4-(pyridine-2'-yl)-butyric acid;

H-$\beta^3$-H4Pal-OH (3 S)-3-Amino-4-(pyridine-4'-yl)-butyric acid;
H-$\beta^3$-HPhg-OH (3R)-3-Amino-3-phenyl-propionic acid;
H-$\beta^3$-HCha-OH (3S)-3-Amino-4-cyclohexyl-butyric acid;
H-$\beta^3$-H$C_4$al-OH (3S)-3-Amino-4-cyclobutyl-butyric acid;
H-$\beta^3$-H$C_5$al-OH (3S)-3-Amino-4-cyclopentyl-butyric acid;
H-$\beta^3$-HNle-OH (3S)-3-Amino-heptanoic acid;
H-$\beta^3$-H2Nal-OH (3S)-3-Amino-4-(2'-naphthyl)-butyric acid;
H-$\beta^3$-H1Nal-OH (3S)-3-Amino-4-(1'-naphthyl)-butyric acid;
H-$\beta^3$-H4ClPhe-OH (3S)-3-Amino-4-(4'-chlorophenyl)-butyric acid;
H-$\beta^3$-H3ClPhe-OH (3S)-3-Amino-4-(3'-chlorophenyl)-butyric acid;
H-$\beta^3$-H3,4$Cl_2$Phe-OH (3 S)-3-Amino-4-(3',4'-dichloro-phenyl)-butyric acid;
H-$\beta^3$-H4FPhe-OH (3S)-3-Amino-4-(4'-fluorophenyl)-butyric acid;
H-$\beta^3$-H3FPhe-OH (3S)-3-Amino-4-(3'-fluorophenyl)-butyric acid;
H-$\beta^3$-H2FPhe-OH (3S)-3-Amino-4-(2'-fluorophenyl)-butyric acid;
H-$\beta^3$-HThi-OH (3R)-3-Amino-4-(2'-thienyl)-butyric acid;
H-$\beta^3$-HTza-OH (3R)-3-Amino-4-(2'-thiazolyl)-butyric acid;
H-$\beta^3$-HMso-OH (3R)-3-Amino-4-methylsulfoxyl-butyric acid;
H-$\beta^3$-HAcLys-OH (3 S)-7-Acetylamino-3-amino-heptanoic acid;
H-$\beta^3$-HDpr-OH (3R)-3,4-diamino-butyric acid;
H-$\beta^3$-H$A_2$Bu-OH (3S)-3,5-Diamino-pentanoic acid;
H-$\beta^3$-HDbu-OH (3R)-3,4-Diamino-pentanoic acid;
H-$\beta^3$-HAib-OH Amino-dimethyl acetic acid;
H-$\beta^3$-HCyp-OH 1-Amino-cyclopentane-1-yl-acetic acid;
H-$\beta^3$-HY(Bzl)-OH (3S)-3-Amino-4-(4'-benzyloxyphenyl)-butyric acid;
H-$\beta^3$-HH(Bzl)-OH (3 S)-3-Amino-4-(1'-benzylimidazole-4'-yl)-butyric acid;
H-$\beta^3$-HBip-OH (3S)-3-Amino-4-biphenylyl-butyric acid;
H-$\beta^3$-HS(Bzl)-OH (3 S)-3-Amino-4-(benzyloxy)-butyric acid;
H-$\beta^3$-HT(Bzl)-OH (3R,4R)-3-Amino-4-benzyloxy-pentanoic acid;
H-$\beta^3$-HalloT-OH (3R,4S)-3-Amino-4-hydroxy-pentanoic acid;
H-$\beta^3$-HLeu3 OH—OH (3R,4R)-3-Amino-4-hydroxy-5-methyl-hexanoic acid;
H-$\beta^3$-HhAla-OH (3S)-3-Amino-pentanoic acid;
H-$\beta^3$-HhArg-OH (3 S)-3-Amino-7-guanidino-heptanoic acid;
H-$\beta^3$-HhCys-OH (3R)-Amino-5-mercapto-pentanoic acid;
H-$\beta^3$-HhGlu-OH (3 S)-3-Amino-heptanedioic acid;
H-$\beta^3$-HhGln-OH (3S)-3-Amino-6-carbamoyl hexanoic acid;
H-$\beta^3$-HhHis-OH (3S)-3-Amino-5-(imidazole-4'-yl)-pentanoic acid;
H-$\beta^3$-HhIle-OH (3S,5S)-3-Amino-5-methyl-heptanoic acid;
H-$\beta^3$-HhNle-OH (3S)-3-Amino-octanoic acid;
H-$\beta^3$-DiAoc-OH (3S)-3,8-Diamino-octanoic acid;
H-$\beta^3$-HhMet-OH (3 S)-3-Amino-6-methylthio-hexanoic acid;
H-$\beta^3$-HhPe-OH (3S)-3-Amino-5-phenyl-pentanoic acid;
H-$\beta^3$-HhSer-OH (3 S)-3-Amino-5-hydroxy-pentanoic acid;
H-$\beta^3$-HhThr-OH (3S,5R)-3-Amino-5-hydroxy-hexanoic acid;
H-$\beta^3$-HhTrp-OH (3 S)-3-Amino-5-(indol-3'-yl)-pentanoic acid;
H-$\beta^3$-HhThr-OH (3 S)-3-Amino-5-(4'-hydroxyphenyl)-pentanoic acid;
H-$\beta^3$-HhCha-OH (3S)-3-Amino-5-cyclohexyl-pentanoic acid;
H-$\beta^3$-HBpa-OH (3S)-3-Amino-4-(4'-benzoylphenyl)-butyric acid;
H-$\beta^3$-HOctG-OH (3S)-3-Amino-undecanoic acid;
H-$\beta^3$-HNle-OH (3S)-3-Amino-heptanoic acid;
H-$\beta^3$-HTic-OH (3 S)-1,2,3,4-Tetrahydroisoquinoline-3-yl-acetic acid;
H-$\beta^3$-HTiq-OH (1S)-1,2,3,4-Tetrahydroisoquinoline-1-acetic acid;
H-$\beta^3$-HOic-OH (2S,3aS,7aS)-1-Octahydro-1H-indole-2-yl-acetic acid;
H-$\beta^3$-H4AmPyrr1-OH (2S,4S)-4-Amino-pyrrolidine-2-acetic acid;
H-$\beta^3$-H4AmPyrr2-OH (2S,4R)-4-Amino-pyrrolidine-2-acetic acid;
H-$\beta^3$-H4PhePyrr1-OH (2S,4R)-4-Phenyl-pyrrolidine-2-acetic acid;
H-$\beta^3$-H4PhePyrr2-OH (2S,4S)-4-Phenyl-pyrrolidine-2-acetic acid;
H-$\beta^3$-H5PhePyrr1-OH (2S,5R)-5-Phenyl-pyrrolidine-2-acetic acid;
H-$\beta^3$-H5PhePyrr2-OH (2S,5S)-5-Phenyl-pyrrolidine-2-acetic acid;
H-$\beta^3$-H4Hyp1-OH (2S,4S)-4-Hydroxy-pyrrolidine-2-acetic acid;
H-$\beta^3$-H4Hyp2-OH (2S,4R)-4-Hydroxy-pyrrolidine-2-acetic acid;
H-$\beta^3$-H4Mp1-OH (2R,4S)-4-Mercapto-pyrrolidine-2-acetic acid;
H-$\beta^3$-H4Mp2-OH (2R,4R)-4-Mercapto-pyrrolidine-2-acetic acid;
H-$\beta^3$-HPip-OH (2S)-Piperidine-2-acetic acid;
H-$\beta^3$-HPro-OH (2S)-Pyrrolidine-2-acetic acid;
Ahb 4-Amino-2-hydroxy butyric acid;
H-$\gamma^4$-DiHCit-OH (4S)-4-Amino-7-carbamidyl-heptanoic acid;
H-$\gamma^4$-DiHOrn-OH (4S)-4,7-Diamino-heptanoic acid;
H-$\gamma^4$-DiHtBuA-OH (4R)-4-Amino-6,6-dimethyl-heptanoic acid;
H-$\gamma^4$-DiHSar-OH N-Methyl-4-amino-butyric acid;
H-$\gamma^4$-DiHPen-OH (4R)-4-Amino-5-methyl-5-mercapto-hexanoic acid;
H-$\gamma^4$-DiHtBuG-OH (4R)-4-Amino-5,5-dimethyl-hexanoic acid;
H-$\gamma^4$-DiH4AmPhe-OH (4R)-4-Amino-5-(4'-aminophenyl)-pentanoic acid;
H-$\gamma^4$-DiH3 AmPhe-OH (4R)-4-Amino-5-(3'-aminophenyl)-pentanoic acid;
H-$\gamma^4$-DiH2AmPhe-OH (4R)-4-Amino-5-(2'-aminophenyl)-pentanoic acid;
H-$\gamma^4$-DiHPhe(mC($NH_2$)═NH)—OH (4R)-4-Amino-5-(3'-amidinophenyl)-pentanoic acid;
H-$\gamma^4$-DiHPhe(pC($NH_2$)═NH)—OH (4R)-4-Amino-5-(4'-amidinophenyl)-pentanoic acid;

H-$\gamma^4$-DiHPhe(mNHC($NH_2$)═NH)—OH (4R)-4-Amino-5-(3'-guanidino-phenyl)-pentanoic acid;
H-$\gamma^4$-DiHPhe(pNHC($NH_2$)═NH)—OH (4R)-4-Amino-5-(4'-guanidino-phenyl)-pentanoic acid;
H-$\gamma^4$-DiH2Pal-OH (4R)-4-Amino-5-(pyridine-4'-yl)-pentanoic acid;
H-$\gamma^4$-DiH4Pal-OH (4R)-4-Amino-5-(pyridine-4'-yl)-pentanoic acid;
H-$\gamma^4$-DiHPhg-OH (4R)-4-Amino-4-phenyl-butyric acid;
H-$\gamma^4$-DiHCha-OH (4R)-4-Amino-5-cyclohexyl-pentanoic acid;
H-$\gamma^4$-DiH$C_4$al-OH (4R)-4-Amino-5-cyclobutyl-pentanoic acid;
H-$\gamma^4$-DiH$C_5$al-OH (4R)-4-Amino-5-cyclopentyl-pentanoic acid;
H-$\gamma^4$-DiHNle-OH (4S)-4-Amino-octanoic acid;
H-$\gamma^4$-DiH2Nal-OH (4S)-4-Amino-5-(2'-naphthyl)-pentanoic acid;
H-$\gamma^4$-DiH1Nal-OH (4S)-4-Amino-5-(1'-naphthyl)-pentanoic acid;
H-$\gamma^4$-DiH4ClPhe-OH (4R)-4-Amino-5-(4'-chlorophenyl)-pentanoic acid;
H-$\gamma^4$-DiH3ClPhe-OH (4R)-4-Amino-5-(3'-chlorophenyl)-pentanoic acid;
H-$\gamma^4$-DiH2ClPhe-OH (4R)-4-Amino-5-(2'-chlorophenyl)-pentanoic acid;
H-$\gamma^4$-DiH3,4$Cl_2$Phe-OH (4R)-4-Amino-5-(3',4'-dichlorophenyl)-pentanoic acid;
H-$\gamma^4$-DiH4FPhe-OH (4R)-4-Amino-5-(4'-fluorophenyl)-pentanoic acid;
H-$\gamma^4$-DiH3FPhe-OH (4R)-4-Amino-5-(3'-fluorophenyl)-pentanoic acid;
H-$\gamma^4$-DiH2FPhe-OH (4R)-4-Amino-5-(2'-fluorophenyl)-pentanoic acid;
H-$\gamma^4$-DiHThi-OH (4R)-4-Amino-5-(2'-thienyl)-pentanoic acid;
H-$\gamma^4$-DiHTza-OH (4R)-4-Amino-5-(2'-thiazolyl)-pentanoic acid;
H-$\gamma^4$-DiHMso-OH (4R)-4-Amino-5-methylsulfoxyl-pentanoic acid;
H-$\gamma^4$-DiHAcLys-OH (4S)-8-Acetylamino-4-amino-ocatanoic acid;
H-$\gamma^4$-DiHDpr-OH (4R)-4,5-diamino-pentanoic acid;
H-$\gamma^4$-DiH$A_2$Bu-OH (4R)-4,5-Diamino-hexanoic acid;
H-$\gamma^4$-DiHDbu-OH (4R)-4,5-Diamion-hexanoic acid;
H-$\gamma^4$-DiHAib-OH 3-Amino-3,3-dimethyl propionic acid;
H-$\gamma^4$-DiHCyp-OH (1'-Amino-cyclopentane-1'-yl)-3-propionic acid;
H-$\gamma^4$-DiHY(Bzl)-OH (4R)-4-Amino-5-(4'-benzyloxyphenyl)-pentanoic acid;
H-$\gamma^4$-DiBH(Bzl)-OH (4R)-4-Amino-5-(1'-benzylimidazole-4'-yl)-pentanoic acid;
H-$\gamma^4$-DiHBip-OH (4R)-4-Amino-5-biphenylyl-pentanoic acid;
H-$\gamma^4$-DiHS(Bzl)-OH (4S)-4-Amino-5-(benzyloxy)-pentanoic acid;
H-$\gamma^4$-DiHT(Bzl)-OH (4R,5R)-4-Amino-5-benzyloxy-hexanoic acid;
H-$\gamma^4$-DiHalloT-OH (4R,5S)-4-Amino-5-hydroxy-hexanoic acid;
H-$\gamma^4$-DiHLeu3OH—OH (4R,5R)-4-Amino-5-hydroxy-6-methyl-heptanoic acid;
H-$\gamma^4$-DiHhAla-OH (4S)-4-Amino-hexanoic acid;
H-$\gamma^4$-DiHhArg-OH (4S)-4-Amino-8-guanidino-octanoic acid;
H-$\gamma^4$-DiHhCys-OH (4R)-Amino-6-mercapto-hexanoic acid;
H-$\gamma^4$-DiHhGlu-OH (4S)-4-Amino-ocatanedioic acid;
H-$\gamma^4$-DiHhGln-OH (4S)-4-Amino-7-carbamoyl-heptanoic acid;
H-$\gamma^4$-DiHhIle-OH (4S,6S)-4-Amino-6-methyl-octanoic acid;
H-$\gamma^4$-DiHhLeu-OH (4S)-4-Amino-7-methyl-ocatanoic acid;
H-$\gamma^4$-DiHhNle-OH (4S)-4-Amino-nonanoic acid;
H-$\gamma^4$-DiHhLys-OH (4S)-4,9-Diamino-nonanoic acid;
H-$\gamma^4$-DiHhMet-OH (4R)-4-Amino-7-methylthioheptanoic acid;
H-$\gamma^4$-DiHhPhe-OH (4S)-4-Amino-6-phenyl-hexanoic acid;
H-$\gamma^4$-DiHhSer-OH (4R)-4-Amino-6-hydroxy-hexanoic acid;
H-$\gamma^4$-DiHhThr-OH (4R,6R)-4-Amino-6-hydroxy-heptanoic acid;
H-$\gamma^4$-DiHhTrp-OH (4S)-4-Amino-6-(indol-3'-yl)-hexanoic acid;
H-$\gamma^4$-DiHhTyr-OH (4S)-4-Amino-6-(4'-hydroxyphenyl)-hexanoic acid;
H-$\gamma^4$-DiHhCha-OH (4R)-4-Amino-5-cyclohexyl-pentanoic acid;
H-$\gamma^4$-DihBpa-OH (4R)-4-Amino-5-(4'-benzoylphenyl)-pentanoic acid;
H-$\gamma^4$-DiHOctG-OH (4S)-4-Amino-dodecanoic acid;
H-$\gamma^4$-DiHNle-OH (4S)-4-Amino-octanoic acid;
H-$\gamma^4$-DiHTic-OH (3R)-1',2',3',4'-Tetrahydroisoquinoline-3'-yl-3-propionic acid;
H-$\gamma^4$-DiHTiq-OH (1'R)-1',2',3',4'-Tetrahydroisoquinoline-1'-yl-3-propionic acid;
H-$\gamma^4$-DiHOic-OH (2'S,3'aS,7'aS)-1'-Octahydro-1H-indole-2'-yl-3-propionic acid;
H-$\gamma^4$-DiH4AmPyrr1-OH (2'R,4'S)-4'-Amino-pyrrolidine-2'-yl-3-propionic acid;
H-$\gamma^4$-DiH4AmPyrr2-OH (2'R,4'R)-4'-Amino-pyrrolidine-2'-yl-3-propionic acid;
H-$\gamma^4$-DiH4PhePyrr1-OH (2'R,4'R)-4'-Phenyl-pyrrolidine-2'-yl-3-propionic acid;
H-$\gamma^4$-DiH4PhePyrr2-OH (2'R,4'S)-4'-Phenyl-pyrrolidine-2'-yl-3-propionic acid;
H-$\gamma^4$-DiH5PhePyrr1-OH (2'S, 5'R)-5'-Phenyl-pyrrolidine-2'-yl-3-propionic acid;
H-$\gamma^4$-DiH5PhePyrr2-OH (2'S, 5'S)-5'-Phenyl-pyrrolidine-2'-yl-3-propionic acid;
H-$\gamma^4$-DiH4Hyp1-OH (2'R,4'S)-4'-Hydroxy-pyrrolidine-2'-yl-2-propionic acid;
H-$\gamma^4$-DiH4Hyp2-OH (2'R,4'R)-4'-Hydroxy-pyrrolidine-2'-yl-3-propionic acid;
H-$\gamma^4$-DiH4Mp1-OH (2'R,4'S)-4'-Mercapto-pyrrolidine-2'-yl-3-propionic acid;
H-$\gamma^4$-DiH4Mp2-OH (2'R,4'R)-4'-Mercapto-pyrrolidine-2'-yl-3-propionic acid;
H-$\gamma^4$-DiHPip-OH (2'S)-Piperidine-2'-yl-3-propionic acid;
H-$\gamma^4$-DiHPro-OH (2'S)-Pyrrolidine-2'-yl-3-propionic acid;
(AEt)G N-(2-Aminoethyl)glycine;
(APr)G N-(3-Amino-n-propyl)glycine;
(ABu)G N-(4-Amino-n-butyl)glycine;
(APe)G N-(5-Amino-n-pentyl)glycine;
(GuEt)G N-(2-Guanidinoethyl)glycine;
(GuPr)G N-(3-Guanidino-n-propyl)glycine;
(GuBu)G N-(4-Guanidino-n-butyl)glycine;
(GuPe)G N-(5-Guanidino-n-pentyl)glycine;
($PEG_3$-$NH_2$)G N-[$H_2N$—$(CH_2)_3$—$(OCH_2$—$CH_2)_2$—O $(CH_2)_3$]glycine;

(Me)G N-Methylglycine;
(Et)G N-Ethylglycine;
(Bu)G N-Butylglycine;
(Pe)G N-Pentylglycine;
(Ip)G N-Isopropylglycine;
(2MePr)G N-(2-Methylpropyl)glycine;
(3MeBu)G N-(3-Methylbutyl)glycine;
(1MePr)G (1S)-N-(1-Methylpropyl)glycine;
(2MeBu)G (2 S)-N-(2-Methylbutyl)glycine;
(MthEt)G N-(Methylthioethyl)glycine;
(MthPr)G N-(Methylthiopropyl)glycine;
(Ben)G N-(Benzyl)glycine;
(PhEt)G N-(2-Phenylethyl)glycine;
(HphMe)G N-([4'-hydroxyphenyl]methyl)glycine;
(HphEt)G N-(2-[4'-hydroxyphenyl]ethyl)glycine;
(ImMe)G N-(Imidazol-5-yl-methyl)glycine;
(ImEt)G N-(2-(Imidazol-5'-yl)ethyl)glycine;
(InMe)G N-(Indol-2-yl-methyl)glycine;
(InEt)G N-(2-(Indol-2'-yl)ethyl)glycine;
(CboMe)G N-(Carboxymethyl)glycine;
(CboEt)G N-(2-Carboxyethyl)glycine;
(CboPr)G N-(3-Carboxypropyl)glycine;
(CbaMe)G N-(Carbamoylmethyl)glycine;
(CbaEt)G N-(2-Carbamoylethyl)glycine;
(CbaPr)G N-(3-Carbamoylpropyl)glycine;
(HyEt)G N-(2-Hydroxyethyl)glycine;
(HyPr)G (2R)-N-(2-Hydroxypropyl)glycine;
(Mcet)G N-(2-Mercaptoethyl)glycine;
Nip (S)-Nipecotic acid/(S)-3-Piperidinecarboxylic acid;
INip Isonipecotic acid/4-Piperidinecarboxylic acid;
PCA (S)-2-Piperazinecarboxylic acid; or
(S)betaPro (S)-β-Proline/(S)-Pyrrolidine-3-carboxylic acid;

or a respective stereoisomer or N-methyl derivative.

7. A compound according to claim 1 selected from:

benzyl N-[(12R,16S,18S)-16-[(tert-butoxycarbonyl)amino]-8,13-dioxo-20-oxa-9,14-diazatetracyclo[19.3.1.$0^{2,7}$.$0^{14,18}$]pentacosa-1(25),2,4,6,21,23-hexaen-12-yl]carbamate;

tert-butyl N-[(12R,16S,18S)-12-amino-8,13-dioxo-20-oxa-9, 14-diazatetracyclo[19.3.1.$0^{2,7}$.$0^{14,18}$]pentacosa-1(25),2,4,6,21,23-hexaen-16-yl]carbamate;

benzyl N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]carbamate;

tert-butyl N-[(12R,16S,18S)-12-{[2-(1-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]carbamate;

N-[(12R,16S,18S)-16-amino-8,13-dioxo-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide;

methyl N-[(12R,16S,18S)-12-{[2-(1-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-16-yl]carbamate;

N-[(12R,16S,18S)-8,13-dioxo-16-{[2-(1-pyrrolidinyl)acetyl]amino}-20-oxa-9,14-diazatetracyclo[19.3.1.$0^{2,7}$. $0^{14,18}$]pentacosa-1(25),2,4,6,21,23-hexaen-12-yl]-2-(1-naphthyl)acetamide;

N-[(12R,16S,18S)-16-(dimethylamino)-8,13-dioxo-20-oxa-9,14-diazatetracyclo[19.3.1.$0^{2,7}$.$0^{14,18}$]pentacosa-1(25),2,4,6,21,23-hexaen-12-yl]-2-(1-naphthyl)acetamide;

(12R,16S,18S)-12,16-diamino-20-oxa-9,14-diazatetracyclo[19.3.1.$0^{2,7}$.$0^{14,18}$]pentacosa-1(25),2,4,6,21,23-hexaene-8,13-dione;

benzyl N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]carbamate;

N-[(12R,16S,18S)-12-amino-8,13-dioxo-20-oxa-9,14-diazatetracyclo[19.3.1.$0^{2,7}$.$0^{14,18}$]pentacosa-1(25),2,4,6,21,23-hexaen-16-yl]-2-(2-naphthyl)acetamide;

2-(dimethylamino)-N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]acetamide;

3-methyl-N-[(12R,16S,18S)-16-{[2-(2-naphthyl)acetyl]amino}-8,13-dioxo-20-oxa-9,14-diazatetracyclo[19.3.1.$0^{2,7}$.$0^{14,18}$]pentacosa-1(25),2,4,6,21,23-hexaen-12-yl]butanamide;

benzyl N-[(12R,16S,18S)-8,13-dioxo-16-[(phenoxycarbonyl)amino]-20-oxa-9,14-diazatetracyclo[19.3.1.$0^{2,7}$.$0^{14,18}$]pentacosa-1(25),2,4,6,21,23-hexaen-12-yl]carbamate;

benzyl N-[(10S,12S,16S)-12-[(tert-butoxycarbonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]carbamate;

tert-butyl N-[(10S,12S,16S)-16-amino-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]carbamate;

benzyl N-[(10S,12S,16S)-12-amino-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]carbamate;

benzyl N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]carbamate;

N-[(10S,12S,16S)-16-amino-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide;

2-(dimethylamino)-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

N-[(10S,12S,16S)-16-[(cyclopropylsulfonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide;

N-[(10S,12S,16S)-20-methyl-16-{[(methylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide;

2-methoxy-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

3-methyl-N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]butanamide;

N-[(10S,12S,16S)-20-methyl-15,21-dioxo-16-[(2-phenylacetyl)amino]-8-oxa-14,20-diazatetracyclo[20.3.1.$0^{2,7}$.$0^{10,14}$]hexacosa-1(26),2,4,6,22,24-hexaen-12-yl]-2-(2-naphthyl)acetamide;

N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]benzamide;

N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]butanamide;

N-[(10S,12S,16S)-20-methyl-12-{[2-(2-naphthyl)acetyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]pentanamide;

2-{[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]amino}acetic acid;

2-(dimethylamino)-N-[(10S,12S,16S)-20-methyl-12-{[(methylamino)carbothioyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

2-(dimethylamino)-N-[(10S,12S,16S)-20-methyl-15,21-dioxo-12-[(2-sulfanylacetyl)amino]-8-oxa-14,20-diazatetracyclo[20.3.1.$0^{2,7}$.$0^{10,14}$]hexacosa-1(26),2,4,6,22,24-hexaen-16-yl]acetamide;

2-(dimethylamino)-N-[(10S,12S,16S)-20-methyl-15,21-dioxo-12-{[2-(tritylsulfanyl)acetyl]amino}-8-oxa-14,20-diazatetracyclo[20.3.1.$0^{2,7}$.$0^{10,14}$]hexacosa-1(26),2,4,6,22,24-hexaen-16-yl]acetamide;

2-(dimethylamino)-N-[(10S,12S,16S)-20-methyl-12-{[(methylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

2-(dimethylamino)-N-[(10S,12S,16S)-12-({[3-(dimethylamino)anilino]carbonyl}amino)-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

2-(dimethylamino)-N-[(10S,12S,16S)-20-methyl-12-{[(2-naphthylamino)carbonyl]amino}-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

2-(dimethylamino)-N-[(10S,12S,16S)-20-methyl-12-[(methylsulfonyl)amino]-15,21-dioxo-8-oxa-14,20-diazatetracyclo[20.3.1.$0^{2,7}$.$0^{10,14}$]hexacosa-1(26),2,4,6,22,24-hexaen-16-yl]acetamide;

N-[(10S,12S,16S)-12-[(benzylsulfonyl)amino]-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]-2-(dimethylamino)acetamide;

tert-butyl N-[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl]carbamate;

N-[(10S,12S,16S)-12-amino-20-methyl-15,21-dioxo-8-oxa-14,20-diazatetracyclo[20.3.1.$0^{2,7}$.$0^{10,14}$]hexacosa-1(26),2,4,6,22,24-hexaen-16-yl]-2-(dimethylamino)acetamide;

ethyl 2-{[(10S,12S,16S)-16-{[2-(dimethylamino)acetyl]amino}-20-methyl-15,21-dioxo-8-oxa-14,20-diazatetracyclo[20.3.1.$0^{2,7}$.$0^{10,14}$]hexacosa-1(26),2,4,6,22,24-hexaen-12-yl}amino acetate;

benzyl (10R,15S)-4-methoxy-10,16-dimethyl-12,17-dioxo-8-oxa-11,16-diazatricyclo[16.3.1.$0^{2,7}$]docosa-1(22),2,4,6,18,20-hexaene-15-carboxylate;

(10R,15S)-4-methoxy-10,16-dimethyl-12,17-dioxo-8-oxa-11,16-diazatricyclo[16.3.1.$0^{2,7}$]docosa-1(22),2,4,6,18,20-hexaene-15-carboxylic acid;

(10R,15S)-4-methoxy-10,16-dimethyl-12,17-dioxo-8-oxa-11,16-diazatricyclo[16.3.1.$0^{2,7}$]docosa-1(22),2,4,6,18,20-hexaene-15-carboxamide;

(10R,15S)-4-methoxy-N,10,16-trimethyl-12,17-dioxo-8-oxa-11,16-diazatricyclo[16.3.1.$0^{2,7}$]docosa-1(22),2,4,6,18,20-hexaene-15-carboxamide;

(10R,15S)-4-methoxy-10,16-dimethyl-12,17-dioxo-N-phenyl-8-oxa-11,16-diazatricyclo[16.3.1.$0^{2,7}$]docosa-1(22),2,4,6,18,20-hexaene-15-carboxamide;

(10R,15S)-4-methoxy-10,16-dimethyl-15-(1-pyrrolidinylcarbonyl)-8-oxa-11,16-diazatricyclo[16.3.1.$0^{2,7}$]docosa-1(22),2,4,6,18,20-hexaene-12,17-dione;

(10R,15S)-N-[2-(dimethylamino)ethyl]-4-methoxy-10,16-dimethyl-12,17-dioxo-8-oxa-11,16-diazatricyclo[16.3.1.$0^{2,7}$]docosa-1(22),2,4,6,18,20-hexaene-15-carboxamide;

tert-butyl N-[3-({[(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]carbonyl}amino)propyl]carbamate;

(10R,15S)-N-(3-aminopropyl)-4-methoxy-10,16-dimethyl-12,17-dioxo-8-oxa-11,16-diazatricyclo[16.3.1.$0^{2,7}$]docosa-1(22),2,4,6,18,20-hexaene-15-carboxamide;

(10R,15S)-4-methoxy-10,16-dimethyl-12,17-dioxo-N-(3-pyridinylmethyl)-8-oxa-11,16-diazatricyclo[16.3.1.$0^{2,7}$]docosa-1(22),2,4,6,18,20-hexaene-15-carboxamide;

(10R,15S)-4-methoxy-N-(2-methoxyethyl)-10,16-dimethyl-12,17-dioxo-8-oxa-11,16-diazatricyclo[16.3.1.$0^{2,7}$]docosa-1(22),2,4,6,18,20-hexaene-15-carboxamide;

(10R,15S)-N-cyclopropyl-4-methoxy-10,16-dimethyl-12,17-dioxo-8-oxa-11,16-diazatricyclo[16.3.1.$0^{2,7}$]docosa-1(22),2,4,6,18,20-hexaene-15-carboxamide;

(10R,15S)-4-methoxy-10,16-dimethyl-12,17-dioxo-N-(2,2,2-trifluoroethyl)-8-oxa-11,16-diazatricyclo[16.3.1.$0^{2,7}$]docosa-1(22),2,4,6,18,20-hexaene-15-carboxamide (10R,15S)-N-isobutyl-4-methoxy-10,16-dimethyl-12,17-dioxo-8-oxa-11,16-diazatricyclo[16.3.1.$0^{2,7}$]docosa-1(22),2,4,6,18,20-hexaene-15-carboxamide;

(10R,15S)-N-(2-hydroxyethyl)-4-methoxy-10,16-dimethyl-12,17-dioxo-8-oxa-11,16-diazatricyclo[16.3.1.$0^{2,7}$]docosa-1(22),2,4,6,18,20-hexaene-15-carboxamide;

tert-butyl 2-({[(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]carbonyl}amino)acetate;

2-({[(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]carbonyl}amino)acetic acid;

(10R,15S)-4-methoxy-10,16-dimethyl-12,17-dioxo-N-[(1S)-1-phenylethyl]-8-oxa-11,16-diazatricyclo[16.3.1.$0^{2,7}$]docosa-1(22),2,4,6,18,20-hexaene-15-carboxamide;

(10R,15S)-N-[2-(dimethylamino)ethyl]-4-methoxy-N,10,16-trimethyl-12,17-dioxo-8-oxa-11,16-diazatricyclo[16.3.1.$0^{2,7}$]docosa-1(22),2,4,6,18,20-hexaene-15-carboxamide;

(10R,15S)-4-methoxy-10,16-dimethyl-N-(1-naphthylmethyl)-12,17-dioxo-8-oxa-11,16-diazatricyclo[16.3.1.$0^{2,7}$]docosa-1(22),2,4,6,18,20-hexaene-15-carboxamide;

(10R,15S)-4-methoxy-10,16-dimethyl-N-(2-naphthylmethyl)-12,17-dioxo-8-oxa-11,16-diazatricyclo[16.3.1.$0^{2,7}$]docosa-1(22),2,4,6,18,20-hexaene-15-carboxamide;

(10R,15S)-15-(hydroxymethyl)-4-methoxy-10,16-dimethyl-8-oxa-11,16-diazatricyclo[16.3.1.$0^{2,7}$]docosa-1(22),2,4,6,18,20-hexaene-12,17-dione;

(10R,15S)-4-methoxy-10,16-dimethyl-15-[(3-pyridinyloxy)methyl]-8-oxa-11,16-diazatricyclo[16.3.1.$0^{2,7}$]docosa-1(22),2,4,6,18,20-hexaene-12,17-dione;

(10R,15S)-15-(azidomethyl)-4-methoxy-10,16-dimethyl-8-oxa-11,16-diazatricyclo[16.3.1.$0^{2,7}$]docosa-1(22),2,4,6,18,20-hexaene-12,17-dione;

(10R,15S)-15-(aminomethyl)-4-methoxy-10,16-dimethyl-8-oxa-11,16-diazatricyclo[16.3.1.$0^{2,7}$]docosa-1(22),2,4,6,18,20-hexaene-12,17-dione;

N-{[(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]methyl}-2-phenylacetamide;

[(10R,15S)-4-methoxy-10,16-dimethyl-12,17-dioxo-8-oxa-11,16-diazatricyclo[16.3.1.$0^{2,7}$]docosa-1(22),2,4,6,18,20-hexaen-15-yl]methyl N-phenylcarbamate;

benzyl (9S,14S)-9,15-dimethyl-11,16-dioxo-7-oxa-10,15-diazatricyclo[15.3.1.$1^{2,6}$]docosa-1(21),2(22),3,5,17,19-hexaene-14-carboxylate;

(9S,14S)-9,15-dimethyl-11,16-dioxo-7-oxa-10,15-diazatricyclo[15.3.1.$1^{2,6}$]docosa-1(21),2(22),3,5,17,19-hexaene-14-carboxylic acid;

(9S,14S)-N,9,15-trimethyl-11,16-dioxo-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-N-phenyl-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-N-phenethyl-7-oxa-10,15-diazatricyclo[15.3.1.$1^{2,6}$]docosa-1(21),2(22),3,5,17,19-hexaene-14-carboxamide;

(9S,14S)-9,15-dimethyl-N-(1-naphthylmethyl)-11,16-dioxo-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-N-(3-pyridinylmethyl)-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-N-[(1S)-1-phenylethyl]-7-oxa-10,15-diazatricyclo[15.3.1.$1^{2,6}$]docosa-1(21),2(22),3,5,17,19-hexaene-14-carboxamide;

(9S,14S)-N-(2-methoxyethyl)-9,15-dimethyl-11,16-dioxo-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-N-(2,2,2-trifluoroethyl)-7-oxa-10,15-diazatricyclo[15.3.1.$1^{2,6}$]docosa-1(21),2(22),3,5,17,19-hexaene-14-carboxamide;

(9S,14S)-N-cyclopropyl-9,15-dimethyl-11,16-dioxo-7-oxa-10,15-diazatricyclo[15.3.1.$1^{2,6}$]docosa-1(21),2(22),3,5,17,19-hexaene-14-carboxamide;

(9S,14S)-N-isobutyl-9,15-dimethyl-11,16-dioxo-7-oxa-10,15-diazatricyclo[15.3.1.$1^{2,6}$]docosa-1(21),2(22),3,5,17,19-hexaene-14-carboxamide;

(9S,14S)-N-(2-hydroxyethyl)-9,15-dimethyl-11,16-dioxo-7-oxa-10,15-diazatricyclo[15.3.1.$1^{2,6}$]docosa-1(21),2(22),3,5,17,19-hexaene-14-carboxamide;

tert-butyl 2-({[(9S,14S)-9,15-dimethyl-11,16-dioxo-7-oxa-10,15-diazatricyclo[15.3.1.$1^{2,6}$]docosa-1(21),2(22),3,5,17,19-hexaen-14-yl]carbonyl}amino)acetate;

2-({[(9S,14S)-9,15-dimethyl-11,16-dioxo-7-oxa-10,15-diazatricyclo[15.3.1.$1^{2,6}$]docosa-1(21),2(22),3,5,17,19-hexaen-14-yl]carbonyl}amino)acetic acid;

(9S,14S)-N-[2-(dimethylamino)ethyl]-9,15-dimethyl-11,16-dioxo-7-oxa-10,15-diazatricyclo[15.3.1.$1^{2,6}$]docosa-1(21),2(22),3,5,17,19-hexaene-14-carboxamide;

(9S,14S)-9,15-dimethyl-11,16-dioxo-N-[3-(1-pyrrolidinyl)propyl]-7-oxa-10,15-diazatricyclo[15.3.1.$1^{2,6}$]docosa-1(21),2(22),3,5,17,19-hexaene-14-carboxamide;

(9S,14S)-14-(1-azetanylcarbonyl)-9,15-dimethyl-7-oxa-10,15-diazatricyclo[15.3.1.$1^{2,6}$]docosa-1(21),2(22),3,5,17,19-hexaene-11,16-dione;

(9S,14S)-9,15-dimethyl-14-(morpholinocarbonyl)-7-oxa-10,15-diazatricyclo[15.3.1.$1^{2,6}$]docosa-1(21),2(22),3,5,17,19-hexaene-11,16-dione;

(9S,14S)-9,15-dimethyl-N-[(1-methyl-1H-imidazol-4-yl)methyl]-11,16-dioxo-7-oxa-10,15-diazatricyclo[15.3.1.$1^{2,6}$]docosa-1(21),2(22),3,5,17,19-hexaene-14-carboxamide;

(9S,14S)-9,15-dimethyl-N-(2-naphthylmethyl)-11,16-dioxo-7-oxa-10,15-diazatricyclo[15.3.1.$1^{2,6}$]docosa-1(21),2(22),3,5,17,19-hexaene-14-carboxamide;

benzyl (9S,11R)-11-[(tert-butoxycarbonyl)amino]-14,20-dioxo-7-oxa-13,16,19,23-tetraazatetracyclo[19.3.1.$1^{2,6}$.$0^{9,13}$]hexacosa-1(25),2(26),3,5,21,23-hexaene-16-carboxylate;

tert-butyl N-[(9S,11R)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate;

benzyl (9S,11R)-11-amino-14,20-dioxo-7-oxa-13,16,19,23-tetraazatetracyclo[19.3.1.$1^{2,6}$.$0^{9,13}$]hexacosa-1(25),2(26),3,5,21,23-hexaene-16-carboxylate;

(9S,11R)-11-amino-7-oxa-13,16,19,23-tetraazatetracyclo[19.3.1.$1^{2,6}$.$0^{9,13}$]hexacosa-1(25),2(26),3,5,21,23-hexaene-14,20-dione;

tert-butyl N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate;

(9S,11R)-11-amino-16-methyl-7-oxa-13,16,19,23-tetraazatetracyclo[19.3.1.$1^{2,6}$.$0^{9,13}$]hexacosa-1(25),2(26),3,5,21,23-hexaene-14,20-dione;

N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-2-(2-naphthyl)acetamide;

tert-butyl N-[(9S,11R)-16-(3-fluorobenzyl)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]carbamate;

(9S,11R)-11-amino-16-(3-fluorobenzyl)-7-oxa-13,16,19,23-tetraazatetracyclo[19.3.1.$1^{2,6}$.$0^{9,13}$]hexacosa-1(25),2(26),3,5,21,23-hexaene-14,20-dione;

N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]acetamide;

N-[(9S,11R)-16-(3-fluorobenzyl)-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]acetamide;

N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-2-(1-naphthyl)acetamide;

N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]-N-phenylurea;

N-[(9S,11R)-16-methyl-14,20-dioxo-7-oxa-13,16,19,23-tetraazatetracyclo[19.3.1.$1^{2,6}$.$0^{9,13}$]hexacosa-1(25),2(26),3,5,21,23-hexaen-11-yl]benzenesulfonamide;

tert-butyl N-[(9S,11R)-16-[2-(dimethylamino)acetyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate;

(9S,11R)-11-amino-16-[2-(dimethylamino)acetyl]-7-oxa-13,16,19,23-tetraazatetracyclo[19.3.1.1$^{2,6}$.0$^{9,13}$]hexacosa-1(25),2(26),3,5,21,23-hexaene-14,20-dione;

N-[(9S,11R)-16-[2-(dimethylamino)acetyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-phenylacetamide;

N-[(9S,11R)-16-[2-(dimethylamino)acetyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]cyclopropanesulfonamide;

N-[(9S,11R)-16-[2-(dimethylamino)acetyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-N-methylurea;

tert-butyl N-[(9S,11R)-16-(cyclopropylsulfonyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate;

(9S,11R)-11-amino-16-(cyclopropylsulfonyl)-7-oxa-13,16,19,23-tetraazatetracyclo[19.3.1.1$^{2,6}$.0$^{9,13}$]hexacosa-1(25),2(26),3,5,21,23-hexaene-14,20-dione;

N-[(9S,11R)-16-(cyclopropylsulfonyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]benzamide;

tert-butyl N-[(9S,11R)-16-[(methylamino)carbonyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate;

(9S,11R)-11-amino-N-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxamide;

(9S,11R)-11-[(3-fluorobenzoyl)amino]-N-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxamide;

allyl N-[(13S,16R)-16-methyl-14-oxo-18-oxa-8-thia-15-azatricyclo[17.3.1.0$^{2,7}$]tricosa-1(23),2,4,6,19,21-hexaen-13-yl]carbamate;

(13S,16R)-13-amino-16-methyl-18-oxa-8-thia-15-azatricyclo[17.3.1.0$^{2,7}$]tricosa-1(23),2,4,6,19,21-hexaen-14-one;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-naphthyl)acetamide;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(2-naphthyl)acetamide;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-pyrrolidinyl)acetamide;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]nicotinamide;

3-methyl-N-[(13S,16R)-16-methyl-14-oxo-18-oxa-8-thia-15-azatricyclo[17.3.1.0$^{2,7}$]tricosa-1(23),2,4,6,19,21-hexaen-13-yl]butanamide;

methyl N-[(13S,16R)-16-methyl-14-oxo-18-oxa-8-thia-15-azatricyclo[17.3.1.0$^{2,7}$]tricosa-1(23),2,4,6,19,21-hexaen-13-yl]carbamate;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]cyclopropanesulfonamide;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]benzenesulfonamide;

N-methyl-N'-[(13S,16R)-16-methyl-14-oxo-18-oxa-8-thia-15-azatricyclo[17.3.1.0$^{2,7}$]tricosa-1(23),2,4,6,19,21-hexaen-13-yl]urea;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]-N'-(3-pyridinyl)urea;

(13S,16R)-13-(isobutylamino)-16-methyl-18-oxa-8-thia-15-azatricyclo[17.3.1.0$^{2,7}$]tricosa-1(23),2,4,6,19,21-hexaen-14-one;

(13S,16R)-13-(isopentylamino)-16-methyl-18-oxa-8-thia-15-azatricyclo[17.3.1.0$^{2,7}$]tricosa-1(23),2,4,6,19,21-hexaen-14-one;

allyl N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]carbamate;

(13S,16R)-13-amino-16-methyl-18-oxa-8λ$^{6}$-thia-15-azatricyclo[17.3.1.0$^{2,7}$]tricosa-1(23),2,4,6,19,21-hexaene-8,8,14-trione;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]-2-(1-naphthyl)acetamide;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]-2-(2-naphthyl)acetamide;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]-2-(1-pyrrolidinyl)acetamide;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]nicotinamide;

3-methyl-N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]butanamide;

methyl N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]carbamate;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]cyclopropanesulfonamide;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]benzenesulfonamide;

N-methyl-N'-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]urea;

N-[(13S,16R)-16-methyl-8,8,14-trioxo-18-oxa-8λ$^{6}$-thia-15-azatricyclo[17.3.1.0$^{2,7}$]tricosa-1(23),2,4,6,19,21-hexaen-13-yl]-N'-(3-pyridinyl)urea;

(13S,16R)-13-(isobutylamino)-16-methyl-18-oxa-8λ$^{6}$-thia-15-azatricyclo[17.3.1.0$^{2,7}$]tricosa-1(23),2,4,6,19,21-hexaene-8,8,14-trione;

(13S,16R)-13-(isopentylamino)-16-methyl-18-oxa-8λ$^{6}$-thia-15-azatricyclo[17.3.1.0$^{2,7}$]tricosa-1(23),2,4,6,19,21-hexaene-8,8,14-trione;

allyl N-[(10R,13S)-10-methyl-12-oxo-8-oxa-18-thia-11,21-diazatricyclo[17.3.1.0$^{2,7}$]tricosa-1(23),2,4,6,19,21-hexaen-13-yl]carbamate;

(10R,13S)-13-amino-10-methyl-8-oxa-18-thia-11,21-diazatricyclo[17.3.1.0$^{2,7}$]tricosa-1(23),2,4,6,19,21-hexaen-12-one;

(10R,13S)-13-(dimethylamino)-10-methyl-8-oxa-18-thia-11,21-diazatricyclo[17.3.1.$0^{2,7}$]tricosa-1(23),2,4,6,19,21-hexaen-12-one;

(10R,13S)-13-(isobutylamino)-10-methyl-8-oxa-18-thia-11,21-diazatricyclo[17.3.1.$0^{2,7}$]tricosa-1(23),2,4,6,19,21-hexaen-12-one;

(10R,13S)-13-[(3-fluorobenzyl)amino]-10-methyl-8-oxa-18-thia-11,21-diazatricyclo[17.3.1.$0^{2,7}$]tricosa-1(23),2,4,6,19,21-hexaen-12-one;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]acetamide;

2-methoxy-N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]acetamide;

2-(dimethylamino)-N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]acetamide;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]nicotinamide;

3-methyl-N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]butanamide;

tert-butyl N-(3-{[(10R,13S)-10-methyl-12-oxo-8-oxa-18-thia-11,21-diazatricyclo[17.3.1.$0^{2,7}$]tricosa-1(23),2,4,6,19,21-hexaen-13-yl]amino}-3-oxopropyl)carbamate;

3-amino-N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]propanamide;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]-2-(1-naphthyl)acetamide;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]-2-(2-naphthyl)acetamide;

3,3,3-trifluoro-N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]propanamide;

3-fluoro-N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]benzamide;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]-N'-(3-pyridinyl)urea N-methyl-N'-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]urea;

tert-butyl 3-[({[(10R,13S)-10-methyl-12-oxo-8-oxa-18-thia-11,21-diazatricyclo[17.3.1.$0^{2,7}$]tricosa-1(23),2,4,6,19,21-hexaen-13-yl]amino}carbonyl)amino]propanoate;

3-[({[(10R,13S)-10-methyl-12-oxo-8-oxa-18-thia-11,21-diazatricyclo[17.3.1.$0^{2,7}$]tricosa-1(23),2,4,6,19,21-hexaen-13-yl]amino}carbonyl)amino]propanoic acid;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]methanesulfonamide;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]cyclopropanesulfonamide;

N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]benzenesulfonamide;

methyl N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]carbamate;

2-methoxyethyl N-[(10R,13S)-10-methyl-12-oxo-8-oxa-18-thia-11,21-diazatricyclo[17.3.1.$0^{2,7}$]tricosa-1(23),2,4,6,19,21-hexaen-13-yl]carbamate;

allyl N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]carbamate;

(10R,13S)-13-amino-10-methyl-8-oxa-18λ$^6$-thia-11,21-diazatricyclo[17.3.1.$0^{2,7}$]tricosa-1(23),2,4,6,19,21-hexaene-12,18,18-trione;

(10R,13S)-13-(dimethylamino)-10-methyl-8-oxa-18λ$^6$-thia-11,21-diazatricyclo[17.3.1.$0^{2,7}$]tricosa-1(23),2,4,6,19,21-hexaene-12,18,18-trione;

(10R,13S)-13-(isobutylamino)-10-methyl-8-oxa-18λ$^6$-thia-11,21-diazatricyclo[17.3.1.$0^{2,7}$]tricosa-1(23),2,4,6,19,21-hexaene-12,18,18-trione;

(10R,13S)-13-[(3-fluorobenzyl)amino]-10-methyl-8-oxa-18λ$^6$-thia-11,21-diazatricyclo[17.3.1.$0^{2,7}$]tricosa-1(23),2,4,6,19,21-hexaene-12,18,18-trione;

N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]acetamide;

2-methoxy-N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]acetamide;

2-(dimethylamino)-N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]acetamide;

N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]nicotinamide;

3-methyl-N'-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]butanamide;

tert-butyl N-(3-{[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]amino}-3-oxopropyl)carbamate;

3-amino-N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]propanamide;

N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]-2-(1-naphthyl)acetamide;

N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]-2-(2-naphthyl)acetamide;

3,3,3-trifluoro-N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]propanamide;

3-fluoro-N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]benzamide;

N-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]-N'-(3-pyridinyl)urea;

N-methyl-N'-[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]urea;

tert-butyl 3-[({[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]amino}carbonyl)amino]propanoate;

3-[({[(10R,13S)-10-methyl-12,18,18-trioxo-8-oxa-18λ$^6$-thia-11,21-diazatricyclo[17.3.1.$0^{2,7}$]tricosa-1(23),2,4,6,19,21-hexaen-13-yl]amino}carbonyl)amino]propanoic acid;

N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]methanesulfonamide;

N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]cyclopropanesulfonamide;

N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]benzenesulfonamide;

methyl N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]carbamate;

2-methoxyethyl N-[(10R,13S)-10-methyl-12,18,18-trioxo-8-oxa-18λ$^{6}$-thia-11,21-diazatricyclo[17.3.1.0$^{2,7}$]tricosa-1(23),2,4,6,19,21-hexaen-13-yl]carbamate;

(9S,16S,19R)-16-benzyl-19,20-dimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione;

(9S,19S)-19-benzyl-20-methyl-7-oxa-13,17,20,24-tetraazatetracyclo[20.3.1.1$^{2,6}$.0$^{9,13}$]heptacosa-1(26),2(27),3,5,22,24-hexaene-14,18,21-trione;

(9S,19S)-19-benzyl-7-oxa-13,17,20,24-tetraazatetracyclo[20.3.1.1$^{2,6}$.0$^{9,13}$]heptacosa-1(26),2(27),3,5,22,24-hexaene-14,18,21-trione;

(9S,16R,19S)-19-benzyl-16,17,20-trimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione;

(9S,16R)-16,17,20-trimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione;

(9S,16R,19S)-19-benzyl-16,17-dimethyl-7-oxa-13,17,20,24-tetraazatetracyclo[20.3.1.1$^{2,6}$.0$^{9,13}$]heptacosa-1(26),2(27),3,5,22,24-hexaene-14,18,21-trione;

(9S,16S)-16-benzyl-21-methyl-7-oxa-13,17,21,25-tetraazatetracyclo[21.3.1.1$^{2,6}$.0$^{9,13}$]octacosa-1(27),2(28),3,5,23,25-hexaene-14,18,22-trione;

3-[(9S,16R,19S)-16,17,20-trimethyl-14,18,21-trioxo-7-oxa-13,17,20,24-tetraazatetracyclo[20.3.1.1$^{2,6}$.0$^{9,13}$]heptacosa-1(26),2(27),3,5,22,24-hexaen-19-yl]propanoic acid;

(9S,16R,22S)-16,17,20,22,23-pentamethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone;

(9S,16R,22S)-16,17,22-trimethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone;

(9S,19R,22S)-16,19,20,22,23-pentamethyl-7-oxa-13,16,20,23,27-pentaazatetracyclo[23.3.1.1$^{2,6}$.0$^{9,13}$]triaconta-1(29),2(30),3,5,25,27-hexaene-14,17,21,24-tetrone;

(9S,18S,22R)-16,18,19,22,23-pentamethyl-7-oxa-13,16,19,23,27-pentaazatetracyclo[23.3.1.1$^{2,6}$.0$^{9,13}$]triaconta-1(29),2(30),3,5,25,27-hexaene-14,17,20,24-tetrone;

(9S,18S,21R)-18-benzyl-21,22-dimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone;

(9S,18S,21R)-18-benzyl-16,21-dimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone;

(9S,18S,21R)-18-benzyl-16,21,22-trimethyl-7-oxa-13,16,19,22,26-pentaazatetracyclo[22.3.1.1$^{2,6}$.0$^{9,13}$]nonacosa-1(28),2(29),3,5,24,26-hexaene-14,17,20,23-tetrone;

3-[(9S,16R,19S,22S)-16,17,19,23-tetramethyl-14,18,21,24-tetraoxo-7-oxa-13,17,20,23,27-pentaazatetracyclo[23.3.1.1$^{2,6}$.0$^{9,13}$]triaconta-1(29),2(30),3,5,25,27-hexaen-22-yl]propanoic acid;

3-[(9S,15S,18R,21S)-18-benzyl-15,22-dimethyl-14,17,20,23-tetraoxo-7-oxa-13,16,19,22,26-pentaazatetracyclo[22.3.1.1$^{2,6}$.0$^{9,13}$]nonacosa-1(28),2(29),3,5,24,26-hexaen-21-yl]propanoic acid;

3-[(9S,15R,18S,21S)-18-benzyl-15,22-dimethyl-14,17,20,23-tetraoxo-7-oxa-13,16,19,22,26-pentaazatetracyclo[22.3.1.1$^{2,6}$.0$^{9,13}$]nonacosa-1(28),2(29),3,5,24,26-hexaen-21-yl]propanoic acid;

(9S,16R,19S,22R)-19-(4-aminobutyl)-16,17,22-trimethyl-7-oxa-13,17,20,23,27-pentaazatetracyclo[23.3.1.1$^{2,6}$.0$^{9,13}$]triaconta-1(29),2(30),3,5,25,27-hexaene-14,18,21,24-tetrone;

benzyl (10S,12S)-12-[(tert-butoxycarbonyl)amino]-15,21-dioxo-8-oxa-3,14,17,20-tetraazatetracyclo[20.2.2.0$^{2,7}$.0$^{10,14}$]hexacosa-1(24),2,4,6,22,25-hexaene-17-carboxylate;

benzyl (10S,12S)-12-amino-15,21-dioxo-8-oxa-3,14,17,20-tetraazatetracyclo[20.2.2.0$^{2,7}$.0$^{10,14}$]hexacosa-1(24),2,4,6,22,25-hexaene-17-carboxylate;

tert-butyl N-[(10S,12S)-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]carbamate;

tert-butyl N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]carbamate;

(10S,12S)-12-amino-17-methyl-8-oxa-3,14,17,20-tetraazatetracyclo[20.2.2.0$^{2,7}$.0$^{10,14}$]hexacosa-1(24),2,4,6,22,25-hexaene-15,21-dione;

N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-2-(1-naphthyl)acetamide;

3-methyl-N'-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]butanamide;

N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-N'-(3 pyridinyl)urea;

N-[(10S,12S)-17-methyl-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]benzenesulfonamide;

tert-butyl N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]carbamate;

(10S,12S)-12-amino-17-[2-(dimethylamino)acetyl]-8-oxa-3,14,17,20-tetraazatetracyclo[20.2.2.0$^{2,7}$.0$^{10,14}$]hexacosa-1(24),2,4,6,22,25-hexaene-15,21-dione;

N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-2-phenylacetamide;

N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]-N-methylurea;

N-[(10S,12S)-17-[2-(dimethylamino)acetyl]-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]cyclopropanesulfonamide;

benzyl (10S,12S)-12-(acetylamino)-15,21-dioxo-8-oxa-3,14,17,20-tetraazatetracyclo[20.2.2.0$^{2,7}$.0$^{10,14}$]hexacosa-1(24),2,4,6,22,25-hexaene-17-carboxylate;

N-[(10S,12S)-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]acetamide;

N-[(10S,12S)-17-(3-fluorobenzyl)-15,21-dioxo-8-oxa-3,14,17,20-tetraazatetracyclo[20.2.2.0$^{2,7}$.0$^{10,14}$]hexacosa-1(24),2,4,6,22,25-hexaen-12-yl]acetamide;

N-[(10S,12S)-15,21-dioxo-17-[2-(1-pyrrolidinyl)acetyl]-8-oxa-3,14,17,20-tetraazatetracyclo[20.2.2.0$^{2,7}$.0$^{10,14}$]hexacosa-1(24),2,4,6,22,25-hexaen-12-yl]acetamide;

(10S,12S)-12-(acetylamino)-15,21-dioxo-N-phenyl-8-oxa-3,14,17,20-tetraazatetracyclo[20.2.2.0$^{2,7}$.0$^{10,14}$]hexacosa-1(24),2,4,6,22,25-hexaene-17-carboxamide;

N-[(10S,12S)-15,21-dioxo-17-(phenylsulfonyl)-8-oxa-3,14,17,20-tetraazatetracyclo[20.2.2.0$^{2,7}$.0$^{10,14}$]hexacosa-1(24),2,4,6,22,25-hexaen-12-yl]acetamide;

3-({[(10S,12S)-12-(acetylamino)-15,21-dioxo-8-oxa-3,14,17,20-tetraazatetracyclo[20.2.2.0$^{2,7}$.0$^{10,14}$]hexacosa-1(24),2,4,6,22,25-hexaen-17-yl]carbonyl}amino)propanoic acid;

tert-butyl 3-({[(10S,12S)-12-(acetylamino)-15,21-dioxo-8-oxa-3,14,17,20-tetraazatetracyclo[20.2.2.0$^{2,7}$.0$^{10,14}$]hexacosa-1(24),2,4,6,22,25-hexaen-17-yl]carbonyl}amino)propanoate;

methyl (8S,17S,19S)-17-[(tert-butoxycarbonyl)amino]-24-fluoro-6,14-dioxo-10,21-dioxa-4-thia-7,15-diazatetracyclo[20.3.1.1$^{2,5}$.0$^{15,19}$]heptacosa-1(26),2,5 (27),22,24-pentaene-8-carboxylate;

methyl (8S,17S,19S)-17-amino-24-fluoro-6,14-dioxo-10,21-dioxa-4-thia-7,15-diazatetracyclo[20.3.1.1$^{2,5}$.0$^{15,19}$]heptacosa-1(26),2,5(27),22,24-pentaene-8-carboxylate;

methyl (8S,17S,19S)-24-fluoro-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxylate;

(8S,17S,19S)-24-fluoro-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxylic acid;

(8S,17S,19S)-24-fluoro-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxamide;

(8S,17S,19S)-24-fluoro-N-isobutyl-6,14-dioxo-17-[(2-phenylacetyl)amino]-10,21-dioxa-4-thia-7,15-diazatetracyclo[20.3.1.1$^{2,5}$.0$^{15,19}$]heptacosa-1(26),2,5(27),22,24-pentaene-8-carboxamide;

methyl (8S,12E,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylate;

(8S,12E,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid;

methyl (8S,12E,18S,20S)-18-amino-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylate;

methyl (8S,12E,18S,20S)-25-fluoro-18-[2-(2-naphthyl)acetyl]amino-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylate;

tert-butyl N-[(8S,12E,18S,20S)-25-fluoro-8-[(isobutylamino)carbonyl]-6,15-dioxo-10,22-dioxa-4-thia-7,16-diazatetracyclo[21.3.1.1$^{2,5}$.0$^{16,20}$]octacosa-1(27),2,5(28),12,23,25-hexaen-18-yl]carbamate;

(8S,12E,18S,20S)-18-amino-25-fluoro-N-isobutyl-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxamide;

(8S,12E,18S,20S)-25-fluoro-N-isobutyl-6,15-dioxo-18-[(3-pyridinylcarbonyl)amino]-10,22-dioxa-4-thia-7,16-diazatetracyclo[21.3.1.1$^{2,5}$.0$^{16,20}$]octacosa-1(27),2,5(28),12,23,25-hexaene-8-carboxamide;

tert-butyl N-[(8S,12E,18S,20S)-8-(anilinocarbonyl)-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaen-18-yl]carbamate;

(8S,12E,18S,20S)-18-amino-25-fluoro-6,15-dioxo-N-phenyl-10,22-dioxa-4-thia-7,16-diazatetracyclo[21.3.1.1$^{2,5}$.0$^{16,20}$]octacosa-1(27),2,5(28),12,23,25-hexaene-8-carboxamide;

methyl (8S,12E,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$]octacosa-1(27),2,5(28),12,23,25-hexaene-8-carboxylate;

(8S,12E,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$]octacosa-1(27),2,5(28),12,23,25-hexaene-8-carboxylic acid;

methyl (8S,12E,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylate;

(8S,12E,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid;

(8S,12E,18S,20S)-25-fluoro-N-isobutyl-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxamide;

(8S,12E,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),12,23,25-hexaene-8-carboxylic acid;

methyl (8S,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate;

(8S,18S,20S)-18-[(tert-butoxycarbonyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylic acid;

methyl (8S,18S,20S)-18-amino-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate;

methyl (8S,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate;

tert-butyl N-[(8S,18S,20S)-8-(anilinocarbonyl)-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate;

(8S,18S,20S)-18-amino-25-fluoro-6,15-dioxo-N-phenyl-10,22-dioxa-4-thia-7,16-diazatetracyclo[21.3.1.1$^{2,5}$.0$^{16,20}$]octacosa-1(27),2,5(28),23,25-pentaene-8-carboxamide;

methyl (8S,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$]octacosa-1(27),2,5(28),23,25-pentaene-8-carboxylate;

(8S,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylic acid;

methyl (8S,18S,20S)-18-[(3-chlorobenzoyl)amino]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylate;

(8S,18S,20S)-25-fluoro-6,15-dioxo-18-[(2-phenylacetyl)amino]-10,22-dioxa-4-thia-7,16-diazatetracyclo[21.3.1.1$^{2,5}$.0$^{16,20}$]octacosa-1(27),2,5(28),23,25-pentaene-8-carboxylic acid;

(8S,18S,20S)-25-fluoro-18-{[2-(2-naphthyl)acetyl]amino}-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxylic acid;

tert-butyl N-[(8S,18S,20S)-25-fluoro-8-[(isobutylamino)carbonyl]-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate;

(8S,18S,20S)-18-amino-25-fluoro-N-isobutyl-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide;

(8S,18S,20S)-25-fluoro-N-isobutyl-6,15-dioxo-18-[(3-pyridinylcarbonyl)amino]-10,22-dioxa-4-thia-7,16-diazatetracyclo[21.3.1.1$^{2,5}$.0$^{16,20}$]octacosa-1(27),2,5(28),23,25-pentaene-8-carboxamide;

tert-butyl N-[(8S,18S,20S)-8-[(4-chloroanilino)carbonyl]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate;

(8S,18S,20S)-18-amino-N-(4-chlorophenyl)-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide;

tert-butyl N-[(8S,18S,20S)-25-fluoro-6,15-dioxo-8-(3-toluidinocarbonyl)-10,22-dioxa-4-thia-7,16-diazatetracyclo[21.3.1.1$^{2,5}$.0$^{16,20}$]octacosa-1(27),2,5(28),23,25-pentaen-18-yl]carbamate;

(8S,18S,20S)-18-amino-25-fluoro-N-(3-methylphenyl)-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide;

tert-butyl N-[(8S,18S,20S)-8-[(benzylamino)carbonyl]-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaen-18-yl]carbamate;

(8S,18S,20S)-18-amino-N-benzyl-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide;

benzyl N-[(9S,11S,15S)-11-[(4-bromobenzyl)oxy]-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]carbamate;

(9S,11S,15S)-15-amino-11-hydroxy-18,21-dimethyl-7-oxa-3-thia-13,18,21,22-tetraazatetracyclo[18.2.1.0$^{2,6}$.0$^{9,13}$]tricosa-1(22),2(6),4,20(23)-tetraene-14,19-dione;

(9S,11S,15S)-15-amino-11-(benzyloxy)-18,21-dimethyl-7-oxa-3-thia-13,18,21,22-tetraazatetracyclo[18.2.1.0$^{2,6}$. 0$^{9,13}$]tricosa-1(22),2(6),4,20(23)-tetraene-14,19-dione;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(2-naphthyl)acetamide;

N-[(9S,11S,15S)-11-(benzyloxy)-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]acetamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(1-naphthyl)acetamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-3-methylbutanamide;

3-fluoro-N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]benzamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]benzenesulfonamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]methanesulfonamide;

methyl N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]carbamate;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N-methylurea;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N'-(3-pyridinyl)urea;

N-[(9S,11S,15S)-11-methoxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(2-naphthyl)acetamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N'-(2-naphthyl)urea;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-phenylacetamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-3-methoxybenzamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-naphthalenesulfonamide;

3-(4-fluorophenyl)-N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]propanamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(1H-indol-3-yl)acetamide;

(9S,11S,15S)-11-hydroxy-18,21-dimethyl-15-{[2-(2-naphthyl)ethyl]amino}-7-oxa-3-thia-13,18,21,22-tetraazatetracyclo[18.2.1.0$^{2,6}$.0$^{9,13}$]tricosa-1(22),2(6),4,20(23)-tetraene-14,19-dione;

(9S,11S,15S)-15-[(4-fluorobenzyl)amino]-11-hydroxy-18,21-dimethyl-7-oxa-3-thia-13,18,21,22-tetraazatetracyclo[18.2.1.0$^{2,6}$.0$^{9,13}$]tricosa-1(22),2(6),4,20(23)-tetraene-14,19-dione;

benzyl N-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate;

benzyl N-[(13R,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate;

(13S,19S)-13-amino-4,8-dimethyl-23-nitro-21-oxa-3,8,15,27-tetraazatetracyclo[20.2.2.1$^{2,6}$.0$^{15,19}$]heptacosa-1(24),2(27),3,5,22,25-hexaene-7,14-dione;

benzyl N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate;

benzyl N-[(13S,19S)-23-(acetylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate;

N-[(13S,19S)-13-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide;

N-(2-chlorophenyl)-N'-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]urea;

N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-N'-(2-chlorophenyl)urea;

N-[(13S,19S)-13-{[(2-chloroanilino)carbonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide;

N-[(13S,19S)-4,8-dimethyl-23-nitro-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide;

N-[(13S,19S)-23-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide;

N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]cyclopropanecarboxamide;

N-[(13S,19S)-13-amino-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide;

benzyl N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]carbamate;

benzyl N-[(13S,19S)-4,8-dimethyl-7,14-dioxo-23-(2-pyrimidinylamino)-21-oxa-3,8,15,27-tetraazatetracyclo[20.2.2.1$^{2,6}$.0$^{15,19}$]heptacosa-1(24),2(27),3,5,22,25-hexaen-13-yl]carbamate;

(13S,19S)-13-amino-4,8-dimethyl-23-(2-pyrimidinylamino)-21-oxa-3,8,15,27-tetraazatetracyclo[20.2.2.1$^{2,6}$.0$^{15,19}$]heptacosa-1(24),2(27),3,5,22,25-hexaene-7,14-dione;

N-[(13S,19S)-13-(dimethylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide;

N-[(13S,19S)-23-(acetylamino)-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-2-phenylacetamide;

N-[(13S,19S)-13-{[(3-chlorophenyl)sulfonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide;

N-[(13S,19S)-13-{[(isobutylamino)carbonyl]amino}-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]acetamide;

N-[(13S,19S)-4,8-dimethyl-23-[(methylsulfonyl)amino]-7,14-dioxo-21-oxa-3,8,15,27-tetraazatetracyclo[20.2.2.1$^{2,6}$.0$^{15,19}$]heptacosa-1(24),2(27),3,5,22,25-hexaen-13-yl]-4-fluorobenzamide;

N-[(13S,19S)-13-[(3-fluorobenzyl)amino]-4,8-dimethyl-7,14-dioxo-21-oxa-3,8,15,27-tetraazatetracyclo[20.2.2.1$^{2,6}$.0$^{15,19}$]heptacosa-1(24),2(27),3,5,22,25-hexaen-23-yl]methanesulfonamide;

benzyl N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]carbamate;

(15R,16aS)-15-amino-10-methyl-10,11,15,16,16a,17-hexahydro-14H-dibenzo[i,k]pyrrolo[2,1-c][1,4,7]oxadiazacyclododecine-9,12-dione;

(15R,16aS)-15-(dimethylamino)-10-methyl-10,11,15,16,16a,17-hexahydro-14H-dibenzo[i,k]pyrrolo[2,1-c][1,4,7]oxadiazacyclododecine-9,12-dione;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]acetamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-methylbutanamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(2-naphthyl)acetamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(1-naphthyl)acetamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-2-(dimethylamino)acetamide;

tert-butyl N-(3-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino-3-oxopropyl)carbamate;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-aminopropanamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-3-fluorobenzamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]isonicotinamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N-methylurea;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N'-(3-pyridinyl)urea;

2-methoxyethyl N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]carbamate;

tert-butyl 3-[({[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino}carbonyl)amino]propanoate;

3-[({[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]amino}carbonyl)amino]propanoic acid;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]methanesulfonamide;

N-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]benzenesulfonamide;

(15R,16aS)-15-[(3-fluorobenzyl)amino]-10-methyl-10,11,15,16,16a,17-hexahydro-14H-dibenzo[i,k]pyrrolo[2,1-c][1,4,7]oxadiazacyclododecine-9,12-dione;

(15R,16aS)-15-(isobutylamino)-10-methyl-10,11,15,16,16a,17-hexahydro-14H-dibenzo[i,k]pyrrolo[2,1-c][1,4,7]oxadiazacyclododecine-9,12-dione;

N"-[(15R,16aS)-10-methyl-9,12-dioxo-9,10,11,12,15,16,16a,17-octahydro-14H-dibenzo[i,k]pyrrolo[2,1-c][1,4,7]oxadiazacyclododecin-15-yl]-N,N,N,N-tetramethylguanidine;

benzyl (16S,18S)-16-[(tert-butoxycarbonyl)amino]-7,13-dioxo-4-(trifluoromethyl)-5,20-dioxa-3,8, 11,14-tetraazatetracyclo[19.3.1.0$^{2,6}$.0$^{14,18}$]pentacosa-1(25),2(6),3,21,23-pentaene-11-carboxylate;

tert-butyl N-[(16S,18S)-7,13-dioxo-4-(trifluoromethyl)-5,20-dioxa-3,8, 11,14-tetraazatetracyclo[19.3.1.0$^{2,6}$.0$^{14,18}$]pentacosa-1(25),2(6),3,21,23-pentaen-16-yl]carbamate;

benzyl (16S,18S)-16-amino-7,13-dioxo-4-(trifluoromethyl)-5,20-dioxa-3,8, 11,14-tetraazatetracyclo[19.3.1.0$^{2,6}$.0$^{14,18}$]pentacosa-1(25),2(6),3,21,23-pentaene-11-carboxylate;

allyl N-[(12R,16S,18S)-16-[(tert-butoxycarbonyl)amino]-8,13-dioxo-20-oxa-9,14-diazatetracyclo[19.3.1.0$^{2,7}$.0$^{14,18}$]pentacosa-1(25),2,4,6,21,23-hexaen-12-yl]carbamate;

allyl N-[(12R,16S,18S)-16-amino-8,13-dioxo-20-oxa-9,14-diazatetracyclo[19.3.1.0$^{2,7}$.0$^{14,18}$]pentacosa-1(25),2,4,6,21,23-hexaen-12-yl]carbamate;

2-(1H-imidazol-1-yl)-N-[(12R,16S,18S)-12-{[2-(1-naphthyl)acetyl]amino}-8,13-dioxo-20-oxa-9,14-diazatetracyclo[19.3.1.0$^{2,7}$.0$^{14,18}$]pentacosa-1 (25),2,4,6,21,23-hexaen-16-yl]acetamide;

N-[(12R,16S,18S)-8,13-dioxo-16-{[(3-pyridinylamino)carbonyl]amino}-20-oxa-9,14-diazatetracyclo[19.3.1.0$^{2,7}$.0$^{14,18}$]pentacosa-1(25),2,4,6,21,23-hexaen-12-yl]-2-(1-naphthyl)acetamide;

2-(3-chlorophenyl)-N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]acetamide;

2-cyclohexyl-N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]acetamide;

N-[(12R,16S,18S)-12-{[(1-naphthylamino)carbonyl]amino}-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide;

N-[(12R,16S,18S)-12-[(benzylsulfonyl)amino]-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide;

benzyl N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]carbamate;

N-[(12R,16S,18S)-12-amino-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide;

N-[(12R,16S,18S)-12-{[2-(1-naphthyl)ethyl]amino}-8,13-dioxo-20-oxa-9,14-diazatetracyclo[19.3.1.0$^{2,7}$.0$^{14,}$$_{18}$]pentacosa-1(25),2,4,6,21,23-hexaen-16-yl]-2-(1-pyrrolidinyl)acetamide;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(1-naphthyl)acetamide;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-N'-(2-naphthyl)urea;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-naphthalenesulfonamide;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-3-(2-naphthyl)propanamide;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-3-phenylpropanamide;

2-(dimethylamino)-N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]acetamide;

benzyl (9S,11R)-11-{[2-(2-naphthyl)acetyl]amino}-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxylate;

N-[(9S,11R)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-16-(3-fluorobenzoyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-16-benzyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-14,20-dioxo-16-phenethyl-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-14,20-dioxo-16-(3-phenylpropyl)-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-16-isopentyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-16-isobutyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

2-(dimethylamino)ethyl (9S,11R)-11-{[2-(2-naphthyl)acetyl]amino}-14,20-dioxo-7-oxa-13,16,19,23-tetraazatetracyclo[19.3.1.1$^{2,6}$.0$^{9,13}$]hexacosa-1(25),2(26),3,5,21,23-hexaene-16-carboxylate;

N-[(9S,11R)-16-[2-(dimethylamino)ethyl]-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide; or 3,3-dimethyl-N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]butanamide.

8. A compound according to claim 1 selected from:

tert-butyl N-[(12R,16S,18S)-12-amino-8,13-dioxo-20-oxa-9,14-diazatetracyclo[19.3.1.0$^{2,7}$.0$^{14,18}$]pentacosa-1(25),2,4,6,21,23-hexaen-16-yl]carbamate;

N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]-2-(1-naphthyl)acetamide;

benzyl N-[(12R,16S,18S)-8,13-dioxo-16-[(phenoxycarbonyl)amino]-20-oxa-9,14-diazatetracyclo[19.3.1.0$^{2,7}$.0$^{14,18}$]pentacosa-1(25),2,4,6,21,23-hexaen-12-yl]carbamate;

benzyl N-[(10S,12S,16S)-20-methyl-12-{[2-(2-naphthyl)acetyl]amino}-15,21-dioxo-8-oxa-14,20-diazatetracyclo[20.3.1.0$^{2,7}$.0$^{10,14}$]hexacosa-1(26),2,4,6,22,24-hexaen-16-yl]carbamate;

2-(dimethylamino)-N-[(10S,12S,16S)-20-methyl-12-{[2-(2-naphthyl)acetyl]amino}-15,21-dioxo-8-oxa-14,20-diazatetracyclo[20.3.1.0$^{2,7}$.0$^{10,14}$]hexacosa-1(26),2,4,6,22,24-hexaen-16-yl]acetamide;

N-[(10S,12S,16S)-16-[(cyclopropylsulfonyl)amino]-20-methyl-15,21-dioxo-8-oxa-14,20-diazatetracyclo[20.3.1.0$^{2,7}$.0$^{10,14}$]hexacosa-1(26),2,4,6,22,24-hexaen-12-yl]-2-(2-naphthyl)acetamide;

3-methyl-N'-[(10S,12S,16S)-20-methyl-12-{[2-(2-naphthyl)acetyl]amino}-15,21-dioxo-8-oxa-14,20-diazatetracyclo[20.3.1.0$^{2,7}$.0$^{10,14}$]hexacosa-1(26),2,4,6,22,24-hexaen-16-yl]butanamide;

N-[(10S,12S,16S)-20-methyl-15,21-dioxo-16-[(2-phenylacetyl)amino]-8-oxa-14,20-diazatetracyclo[20.3.1.0$^{2,7}$.0$^{10,14}$]hexacosa-1(26),2,4,6,22,24-hexaen-12-yl]-2-(2-naphthyl)acetamide;

N-[(10S,12S,16S)-20-methyl-12-{[2-(2-naphthyl)acetyl]amino}-15,21-dioxo-8-oxa-14,20-diazatetracyclo[20.3.1.0$^{2,7}$.0$^{10,14}$]hexacosa-1(26),2,4,6,22,24-hexaen-16-yl]benzamide;

N-[(10S,12S,16S)-20-methyl-12-{[2-(2-naphthyl)acetyl]amino}-15,21-dioxo-8-oxa-14,20-diazatetracyclo[20.3.1.0$^{2,7}$.0$^{10,14}$]hexacosa-1(26),2,4,6,22,24-hexaen-16-yl]butanamide;

N-[(10S,12S,16S)-20-methyl-12-{[2-(2-naphthyl)acetyl]amino}-15,21-dioxo-8-oxa-14,20-diazatetracyclo[20.3.1.0$^{2,7}$.0$^{10,14}$]hexacosa-1(26),2,4,6,22,24-hexaen-16-yl]pentanamide;

(10R,15S)-4-methoxy-10,16-dimethyl-12,17-dioxo-N'-(3-pyridinylmethyl)-8-oxa-11,16-diazatricyclo[16.3.1.0$^{2,7}$]docosa-1(22),2,4,6,18,20-hexaene-15-carboxamide;

tert-butyl N-[(9S,11R)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate;

tert-butyl N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]carbamate;

N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(2-naphthyl)acetamide;

N-[(9S,11R)-16-(3-fluorobenzyl)-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]acetamide;

N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]-2-(1-naphthyl)acetamide;

N-[(9S,11R)-16-methyl-14,20-dioxo-7-oxa-13,16,19,23-tetraazatetracyclo[19.3.1.1$^{2,6}$.0$^{9,13}$]hexacosa-1(25),2(26),3,5,21,23-hexaen-11-yl]benzenesulfonamide;

(13S,16R)-13-amino-16-methyl-18-oxa-8-thia-15-azatricyclo[17.3.1.0$^{2,7}$]tricosa-1(23),2,4,6,19,21-hexaen-14-one;

N-[(13S,16R)-16-methyl-14-oxo-18-oxa-8-thia-15-azatricyclo[17.3.1.0$^{2,7}$]tricosa-1(23),2,4,6,19,21-hexaen-13-yl]-2-(1-pyrrolidinyl)acetamide;

(10R,13S)-13-amino-10-methyl-8-oxa-18-thia-11,21-diazatricyclo[17.3.1.0$^{2,7}$]tricosa-1(23),2,4,6,19,21-hexaen-12-one;

(8S,18S,20S)-18-amino-25-fluoro-6,15-dioxo-N-phenyl-10,22-dioxa-4-thia-7,16-diazatetracyclo[21.3.1.1$^{2,5}$.0$^{16,20}$]octacosa-1(27),2,5(28),23,25-pentaene-8-carboxamide;

(8S,18S,20S)-18-amino-N-(4-chlorophenyl)-25-fluoro-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide;

(8S,18S,20S)-18-amino-25-fluoro-N-(3-methylphenyl)-6,15-dioxo-10,22-dioxa-4-thia-7,16-diazatetracyclo[21.3.1.1$^{2,5}$.0$^{16,20}$]octacosa-1(27),2,5(28),23,25-pentaene-8-carboxamide;

N-[(9S,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(2-naphthyl)acetamide;

N-[(95,11S,15S)-11-hydroxy-18,21-dimethyl-14,19-dioxo-7-oxa-3-thia-13,18,21,22-tetraazatetracyclo

[18.2.1.0$^{2,6}$.0$^{9,13}$]tricosa-1(22),2(6),4,20(23)-tetraen-15-yl]-2-(1-naphthyl)acetamide;
N-[(9S,11S,15S)-11-methoxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-2-(2-naphthyl)acetamide;
N-[(95,11S,15S)-11-hydroxy-18,21-dimethyl-14,19-dioxo-7-oxa-3-thia-13,18,21,22-tetraazatetracyclo[18.2.1.0$^{2,6}$.0$^{9,13}$]tricosa-1(22),2(6),4,20(23)-tetraen-15-yl]-N'-(2-naphthyl)urea;
(9S,11S,15S)-11-hydroxy-18,21-dimethyl-15-{[2-(2-naphthyl)ethyl]amino}-7-oxa-3-thia-13,18,21,22-tetraazatetracyclo[18.2.1.0$^{2,6}$.0$^{9,13}$]tricosa-1(22),2(6),4,20(23)-tetraene-14,19-dione;
2-(1H-imidazol-1-yl)-N-[(12R,16S,18S)-12-{[2-(1-naphthyl)acetyl]amino}-8,13-dioxo-20-oxa-9,14-diazatetracyclo[19.3.1.0$^{2,7}$.0$^{14,18}$]pentacosa-1(25),2,4,6,21,23-hexaen-16-yl]acetamide;
N-[(12R,16S,18S)-8,13-dioxo-16-{[(3-pyridinylamino)carbonyl]amino}-20-oxa-9,14-diazatetracyclo[19.3.1.0$^{2,7}$.0$^{14,18}$]pentacosa-1(25),2,4,6,21,23-hexaen-12-yl]-2-(1-naphthyl)acetamide;
2-(3-chlorophenyl)-N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]acetamide;
2-cyclohexyl-N-[(12R,16S,18S)-8,13-dioxo-16-{[2-(1-pyrrolidinyl)acetyl]amino}-20-oxa-9,14-diazatetracyclo[19.3.1.0$^{2,7}$.0$^{14,18}$]pentacosa-1(25),2,4,6,21,23-hexaen-12-yl]acetamide; or
N-[(12R,16S,18S)-12-{[(1-naphthylamino)carbonyl]amino}-8,13-dioxo-20-oxa-9,14-diazatetracyclo[19.3.1.0$^{2,7}$.0$^{14,18}$]pentacosa-1(25),2,4,6,21,23-hexaen-16-yl]-2-(1-pyrrolidinyl)acetamide.

9. A pharmaceutical composition comprising a compound or a mixture of compounds according to claim 1, or pharmaceutically acceptable salt(s) thereof, and at least one therapeutically inert excipient.

10. A method for the treatment of diseases, comprising:
administering the compound according to claim 1, or a pharmaceutically acceptable salt thereof, to a subject in need thereof,
said diseases to be treated are selected from the group consisting of pulmonary hypertension, asthma, psoriasis, allergic rhinitis, preterm delivery, cancer, and Alzheimer's disease.

11. The method according to claim 10,
wherein said administering occurs by oral, topical, transdermal, injection, buccal, transmucosal, pulmonary or inhalation administration, particularly in form of tablets, dragees, capsules, solutions, liquids, gels, plaster, creams, ointments, syrup, slurries, suspensions, spray, nebulizer or suppositories.

12. A compound according to claim 2 wherein
$R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})_qe$; $—(CR^{32}R^{33})_qR^{41}$; or $—(CR^{32}R^{33})_qR^{44}$;
$R^3$ and $R^4$ are independently defined as H; F; Cl; $CF_3$; $OCF_3$; $OCHF_2$; $NO_2$; CN; $C_{1-6}$-alkyl; cycloalkyl; $C_{1-6}$-alkoxy or aryloxy;
$R^5$ is H; $CF_3$; $C_{1-6}$-alkyl; or cycloalkyl;
$R^6$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})R^{40}$; $—(CR^{32}R^{33})_qR^{41}$; or $—(CR^{32}R^{33})_qR^{44}$;
$R^7$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;
$R^8$ and $R^9$ are independently defined as H; $CF_3$; $C_{1-6}$-alkyl; cycloalkyl; heterocycloalkyl;
$R^{10}$, $R^{11}$ and $R^{12}$ are independently defined as H; $C_{1-6}$-alkyl; or cycloalkyl;
$R^{13}$ is $C_{1-6}$-alkyl;
$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qSO_2R^{38}$; $—(CR^{32}R^{33})_qR^{39}$; $—(CR^{32}R^{33})R^{40}$; $—(CR^{32}R^{33})_qR^{41}$; or $—(CR^{32}R^{33})_qR^{44}$;
$R^{15}$, $R^{17}$, $R^{19}$, $R^{21}$, $R^{23}$, $R^{25}$, $R^{27}$, and $R^{31}$ are independently defined as H; or $C_{1-6}$-alkyl;
$R^{16}$, $R^{22}$ and $R^{28}$ are independently defined as H; $CF_3$; or $C_{1-6}$-alkyl;
$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; $—(CR^{32}R^{33})_qOR^{34}$; $—(CR^{32}R^{33})_rNR^7R^{35}$; $—(CR^{32}R^{33})_qOCONR^7R^{35}$; $—(CR^{32}R^{33})_rNR^7COOR^{36}$; $—(CR^{32}R^{33})_rNR^7COR^{37}$; $—(CR^{32}R^{33})_rNR^7CONR^7R^{35}$; $—(CR^{32}R^{33})_rNR^7SO_2R^{38}$; $—(CR^{32}R^{33})_rNR^7SO_2NR^7R^{35}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; or $—(CR^{32}R^{33})_qR^{44}$;
$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{51})_qOR^{45}$; $—(CR^{42}R^{51})_qSR^{45}$; $—(CR^{42}R^{51})_rNR^7R^{45}$; $—(CR^{42}R^{51})_qOCONR^7R^{45}$; $—(CR^{42}R^{51})_rNR^7COOR^{36}$; $—(CR^{42}R^{51})_rNR^7COR^{38}$; $—(CR^{42}R^{51})_rNR^7CONR^7R^{45}$; $—(CR^{42}R^{51})_rNR^7SO_2R^{38}$; $—(CR^{42}R^{51})_rNR^7SO_2NR^7R^{45}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_qCOR^{38}$; $—(CR^{42}R^{51})_qSO_2R^{38}$; $—(CR^{42}R^{51})_qR^{39}$; $—(CR^{42}R^{51})_qR^{40}$; $—(CR^{42}R^{51})_qR^{41}$; or $—(CR^{42}R^{51})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; heteroaryl-$C_{1-6}$-alkyl; $—(CR^{42}R^{51})_rOR^{45}$; $—(CR^{42}R^{51})_rNR^7R^{45}$; $—(CR^{42}R^{51})_rOCONR^7R^{35}$; $—(CR^{42}R^{51})_rNR^7COOR^{36}$; $—(CR^{42}R^{51})_rNR^7COR^{38}$; $—(CR^{42}R^{51})_rNR^7CONR^7R^{45}$; $—(CR^{42}R^{51})_rNR^7SO_2R^{38}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_qCOR^{38}$; $—(CR^{42}R^{51})_qSO_2R^{38}$; $—(CR^{42}R^{51})_qR^{39}$; $(CR^{42}R^{51})_sR^{40}$; $(CR^{42}R^{51})_qR^{41}$; or $(CR^{42}R^{51})_rR^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{32}R^{33})_rOR^{45}$; $—(CR^{32}R^{33})_rNR^7R^{45}$; $—(CR^{32}R^{33})_rOCONR^7R^{45}$; $—(CR^{32}R^{33})_rNR^7COOR^{36}$; $—(CR^{32}R^{33})_rNR^7COR^{37}$; $—(CR^{32}R^{33})_rNR^7CONR^7R^{45}$; $—(CR^{32}R^{33})_rNR^7SO_2R^{38}$; $—(CR^{32}R^{33})_rNR^7SO_2NR^7R^{45}$; $—(CR^{32}R^{33})_qCOOR^{36}$; $—(CR^{32}R^{33})_qCONR^7R^{45}$; $—(CR^{32}R^{33})_qCOR^{37}$; $—(CR^{32}R^{33})_qSO_2R^{38}$; $—(CR^{32}R^{33})_qSO_2NR^7R^{50}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{36}$ is H; $C_{1-6}$-alkyl; cycloalkyl; aryl; aryl-$C_{1-6}$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; $—(CR^{42}R^{51})_qOR^{45}$; $—(CR^{42}R^{51})_qSR^{45}$; $—(CR^{42}R^{51})_rNR^7R^{45}$; $—(CR^{42}R^{51})_rOCONR^7R^{45}$; $—(CR^{42}R^{51})_rNR^7COOR^{36}$; $—(CR^{42}R^{51})_rNR^7COR^{44}$; $—(CR^{42}R^{51})_rNR^7CONR^7R^{45}$; $—(CR^{42}R^{51})_rNR^7SO_2R^{38}$; $—(CR^{42}R^{51})_rNR^7SO_2NR^7R^{45}$; $—(CR^{42}R^{51})_qCOOR^{36}$; $—(CR^{42}R^{51})_qCONR^7R^{45}$; $—(CR^{42}R^{51})_qSO_2NR^7R^{45}$; $—(CR^{42}R^{51})_rCOR^{38}$; $—(CR^{42}R^{51})_qSO_2R^{38}$; $—(CR^{42}R^{51})_rR^{39}$; $—(CR^{42}R^{51})_uR^{40}$; $—(CR^{42}R^{51})_rR^{41}$; or $—(CR^{42}R^{51})_rR^{44}$;

$R^{38}$ is $C_{1-6}$-alkyl; $C_{2-6}$-alkenyl; cycloalkyl; heterocycloalkyl; aryl; heteroaryl; aryl-$C_{1-6}$-alkyl; or heteroaryl-$C_{1-6}$-alkyl;

$R^{42}$ and $R^{43}$ are independently defined as H; F; $CF_3$; $C_{1-6}$-alkyl; $C_{2-6}$-alkenyl; cycloalkyl; heterocycloalkyl; aryl-$C_{1-6}$-alkyl; or heteroaryl-$C_{1-6}$-alkyl;

$R^{44}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or a group of one of the formulae

H51

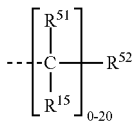

H52

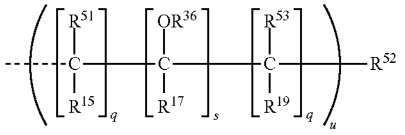

H53

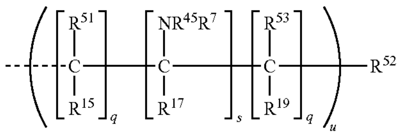

-continued

H54

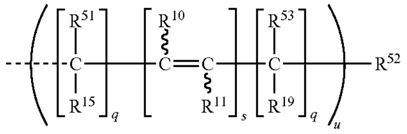

H55

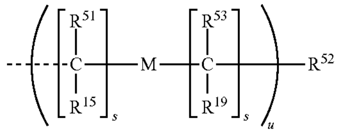

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{42}R^{51})_rOR^{36}$; $—(CR^{42}R^{51})_rNR^7R^{57}$; $—(CR^{42}R^{51})_rOCONR^7R^{57}$; $—(CR^{42}R^{51})_rNR^7CONR^7R^{57}$; $—(CR^{42}R^{51})_rNR^7COR^{38}$; $—(CR^{42}R^{51})_rNR^7SO_2R^{38}$; $—(CR^{42}R^{51})_rNR^7SO_2NR^7R^{57}$; $—(CR^{42}R^{51})—COOR^{36}$; $—(CR^{42}R^{51})_qCOR^{38}$; $—(CR^{42}R^{51})—SO_2R^{33}$; $—(CR^{42}R^{51})_qR^{39}$; $—(CR^{42}R^{51})_sR^{40}$; $—(CR^{42}R^{51})_qR^{41}$; or $—(CR^{42}R^{51})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—(CR^{42}R^{51})_qOR^{36}$; $—(CR^{42}R^{51})_qSR^{36}$; $—(CR^{42}R^{51})—NR^7R^{57}$; $—(CR^{42}R^{51})—OCONR^7R^{57}$; $—(CR^{42}R^{51})_qNR^{44}COOR^{36}$; $—(CR^{42}R^{51})_qNR^7COR^{38}$; $—(CR^{42}R^{51})_qNR^7CONR^7R^{45}$; $—(CR^{42}R^{51})_qNR^7SO_2R^{38}$; $—(CR^{42}R^{51})_qNR^7SO_2NR^7R^{45}$; $—(CR^{42}R^{51})_qCOOR^{36}$; $—(CR^{42}R^{51})_qCONR^7R^{45}$; $—(CR^{42}R^{51})—SO_2NR^7R^{45}$; $—(CR^{42}R^{51})_qCOR^{38}$; $—(CR^{42}R^{51})—SO_2R^{38}$; or $—(CR^{42}R^{51})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $—NR^7R^{45}$;

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{42}R^{51})_rOR^{45}$; $—(CR^{42}R^{51})_rSR^{45}$; $—(CR^{42}R^{51})_rNR^7R^{45}$; $—(CR^{42}R^{51})_rOCONR^7R^{45}$; $—(CR^{42}R^{51})_rNR^7COOR^{36}$; $—(CR^{42}R^{51})_rNR^7COR^{38}$; $—(CR^{42}R^{51})_rNR^7CONR^7R^{45}$; $—(CR^{42}R^{51})_rNR^7SO_2R^{38}$; $—(CR^{42}R^{51})_rNR^7SO_2NR^7R^{45}$; $—(CR^{42}R^{51})—COOR^{36}$; $—(CR^{42}R^{51})_qCONR^7R^{45}$; $—(CR^{42}R^{51})_rSO_2NR^7R^{45}$; $—(CR^{42}R^{51})_qCOR^{38}$; $—(CR^{42}R^{51})—SO_2R^{38}$; or $—(CR^{42}R^{51})_sR^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{51})_qOR^{36}$; $—(CR^{42}R^{51})_qSR^{36}$; $—(CR^{42}R^{51})_qNR^7R^{45}$; $—(CR^{42}R^{51})_qNR^7COOR^{36}$; $—(CR^{42}R^{51})_qNR^7COR^{38}$; $—(CR^{42}R^{51})_qNR^7SO_2R^{38}$; $—(CR^{42}R^{51})_qNR^7CONR^7R^{45}$; $—(CR^{42}R^{51})_qCOOR^{36}$; $—(CR^{42}R^{51})_qCONR^7R^{45}$; $—(CR^{42}R^{51})_qCOR^{38}$; or $—(CR^{42}R^{51})_qR^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_tOR^{36}$; $—(CR^{42}R^{43})_tNR^7R^{57}$; $—(CR^{42}R^{43})_tCOOR^{36}$; or $—(CR^{42}R^{43})_tCONR^7R^{57}$;

$R^{52}$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$OR^{36}$; —$NR^7R^{57}$; —$NR^7COR^{38}$; —$NR^7COOR^{36}$; —$NR^7SO_2R^{38}$; —$NR^7CONR^7R^{57}$; —$COOR^{36}$; —$CONR^7R^{57}$; —C(=$NR^7$)$NR^7R^{57}$; —$NR^7$C(=$NR^7$)$NR^7R^{57}$; or a group of one of the formulae
H56
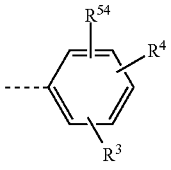
H57
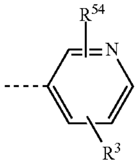
H58
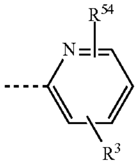
H59
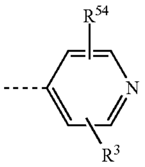
H60
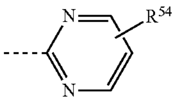
H61
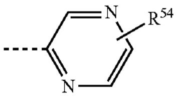
H62
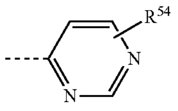
H63
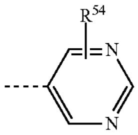
H64
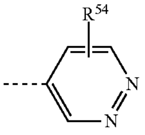
-continued
H65
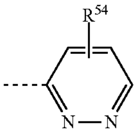
H66
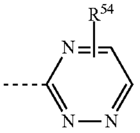
H67
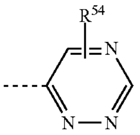
H68
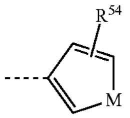
H69
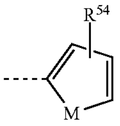
H70
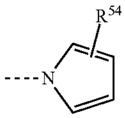
H71
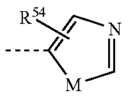
H72
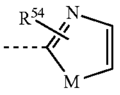
H73
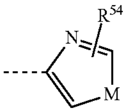
H74
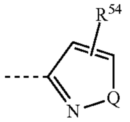
H75
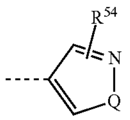
H76
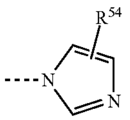

-continued
H77
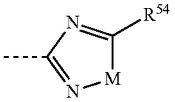
H78
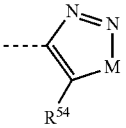
H79
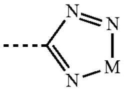
H80
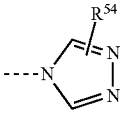
H81
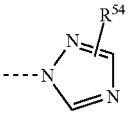
H82
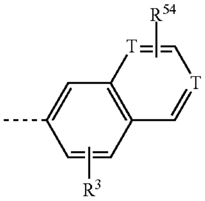
H83
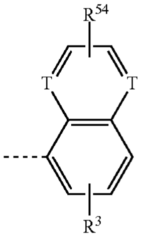
H84
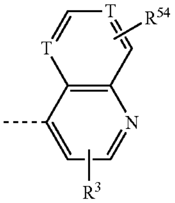
H85
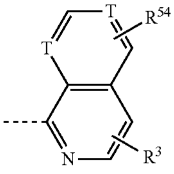
-continued
H86
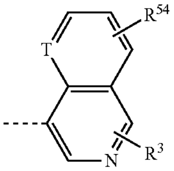
H87
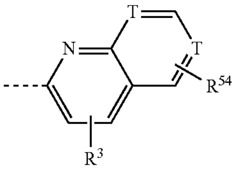
H88
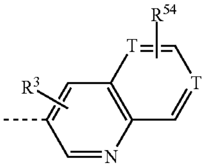
H89
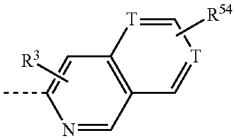
H90
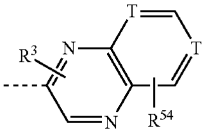
H91
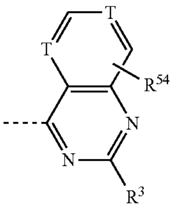
H92
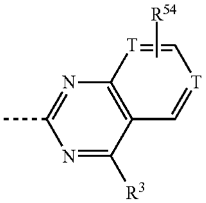
H93
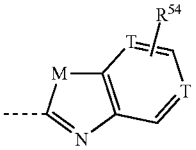
H94
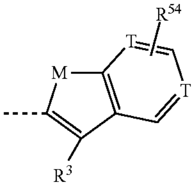

-continued

H95

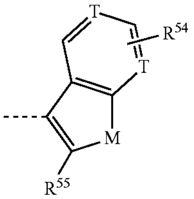

H96

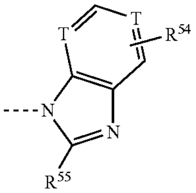

H97

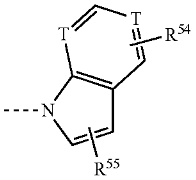

H98

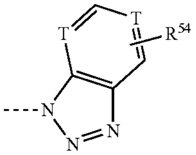

H99

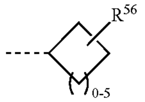

H100

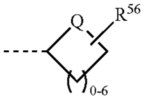

H101

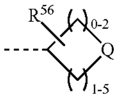

H102

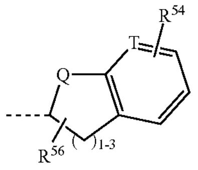

H103

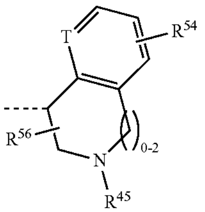

-continued

H104

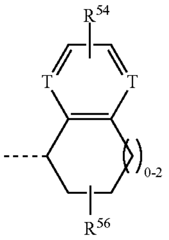

H105

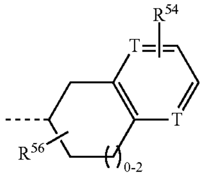

H106

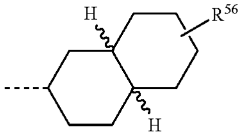

H107

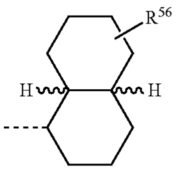

H108

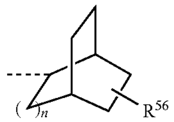

H109

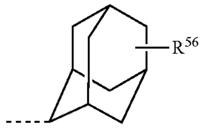

H110

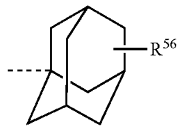

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$OR^{36}$; —$NR^7R^{57}$; —$NR^7COR^{38}$; —$NR^7SO_2R^{38}$; —$NR^7CONR^7R^{57}$; —$COR^{38}$; or —$SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; —$COOR^{36}$; or —$CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_rOR^{36}$; —$(CR^{42}R^{43})_rNR^7R^{45}$; —$(CR^{42}R^{43})_qCOOR^{36}$; or —$(CR^{42}R^{43})_qCONR^7R^{45}$;

$R^{57}$ is H; $C_{1-6}$-alkyl; $C_{2-6}$-alkenyl; cycloalkyl; aryl-$C_{1-6}$-alkyl; or an N-protecting group;

or a stereoisomer of such a compound; or a salt, solvate, clathrate, N-oxide, isotopically enriched or enantiomerically enriched version thereof.

13. A compound according to claim 2 wherein the Template A is selected from $A_B1$-$A_C1$; $A_B1$-$A_C4$; $A_B1$-$A_C6$; $A_B1$-$A_C8$; $A_B1$-$A_C9$; $A_B1$-$A_C11$; $A_B1$-$A_C13$; $A_B1$-$A_C19$; $A_B1$-$A_C22$; $A_B1$-$A_C24$; $A_B1$-$A_C49$; $A_B1$-$A_C51$; $A_B2$-$A_C4$; $A_B2$-$A_C51$; $A_B4$-$A_C1$; $A_B4$-$A_C4$; $A_B4$-$A_C6$; $A_B4$-$A_C19$; $A_B4$-$A_C22$; $A_B4$-$A_C24$; $A_B4$-$A_C49$; $A_B4$-$A_C51$; $A_B4$-$A_C59$; $A_B5$-$A_C51$; $A_B5$-$A_C59$; $A_B6$-$A_C1$; $A_B6$-$A_C4$; $A_B6$-$A_C8$; $A_B6$-$A_C9$; $A_B6$-$A_C11$; $A_B6$-$A_C13$; $A_B6$-$A_C16$; $A_B6$-$A_C18$; $A_B6$-$A_C19$; $A_B6$-$A_C20$; $A_B6$-$A_C30$; $A_B6$-$A_C31$; $A_B6$-$A_C49$; $A_B6$-$A_C51$; $A_B9$-$A_C6$; $A_B9$-$A_C49$; $A_B14$-$A_C49$; $A_B20$-$A_C6$; $A_B20$-$A_C49$; $A_B23$-$A_C4$; $A_B23$-$A_C49$; $A_B45$-$A_C49$; $A_B45$-$A_C52$; $A_B45$-$A_C57$; $A_B45$-$A_C58$; $A_B45$-$A_C65$; $A_B45$-$A_C66$; $A_B46$-$A_C57$; $A_B46$-$A_C58$; $A_B49$-$A_C49$; $A_B50$-$A_C57$; $A_B50$-$A_C58$; $A_B50$-$A_C61$; $A_B51$-$A_C49$; $A_B51$-$A_C61$; or $A_B59$-$A_C61$;

the Modulator B is selected from

B1; B4; B5; B6; or B7;

and wherein $R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_q NR^7CONR^7R^{35}$; —$(CR^{32}R^{33})_qNR^7SO_2R^{38}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qR^{39}$; —$(CR^{32}R^{33})_qR^{40}$; —$(CR^{32}R^{33})_q R^{41}$; or —$(CR^{32}R^{33})_qR^{44}$;

$R^3$ and $R^4$ are independently defined as H; F; Cl; $CF_3$; $OCF_3$; $OCHF_2$; $NO_2$; CN; $C_{1-6}$-alkyl; or $C_{1-6}$-alkoxyl;

$R^5$ is H; $CF_3$; or $C_{1-6}$-alkyl;

$R^6$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_qNR^7CONR^7R^{35}$; —$(CR^{32}R^{33})_qNR^7SO_2R^{38}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qR^{39}$; —$(CR^{32}R^{33})_sR^{40}$; —$(CR^{32}R^{33})_qR^{41}$; or —$(CR^{32}R^{33})_qR^{44}$;

$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{32}R^{33})_qOR^{34}$; —$(CR^{32}R^{33})_qSR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_q NR^7CONR^7R^{35}$; —$(CR^{32}R^{33})_qNR^7SO_2R^{38}$; —$(CR^{32}R^{33})_qCOOR^{36}$; —$(CR^{32}R^{33})_qCONR^7R^{35}$; —$(CR^{32}R^{33})_qSO_2NR^7R^{35}$; —$(CR^{32}R^{33})_qCOR^{37}$; —$(CR^{32}R^{33})_qR^{39}$; —$(CR^{32}R^{33})_sR^{40}$; —$(CR^{32}R^{33})_q R^{41}$; or —$(CR^{32}R^{33})_qR^{44}$;

$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; —$(CR^{32}R^{33})_qOR^{34}$; —$(CR^{32}R^{33})_qNR^7R^{35}$; —$(CR^{32}R^{33})_qOCONR^7R^{35}$; —$(CR^{32}R^{33})_qNR^7COOR^{36}$; —$(CR^{32}R^{33})_qNR^7COR^{37}$; —$(CR^{32}R^{33})_rNR^7CONR^7R^{35}$; —$(CR^{32}R^{33})_qNR^7SO_2R^{38}$; —$(CR^{32}R^{33})_qCOOR^{36}$; —$(CR^{32}R^{33})_qCONR^7R^{35}$; —$(CR^{32}R^{33})_qCOR^{37}$; or —$(CR^{32}R^{33})_qR^{44}$;

$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; —$(CR^{42}R^{43})_qOR^{45}$; —$(CR^{42}R^{43})_qSR^{45}$; —$(CR^{42}R^{43})_rNR^7R^{45}$; —$(CR^{42}R^{43})_r NR^7COOR^{36}$; —$(CR^{42}R^{43})_rNR^7COR^{38}$; —$(CR^{42}R^{43})_qCOOR^{36}$; —$(CR^{42}R^{43})_qCONR^7R^{45}$; —$(CR^{42}R^{43})_qCOR^{38}$; —$(CR^{42}R^{43})_qR^{39}$; —$(CR^{42}R^{43})_sR^{40}$; —$(CR^{42}R^{43})_qR^{41}$; or —$(CR^{42}R^{43})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; —$(CR^{42}R^{43})_rOR^{45}$; —$(CR^{42}R^{43})_rNR^7R^{45}$; —$(CR^{42}R^{43})_rOCONR^7R^{35}$; —$(CR^{42}R^{43})_rNR^7COOR^{36}$; —$(CR^{42}R^{43})_rNR^7COR^{38}$; —$(CR^{42}R^{43})_rNR^7CONR^7R^{45}$; —$(CR^{42}R^{43})_rNR^7SO_2R^{38}$; —$(CR^{42}R^{43})_qCOOR^{36}$; —$(CR^{42}R^{43})_qCONR^7R^{45}$; —$(CR^{42}R^{43})_qCOR^{38}$; —$(CR^{42}R^{43})_qR^{39}$; —$(CR^{42}R^{43})_sR^{40}$; —$(CR^{42}R^{43})_qR^{41}$; or —$(CR^{42}R^{43})_q R^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{32}R^{33})_rOR^{45}$; $(CR^{32}R^{33})_rNR^7R^{45}$; —$(CR^{32}R^{33})_rOCONR^7R^{45}$; —$(CR^{32}R^{33})_rNR^7COOR^{36}$; —$(CR^{32}R^{33})_rNR^7COR^{37}$; —$(CR^{32}R^{33})_rNR^7CONR^7R^{50}$; —$(CR^{32}R^{33})_rNR^7SO_2R^{38}$; —$(CR^{32}R^{33})_qCOOR^{36}$; —$(CR^{32}R^{33})_qCONR^7R^{45}$; —$(CR^{32}R^{33})_qCOR^{38}$; —$(CR^{32}R^{33})_qR^{39}$; —$(CR^{32}R^{33})_sR^{40}$; —$(CR^{32}R^{33})_qR^{41}$; or —$(CR^{32}R^{33})_q R^{44}$;

$R^{36}$ is H; $C_{1-6}$-alkyl; cycloalkyl; aryl; aryl-$C_{1-6}$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; —$(CR^{42}R^{43})_qOR^{45}$; —$(CR^{42}R^{43})_qSR^{45}$; —$(CR^{42}R^{43})_rNR^7R^{45}$; —$(CR^{42}R^{43})_sOCONR^7R^{45}$; —$(CR^{42}R^{43})_rNR^7COOR^{36}$; —$(CR^{42}R^{43})_rNR^7COR^{44}$; —$(CR^{42}R^{43})_rNR^7CONR^7R^{45}$; —$(CR^{42}R^{43})_rNR^7SO_2R^{38}$; —$(CR^{42}R^{43})_qCOOR^{36}$; —$(CR^{42}R^{43})_qCONR^7R^{45}$; —$(CR^{42}R^{43})_tCOR^{38}$; —$(CR^{42}R^{43})_tR^{39}$; —$(CR^{42}R^{43})_u R^{40}$; —$(CR^{42}R^{43})_tR^{41}$; or —$(CR^{42}R^{43})_tR^{44}$;

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{42}R^{43})_rOR^{36}$; —$(CR^{42}R^{43})_rNR^7R^{57}$; —$(CR^{42}R^{43})_rOCONR^7R^{57}$; —$(CR^{42}R^{43})_rNR^7CONR^7R^{57}$; —$(CR^{42}R^{43})_rNR^7COR^{38}$; —$(CR^{42}R^{43})_rNR^7SO_2R^{38}$; —$(CR^{42}R^{43})_qCOOR^{36}$; —$(CR^{42}R^{43})_qCOR^{38}$; —$(CR^{42}R^{43})_qR^{39}$; —$(CR^{42}R^{43})_sR^{40}$; $(CR^{42}R^{43})^{41}$; or —$(CR^{42}R^{43})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; —$(CR^{42}R^{43})_qOR^{36}$; —$(CR^{42}R^{43})_qNR^7R^{57}$; —$(CR^{42}R^{43})_qNR^7COR^{38}$; —$(CR^{42}R^{43})_qCOOR^{36}$; —$(CR^{42}R^{43})_qCONR^7R^{45}$; —$(CR^{42}R^{43})_qSO_2NR^7R^{45}$; —$(CR^{42}R^{43})_qCOR^{38}$; or —$(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or —$NR^7R^{45}$;

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; —$(CR^{42}R^{43})_rOR^{45}$; —$(CR^{42}R^{43})_rSR^{45}$; —$(CR^{42}R^{43})_rNR^7R^{45}$; —$(CR^{42}R^{43})_rOCONR^7R^{45}$; —$(CR^{42}R^{43})_rNR^7COOR^{36}$; —$(CR^{42}R^{43})_rNR^7COR^{38}$; —$(CR^{42}R^{43})_rNR^7CONR^7R^{45}$; —$(CR^{42}R^{43})_rNR^7SO_2R^{38}$;

$—(CR^{42}R^{43})_qCOOR^{36}$; $—(CR^{42}R^{43})_qCONR^7R^{45}$; $—(CR^{42}R^{43})_qCOR^{38}$; or $—(CR^{42}R^{43})_sR^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_qOR^{36}$; $—(CR^{42}R^{43})_qNR^7R^{45}$; $—(CR^{42}R^{43})_qNR^7COR^{38}$; $—(CR^{42}R^{43})_qNR^7SO_2R^{38}$; $—(CR^{42}R^{43})_qCOOR^{36}$; $—(CR^{42}R^{43})_qCONR^7R^{45}$; $—(CR^{42}R^{43})_qCOR^{38}$; or $—(CR^{42}R^{43})_qR^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_tOR^{36}$; $—(CR^{42}R^{43})_tNR^7R^{57}$; $—(CR^{42}R^{43})_tCOOR^{36}$; or $—(CR^{42}R^{43})_tCONR^7R^{57}$;

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—OR^{36}$; $—NR^7R^{57}$; $—NR^7COR^{38}$; $—NR^7SO_2R^{38}$; $—NR^7CONR^7R^{57}$; $—COR^{38}$; or $—SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; $—COOR^{36}$; or $—CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_rOR^{36}$; $—(CR^{42}R^{43})_rNR^7R^{45}$; $—(CR^{42}R^{43})_qCOOR^{36}$; or $—(CR^{42}R^{43})_qCONR^7R^{45}$;

or a stereoisomer of such a compound; or a salt, solvate, clathrate, N-oxide, isotopically enriched or enantiomerically enriched version thereof.

14. A compound according to claim 3 wherein the Template A is selected from $A_B1$-$A_C1$; $A_B1$-$A_C4$; $A_B1$-$A_C6$; $A_B1$-$A_C8$; $A_B1$-$A_C9$; $A_B1$-$A_C11$; $A_B1$-$A_C13$; $A_B1$-$A_C19$; $A_B1$-$A_C22$; $A_B1$-$A_C24$; $A_B1$-$A_C49$; $A_B1$-$A_C51$; $A_B2$-$A_C4$; $A_B2$-$A_C51$; $A_B4$-$A_C1$; $A_B4$-$A_C4$; $A_B4$-$A_C6$; $A_B4$-$A_C19$; $A_B4$-$A_C22$; $A_B4$-$A_C24$; $A_B4$-$A_C49$; $A_B4$-$A_C51$; $A_B4$-$A_C59$; $A_B5$-$A_C51$; $A_B5$-$A_C59$; $A_B6$-$A_C1$; $A_B6$-$A_C4$; $A_B6$-$A_C8$; $A_B6$-$A_C9$; $A_B6$-$A_C11$; $A_B6$-$A_C13$; $A_B6$-$A_C16$; $A_B6$-$A_C18$; $A_B6$-$A_C19$; $A_B6$-$A_C20$; $A_B6$-$A_C30$; $A_B6$-$A_C31$; $A_B6$-$A_C49$; $A_B6$-$A_C51$; $A_B9$-$A_C6$; $A_B9$-$A_C49$; $A_B14$-$A_C49$; $A_B20$-$A_C6$; $A_B20$-$A_C49$; $A_B23$-$A_C4$; $A_B23$-$A_C49$; $A_B45$-$A_C49$; $A_B45$-$A_C52$; $A_B45$-$A_C57$; $A_B45$-$A_C58$; $A_B45$-$A_C65$; $A_B45$-$A_C66$; $A_B46$-$A_C57$; $A_B46$-$A_C58$; $A_B49$-$A_C49$; $A_B50$-$A_C57$; $A_B50$-$A_C58$; $A_B50$-$A_C61$; $A_B51$-$A_C49$; $A_B51$-$A_C61$; or $A_B59$-$A_C61$;

the Modulator B is selected from

B1; B4; B5; B6; or B7;

and wherein $R^1$ and $R^2$ are independently defined as H; F; Cl; Br; I; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qR^{39}$; $—(CR^{32}R^{33})_qR^{40}$; $—(CR^{32}R^{33})_qR^{41}$; or $—(CR^{32}R^{33})_rR^{44}$;

$R^3$ and $R^4$ are independently defined as H; F; Cl; $CF_3$; $OCF_3$; $OCHF_2$; $NO_2$; CN; $C_{1-6}^-$ alkyl; or $C_{1-6}$-alkoxyl;

$R^5$ is H; $CF_3$; or $C_{1-6}$-alkyl;

$R^6$ is H; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{14}$, $R^{20}$ and $R^{26}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{32}R^{33})_qOR^{34}$; $—(CR^{32}R^{33})_qSR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_qNR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qSO_2NR^7R^{35}$; $—(CR^{32}R^{33})_qCOR^{37}$; $—(CR^{32}R^{33})_qR^{39}$; $—(CR^{32}R^{33})_sR^{40}$; $—(CR^{32}R^{33})_qR^{41}$; or $—(CR^{32}R^{33})_rR^{44}$;

$R^{18}$, $R^{24}$ and $R^{30}$ are independently defined as H; F; $CF_3$; $C_{1-6}$-alkyl; $C_{2-6}$-alkenyl; cycloalkyl; heterocycloalkyl; aryl-$C_{1-6}$-alkyl; heteroaryl-$C_{1-6}$-alkyl; $—(CR^{32}R^{33})_qOR^{34}$; $—(CR^{32}R^{33})_qNR^7R^{35}$; $—(CR^{32}R^{33})_qOCONR^7R^{35}$; $—(CR^{32}R^{33})_qNR^7COOR^{36}$; $—(CR^{32}R^{33})_qNR^7COR^{37}$; $—(CR^{32}R^{33})_rNR^7CONR^7R^{35}$; $—(CR^{32}R^{33})_qNR^7SO_2R^{38}$; $—(CR^{32}R^{33})_qCOOR^{36}$; $—(CR^{32}R^{33})_qCONR^7R^{35}$; $—(CR^{32}R^{33})_qCOR^{37}$; or $—(CR^{32}R^{33})_qR^{44}$;

$R^{32}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $—(CR^{42}R^{43})_qOR^{45}$; $—(CR^{42}R^{43})_qSR^{45}$; $—(CR^{42}R^{43})_rNR^7R^{45}$; $—(CR^{42}R^{43})_rNR^7COOR^{36}$; $—(CR^{42}R^{43})_rNR^7COR^{38}$; $—(CR^{42}R^{43})_q COOR^{36}$; $—(CR^{42}R^{43})_qCONR^7R^{45}$; $—(CR^{42}R^{43})_q COR^{38}$; $—(CR^{42}R^{43})_qR^{39}$; $—(CR^{42}R^{43})_sR^{40}$; $—(CR^{42}R^{43})_qR^{41}$; or $—(CR^{42}R^{43})_qR^{44}$;

$R^{33}$ is H; or $C_{1-6}$-alkyl;

$R^{34}$ is H; $C_{1-6}$-alkyl; $C_{2-6}$-alkenyl; cycloalkyl; aryl; heteroaryl; aryl-$C_{1-6}$-alkyl; $—(CR^{42}R^{43})_rOR^{45}$; $—(CR^{42}R^{43})_rNR^7R^{45}$; $—(CR^{42}R^{43})_rOCONR^7R^{35}$; $—(CR^{42}R^{43})_rNR^7COOR^{36}$; $—(CR^{42}R^{43})_rNR^7COR^{38}$; $—(CR^{42}R^{43})_rNR^7CONR^7R^{45}$; $—(CR^{42}R^{43})_rNR^7SO_2R^{38}$; $—(CR^{42}R^{43})_qCOOR^{36}$; $—(CR^{42}R^{43})_qCONR^7R^{45}$; $—(CR^{42}R^{43})_qCOR^{38}$; $—(CR^{42}R^{43})_qR^{39}$; $—(CR^{42}R^{43})_sR^{40}$; $—(CR^{42}R^{43})_qR^{41}$; or $—(CR^{42}R^{43})_qR^{44}$;

$R^{35}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $—(CR^{32}R^{33})_rOR^{45}$; $(CR^{32}R^{33})_rNR^7R^{45}$; $—(CR^{32}R^{33})_rOCONR^7R^{45}$; $—(CR^{32}R^{33})_rNR^7COOR^{36}$; $—(CR^{32}R^{33})_rNR^7COR^{37}$; $—(CR^{32}R^{33})_rNR^7CONR^7R^{50}$; $—(CR^{32}R^{33})_rNR^7SO_2R^{38}$; $—(CR^{32}R^{33})_qCOOR^{36}$; $—(CR^{32}R^{33})_qCONR^7R^{45}$; $—(CR^{32}R^{33})_qCOR^{38}$; $—(CR^{32}R^{33})_qR^{39}$; $—(CR^{32}R^{33})_sR^{40}$; $—(CR^{32}R^{33})_qR^{41}$; or $—(CR^{32}R^{33})_qR^{44}$;

$R^{36}$ is H; $C_{1-6}$-alkyl; cycloalkyl; aryl; aryl-$C_{1-6}$-alkyl; or an O/S-protecting group;

$R^{37}$ is $C_{1-6}$-alkyl; cycloalkyl; heterocycloalkyl; aryl; heteroaryl; aryl-$C_{1-6}$-alkyl; heteroaryl-$C_{1-6}$-alkyl; $—(CR^{42}R^{43})_qOR^{45}$; $—(CR^{42}R^{43})_qSR^{45}$; $—(CR^{42}R^{43})_rNR^7R^{45}$; $—(CR^{42}R^{43})_sOCONR^7R^{45}$; $—(CR^{42}R^{43})_rNR^7COOR^{36}$; $—(CR^{42}R^{43})_rNR^7COR^{44}$; $—(CR^{42}R^{43})_r$ $NR^7CONR^7R^{45}$; $-(CR^{42}R^{43})_rNR^7SO_2R^{38}$; $-(CR^{42}R^{43})_qCOOR^{36}$; $-(CR^{42}R^{43})_qCONR^7R^{45}$; $-(CR^{42}R^{43})_rCOR^{38}$; $-(CR^{42}R^{43})_rR^{39}$; $-(CR^{42}R^{43})_uR^{40}$; $-(CR^{42}R^{43})_rR^{41}$; or $-(CR^{42}R^{43})_rR^{44}$;

$R^{45}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $-(CR^{42}R^{43})_rOR^{36}$; $-(CR^{42}R^{43})_rNR^7R^{57}$; $-(CR^{42}R^{43})_rOCONR^7R^{57}$; $-(CR^{42}R^{43})_rNR^7CONR^7R^{57}$; $-(CR^{42}R^{43})_rNR^7COR^{38}$; $-(CR^{42}R^{43})_rNR^7SO_2R^{38}$; $-(CR^{42}R^{43})_qCOOR^{36}$; $-(CR^{42}R^{43})_qCOR^{38}$; $-(CR^{42}R^{43})_qR^{39}$; $-(CR^{42}R^{43})_sR^{40}$; $(CR^{42}R^{43})^{41}$; or $-(CR^{42}R^{43})_sR^{44}$;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $-(CR^{42}R^{43})_qOR^{36}$; $-(CR^{42}R^{43})_qNR^7R^{57}$; $-(CR^{42}R^{43})_qNR^7COR^{38}$; $-(CR^{42}R^{43})_qCOOR^{36}$; $-(CR^{42}R^{43})_qCONR^7R^{45}$; $-(CR^{42}R^{43})_qSO_2NR^7R^{45}$; $-(CR^{42}R^{43})_qCOR^{38}$; or $-(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $-NR^7R^{45}$;

$R^{48}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; an N-protecting group; $-(CR^{42}R^{43})_rOR^{45}$; $-(CR^{42}R^{43})_rSR^{45}$; $-(CR^{42}R^{43})_rNR^7R^{45}$; $-(CR^{42}R^{43})_rOCONR^7R^{45}$; $-(CR^{42}R^{43})_rNR^7COOR^{36}$; $-(CR^{42}R^{43})_rNR^7COR^{38}$; $-(CR^{42}R^{43})_rNR^7CONR^7R^{45}$; $-(CR^{42}R^{43})_rNR^7SO_2R^{38}$; $-(CR^{42}R^{43})_qCOOR^{36}$; $-(CR^{42}R^{43})_qCONR^7R^{45}$; $-(CR^{42}R^{43})_qCOR^{38}$; or $-(CR^{42}R^{43})_sR^{44}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $-(CR^{42}R^{43})_qOR^{36}$; $-(CR^{42}R^{43})_qNR^7R^{45}$; $-(CR^{42}R^{43})_qNR^7COR^{38}$; $-(CR^{42}R^{43})_qNR^7SO_2R^{38}$; $-(CR^{42}R^{43})_qCOOR^{36}$; $-(CR^{42}R^{43})_qCONR^7R^{45}$; $-(CR^{42}R^{43})_qCOR^{38}$; or $-(CR^{42}R^{43})_qR^{44}$;

$R^{50}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or an N-protecting group;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $-(CR^{42}R^{43})_tOR^{36}$; $-(CR^{42}R^{43})_tNR^7R^{57}$; $-(CR^{42}R^{43})_tCOOR^{36}$; or $-(CR^{42}R^{43})_tCONR^7R^{57}$;

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $-OR^{36}$; $-NR^7R^{57}$; $-NR^7COR^{38}$; $-NR^7SO_2R^{38}$; $-NR^7CONR^7R^{57}$; $-COR^{38}$; or $-SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; $-COOR^{36}$; or $-CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $-(CR^{42}R^{43})_rOR^{36}$; $-(CR^{42}R^{43})_rNR^7R^{45}$; $-(CR^{42}R^{43})_qCOOR^{36}$; or $-(CR^{42}R^{43})_qCONR^7R^{45}$;

or a stereoisomer of such a compound; or a salt, solvate, clathrate, N-oxide, isotopically enriched or enantiomerically enriched version thereof.

15. A compound according to claim 2 wherein the Template A is selected from $A_B1$-$A_C1$; $A_B1$-$A_C4$; $A_B1$-$A_C19$; $A_B2$-$A_C4$; $A_B4$-$A_C1$; $A_B4$-$A_C4$; $A_B4$-$A_C19$; $A_B4$-$A_C59$; $A_B5$-$A_C51$; $A_B5$-$A_C59$; $A_B6$-$A_C31$; $A_B9$-$A_C6$; or $A_B46$-$A_C58$;

and wherein $R^3$ and $R^4$ are independently defined as H; F; $CF_3$; $OCF_3$; $OCHF_2$; CN; or $C_{1-6}$-alkoxyl;

$R^5$ is H; $CF_3$; or $C_{1-6}$-alkyl;

$R^{33}$ is H; or $C_{1-6}$-alkyl;

$R^{46}$ is H; F; Cl; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $-(CR^{42}R^{43})_qR^{44}$;

$R^{47}$ is H; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; or $-NR^7R^{45}$;

$R^{49}$ is H; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; or $-(CR^{42}R^{43})_qR^{44}$;

$R^{51}$ and $R^{53}$ are independently defined as H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $-(CR^{42}R^{43})_tOR^{36}$; $-(CR^{42}R^{43})NR^7R^{57}$; $-(CR^{42}R^{43})_tCOOR^{36}$; or $-(CR^{42}R^{43})_tCONR^7R^{57}$;

$R^{54}$ is H; F; $CF_3$; $OCF_3$; $OCHF_2$; $NO_2$; CN; $C_{1-6}$-alkyl; $C_{2-6}$-alkenyl; $C_{2-6}$-alkynyl; cycloalkyl; heterocycloalkyl; aryl-$C_{1-6}$-alkyl; heteroaryl-$C_{1-6}$-alkyl; $-OR^{36}$; $-NR^7R^{57}$; $-NR^7COR^{38}$; $-NR^7SO_2R^{38}$; $-NR^7CONR^7R^{57}$; $-COR^{38}$; or $-SO_2R^{38}$;

$R^{55}$ is H; $CF_3$; $C_{1-6}$-alkyl; $C_{2-6}$-alkenyl; $C_{2-6}$-alkynyl; cycloalkyl; heterocycloalkyl; aryl; heteroaryl; aryl-$C_{1-6}$-alkyl; heteroaryl-$C_{1-6}$-alkyl; $-COOR^{36}$; or $-CONR^7R^{45}$;

$R^{56}$ is H; F; $CF_3$; $C_{1-6}$-alkyl; $C_{2-6}$-alkenyl; cycloalkyl; heterocycloalkyl; aryl; heteroaryl; aryl-$C_{1-6}$-alkyl; heteroaryl-$C_{1-6}$-alkyl; $-(CR^{42}R^{43})_rOR^{36}$; $-(CR^{42}R^{43})_rNR^7R^{45}$; $-(CR^{42}R^{43})_qCOOR^{36}$; or $-(CR^{42}R^{43})_qCONR^7R^{45}$;

or a stereoisomer of such a compound; or a salt, solvate, clathrate, N-oxide, isotopically enriched or enantiomerically enriched version thereof.

* * * * *